(12) United States Patent
Kishi et al.

(10) Patent No.: US 11,548,898 B2
(45) Date of Patent: Jan. 10, 2023

(54) SYNTHESIS OF HALICHONDRINS

(71) Applicants: President and Fellows of Harvard College, Cambridge, MA (US); Eisai R&D Management Co., LTD., Tokyo (JP)

(72) Inventors: Yoshito Kishi, Cambridge, MA (US); Yanran Ai, Wilmington, DE (US); Ning Ye, Suzhou (CN); Qiaoyi Wang, Waltham, MA (US); Kenzo Yahata, Osaka (JP); Kentaro Iso, Tsukuba (JP); Santhosh Reddy Naini, Arlington, MA (US); Shuji Yamashita, Yokohama (JP); Jihoon Lee, Gyeonggi-do (KR); Isao Ohashi, Tsukuba (JP); Takashi Fukuyama, Tsukuba (JP)

(73) Assignees: President and Fellows of Harvard College, Cambridge, MA (US); Eisai R&D Management Co., LTD., Tokyo (JP)

( * ) Notice: Subject to any disclaimer, the term of this patent is extended or adjusted under 35 U.S.C. 154(b) by 166 days.

(21) Appl. No.: 16/628,504

(22) PCT Filed: Jul. 6, 2018

(86) PCT No.: PCT/US2018/041005
§ 371 (c)(1),
(2) Date: Jan. 3, 2020

(87) PCT Pub. No.: WO2019/010363
PCT Pub. Date: Jan. 10, 2019

(65) Prior Publication Data
US 2021/0230177 A1    Jul. 29, 2021

Related U.S. Application Data

(60) Provisional application No. 62/529,333, filed on Jul. 6, 2017, provisional application No. 62/529,310, filed on Jul. 6, 2017.

(51) Int. Cl.
*C07D 493/22*    (2006.01)

(52) U.S. Cl.
CPC ................. *C07D 493/22* (2013.01)

(58) Field of Classification Search
CPC .................................... C07D 493/22
(Continued)

(56) References Cited

U.S. PATENT DOCUMENTS

| 5,338,865 A | 8/1994 | Kishi et al. |
| 5,436,238 A | 7/1995 | Kishi et al. |

(Continued)

FOREIGN PATENT DOCUMENTS

| CO | 2018008667 A2 | 8/2018 |
| CO | 2019009000 A2 | 1/2020 |

(Continued)

OTHER PUBLICATIONS

US 9,029,573 B2, 05/2015, Hu (withdrawn)
(Continued)

*Primary Examiner* — Taylor V Oh
(74) *Attorney, Agent, or Firm* — Wolf, Greenfield & Sacks, P.C.

(57) ABSTRACT

The present invention provides methods for the synthesis of ketones involving a Ni/Zr-mediated coupling reaction. The Ni/Zr-mediated ketolization reactions can be used in the synthesis of halichondrins (e.g., halichondrin A, B, C; homohalichondrin A, B, C; norhalichondrin A, B, C), and analogs thereof. Therefore, the present invention also provides synthetic methods useful for the synthesis of halichondrins, and analogs thereof. Also provided herein are compounds (i.e., intermediates) useful in the synthesis of halichondrins, and analogs thereof. In particular, the present invention provides methods and compounds useful in the synthesis of compound of Formula (H3-A).

(Continued)

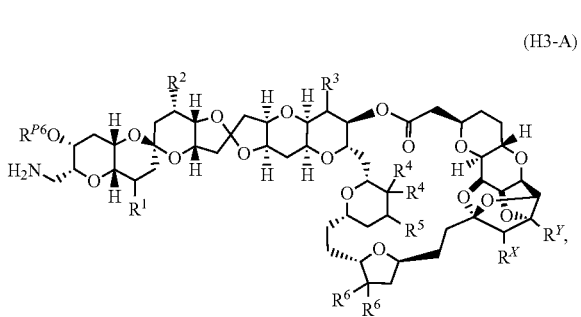

(H3-A)

66 Claims, 28 Drawing Sheets

(58) Field of Classification Search
USPC .......................................................... 549/344
See application file for complete search history.

(56) References Cited

U.S. PATENT DOCUMENTS

| | | | |
|---|---|---|---|
| 5,786,492 A | 7/1998 | Gravalos et al. | |
| 6,214,865 B1 | 4/2001 | Littlefield et al. | |
| 6,469,182 B1 | 10/2002 | Littlefield et al. | |
| 6,653,341 B1 | 11/2003 | Littlefield et al. | |
| 7,470,720 B2 | 12/2008 | Littlefield et al. | |
| 7,982,060 B2 | 7/2011 | Austad et al. | |
| 8,093,410 B2 | 1/2012 | Chase et al. | |
| 8,097,648 B2 | 1/2012 | Littlefield et al. | |
| 8,203,010 B2 | 6/2012 | Endo et al. | |
| 8,350,067 B2 | 1/2013 | Endo et al. | |
| 8,445,701 B2 | 5/2013 | Austad et al. | |
| 8,598,373 B2 | 12/2013 | Hu | |
| 8,618,313 B2 | 12/2013 | Benayoud et al. | |
| 8,884,031 B2 | 11/2014 | Chase et al. | |
| RE45,324 E | 1/2015 | Austad et al. | |
| 8,927,597 B2 | 1/2015 | Endo et al. | |
| 8,975,422 B2 | 3/2015 | Fang et al. | |
| 8,987,479 B2 | 3/2015 | Chase et al. | |
| 9,206,194 B2 | 12/2015 | Hu | |
| 9,278,979 B2 | 3/2016 | Souza et al. | |
| 9,303,039 B2 | 4/2016 | Zhang et al. | |
| 9,303,050 B2 | 4/2016 | Benayoud et al. | |
| 9,382,262 B2 | 7/2016 | Endo et al. | |
| 9,469,651 B2 | 10/2016 | Hu | |
| 9,938,288 B1 | 4/2018 | Kishi et al. | |
| 10,344,038 B2 | 7/2019 | Kishi et al. | |
| 10,556,910 B2 | 2/2020 | Kishi et al. | |
| 10,633,392 B2 | 4/2020 | Kishi et al. | |
| 10,844,073 B2 | 11/2020 | Lee et al. | |
| 10,954,249 B2 | 3/2021 | Kishi et al. | |
| 11,155,562 B2 | 10/2021 | Kishi et al. | |
| 11,220,513 B2 | 1/2022 | Kishi et al. | |
| 2004/0198806 A1 | 10/2004 | Eisai et al. | |
| 2006/0104984 A1 | 5/2006 | Littlefield et al. | |
| 2006/0154312 A1 | 7/2006 | Agoulnik et al. | |
| 2007/0244187 A1 | 10/2007 | Austad et al. | |
| 2009/0198074 A1 | 8/2009 | Chase et al. | |
| 2009/0203771 A1 | 8/2009 | Inanaga et al. | |
| 2010/0254996 A1 | 10/2010 | Brantley-Sieders et al. | |
| 2011/0054194 A1 | 3/2011 | Hu et al. | |
| 2011/0184190 A1 | 7/2011 | Endo et al. | |
| 2013/0336974 A1 | 12/2013 | Collier et al. | |
| 2014/0198806 A1 | 7/2014 | Pani et al. | |
| 2016/0090391 A1 | 3/2016 | Souza et al. | |
| 2017/0137437 A1 | 5/2017 | Kishi et al. | |
| 2018/0155361 A1 | 6/2018 | Lee et al. | |
| 2018/0230164 A1 | 8/2018 | Kishi et al. | |
| 2020/0002352 A1 | 1/2020 | Lee et al. | |
| 2020/0148698 A1 | 3/2020 | Kishi et al. | |
| 2020/0165183 A1 | 5/2020 | Kishi et al. |
| 2020/0223863 A1 | 7/2020 | Kishi et al. |
| 2020/0325152 A1 | 10/2020 | Kishi et al. |
| 2021/0009605 A1 | 1/2021 | Kishi et al. |
| 2021/0261566 A1 | 8/2021 | Kishi et al. |

FOREIGN PATENT DOCUMENTS

| | | |
|---|---|---|
| JP | S6-1191687 A | 8/1986 |
| JP | 6-122687 | 5/1994 |
| JP | 6-279450 | 10/1994 |
| JP | 6-279451 A | 10/1994 |
| JP | H07-504664 A | 5/1995 |
| JP | H08-208600 A | 8/1996 |
| JP | 2001-305734 A | 11/2001 |
| JP | 2003-261447 A | 9/2003 |
| RU | 2517167 C2 | 5/2014 |
| WO | WO 1993/017690 A1 | 9/1993 |
| WO | WO 1999/065894 A1 | 12/1999 |
| WO | WO 2005/118565 A1 | 12/2005 |
| WO | WO 2006/076100 A2 | 7/2006 |
| WO | WO 2007/139149 A1 | 12/2007 |
| WO | WO 2009/046308 A1 | 4/2009 |
| WO | WO 2009/064029 A1 | 5/2009 |
| WO | WO 2009/124237 A1 | 10/2009 |
| WO | WO 2011/094339 A1 | 8/2011 |
| WO | WO 2012/147900 A1 | 11/2012 |
| WO | WO 2013/086634 A1 | 6/2013 |
| WO | WO 2013/097042 A1 | 7/2013 |
| WO | WO 2013/142999 A1 | 10/2013 |
| WO | WO 2015/000070 A1 | 1/2015 |
| WO | WO 2015/066729 A1 | 5/2015 |
| WO | WO 2015/085193 A1 | 6/2015 |
| WO | WO 2016/003975 A1 | 1/2016 |
| WO | WO 2016/038624 A1 | 3/2016 |
| WO | WO 2016/176560 A1 | 11/2016 |
| WO | WO 2016/179607 A1 | 11/2016 |
| WO | WO 2017/151979 A1 | 9/2017 |
| WO | WO 2018/149552 A1 | 8/2018 |
| WO | WO 2018/187331 A1 | 10/2018 |
| WO | WO 2019/009956 A1 | 1/2019 |
| WO | WO 2019/010363 A1 | 1/2019 |

OTHER PUBLICATIONS

Extended European Search Report for EP 15814059.0, dated Nov. 24, 2017.
International Search Report and Written Opinion for PCT/US2015/038439, dated Sep. 29, 2015.
International Preliminary Report on Patentability for PCT/US2015/038439, dated Jan. 12, 2017.
International Search Report and Written Opinion for PCT/US2016/030064, dated Aug. 8, 2016.
International Preliminary Report on Patentability for PCT/US2016/030064, dated Nov. 9, 2017.
International Search Report and Written Opinion for PCT/US2018/025887, dated Jun. 21, 2018.
International Preliminary Report on Patentability for Application No. PCT/US2018/025887 dated Oct. 17, 2019.
Invitation to Pay Additional Fees for PCT/US2018/041005, dated Sep. 14, 2018.
International Preliminary Report on Patentability for PCT/US2018/041005, dated Jan. 16, 2020.
Invitation to Pay Additional Fees for PCT/US2018/061250, dated Feb. 26, 2019.
International Search Report and Written Opinion for PCT/US2018/061250, dated Apr. 16, 2019.
International Search Report and Written Opinion for PCT/US2018/031765, dated Jul. 2, 2018.
International Preliminary Report on Patentability for PCT/US2018/031765, dated Jan. 16, 2020.
[No Author Listed] American Chemical Society. STN Database. Apr. 11, 2014. RN # 1583253-64-8.
[No Author Listed] Application for Product Designation Under the SAKIGAKE Designation System. Generic name E7130. Eisai Co., Ltd. Nov. 22, 2017.

(56) References Cited

OTHER PUBLICATIONS

[No Author Listed] Evidentiary Document for Applicability of E7130 to Designation Requirements. Eisai Co., Ltd. Nov. 22, 2017.
[No Author Listed] Overview Relating to the Suitability for Designation Requirements Under the SAKIGAKE Designation System. Generic name E7130. Eisai Co., Ltd.
Aicher et al., Synthetic studies towards halichondrins. Tetrahedron Lett. 1987;28(30):3463-66.
Aicher et al., Synthetic Studies towards Halichondrins: Synthesis of the C.27-C.38 Segment. Tetrahedron Lett. 1992;33(12):1549-52.
Aicher et al., Total synthesis of halichondrin B and norhalichondrin B. J. Am. Chem. Soc., 1992, 114(8), pp. 3162-3164.
Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.
Berge et al., Pharmaceutical Salts. J. Pharmaceutical Sciences 1977;66(1):1-19.
Bringans, Studies on natural product derivatives : HIV therapies incorporating marine natural products. Dissertation. University of Canterbury, 2001.
Buszek et al., Synthetic Studies Towards Halichondrins: Synthesis of the Left Half of Halichondrins. Tetrahedron Lett. 1992;33:1553.
Chen et al., Ni(II)/Cr(II)-mediated coupling reaction: an asymmetric process. J. Org. Chem., 1995, 60 (17), pp. 5386-5387.
Cherney et al., Catalytic Asymmetric Reductive Acyl Cross-Coupling: Synthesis of Enantioenriched Acyclic α,α-Disubstituted Ketones. J. Am. Chem. Soc., 2013, 135 (20), pp. 7442-7445. doi: 10.1021/ja402922w.
Cherney et al., Pd-catalyzed Fukuyama cross-coupling of secondary organozinc reagents for the direct synthesis of unsymmetrical ketones. Tetrahedron 2014;70(20):3259-65.
Choi et al., Asymmetric Ni(II)/Cr(II)-Mediated Coupling Reaction: Catalytic Process. Org. Lett., 2002, 4 (25), pp. 4435-4438. doi: 10.1021/ol026981x.
Choi et al., Synthetic studies on the marine natural product halichondrins. Pure Appl. Chem., 2003, vol. 75, No. 1, pp. 1-17.
Dong et al., New syntheses of E7389 C14-C35 and halichondrin C14-C38 building blocks: reductive cyclization and oxy-Michael cyclization approaches. J Am Chem Soc. Nov. 4, 2009;131(43):15642-6. doi: 10.1021/ja9058487.
Fang et al., Synthetic Studies Towards Halichondrins: Synthesis of the Left Halves of Norhalichondrins and Homohalichondrins. Tetrahedron Lett. 1992;33(12):1557-60.
Fukuyama et al., Application of a Rotor—Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.
Fukuyama et al., Application of Continuous Flow for DIBAL-H Reduction and n-BuLi Mediated Coupling Reaction in the Synthesis of Eribulin Mesylate. Org. Process Res. Dev., 2016, 20 (2), pp. 503-509. doi: 10.1021/acs.oprd.5b00353.
Gould et al., Salt selection for basic drugs. International Journal of Pharmaceutics Nov. 1986;33(1-3):201-217. https://doi.org/10.1016/0378-5173(86)90055-4.
Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Hirata et al., Halichondrins—antitumor polyether macrolides from a marine sponge. Pure Appl. Chem., 1986, vol. 58, No. 5, pp. 701-710.
Jackson et al., A total synthesis of norhalichondrin B. Angew Chem Int Ed Engl. 2009;48(13):2346-50. doi: 10.1002/anie.200806111.
Kaburagi et al., Effective procedure for selective ammonolysis of monosubstituted oxiranes: application to E7389 synthesis. Tetrahedron Lett. 2007;48(51):8967-71.
Kim et al., New syntheses of E7389 C14-C35 and halichondrin C14-C38 building blocks: double-inversion approach. J Am Chem Soc. Nov. 4, 2009; 131(43):15636-41. doi: 10.1021/ja9058475.
Kress et al., Investigations of the intramolecular Ni(II)/Cr(II)-mediated coupling reaction: Application to the taxane ring system. Tetrahedron Letters 1993;34(38);6003-6.
Kumar et al., Fe/Cu-Mediated One-Pot Ketone Synthesis. Org Lett. May 19, 2017;19(10):2766-2769. doi: 10.1021/acs.orglett.7b01128. Epub May 10, 2017.
Lee et al., One-Pot Ketone Synthesis with Alkylzinc Halides Prepared from Alkyl Halides via a Single Electron Transfer (SET) Process: New Extension of Fukuyama Ketone Synthesis. J. Am. Chem. Soc., 2016, 138 (22), pp. 7178-7186. doi: 10.1021/jacs.6b03897.
Li et al., Unified Synthesis of C1-C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.
Lill, Studies on New Zealand marine natural products. Dissertation. University of Canterbury, 1999.
Liu et al., Catalytic enantioselective Cr-mediated propargylation: application to halichondrin synthesis. Org Lett. Oct. 15, 2009;11(20):4520-3. doi: 10.1021/ol9016595.
Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.
Liu et al., Synthesis of Alcohols from m-Fluorophenylsulfones and Dialkylboranes: Application to the C14-C35 Building Block of E7389. Org. Lett., 2012, 14 (9), pp. 2262-2265. doi: 10.1021/ol300672q.
Mori et al., A Practical Synthesis of Multifunctional Ketones through the Fukuyama Coupling Reaction. Adv. Synth. Catal. 2007;349(11-12);2027.
Namba et al., New catalytic cycle for couplings of aldehydes with organochromium reagents. Org Lett. Dec. 23, 2004;6(26):5031-3.
Narayan et al., Novel second generation analogs of eribulin. Part I: Compounds containing a lipophilic C32 side chain overcome P-glycoprotein susceptibility. Bioorg Med Chem Lett, Mar. 15, 2011;21(6):1630-3.
Narayan et al., Novel second generation analogs of eribulin. Part II: Orally available and active against resistant tumors in vivo. Bioorg Med Chem Lett, Mar. 15, 2011;21(6):1634-8.
Narayan et al., Novel second generation analogs of eribulin. Part III: Blood-brain barrier permeability and in vivo activity in a brain tumor model. Bioorg Med Chem Lett, Mar. 15, 2011;21(6):1639-43.
Ortega et al., Potential clinical applications of halichondrins in breast cancer and other neoplasms. Breast Cancer (Dove Med Press). Feb. 8, 2012;4:9-19. doi: 10.2147/BCTT.S12423.
Seletsky et al., Structurally simplified macrolactone analogues of halichondrin B. Bioorg Med Chem Lett, Nov. 15, 2004;14(22):5547-50.
Shan et al., Concise and Highly Stereoselective Synthesis of the C20-C26 Building Block of Halichondrins and Eribulin. Org. Lett., 2012, 14 (2), pp. 660-663. doi: 10.1021/ol203373d.
Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.
Stamos et al., Synthetic studies on halichondrins: A practical synthesis of the C.1−C.13 segment. Tetrahedron Letters Nov. 25, 1996;37(48):8643-8646.
Tokuyama et al., A novel ketone synthesis by a palladium-catalyzed reaction of thiol esters and organozinc reagents. Tetrahedron Lett. 1998;39(20):3189-92.
Ueda et al., Total synthesis of halichondrin A, the missing member in the halichondrin class of natural products. J Am Chem Soc. Apr. 2, 2014;136(13):5171-6. doi: 10.1021/ja5013307. Epub Mar. 19, 2014.
Uemura et al., Norhalichondrin A: an antitumor polyether macrolide from a marine sponge. J. Am. Chem. Soc., 1985, 107 (16), pp. 4796-4798. doi: 10.1021/ja00302a042.

(56) References Cited

OTHER PUBLICATIONS

Uemura, Exploratory research on bioactive natural products with a focus on biological phenomena. Proc Jpn Acad Ser B Phys Biol Sci. 2010;86(3):190-201.
Wan et al., Asymmetric Ni(II)/Cr(II)-mediated coupling reaction: stoichiometric process. Org Lett. Dec. 12, 2002;4(25):4431-4.
Wang et al., Structure-activity relationships of Halichondrin B analogues: modifications at C.30-C.38. Bioorg Med Chem Lett, May 15, 2000; 10(10):1029-32.
Wotal et al., Stoichiometric Reactions of Acylnickel(II) Complexes with Electrophiles and the Catalytic Synthesis of Ketones. Organometallics, 2014, 33 (20), pp. 5874-5881. doi: 10.1021/om5004682.
Wotal et al., Synthesis of Functionalized Dialkyl Ketones from Carboxylic Acid Derivatives and Alkyl Halides. Org. Lett., 2012, 14 (6), pp. 1476-1479. doi: 10.1021/ol300217x.
Xie et al., Synthesis of the C20-C26 Building Block of Halichondrins via a Regiospecific and Stereoselective SN2' Reaction. Org. Lett., 2002;4(25):4427-4429.DOI: 10.1021/ol026982p.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Total synthesis of halichondrin C. J Am Chem Soc. Jan. 18, 2012;134(2):893-6. doi: 10.1021/ja2108307. Epub Dec. 23, 2011.
Yan et al., Selective Activation/Coupling of Polyhalogenated Nucleophiles in Ni/Cr-Mediated Reactions: Synthesis of C1-C19 Building Block of Halichondrin Bs. J. Am. Chem. Soc., 2015, 137 (19), pp. 6219-6225.
Zheng et al., Macrocyclic ketone analogues of halichondrin B. Bioorg Med Chem Lett. Nov. 15, 2004;14(22):5551-4.
Araki et al., A Convenient Method for the Preparation of Ketones by the Reaction of Grignard Reagents with Carboxylic Acid Derivatives. Chem. Soc. Jpn. 1974;47:1777-80.
Britovsek et al., Synthesis of iron(ii), manganese(ii) cobalt(ii) and ruthenium(ii) complexes containing tridentate nitrogenligands and their application in the catalytic oxidation of alkanes. Dalton Trans. 2005, 945-55.
Buchwald et al., Synthesis, structure, and reactions of (1-ethoxyethyl)zirconocene chloride, a stable acyclic secondary zirconocene alkyl. Organometallics. 1988;7(11):2324-2328.
Cardellicchio et al., A highly efficient synthetic route to ketones through sequential coupling reactions of grignard reagents with s-phenyl carbonochloridothioate in the presence of nickel or iron catalysts. Tetrahedron Lett. 1985;26(30):3595-98.
Chen et al., Attempts to Improve the Overall Stereoselectivity of the Ireland-Claisen Rearrangement. Org. Lett. Jan. 15, 2009; 11(2):409-12.
Corey et al., Synthesis of 1,n-Dicarbonyl Derivates Using Carbanions from 1,3-Dithianes. Angew. Chem. Int. Ed. 1965;4(12):1077-78.
Dieter, Reaction of acyl chlorides with organometallic reagents: A banquet table of metals for ketone synthesis. Tetrahedron. 1999;55:4177-4236.
Eliel et al., Conformational analysis. 42. Monosubstituted tetrahydropyrans. J. Am. Chem. Soc. 1982; 104(13):3635-43.
Fiandanese et al., One-step synthesis of ketones from carylic acids and grignard reagents in the presence of a nickel(II)-phosphine catalyst. Tetrahedron Lett. 1983;24(34):3677-80.
Fleming et al., Grignard Reagents: Alkoxide-Directed Iodine-Magnesium Exchange at sp3 Centers. Org. Lett. 2007; 9(22):4507-09.
Gerlach et al., Bildung von Estern und Lactonen durch Silberionen-Katalyse. Helv. Chim. Acta. 1974; 57(8): 2661-63.
Hayashi et al., Diarylprolinol in an Asymmetric, Direct Cross-Aldol Reaction with Alkynyl Aldehydes. ChemCatChem. 2013; 5:2887-92.
Hayashi et al., A diarylprolinol in an asymmetric, catalytic, and direct crossed-aldol reaction of acetaldehyde. Angew Chem Int Ed Engl. 2008;47(11):2082-4. doi: 10.1002/anie.200704870.

Hoveyda et al., The remarkable metal-catalysed olefin metathesis reaction. Nature. 2007;450:243-51.
Johannes et al., Biomimetic macrocycle-forming Diels-Alder reaction of an iminium dienophile: synthetic studies directed toward gymnodimine. Org Lett. Sep. 1, 2005;7(18):3997-4000. doi: 10.1021/ol051553n.
Jung et al., Synthesis of 1,4-, 2,4-, and 3,4-dimethylphenanthrenes: a novel deoxygenation of arene 1,4-endoxides with trimethylsilyl iodide. J. Org. Chem. 1989; 54:5667-75.
Kaburagi, Operationally Simple and Efficient Workup Procedure for TBAF-Mediated Desilylation: Application to Halichondrin Synthesis. Org. Lett. 2007; 9(4):723-26.
Katsuki et al., The first practical method for asymmetric epoxidation. J. Am. Chem. Soc. 1980, 102(18) 5974-76.
Kim et al., Copper ion promoted esterification of (S)-2-pyridyl thioates and 2-pyridyl esters. Efficient methods for the preparation of hindered esters. J. Org. Chem. 1984;49(10):1712-16.
Knochel et al., Modern Organocopper Chemistry. 2002. Wiley-VCH, Eds.
Kobayashi et al., Complete Stereochemistry of Tetrafibricin. Org. Lett. 2003; 5(1):93-96.
Lee et al., Extension of Pd-Mediated One-Pot Ketone Synthesis to Macrocyclization: Application to a New Convergent Synthesis of Eribulinv. J. Am. Chem. Soc. 2016;138(50):16248-51.
Lewis et al., Highly stereoselective approaches to .alpha.- and .beta.-C-glycopyranosides. J. Am. Chem. Soc. 1982;104(18):4976-78.
Li et al., Stereocontrolled Synthesis of α-Amino-α'-alkoxy Ketones by a Copper-Catalyzed Cross-Coupling of Peptidic Thiol Esters and α-Alkoxyalkylstannanes. Org. Lett. 2011;13(14):3682-85.
Liebeskind et al., Thiol Ester-Boronic Acid Coupling. A Mechanistically Unprecedented and General Ketone Synthesis. J. Am. Chem. Soc. 2000;122(45):11260-61.
Lipschutz, Applications of Higher-Order Mixed Organocuprates to Organic Synthesis. Synthesis. Apr. 1987;325-41.
Loots et al., Nickel-catalyzed conjugate addition of zirconium alkenyls to .alpha.,.beta.-unsaturated ketones. J. Am. Chem. Soc. 1977;99(24):8045-46.
Lu et al., Alkyl-Alkyl Suzuki Cross-Coupling of Unactivated Secondary Alkyl Chlorides. C. Angew. Chem. Int. Ed. 2010;49(37):6676-78.
Masashi et al., A Convenient Method for the Preparation of Ketones by the Reaction of Grignard Reagents with Carboxylic Acid Derivatives. Chem. Soc. Jpn. 1974;47:1777-80.
Mcgee et al., Synthesis and Isolation of Organogold Complexes through a Controlled 1,2-Silyl Migration. Chem. Eur. J. 2015;21(27): 9662-9665.
Miyajima et al., Electric-field-responsive handle for large-area orientation of discotic liquid-crystalline molecules in millimeter-thick films. Angew. Chem., Int. Ed. 2011;123:8011-15.
Nahm et al., N-methoxy-n-methylamides as effective acylating agents. Tetrahedron Lett. 1981;22(39):3815-18.
Negishi et al., Palladium-catalyzed acylation of organozincs and other organometallics as a convenient route to ketones. Tetrahedron Lett. 1983;24(47): 5181-4.
Negri et al., A total synthesis of polyether antibiotic (−)-A23187 (calcimycin). Tetrahedron Lett. 1987; 28(10):1063-66.
Normant, Organocopper(I) Compounds and Organocuprates in Synthesis. Synthesis. Feb. 1972; 1972(2):63-80.
Onaka et al., A Convenient Method for the Direct Preparation of Ketones From 2-(6-(2-Methoxyethyl)Pyridyl)Carboxylates and Alkyl Iodides by Use of Zinc Dust and a Catalytic Amount of Nickel Dichloride. Chem. Lett. 1981;10(4):531-34.
Ruscoe et al., Copper-Catalyzed Double Additions and Radical Cyclization Cascades in the Re-Engineering of the Antibacterial Pleuromutilin. J. Chem. Eur. J. 2016; 22:116-119.
Schrock, Multiple Metal-Carbon Bonds for Catalytic Metathesis Reactions. Adv. Synth Catal. 2007;349: 41-53.
Scriven et al., Azides: their preparation and synthetic uses. Chem Rev. 1988;88(2):297-368.
Seebach, Methods of Reactivity Umpolung. Angew. Chem. Int. Ed. 1979;18(4):239-58.

(56) References Cited

OTHER PUBLICATIONS

Seebach et al., Generation and synthetic applications of 2-lithio-1,3-dithianes. J. Org. Chem. 1975;40(2): 231-37.
Serrano et al., Nickel-Catalyzed Reductive Amidation of Unactivated Alkyl Bromides. Angew. Chem. Int. Ed. 2016;55(37):11207-11.
Sharpless et al., High stereo- and regioselectivities in the transition metal catalyzed epoxidations of olefinic alcohols by tert-butyl hydroperoxide. J. Am. Chem. Soc. 1973;95(18):6136-37.
Shiina, An Adventurous Synthetic Journey with MNBA from Its Reaction Chemistry to the Total Synthesis of Natural Products. Bull Chem. Soc. Jpn. 2014; 87(2):196-233.
Shiina et al., A novel and efficient macrolactonization of ω-hydroxycarboxylic acids using 2-methyl-6-nitrobenzoic anhydride (MNBA). Tetrahedron Lett. Oct. 14, 2002;43(42):7535-39.
Shiina et al., A Novel Method for the Preparation of Macrolides from ω-Hydroxycarboxylic Acids. Chem. Lett. 1994;23(4):677-80.
Smith III et al., Evolution of Dithiane-Based Strategies for the Construction of Architecturally Complex Natural Products. Acc. Chem. Rev. 2004; 37(6): 365-77.
Takai et al., A practical transformation of aldehydes into (E)-iodoalkenes with geminal dichromium reagents. Synlett. 1999;8:1268-70.
Takai et al., Simple and selective method for aldehydes (RCHO) → (E)-haloalkenes (RCH:CHX) conversion by means of a haloform-chromous chloride system. J. Am. Chem. Soc. 1986;108(23):7408-10.
Takaya et al., Investigation of Organoiron Catalysis in Kumada-Tamao-Corriu-Type Cross-Coupling Reaction Assisted by Solution-Phase X-ray Absorption Spectroscopy. Bull. Chem. Soc. Jpn. 2015;88(3): 410-418.
Takuji et al., Kumada-Tamao-Corriu Coupling of Alkyl Halides Catalyzed by an Iron-Bisphosphine Complex. Chem. Lett. 2011, 40(9):1030-32.
Thornton et al., π-Nucleophile Traps for Metallonitrene/Alkyne Cascade Reactions: A Versatile Process for the Synthesis of α-Aminocyclopropanes and β-Aminostyrenes. J. Am. Chem. Soc. 2009;131(7): 2434-2435.
Trnka et al., The Development of L2X2RuCHR Olefin Metathesis Catalysts: An Organometallic Success Story. Acc. Chem. Res. 2001;34(1):18-29.
Turhanen et al., A powerful tool for acid catalyzed organic addition and substitution reactions. RSC Adv. 2015; 5:26218-26222.
Velder et al., Modular Synthesis of Chiral Phosphine-Phosphite-Ligands from Phenolic Precursors: A New Approach to Bidentate Chelate Ligands Exploiting a P☐O to P☐C Migration Rearrangement. Adv Synth Catal. 2008; 350(9):1309-15.
Weix et al., Nickel-Catalyzed Cross-Electrophile Coupling with Organic Reductants in Non-Amide Solvents. Chem. Eur. J. 2016; 22(33):11564-11567.
Williams et al., Competitive oxidation processes in the reaction between (dicyclopentadienyl)zirconium bis(phosphine) complexes and alkyl halides. J. Am. Chem. Soc. 1980; 102(10):3660-62.
Williams et al., Direct observation of metal-centered radicals in an oxidative-addition reaction. J. Am. Chem. Soc. 1982; 104(4):1122-24.
Wipf et al., Transmetalation reactions of alkylzirconocenes: copper-catalyzed conjugate addition to enones. J. Org. Chem. 1991;56(23): 6494-96.
Wittenberg et al., Ketone synthesis under neutral conditions. Cu(I) diphenylphosphinate-mediated, palladium-catalyzed coupling of thiol esters and organostannanes. Org Lett. Aug. 21, 2003;5(17):3033-5. doi: 10.1021/ol034962x.
Wu et al., Ketone Formation via Mild Nickel-Catalyzed Reductive Coupling of Alkyl Halides with Aryl Acid Chlorides. Org. Lett. 2012; 14(12):3044-47.
Yoneda et al., Asymmetric Synthesis of Spiroketals with Aminothiourea Catalysts. Angew Chem Int Ed Engl. Dec. 14, 2015;54(51):15497-500. doi: 10.1002/anie.201508405.
Yus et al., The role of 1,3-dithianes in natural product synthesis. Tetrahedron. Aug. 11, 2003; 59(33):6147-6212.
Zhang et al., Alcohols as Latent Coupling Fragments for Metallaphotoredox Catalysis: sp3-sp2 Cross-Coupling of Oxalates with Aryl Halides. J. Am. Chem. Soc. 2016; 138(42):13862-65.
Zhang et al., A Unique Catalyst Effects the Rapid Room-Temperature Cross-Coupling of Organozinc Reagents with Carboxylic Acid Fluorides, Chlorides, Anhydrides, and Thioesters. J. Am. Chem. Soc. 2004;126(49):15964-65.
Zhao et al., Ni-Catalyzed Reductive Coupling of Alkyl Acids with Unactivated Tertiary Alkyl and Glycosyl Halides. J. Am. Chem. Soc. 2014;136(50):17645-51.
International Preliminary Report on Patentability in connection with Application No. PCT/US2018/061250, dated May 28, 2020.
U.S. Appl. No. 15/322,756, filed Dec. 29, 2016, Kishi et al.
U.S. Appl. No. 16/746,233, filed Jan. 17, 2020, Kishi et al.
U.S. Appl. No. 15/570,593, filed Oct. 30, 2017, Kishi et al.
U.S. Appl. No. 16/441,843, filed Jun. 14, 2019, Kishi et al.
U.S. Appl. No. 15/814,105, filed Nov. 15, 2017, Kishi et al.
U.S. Appl. No. 16/500,924, filed Oct. 4, 2019, Kishi et al.
U.S. Appl. No. 15/809,845, filed Nov. 10, 2017, Lee et al.
U.S. Appl. No. 16/459,120, filed Jul. 1, 2019, Lee et al.
U.S. Appl. No. 16/628,419, filed Jan. 3, 2020, Kishi et al.
PCT/US2015/038439, Sep. 29, 2015, International Search Report and Written Opinion.
PCT/US2015/038439, Jan. 12, 2017, International Preliminary Report on Patentability.
EP 15814059.0, Nov. 24, 2017, Extended European Search Report.
PCT/US2016/030064, Nov. 9, 2017, International Preliminary Report on Patentability.
PCT/US2016/030064, Aug. 8, 2016, International Search Report and Written Opinion.
PCT/US2018/025887, Jun. 21, 2018, International Search Report and Written Opinion.
PCT/US2018/025887, Oct. 17, 2019, International Preliminary Report on Patentability.
PCT/US2018/04100, Sep. 14, 2018, Invitation to Pay Additional Fees.
PCT/US2018/04100, Jan. 16, 2020, International Preliminary Report on Patentability.
PCT/US2018/061250, Feb. 26, 2019, Invitation to Pay Additional Fees.
PCT/US2018/061250, Apr. 16, 2019, International Search Report and Written Opinion.
PCT/US2018/031765, Jul. 2, 2018, International Search Report and Written Opinion.
PCT/US2018/031765, Jan. 16, 2020, International Preliminary Report on Patentability.
U.S. Appl. No. 16/859,018, filed Apr. 27, 2020, Kishi et al.
U.S. Appl. No. 17/167,480, filed Feb. 4, 2021, Kishi et al.
PCT/US2020/043501, Dec. 3, 2020, International Search Report and Written Opinion.
International Search Report and Written Opinion for PCT/US2020/043501, dated Dec. 3, 2020.
Bockus et al. Form and Function in Cyclic Peptide Natural Products: A Pharmacokinetic Perspective. Curr Top Med Chem. 2013;13(7):821-36. doi: 10.2174/1568026611313070005.
Dybdal-Hargreaves et al. Eribulin Mesylate: Mechanism of Action of a Unique Microtubule-Targeting Agent. Clin Cancer Res. Jun. 2015 1;21(11):2445-52. doi: 10.1158/1078-0432.CCR-14-3252. Epub Apr. 2, 2015.
Horita et al. Synthetic Studies of Halichondrin B, an Antitumor Polyether Macrolide Isolated from a Marine Sponge. 7. Synthesis of Two C27-C36 Units via Construction of the F Ring and Completely Stereoselective C-Glycosylation Using Mixed Lewis Acids. Chemical & Pharmaceutical Bulletin. 1997; 45(10): 1558-1572. doi:10.1248/cpb.45.1558.
Jackson et al. The Halichondrins and E7389. Chem Rev. Jul. 2009;109(7):3044-79. doi: 10.1021/cr900016w.
Ogawa et al., Total synthesis of resolvin E1. Tetrahedron Letters. Nov. 4, 2009; 50(44): 6079-82.
Melzig et al., Preparation of Polyfunctional Zinc Organometallics Using an Fe- or Co-Catalyzed Cl/Zn-Exchange. Org Lett. 2011; 13(12): 3174-3177.

(56) References Cited

OTHER PUBLICATIONS

Mori et al. Pd(OH)2/C (Pearlman's catalyst): a highly active catalyst for Fukuyama, Sonogashira, and Suzuki coupling reactions. J Org Chem. Feb. 21, 2003;68(4):1571-4. doi: 10.1021/jo0265277.

Mori et al. A novel procedure for the synthesis of multifunctional ketones through the Fukuyama coupling reaction employing dialkylzincs. Tetrahedron Letters. Sep. 20, 2004; 45(39):7343-45.

Mori et al. Synthesis of Multi-Functionalized Ketones Through The Fukuyama Coupling Reaction Catalyzed by Pearlman's Catalyst: Preparation of Ethyl 6-Oxotridecanoate (Tridecanoic Acid, 6-Oxo-, Ethyl Ester).Organic Syntheses. 2007;84: 285-294.

Movassaghi et al. Enantioselective total synthesis of (−)-acylfulvene and (−)-irofulven. Angew Chem Int Ed Engl. Sep. 4, 2006;45(35):5859-63. doi: 10.1002/anie.200602011.

Sabitha et al., Synthesis of the C45-C53 tetrahydropyran domain of norhalichondrins and the C14-C22 tetrahydrofuran domain of the halichondrin family. RSC Advances. 2012; 2: 10157-10159.

Swami et al. Eribulin in Cancer Treatment. Mar Drugs. Aug. 7, 2015;13(8):5016-58. doi: 10.3390/md13085016.

Ueda et al. Total synthesis of (+)-haplophytine. Angew Chem Int Ed Engl. 2009;48(41):7600-3. doi: 10.1002/anie.200902192.

Umehara et al. Further Studies on Ni/Zr-mediated One-pot Ketone Synthesis: Use of a 1-6 Mixture of NiI- and NiII-catalysts Greatly Improves the Molar Ratio of Coupling Partners. Chem Lett. 2019;48:947-950.

International Search Report and Written Opinion for PCT/US2018/041005, dated Nov. 19, 2018.

No Author Listed, Presentation material for The 63rd Symposium on the Chemistry of Natural Products. Sep. 15-17, 2021. 26 pages.

No Author Listed, Small Medical Encyclopedia. Soviet Medicine. 1996; 5: 90-96.

Durnov et al., Pediatric Oncology. Moscow Medicine. 2002; 139.

Kaburagi et al., Gram-Scale Synthesis of a Halichondrin-Class Anticancer Drug Candidate E7130. Abstract. Japanese language. 2021. 5 pages.

Kaburagi et al., Gram-Scale Synthesis of a Halichondrin-Class Anticancer Drug Candidate E7130. Abstract. English language. 2021. 2 pages.

Kaburagi, A landmark in drug discovery based on complex natural product synthesis. Abstract. 2021. 1 page.

Kira, Gram-scale synthesis of a structurally complex drug candidate E7130. Abstract. 2021. 1 page.

Kümmerer, Pharmaceuticals in the environment. Annu Rev Environ Resour. 2010;35:57-75.

U.S. Appl. No. 17/501,037, filed Oct. 14, 2021, Kishi et al.

Weix System (X = I; Y = SPy): 39% yield
 NiCl₂(dtbbpy), Mn, DMA, rt, 12 hr
Reisman System (X = I; Y = Cl): 21% yield
 NiCl₂(dme), bis(oxazoline), Mn, 2,6-di-MePhCO₂H, DMA-THF, 20 °C, 24 hr
Gong System (X = Br; Y = OH): no desired product formation
 (Boc)₂O, NiCl₂(dtbbpy), TBAI, MgCl₂, Zn, DMF-THF, 20 °C, 14 hr

| Entry | Ni(dtbbpy)X$_2$ | Reaction times (h) | Results (%) |
| --- | --- | --- | --- |
| 1 | Cl | 1 | 89 |
| 2 | Br | 0.5 | 93 |
| 3 | I | 1 | 57 |

| Entry | Solvent | Reaction times (h) | Results (%) |
|---|---|---|---|
| 1 | DMI | 0.5 | 89 |
| 2 | DMF | 1 | <10 |
| 3 | DMA | 1 | 75 |
| 4 | DMPU | 1 | 67 |
| 5 | DMSO | 1 | 60 |
| 6 | HMPU | 1 | 63 |
| 7 | THF | 4 | 57 |
| 8 | Et$_2$O | 6 | 40 |
| 9 | MeCN | 1 | 30 |
| 10 | toluene | 12 | 36 |
| 11 | 1,4-dioxane | 2 | 56 |
| 12 | CH$_2$Cl$_2$ | 4 | 44 |
| 13 | DME | 2 | 50 |
| 14 | NMP | 1 | 70 |
| 15 | HFIP | 12 | <10 |
| 16 | EtOAc | 12 | <10 |

| Entry | Co-Solvent | Results (%) |
| --- | --- | --- |
| 1 | DMI-EtOAc (1:1) | 78 |
| 2 | DMI-MeCN (1:1) | 45 |
| 3 | DMI-THF (1:1) | 55 |
| 4 | DMI-DME (1:1) | 20 |
| 5 | DMI-iPrCN (1:1) | 20 |
| 6 | DMA-EtOAc (1:1) | 64 |
| 7 | DMI-EtOAc (5:1) | 88 |
| 8 | DMI-EtOAc (3:1) | 83 |
| 9 | DMI-EtOAc (2:1) | 78 |
| 10 | DMI-EtOAc (1:1) | 70 |
| 11 | DMI-EtOAc (1:2) | 40 |
| 12 | DMI-EtOAc (1:4) | <10 |
| 13 | DMI-EtOAc (1:20) | <10 |

| Entry | additive | Results (%) |
| --- | --- | --- |
| 1 | none | 50 |
| 2 | Cp$_2$ZrCl$_2$ | 92 |
| 3 | TESCl | 60 |
| 4 | TMSCl | <10 |
| 5 | CoPc (1 mol%) | 30 |
| 6 | CrCl$_2$ (25 mol%) | 46 |
| 7 | LiI | 51 |
| 8 | MgCl$_2$ | 34 |
| 9 | p-F-styrene (10 mol%) | 76 |
| 10 | p-CF$_3$-styrene (10 mol%) | 55 |

| Entry | equiv. Cp₂ZrCl | Reaction times (h) | Results (%) |
|---|---|---|---|
| 1 | 0 | 12 | 45 |
| 2 | 0.1 | 12 | 51 |
| 3 | 0.5 | 3 | 51 |
| 4 | 1.0 | <1 | 94 |
| 5 | 2.0 | <1 | 90 |

| Entry | X | Results (%) |
|---|---|---|
| 1 | I | 90 |
| 2 | Br | <10 |
| 3 | Br+LiI | 85 |

| Entry | Reductant | Results (%) |
|---|---|---|
| 1 | Zn | 90 |
| 2 | Mn | 80 |
| 3 | Mg | 25 |
| 4 | tetrakis(dimethylamino)ethylene | 20 |

| Entry | Concentration (M) | Time (h) | Results (%) |
| --- | --- | --- | --- |
| 1 | 0.5 | 0.5 | 92 |
| 2 | 0.25 | 1 | 72 |
| 3 | 0.1 | 4 | 30 |
| 4 | 0.05 | 12 | 17 |
| 5 | 0.025 | 12 | <10 |
| 6 | 0.001 | 12 | <10 |
| 7 | 0.1 (3 eq. $Cp_2ZrCl_2$, 30 mol% Ni(dtbbpy)$Br_2$) | 1.5 | 85 |
| 8 | 0.05 (3 eq. $Cp_2ZrCl_2$, 30 mol% Ni(dtbbpy)$Br_2$) | 3 | 76 |
| 9 | 0.001 (5 eq. $Cp_2ZrCl_2$, 50 mol% Ni(dtbbpy)$Br_2$) | 6 | 55 |

| Entry | ratio of 1 and 2 | Results (%) |
| --- | --- | --- |
| 1 | 1.5:1.0 | 89 |
| 2 | 1.2:1.0 | 89 |
| 3 | 1.1:1.0 | 80 |
| 4 | 1.0:1.0 | 75 |
| 5 | 0.8:1.0 | 75 |

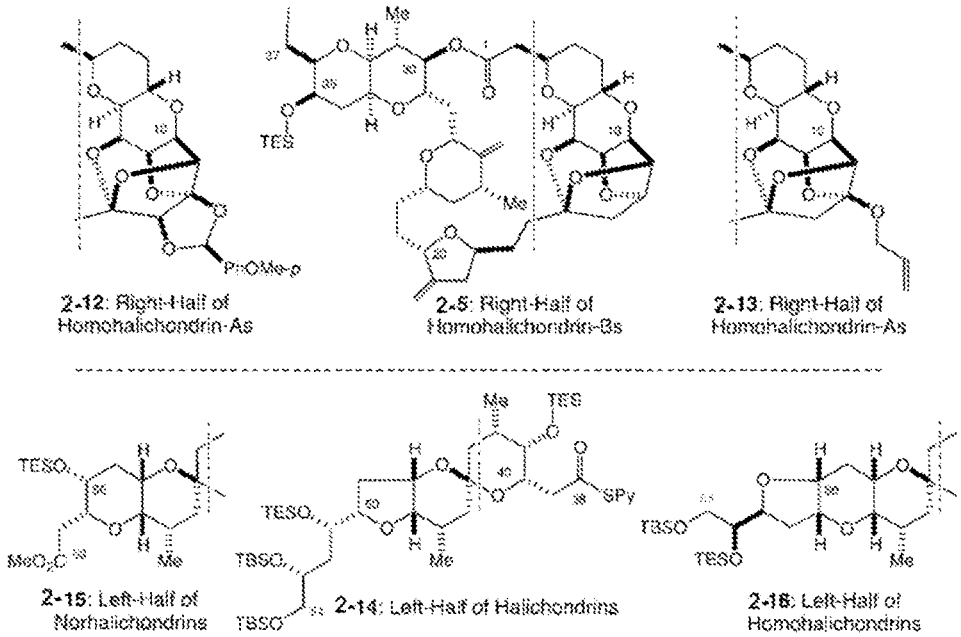

Figure 8A

Halichondrin-B Series

| | | | |
|---|---|---|---|
| 2-5 + 2-14 | a-1; yields: i = 88%, ii = 77% | → | Halichondrin B (17) |
| 2-5 + 2-15 | a-2; yields: i = 84%, ii = 72% | → | Norhalichondrin B (18) |
| 2-5 + 2-16 | a-3; yields: i = 82%, ii = 75% | → | Homohalichondrin B (19) |

Halichondrin-A Series

| | | | |
|---|---|---|---|
| 2-12 + 2-14 | b-1; yields: i = 86%, ii = 61% | → | Halichondrin A (20) |
| 2-12 + 2-15 | b-2; yields: i = 87%, ii = 64% | → | Norhalichondrin A (21) |
| 2-12 + 2-16 | b-3; yields: i = 85%, ii = 71% | → | Homohalichondrin A (22) |

Halichondrin-C Series

| | | | |
|---|---|---|---|
| 2-13 + 2-14 | c-1; yields: i = 85%, ii = 55% | → | Halichondrin C (23) |
| 2-13 + 2-15 | c-2; yields: i = 85%, ii = 58% | → | Norhalichondrin C (24) |
| 2-13 + 2-16 | c-3; yields: i = 85%, ii = 65% | → | Homohalichondrin C (25) |

Figure 8B

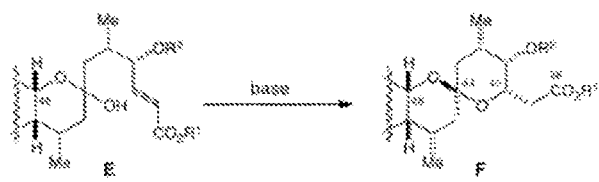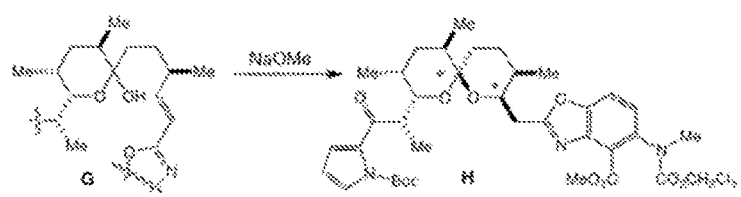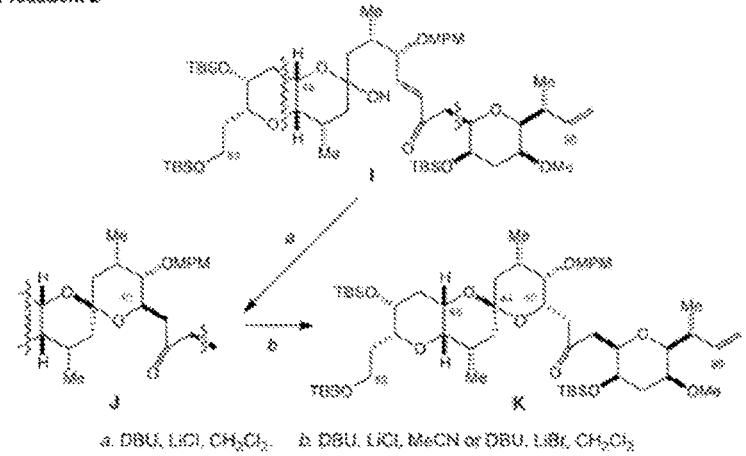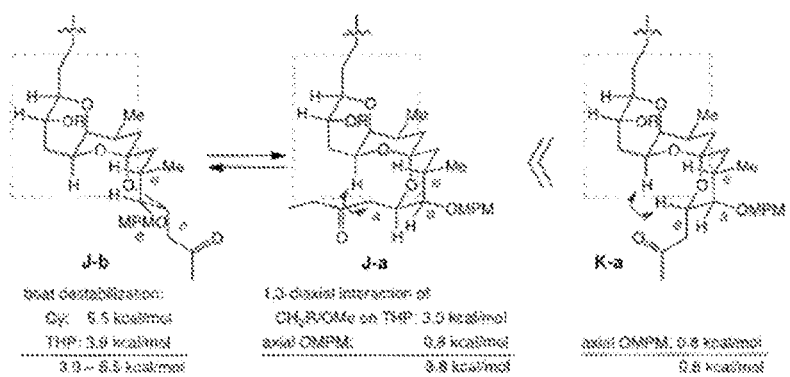
Figure 15

SYNTHESIS OF HALICHONDRINS

RELATED APPLICATIONS

This application is a national stage filing under 35 U.S.C. § 371 of international PCT application, PCT/US2018/041005, filed Jul. 6, 2018, which claims priority under 35 U.S.C. § 119(e) to U.S. provisional patent applications, U.S. Ser. No. 62/529,333, filed Jul. 6, 2017; and U.S. Ser. No. 62/529,310, filed Jul. 6, 2017; the entire contents of each of which is incorporated herein by reference.

BACKGROUND OF THE INVENTION

Halichondrins are polyether natural products, originally isolated from the marine scavenger *Halichondria okadai* by Uemura, Hirata, and coworkers. See, e.g., Uemura, D.; Takahashi, K.; Yamamoto, T.; Katayama, C.; Tanaka, J.; Okumura, Y.; Hirata, Y. *J. Am. Chem. Soc.* 1985, 107, 4796; Hirata, Y.; Uemura, D. *Pure Appl. Chem.* 1986, 58, 701. Several additional members, including halistatin, were isolated from various marine scavengers. This class of natural products displays interesting structural diversity, such as the oxidation state of the carbons of the C8-C14 polycycle, and the length of the carbon backbone. Thus, this class of natural products is sub-grouped into the norhalichondrin series (e.g., norhalichondrin A, B, and C), the halichondrin series (e.g., halichondrin A, B, C), and the homohalichondrin series (e.g., homohalichondrin A, B, C) (see FIG. 1). Except halichondrin A, all the members have been isolated from natural sources. Due to their intriguing structural architecture and extraordinary antitumor activity, halichondrins have received much attention from the scientific community.

SUMMARY OF THE INVENTION

The present invention provides new synthetic methods useful in the synthesis of halichondrin natural products and related molecules. As described herein, a novel nickel/zirconium-mediated coupling reaction has been developed as a key step in the synthesis. In addition to synthetic methods, the present invention also provides compounds which are useful synthetic intermediates in the synthesis of halichondrin natural products and analogs thereof.

For example, in certain embodiments, provided herein are compounds and methods useful in the synthesis of Compound (1):

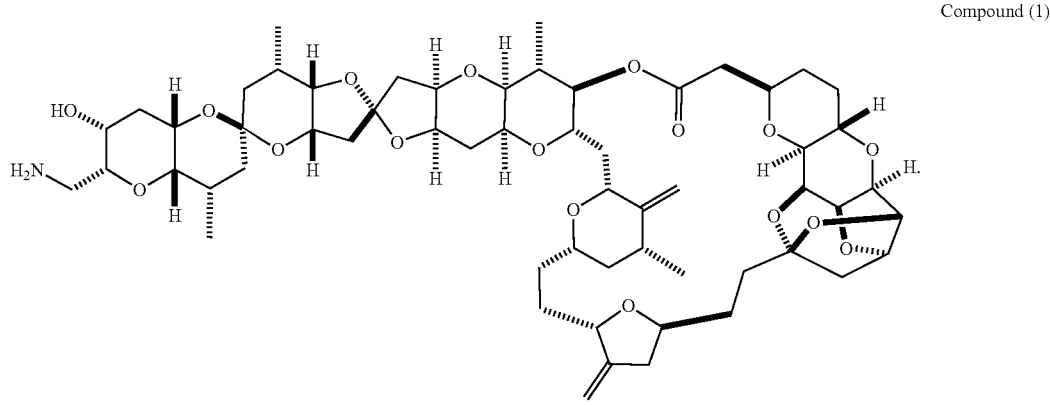

Compound (1)

In one aspect, the present invention provides methods for preparing ketones using a Ni/Zr-mediated coupling reaction, as outlined in Scheme 1A. These coupling reactions can be applied to the synthesis of halichondrins (e.g., halichondrin A, B, C; homohalichondrin A, B, C; norhalichondrin A, B, C), and analogs thereof.

Scheme 1A

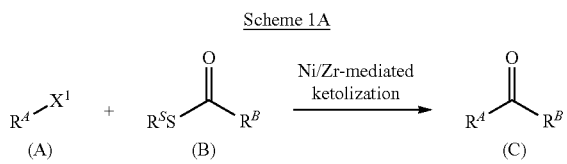

Application of Ni/Zr-mediated coupling reactions provided herein to the preparation of compounds in the halichondrin series (e.g., halichondrin A, B, C, and analogs thereof) is outlined in Scheme 2A, for example. This strategy involves a coupling of a "left half" building block with a "right half" building block via a Ni/Zr-mediated ketolization reaction described herein.

Scheme 2A
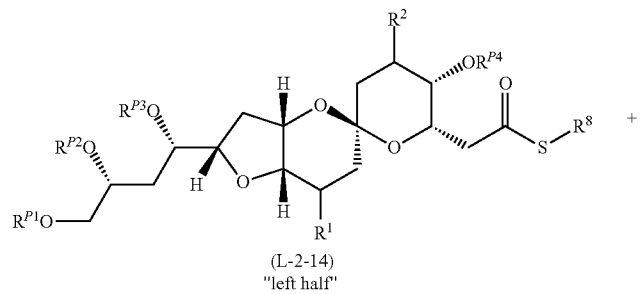
(L-2-14)
"left half"
+
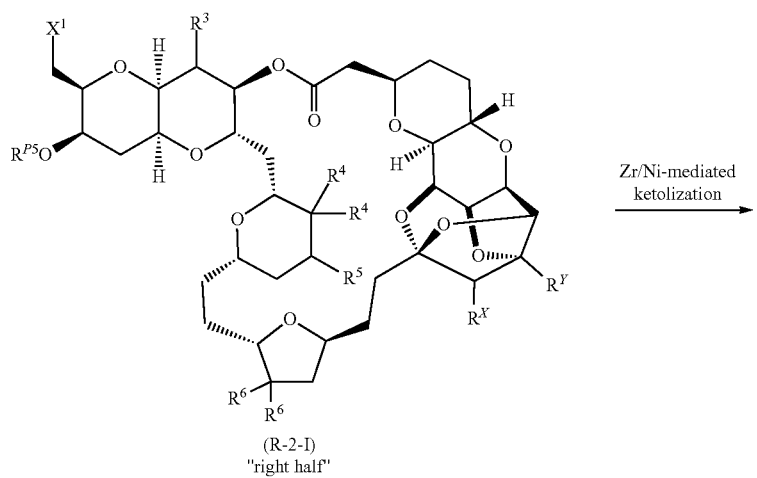
(R-2-I)
"right half"
Zr/Ni-mediated ketolization →
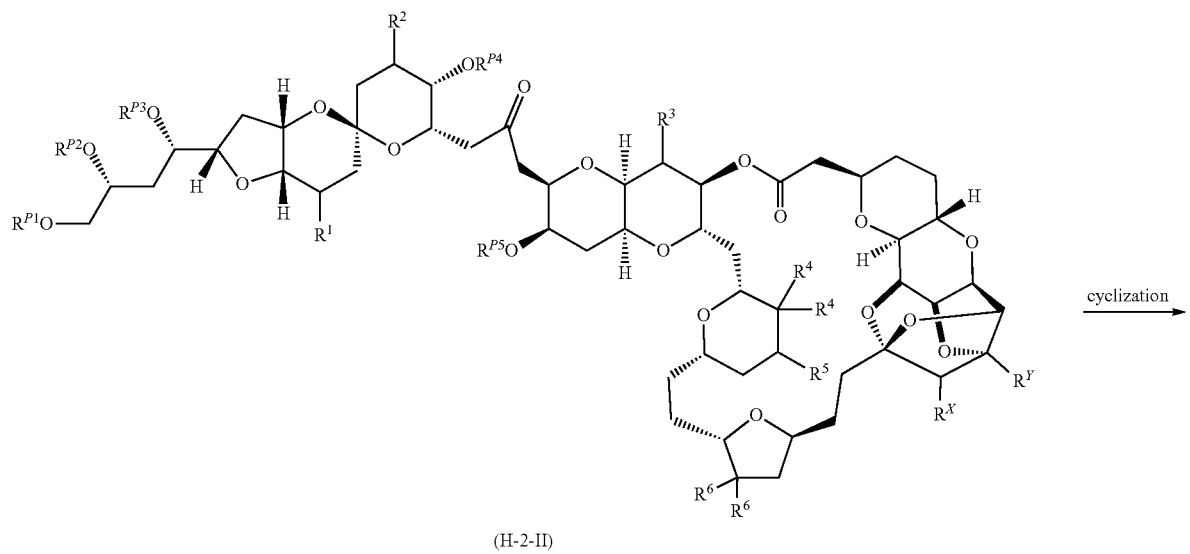
(H-2-II)
cyclization →

-continued

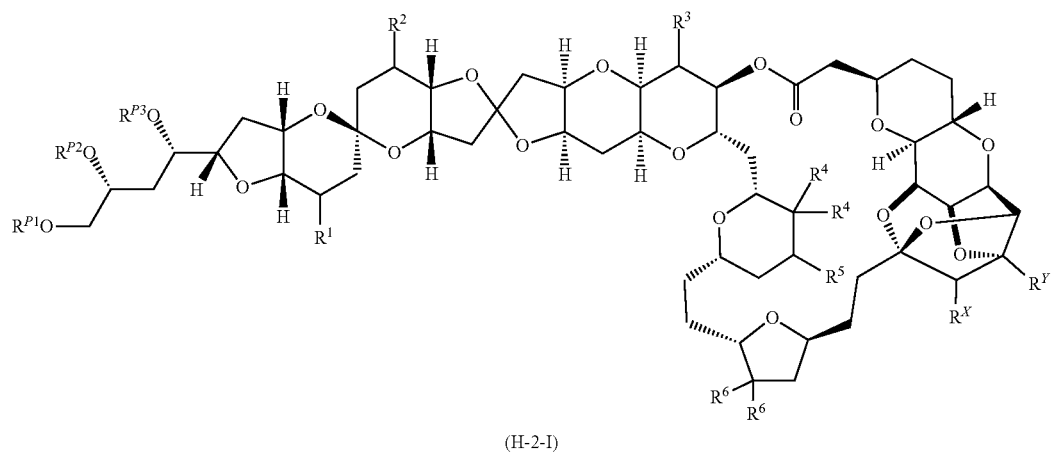

(H-2-I)

Application of Ni/Zr-mediated coupling reactions provided herein to the preparation of compounds in the homohalichondrin series (e.g., homohalichondrin A, B, C, and analogs thereof) is outlined in Scheme 2B, for example. This strategy involves a coupling of a "left half" building block with a "right half" building block via a Ni/Zr-mediated ketolization reaction described herein.

Scheme 2B

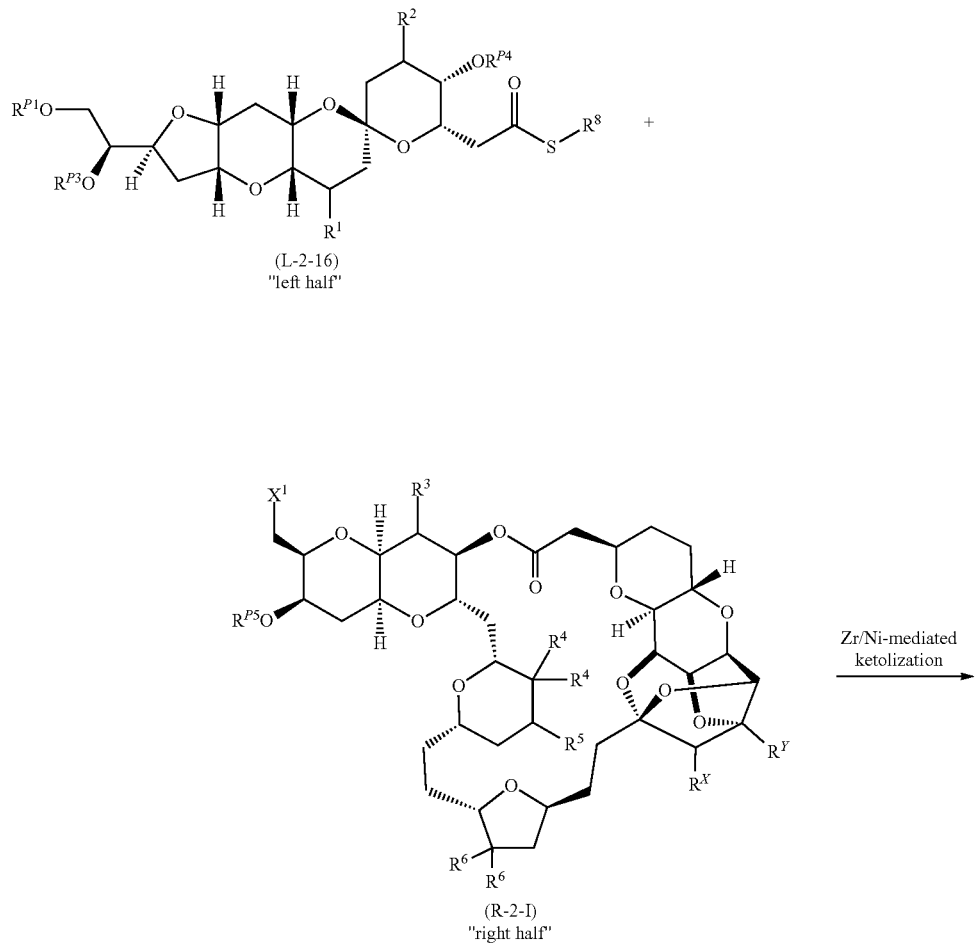

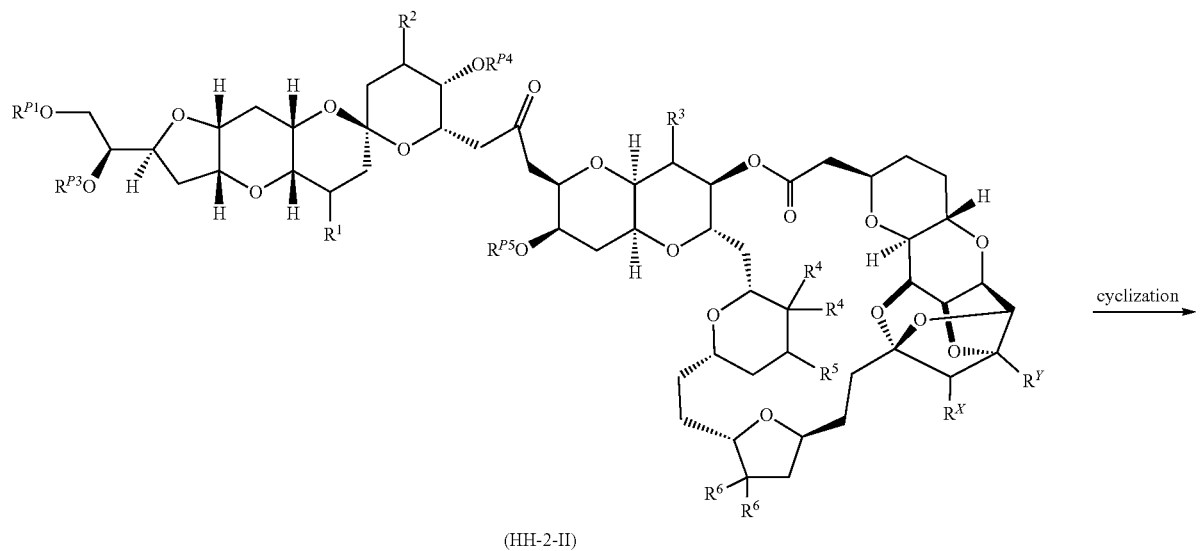

(HH-2-II)

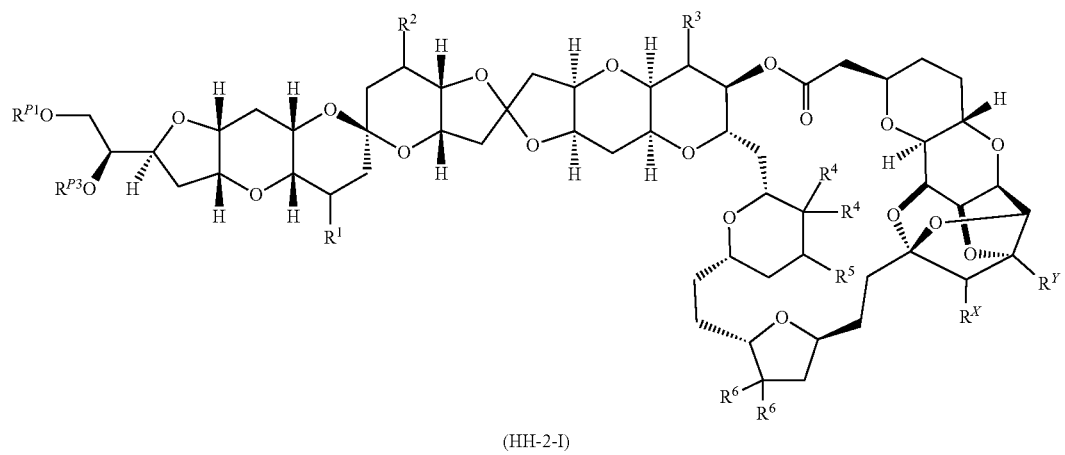

(HH-2-I)

Application of Ni/Zr-mediated coupling reactions provided herein to the preparation of compounds in the norhalichondrin series (e.g., norhalichondrin A, B, C, and analogs thereof) is outlined in Scheme 2C, for example. This strategy involves coupling of a "left half" building block with a "right half" building block via a Ni/Zr-mediated ketolization reaction described herein.

Scheme 2C

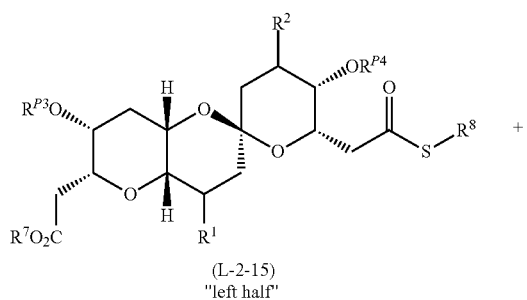

(L-2-15)
"left half"

+

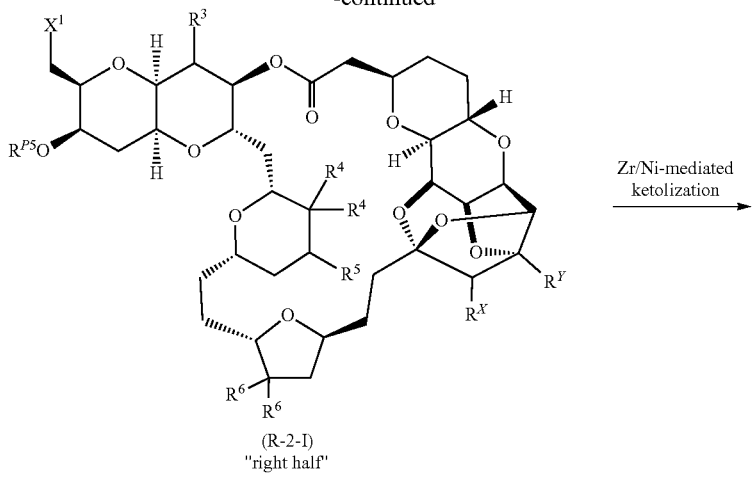

(R-2-I)
"right half"

Zr/Ni-mediated ketolization

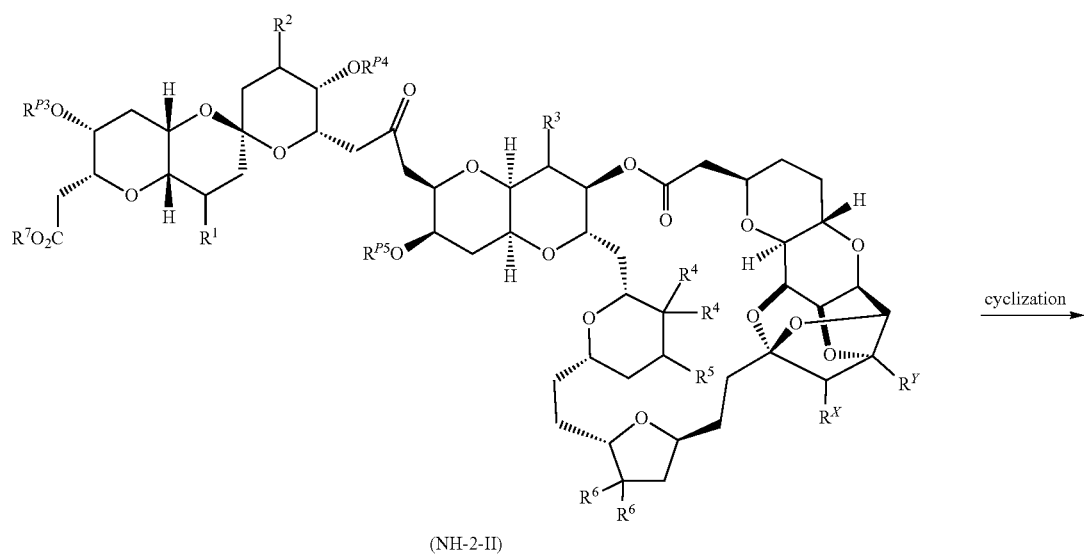

(NH-2-II)

cyclization

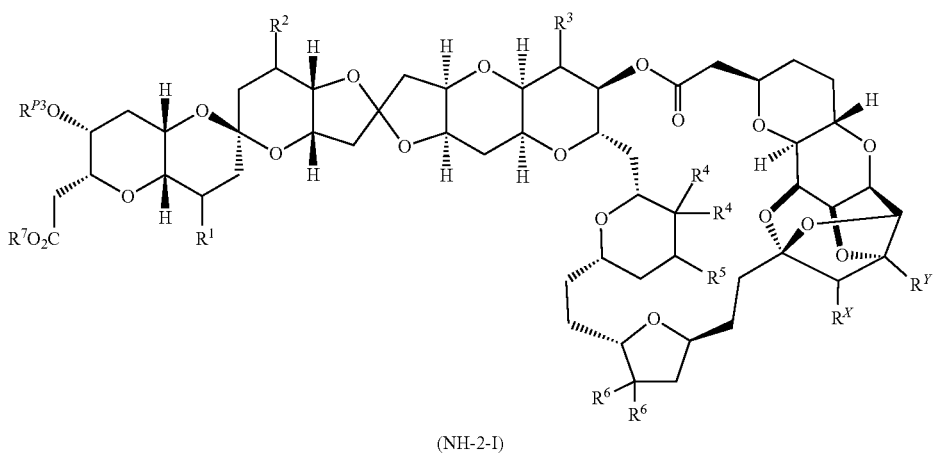

(NH-2-I)

Application of Ni/Zr-mediated coupling reactions provided herein to the preparation of additional halichondrin analogs is outlined in Scheme 2D, for example. This strategy involves a coupling of a "left half" building block with a "right half" building block via a Ni/Zr-mediated ketolization reaction described herein.

Scheme 2D
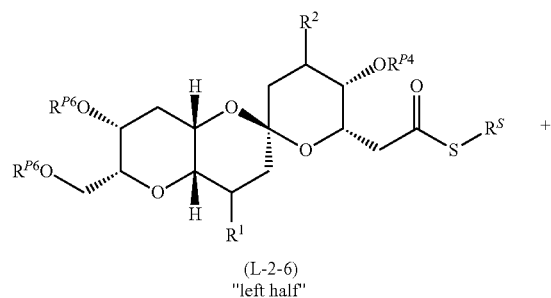
(L-2-6)
"left half"
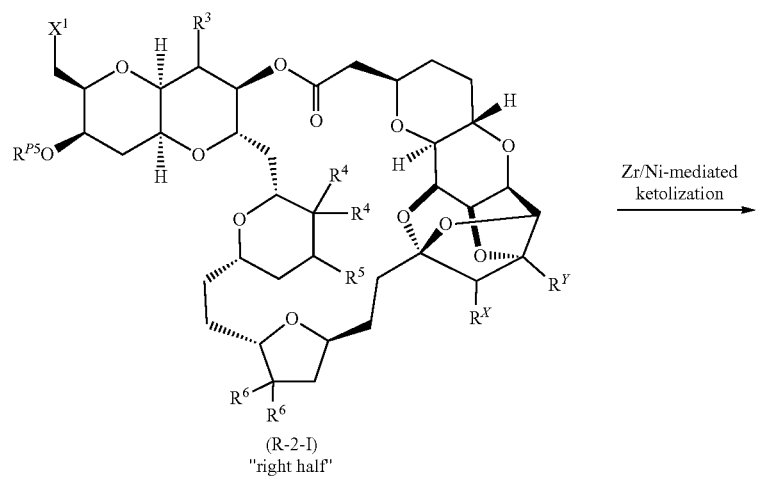
(R-2-I)
"right half"
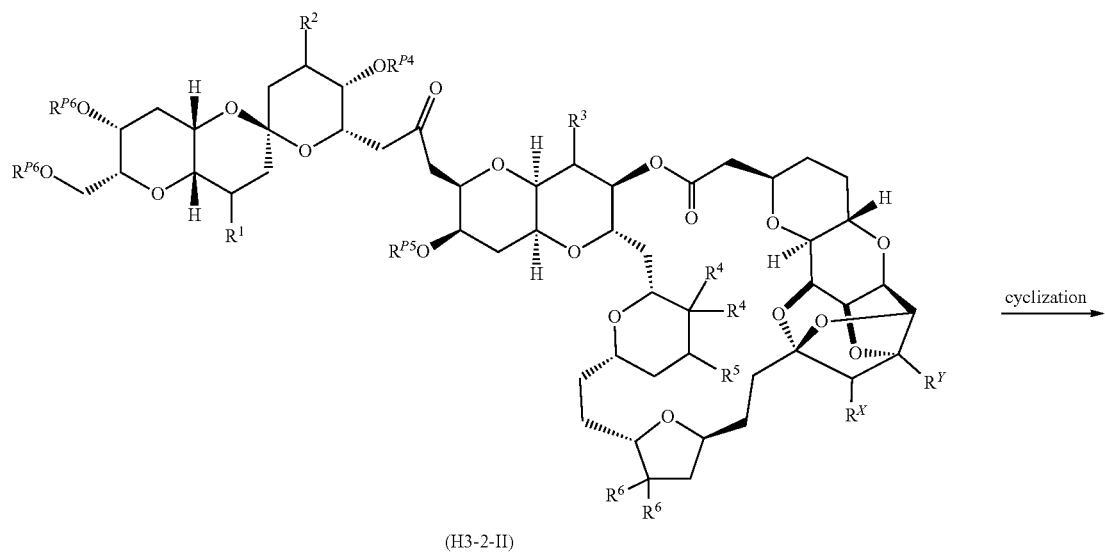
(H3-2-II)

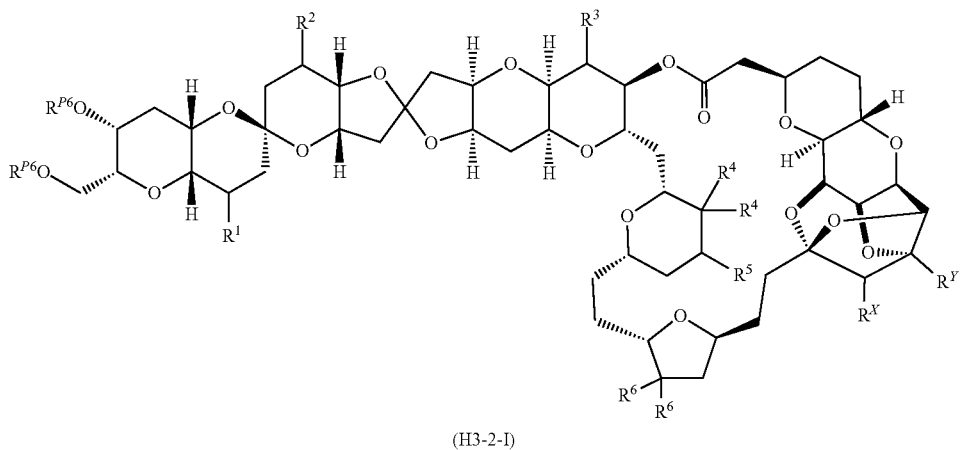

(H3-2-I)

In general, the provided methods for the preparation of halichondrins (e.g., halichondrin A, B, C; homohalichondrin A, B, C; norhalichondrin A, B, C), and analogs thereof, involve the coupling of a "left half" fragment with a "right half" fragment. In another aspect, the present invention provides methods useful in the preparation of said "right half" and "left half" building blocks.

In another aspect, the present invention provides compounds which are useful intermediates en route to halichondrins (e.g., halichondrin A, B, C; homohalichondrin A, B, C; norhalichondrin A, B, C), and analogs thereof. For example, in one aspect, the present invention provides novel "left half" and "right half" building blocks of halichondrins (e.g., halichondrin A, B, C; homohalichondrin A, B, C; norhalichondrin A, B, C), and analogs thereof, and intermediates useful in the preparation of said building blocks.

In yet another aspect, the present invention provides methods useful in the preparation of halichondrin analogs; in particular, the preparation of Compound (1). The present invention also provides compounds (i.e., synthetic intermediates) useful in the synthesis of Compound (1).

In one aspect, the present invention provides methods for preparing Compound (1) that involve substituting the primary hydroxyl group of Compound (2) (—OH; denoted by * in Scheme 1) with an amino group (—NH$_2$). The substitution may be carried out in one or more steps. For example, the substitution may be carried out by converting the primary hydroxyl group of Compound (2) to a leaving group (e.g., —OR$^1$), followed by substitution of the leaving group with an amine or amine precursor (e.g., azide).

Scheme 1

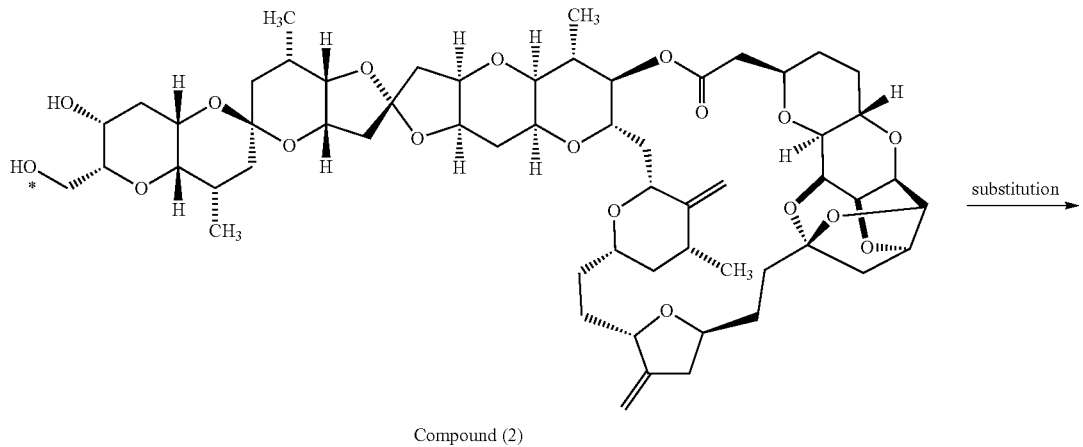

Compound (2)

-continued

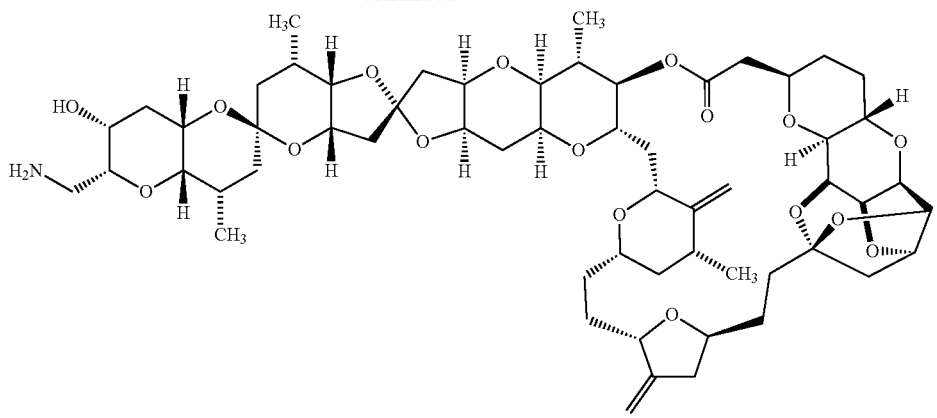

Compound (1)

Current methods for the synthesis of halichondrins can be found, for example, in international PCT publications, WO 2016/176560, published Nov. 3, 2016, and WO 2016/003975, published Jan. 7, 2016; the entire contents of each of which is incorporated herein by reference.

Other current methods for the synthesis of halichondrins can be found, for example, in U.S. Pat. No. 9,938,288, issued Apr. 10, 2018; U.S. Provisional Patent Application Ser. No. 62/586,416, filed Nov. 15, 2017; International Application No. PCT/US2018/031765, filed May 9, 2018; U.S. Patent Application Publication No. US 2018/0155361, published Jun. 7, 2018; the entire contents of each of which is incorporated herein by reference.

The details of certain embodiments of the invention are set forth in the Detailed Description of Certain Embodiments, as described below. Other features, objects, and advantages of the invention will be apparent from the Definitions, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{23}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{24}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 t electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 nt electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X, —NH$_2$(C$_{1-6}$ alkyl)+X, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ ($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(=NH)NH($C_{1-6}$ alkyl), —OC(=NH)NH$_2$, —NHC(=NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$($C_{1-6}$ alkyl), —SO$_2$O($C_{1-6}$ alkyl), —OSO$_2$($C_{1-6}$ alkyl), —SO($C_{1-6}$ alkyl), —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, carbon atom substituents include: halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —CO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(=NH)NH($C_{1-6}$ alkyl), —OC(=NH)NH$_2$, —NHC(=NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$($C_{1-6}$ alkyl), —SO$_2$O($C_{1-6}$ alkyl), —OSO$_2$($C_{1-6}$ alkyl), —SO($C_{1-6}$ alkyl), —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(ORc)$_2$, and —OP(=O)(N(R$^{bb}$)$_2$)$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and RC are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (e.g., —C(=O)$R^{aa}$), carboxylic acids (e.g., —CO$_2$H), aldehydes (—CHO), esters (e.g., —CO$_2R^{aa}$, —C(=O)S$R^{aa}$, —C(=S)S$R^{aa}$), amides (e.g., —C(=O)N($R^{bb}$)$_2$, —C(=O)N$R^{bb}$SO$_2R^{aa}$, —C(=S)N($R^{bb}$)$_2$), and imines (e.g., —C(=N$R^{bb}$)$R^{aa}$, —C(=N$R^{bb}$)O$R^{aa}$), —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methyl sulfinylbenzyl carbamate (Msz), 9-anthrylmethyl carbamate, diphenylmethyl carbamate, 2-methylthioethyl carbamate, 2-methyl sulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethyl sulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methyl amine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxyethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenyl acetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethyl silylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB, MPM), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-butyl, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HCO$_3{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4{}^-$, PF$_4{}^-$, PF$_6{}^-$, AsF$_6{}^-$, SbF$_6{}^-$, B[3,5-(CF$_3$)$_2$C$_6$H$_3$]$_4{}^-$, B(C$_6$F$_5$)$_4{}^-$, BPh$_4{}^-$, Al(OC(CF$_3$)$_3$)$_4{}^-$, and carborane anions (e.g., CB$_{11}$H$_{12}{}^-$ or (HCB$_{11}$Me$_5$Br$_6$)$^-$). Exemplary counterions which may be multivalent include CO$_3{}^{2-}$, HPO$_4{}^{2-}$, PO$_4{}^{3-}$, B$_4$O$_7{}^{2-}$, SO$_4{}^{2-}$, S$_2$O$_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such asp-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., $-OC(=O)SR^{aa}$, $-OC(=O)R^{aa}$, $-OCO_2R^{aa}$, $-OC(=O)N(R^{bb})_2$, $-OC(=NR^{bb})Ra$, $-OC(=NR^{bb})OR$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The following definitions are more general terms used throughout the present application.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)).

The term "catalysis," "catalyze," or "catalytic" refers to the increase in rate of a chemical reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have lower activation energy (rate-limiting free energy of activation) than the corresponding uncatalyzed reaction, resulting in a higher reaction rate at the same temperature. Catalysts may affect the reaction environment favorably, bind to the reagents to polarize bonds, form specific intermediates that are not typically produced by a uncatalyzed reaction, or cause dissociation of reagents to reactive forms.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

BRIEF DESCRIPTION OF THE DRAWINGS

The accompanying drawings, which constitute a part of this specification, illustrate several embodiments of the invention and together with the description, serve to explain the principles of the invention.

FIG. 8A shows exemplary right- and left-halves of halichondrins, homohalichondrins, and norhalichondrins. FIG. 8B shows an exemplary synthesis of halicondrins. Reagents and conditions: For all the cases, step #1 was ketone coupling under the conditions specified in Scheme 3; step #2 was TBAF (10 equiv.), pivalic acid (5 equiv.), DMF, rt, 3-8 hr; step #3 was PPTS, CH$_2$Cl$_2$, ~20° C., 2-4 hours. Epimerization of C38-epi-halichondrins was done with TMSOTf, CH$_2$Cl$_2$, –78° C. For the halichondrin-A or -C series, these steps were followed by PPTS, 2,2-dimethyl-propan-1,3-diol, i-PrOH, rt, overnight or by Pd(PPh$_3$)$_4$, dimedone, CH$_2$Cl$_2$, rt, 4-8 hours, respectively. In the norhalichondrin series, the methyl ester at C53 was hydrolyzed by treatment with aq. LiOH, THF, rt, at the end of transformation. Numbers after i and ii indicate the yield for ketone couplings and overall yield after ketone coupling, respectively.

FIG. 15 shows exemplary stereocontrolled [6,6]-spiroketal synthesis. Abbreviation: MPM=p-MeOC$_6$H4CH$_2$—.

DBU=1,8-diazabicyclo[5.4.0]-undec-7-ene; DDQ=2,3-dichloro-5,6-dicyano-p-benzoquinone.

Figure 17:
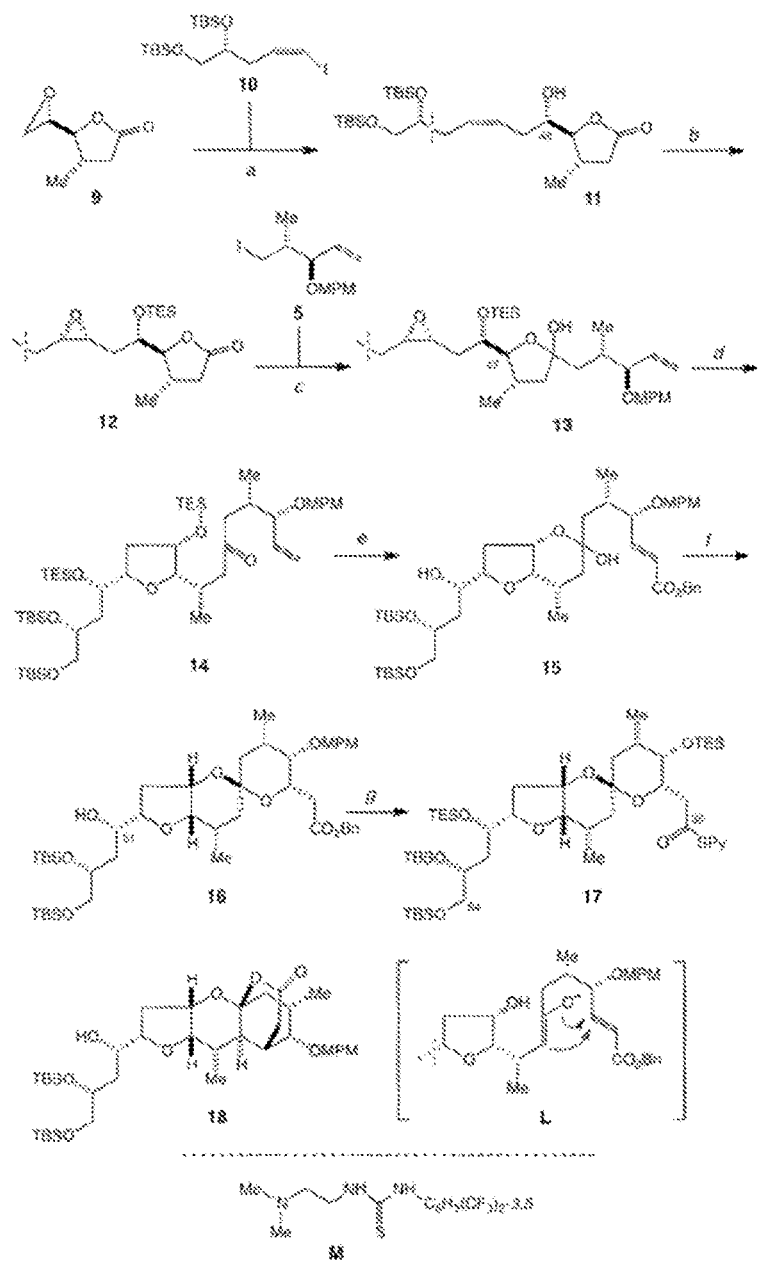

FIG. 17 shows an exemplary synthesis of a left hand building block of halichondrins. Reagents and conditions: a. 10 (1.8 equiv.), n-BuLi (1.75 equiv.), Li(thienylCuCN) (2.0 equiv.), $BF_3 \cdot Et_2O$ (1.6 equiv.), $Et_2O$, −78° C., 1 hour (81%). b. 1. $VO(TMHD)_2$ (5 mol %), tBuOOH (5.5 M in decane, 2 equiv.), toluene, rt, 5 hours. 2. TESCl (2.0 equiv.), imidazole (4.0 equiv.), $CH_2Cl_2$, 0° C., 2 hr (85% for 2 steps). c. t-BuLi (2.6 equiv.), THF, −78° C., 0.5 hours (85%). d. 1. $(PhO)_2P(=O)OH$ (5 mol %), toluene (0.05M), 0° C. to rt, 12 hours. 2. TESCl (3.0 equiv.), imidazole (6.0 equiv.), $CH_2Cl_2$, rt, 2 hours (85% for 2 steps). e. 1. $OsO_4$ (5% mol), NMMO (2.0 equiv.), acetone/$H_2O$, rt, 12 hours. 2. $Pb(OAc)_4$ (1.5 equiv.), $K_2CO_3$ (10 equiv.), $CH_2Cl_2$, rt, 10 minutes. 3. $(MeO)_2P(=O)COOBn$ (4 equiv.), $K_3PO_4$ (8 equiv.), toluene, rt, 15 hours (82% for 3 steps). 4. $(PhO)_2P(=O)OH$ (5 mol %), THF-$H_2O$ (4:1, 0.02M), rt, 24 hours. 5. TBSCl (1.5 equiv.), imidazole (3.0 equiv.), $CH_2Cl_2$, rt, 2 hours (80% for 2 steps). f BnOAc (1 equiv.), and LiCl (10 equiv.), DBU (20 equiv.), MeCN (0.05M), 24 hr (86% alone with 8% 18). or BnOAc (1 equiv.), and LiCl (10 equiv.), DBU (20 equiv.), M (50 mol %), MeCN (0.05M), 2 hours; then BnOAc (1 equiv.), and LiCl (10 equiv.), DBU (20 equiv.), MeCN (0.05M), 24 hours (93%). g. 1. DDQ (1.6 equiv.), $CH_2Cl_2$, phosphate buffer, 0° C., 0.5 hours. 2. TESCl (3 equiv.), imidazole (6 equiv.), $CH_2Cl_2$, rt, 2 hours (90% for 2 steps). 3. Pd/C, $H_2$ balloon, EtOAc, rt, 1 hour. 4. $(PyS)_2$ (1.4 equiv.), $PPh_3$ (1.3 equiv.), toluene, rt, 3 hr (91% for 2 steps). Abbreviation: TMHD=tris (2,2,6,6-tetramethyl-3,5-heptanedionate).

Figure 18:
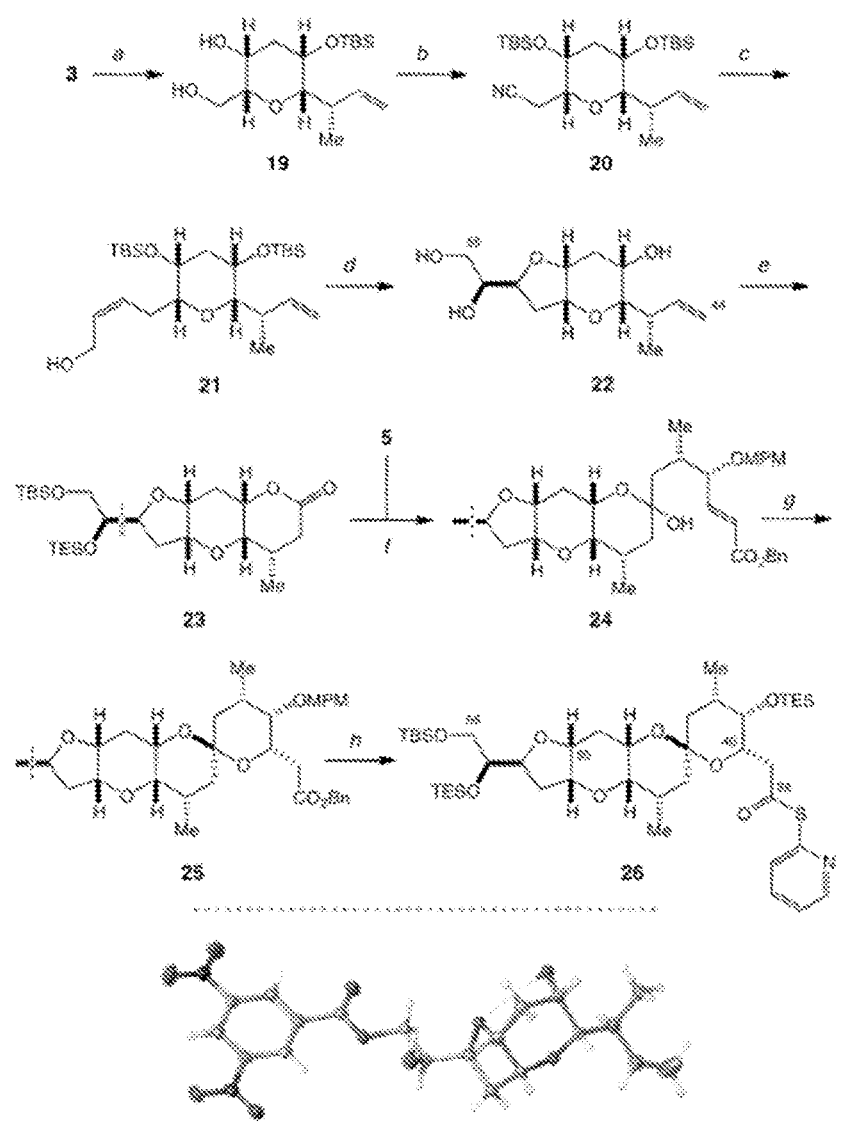

FIG. 18 shows an exemplary synthesis of a left half building block in the homohalichondrin series. Reagents and conditions: a. 1. DIBAL (1.3 equiv.), $CH_2Cl_2$, −78° C., 15 min. 2. $MePPh_3Br$ (4 equiv.), t-BuOK (3 equiv.), THF, 0° C.-rt, 20 minutes. 3. TBSOTf (1.3 equiv.), 2,6-lutidine (2 equiv.), $CH_2Cl_2$, 0° C.-rt, 1 hour. 4. HF.py (ca. 8 equiv.), pyridine, MeCN, −10° C.-rt, 1.5 hours (96% for 4 steps). b. 1. $Tf_2O$ (1.2 equiv.), 2,6-lutidine (4 equiv.), $CH_2Cl_2$, −78° C., 10 minutes. 2. NaCN (10 equiv.), DMSO, rt, 1 hour. 3. TBSCl (3 equiv.), pyridine (8 equiv.), $AgNO_3$ (3 equiv.), DMF, 0° C.-rt, 18 hours (87% for 3 steps). c. 1. DIBAL (1.1 equiv.), $CH_2Cl_2$, hexanes, −78° C., 30 minutes. 2. $(CF_3CH_2O)_2P(O)CH_2CO_2Me$ (1.5 equiv.), 18-Crown-6 (8 equiv.), KHMDS (1.5 equiv.), THF, −78° C. (84% for 2 steps). 3. DIBAL (4 equiv.), THF, −78° C.-0° C., 30 minutes (99%). d. 1. (+)-DET (20 mol %), $Ti(OPr-i)_4$ (15 mol %), TBHP (1.5 equiv.), MS 4A, $CH_2Cl_2$, −10° C., 15 hours (86% for desired isomer, 11% for undesired isomer). 2. TBAF (6 equiv.), MS 4Å, THF (96%). e. 1. TBSCl (1.5 equiv.), $Et_3N$ (4 equiv.), $CH_2Cl_2$, rt, 5 hours (99%). 2. TESCl (1.2 equiv.), imidazole (3 equiv.), $CH_2Cl_2$, 0° C.-rt, 15 minutes. 3. 9-BBN (3 equiv.), THF, 0° C.-rt, 1 hour then $NaBO_3 \cdot H_2O$ aq. (94% for 2 steps). 4. TEMPO (20 mol %), $PhI(OAc)_2$ (3 equiv.), $CH_2Cl_2$, rt, 36 hours (95%). f 1. 5 (1.3 equiv.), t-BuLi (2.5 equiv.), THF, −78° C., 30 minutes. 2. $OsO_4$ (10 mol %), NMMO (2 equiv.), $H_2O$, acetone, rt, 4 hours. 3. $Pb(OAc)_4$ (1.5 equiv.), $K_2CO_3$ (10 equiv.), $CH_2Cl_2$, rt, 15 minutes (68% for 3 steps). 4. $(MeO)_2P(=O)CH_2CO_2Bn$ (5 equiv.), NaH (4 equiv.), THF, 0° C., 3 hours (88%). g. 1. LiBr (10 equiv.), DBU (20 equiv.), MeCN, rt, 11 hours (70%). h. DDQ (3 equiv.), $CH_2Cl_2$, t-BuOH, pH 7 buffer, rt, 15 minutes (86%). 2. TESCl (1.5 equiv.), imidazole (3 equiv.), $CH_2Cl_2$, rt, 4 hr (97%). 3. $H_2$ (1 atm), Pd/C, AcOEt, rt, 2 hours (89%). 4. $(PyS)_2$ (1.2 equiv.), $PPh_3$ (3 equiv.), toluene, rt, 12 hours (97%). Abbreviation: 18-Crown-6=1,4,7,10,13,16-hexa-oxacyclooctadecane; KHMDS=potassium bis(trimethylsilyl)amide; 9-BBN=9-borabicyclononane; DET=diethyl tartrate; TBHP=tert-butyl hydroperoxide; MS=molecular sieves; TBAF=tetrabutylammonium fluoride.

Figure 19:
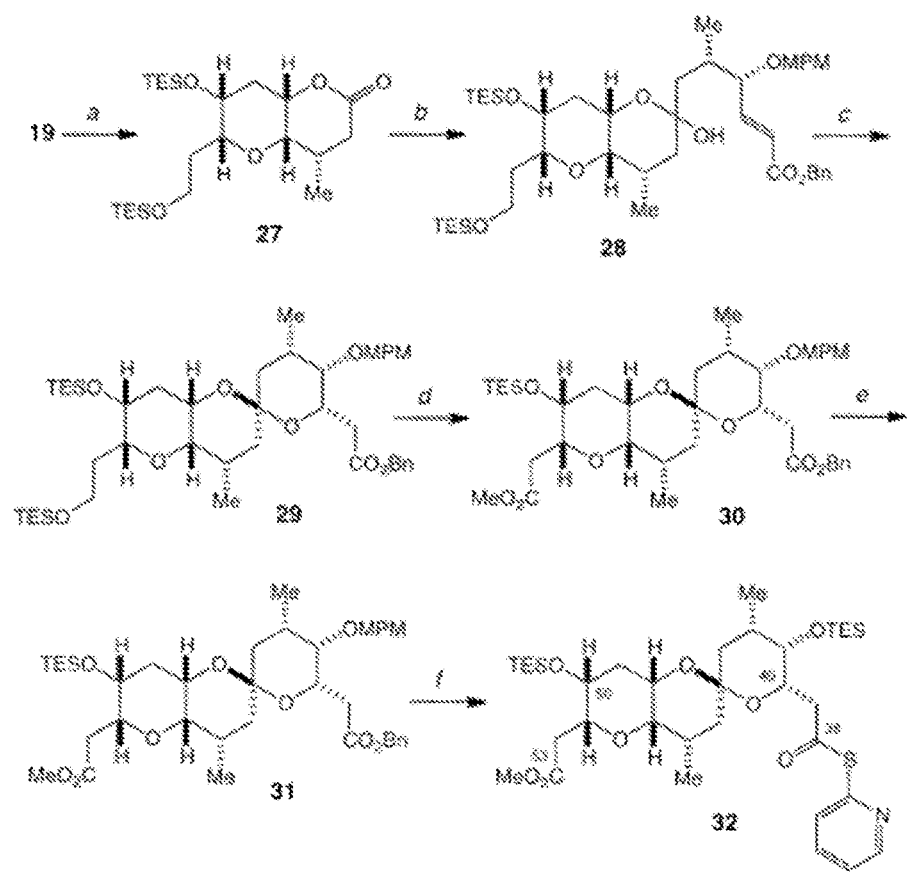

FIG. 19 shows an exemplary synthesis of a left hand $C_{38}$-$C_{53}$ building block in the norhalichondrin series. Reagents and conditions: a. 1. $Tf_2O$ (1.2 equiv.), 2,6-lutidine (4 equiv.), $CH_2Cl_2$, −78° C., 10 minutes. 2. NaCN (10 equiv.), DMSO, rt, 1 hour (87% for two steps). 3. DIBAL (4.5 equiv.), $CH_2Cl_2$, −78° C., 30 minutes. 4. $NaBH_4$ (5 equiv), MeOH, rt, 30 minutes. 5. TBSOTf (3 equiv.), 2,6-lutidine (3.5 equiv.), $CH_2Cl_2$, rt, 30 minutes (90% for 3 steps). 6. 9-BBN (2 equiv.), THF, rt, 2 hours, then NaOH, $H_2O_2$, $H_2O$, rt, 3 hr (91%). 7. TEMPO (0.5 equiv.), $PhI(OAc)_2$ (5.0 equiv.), $CH_3CN$, $H_2O$, THF, rt, 12 hours (90%). 8. p-TsOH.$H_2O$ (1.0 equiv.), $H_2O$ (10 equiv.), $CH_2Cl_2$, rt, 24 hours. 9. TESOTf (10 equiv), 2,6-lutidine (12 equiv.), $CH_2Cl_2$, rt, 1 hour (76% for 2 steps). b. 1. 5, t-BuLi (2.2 equiv.), toluene, $Et_2O$, −78° C., 10 minutes (82%). 2. $OsO_4$ (5 mol %), NMMO (2 equiv.), $H_2O$, acetone, rt, 12 hours. 3. $Pb(OAc)_4$ (2 equiv.), $K_2CO_3$ (10 equiv.), rt, 30 minutes (86% for 2 steps). 4. $(MeO)_2P(=O)CH_2CO_2Bn$ (4 equiv.), $K_3PO_4$ (3 equiv.), rt, 36 hours (93%). c. LiBr (10 equiv.), DBU (5 equiv.), BnOAc (2 equiv.), $CH_3CN$, rt, 12 hours (82%). d. 1. TBAF (1.5 equiv.), HOAc (1.0 equiv.), THF, 0° C., 5 hours (81%). 2. Dess-Martin periodinane (2.0 equiv.), $NaHCO_3$ (10 equiv.), $CH_2Cl_2$, rt, 30 min. 3. $NaClO_2$ (3 equiv.), $NaH_2PO_4$ (4 equiv.), 2-methyl-2-butene, t-BuOH, $H_2O$, rt, 30 minutes. 4. $TMSCH_2N_2$(3.0 equiv.), benzene, MeOH, rt, 5 minutes (87% for 3 steps). e. 1. DDQ (2.0 equiv.), $CH_2Cl_2$, aqueous pH7 buffer, rt, 1 hour. 2. TESOTf (2.0 equiv.), 2,6-lutidine (2.5 equiv.), $CH_2Cl_2$, rt, 30 minutes (83% for 2 steps). f 1. Pd/C (10 wt %), $H_2$, EtOAc, rt, 3 hours. 2. $(SPy)_2$ (1.4 equiv.), $PPh_3$ (1.2 equiv.), toluene, rt, 12 hours (88% for 2 steps). Abbreviation: p-TsOH=p-toluenesulfonic acid.

Figure 20:
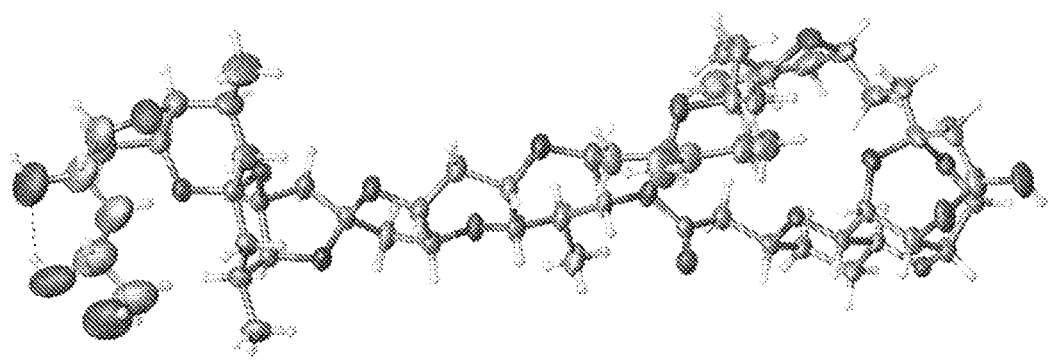

FIG. 20 shows an X-Ray Structure for Halichondrin C prepared using the methods described herein. A colorless single crystal of Halichondrin C was obtained by recrystallization from MeOH:$CH_2Cl_2$=1:1.

Figure 21:
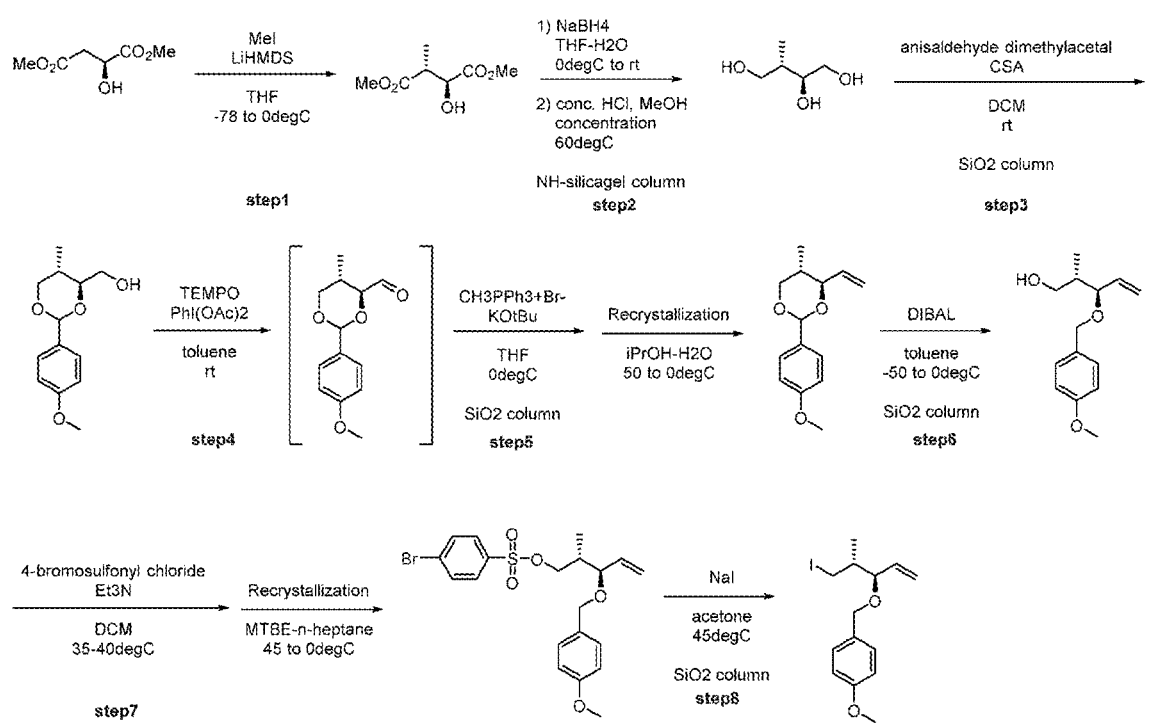

FIG. 21 shows an exemplary synthetic scheme for the preparation of an exemplary C33-C43 fragment of halichondrins and analogs thereof.

Figure 22:
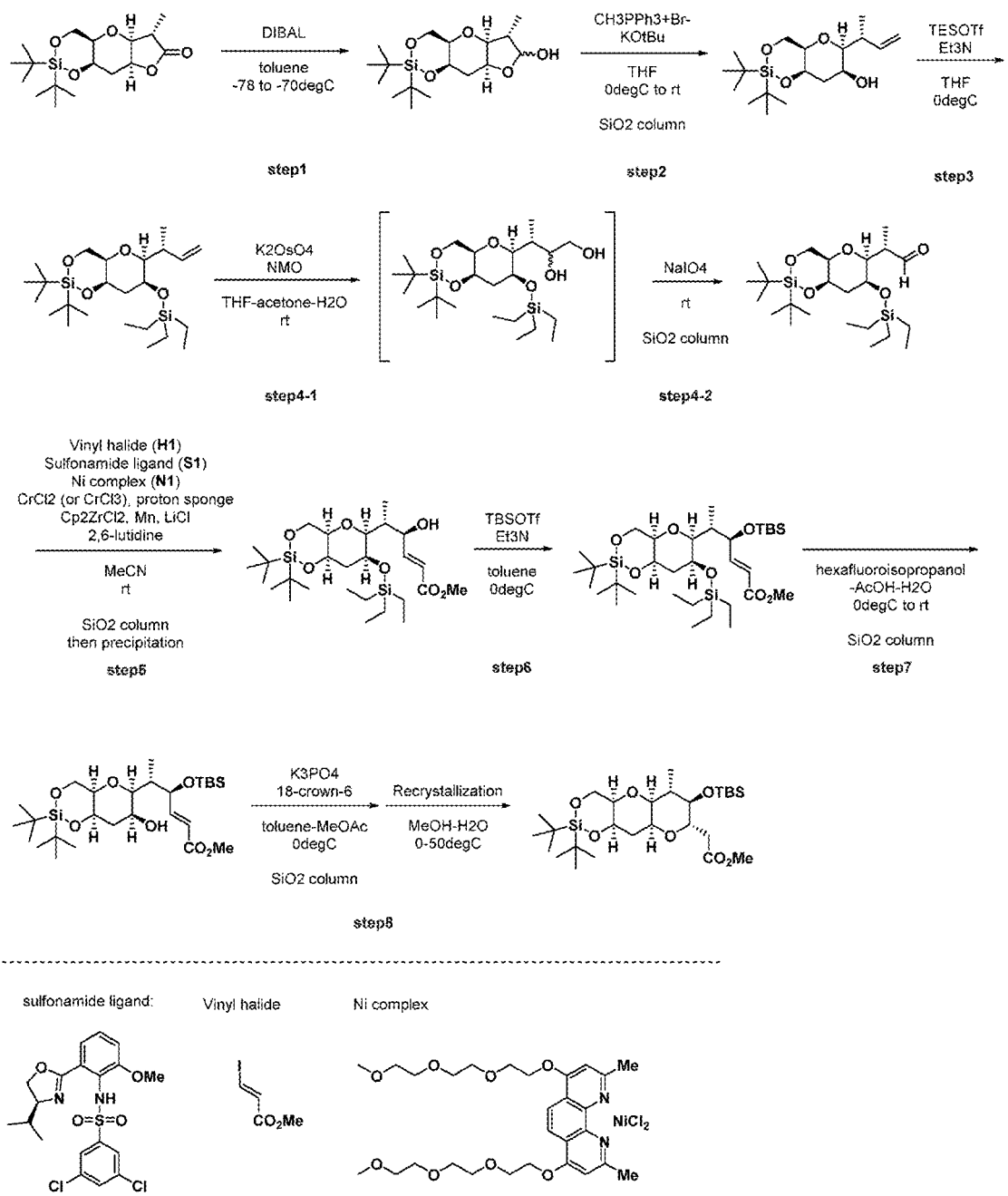

FIG. 22 shows an exemplary synthetic scheme for the preparation of an exemplary C27-C37 fragment of halichondrins and analogs thereof.

Figure 23:
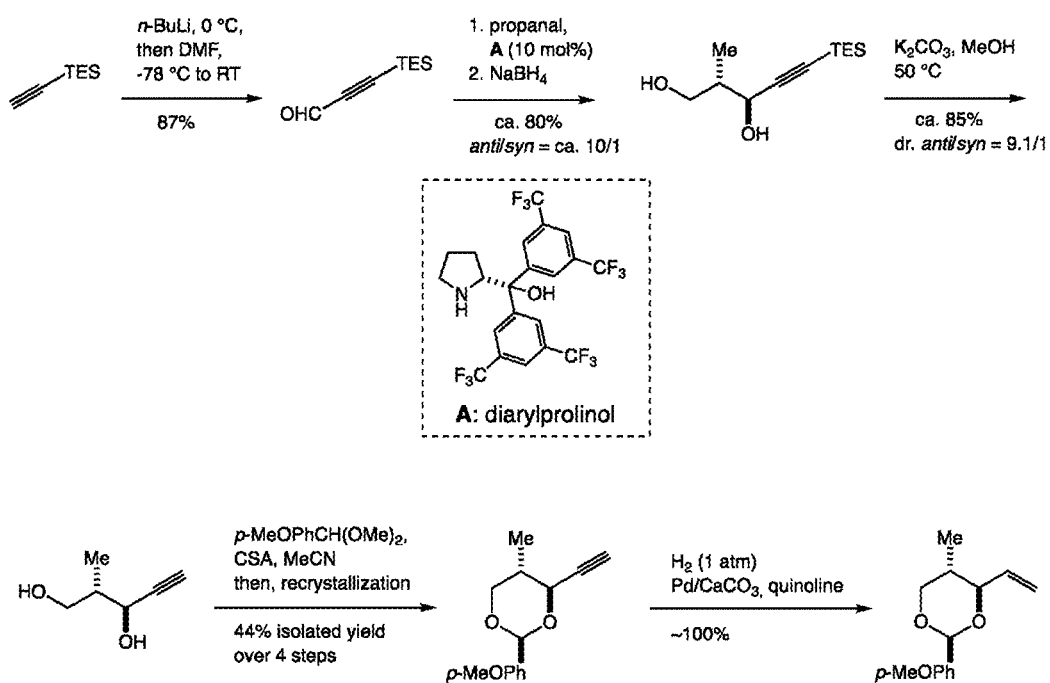

FIG. 23 shows an exemplary synthetic scheme for the preparation of an exemplary C39-C43 fragment of halichondrins and analogs thereof.

DETAILED DESCRIPTION OF CERTAIN EMBODIMENTS

Provided herein are Ni/Zr-mediated coupling reactions useful in the preparation of ketone-containing compounds. The Ni/Zr-mediated ketolization reactions provided herein are particularly useful in the synthesis of halichondrins and analogs thereof. Therefore, also provided herein are methods for the preparation of halichondrins (e.g., halichondrin A, B, C; homohalichondrin A, B, C; norhalichondrin A, B, C) and analogs thereof.

In certain embodiments, provided herein are methods useful in the preparation of compounds of Formula (H3-A), including Compound (1):

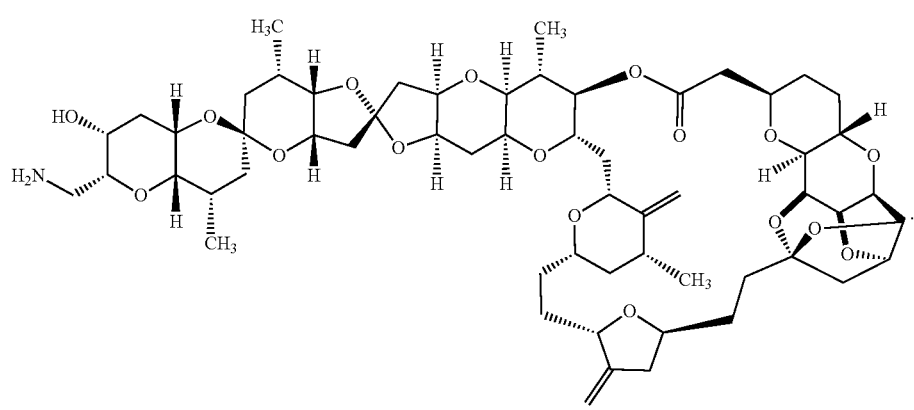

Compound (1)

The present invention also provides compounds (i.e., intermediates) useful in the methods provided herein. In certain embodiments, the compounds provided herein are useful as synthetic intermediates en route to halichondrins and analogs thereof. Furthermore, the present invention provides reagents and catalysts useful in the methods described herein.

Ni/Zr-Mediated Ketolization Reactions

In one aspect, provided herein are nickel/zirconium-mediated ketolization reactions ("Ni/Zr-mediated ketolization reactions") involving a coupling of a thioester and an alkyl halide (e.g., alkyl iodide, alkyl bromide, alkyl chloride, etc.) or alkyl leaving group (e.g., alkyl sulfonate) (Scheme 1A). The ketolization reactions may be intermolecular or intramolecular (i.e., in Scheme 1A, $R^A$ and $R^B$ are optionally joined by a linker). In certain embodiments, the compound of Formula (A) is a primary or secondary alkyl halide ($X^1$=halogen), and the compound of Formula (B) is an alkyl thioester ($R^B$=optionally substituted alkyl), as shown in Scheme 1B.

Scheme 1A

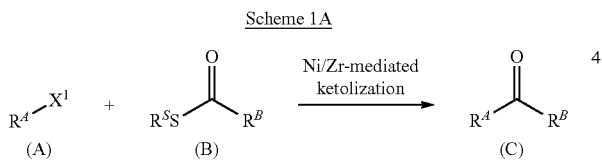

Scheme 1B

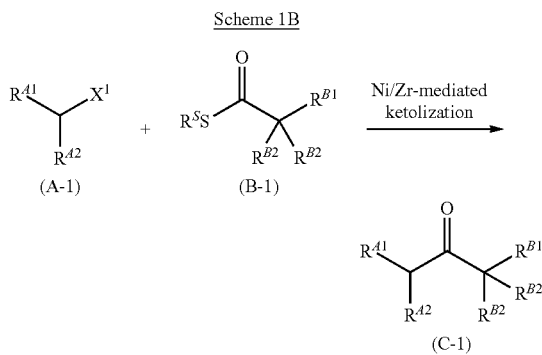

As represented in Scheme 1A, provided herein are methods for preparing a compound of Formula (C):

or a salt thereof, the methods comprising reacting a compound of Formula (A):

or a salt thereof, with a compound of Formula (B):

or a salt thereof, in the presence of nickel and zirconium;
wherein:
  $R^A$ is optionally substituted alkyl;
  $R^B$ is optionally substituted alkyl, optionally substituted alkenyl, optionally substituted alkynyl, optionally substituted aryl, optionally substituted carbocyclyl, optionally substituted heteroaryl, or optionally substituted heterocyclyl;
  optionally wherein $R^A$ and $R^B$ are joined together via a linker, wherein the linker is selected from the group consisting of optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocyclylene, optionally substituted heterocyclylene, optionally substituted acylene, and combinations thereof;
  $X^1$ is halogen or a leaving group; and
  $R^S$ is optionally substituted alkyl, optionally substituted carbocyclyl, optionally substituted aryl, optionally substituted heterocyclyl, or optionally substituted heteroaryl.

In certain embodiments, $R^A$ is a small molecule. In certain embodiments, $R^B$ is a small molecule. Small molecules encompass complex small molecules, such as natural products, pharmaceutical agents, and fragments thereof, and intermediates thereto.

As generally defined herein, a "linker" is a group comprising optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocyclylene, optionally substituted heterocyclylene, optionally substituted acylene, or any combination thereof.

In certain embodiments, the compound of Formula (A) is of Formula (A-1):

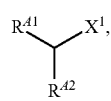
(A-1)

or a salt thereof; the compound of Formula (B) is of Formula (B-1):

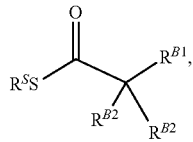
(B-1)

or a salt thereof; and the compound of Formula (C) is of Formula (C-1):

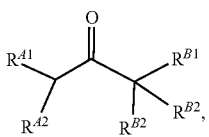
(C-1)

or a salt thereof, wherein:
$X^1$ is halogen or a leaving group;
$R^S$ is optionally substituted alkyl, optionally substituted carbocyclyl, optionally substituted aryl, optionally substituted heterocyclyl, or optionally substituted heteroaryl;
each instance of $R^{A1}$, $R^{A2}$, $R^{B1}$, and $R^{B2}$ is independently hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl; optionally wherein $R^{A1}$ and $R^{B1}$ are joined together via a linker.

In certain embodiments, $R^{A1}$ is a small molecule. In certain embodiments, $R^{B1}$ and $R^{B2}$ are independently a small molecules. Small molecules encompass complex small molecules, such as natural products, pharmaceutical agents, and fragments thereof, and intermediates thereto.

The Ni/Zr-mediated ketolization reactions provided herein may be performed in an intramolecular fashion to yield cyclic ketones as shown in Scheme 1C.

Scheme 1C

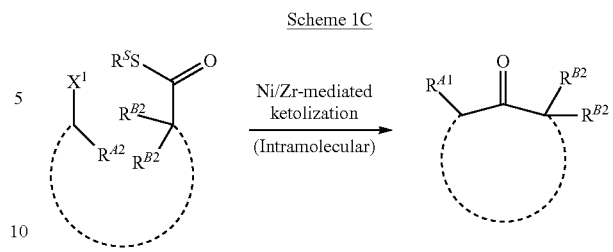

As shown in Scheme 1C, provided herein are methods for preparing a compound of Formula (C-2):

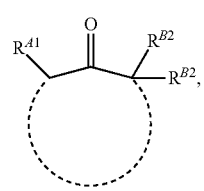
(C-2)

or salt thereof, comprising reacting a compound of Formula (A-B):

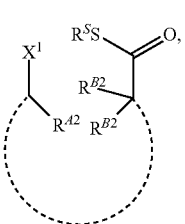
(A-B)

or a salt thereof, in the presence of nickel and zirconium; wherein:
$R^{A2}$ and $R^{B2}$ are optionally substituted alkyl, optionally substituted alkenyl, optionally substituted alkynyl, optionally substituted aryl, optionally substituted carbocyclyl, optionally substituted heteroaryl, or optionally substituted heterocyclyl;
$X^1$ is halogen or a leaving group;
$R^S$ is optionally substituted alkyl, optionally substituted carbocyclyl, optionally substituted aryl, optionally substituted heterocyclyl, or optionally substituted heteroaryl; and ⌣ represents a linker.

Ni/Zr-mediated ketolization reactions provided herein are carried out in the presence of nickel. In certain embodiments, the ketolization reaction is carried out in the presence of a nickel complex. Any nickel complex (e.g., nickel salt, nickel complex, nickel catalyst, or nickel pre-catalyst) known or available in the art may be used in the reaction. In certain embodiments, the ketolization reaction is carried out in the presence of nickel (II). In certain embodiment, the ketolization reaction is carried out in the presence of a nickel (0). In certain embodiments, the nickel complex is of the formula: $NiX_2 \cdot (ligand)$, wherein X is halogen (e.g., Cl, Br, I, or F). In certain embodiments, "ligand" is a bidendate ligand. In certain embodiments, the ligand is an optionally substituted bispyridyl ligand. In certain embodiments, the nickel complex is $NiX_2 \cdot (tbbpy)$, wherein X is halogen (e.g., Cl, Br, I, or F), and "tbbpy" is 4,4'-bis(tert-butyl)-2,2'-bipyridine, having the structure:

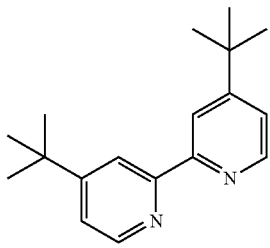 [SMILES: CC(C)(C)c1ccnc(-c2cc(C(C)(C)C)ccn2)c1]

In certain embodiments, the nickel complex is NiCl$_2$.(tbbpy). In certain embodiments, the nickel complex is NiBr$_2$.(tbbpy).

In certain embodiments, the nickel complex is used after complexation of a nickel source and a "ligand" in solution. In certain embodiments, the nickel complex is of the formula: NiX$_2$e(ligand); wherein X is halogen and "ligand" is a bidentate ligand. In certain embodiments, the nickel source is NiCl$_2$; the "ligand" is 4,4'-di-tert-butyl-2,2'-dipyridyl (tbbpy); and the resulting nickel complex is of the formula NiCl$_2$.(tbbpy). In certain embodiments, the nickel source is NiBr$_2$; and the "ligand" is 4,4'-di-tert-butyl-2,2'-dipyridyl (tbbpy); and the resulting nickel complex is of the formula NiBr$_2$.(tbbpy).

In certain embodiments, the nickel is present in a catalytic amount. In certain embodiments, the nickel is present at approximately 1-5 mol %, 5-10 mol %, 1-10 mol %, 5-20 mol %, 10-20 mol %, 20-30 mol %, 20-40 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the nickel is present in from 1-50 mol %. In certain embodiments, the nickel is present in from 1-10 mol %. In certain embodiments, the nickel is present in approximately 5 mol %. In certain embodiments, the nickel is present in approximately 30 mol %. In certain embodiments, the nickel is present in a stoichiometric or excess amount relative to a compound of Formula (A) or (B) in the reaction mixture. In certain embodiments, approximately 1 equivalent of nickel is present (i.e., stoichiometric). In other embodiments, greater than 1 equivalent of nickel is present (i.e., excess).

As described above, the Ni/Zr-mediated ketolization reactions are carried out in the presence of zirconium. In certain embodiments, the reaction is carried out in the presence of a zirconium complex. Any zirconium source (e.g., zirconium salt, complex, catalyst or precatalyst) known or available in the art may be used in the reaction. In certain embodiments, the zirconium source is of the formula (ligand)$_n$ZrX$_2$; wherein n is the number of ligands (e.g., 0, 1, 2, 3, 4), and X is halogen (e.g., Cl, Br, I, or F). In certain embodiments, n is 2, and the ligand is cyclopentadienyl. In certain embodiments, the zirconium source is Cp$_2$ZrX$_2$. In certain embodiments, the zirconium source is Cp$_2$ZrCl$_2$.

In certain embodiments, the zirconium is present in a catalytic amount. In certain embodiments, the zirconium is present in between 1-5 mol %, 5-10 mol %, 1-10 mol %, 5-20 mol %, 10-20 mol %, 20-30 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the zirconium is present in a stoichiometric or excess amount relative to a compound of Formula (A) or (B) in the reaction mixture.

In certain embodiments, approximately 1 equivalent of zirconium is present (i.e., stoichiometric). In other embodiments, greater than 1 equivalent of zirconium is present (i.e., excess). In certain embodiments, approximately 1.1, 1.2, 1.3, 1.4, 1.5, 1.6, 1.7, 1.8, 1.9, 2, 2.5, 3, 3.5, 4, 4.5, 5, 6, 7, 8, 9, or 10 equivalents of zirconium is present. In certain embodiments, approximately 3 equivalents of zirconium is present.

In certain embodiments, a Ni/Zr-mediated ketolization reaction provided herein is performed in the presence of one or more additional reagents or catalysts, such as a reducing metal. In certain embodiments, the reducing metal is zinc. In certain embodiments, the reducing metal is magnesium. In certain embodiments, zinc metal is used (i.e., zinc(0)). In certain embodiments, magnesium metal is used (i.e., magnesium(0)). In certain embodiments, the reaction is carried out in the presence of zinc powder, zinc foil, zinc beads, or any other form of zinc metal. In certain embodiments, a zinc salt is employed such as zinc acetate, zinc sulfate, zinc chloride, zinc bromide, zinc iodide, zinc fluoride, zinc sulfide, or zinc phosphate. The zinc may be present in a catalytic, stoichiometric, or excess amount. In certain embodiments, the zinc is present in excess (i.e., greater than 1 equivalent) relative to a compound of Formula (A) or Formula (B). In certain embodiments, between 1 and 10 equivalents of zinc are used. In certain embodiments, approximately 1.5, 2, 2.5, 3, 3.5, 4, 4.5, 5, 5.5, 6, 7, 8, 9, or 10 equivalents of zinc are present. In certain embodiments, approximately 6 equivalents of zinc are used.

In certain embodiments, the ketolization reaction is carried out in the presence of one or more reagents which help activate zinc metal in the reaction (e.g., by clearing the surface of zinc oxide). In certain embodiments, the reaction is carried out in the presence of a trialkylsilyl halide (e.g., triethylsilyl chloride (TESCl)). This reagent may be present in a catalytic, stoichiometric, or excess amount. In certain embodiments, approximately 1.5, 2, 2.5, 3, 3.5, 4, 4.5, 5, 5.5, 6, 7, 8, 9, or 10 equivalents of this reagent is present. In certain embodiments, approximately 1.5 equivalents of this reagent is present.

In certain embodiments, the Ni/Zr-mediated ketolization is carried out in the presence of one or more additional reagents (i.e., in addition to nickel, zirconium, and zinc).

In certain embodiments, the Ni/Zr-mediated ketolization reaction is carried out in the presence of a base or proton scavenger. In certain embodiments, the base is a pyridine base. In certain embodiments, the base is 2,6-di-tert-butyl pyridine. In certain embodiments, the base is 2,6-lutidine. In certain embodiments, the base is 2,6-di-tert-butyl-4-methylpyridine. In certain embodiments, the base is used in a stoichiometric or excess amount. In certain embodiments, approximately 1.5, 2, 2.5, 3, 3.5, 4, 4.5, 5, 5.5, 6, 7, 8, 9, or 10 equivalents of the base or proton scavenger is present. In certain embodiments, approximately 4 equivalents of the base or proton scavenger is employed.

In certain embodiments, the Ni/Zr-mediated ketolization described herein is carried out in a solvent. Any solvent may be used, and the scope of the method is not limited to any particular solvent or mixture of solvents. The solvent may be polar or non-polar, protic or aprotic, or a combination of solvents (e.g., co-solvents). Examples of useful organic solvents are provided herein. In certain embodiments, the ketolization reaction is carried out in 1,3-dimethyl-2-imidazolidinone (DMI). In certain embodiments, the ketolization reaction is carried out in a 1,3-dimethyl-2-imidazolidinone (DMI)/tetrahydrofuran (THF) mixture. In certain embodiments, the ketolization reaction is carried out in a 1,3-dimethyl-2-imidazolidinone (DMI)/ethyl acetate (EtOAc) mixture.

The Ni/Zr-mediated ketolization reactions described herein may be carried out at any concentration in solvent. Concentration refers to the molar concentration (mol/L) of a coupling partners (e.g., compounds of Formula (A) or (B)) in a solvent. In certain embodiments, the concentration is about 0.1 M. In certain embodiments, the concentration is approximately 0.5 M. In certain embodiments, the concentration is approximately 0.1, 0.2, 0.3, 0.4, 0.5, 0.6, 0.7, 0.8, or 0.9 M. In certain embodiments, the concentration is greater than 1 M. In certain embodiments, the concentration is less than 0.1 M.

The Ni/Zr-mediated ketolization reactions described herein can be carried out at any temperature. In certain embodiments, the reaction is carried out at around room temperature (i.e., between 18 and 24° C.). In certain embodiments, the reaction is carried out below room temperature (e.g., between 0° C. and room temperature). In certain embodiments, the reaction is carried out at above room temperature (e.g., between room temperature and 100° C.). In certain embodiments, the reaction is carried out at a temperature ranging from approximately room temperature to approximately 100° C. In certain embodiments, the reaction is carried out at a temperature ranging from approximately room temperature to approximately 50° C.

In certain embodiments, the Ni/Zr-mediated ketolization reaction is carried out in the presence of a nickel complex, a zirconium complex, and a reducing metal. In certain embodiments, the nickel complex is $NiBr_2(dtbbpy)$. In certain embodiments, the zirconium complex is $Cp_2ZrCl_2$. In certain embodiments, the reducing metal is zinc. In certain embodiments, the reaction is carried out in the presence of $NiBr_2(dtbbpy)$, $Cp_2ZrCl_2$, and zinc metal. In certain embodiments, the reaction is carried out in a polar solvent such as DMI (1,3-dimethyl-2-imidazolidinone). In certain embodiments, the reaction is carried out at around room temperature. In certain embodiments, the reaction is carried out at a temperature ranging from approximately room temperature to approximately 100° C. In certain embodiments, the reaction is carried out at a temperature ranging from approximately room temperature to approximately 50° C. For example, in certain embodiments, the coupling is carried out under the following conditions: 5 mol % $NiBr_2$(dtbbpy), 1.0 equivalent $Cp_2ZrCl_2$, excess zinc metal, in DMI at room temperature.

In certain embodiments, the reaction is carried out in the presence of $NiBr_2$(dtbbpy), $Cp_2ZrCl_2$, zinc metal, and a base or proton scavenger. In certain embodiments, the reaction is carried out in the presence of $NiBr_2$(dtbbpy), $Cp_2ZrCl_2$, zinc metal, and $(t-Bu)_2(Me)Py$. In certain embodiments, the reaction is carried out in a mixture of DMI and EtOAc (ethyl acetate). In certain embodiments, the reaction is carried out at around room temperature. In certain embodiments, the reaction is carried out at a temperature ranging from approximately room temperature to approximately 100° C. In certain embodiments, the reaction is carried out at a temperature ranging from approximately room temperature to approximately 50° C. For example, in certain embodiments, the coupling is carried out under the following conditions: 30 mol % $NiBr_2$(dtbbpy), 3.0 equivalents $Cp_2ZrCl_2$, 6.0 equivalents zinc metal, and 4.0 equivalents $(t-Bu)_2(Me)Py$, in DMI-EtOAc at room temperature.

Synthesis of Halichondrins and Analogs

The Ni/Zr-mediated ketolization reactions provided herein can be applied to the synthesis of halichondrins (e.g., halichondrin A, B, C; homohalichondrin A, B, C, norhalichondrin A, B, C) and analogs thereof. In certain embodiments, methods are useful in the synthesis of compounds of Formula (H3-A), such as Compound (1). In certain embodiments, the methods comprise the steps of: (1) coupling a "left half" building block with a "right half" building block via a Ni/Zr-mediated ketolization reaction provided herein; followed by (2) cyclizing the resulting coupling product (e.g., acid-mediated cyclization); optionally, followed by any necessary synthetic transformations to arrive at a desired product.

Synthesis of Halichondrins

The Ni/Zr-mediated ketolization reactions provided herein can be applied to the preparation of halichondrins (e.g., halichondrin A, B, C) and analogs thereof. For example, as shown in Scheme 2A, coupling of a left half of Formula (L-2-14) with a right half of Formula (R-2-I) via a Ni/Zr-mediated ketolization yields a ketone of Formula (H-2-II), cyclization of which provides a compound of Formula (H-2-I), which is a halichondrin or an analog thereof, or an intermediate thereto.

Scheme 2A

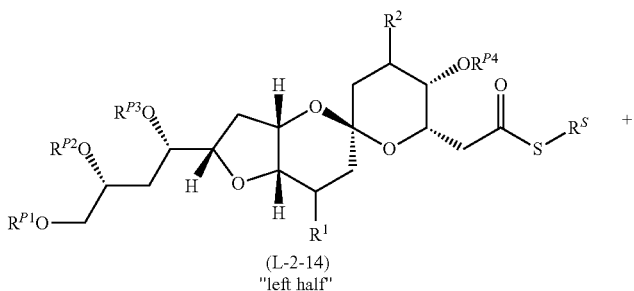

(L-2-14)
"left half"

-continued
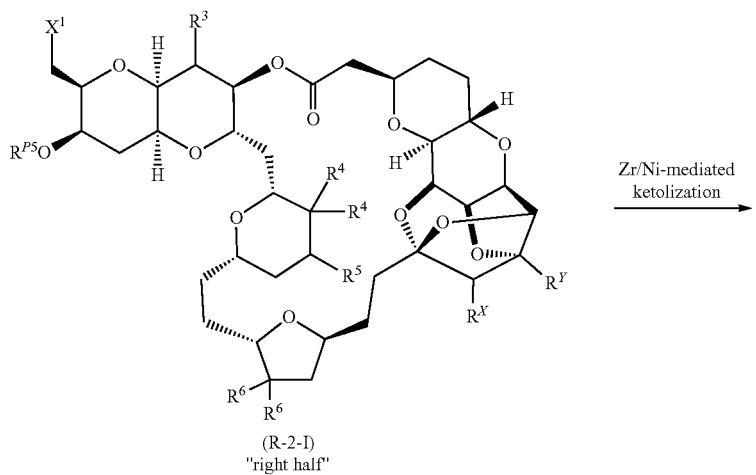
(R-2-I)
"right half"
→ Zr/Ni-mediated ketolization
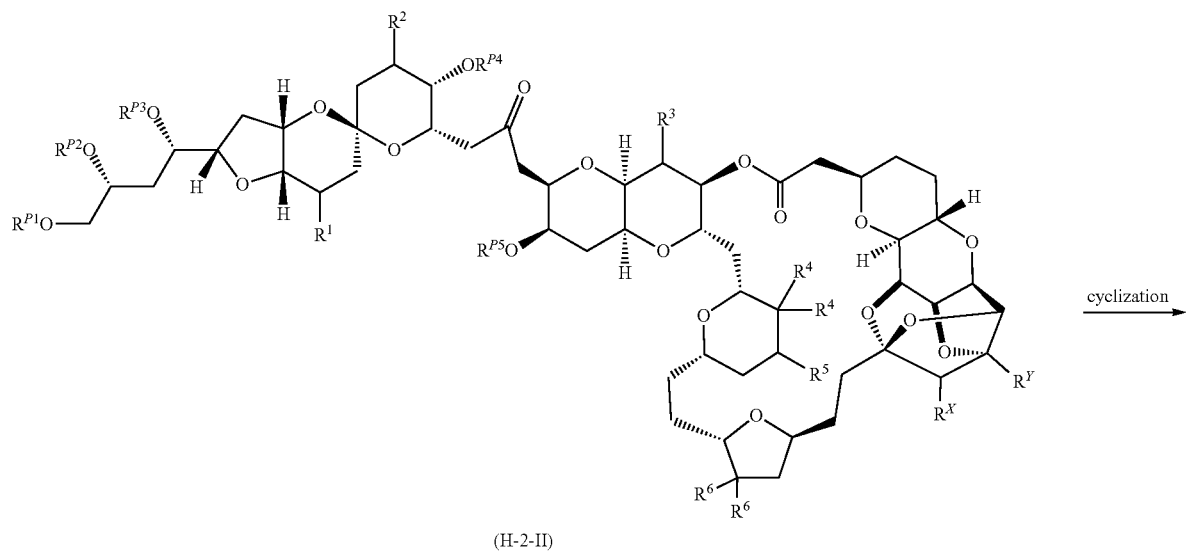
(H-2-II)
→ cyclization
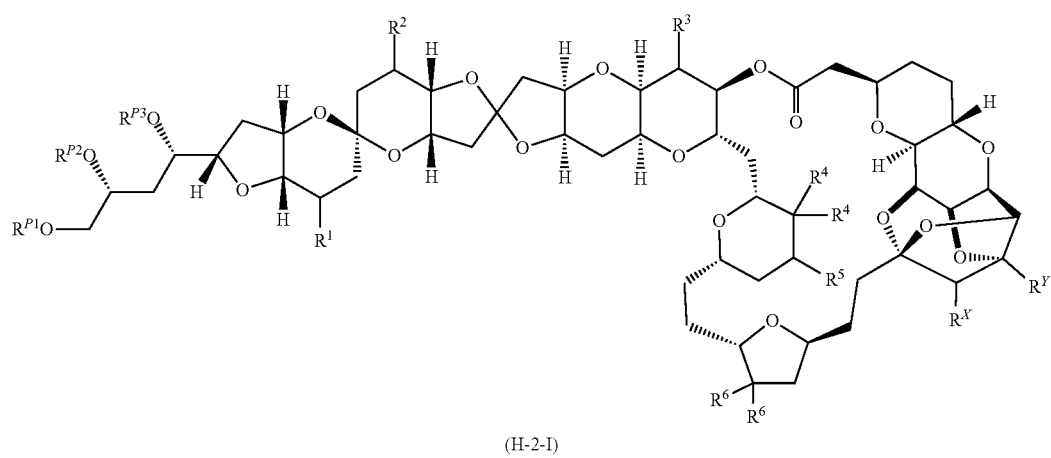
(H-2-I)

Provided herein is a method of preparing a compound of Formula (H-2-I):

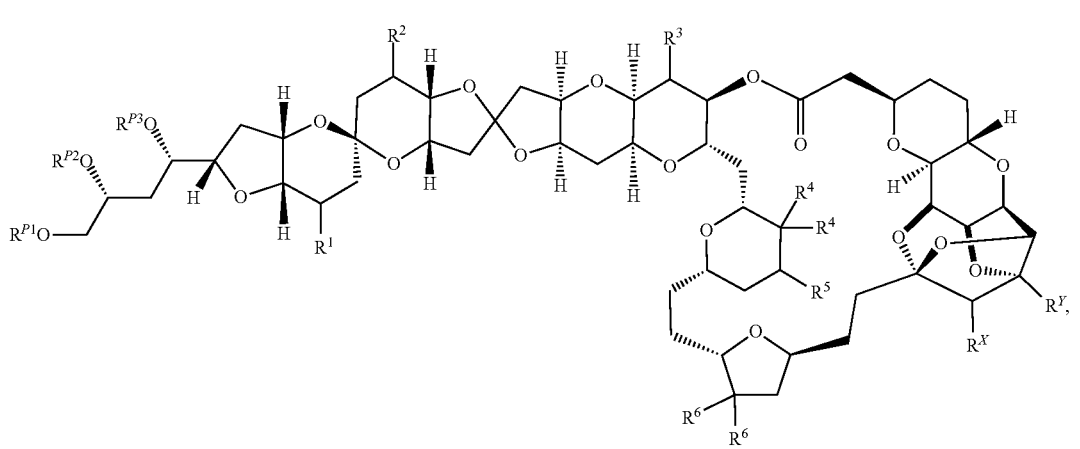

(H-2-I)

or a salt thereof, the method comprising cyclizing a compound of Formula (H-2-II):

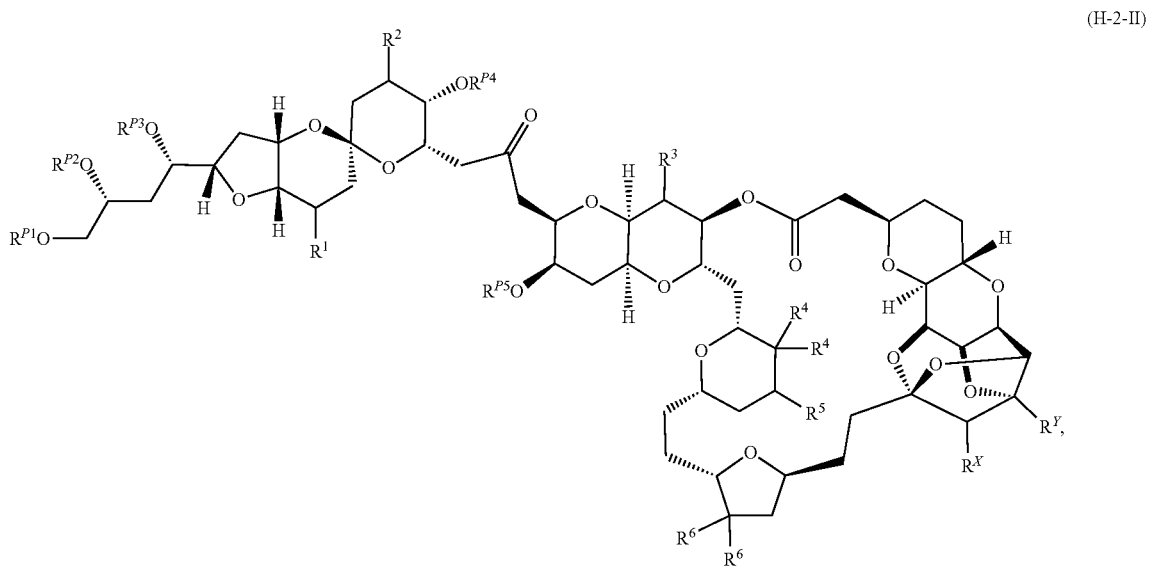

(H-2-II)

or a salt thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

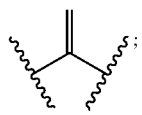 [SMILES: *C(*)=C]

each instance of $R^6$ is independently hydrogen, halogen, optionally substituted alkyl, or two $R^6$ groups are taken together to form:

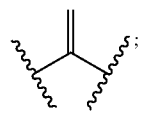

$R^{P1}$, $R^{P2}$, $R^{P3}$, $R^{P4}$, and $R^{P5}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the step of cyclizing a compound of Formula (H-2-II), or a salt thereof, is carried out in the presence of an acid. The acid may be a Lewis acid or a Brønsted acid. In certain embodiments, the acid is a Brønsted acid. In certain embodiments, the acid is a sulfonic acid. In certain embodiments, the acid is a salt of a sulfonic acid. In certain embodiments, the acid is a pyridinium salt. In certain embodiments, the acid is pyridinium p-toluenesulfonate (PPTS). In certain embodiments, the acid is present in a catalytic amount. In certain embodiments, the acid is present in a stoichiometric (e.g., approximately 1 equivalent) or excess amount (e.g., greater than 1 equivalent). In certain embodiments, the acid is present in an excess amount (e.g., about 5 equivalents).

In certain embodiments, the step of cyclizing is carried out in the presence of PPTS. In certain embodiments, the step is carried out in a solvent such as $CH_2Cl_2$. In certain embodiments, the reaction is carried out at a temperature ranging from approximately 0° C. to approximately 50° C. In certain embodiments, the reaction is carried out at around room temperature. In certain embodiments, the reaction is carried out at around 20° C. For example, in certain embodiments, the step of cyclizing is carried out under the following conditions: 5 equivalents of PPTS in $CH_2Cl_2$ at around 20° C. (e.g., for 2 hours).

In certain embodiments, $R^{P1}$, $R^{P2}$, and $R^{P3}$ are silyl protecting groups, and $R^{P4}$ and $R^{P5}$ are hydrogen. In certain embodiments, $R^{P1}$ and $R^{P2}$ are TBS, $R^{P3}$ is TES, and $R^{P4}$ and $R^{P5}$ are hydrogen.

In certain embodiments, the compound of Formula (H-2-II) is of Formula (H-2-IIA):

(H-2-IIA)

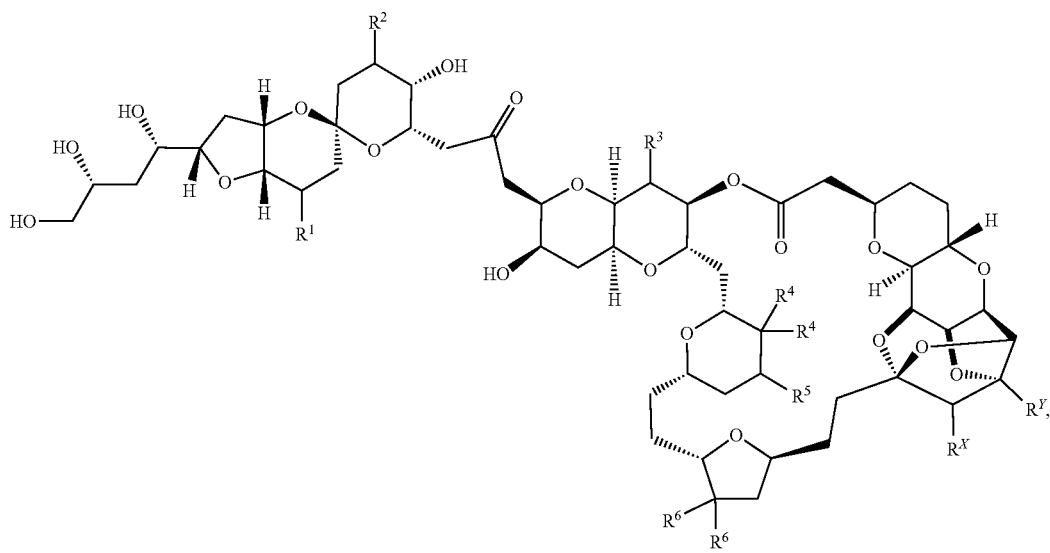

or a salt thereof.

Provided herein is a method of preparing a compound of Formula (H-2-II):

(H-2-II)

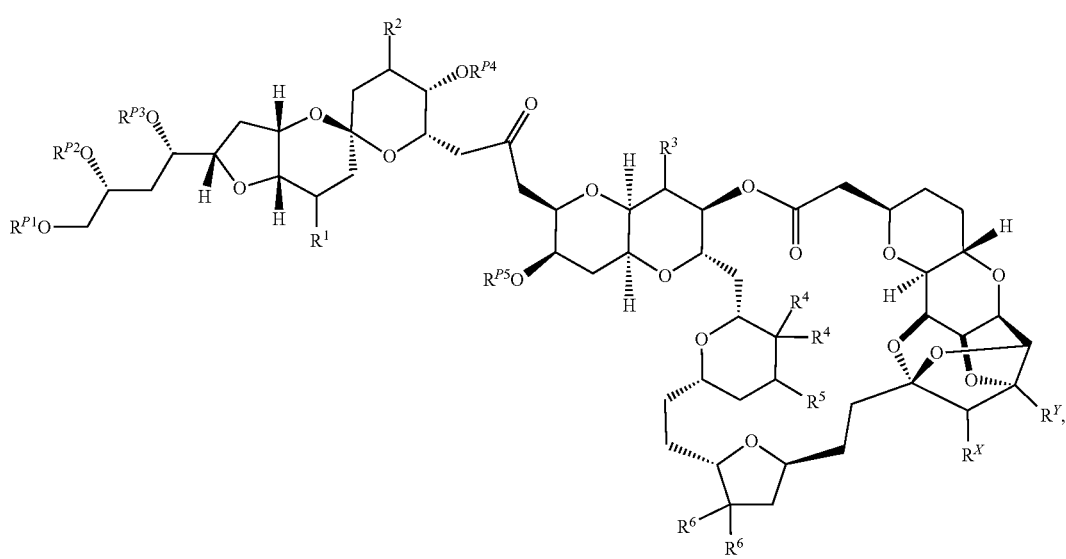

or a salt thereof, the method comprising coupling a compound of Formula (L-2-14):

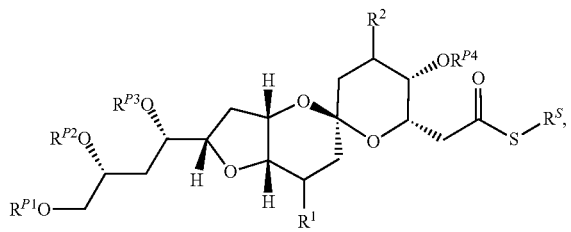
(L-2-14)

or a salt thereof, with a compound of Formula (R-2-I):

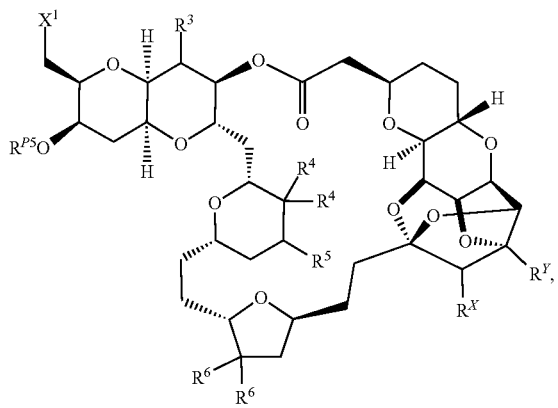
(R-2-I)

or a salt thereof, wherein:

$R^S$ is optionally substituted alkyl, optionally substituted carbocyclyl, optionally substituted aryl, optionally substituted heterocyclyl, or optionally substituted heteroaryl;

$X^1$ is halogen or a leaving group;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

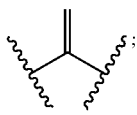 [SMILES: *C(*)=C]

each instance of $R^6$ is independently hydrogen, halogen, or optionally substituted alkyl, or two $R^6$ groups are taken together to form:

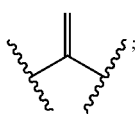

$R^{P1}$, $R^{P2}$, $R^{P3}$, $R^{P4}$, and $R^{P5}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the step of coupling to provide a compound of Formula (H-2-II) is a Ni/Zr-mediated ketolization provided herein. Any reagents or conditions provided herein for the Ni/Zr-mediated ketolization may be used in the coupling. In certain embodiments, the Ni/Zr-mediated ketolization reaction is carried out in the presence of a nickel complex, a zirconium complex, and a reducing metal. The reaction may also be carried out in the presence of one or more additional reagents, such a base or proton scavenger. In certain embodiments, the nickel complex is NiBr$_2$(dtbbpy). In certain embodiments, the zirconium complex is Cp$_2$ZrCl$_2$. In certain embodiments, the reducing metal is zinc. In certain embodiments, the additional base or proton scavenger is (t-Bu)$_2$(Me)Py. In certain embodiments, the reaction is carried out in the presence of NiBr$_2$(dtbbpy), Cp$_2$ZrCl$_2$, and zinc metal. In certain embodiments, the reaction is carried out in the presence of NiBr$_2$(dtbbpy), Cp$_2$ZrCl$_2$, and zinc metal. In certain embodiments, the reaction is carried out in the presence of NiBr$_2$(dtbbpy), Cp$_2$ZrCl$_2$, zinc metal, and (t-Bu)$_2$(Me)Py. In certain embodiments, the reaction is carried out in a polar solvent such as DMI (1,3-dimethyl-2-imidazolidinone). In certain embodiments, the reaction is carried out in a mixture of DMI and EtOAc (ethyl acetate). In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature.

For example, in certain embodiments, the coupling is carried out under the following conditions: 30 mol % NiBr$_2$(dtbbpy), 3.0 equivalents Cp$_2$ZrCl$_2$, 6.0 equivalents zinc metal, and 4.0 equivalents (t-Bu)$_2$(Me)Py, in DMI-EtOAc at room temperature.

In certain embodiments, $R^{P1}$, $R^{P2}$, $R^{P3}$, $R^{P4}$ and $R^{P5}$ are silyl protecting groups. In certain embodiments, $R^{P1}$ and $R^{P2}$ are TBS; and $R^{P3}$, $R^{P4}$ and $R^{P5}$ are TES.

In certain embodiments, the method of preparing a compound of Formula (H-2-II) further comprises one or more steps of deprotecting one or more oxygen atoms of the compound of Formula (H-2-II) (e.g., to yield a compound of Formula (H-2-IIA), or a salt thereof). In certain embodiments, the resulting compound or salt thereof can then be used in the cyclization step to yield a compound of Formula (H-2-I), or a salt thereof. In certain embodiments, the step of deprotecting is carried out in the presence of a fluoride source (e.g., when the one or more oxygen atoms are protected with silyl groups).

Examples of fluoride sources useful in the invention include, but are not limited to, metal fluorides (e.g., sodium fluoride, potassium fluoride, cesium fluoride, silver fluoride)

and tetraalkylammonium fluorides (e.g., tetramethylammonium fluoride, tetraethylammonium fluoride, tetrabutylammonium fluoride). In certain embodiments, the fluoride source is a tetraalkylammonium fluoride. In certain embodiments, the fluoride source is tetrabutylammonium fluoride (TBAF). In certain embodiments, hydrogen fluoride (HF) is used. In certain embodiments, HF.pyridine is used as the HF source. Other examples of protecting groups useful in the present invention, and reagents useful in protection/deprotection reactions can be found in the art, e.g., in *Protecting Groups in Organic Synthesis*, T. W. Greene and P. G. M. Wuts, 3$^{rd}$ edition, John Wiley & Sons, 1999, incorporated herein by reference.

Once a compound of Formula (H-2-I), or salt thereof, is obtained, the method may comprise one or more additional steps (e.g., deprotection, protection, substitution, addition, elimination) to yield a desired compound (e.g., halichondrin A, B, C, or an analog thereof).

Synthesis of Homohalichondrins

The Ni/Zr-mediated ketolization reactions provided herein can be applied to the preparation of homohalichondrins (e.g., homohalichondrin A, B, C), and analogs thereof. For example, as shown in Scheme 2B, coupling of a left half of Formula (L-2-16) with a right half of Formula (R-2-I) via a Ni/Zr-mediated ketolization yields a ketone of Formula (HH-2-II), cyclization of which provides a compound of Formula (HH-2-I), which is a homohalichondrin natural product or an analog thereof, or an intermediate thereto.

Scheme 2B

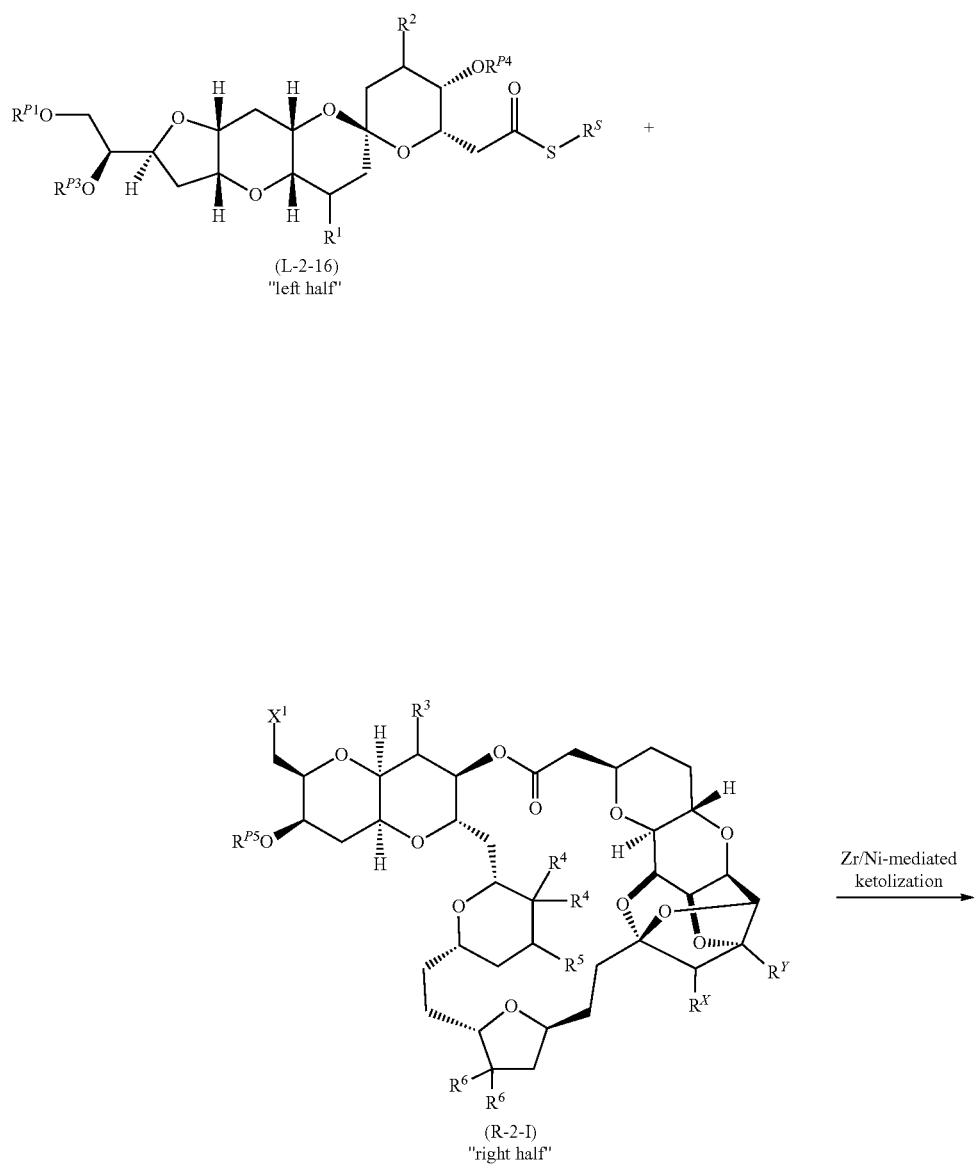

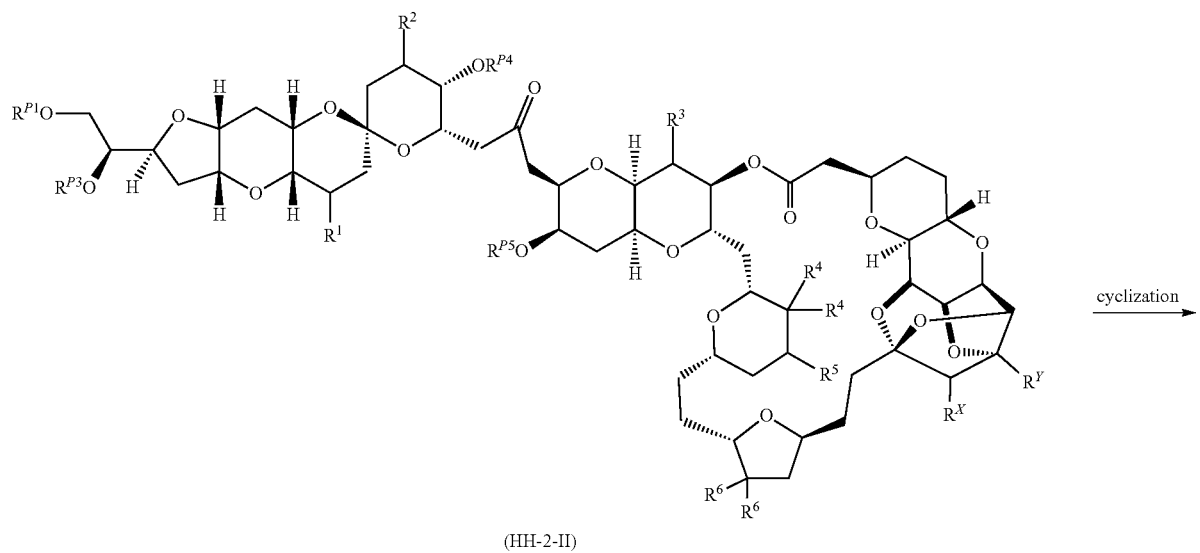
(HH-2-II)
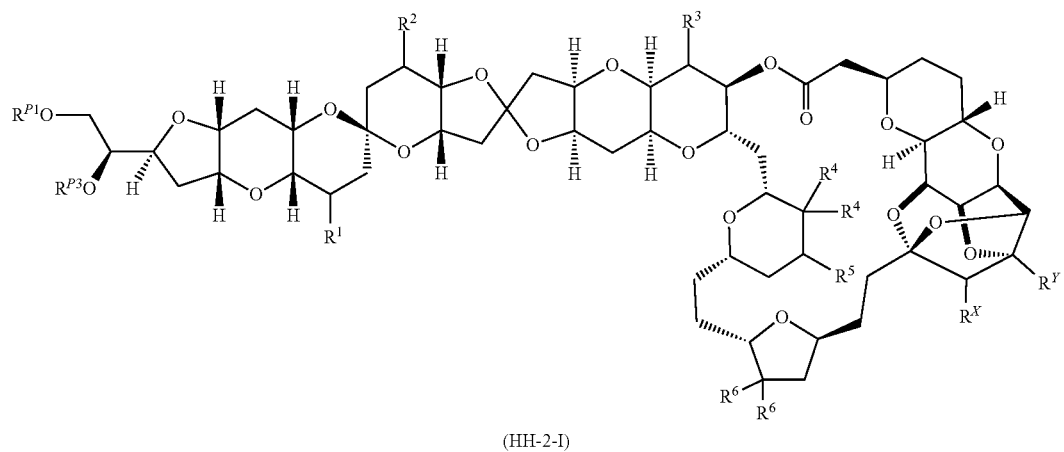
(HH-2-I)
Provided herein is a method of preparing a compound of Formula (HH-2-I):
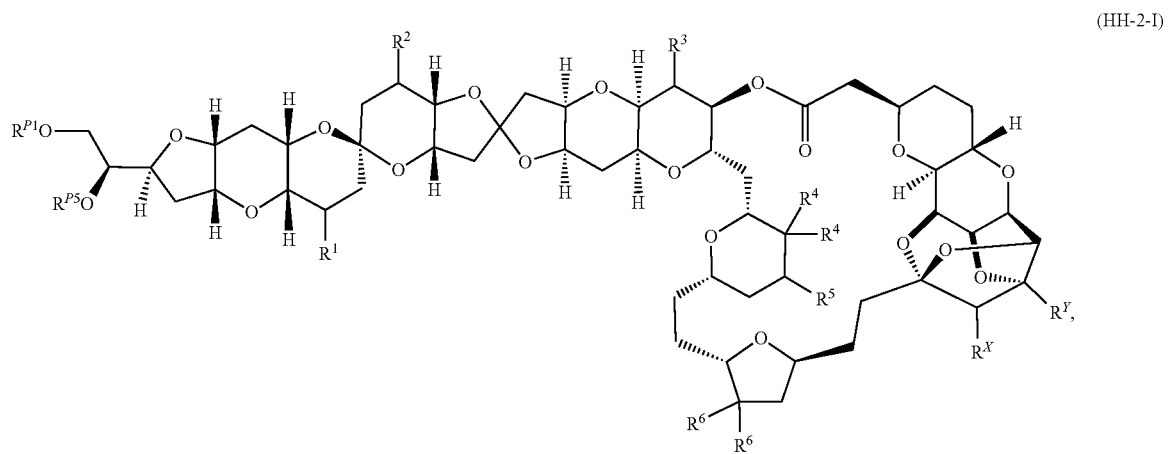
(HH-2-I)

or a salt thereof, the method comprising cyclizing a compound of Formula (HH-2-II):

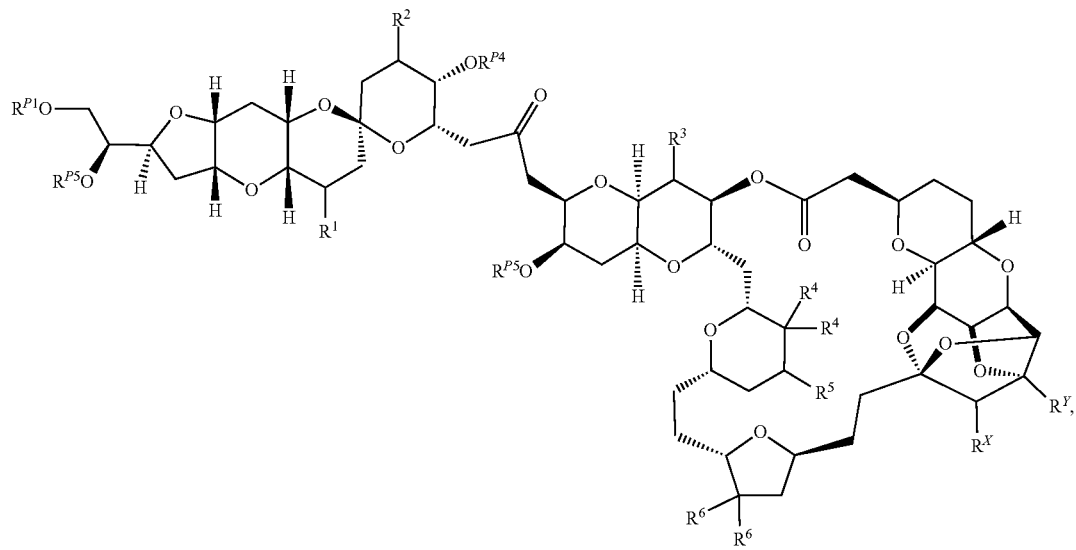

(HH-2-II)

or a salt thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

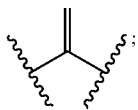 [SMILES: *C(*)=C]

each instance of $R^6$ is independently hydrogen, halogen, or optionally substituted alkyl, or two $R^6$ groups are taken together to form:

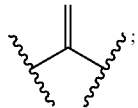

$R^{P1}$, $R^{P3}$, $R^{P4}$, and $R^{P5}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group;

$R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the step of cyclizing a compound of Formula (HH-2-II), or a salt thereof, is carried out in the presence of an acid. The acid may be a Lewis acid or a Brønsted acid. In certain embodiments, the acid is a Brønsted acid. In certain embodiments, the acid is a sulfonic acid. In certain embodiments, the acid is a salt of a sulfonic acid. In certain embodiments, the acid is a pyridinium salt. In certain embodiments, the acid is pyridinium p-toluenesulfonate (PPTS). In certain embodiments, the acid is present in a catalytic amount. In certain embodiments, the acid is present in a stoichiometric (e.g., approximately 1 equivalent) or excess amount (e.g., greater than 1 equivalent). In certain embodiments, the acid is present in an excess amount (e.g., about 5 equivalents).

In certain embodiments, the step of cyclizing is carried out in the presence of PPTS. In certain embodiments, the step is carried out in a solvent such as $CH_2Cl_2$. In certain embodiments, the reaction is carried out at a temperature ranging from approximately 0° C. to approximately 50° C. In certain embodiments, the reaction is carried out at around room temperature. In certain embodiments, the reaction is carried out at around 20° C. For example, in certain embodiments, the step of cyclizing is carried out under the following conditions: 5 equivalents of PPTS in $CH_2Cl_2$ at around 20° C. (e.g., for 2 hours).

In certain embodiments, $R^{P1}$ and $R^{P2}$ are silyl protecting groups; and $R^{P4}$ and $R^{P5}$ are hydrogen. In certain embodiments, $R^{P1}$ is TBS; $R^{P2}$ is TES; and $R^{P4}$ and $R^{P5}$ are hydrogen.

In certain embodiments, the compound of Formula (HH-2-II) is of Formula (HH-2-IIA):
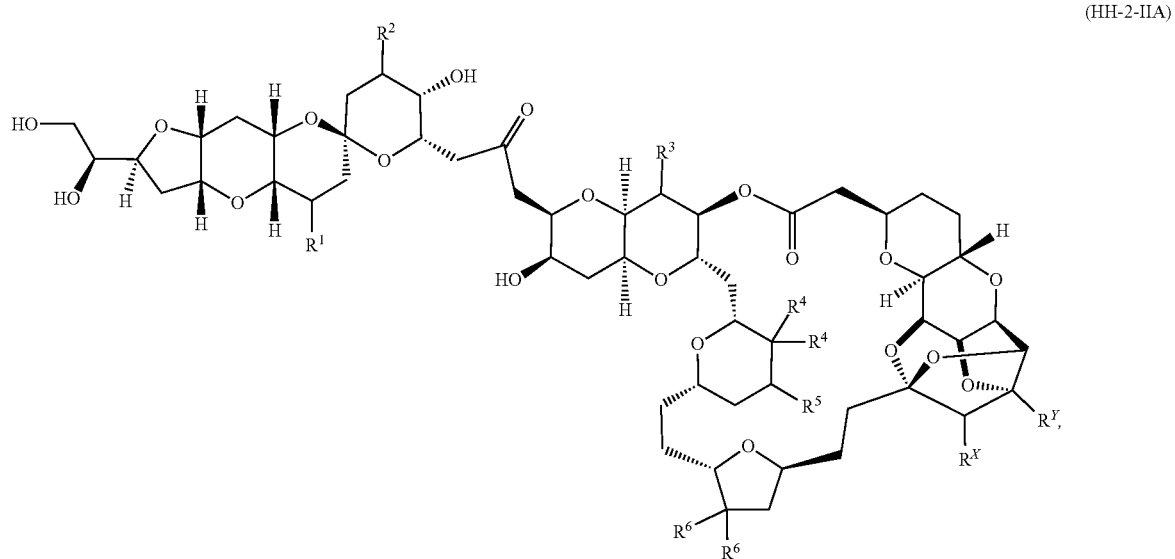
(HH-2-IIA)
or a salt thereof.
Provided herein is a method of preparing a compound of Formula (HH-2-II):
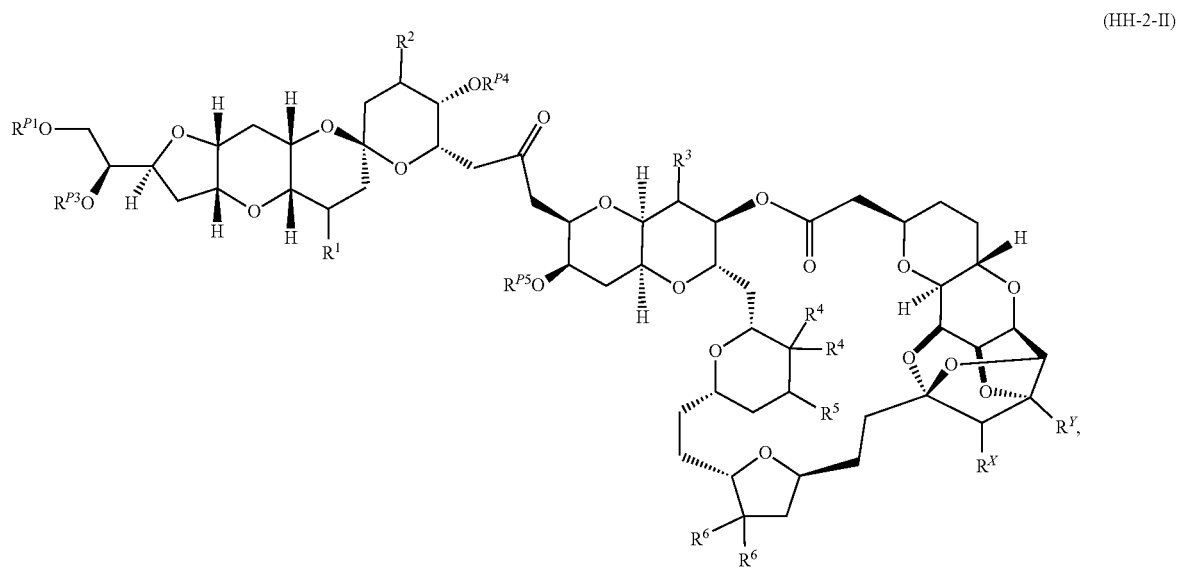
(HH-2-II)

or a salt thereof, the method comprising coupling a compound of Formula (L-2-16):

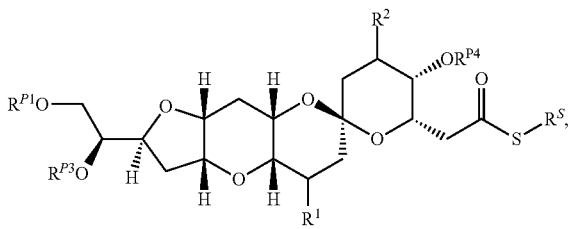

(L-2-16)

or a salt thereof, with a compound of Formula (R-2-I):

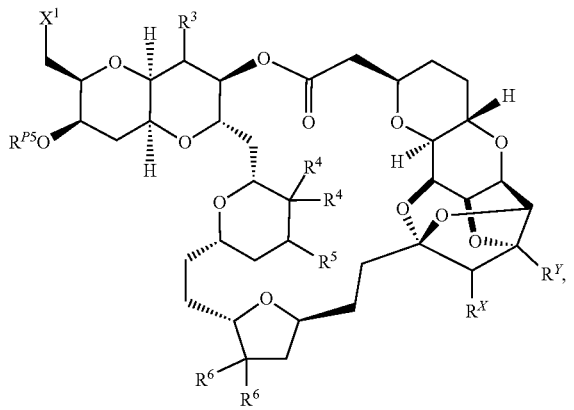

(R-2-I)

or a salt thereof, wherein:

$R^S$ is optionally substituted alkyl, optionally substituted carbocyclyl, optionally substituted aryl, optionally substituted heterocyclyl, or optionally substituted heteroaryl;

$X^1$ is halogen or a leaving group;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

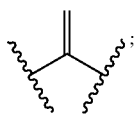 [SMILES: *C(*)=C]

each instance of $R^6$ is independently hydrogen, halogen, or optionally substituted alkyl, or two $R^6$ groups are taken together to form:

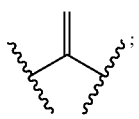

$R^{P1}$, $R^{P3}$, $R^{P4}$, and $R^{P5}$ are each independently hydrogen, optionally substituted alkyl, optionally substituted acyl, or an oxygen protecting group;

$R^X$ is hydrogen or $—OR^{Xa}$, wherein $R^{Xa}$ is hydrogen, optionally substituted alkyl, optionally substituted acyl, or an oxygen protecting group; and $R^Y$ is hydrogen or $—OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the step of coupling to provide a compound of Formula (HH-2-II) is a Ni/Zr-mediated ketolization as provided herein. Any reagents or conditions provided herein for the Ni/Zr-mediated ketolization may be used in the coupling. In certain embodiments, the Ni/Zr-mediated ketolization reaction is carried out in the presence of a nickel complex, a zirconium complex, and a reducing metal. The reaction may also be carried out in the presence of one or more additional reagents, such a base or proton scavenger. In certain embodiments, the nickel complex is $NiBr_2(dtbbpy)$. In certain embodiments, the zirconium complex is $Cp_2ZrCl_2$. In certain embodiments, the reducing metal is zinc. In certain embodiments, the additional base or proton scavenger is $(t-Bu)_2(Me)Py$. In certain embodiments, the reaction is carried out in the presence of $NiBr_2(dtbbpy)$, $Cp_2ZrCl_2$, and zinc metal. In certain embodiments, the reaction is carried out in the presence of $NiBr_2(dtbbpy)$, $Cp_2ZrCl_2$, and zinc metal. In certain embodiments, the reaction is carried out in the presence of $NiBr_2(dtbbpy)$, $Cp_2ZrCl_2$, zinc metal, and $(t-Bu)_2(Me)Py$. In certain embodiments, the reaction is carried out in a polar solvent such as DMI (1,3-dimethyl-2-imidazolidinone). In certain embodiments, the reaction is carried out in a mixture of DMI and EtOAc (ethyl acetate). In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature.

For example, in certain embodiments, the coupling is carried out under the following conditions: 30 mol % $NiBr_2(dtbbpy)$, 3.0 equivalents $Cp_2ZrCl_2$, 6.0 equivalents zinc metal, and 4.0 equivalents $(t-Bu)_2(Me)Py$, in DMI-EtOAc at room temperature.

In certain embodiments, $R^{P1}$, $R^{P2}$, $R^{P3}$, $R^{P4}$ and $R^{P5}$ are silyl protecting groups. In certain embodiments, $R^{P1}$ and $R^{P2}$ are TBS; and $R^{P3}$, $R^{P4}$ and $R^{P5}$ are TES.

In certain embodiments, the method of preparing a compound of Formula (HH-2-II) further comprises one or more steps of deprotecting one or more oxygen atoms of the compound of Formula (HH-2-II) (e.g., to yield a compound of Formula (HH-2-IIA), or a salt thereof). In certain embodiments, the resulting compound, or salt thereof, is then cyclized to yield a compound of Formula (HH-2-I), or a salt thereof. In certain embodiments, a step of deprotecting is carried out in the presence of a fluoride source (e.g., when one or more oxygen atoms are protected with silyl groups). Examples of fluoride sources are provided herein.

Once a compound of Formula (HH-2-I), or salt thereof, is obtained, one or more additional steps (e.g., deprotection, protection, substitution, addition, elimination) may be performed to yield a desired compound (e.g., homohalichondrin A, B, C, or an analog thereof, or intermediate thereto).

Synthesis of Norhalichondrins

The Ni/Zr-mediated ketolization reactions provided herein can be applied to the preparation of norhalichondrins (e.g., norhalichondrin A, B, C) and analogs thereof. For example, as shown in Scheme 2C, coupling of a left half of Formula (L-2-15) with a right half of Formula (R-2-I) via a Ni/Zr-mediated ketolization yields a ketone of Formula (NH-2-II), cyclization of which provides a compound of Formula (NH-2-I), which is a norhalichondrin or an analog thereof, or intermediate thereto.

Scheme 2C

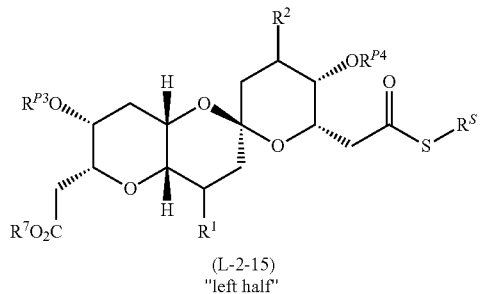

(L-2-15)
"left half"

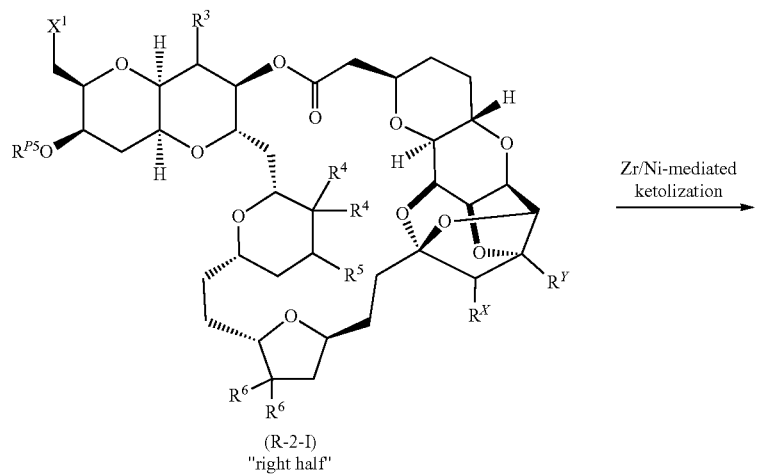

(R-2-I)
"right half"

Zr/Ni-mediated ketolization

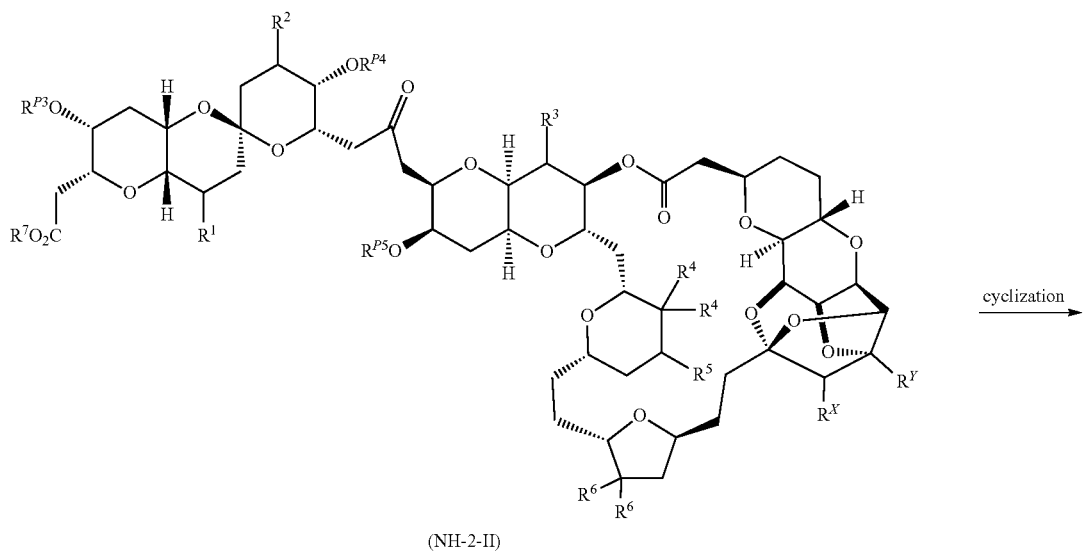

(NH-2-II)

cyclization

-continued
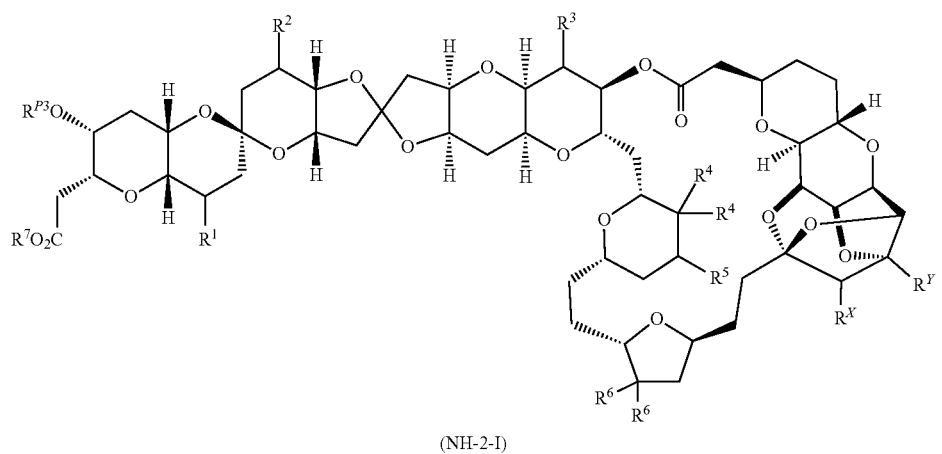
(NH-2-I)
Provided herein is a method of preparing a compound of Formula (NH-2-I):
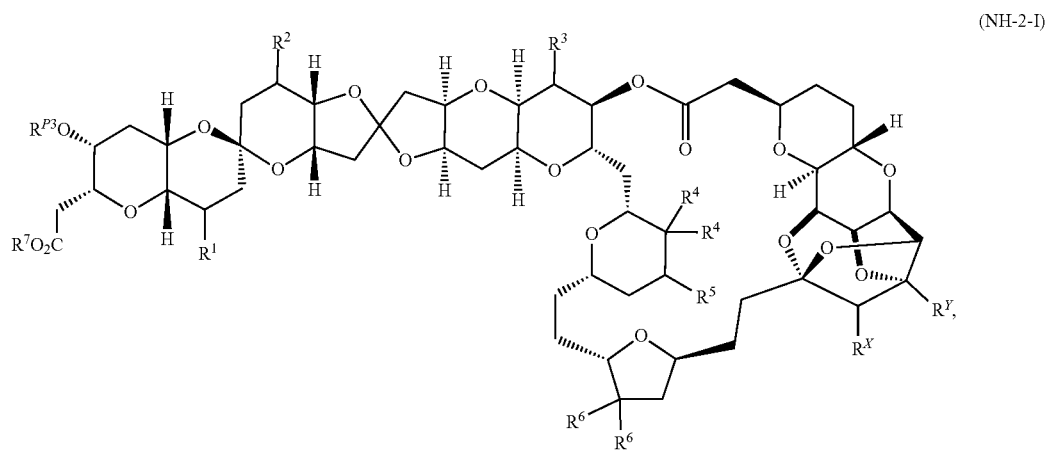
(NH-2-I)

or a salt thereof, the method comprising cyclizing a compound of Formula (NH-2-II):

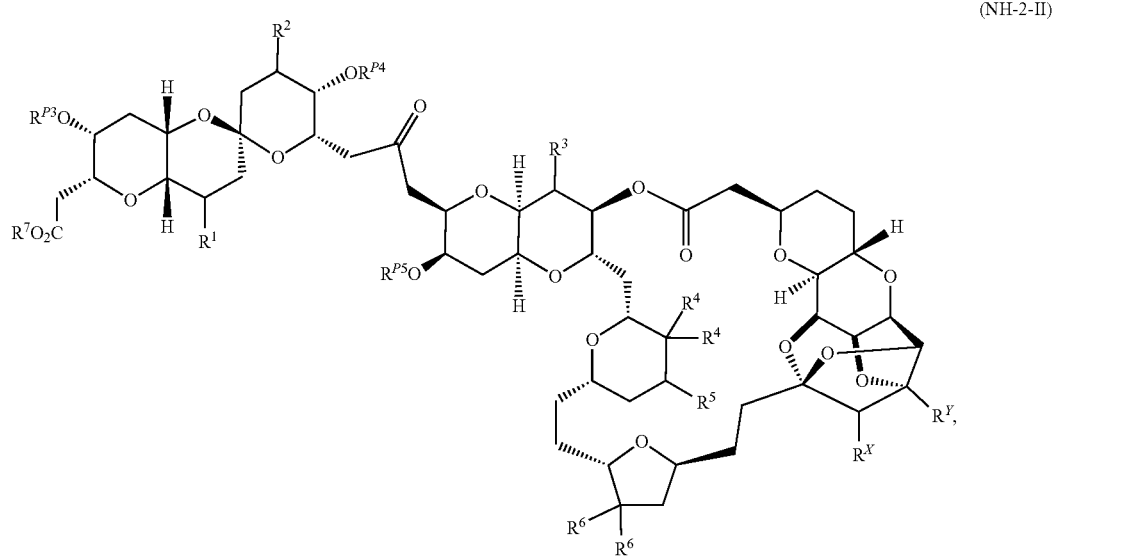

(NH-2-II)

or a salt thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

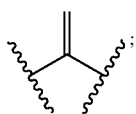 [SMILES: *C(*)=C]

each instance of $R^6$ is independently hydrogen, halogen, or optionally substituted alkyl, or two $R^6$ groups are taken together to form:

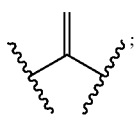

$R^{P3}$, $R^{P4}$, and $R^{P5}$ are each independently hydrogen, optionally substituted alkyl, optionally substituted acyl, or an oxygen protecting group;

$R^7$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the step of cyclizing a compound of Formula (NH-2-II), or a salt thereof, is carried out in the presence of an acid. The acid may be a Lewis acid or a Brønsted acid. In certain embodiments, the acid is a Brønsted acid. In certain embodiments, the acid is a sulfonic acid. In certain embodiments, the acid is a salt of a sulfonic acid. In certain embodiments, the acid is a pyridinium salt. In certain embodiments, the acid is pyridinium p-toluenesulfonate (PPTS). In certain embodiments, the acid is present in a catalytic amount. In certain embodiments, the acid is present in a stoichiometric (e.g., approximately 1 equivalent) or excess amount (e.g., greater than 1 equivalent). In certain embodiments, the acid is present in an excess amount (e.g., about 5 equivalents).

In certain embodiments, the step of cyclizing is carried out in the presence of PPTS. In certain embodiments, the step is carried out in a solvent such as $CH_2Cl_2$. In certain embodiments, the reaction is carried out at a temperature ranging from approximately 0° C. to approximately 50° C. In certain embodiments, the reaction is carried out at around room temperature. In certain embodiments, the reaction is carried out at around 20° C. For example, in certain embodiments, the step of cyclizing is carried out under the following conditions: 5 equivalents of PPTS in $CH_2Cl_2$ at around 20° C. (e.g., for 2 hours).

In certain embodiments, $R^{P3}$ is a silyl protecting group; $R^7$ is optionally substituted alkyl; and $R^{P4}$ and $R^{P5}$ are hydrogen. In certain embodiments, $R^{P3}$ is TES; $R^7$ is methyl; and $R^{P4}$ and $R^{P5}$ are hydrogen.

In certain embodiments, the compound of Formula (NH-2-II) is of Formula (NH-2-IIA):
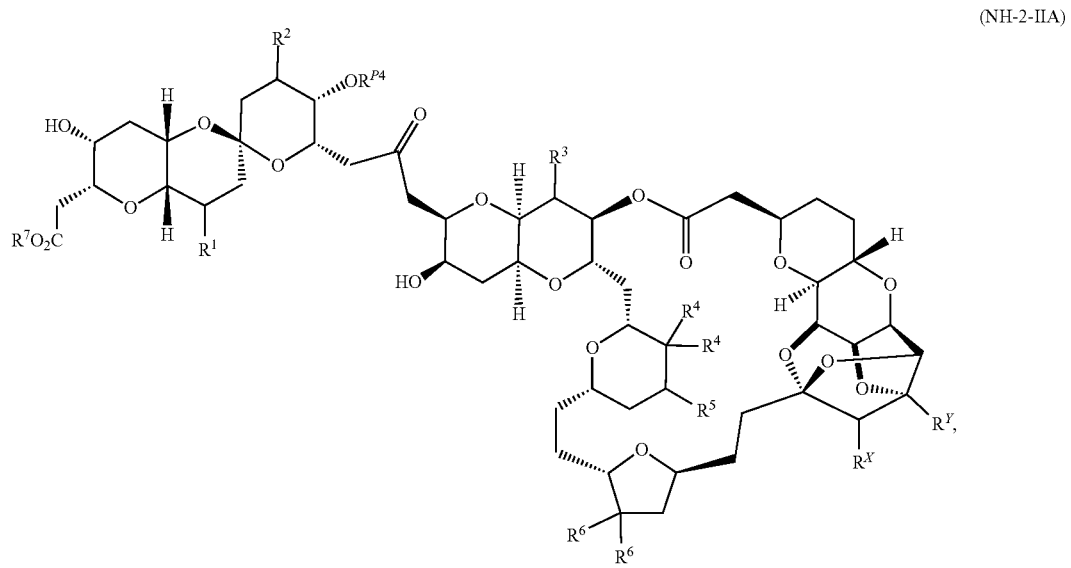
(NH-2-IIA)
or a salt thereof.
Provided herein is a method of preparing a compound of Formula (NH-2-II):
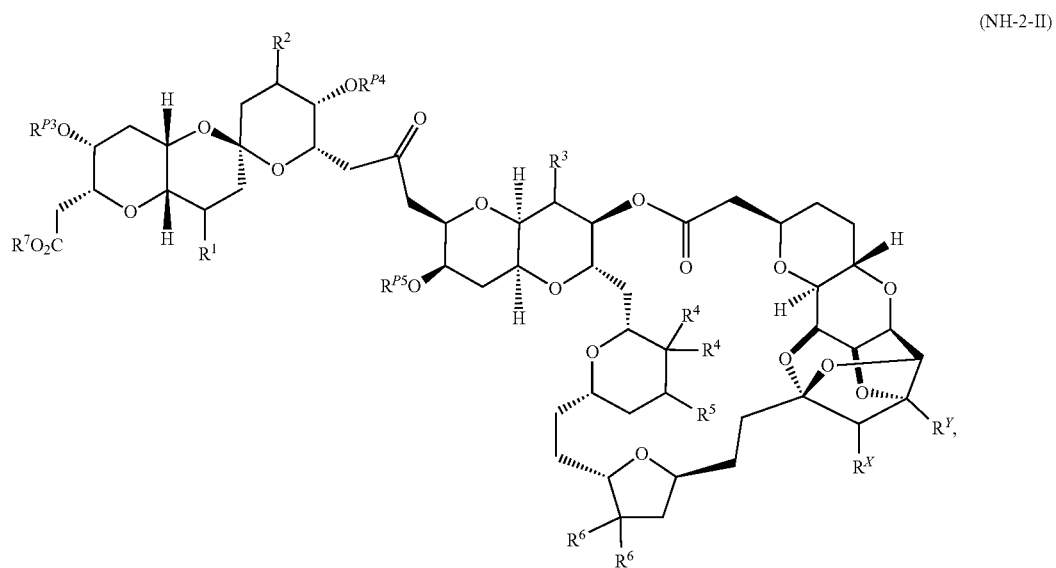
(NH-2-II)

or a salt thereof, the method comprising coupling a compound of Formula (L-2-15):

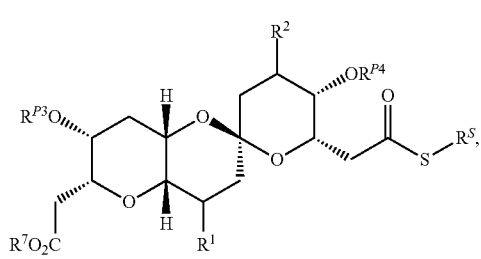

(L-2-15)

or a salt thereof, with a compound of Formula (R-2-I):

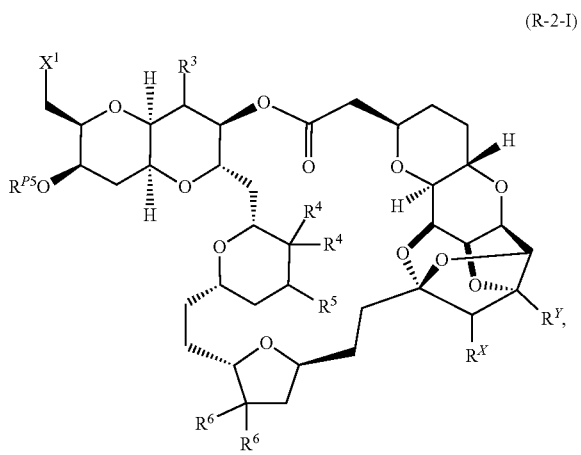

(R-2-I)

or a salt thereof, wherein:

$R^S$ is optionally substituted alkyl, optionally substituted carbocyclyl, optionally substituted aryl, optionally substituted heterocyclyl, or optionally substituted heteroaryl;

$X^1$ is halogen or a leaving group;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

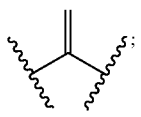 [SMILES: *C(*)=C]

each instance of $R^6$ is independently hydrogen, halogen, or optionally substituted alkyl, or two $R^6$ groups are taken together to form:

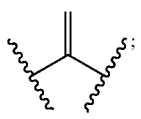 [SMILES: *C(*)=C]

$R^{P3}$, $R^{P4}$, and $R^{P5}$ are each independently hydrogen, optionally substituted alkyl, optionally substituted acyl, or an oxygen protecting group;

$R^7$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the step of coupling to provide a compound of Formula (NH-2-II) is a Ni/Zr-mediated ketolization provided herein. Any reagents or conditions provided herein for the Ni/Zr-mediated ketolization may be used in the coupling. In certain embodiments, the Ni/Zr-mediated ketolization reaction is carried out in the presence of a nickel complex, a zirconium complex, and a reducing metal. The reaction may also be carried out in the presence of one or more additional reagents, such a base or proton scavenger. In certain embodiments, the nickel complex is NiBr$_2$(dtbbpy). In certain embodiments, the zirconium complex is Cp$_2$ZrCl$_2$. In certain embodiments, the reducing metal is zinc. In certain embodiments, the additional base or proton scavenger is (t-Bu)$_2$(Me)Py. In certain embodiments, the reaction is carried out in the presence of NiBr$_2$(dtbbpy), Cp$_2$ZrCl$_2$, and zinc metal. In certain embodiments, the reaction is carried out in the presence of NiBr$_2$(dtbbpy), Cp$_2$ZrCl$_2$, and zinc metal. In certain embodiments, the reaction is carried out in the presence of NiBr$_2$(dtbbpy), Cp$_2$ZrCl$_2$, zinc metal, and (t-Bu)$_2$(Me)Py. In certain embodiments, the reaction is carried out in a polar solvent such as DMI (1,3-dimethyl-2-imidazolidinone). In certain embodiments, the reaction is carried out in a mixture of DMI and EtOAc (ethyl acetate). In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature.

For example, in certain embodiments, the coupling is carried out under the following conditions: 30 mol % NiBr$_2$(dtbbpy), 3.0 equivalents Cp$_2$ZrCl$_2$, 6.0 equivalents zinc metal, and 4.0 equivalents (t-Bu)$_2$(Me)Py, in DMI-EtOAc at room temperature.

In certain embodiments, $R^{P3}$ is a silyl protecting group; $R^7$ is optionally substituted alkyl; and $R^{P4}$ and $R^{P5}$ are silyl protecting groups. In certain embodiments, $R^{P3}$ is TES; $R^7$ is methyl; and $R^{P4}$ and $R^{P5}$ are TES.

In certain embodiments, the method of preparing a compound of Formula (NH-2-II) further comprises one or more steps of deprotecting one or more oxygen atoms of the compound of Formula (NH-2-II) (e.g., to yield a compound of Formula (NH-2-IIA), or a salt thereof). In certain embodiments, the resulting compound, or salt thereof, is then cyclized to yield a compound of Formula (NH-2-I), or a salt thereof. In certain embodiments, a step of deprotecting is carried out in the presence of a fluoride source (e.g., when the one or more oxygen atoms are protected with silyl groups). Examples of fluoride sources are provided herein.

Once a compound of Formula (NH-2-I), or salt thereof, is obtained, the method may comprise one or more additional steps (e.g., deprotection, protection, substitution, addition, elimination) to yield a desired compound (e.g., homohalichondrin A, B, C, or an analog thereof).

Synthesis of Additional Halichondrin Analogs

Methods for the preparation of additional halichondrin analogs are provided herein. The Ni/Zr-mediated ketolization reactions provided herein can be applied to the preparation of additional halichondrin analogs. For example, as shown in Scheme 2D, coupling of a left half of Formula (L-2-6) with a right half of Formula (R-2-I) via a Ni/Zr-mediated ketolization yields a ketone of Formula (H3-2-II), cyclization of which provides a compound of Formula (H3-2-I). The compound of Formula (H3-2-I) can be subjected to further synthetic transformation to yield a desired compound.

Scheme 2D

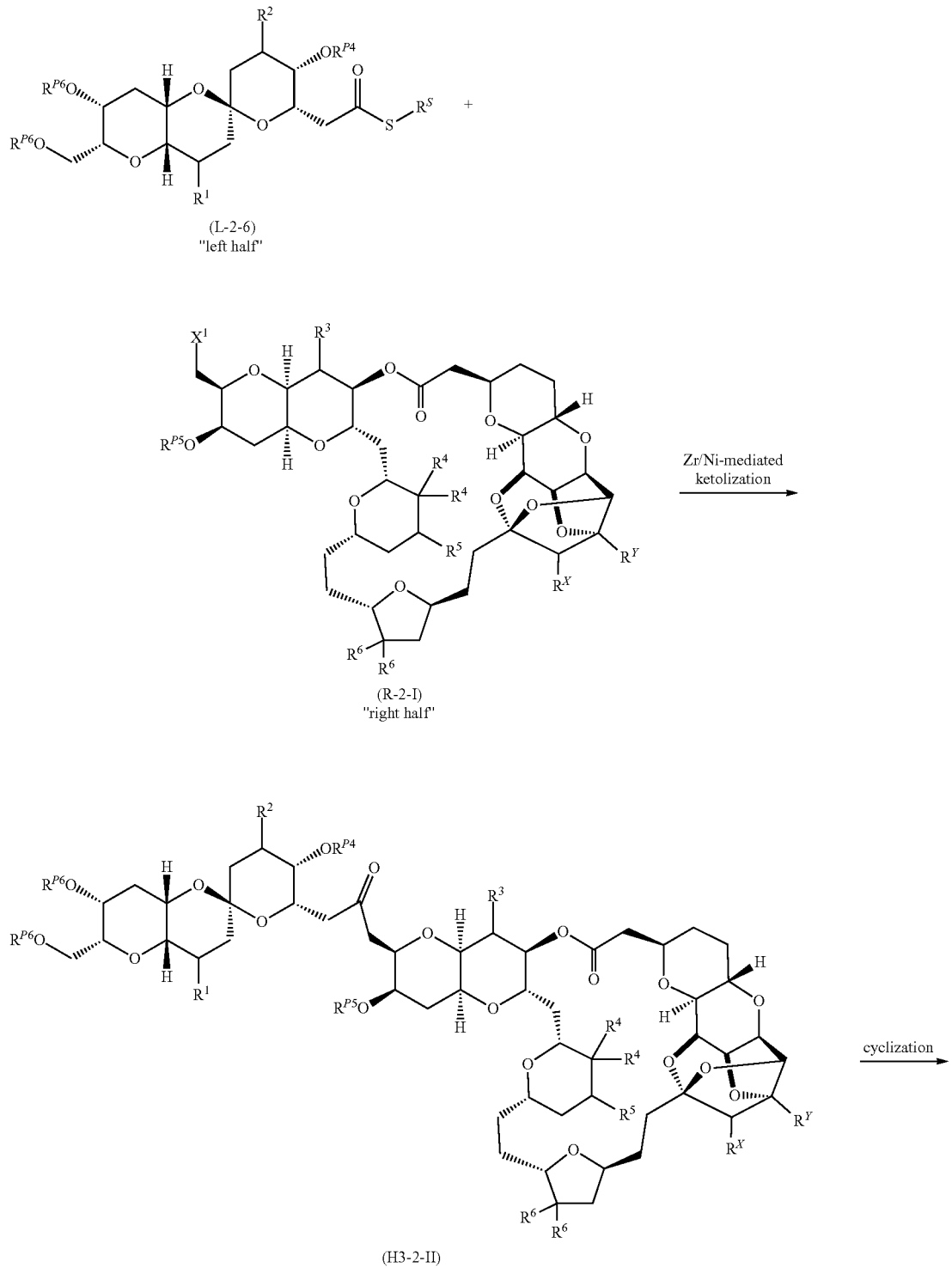

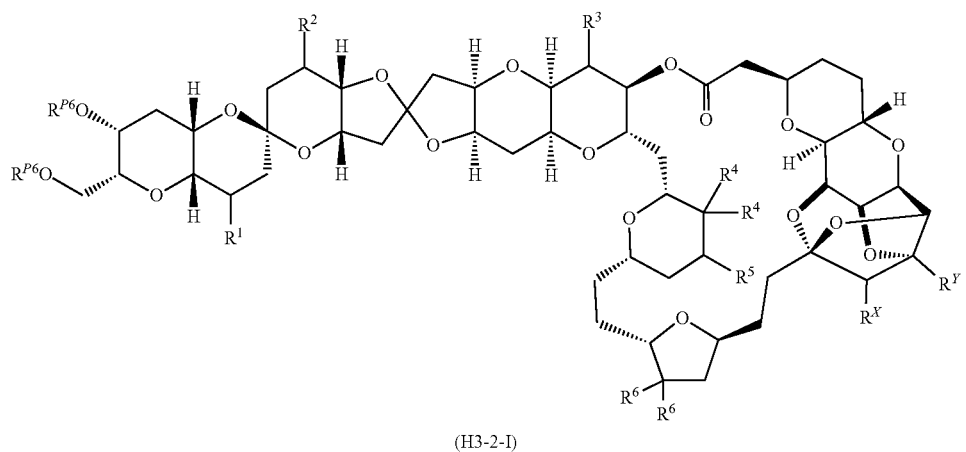
(H3-2-I)
As shown in Scheme 2D, provided herein is a method of preparing a compound of Formula (H3-2-I):
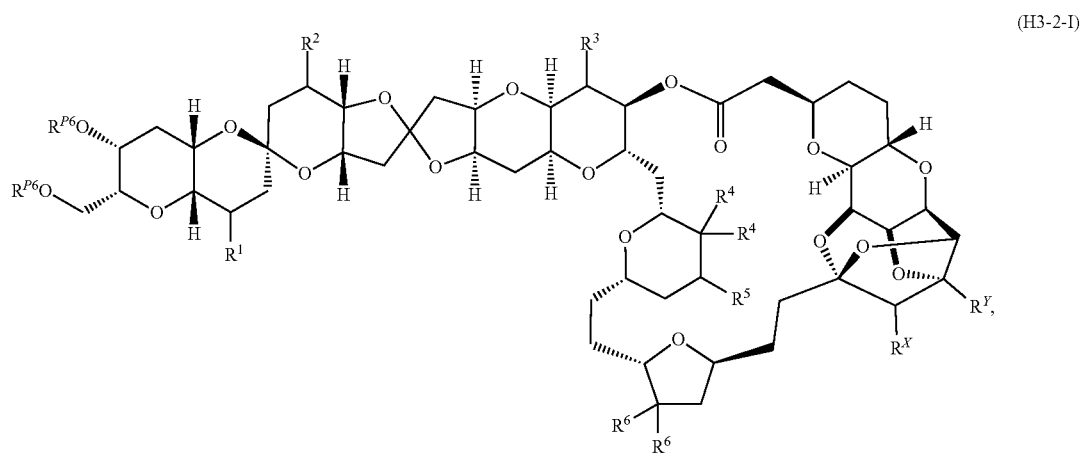
(H3-2-I)

or a salt thereof, the method comprising cyclizing a compound of Formula (H3-2-II):

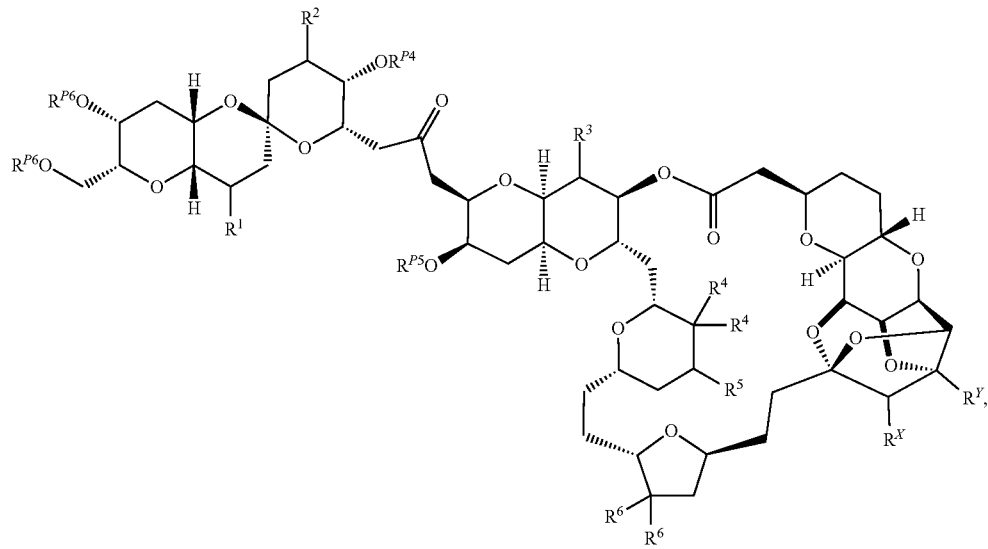

(H3-2-II)

or a salt thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

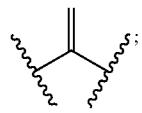 [SMILES: *C(*)=C]

each instance of $R^6$ is independently hydrogen, halogen, or optionally substituted alkyl, or two $R^6$ groups are taken together to form:

$R^{P4}$, $R^{P5}$, and $R^{P6}$ are each independently hydrogen, optionally substituted alkyl, optionally substituted acyl, or an oxygen protecting group; optionally wherein two $R^{P6}$ are joined with the intervening atoms to form optionally substituted heterocyclyl;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound of Formula (H3-2-II) is of Formula (H3-2-IIA):
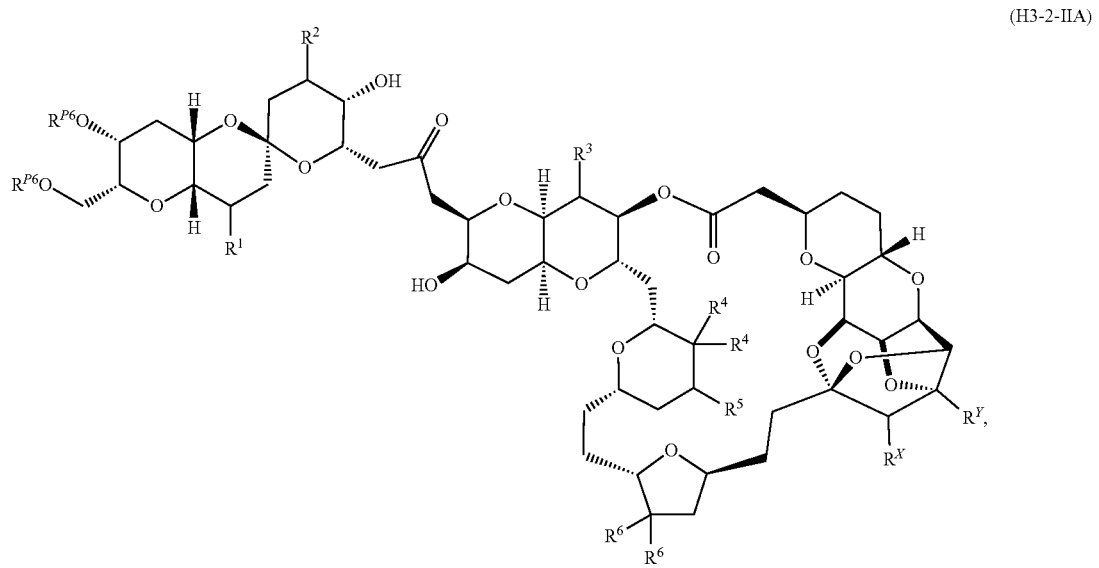
(H3-2-IIA)
or a salt thereof.
In certain embodiments, the method is a method of preparing Compound (2):
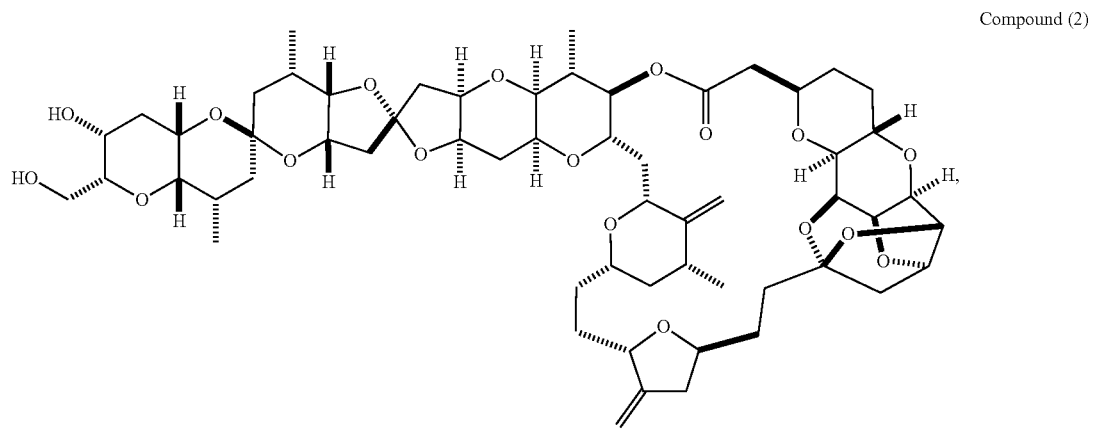
Compound (2)

or a salt thereof, the method comprising cyclizing a compound of the formula:

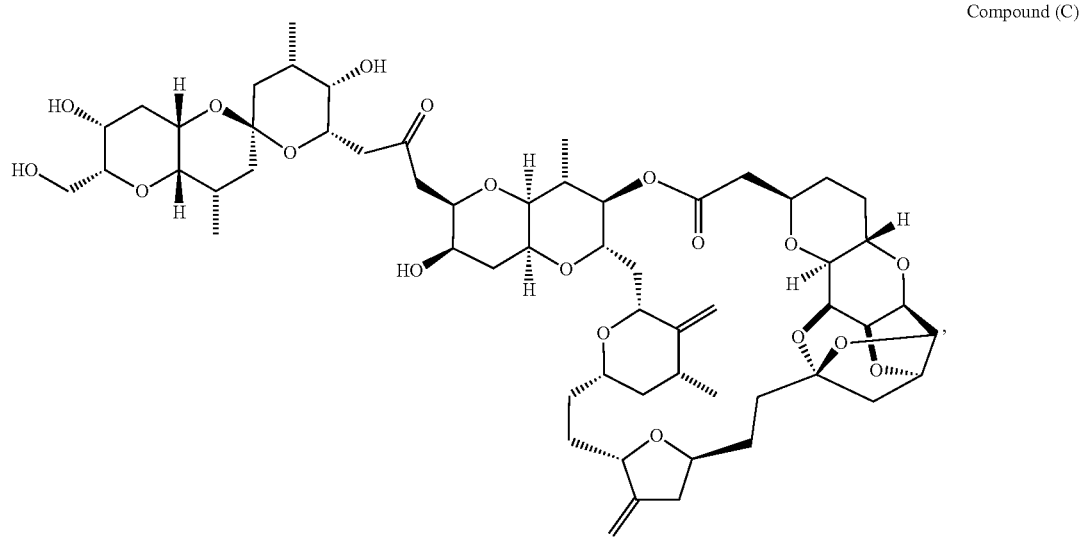 [SMILES: C=C1C[C@@H]2CC[C@@]34C[C@H]5O[C@H]6[C@@H](O3)[C@H]3O[C@H](CC[C@@H]3O[C@H]6C5O4)CC(=O)O[C@@H]3[C@@H](C)[C@@H]4O[C@H](CC(=O)C[C@@H]5O[C@@]6(C[C@H](C)[C@@H]5O)C[C@H](C)[C@@H]5O[C@H](CO)[C@H](O)C[C@@H]5O6)[C@H](O)C[C@@H]4O[C@H]3C[C@H]3O[C@@H](CC[C@@H]1O2)C[C@@H](C)C3=C]

Compound (C)

or a salt thereof.

In certain embodiments, the step of cyclizing a compound of Formula (H3-2-II), Compound (C), or a salt thereof, is carried out in the presence of an acid. The acid may be a Lewis acid or a Brønsted acid. In certain embodiments, the acid is a Brønsted acid. In certain embodiments, the acid is a sulfonic acid. In certain embodiments, the acid is a salt of a sulfonic acid. In certain embodiments, the acid is a pyridinium salt. In certain embodiments, the acid is pyridinium p-toluenesulfonate (PPTS). In certain embodiments, the acid is present in a catalytic amount. In certain embodiments, the acid is present in a stoichiometric (e.g., approximately 1 equivalent) or excess amount (e.g., greater than 1 equivalent). In certain embodiments, the acid is present in an excess amount (e.g., about 5 equivalents). In certain embodiments, the step is carried out in a solvent. In certain embodiments, the reaction is carried out in dichloromethane (DCM). In certain embodiments, the reaction is carried out at a temperature ranging from approximately 0° C. to approximately 50° C. In certain embodiments, the reaction is carried out at a temperature ranging from approximately 0° C. to approximately room temperature. In certain embodiments, the reaction is carried out at around 20° C. In certain embodiments, the reaction is carried out at around room temperature. In certain embodiments, the reaction is carried out at around 9-11° C.

In certain embodiments, the step of cyclizing is carried out in the presence of PPTS. In certain embodiments, the step of cyclizing is carried out in the presence of PPTS in DCM. For example, in certain embodiments, the step of cyclizing is carried out under the following conditions: 5 equivalents of PPTS in DCM at around 20° C. (e.g., for 2 hours). For example, in certain embodiments, the step of cyclizing is carried out under the following conditions: 5 equivalents of PPTS in DCM at around 9-11° C. (e.g., for 3 hours).

In certain embodiments, two $R^{P6}$ are oxygen protecting groups; and $R^{P4}$ and $R^{P5}$ are hydrogen. In certain embodiments, two $R^{P6}$ are joined to form:

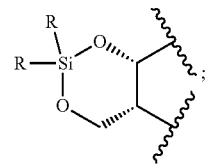

and $R^{P4}$ and $R^{P5}$ are hydrogen. In certain embodiments, two $R^{P6}$ are joined to form:

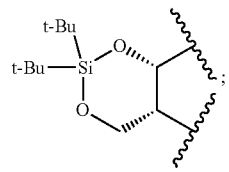

and $R^{P4}$ and $R^{P5}$ are hydrogen. In certain embodiments, each $R^{P6}$, $R^{P4}$, and $R^{P5}$ are each hydrogen. In certain embodiments, one or more free hydroxyl groups of Compound (C) is substituted with an oxygen protecting group (e.g., a silyl protecting group).

As shown in Scheme 2D, provided herein is a method of preparing a compound of Formula (H3-2-II):

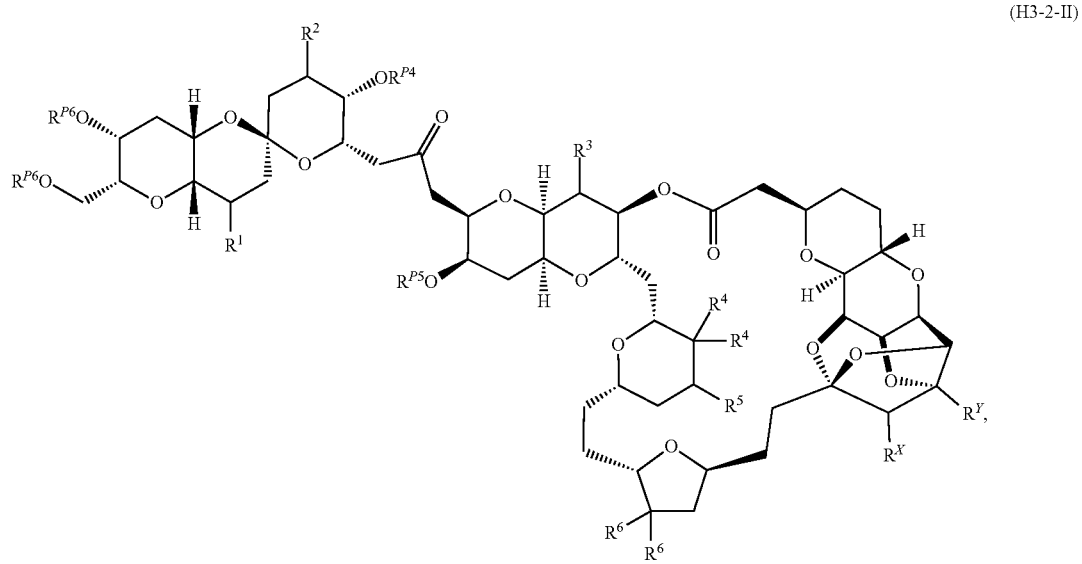

or a salt thereof, the method comprising coupling a compound of Formula (L-2-6):

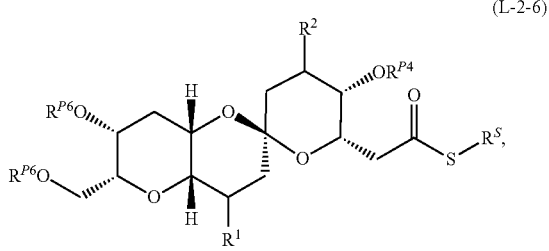

or a salt thereof, with a compound of Formula (R-2-I):

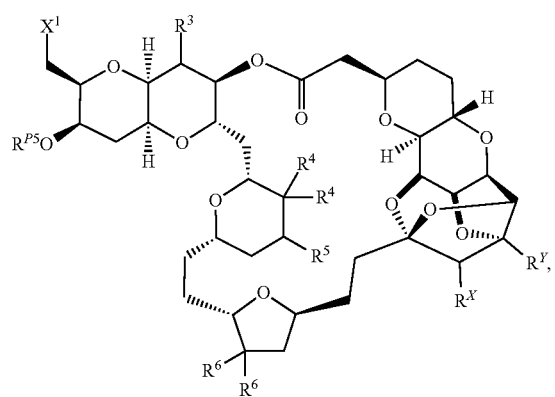

or a salt thereof, wherein:

$R^S$ is optionally substituted alkyl, optionally substituted carbocyclyl, optionally substituted aryl, optionally substituted heterocyclyl, or optionally substituted heteroaryl;

$X^1$ is halogen or a leaving group;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

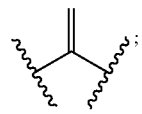 [SMILES: *C(*)=C]

each instance of $R^6$ is independently hydrogen, halogen, or optionally substituted alkyl, or two $R^6$ groups are taken together to form:

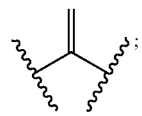 [SMILES: *C(*)=C]

$R^{P4}$, $R^{P5}$, and $R^{P6}$ are each independently hydrogen, optionally substituted alkyl, optionally substituted acyl, or an oxygen protecting group; optionally wherein two $R^{P6}$ are joined with the intervening atoms to form optionally substituted heterocyclyl;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the method comprises coupling a compound of Formula (E-L):

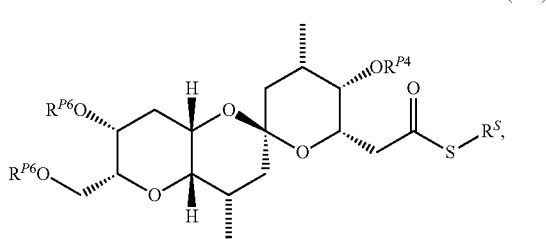

(E-L)

or a salt thereof, with a compound of the formula (E-R):

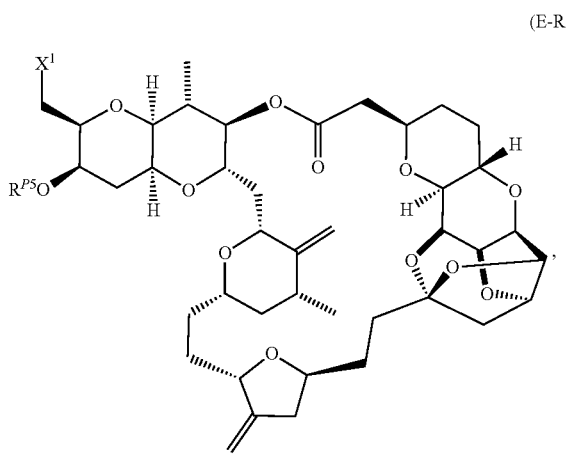

(E-R)

or a salt thereof, to yield a compound of the formula (E-1):

or a salt thereof, wherein:

$R^S$ is optionally substituted alkyl, optionally substituted carbocyclyl, optionally substituted aryl, optionally substituted heterocyclyl, or optionally substituted heteroaryl;

$X^1$ is halogen or a leaving group; and $R^{P4}$, $R^{P5}$, and $R^{P6}$ are each independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the step of coupling to provide a compound of Formula (H3-2-II), (E-1), or a salt thereof, is a Ni/Zr-mediated ketolization provided herein. Any reagents or conditions provided herein for the Ni/Zr-mediated ketolization may be used in the coupling. See, e.g., the section entitled Ni/Zr-Mediated Ketolization Reactions above.

In certain embodiments, the Ni/Zr-mediated ketolization reaction is carried out in the presence of nickel and zirconium complexes. In certain embodiments, the Ni/Zr-mediated ketolization reaction is carried out in the presence of a nickel complex, a zirconium complex, and a reducing metal.

In certain embodiments, the nickel is a nickel complex. In certain embodiments, the nickel is a nickel(II) or nickel(0) complex. In certain embodiments, the nickel complex is of the formula: $NiX_2 \cdot (ligand)$; wherein X is halogen and "ligand" is a bidentate ligand. In certain embodiments, the nickel complex is used after complexation of a nickel source and a "ligand" in solution. In certain embodiments, the nickel source is $NiCl_2$; the "ligand" is 4,4'-di-tert-butyl-2,2'-dipyridyl (tbbpy); and the nickel complex is of the formula $NiCl_2 \cdot (tbbpy)$. In certain embodiments, the nickel source is $NiBr_2$; and the "ligand" is 4,4'-di-tert-butyl-2,2'-dipyridyl (tbbpy); and the nickel complex is of the formula $NiBr_2 \cdot (tbbpy)$.

In certain embodiments, the zirconium complex is $Cp_2ZrCl_2$. In certain embodiments, $Cp_2ZrCl_2$ is present in a stoichiometric or excess amount (e.g., from 1-4 equivalents). In certain embodiments, the reducing metal is zinc metal. In certain embodiments, the reducing metal is manganese metal. In certain embodiments, the zinc or manganese metal is present in an excess amount. The reaction may also be carried out in the presence of one or more additional

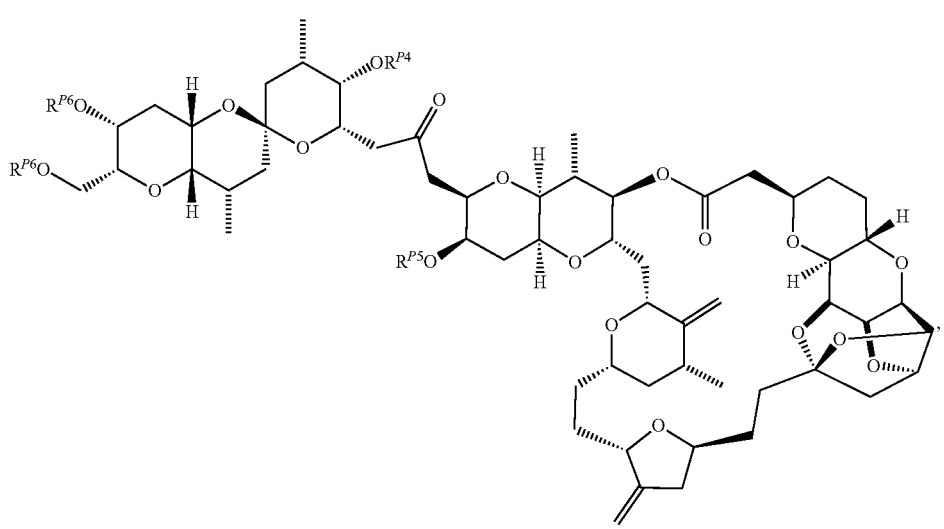

(E-1)

reagents, such a base and/or proton scavenger. In certain embodiments, the reaction is carried out in the presence of $(t\text{-Bu})_2(\text{Me})\text{Py}$. In certain embodiments, the reaction is carried out in the presence of proton sponge (e.g., 1,8-bis(dimethylamino)naphthalene).

In certain embodiments, the reaction is carried out in the presence of $\text{NiBr}_2(\text{dtbbpy})$, $\text{Cp}_2\text{ZrCl}_2$, and zinc metal. In certain embodiments, the reaction is carried out in the presence of $\text{NiBr}_2(\text{dtbbpy})$, $\text{Cp}_2\text{ZrCl}_2$, and manganese metal. In certain embodiments, the reaction is carried out in the presence of $\text{NiBr}_2(\text{dtbbpy})$, $\text{Cp}_2\text{ZrCl}_2$, zinc metal, and $(t\text{-Bu})_2(\text{Me})\text{Py}$. In certain embodiments, the reaction is carried out in the presence of $\text{NiBr}_2(\text{dtbbpy})$, $\text{Cp}_2\text{ZrCl}_2$, manganese metal, and $(t\text{-Bu})_2(\text{Me})\text{Py}$.

In certain embodiments, the reaction is carried out in a polar solvent, such as DMI (1,3-dimethyl-2-imidazolidinone). In certain embodiments, the reaction is carried out in a mixture of DMI and EtOAc (ethyl acetate). In certain embodiments, the reaction is carried out in a mixture of DMI and ethanol. In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature. In certain embodiments, the reaction is carried out at around 30° C.

For example, in certain embodiments, the coupling is carried out under the following conditions: 30 mol % $\text{NiBr}_2(\text{dtbbpy})$, 3.0 equivalents $\text{Cp}_2\text{ZrCl}_2$, 6.0 equivalents zinc metal, and 4.0 equivalents $(t\text{-Bu})_2(\text{Me})\text{Py}$, in DMI-EtOAc at room temperature.

In certain embodiments, the coupling is carried out in the presence of $\text{NiBr}_2(\text{dtbbpy})$, $\text{Cp}_2\text{ZrCl}_2$, and manganese metal in DMI. For example, in certain embodiments, the coupling is carried out under the following conditions: approximately 75 mol % $\text{NiBr}_2(\text{dtbbpy})$, 3.5 equivalents $\text{Cp}_2\text{ZrCl}_2$, and 7 equivalents manganese metal in DMI at around 30° C. (e.g., for 4 hours).

In certain embodiments, the coupling is carried out by reacting a compound of Formula (L-2-6), or a salt thereof, in the presence of a compound of Formula (R-2-I), or a salt thereof, $\text{Cp}_2\text{ZrCl}_2$, and manganese metal; followed by the addition of $\text{NiBr}_2(\text{dtbbpy})$ to the reaction mixture. In certain embodiments, the coupling is carried out by reacting a compound of Formula (L-2-6), or a salt thereof, in the presence of a compound of Formula (R-2-I), or a salt thereof, $\text{Cp}_2\text{ZrCl}_2$, and manganese metal in DMI; followed by the addition of $\text{NiBr}_2(\text{dtbbpy})$ in a solution of DMI to the reaction mixture.

In certain embodiments, the coupling is carried out by reacting a compound of Formula (E-L), or a salt thereof, in the presence of a compound of Formula (R-L), or a salt thereof, $\text{Cp}_2\text{ZrCl}_2$, and manganese metal; followed by the addition of $\text{NiBr}_2(\text{dtbbpy})$ to the reaction mixture. In certain embodiments, the coupling is carried out by reacting a compound of Formula (E-L), or a salt thereof, in the presence of a compound of Formula (R-L), or a salt thereof, $\text{Cp}_2\text{ZrCl}_2$, and manganese metal in DMI; followed by the addition of $\text{NiBr}_2(\text{dtbbpy})$ in a solution of DMI to the reaction mixture.

The coupling reaction to yield a compound of Formula (H3-2-II), (E-1), or a salt thereof, can be carried out to yield any amount of product. In certain embodiments, the reaction is carried out to yield more than 1 g, 2 g, 5 g, 10 g, 20 g, 30 g, 50 g, 100 g, 200 g, 500 g, or 1 kg of product. In certain embodiments, the reaction is carried out to yield less than 1 g of product. In certain embodiments, the reaction is carried out to yield from 1 g to 100 g of product, inclusive. In certain embodiments, the reaction is carried out to yield approximately 1 g, 2 g, 5 g, 10 g, 20 g, 30 g, 40 g, 50 g, 60 g, 70 g, 80 g, 90 g, or 100 g of product.

In certain embodiments, $X^1$ is a halogen and $R^S$ is optionally substituted pyridyl. In certain embodiments, $X^1$ is —I. In certain embodiments, $R^S$ is 2-pyridyl. In certain embodiments, $X^1$ is —I; and $R^S$ is 2-pyridyl.

In certain embodiments, two $R^{P6}$ are joined to form:

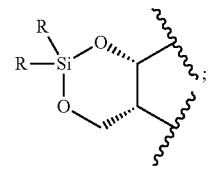

and $R^{P4}$ and $R^{P5}$ are silyl protecting groups. In certain embodiments, two $R^{P6}$ are joined to form:

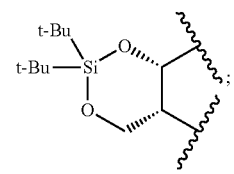 [SMILES: *[C@@H]1CO[Si](C(C)(C)C)(C(C)(C)C)O[C@@H]1*]

and $R^{P4}$ and $R^{P5}$ are TES.

In certain embodiments, the method of preparing a compound of Formula (H3-2-II) further comprises one or more steps of deprotecting one or more oxygen atoms (e.g., removing groups $R^{P4}$, $R^{P5}$, and/or $R^{P6}$) of the compound of Formula (H3-2-II) (e.g., to yield a compound of Formula (HI3-2-IIA), or a salt thereof). In certain embodiments, the resulting compound, or salt thereof, can then be used in the cyclization step to yield a compound of Formula (HI3-2-I), or a salt thereof. Likewise, the method of preparing a compound of Formula (E-1) can further comprise one or more steps of deprotecting one or more oxygen atoms (e.g., removing groups $R^{P4}$, $R^{P5}$, and/or $R^{P6}$) of the compound of Formula (E-1) (e.g., to yield Compound (C), or a salt thereof). In certain embodiments, the resulting compound, or salt thereof, can then be used in the cyclization step to yield Compound (2).

In certain embodiments, a step of deprotecting is carried out in the presence of a fluoride source (e.g., when $R^{P4}$, $R^{P5}$, and/or $R^{P6}$ are silyl protecting groups). Examples of fluoride sources are provided herein. In certain embodiments, the fluoride source is TBAF. In certain embodiments, the step of deprotection is carried out in the presence of an imidazole hydrochloride. In certain embodiments, $R^{P4}$ and $R^{P5}$ are TES; and the step of deprotecting (to remove $R^{P4}$ and $R^{P5}$) is carried out in the presence of TBAF and imidazole hydrochloride. In certain embodiments, two $R^{P6}$ are joined to form:

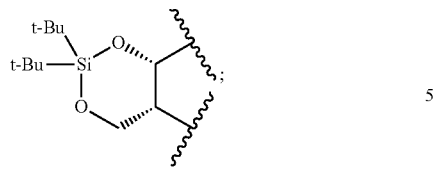
5

$R^{P4}$ and $R^{P5}$ are TES; and the step of deprotecting (to remove $R^{P6}$, $R^{P4}$, and $R^{P5}$) is carried out in the presence of TBAF and imidazole hydrochloride. In certain embodiments, the reaction is carried out in a solvent such as THF.

Once a compound of Formula (H3-2-I), (E-1), or salt thereof, is obtained, the method may comprise one or more additional steps (e.g., deprotection, protection, substitution, addition, elimination) to yield a desired compound.

Synthesis of Amino Analogs of Halichondrins

Provided herein are methods for preparing amino analogs of halichondrins, such as compound of Formula (H3-A). For example, as shown below in Scheme 4, compounds of Formula (H3-A) can be prepared by converting compounds of Formula (H3-OH). The primary hydroxyl group (denoted by * in Scheme 4) is converted to a leaving group —$OR^L$ by treatment of a compound of Formula (H3-A) with a reagent of formula $X^L$-$R^L$. The group —$OR^L$ can then be substituted for an amine or amine precursor. In certain embodiments, the method comprises substituting the primary —$OR^L$ group with an azide (—$N_3$) (i.e., to yield a compound of Formula (H3-N3)). The azide moiety can then be reduced to an amine to yield a compound of Formula (H3-A).

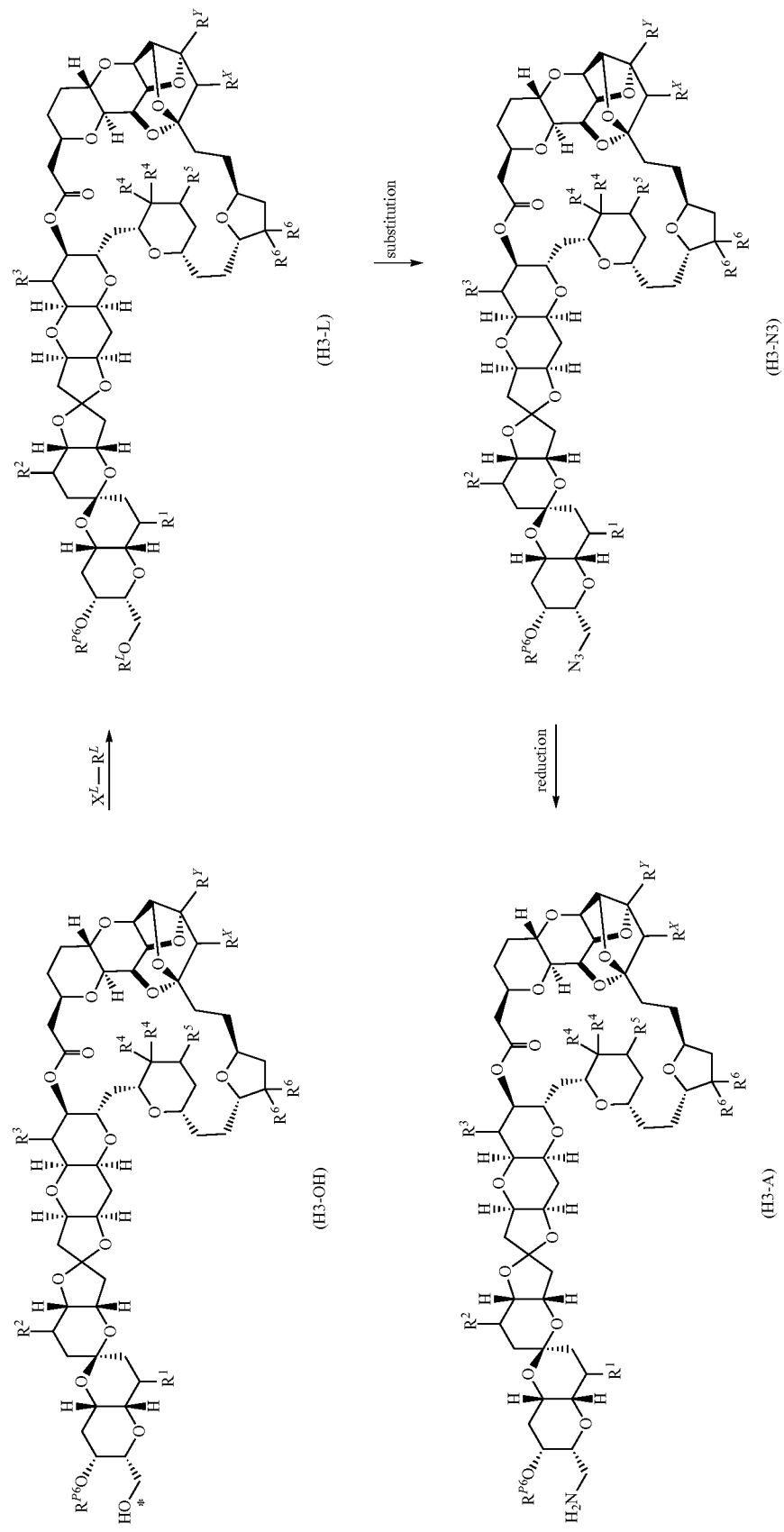

In certain embodiments, the compound of Formula (H3-A) is a Compound (1), or a salt thereof. Therefore, provided herein are methods for preparing Compound (1) and salts thereof. For example, as shown below in Scheme 2, Compound (1) can be prepared by converting Compound (2) to a compound of Formula (A). In this step, the primary hydroxyl group of Compound (2) (denoted by * in Scheme 2) is converted to a leaving group —$OR^L$ by treatment of Compound (2) with a reagent of formula $X^L$-$R^L$. In certain embodiments, the leaving group is a sulfonate (i.e., $R^L$ is optionally substituted sulfonyl). The group —$OR^L$ can then be substituted for an amine or amine precursor. In certain embodiments, the method comprises substituting the primary —$OR^L$ group with an azide (—$N_3$) (i.e., to yield a compound of Formula (B)). The azide moiety of a compound of Formula (B) can then be reduced to an amine to yield Compound (1).

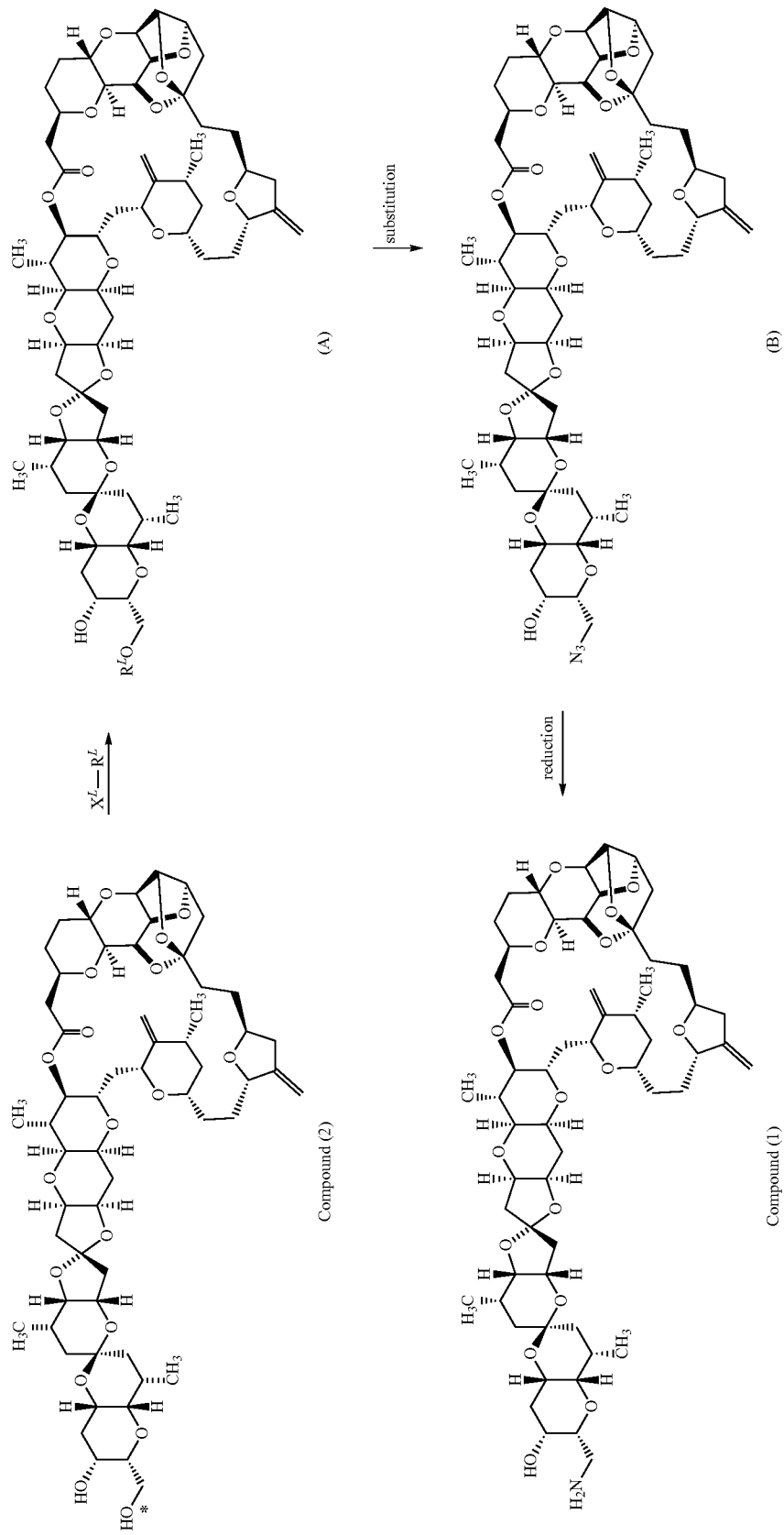

As shown in Scheme 4 above, provided herein is a method of preparing a compound of Formula (H3-A):

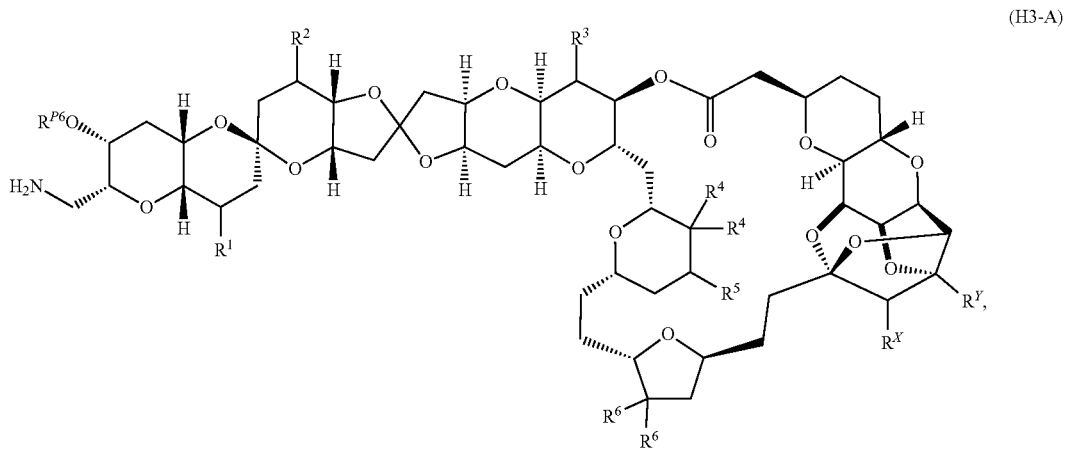

(H3-A)

or a salt thereof, the method comprising a step of reducing a compound of Formula (H3-N3):

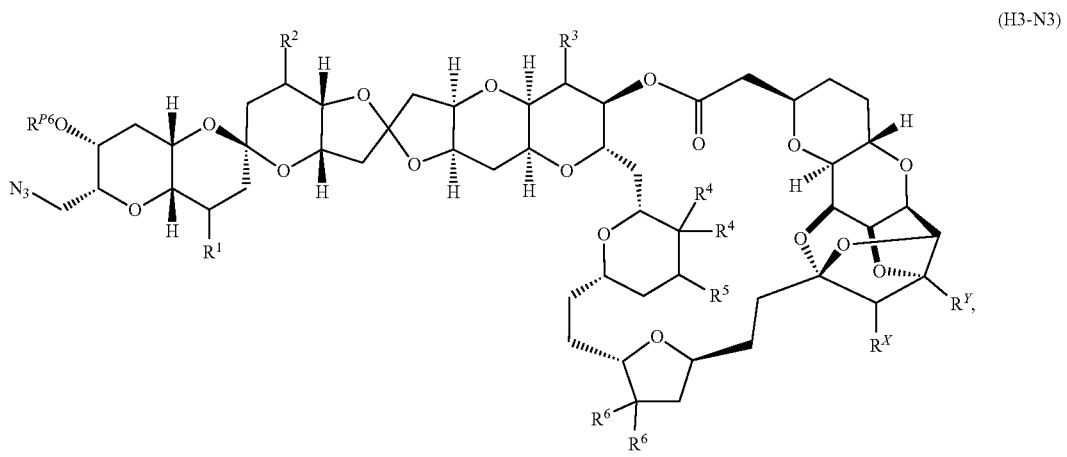

(H3-N3)

or a salt thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

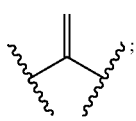

each instance of $R^6$ is independently hydrogen, halogen, or optionally substituted alkyl, or two $R^6$ groups are taken together to form:

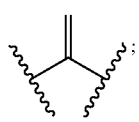 [SMILES: *C(*)=C]

$R^{P4}$, $R^{P5}$, and $R^{P6}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, as shown in Scheme 2, the method provided herein is a method for preparing Compound (1):

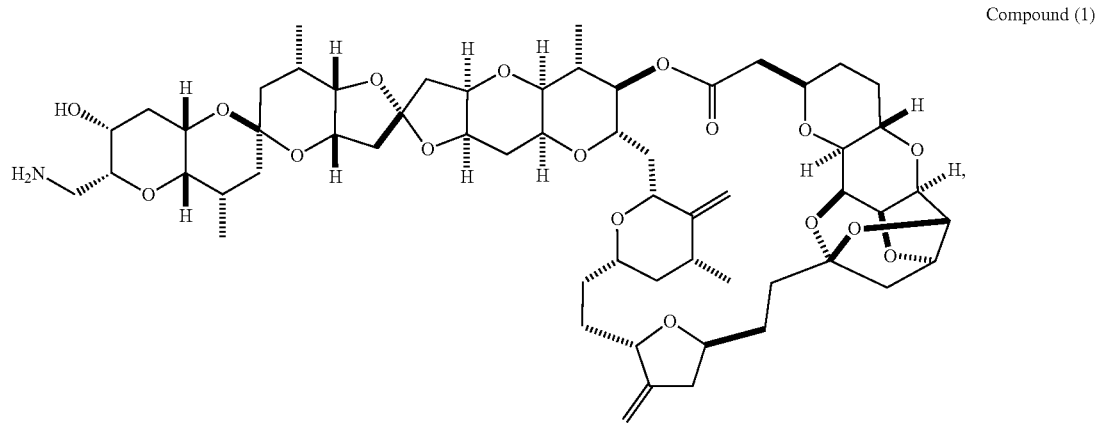

Compound (1)

or a salt thereof, the method comprising reducing a compound of Formula (B):

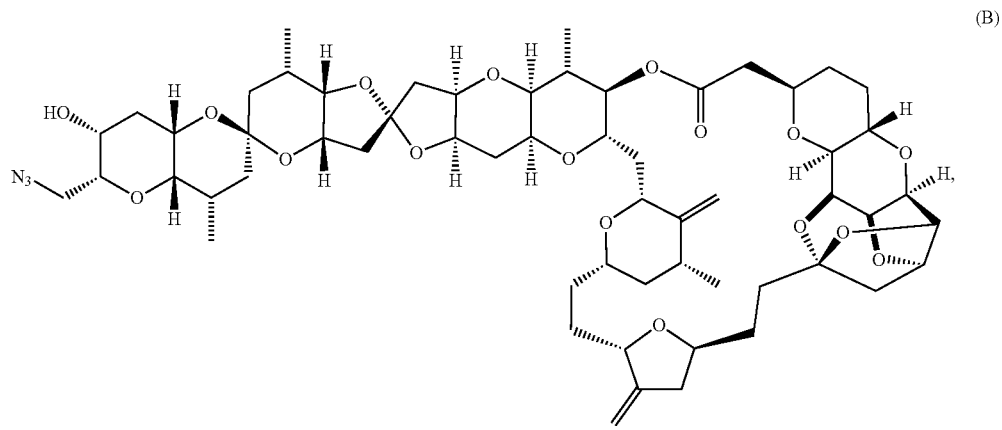

(B)

or a salt thereof.

The step of reducing to form a compound of Formula (H3-A), Compound (1), or a salt thereof, may be carried out in the presence of any reagents or conditions capable of reducing an azide to an amine (see, e.g., *Chem. Rev.*, 1988, 88 (2), pp 297-368). In certain embodiments, the step of reducing is carried out in the presence of a phosphine reagent (i.e., the Staudinger reaction). In certain embodiments, the phosphine is a trialkylphosphine. In certain embodiments, the phosphine is a triarylphosphine. In certain embodiments, the phosphine is triphenylphosphine ($Ph_3P$). In certain embodiments, the phosphine reagent is polymer-bound phosphine. In certain embodiments, the phosphine reagent is polymer-bound triphenylphosphine. In certain embodiments, treatment with the phosphine is followed by treatment with water, e.g., an aqueous work-up.

In certain embodiments, approximately 1 equivalent of the phosphine reagent is used. In certain embodiments, greater than 1 equivalent of the phosphine reagent is used. In certain embodiments, approximately 1-10 equivalents of the phosphine reagent is used. In certain embodiments, approximately 1-5 equivalents of the phosphine reagent is used. In certain embodiments, approximately 3 equivalents of the phosphine is used. In certain embodiments, the reaction is carried out in a solvent. In certain embodiments, the reaction is carried out in THF. In certain embodiments, the reaction is carried out in THF and water. In certain embodiments, the reaction is carried out at a temperature ranging from approximately 0° C. to approximately 50° C. In certain embodiments, the reaction is carried out at a temperature ranging from approximately 0° C. to approximately room temperature. In certain embodiments, the reaction is carried out at a temperature ranging from approximately room temperature to approximately 50° C. In certain embodiments, the reaction is carried out at around room temperature. In certain embodiments, the reactions is carried out at around 25 OC.

In certain embodiments, the reaction is carried out in the presence of polymer-bound $PPh_3$ in THF and water. In certain embodiments, the reaction is carried out under the following conditions: 3 equivalents polymer-bound $PPh_3$ in THF and water at around 25° C. (e.g., for 70 hours).

In certain embodiments, the product is purified and isolated by precipitation. In certain embodiments, the product is purified by column chromatography. In certain embodiments, the product is isolated and purified using a combination of column chromatography and precipitation.

In certain embodiments, $R^{P6}$ is hydrogen. In certain embodiments, $R^{P6}$ is an oxygen protecting group. In certain embodiments, $R^{P6}$ is a silyl protecting group. In certain embodiments, one or more free hydroxyl groups of Compound (B) and Compound (1) is substituted with an oxygen protecting group (e.g., a silyl protecting group).

Other reagents and conditions may be used to convert the azide of Compound (B), or a compound of Formula (H3-N3), to an amine. For example, in certain embodiments, the step of reducing is carried out in the presence of palladium and hydrogen (e.g., Pd/C and $H_2$). In certain embodiments, the step of reducing is carried out in the presence of a hydride (i.e., $H^-$) source.

As shown in Scheme 4, also provided herein is a method of preparing a compound of Formula (H3-N3):

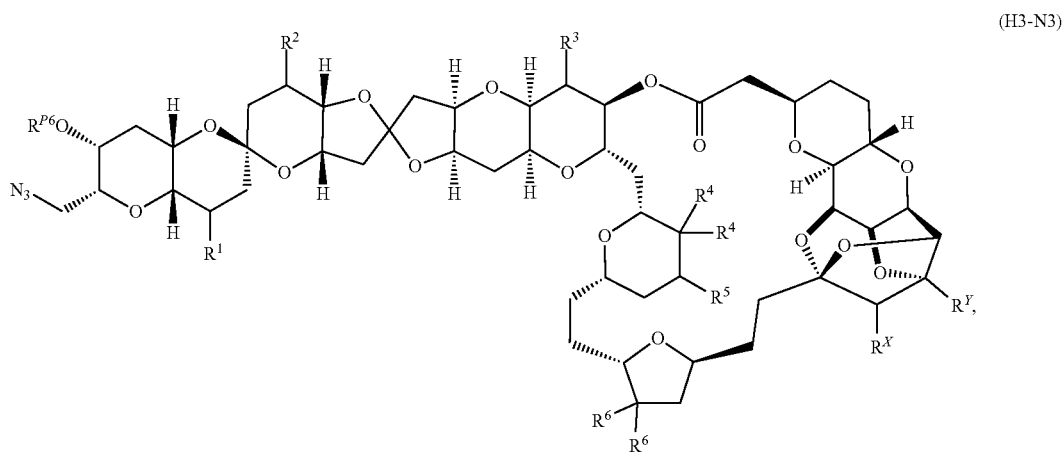

(H3-N3)

or a salt thereof, the method comprising a step of reacting a compound of Formula (H3-L):

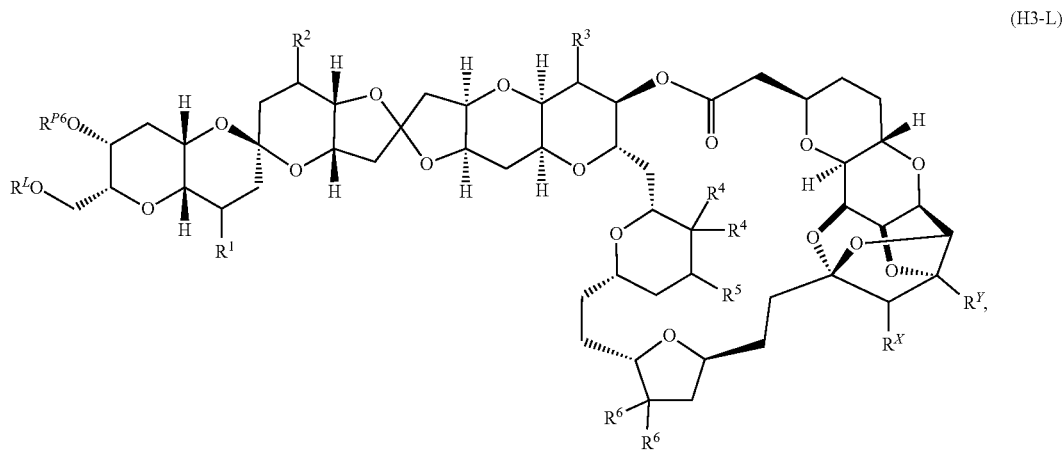

(H3-L)

or a salt thereof, in the presence of an azide, to yield a compound of Formula (H3-N3), or a salt thereof, wherein:

$R^L$ is optionally substituted sulfonyl, optionally substituted sulfinyl, optionally substituted phosphoryl, or optionally substituted acyl;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

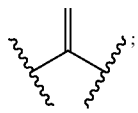

each instance of $R^6$ is independently hydrogen, halogen, or optionally substituted alkyl, or two $R^6$ groups are taken together to form:

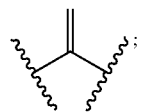 [SMILES: *C(*)=C]

$R^{P4}$, $R^{P5}$, and $R^{P6}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, as shown in Scheme 2, the method is a method of preparing a compound of Formula (B):

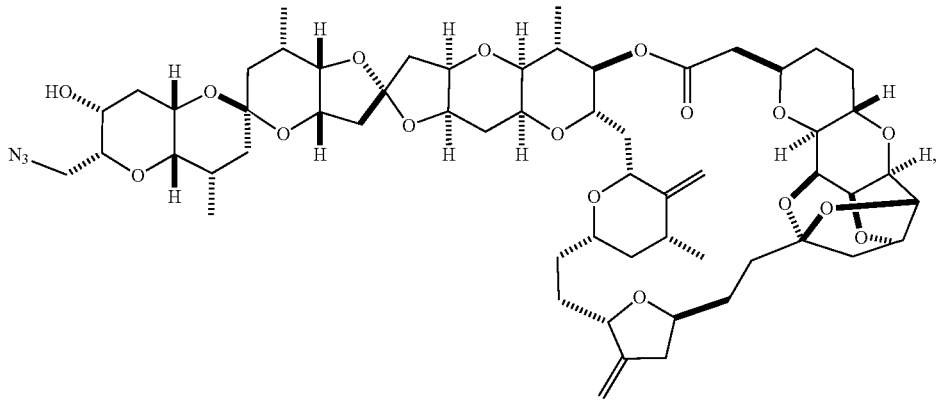

(B)

or a salt thereof, the method comprising reacting a compound of Formula (A):

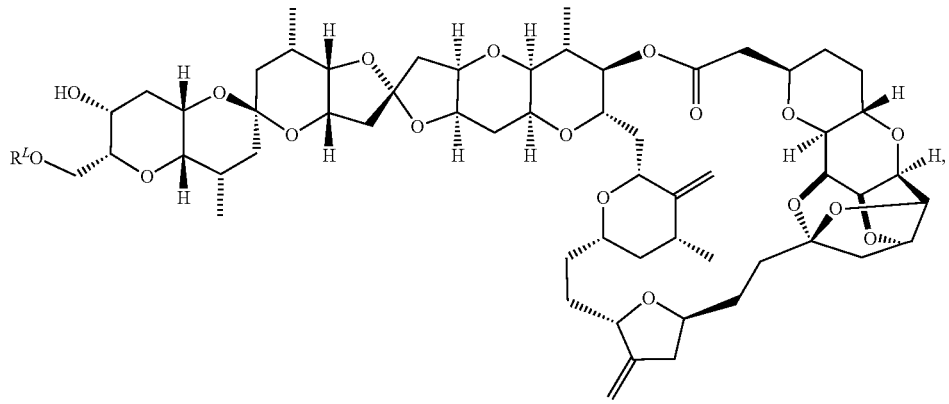

(A)

or a salt thereof, in the presence of an azide, wherein:

$R^L$ is optionally substituted sulfonyl, optionally substituted sulfinyl, optionally substituted phosphoryl, or optionally substituted acyl.

The reaction to form a compound of Formula (H3-N3), Compound (B), or a salt thereof, is carried out in the presence of an azide. In certain embodiments, the azide is an azide salt. In certain embodiments, the azide sodium azide ($NaN_3$) or potassium azide ($KN_3$). In certain embodiments, the azide is a tetraalkylammonium azide (i.e., $[(alkyl)_4N]N_3$). In certain embodiments, the azide is tetrabutylammonium azide ($[n-Bu_4N]N_3$). In certain embodiments, approximately 1 equivalent of the azide is present. In certain embodiments, greater than 1 equivalent of the azide is present. In certain embodiments, approximately 1-10 equivalents of azide are present. In certain embodiments, approximately 5-10 equivalents are present. In certain embodiments, approximately 8 equivalents of azide is present.

In certain embodiments, the reaction is carried out in a solvent. In certain embodiments, the solvent is a polar solvent. In certain embodiments, the solvent is an apolar solvent. In certain embodiments, the solvent is toluene. In certain embodiments, the reaction is carried out at above room temperature. In certain embodiments, the reaction is carried out at a temperature ranging from room temperature to approximately 150° C. In certain embodiments, the reaction is carried out at approximately 100° C.

In certain embodiments, the reaction is carried out in the presence of tetrabutylammonium azide ($[n-Bu_4N]N_3$) in toluene. In certain embodiments, the reaction is carried out in the presence of tetrabutylammonium azide ($[n-Bu_4N]N_3$) in toluene at approximately 100° C. In certain embodiments, the reaction is carried out under the following conditions: 8 equivalents of tetrabutylammonium azide ($[n-Bu_4N]N_3$) in toluene at approximately 100° C. (e.g., for 5 hours).

In certain embodiments, $R^{P6}$ is hydrogen and $R^L$ is Ts. In certain embodiments, $R^{P6}$ is an oxygen protecting group and $R^L$ is Ts. In certain embodiments, $R^{P6}$ is a silyl protecting group and $R^L$ is Ts. In certain embodiments, one or more free hydroxyl groups of Compound (A) and Compound (B) is substituted with an oxygen protecting group (e.g., a silyl protecting group).

In certain embodiments, the compound of Formula (A) is the following:

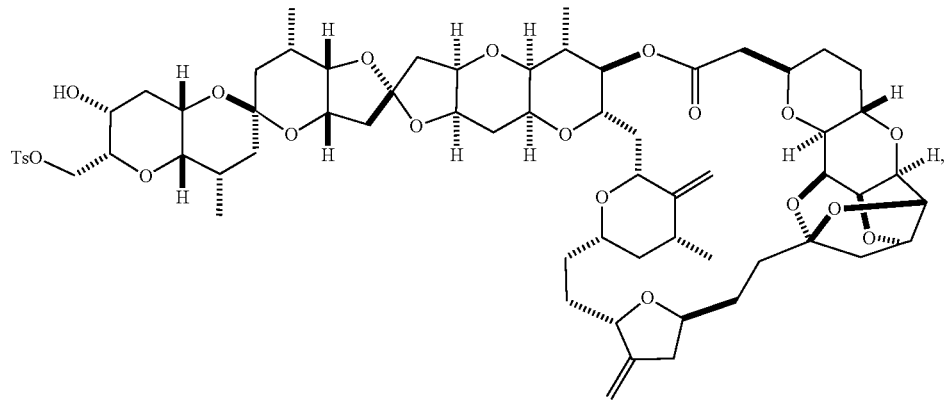

or a salt thereof. "Ts" is a tosyl group of the formula:

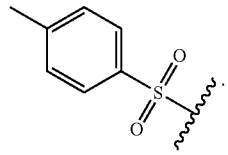 [SMILES: *S(=O)(=O)c1ccc(C)cc1]

Also provided herein is a method of preparing a compound of Formula (H3-L):

(H3-L)

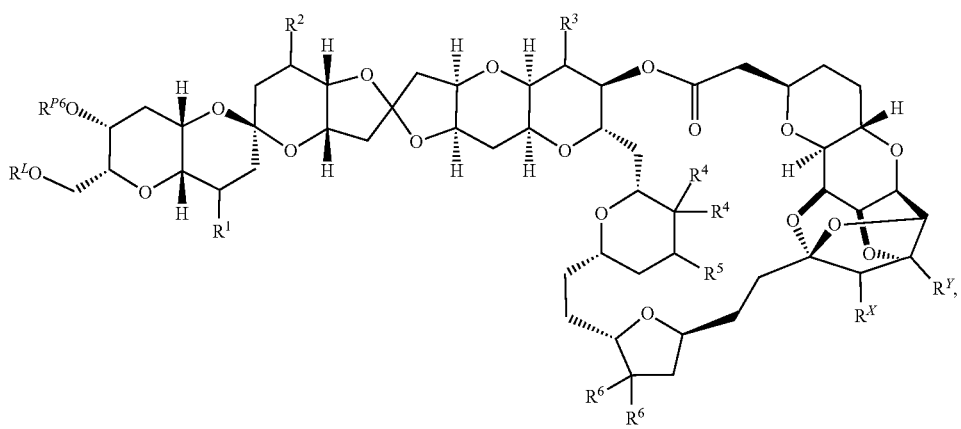

or a salt thereof, the method comprising a step of reacting a compound of Formula (H3-OH):

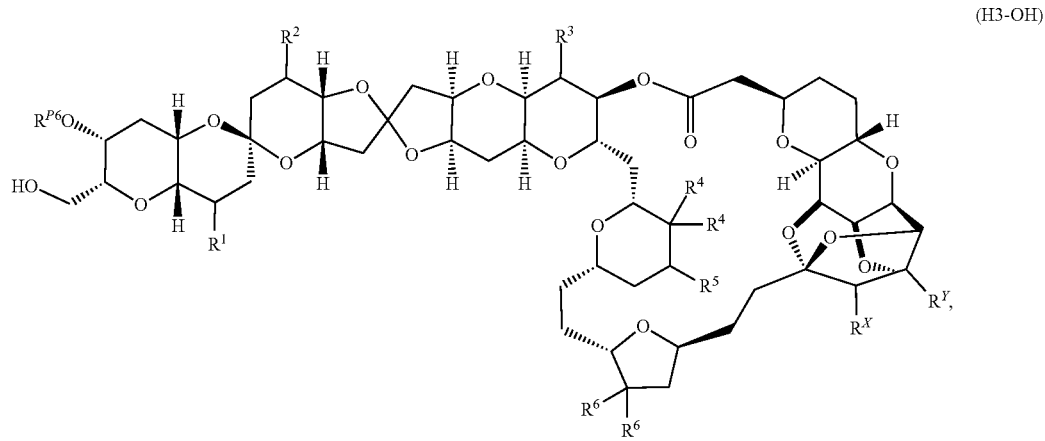

(H3-OH)

or a salt thereof, in the presence of a reagent of the formula $X^L\text{-}R^L$, to yield a compound of Formula (H3-L), or a salt thereof, wherein:

$R^L$ is optionally substituted sulfonyl, optionally substituted sulfinyl, optionally substituted phosphoryl, or optionally substituted acyl;

$X^L$ is halogen or a leaving group;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

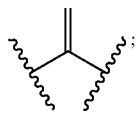 [SMILES: *C(*)=C]

each instance of $R^6$ is independently hydrogen, halogen, or optionally substituted alkyl, or two $R^6$ groups are taken together to form:

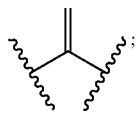 [SMILES: *C(*)=C]

$R^{P4}$, $R^{P5}$, and $R^{P6}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the method is a method of preparing a compound of Formula (A):

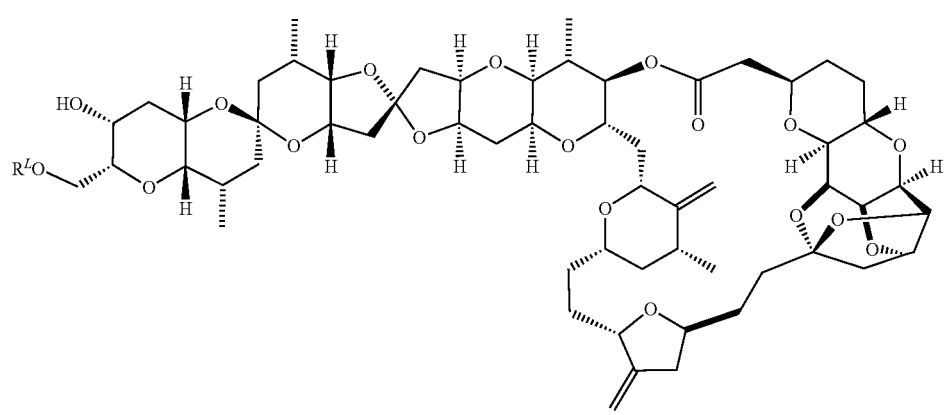

(A)

or a salt thereof, the method comprising reacting Compound (2):

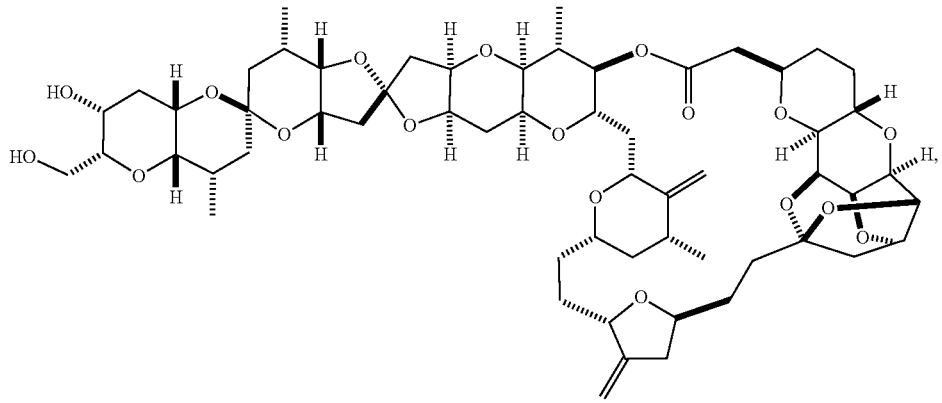

Compound (2)

or a salt thereof, in the presence of a reagent of the formula $X^L$-$R^L$, wherein:

$X^L$ is halogen or a leaving group; and $R^L$ is optionally substituted sulfonyl, optionally substituted sulfinyl, optionally substituted phosphoryl, or optionally substituted acyl.

The reaction to form a compound of Formula (H3-L), Compound (A), or a salt thereof, is carried out in the presence of a reagent of the formula $X^L$-$R^L$. The overall transformation coverts the primary hydroxyl group of the starting material to a leaving group (e.g., a sulfonyl leaving group) of formula —$OR^L$.

In certain embodiments, the reagent of the formula $X^L$-$R^L$ is a sulfonating agent. Sulfonating reagents capable of converting a free hydroxyl group to a sulfonate leaving group are known in the art. In certain embodiments, the reagent of the formula $X^L$-$R^L$ is a sulfonyl halide (i.e., wherein $R^L$ is optionally substituted sulfonyl). In certain embodiments, the reagent is a tosyl halide (i.e., $X^L$-Ts). In certain embodiments, the reagent is a sulfonyl chloride ($X^1$ is chlorine and $R^L$ is optionally substituted sulfonyl). In certain embodiments, the reagent is tosyl chloride (TsCl). In certain embodiments, approximately 1 equivalent of the reagent is used. In certain embodiments, greater than 1 equivalent of the reagent is used. In certain embodiments, approximately 3 equivalents of the reagent is used.

In certain embodiments, the reaction is carried out in the presence of one or more additional reagents. In certain embodiments, the reaction is carried out in the presence of a base. In certain embodiments, the base is a nitrogen base. In certain embodiments, the base is an amine base. In certain embodiments, the base is a trialkylamine base. Examples of amine bases include, but are not limited to, triethylamine (TEA) and diisopropylethylamine (DIPEA). In certain embodiments, the base is triethylamine (TEA). In certain embodiments, the base is a heterocyclic base. Examples of heterocyclic bases include, but are not limited to, pyridine and imidazole bases. In certain embodiments, approximately 1 equivalent of the base is used. In certain embodiments, greater than 1 equivalent of the base is used. In certain embodiments, an excess (e.g., approximately 6 equivalents) of the base is used.

In certain embodiments, the reaction is carried out in the presence of a Lewis acid. In certain embodiments, the Lewis acid is dibutyltin oxide. In certain embodiments, the Lewis acid is present in 1 equivalent or less (e.g., 0.5 equivalents).

In certain embodiments, the reaction is carried out in a solvent. In certain embodiments, the solvent is dichloromethane (DCM). In certain embodiments, the reaction is carried out at a temperature ranging from approximately 0° C. to approximately 50° C. In certain embodiments, the reaction is carried out at a temperature ranging from approximately room temperature to approximately 50° C. In certain embodiments, the reaction is carried out at around room temperature. In certain embodiments, the reaction is carried out at around 25° C.

In certain embodiments, the reaction is carried out in the presence of TsCl, TEA, and a Lewis acid. In certain embodiments, the reaction is carried out in the presence of TsCl, TEA, and dibutyltin oxide. In certain embodiments, the reaction is carried out in the presence of TsCl, TEA, and dibutyltin oxide in DCM. In certain embodiments, the reaction is carried out in the presence of TsCl, TEA, and dibutyltin oxide in DCM at around 25° C. In certain embodiments, the reaction is carried out under the following conditions: 3 equivalents TsCl, excess TEA (e.g., approximately 6 equivalents), and less than 1 equivalent of dibutyltin oxide (e.g., 0.6 equivalents) in DCM at approximately 25° C. (e.g., for 3 hours).

In certain embodiments, $R^{P6}$ is hydrogen and $R^L$ is Ts. In certain embodiments, $R^{P6}$ is an oxygen protecting group, and $R^L$ is Ts. In certain embodiments, $R^{P6}$ is a silyl protecting group, and $R^L$ is Ts. In certain embodiments, one or more free hydroxyl groups of Compound (A) and Compound (2) is substituted with an oxygen protecting group (e.g., a silyl protecting group).

Methods for preparing the starting materials (i.e., compounds of Formula (H3-OH), Compound (2), and salts thereof) are provided herein, e.g., under the subsection entitled Synthesis of Additional Halichondrin Analogs.

Preparation of "Right Half" Building Blocks

Also provided herein are methods useful in the preparation of "right half" building blocks of halichondrins (e.g., halichondrin A, B, C; homohalichondrin A, B, C, norhalichondrin A, B, C, and analogs thereof). For example, as described above, compounds of Formula (R-2-I) are useful as right half building blocks. As shown below in Scheme 3A, a compound of Formula (R-2-I) can be prepared by substitution of a compound of Formula (R-4-11B) (i.e., substitution of the group —OR$^{P7}$ with the group —X$^1$). A compound of Formula (R-4-11B) can be prepared by deprotecting and re-protecting one or more oxygen atoms of a compound of Formula (R-4-11A), thereby converting one occurrence of the group —OR$^{P5}$ to the group —OR$^{P7}$). As also shown in Scheme 3A, a compound of Formula (R-4-11) can be prepared by cyclizing a compound of Formula (R-4-10). Furthermore, a compound of Formula (R-4-10) can be obtained by coupling a compound of Formula (R-4-8) with a compound of Formula (R-4-9).

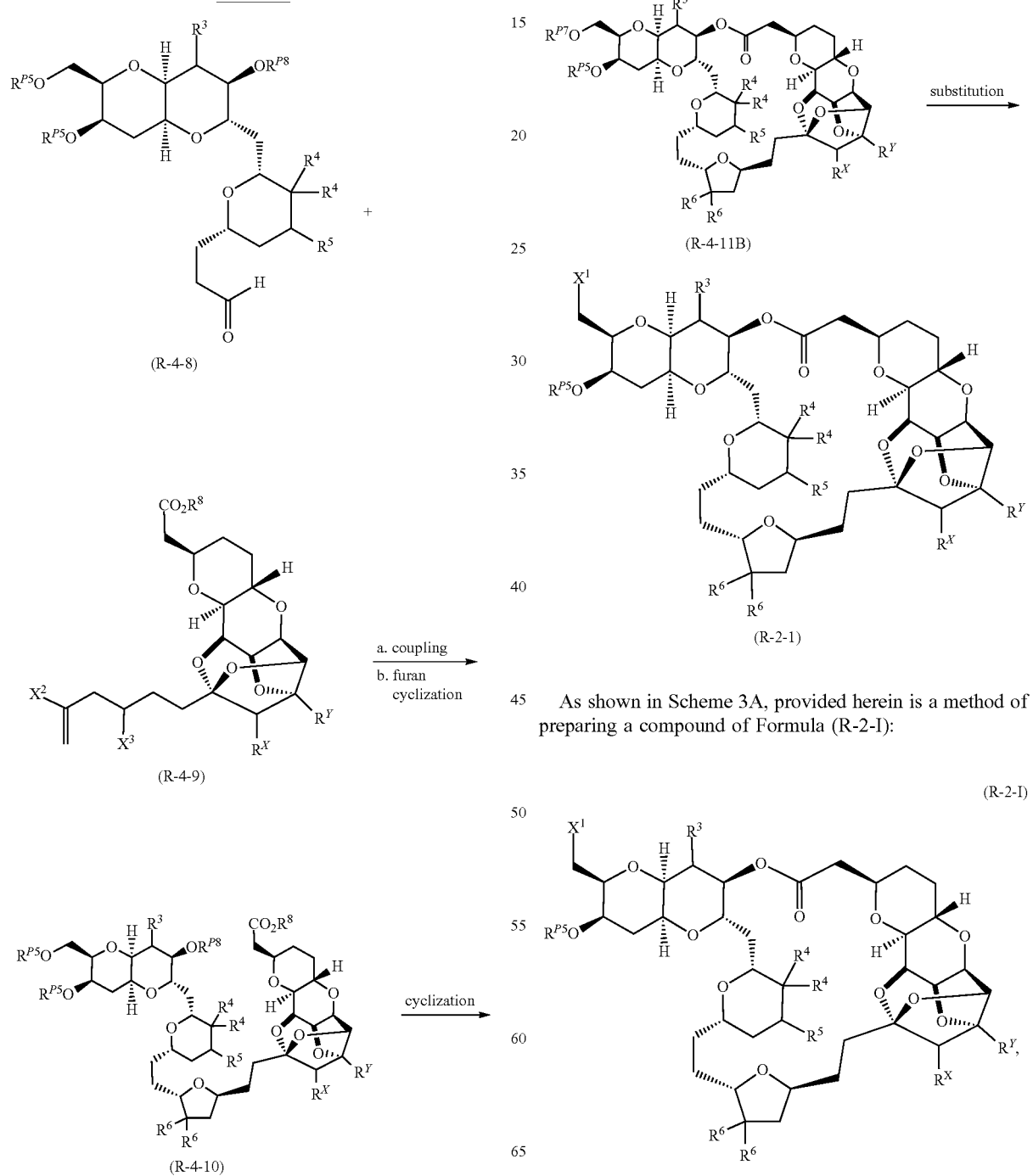

As shown in Scheme 3A, provided herein is a method of preparing a compound of Formula (R-2-I):

or a salt thereof, the method comprising reacting a compound of Formula (R-4-11B):

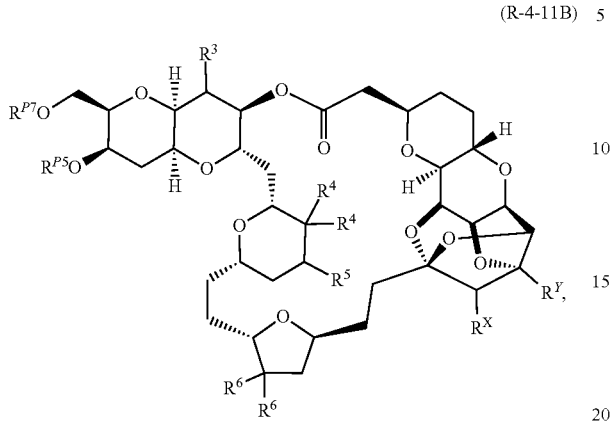
(R-4-11B)

or a salt thereof, in the presence of a nucleophile, thereby substituting the group —OR$^{P7}$ with the group —X$^1$; wherein:

X$^1$ is halogen or a leaving group;

R$^3$ and R$^5$ are each independently hydrogen, halogen, or optionally substituted alkyl;

each instance of R$^4$ is independently hydrogen, halogen, or optionally substituted alkyl, or two R$^4$ groups are taken together to form:

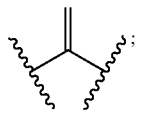 [SMILES: *C(*)=C];

each instance of R$^6$ is independently hydrogen, halogen, or optionally substituted alkyl, or two R$^6$ groups are taken together to form:

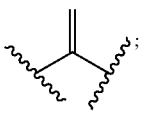;

R$^{P5}$ is hydrogen, optionally substituted alkyl, optionally substituted acyl, or an oxygen protecting group;

R$^{P7}$ is optionally substituted sulfonyl, optionally substituted sulfinyl, optionally substituted phosphoryl, optionally substituted acyl, or an oxygen protecting group;

optionally wherein R$^{P5}$ and R$^{P7}$ are joined with the intervening atoms to form optionally substituted heterocyclyl;

R$^X$ is hydrogen or —OR$^{Xa}$, wherein R$^{Xa}$ is hydrogen, optionally substituted alkyl, optionally substituted acyl, or an oxygen protecting group; and R$^Y$ is hydrogen or —OR$^{Ya}$, wherein R$^{Ya}$ is hydrogen, optionally substituted alkyl, optionally substituted acyl, or an oxygen protecting group;

optionally wherein R$^{Xa}$ and R$^{Ya}$ are joined together with their intervening atoms to form optionally substituted heterocyclyl.

In certain embodiments, method is a method of preparing a compound of Formula (E-R):

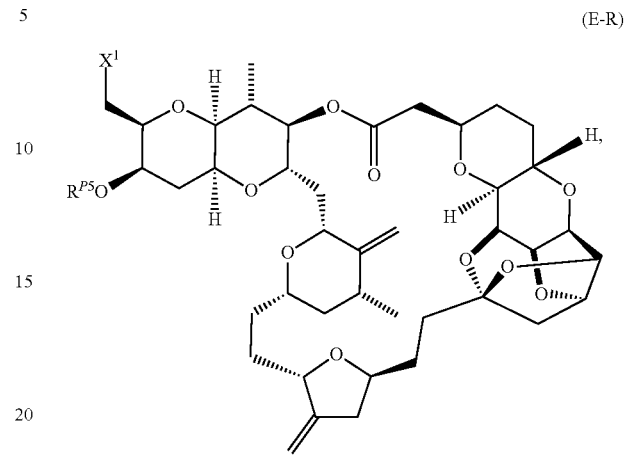
(E-R)

or a salt thereof, the method comprising reacting a compound of Formula (E-R-1):

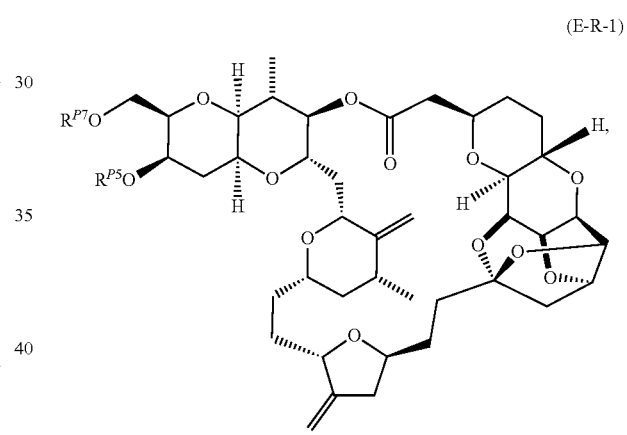
(E-R-1)

or a salt thereof, in the presence of a nucleophile, thereby substituting the group —OR$^{P7}$ with the group —X$^1$; wherein:

X$^1$ is halogen or a leaving group;

R$^{P5}$ is hydrogen, optionally substituted alkyl, optionally substituted acyl, or an oxygen protecting group; and R$^{P7}$ is optionally substituted sulfonyl, optionally substituted sulfinyl, optionally substituted phosphoryl, optionally substituted acyl, or an oxygen protecting group;

optionally wherein R$^{P5}$ and R$^{P7}$ are joined with the intervening atoms to form optionally substituted heterocyclyl.

As described above, the method of preparing a compound of Formula (R-2-I), (E-R), or a salt thereof, comprises a step of reacting a compound of Formula (R-4-11B), or a salt thereof, in the presence of a nucleophile, thereby substituting the leaving group —OR$^{P7}$ with the group —X$^1$. In certain embodiments, the nucleophile is a halide anion (e.g., Cl$^-$, Br$^-$, I$^-$, F$^-$). In certain embodiments, the reaction is carried out in the presence of a halide salt. In certain embodiments, the reaction is carried out in the presence of an iodide salt (e.g., NaI, KI), thereby substituting the leaving group —OR⁷ with the group —I. In certain embodiments, the iodide salt is sodium iodide (NaI). In certain embodiments, the reaction is carried out in the presence of NaI. In certain embodiments, the reaction is carried out in a polar solvent (e.g., DMF or DMI). In certain embodiments, the reaction is carried out at a temperature ranging from approximately 0° C. to approximately 50° C. In certain embodiments, the reaction is carried out at a temperature ranging from approximately room temperature to approximately 50° C. In certain embodiments, the reaction is carried out at around room temperature.

In certain embodiments, the reaction is carried out in the presence of NaI in DMI at around room temperature. For example, in certain embodiments, the reaction is carried out under the following conditions: 5 equivalents of NaI in DMF at room temperature (e.g., for 2-5 hours). For example, in certain embodiments, the reaction is carried out under the following conditions: 5 equivalents of NaI in DMI at room temperature (e.g., for 2-5 hours).

In certain embodiments, the group —OR⁷ is a leaving group. In certain embodiments, the group —OR⁷ is —O-sulfonyl. In certain embodiments, the group —OR⁷ is —OMs. In certain embodiments, the group —OR⁷ is —OTs. In certain embodiments, the group —OR^{P7} is —OTf. In certain embodiments, the group —OR⁷ is —O-acyl. In certain embodiments, the group —OR⁷ is —O-phosphoryl. In certain embodiments, R^{P5} is a silyl protecting group. In certain embodiments, R^{P5} is TES. In certain embodiments, —OR^{P7} is —OTf and R^{P5} is TES.

As shown in Scheme 3A, a compound of Formula (R-4-11B) can be prepared by deprotecting and re-protecting one or more oxygen atoms of a compound of Formula (R-4-11A), thereby converting one occurrence of the group —OR^{P5} to the group —OR^{P7}.

For example, in certain embodiments, provided herein is a method of preparing a compound of Formula (R-4-11B), or a salt thereof, the method comprising:

(a) a step of deprotecting a compound of Formula (R-4-11A):

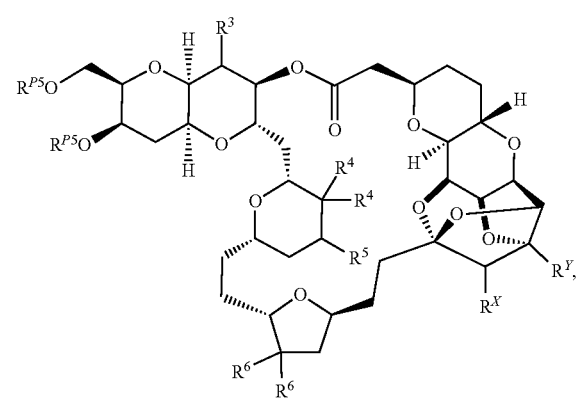

(R-4-11A)

or a salt thereof, to yield a compound of Formula (R-4-11C):

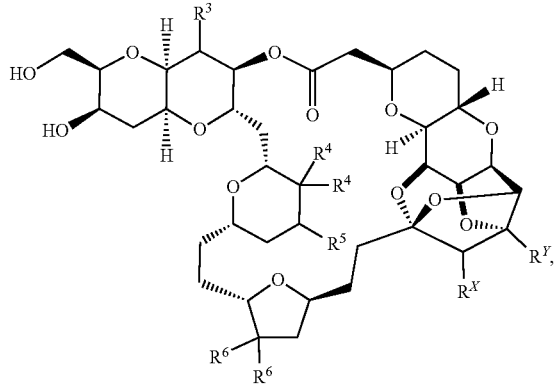

(R-4-11C)

or a salt thereof, following by (b) one or more steps of re-protecting the compound of Formula (R-4-11C), or a salt thereof, to yield a compound of Formula (R-4-11B), or a salt thereof.

In certain embodiments, the method comprises:

(a) a step of deprotecting a compound of Formula (E-R-2):

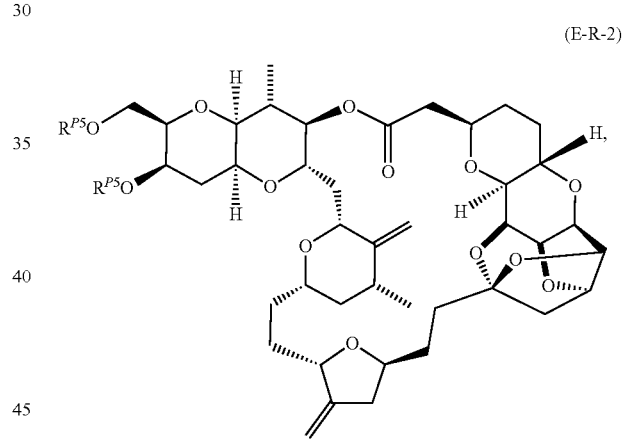

(E-R-2)

or a salt thereof, to yield a compound of the formula:

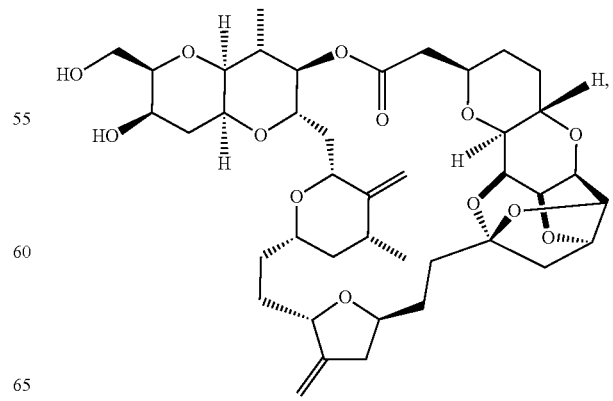

or a salt thereof; and (b) one or more steps of re-protecting the product of step (a) to yield a compound of Formula (E-R-1):

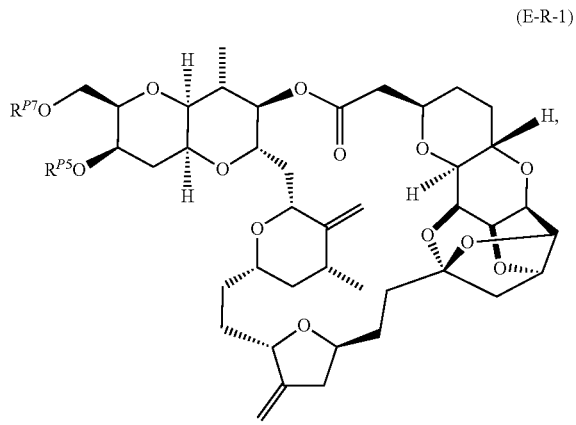

(E-R-1)

or a salt thereof, wherein:

$R^{P5}$ is hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^{P7}$ is optionally substituted sulfonyl, optionally substituted sulfinyl, optionally substituted phosphoryl, optionally substituted acyl, or an oxygen protecting group;

optionally wherein $R^{P5}$ and $R^{P7}$ are joined with the intervening atoms to form optionally substituted heterocyclyl.

As shown above, the compounds of Formula (R-4-11A) and (E-R-2) can be deprotected to remove the groups $R^{P5}$ (i.e., step (a)). In certain embodiments, the $R^{P5}$ groups are silyl protecting groups; and step (a) is carried out in the presence of a fluoride source. In certain embodiments, the fluoride source is tetrabutylammonium fluoride (TBAF). In certain embodiments, two $R^{P5}$ are joined with the intervening atoms to form a ring of the formula:

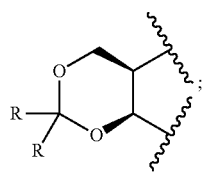

and step (a) is carried out in the presence of an acid. In certain embodiments, two $R^{P5}$ are joined with the intervening atoms to form a ring of the formula:

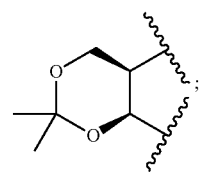 [SMILES: *[C@@H]1COC(C)(C)O[C@@H]1*]

and step (a) is carried out in the presence of an acid. In certain embodiments, the acid isp-toluenesulfonic acid (TsOH). In certain embodiments, the acid is p-toluenesulfonic acid monohydrate (TsOH.H$_2$O). In certain embodiments, the acid is present in a catalytic amount.

In certain embodiments, the step of deprotecting is carried out in DCM and an alcohol (e.g., ROH). In certain embodiments, the deprotection is carried out in DCM and MeOH. In certain embodiments, the reaction is carried out at a temperature ranging from approximately 0° C. to approximately 50° C. In certain embodiments, the deprotection is carried out at around room temperature. In certain embodiments, the deprotection is carried out at around 25° C.

In certain embodiments, two $R^{P5}$ are joined with the intervening atoms to form a ring of the formula:

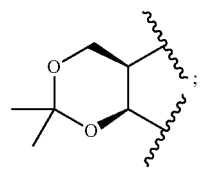 [SMILES: *[C@@H]1COC(C)(C)O[C@@H]1*]

and the deprotection is carried out in the presence of TsOH.H$_2$O in DCM and an alcohol. In certain embodiments, the deprotection is carried out under the following conditions: catalytic TsOH.H$_2$O (e.g., 0.02 equiv) in DCM and MeOH at around 25° C. (e.g., for 4 hours).

In certain embodiments, on compound of Formula (R-4-11B) or (E-R-1), —OR$^{P7}$ is a sulfonate leaving group and $R^{P5}$ is a silyl protecting group; and step (b) is carried out in the presence of a sulfonating reagent and a base (thereby installing $R^{P7}$ as a sulfonyl group), followed by a silylating reagent and a base (thereby installing $R^{P5}$ as a silyl group). In certain embodiments, the sulfonating reagent is a triflating agent. In certain embodiments, the sulfonating reagent is Tf$_2$O. In certain embodiments, the silylating reagent is TESOTf. In certain embodiments, the base is an amine or pyridine base. In certain embodiments, the base is 2,4,6-collidine.

In certain embodiments, the steps of protecting are carried out in a solvent. In certain embodiments, the solvent is DCM. In certain embodiments, the steps of protecting are carried out at below room temperature (e.g., from about −78° C. to −40° C.; from about −78° C. to 0° C.; from about −78° C. to room temperature).

In certain embodiments, —OR$^{P7}$ is —OTf and $R^{P5}$ is TES; and step (b) is carried out in the presence of Tf$_2$O and a base, followed by TESOTf and a base. In certain embodiments, the reaction is carried out in the presence of Tf$_2$O and 2,4,6-collidine in DCM, followed by addition of TESOTf. In certain embodiments, the reaction is carried out under the following conditions: approximately 1.4 equivalents of Tf$_2$O and 5 equivalents of 2,4,6-collidine in DCM at around −78° C., followed by addition of 1.4 equivalents of TESOTf and warming to around −40° C.

As shown in Scheme 3A, also provided herein is a method of preparing a compound of Formula (R-4-11A):

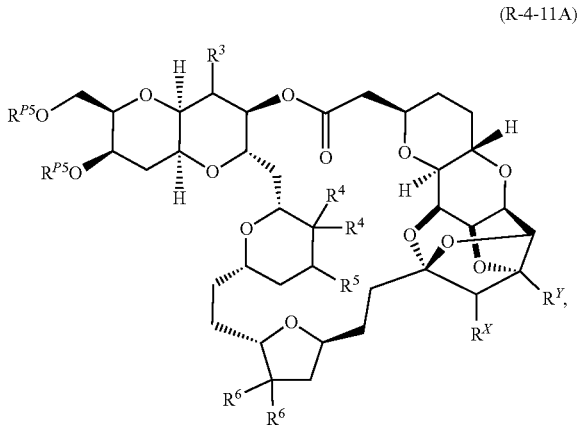
(R-4-11A)

or a salt thereof, the method comprising cyclizing a compound of Formula (R-4-10):

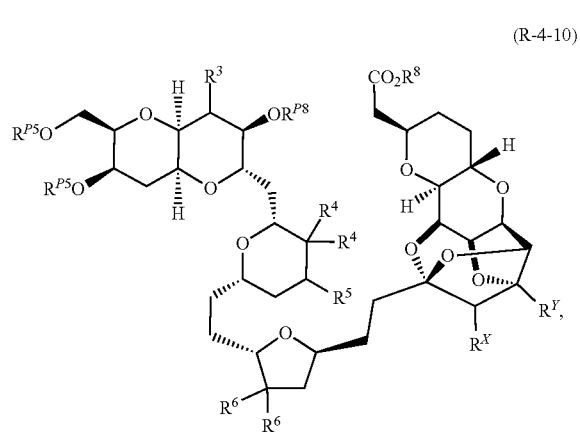
(R-4-10)

or a salt thereof, wherein:

$R^3$ and $R^5$ are each independently hydrogen, halogen, or optionally substituted alkyl;

each instance of $R^4$ is independently hydrogen, halogen, optionally substituted alkyl, or two $R^4$ groups are taken together to form:

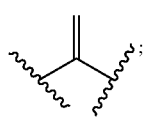 [SMILES: *C(*)=C]

each instance of $R^6$ is independently hydrogen, halogen, optionally substituted alkyl, or two $R^6$ groups are taken together to form:

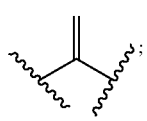

each instance of $R^{P5}$ and $R^{P8}$ is independently hydrogen, optionally substituted alkyl, optionally substituted acyl, or an oxygen protecting group; optionally, wherein two $R^{P5}$ groups are joined together with the intervening atoms to form an optionally substituted heterocyclyl ring;

$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or $-OR^{Xa}$, wherein $R^{Xa}$ is hydrogen, optionally substituted alkyl, optionally substituted acyl, or an oxygen protecting group; and $R^Y$ is hydrogen or $-OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the method comprises cyclizing a compound of Formula (E-R-3):

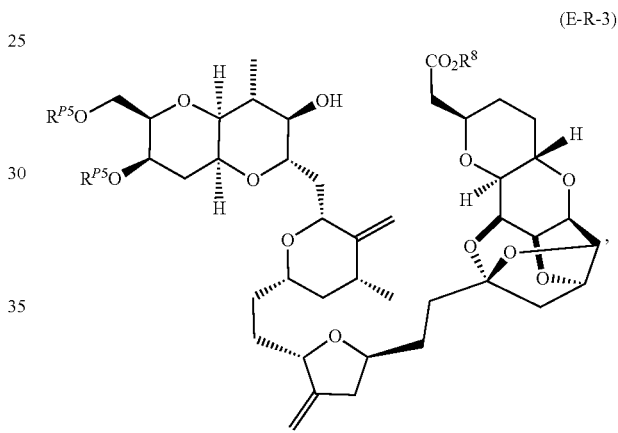
(E-R-3)

or a salt thereof, to yield a compound of Formula (E-R-2):

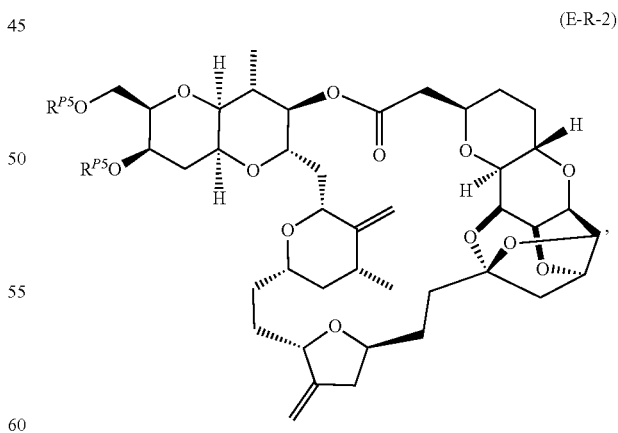
(E-R-2)

or a salt thereof, wherein:

each instance of $R^{P5}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (R-4-10), (E-R-3), or a salt thereof, is carried out in the presence of an anhydride reagent. In certain embodiments, the anhydride reagent is a benzoic anhydride. In certain embodiments, the reagent is a nitrobenzoic anhydride. In certain embodiments, the anhydride is 2-methyl-6-nitrobenzoic anhydride (MNBA). The anhydride reagent may be present in a catalytic, stoichiometric, or excess amount. In certain embodiments, the anhydride reagent is present in excess (i.e., greater than 1 equivalent) relative to a compound of Formula (R-4-10) or (E-R-3). In certain embodiments, the anhydride is present in approximately 3 equivalents.

In certain embodiments, the reaction is carried out in the presence of a nucleophilic reagent capable of activating the carboxyl group —$CO_2R^8$ or —$CO_2H$. In certain embodiments, the nucleophilic reagent is a pyridine. In certain embodiments, the nucleophilic reagent is 4-dimethylaminopyridine (DMAP). In certain embodiments, the nucleophilic reagent is present in excess (i.e., greater than 1 equivalent) relative to a compound of Formula (R-4-10) or (E-R-3). In certain embodiments, the reagent is present in approximately 6 equivalents.

In certain embodiments, the step of cyclizing is carried out in the presence of a base. In certain embodiments, the base is a nitrogen base. In certain embodiments, the base is an amine base. In certain embodiments, the base is a trialkylamine base (e.g., trimethylamine, triethylamine, tributylamine, diisopropyl ethylamine). In certain embodiments, the base is a heteroaryl base (e.g., a pyridine base, an imidazole base). In certain embodiments, the base is diisopropyl ethylamine (DIPEA). In certain embodiments, the base is present in excess (i.e., greater than 1 equivalent) relative to a compound of Formula (R-4-10). IN certain embodiments, the base is present in approximately 6 equivalents.

In certain embodiments, the step of cyclizing is carried out in a solvent (e.g., toluene). In certain embodiments, the reaction is carried out at above room temperature. In certain embodiments, the deprotection is carried out in DCM and MeOH. In certain embodiments, the reaction is carried out at a temperature ranging from approximately room temperature to approximately 100° C. In certain embodiments, the reaction is carried out at approximately 70° C. or 80° C.

In certain embodiments, the step of cyclizing is carried out in the presence of an anhydride reagent, a nucleophilic reagent, and a base. In certain embodiments, the anhydride reagent is 2-methyl-6-nitrobenzoic anhydride. In certain embodiments, the nucleophilic reagent is DMAP. In certain embodiments, the base is a trialkylamine base such as DIPEA. In certain embodiments, the step is carried out in the presence of 2-methyl-6-nitrobenzoic anhydride (MNBA), 4-dimethylaminopyridine (DMAP), and diisopropyl ethylamine (DIPEA).

For example, in certain embodiments, the step of cyclizing is carried out under the following conditions: 6 equivalents MNBA, 12 equivalents DMAP, and 6 equivalents DIPEA, in toluene at around 70° C. For example, in certain embodiments, the step of cyclizing is carried out under the following conditions: 3 equivalents MNBA, 6 equivalents DMAP, and 6 equivalents DIPEA, in toluene at around 80° C. (e.g., for 6 hours). In certain embodiments, the reaction entails slow addition (i.e., dropwise addition) of the compound of Formula (R-4-10) or (E-R-3), or salt thereof, to the reaction mixture.

In certain embodiments, the compound of Formula (R-4-10) is of the Formula (R-4-10A):

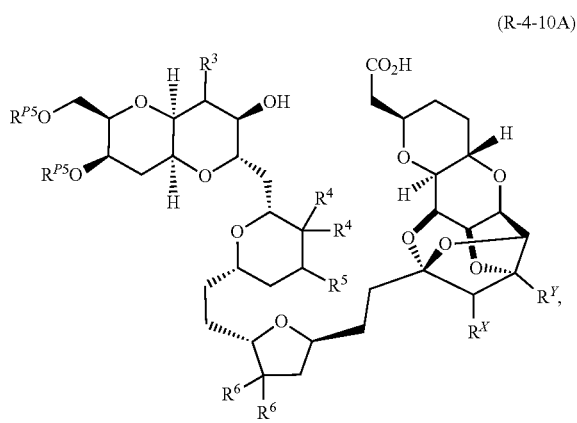

(R-4-10A)

or a salt thereof.

In certain embodiments, two $R^{P5}$ are joined with the intervening atoms to form a ring of the formula:

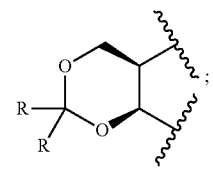

and $R^8$ is hydrogen. In certain embodiments, two $R^{P5}$ are joined with the intervening atoms to form a ring of the formula:

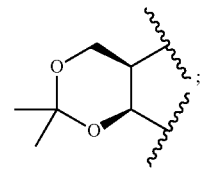 [SMILES: *[C@@H]1COC(C)(C)O[C@@H]1*]

and $R^8$ is hydrogen.

Also provided herein is a method of preparing a compound of Formula (R-4-10):

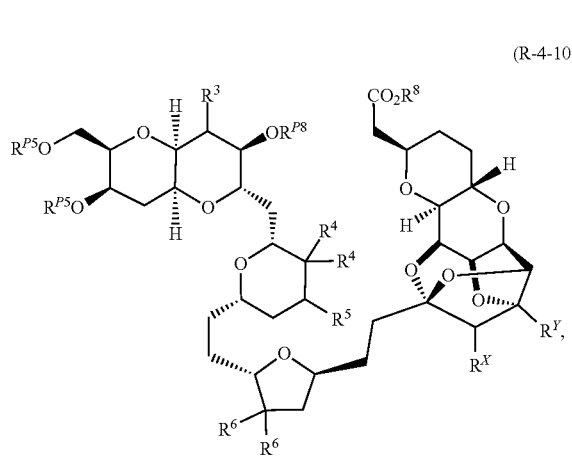

(R-4-10)

or a salt thereof, the method comprising the steps of:
(a) coupling a compound of Formula (R-4-8):

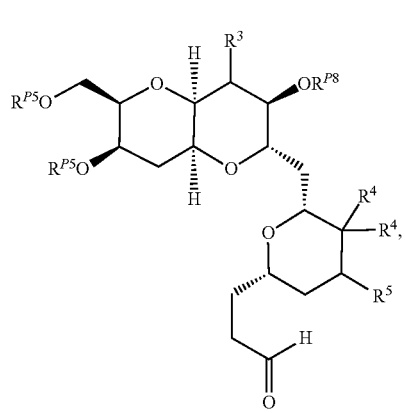

(R-4-8)

or a salt thereof, with a compound of Formula (R-4-9):

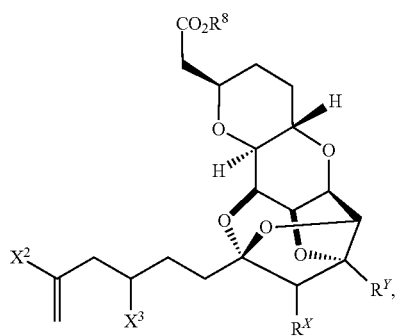

(R-4-9)

or a salt thereof, to yield a compound of Formula (R-4-10B):

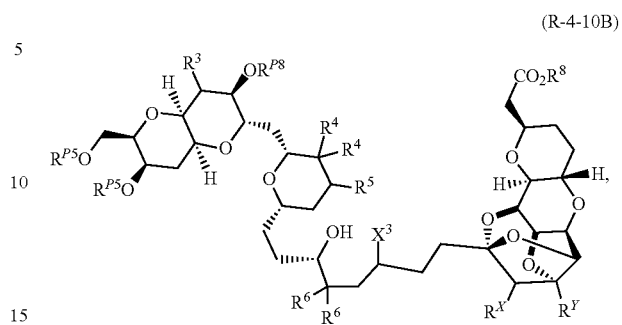

(R-4-10B)

or a salt thereof, followed by (b) cyclizing a compound of Formula (R-4-10B), or a salt thereof, to yield a compound of Formula (R-4-10), or a salt thereof, wherein:

$X^3$ and $X^2$ are each independently halogen or a leaving group;

$R^3$ and $R^5$ are each independently hydrogen, halogen, or optionally substituted alkyl;

each instance of $R^4$ is independently hydrogen, halogen, or optionally substituted alkyl, or two $R^6$ groups are taken together to form:

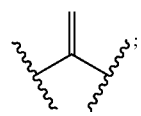

each instance of $R^6$ is independently hydrogen, halogen, or optionally substituted alkyl, or two $R^6$ groups are taken together to form:

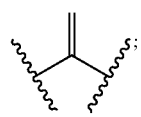 [SMILES: *C(*)=C]

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring;

$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the method comprises:

(a) a step of coupling a compound of Formula (E-R-4):

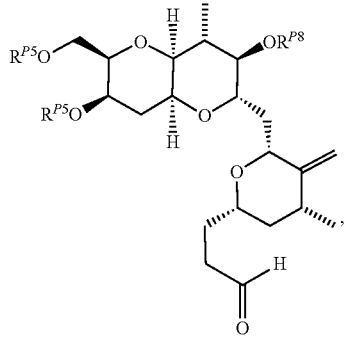

(E-R-4)

or a salt thereof, with a compound of Formula (E-R-5):

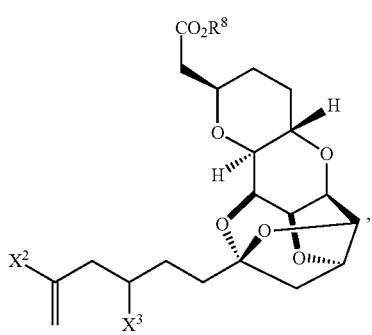

(E-R-5)

or a salt thereof, to yield a compound of Formula (E-R-6):

(E-R-6)

or a salt thereof, followed by (b) a step of cyclizing a compound of Formula (E-R-6), or a salt thereof, to yield a compound of Formula (E-R-7):

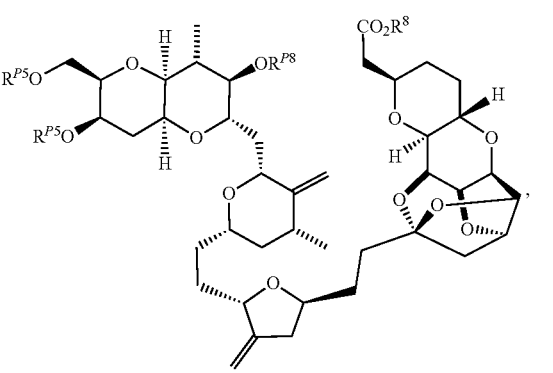

(E-R-7)

or a salt thereof, or a salt thereof, wherein:

$X^3$ and $X^2$ are each independently halogen or a leaving group;

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, step (a) above (to prepare a compound of Formula (R-4-10B), (E-R-6), or a salt thereof) is a Ni/Cr-mediated reductive coupling reaction; and step (b) above (to prepare a compound of Formula (R-4-10), (E-R-7), or a salt thereof) is an acid-promoted or base-promoted intramolecular furan cyclization. Reagents and conditions for steps (a) and (b) can be found in, e.g., international PCT application publications, WO 2016/176560, published Nov. 3, 2016, and WO 2016/003975, published Jan. 7, 2016, the entire contents of which is incorporated herein by reference.

The Ni/Cr-mediated reductive coupling (i.e., step (a)) is carried out in the presence of nickel and chromium. In certain embodiments, the nickel is a nickel complex. Examples of nickel complexes include, but are not limited to, those shown in FIG. 9B. In certain embodiments, the nickel complex is (Et)$_2$Phen.NiCl$_2$. In certain embodiments, the nickel complex is the following:

In certain embodiments, the nickel complex is present in a catalytic amount.

In certain embodiments, the chromium is a chromium complex. In certain embodiments, the chromium complex is prepared from a chromium salt and a chiral ligand. In certain embodiments, the chromium salt is CrCl₂ or CrCl₃. In certain embodiments, the chiral ligand is a chiral sulfonamide. Examples of chiral ligands include, but are not limited to, those shown in FIG. 9B. In certain embodiments, the chiral ligand is (S)-4-G. In certain embodiments, the chiral sulfonamide ligand is one of the following:

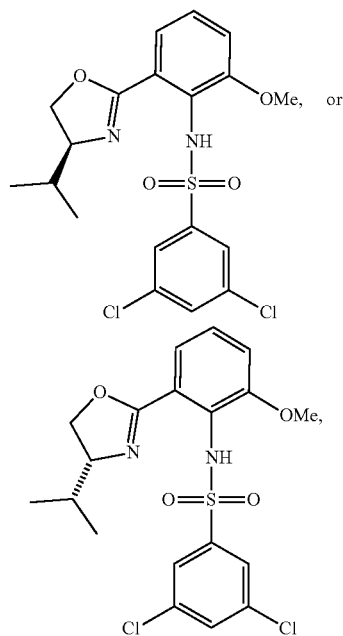

or a salt thereof. In certain embodiments, the chromium complex is present in a catalytic amount.

The Ni/Cr-mediated reductive coupling may be carried out in the presence of one or more additional reagents. In certain embodiments, the coupling is carried out in the presence of a lithium salt (e.g., LiCl or LiBr). In certain embodiments, the coupling is carried out in the presence of a reducing metal such as zinc or manganese (e.g., zinc or manganese metal). In certain embodiments, the coupling is carried out in the presence of zirconium (e.g., ZrCp₂Cl₂). In certain embodiments, the reducing metal is zinc metal. In certain embodiments, the metal is manganese metal. In certain embodiments, the coupling is carried out in the presence of a base or proton scavenger (e.g., 2,6-di-tert-butyl-4-methylpyridine). In certain embodiments, the coupling is carried out in the presence of proton sponge (e.g., 1,8-bis(dimethylamino)naphthalene).

In certain embodiments, the reaction is carried out in a solvent. In certain embodiments, the solvent is acetonitrile (MeCN). In certain embodiments, the deprotection is carried out in DCM and MeOH. In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature. In certain embodiments, the reaction is carried out at around 30 OC.

In certain embodiments, the Ni/Cr-mediated reductive coupling is carried out in the presence of a nickel complex, a chromium salt, a sulfonamide ligand, a lithium salt, a zirconium complex, a reducing metal, and a base or proton scavenger. In certain embodiments, the step of coupling is carried out in the presence of (Et)₂Phen.NiCl₂, CrCl₂, (S)-4-G, LiCl, ZrCp₂Cl₂, manganese metal, and a base or proton scavenger (e.g., 2,6-di-tert-butyl-4-methylpyridine). For example, in certain embodiments, the reaction is carried out under the following conditions: 2 mol % (Et)₂Phen.NiCl₂, 10 mol % CrCl₂, 10 mol % ligand (S)-4-G, 2 equivalents LiCl, 2.5 equivalents ZrCp₂Cl₂, excess manganese metal, and 2.5 equivalents 2,6-di-tert-butyl-4-methylpyridine, in MeCN at room temperature (e.g., for 2 hours).

In certain embodiments, the Ni/Cr-mediated reductive coupling is carried out in the presence of a nickel complex, a chromium salt, a sulfonamide ligand, a zirconium complex, a reducing metal, and a base or proton scavenger. In certain embodiments, the coupling is carried out in the presence of: a nickel complex of the formula:

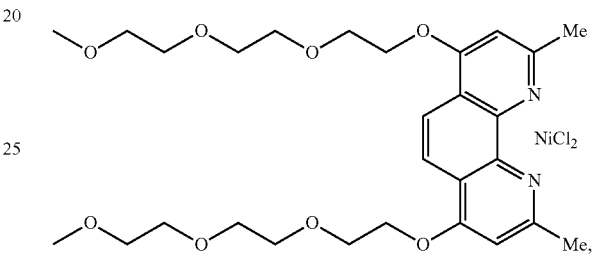

CrCl₃, a sulfonamide ligand of the formula:

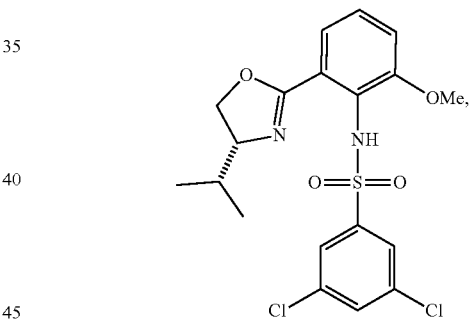

Cp₂ZrCl₂, manganese metal, and a base or proton scavenger (e.g., 2,6-di-tert-butyl-4-methylpyridine and/or proton sponge (e.g., 1,8-bis(dimethylamino)naphthalene)). In certain embodiments, the reaction is carried out in MeCN. In certain embodiments, the reaction is carried out at around 30° C. For example, the coupling can be carried out under the following conditions: 3 mol % of a nickel complex of the formula:

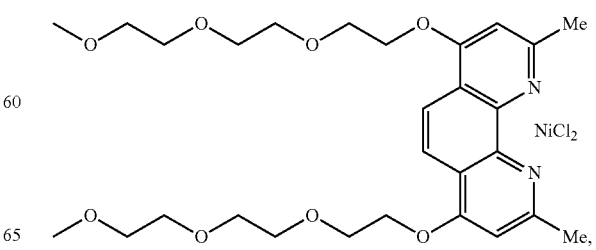

20 mol % CrCl$_3$, 20 mol % of a sulfonamide ligand of the formula:

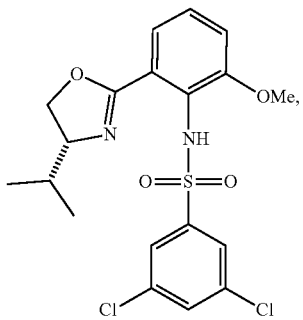 [SMILES: COc1cccc(C2=N[C@H](C(C)C)CO2)c1NS(=O)(=O)c1cc(Cl)cc(Cl)c1]

2.6 equivalents Cp$_2$ZrCl$_2$, 2 equivalents manganese metal, and 2 equivalents of 2,6-di-tert-butyl-4-methylpyridine, and proton sponge in MeCN at around 30° C.

In certain embodiments, step (b) (to prepare a compound of Formula (R-4-10), (E-R-7), or a salt thereof) is carried out in the presence of a Lewis acid. In certain embodiments, the Lewis acid is AgOTf In certain embodiments, the Lewis acid is Ag$_2$O. In certain embodiments, the Lewis acid is SrCO$_3$. The Lewis acid may be present in a catalytic, stoichiometric, or excess amount. In other embodiments, step (b) is carried out in the presence of a base. In certain embodiments, the base is a carbonate salt. In certain embodiments, the base is potassium carbonate (K$_2$CO$_3$).

In certain embodiments, the reaction is carried out in a solvent. In certain embodiments, the solvent is MeOH. In certain embodiments, the solvent is MeCN. In certain embodiments, the reaction is carried out in MeOH and water. In certain embodiments, the reaction is carried out at above room temperature. In certain embodiments, the reaction is carried out at a temperature ranging from approximately room temperature to approximately 100° C. In certain embodiments, the reaction is carried out at from 50-60° C. In certain embodiments, the reaction is carried out at around 60° C. In certain embodiments, the reaction is carried out at around 55° C.

In certain embodiments, in addition to affecting the furan cyclization, the reaction conditions are sufficient to hydrolyze the ester —CO$_2$R$^8$ (wherein R$^8$ is hydrogen in the product (E-R-7) or (R-4-10)).

For example, in certain embodiments, the reaction is carried out under the following conditions: 10 equivalents K$_2$CO$_3$ in MeCN at 60° C. (e.g., for 3 hours). In certain embodiments, the reaction is carried out in the presence of K$_2$CO$_3$, in MeOH and water, at around 55° C. As another example, the reaction can be carried out under the following conditions: 10 equivalents K$_2$CO$_3$ in MeOH and water at around 55° C. (e.g., for 23 hours).

In certain embodiments, two R$^{P5}$ are joined with the intervening atoms to form a ring of the formula:

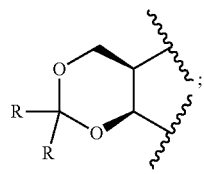

R$^{P8}$ is hydrogen; and R$^8$ is optionally substituted alkyl or hydrogen. In certain embodiments, two R$^{P5}$ are joined with the intervening atoms to form a ring of the formula:

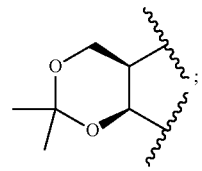 [SMILES: *[C@@H]1COC(C)(C)O[C@@H]1*]

R$^{P8}$ is hydrogen; and R$^8$ is methyl. In certain embodiments, two R$^{P5}$ are joined with the intervening atoms to form a ring of the formula:

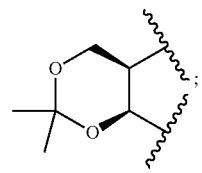 [SMILES: *[C@@H]1COC(C)(C)O[C@@H]1*]

R$^{P8}$ is hydrogen; and R$^8$ is hydrogen.

As shown in Scheme 3B, a compound of Formula (R-4-8) can be prepared by reducing the ester moiety (—CO$_2$R$^8$) of a compound of Formula (R-4-7) to an aldehyde moiety. A compound of Formula (R-4-7) can be prepared by coupling a compound of Formula (R-4-5B) with a compound of Formula (R-4-6), followed by formation of the pyran ring via cyclization of the adduct, or a deprotected form of the adduct. In turn, a compound of Formula (R-4-5B) can be prepared by reducing the ester moiety (—CO$_2$R$^8$) of a compound of Formula (R-4-5A) to an aldehyde moiety. A compound of Formula (R-4-5A) can be prepared by cyclization of a compound of Formula (R-4-4), which can be prepared by coupling a compound of Formula (R-4-2) with an olefin of Formula (R-4-3). As shown in Scheme 3B, a compound of Formula (R-4-2) can be prepared by reducing the lactone of a compound of Formula (R-4-1).

Scheme 3B

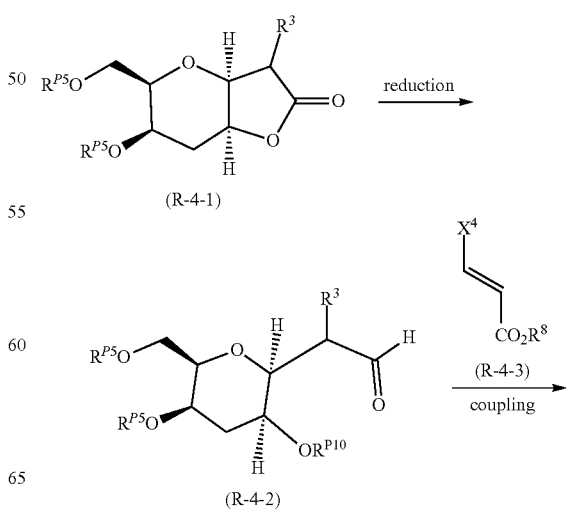

-continued

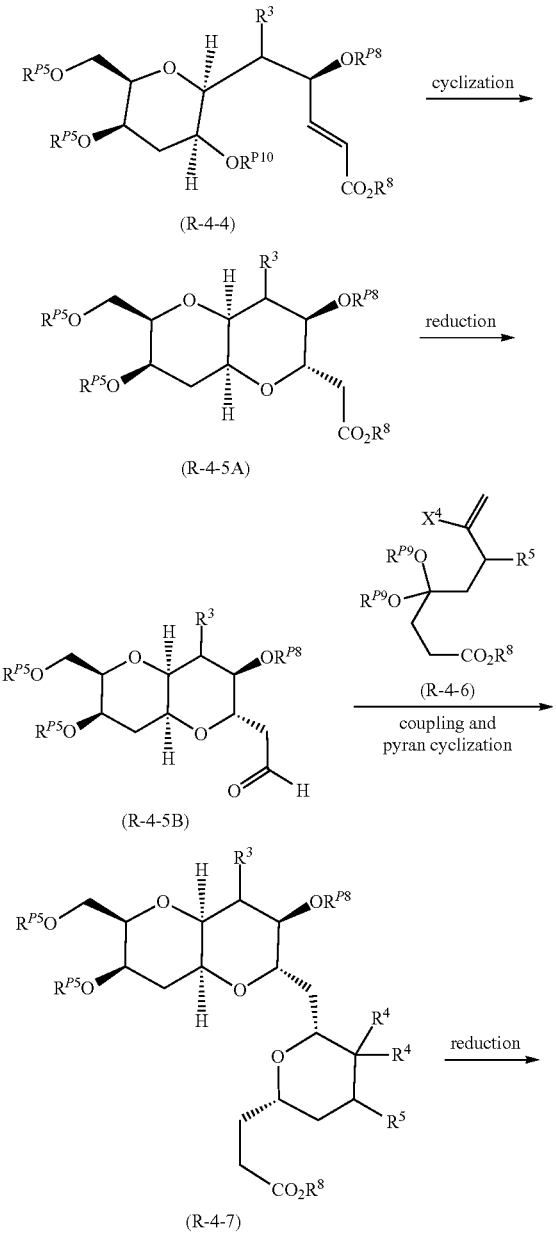

(R-4-4)

(R-4-5A)

(R-4-5B)

(R-4-7)

(R-4-8)

As shown in Scheme 3B, provided herein is a method of preparing a compound of Formula (R-4-8):

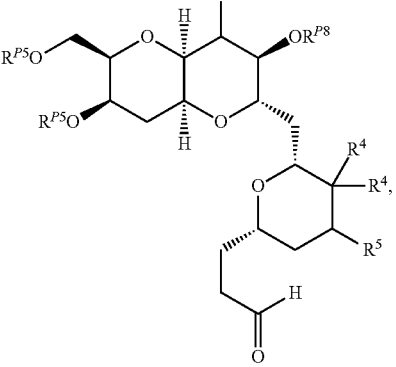

(R-4-8)

or a salt thereof, the method comprising reducing a compound of Formula (R-4-7):

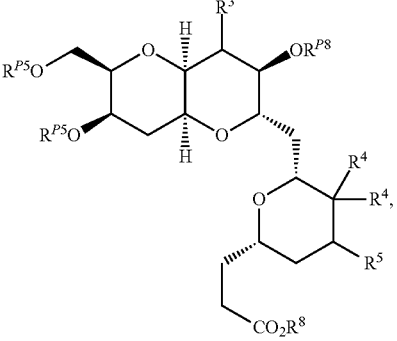

(R-4-7)

or a salt thereof, wherein:

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

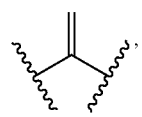

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method comprises a step of reducing a compound of Formula (E-R-8):

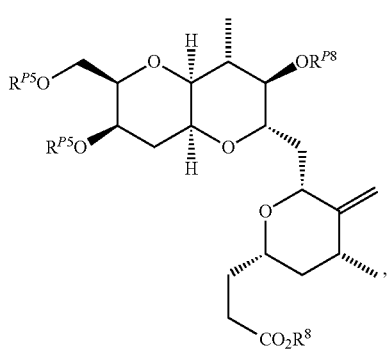

(E-R-8)

or a salt thereof, to yield a compound of Formula (E-R-4):

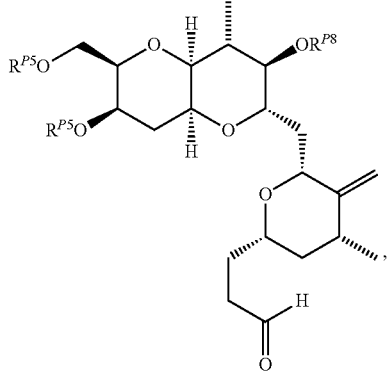

(E-R-4)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

The step of reducing a compound of Formula (R-4-7), (E-R-8), or a salt thereof, converts the ester group —CO$_2$R$^8$ to an aldehyde group. In certain embodiments, the step of reducing is carried out in the presence of a hydride (i.e., H) source. Any hydride source known in the art may be used in this transformation. Examples of hydride sources include, but are not limited to, lithium aluminum hydride (LAH), sodium borohydride (NaBH$_4$), lithium borohydride, and diisobutylaluminum hydride (DIBAL). In certain embodiments, the hydride source is diisobutylaluminum hydride (DIBAL). In certain embodiments, the hydride source is present in a stoichiometric or excess amount.

The step of reducing may optionally comprise reducing the —CO$_2$R$^8$ moiety to an alcohol, followed by oxidation of the resulting alcohol to an aldehyde to yield a compound of Formula (R-4-7), (E-R-8), or a salt thereof.

In certain embodiments, the step of reducing is carried out in the presence of DIBAL. In certain embodiments, the reaction is carried out in a solvent. In certain embodiments, the solvent is DCM. In certain embodiments, the reaction is carried out at below room temperature. In certain embodiments, the reaction is carried out at a temperature ranging from approximately −78° C. to approximately room temperature. In certain embodiments, the reaction is carried out at a temperature ranging from approximately −78° C. to approximately 0° C. In certain embodiments, the reaction is carried out at around −78° C. For example, in certain embodiments, the reaction is carried out under the following conditions: DIBAL in DCM at around −78° C. For example, in certain embodiments, the reaction is carried out under the following conditions: approximately 2.3 equivalents DIBAL in DCM at around −78° C. (e.g., for 1-2 hours).

In certain embodiments, two $R^{P5}$ are joined with the intervening atoms to form a ring of the formula:

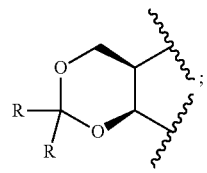

$R^{P8}$ is hydrogen; and $R^8$ is optionally substituted alkyl. In certain embodiments, two $R^{P5}$ are joined with the intervening atoms to form a ring of the formula:

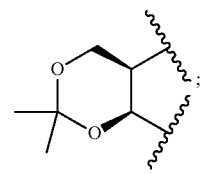 [SMILES: *[C@@H]1COC(C)(C)O[C@@H]1*]

$R^{P8}$ is hydrogen, and $R^8$ is ethyl. In certain embodiments, two $R^{P5}$ are joined with the intervening atoms to form a ring of the formula:

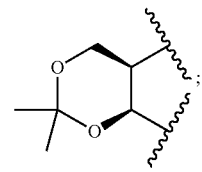 [SMILES: *[C@@H]1COC(C)(C)O[C@@H]1*]

$R^{P8}$ is hydrogen, and $R^8$ is methyl.

As shown in Scheme 3B, also provided herein is a method of preparing a compound of Formula (R-4-7):

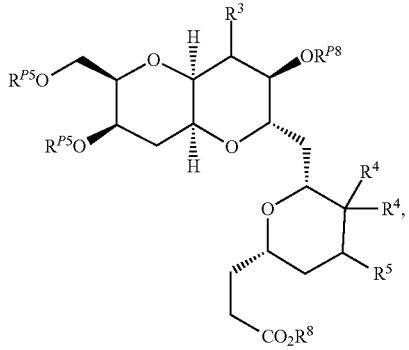
(R-4-7)

or a salt thereof, the method comprising the steps of:

(a) coupling a compound of Formula (R-4-5B):

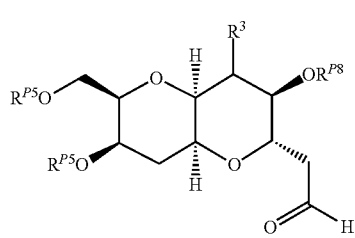
(R-4-5B)

or a salt thereof, with a compound of Formula (R-4-6):

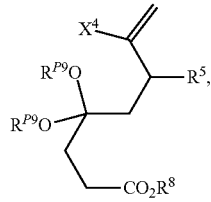
(R-4-6)

or a salt thereof, to yield a compound of Formula (R-4-7A):

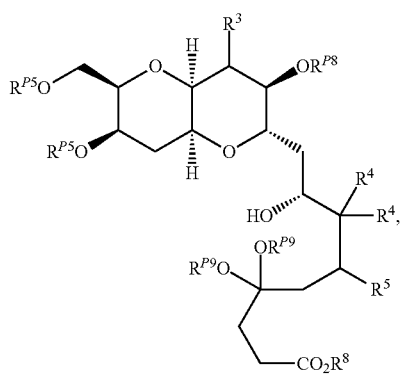
(R-4-7A)

or a salt thereof; and (a-i) deprotecting and cyclizing a compound of Formula (R-4-7A), or a salt thereof, to give a compound of Formula (R-4-7), or a salt thereof; wherein:

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

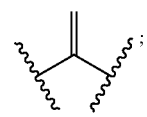

each instance of $R^{P5}$, $R^{P8}$, and $R^{P9}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and optionally, wherein two $R^{P9}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, after the step of coupling the compounds of Formulae (R-4-5B) and (R-4-6) (i.e., step (a)), the method comprises:

(b) a step of deprotecting a compound of Formula (R-4-7A), or a salt thereof, to yield a compound of Formula (R-4-7B):

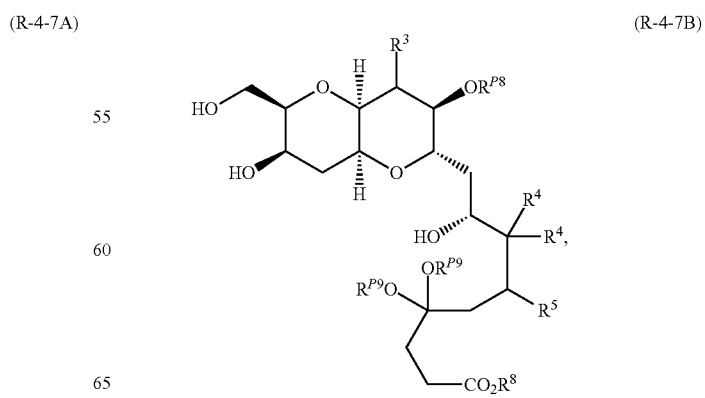
(R-4-7B)

or a salt thereof, (c) a step of cyclizing to yield a compound of Formula (R-4-7C):

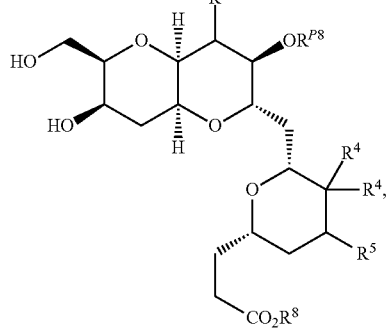
(R-4-7C)

or a salt thereof; and optionally (d) a step of re-protecting the compound of Formula (R-4-7C), or a salt thereof, at one or more oxygen atoms to yield a compound of Formula to yield a compound of Formula (R-4-7B):

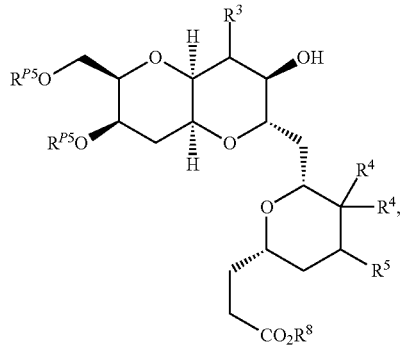
(R-4-7B)

or a salt thereof.

In certain embodiments, the method comprises:

(a) a step of coupling a compound of Formula (E-R-9):

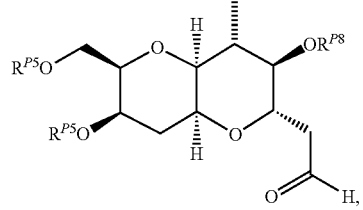
(E-R-9)

or a salt thereof, with a compound of Formula (E-R-10):

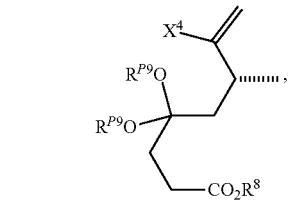
(E-R-10)

or a salt thereof, to yield a compound of Formula (E-R-11):

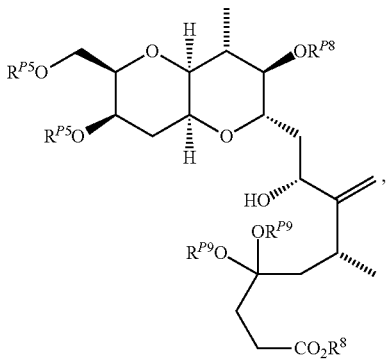
(E-R-11)

or a salt thereof;

(b) a step of deprotecting a compound of Formula (E-R-11), or a salt thereof, under conditions sufficient to remove the groups $R^{P5}$ and $R^{P8}$, to yield a compound of Formula (E-R-12):

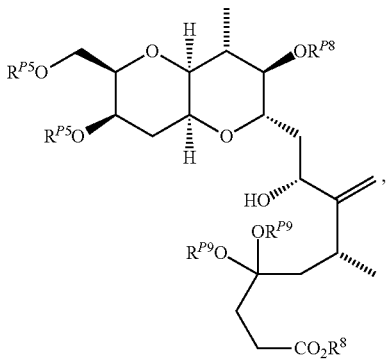
(E-R-12)

or a salt thereof; and (c) a step of deprotecting and cyclizing the compound of Formula (E-R-12), or salt thereof, to yield a compound of Formula (E-R-13):

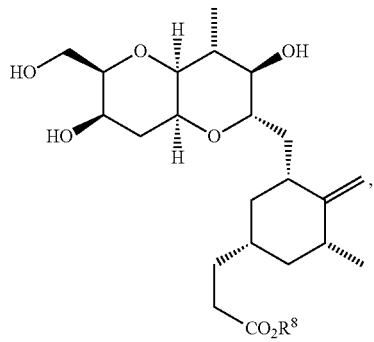

(E-R-13)

or a salt thereof;

(d) a step of protecting the compound of Formula (E-R-13), or a salt thereof, to yield a compound of Formula (E-R-14):

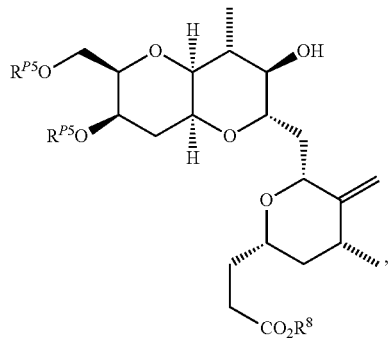

(E-R-14)

or a salt thereof, or a salt thereof; wherein:

each instance of $R^{P5}$, $R^{P8}$, and $R^{P9}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and optionally wherein two $R^{P9}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, step (a) above (to form a compound of Formula (R-4-7A), (E-R-11), or a salt thereof) is a Ni/Cr-mediated reductive coupling reaction; and step (a-i) or (c) (to form a compound of Formula (R-4-7), (E-R-13), or a salt thereof) is a ketal deprotection and an acid-promoted intramolecular pyran cyclization. Reagents and conditions for steps (a), (a-i), and/or (c) above can be found in, e.g., international PCT publications, WO 2016/176560, published Nov. 3, 2016, and WO 2016/003975, published Jan. 7, 2016; the entire contents of each of which is incorporated herein by reference.

The Ni/Cr-mediated reductive coupling (i.e., steps (a)) is carried out in the presence of nickel and chromium. In certain embodiments, the nickel is a nickel complex. Examples of nickel complexes include, but are not limited to, those shown in FIG. 9B. In certain embodiments, the nickel complex is $(Et)_2Phen.NiCl_2$. In certain embodiments, the nickel complex is the following:

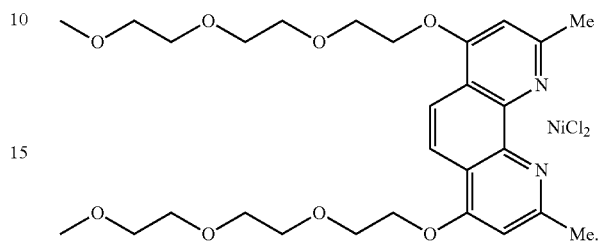

In certain embodiments, the nickel complex is present in a catalytic amount.

In certain embodiments, the chromium is a chromium complex. In certain embodiments, the chromium complex is prepared from a chromium salt and a chiral ligand. In certain embodiments, the chromium salt is $CrCl_2$ or $CrCl_3$. In certain embodiments, the chiral ligand is a chiral sulfonamide. Examples of chiral ligands include, but are not limited to, those shown in FIG. 9B. In certain embodiments, the chiral ligand is (S)-4-G. In certain embodiments, the sulfonamide ligand is one of the following:

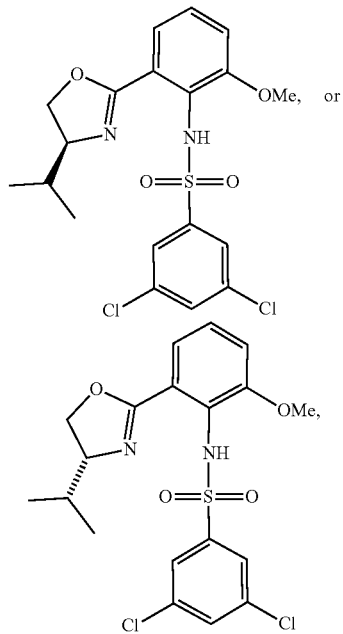

or a salt thereof. In certain embodiments, the chromium complex is present in a catalytic amount.

The Ni/Cr-mediated reductive coupling may be carried out in the presence of one or more additional reagents. In certain embodiments, the coupling is carried out in the presence of a lithium salt (e.g., LiCl). In certain embodiments, the coupling is carried out in the presence of a reducing metal such as zinc or manganese (e.g., zinc or manganese metal). In certain embodiments, the reducing metal is zinc metal. In certain embodiments, the reducing metal is manganese metal. In certain embodiments, the coupling is carried out in the presence of zirconium (e.g., ZrCp$_2$Cl$_2$). In certain embodiments, the coupling is carried out in the presence of a base or proton scavenger (e.g., 2,6-di-tert-butyl-4-methylpyridine). In certain embodiments, the coupling is carried out in the presence of a proton sponge (e.g., 1,8-bis(dimethylamino)naphthalene).

In certain embodiments, the reaction is carried out in a solvent. In certain embodiments, the solvent is MeCN. In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature. In certain embodiments, the reaction is carried out at around 40° C.

In certain embodiments, the Ni/Cr-mediated reductive coupling is carried out in the presence of a nickel complex, a chromium salt, a sulfonamide ligand, a lithium salt, a zirconium complex, a reducing metal, and a base or proton scavenger. In certain embodiments, the step of coupling is carried out in the presence of (Et)$_2$Phen.NiCl$_2$, CrCl$_2$, (S)-4-F, LiCl, manganese metal, and ZrCp$_2$Cl$_2$. For example, in certain embodiments, the reaction is carried out under the following conditions: 2 mol % (Et)$_2$Phen.NiCl$_2$, 10 mol % CrCl$_2$, 10 mol % ligand (S)-4-F, 2 equivalents LiCl, excess manganese metal, 2.5 equivalents ZrCp$_2$Cl$_2$, in MeCN at room temperature (e.g., for 3 hours).

In certain embodiments, the coupling is carried out in the presence of: a nickel complex of the formula:

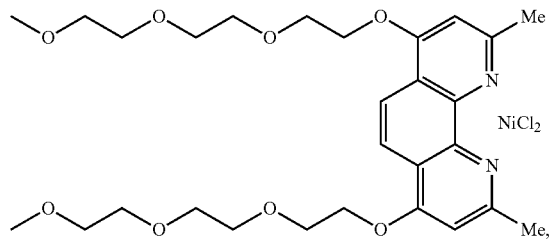

CrCl$_2$, a sulfonamide ligand of the formula:

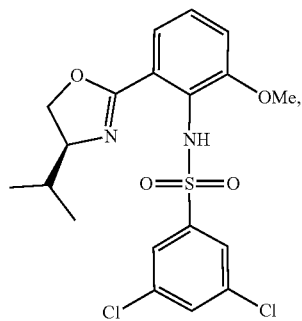 [SMILES: COc1cccc(C2=N[C@@H](C(C)C)CO2)c1NS(=O)(=O)c1cc(Cl)cc(Cl)c1]

Cp$_2$ZrCl$_2$, manganese metal, and a base or proton scavenger (e.g., 2,6-di-tert-butyl-4-methylpyridine and/or proton sponge (e.g., 1,8-Bis(dimethylamino)naphthalene)). In certain embodiments, the reaction is carried out in MeCN at around 40° C. For example, in certain embodiments, the reaction is carried out under the following conditions: 0.5 mol % or more of a nickel complex of the formula:

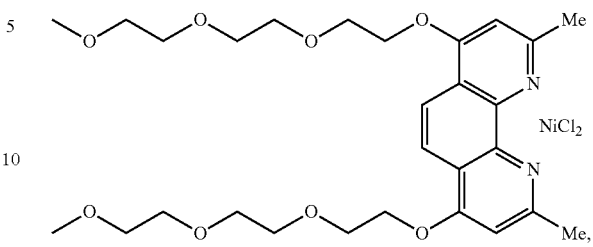

20 mol % CrCl$_2$, 20 mol % a sulfonamide ligand of the formula:

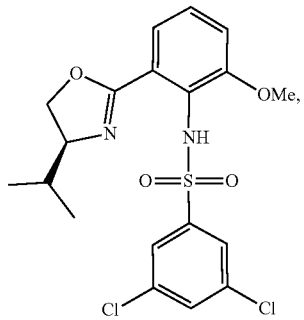 [SMILES: COc1cccc(C2=N[C@@H](C(C)C)CO2)c1NS(=O)(=O)c1cc(Cl)cc(Cl)c1]

1.1 equivalent Cp$_2$ZrCl$_2$, 4 equivalents manganese metal, and proton sponge in MeCN at around 40° C. (e.g., for 19 hours).

In certain embodiments, R$^{P5}$ and R$^{P8}$ are silyl protecting groups; and the deprotection in step (b) is carried out in the presence of a fluoride source. In certain embodiments, the fluoride source is tetrabutylammonium fluoride (TBAF).

In certain embodiments, two R$^{P5}$ are joined with the intervening atoms to form a ring of the formula:

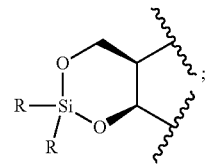

two R$^{P9}$ are joined together to form:

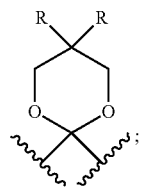

R$^{P8}$ is optionally substituted benzyl or optionally substituted silyl protecting group; and R$^8$ is optionally substituted alkyl. In certain embodiments, two R$^{P5}$ are joined with the intervening atoms to form a ring of the formula:

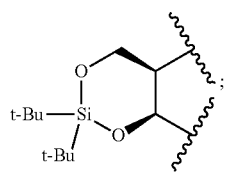 [SMILES: *[C@@H]1CO[Si](C(C)(C)C)(C(C)(C)C)O[C@@H]1*]

two $R^{P9}$ are joined together to form

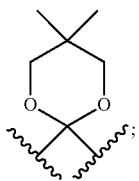

$R^{P8}$ is MPM; $R^8$ is ethyl. In certain embodiments, two $R^{P5}$ are joined with the intervening atoms to form a ring of the formula:

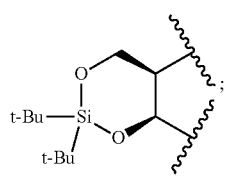 [SMILES: *[C@@H]1CO[Si](C(C)(C)C)(C(C)(C)C)O[C@@H]1*]

two $R^{P9}$ are joined together to form

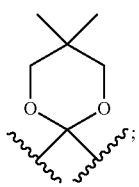

$R^{P8}$ is TBS; and $R^8$ is methyl.

The ketal deprotection and acid-promoted intramolecular pyran cyclization in steps (a-i) and (c) (to form a compound of Formula (R-4-7), (E-R-13), or a salt thereof) involves deprotecting the ketal of the starting material, followed by a cyclization reaction to provide the new six-membered ring of the compound of Formula (R-4-7) or (E-R-13). The deprotecting and cyclizing may be done in the same step, or in separate steps, and in either order. In certain embodiments, the step of deprotecting and cyclizing is carried out in the presence of an acid (e.g., Lewis acid or Brønsted acid). In certain embodiments, the acid is a Lewis acid. In certain embodiments, the step of deprotecting and cyclizing is carried out in the presence of a hydride source.

In certain embodiments, the step of deprotecting and cyclizing is carried out in the presence of a trialkylsilyl sulfonate or trialkylsilyl halide. In certain embodiments, the step of deprotecting and cyclizing is carried out in the presence of triethylsilyl trifluoromethylsulfonate (TESOTf). In certain embodiments, the step of deprotecting and cyclizing is carried out in the presence of trimethylsilyl trifluoromethylsulfonate (TMSOTf). In certain embodiments, the TESOTf or TMSOTf is present in a stoichiometric or excess amount.

In certain embodiments, the step of deprotecting and cyclizing is carried out in the presence of a trialkylsilane. In certain embodiments, the step of deprotecting and cyclizing is carried out in the presence of triethylsilane ($Et_3SiH$). In certain embodiments, the $Et_3SiH$ is present in a stoichiometric or excess amount.

In certain embodiments, the reaction is carried out in a solvent (e.g., $CH_2Cl_2$). In certain embodiments, the reaction is carried out at below room temperature. In certain embodiments, the reaction is carried out at approximately 0° C. In certain embodiments, the reaction is carried out at a temperature ranging from approximately −78° C. to approximately 0° C. In certain embodiments, the reaction is carried out at a temperature ranging from approximately −78° C. to approximately room temperature.

In certain embodiments, the step of deprotecting and cyclizing is carried out in the presence of a Lewis acid and a hydride source. In certain embodiments, the reaction is carried out in the presence of TESOTf and triethylsilane. In certain embodiments, the reaction is carried out in the presence of TESOTf and triethylsilane in DCM at around 0° C. In certain embodiments, the reaction is carried out in the presence of TMSOTf and triethylsilane. In certain embodiments, the reaction is carried out in the presence of TMSOTf and triethylsilane in DCM at a temperature ranging from approximately −78° C. to approximately 0° C. In certain embodiments, the reaction is carried out under the following conditions: 10 equivalents triethylsilane, 5 equivalents TESOTf, in DCM at around 0° C. (e.g., for 3 hours). As another example, in certain embodiments, the reaction is carried out under the following conditions: 5 equivalents triethylsilane, 5 equivalents TMSOTf, in DCM at temperature ranging from approximately −78° C. to approximately 0° C. (e.g., for 1 hour).

In certain embodiments, the step or re-protecting a compound of Formula (R-4-7C), (E-R-13), or a salt thereof (i.e., step (d)), is carried out to install the $R^{P5}$ groups. In certain embodiments, the resulting $R^{P5}$ groups are joined together to form the following formula:

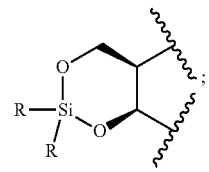

In certain embodiments, the $R^{P5}$ groups are of the following formula:

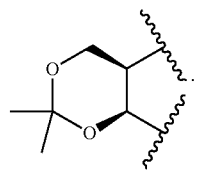

In certain embodiments, the reaction is carried out in the presence of a ketal or ketone; and an acid. In certain embodiments, the ketal is of the formula:

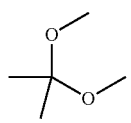

(2,2-dimethoxypropane). In certain embodiments, the acid is pyridinium p-toluenesulfonate (PPTS). In certain embodiments, the reaction is carried out in the presence of 2,2-dimethoxypropane and PPTS. In certain embodiments, the reaction is carried out in a solvent (e.g., THF). In certain embodiments, the reaction is carried out in the presence of 2,2,-dimethoxypropane and PPTS in THF at around 40° C. In certain embodiments, the protection is carried out under the following conditions: 4 equivalents 2,2,-dimethoxypropane and 5 mol % PPTS in THF at around 40° C. (e.g., for 4-5 hours).

In certain embodiments, the compound of Formula (E-R-14), (E-R-8), (R-4-7), or (R-4-7B), or salt thereof, is purified by any combination of silica gel column chromatography, ODS (octadecylsilyl) column chromatography, and recrystallization.

As also shown in Scheme 3B, provided herein is a method of preparing a compound of Formula (R-4-5B):

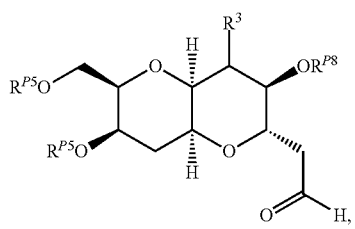

(R-4-5B)

or a salt thereof, the method comprising reducing a compound of Formula (R-4-5A):

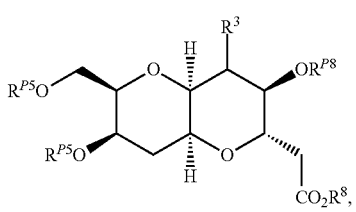

(R-4-5A)

or a salt thereof, wherein:

$R^3$ is hydrogen, halogen, or optionally substituted alkyl;

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method comprises reducing a compound of Formula (E-R-15):

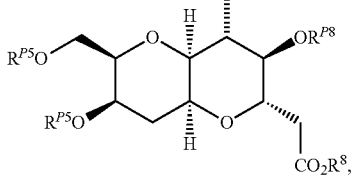

(E-R-15)

or a salt thereof, to yield a compound of Formula (E-R-9):

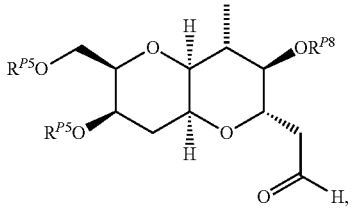

(E-R-9)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

The step of reducing a compound of (R-4-5A), (E-R-15), or a salt thereof, converts the —$CO_2R^8$ moiety to an aldehyde. In certain embodiments, the step of reducing is carried out in the presence of a hydride (i.e., H⁻) source. Any hydride source known in the art may be used in this transformation. Examples of hydride sources are provided herein. In certain embodiments, the hydride source is diisobutylaluminum hydride (DIBAL). In certain embodiments, a stoichiometric or excess amount of DIBAL is used in the reaction.

The step of reducing may optionally comprise reducing the —$CO_2R^8$ moiety to an alcohol, followed by oxidation of the resulting alcohol to an aldehyde to yield a compound of Formula (R-4-5B) or (E-R-9), or a salt thereof.

In certain embodiments, the step of reducing is carried out in the presence of DIBAL. In certain embodiments, the reaction is carried out in a solvent (e.g., DCM). In certain embodiments, the reaction is carried out at below room temperature. In certain embodiments, the reaction is carried out at around −78° C. In certain embodiments, the reaction is carried out at a temperature ranging from approximately −70° C. to approximately −78° C. In certain embodiments, the reaction is carried out at a temperature ranging from approximately −78° C. to approximately 0° C. In certain embodiments, the reaction is carried out at a temperature ranging from approximately −78° C. to approximately room temperature. For example, in certain embodiments, the reaction is carried out under the following conditions: DIBAL in DCM at −78° C. (e.g., for 1-2 hours). For example, in certain embodiments, the reaction is carried out under the following conditions: 2.3 equivalents DIBAL in DCM at −70° C. to −78° C. (e.g., for 1-2 hours).

In certain embodiments, two $R^{P5}$ are joined with the intervening atoms to form a ring of the formula:

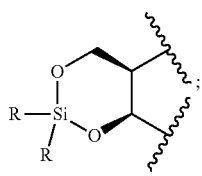

$R^{P8}$ is optionally substituted benzyl or optionally substituted silyl protecting group; and $R^8$ is optionally substituted alkyl. In certain embodiments, two $R^{P5}$ are joined with the intervening atoms to form a ring of the formula:

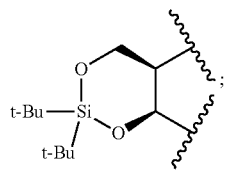 [SMILES: *[C@@H]1CO[Si](C(C)(C)C)(C(C)(C)C)O[C@@H]1*]

$R_{P8}$ is MPM; and $R^8$ is methyl. In certain embodiments, two $R^{P5}$ are joined with the intervening atoms to form a ring of the formula:

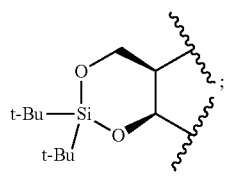 [SMILES: *[C@@H]1CO[Si](C(C)(C)C)(C(C)(C)C)O[C@@H]1*]

$R^{P8}$ is TBS; and $R^8$ is methyl.

Also provided herein is a method of preparing a compound of Formula (R-4-5A):

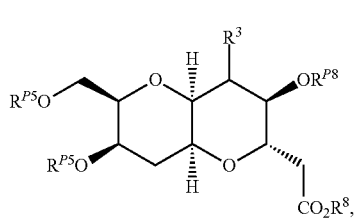

or a salt thereof, the method comprising cyclizing a compound of Formula (R-4-4):

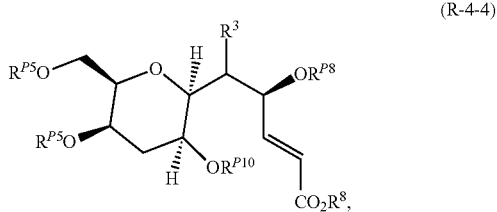

or a salt thereof, wherein:
$R^3$ is hydrogen, halogen, or optionally substituted alkyl;
each instance of $R^{P5}$, $R^{P8}$, and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and
$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method comprises a step of cyclizing a compound of Formula (E-R-16):

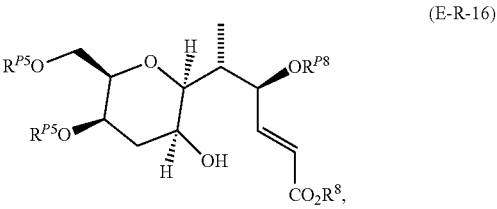

or a salt thereof, to yield a compound of Formula (E-R-15):

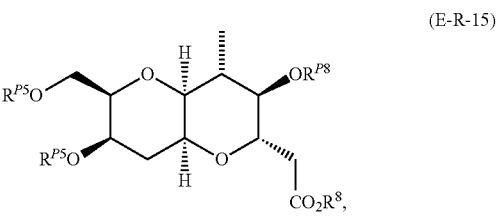

or a salt thereof, wherein:
each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and
$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (R-4-4) or (E-R-16), or a salt thereof, is carried out in the presence of a base. Any base may be used in this cyclization reaction. In certain embodiments, the base is a phosphate salt. In certain embodiments, the base is potassium phosphate ($K_3PO_4$). In certain embodiments, the base is present in 1 equivalent or less. In certain embodiments, the base is present in excess amount.

In certain embodiments, the step of cyclizing is carried out in the presence of one or more additional reagents, such as a metal chelator. In certain embodiments, the reaction is carried out in the presence of a crown ether (e.g., 18-crown-6). In certain embodiments, the reaction is carried out in the presence of 18-crown-6. In certain embodiments, 1 equivalent or less of 18-crown-6 is used.

In certain embodiment, the reaction is carried out in the presence of a solvent. In certain embodiments, the solvent is toluene and/or MeOAc. In certain embodiments, the reaction is carried out at a temperature ranging from approximately 0° C. to approximately 50° C. In certain embodiments, the reaction is carried out at from 0° C. to room temperature. In certain embodiments, the reaction is carried out at around room temperature.

In certain embodiments, the step of cyclizing is carried out in the presence of a base and a crown ether. In certain embodiments, the reaction is carried out in the presence of $K_3PO_4$ and 18-crown-6. For example, in certain embodiments, the reaction is carried out under the following conditions: 1 equivalent $K_3PO_4$, 3 equivalents 18-crown-6, in toluene at room temperature. For example, in certain embodiments, the reaction is carried out under the following conditions: 0.3 equivalents $K_3PO_4$, 0.9 equivalents 18-crown-6, in toluene and MeOAc at around 3° C. (e.g., for 1-2 hours).

In certain embodiments, the compound of Formula (R-4-4) is a compound of Formula (R-4-4A):

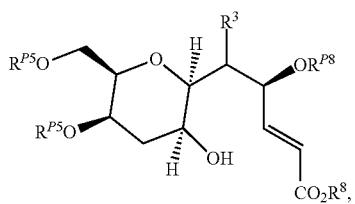

(R-4-4A)

or a salt thereof.

In certain embodiments, two $R^{P5}$ are joined with the intervening atoms to form a ring of the formula:

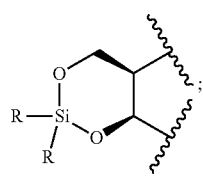

$R^{P8}$ is optionally substituted benzyl or optionally substituted silyl protecting group; and $R^8$ is optionally substituted alkyl. In certain embodiments, two $R^{P5}$ are joined with the intervening atoms to form a ring of the formula:

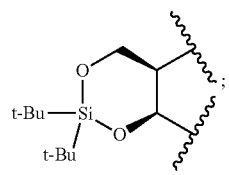 [SMILES: *[C@@H]1CO[Si](C(C)(C)C)(C(C)(C)C)O[C@@H]1*]

$R^{P8}$ is MPM; and $R^8$ is methyl. In certain embodiments, two $R^{P5}$ are joined with the intervening atoms to form a ring of the formula:

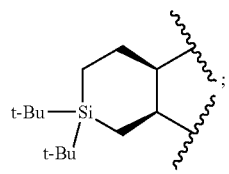 [SMILES: *[C@@H]1CC[Si](C(C)(C)C)(C(C)(C)C)C[C@@H]1*]

$R^{P8}$ is TBS; and $R^8$ is methyl.

In certain embodiments, the compound of Formula (R-4-5A) or (E-R-15), or a salt thereof, is purified by silica gel column chromatography and/or recrystallization.

Also provided herein is a method of preparing a compound of Formula (R-4-4):

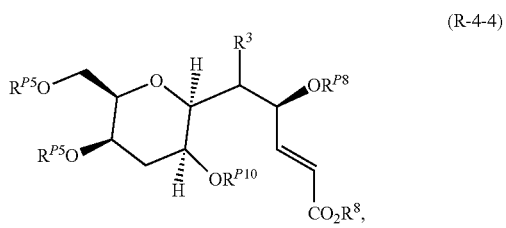

(R-4-4)

or a salt thereof, the method comprising coupling a compound of Formula (R-4-2):

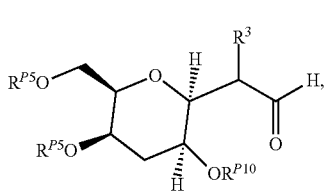

(R-4-2)

or a salt thereof, with a compound of Formula (R-4-3):

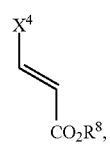

(R-4-3)

or a salt thereof, wherein:
$X^4$ is halogen or a leaving group;
$R^3$ is hydrogen, halogen, or optionally substituted alkyl;
each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the coupling of a compound of Formula (R-4-2) and a compound of Formula (R-4-3) yields a compound of the Formula (R-4-4A):

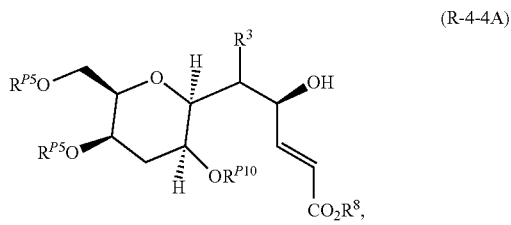

(R-4-4A)

or a salt thereof, and the method of preparing a compound of (R-4-4), or a salt thereof, comprises protecting an oxygen atom of a compound of Formula (R-4-4A), or a salt thereof (e.g., to introduce the group $R^{P8}$). The method may further comprise a step of deprotecting the compound to remove the protecting group $R^{P10}$.

In certain embodiments, the method comprises coupling a compound of Formula (E-R-17):

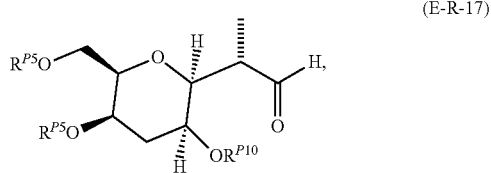

(E-R-17)

or a salt thereof, with a compound of Formula (R-4-3):

(R-4-3)

or a salt thereof, to yield a compound of Formula (E-R-18):

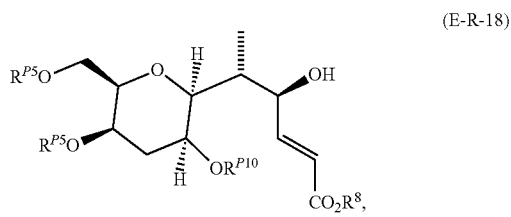

(E-R-18)

or a salt thereof, wherein:
$X^4$ is halogen or a leaving group;
$R^3$ is hydrogen, halogen, or optionally substituted alkyl;

each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method further comprising steps of (a) protecting the free hydroxyl group of the compound of Formula (E-R-18), or a salt thereof; and (b) deprotecting the resulting compound to remove the group $R^{P10}$.

In certain embodiments, the coupling of a compound of Formula (R-4-2) and a compound of Formula (R-4-3) to yield a compound of Formula (R-4-4) (or the coupling of a compound of Formula (E-R-17) and a compound of Formula (R-4-3) to yield a compound of Formula (E-R-18)) is a Ni/Cr-mediated coupling. The Ni/Cr-mediated reductive coupling is carried out in the presence of nickel and chromium. In certain embodiments, the nickel is a nickel complex. Examples of nickel complexes include, but are not limited to, those shown in FIG. 9B. In certain embodiments, the nickel complex is $(Me)_2Phen(OMe)_2 \cdot NiCl_2$. In certain embodiments, the nickel complex is present in a catalytic amount. In certain embodiments, the nickel complex is the following:

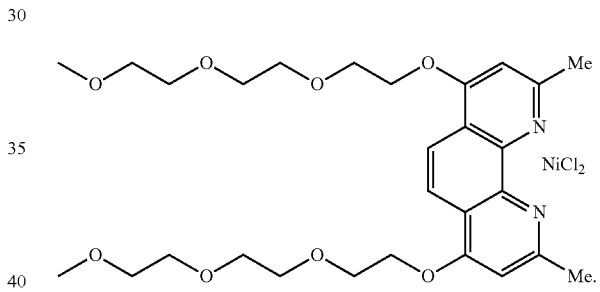

In certain embodiments, the chromium is a chromium complex. In certain embodiments, the chromium complex is prepared from a chromium salt and a chiral ligand. In certain embodiments, the chromium salt is $CrCl_3$ or $CrCl_2$. In certain embodiments, the chiral ligand is a chiral sulfonamide. Examples of chiral ligands include, but are not limited to, those shown in FIG. 9B. In certain embodiments, the chiral ligand is (R)-4-E. In certain embodiments, the chromium complex is present in a catalytic amount. In certain embodiments, the sulfonamide ligand is one of the following:

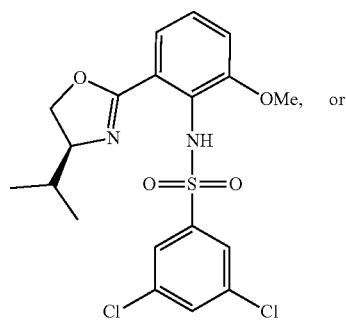

157

-continued

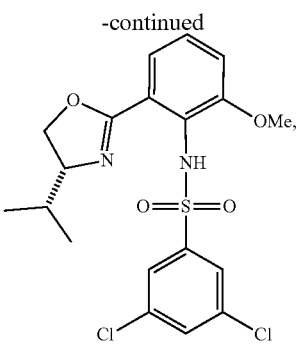

or a salt thereof.

The Ni/Cr-mediated reductive coupling may be carried out in the presence of one or more additional reagents. In certain embodiments, the coupling is carried out in the presence of a lithium salt (e.g., LiCl). In certain embodiments, the coupling is carried out in the presence of a reducing metal such as zinc or manganese (e.g., zinc or manganese metal). In certain embodiments, the coupling is carried out in the presence of zirconium (e.g., ZrCp$_2$Cl$_2$). In certain embodiments, the coupling is carried out in the presence of a base or proton scavenger (e.g., 2,6-di-tert-butyl-4-methylpyridine or 2,6-lutidine). In certain embodiments, the coupling is carried out in the presence of proton sponge (e.g., 1,8-bis(dimethylamino)naphthalene).

In certain embodiments, the reaction is carried out in a solvent (e.g., MeCN). In certain embodiments, the reaction is carried out at a temperature ranging from approximately room temperature to approximately 100° C. In certain embodiments, the reaction is carried out at a temperature ranging from approximately room temperature to approximately 50° C. In certain embodiments, the reaction is carried out at around room temperature. In certain embodiments, the reaction is carried out at around 30° C.

In certain embodiments, the Ni/Cr-mediated reductive coupling is carried out in the presence of a nickel complex, a chromium salt, a sulfonamide ligand, a lithium salt, a zirconium complex, a reducing metal, and a base or proton scavenger. In certain embodiments, the step of coupling is carried out in the presence of (Me)$_2$Phen(OMe)$_2$.NiCl$_2$, CrCl$_2$, ligand (S)-4-E, LiCl, manganese metal, 2,6-lutidine, and ZrCp$_2$Cl$_2$. In certain embodiments, the reaction is carried out in a solvent (e.g., MeCN). In certain embodiments, the reaction is carried out at around room temperature. For example, in certain embodiments, the reaction is carried out under the following conditions: 2 mol % (Me)$_2$Phen(OMe)$_2$.NiCl$_2$, 10 mol % CrCl$_2$, 10 mol % ligand (S)-4-E, 2 equivalents LiCl, 1.1 equivalents Cp$_2$ZrCl$_2$, 1 equivalent 2,6-lutidine, and excess manganese in MeCN at room temperature.

In certain embodiments, the coupling is carried out in the presence of: a nickel complex of the formula:

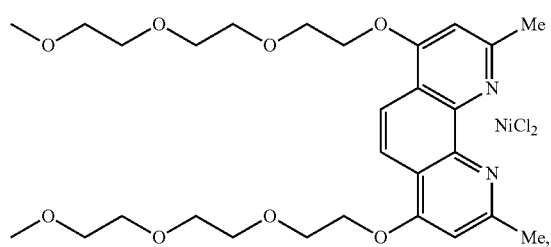

158

CrCl$_2$, a sulfonamide ligand of the formula:

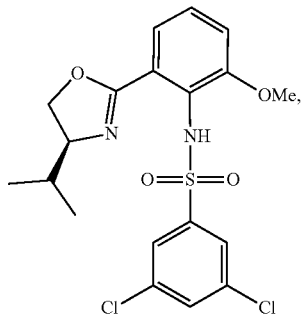 [SMILES: COc1cccc(C2=N[C@@H](C(C)C)CO2)c1NS(=O)(=O)c1cc(Cl)cc(Cl)c1]

Cp$_2$ZrCl$_2$, manganese metal, and a base or proton scavenger (e.g., 2,6-lutidine and/or proton sponge (e.g., 1,8-bis(dimethylamino)naphthalene)). For example, in certain embodiments, the reaction is carried out under the following conditions: 0.5 mol % of a nickel complex of the formula:

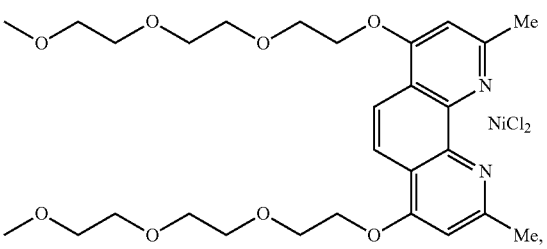

20 ml % CrCl$_2$, 20 mol % of a sulfonamide ligand of the formula:

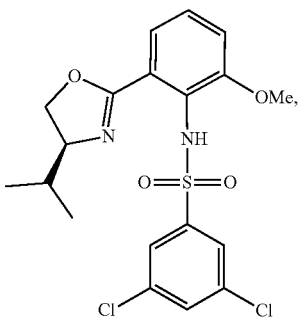 [SMILES: COc1cccc(C2=N[C@@H](C(C)C)CO2)c1NS(=O)(=O)c1cc(Cl)cc(Cl)c1]

1.1 equivalents Cp$_2$ZrCl$_2$, 4 equivalents manganese metal, 2 equivalents 2,6-lutidine, and proton sponge in MeCN at around 30° C. (e.g., for 2-3 hours).

In certain embodiments, two $R^{P5}$ are joined with the intervening atoms to form a ring of the formula:

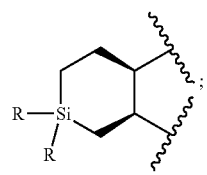

$R^{P8}$ is optionally substituted benzyl or optionally substituted silyl protecting group; $R^8$ is optionally substituted alkyl; and $R^{P10}$ is a silyl protecting group. In certain embodiments, two $R^{P5}$ are joined with the intervening atoms to form a ring of the formula:

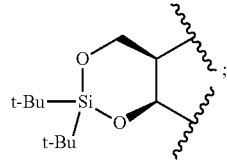 [SMILES: *[C@@H]1CO[Si](C(C)(C)C)(C(C)(C)C)O[C@@H]1*]

$R^{P8}$ is MPM; $R^8$ is methyl; and $R^{P10}$ is TES. In certain embodiments, two $R^{P5}$ are joined with the intervening atoms to form a ring of the formula:

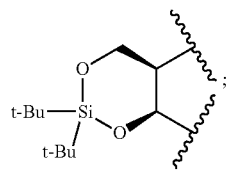 [SMILES: *[C@@H]1CO[Si](C(C)(C)C)(C(C)(C)C)O[C@@H]1*]

$R^{P8}$ is TBS; $R^8$ is methyl; and $R^{P10}$ is TES.

Provided herein a method of preparing a compound of Formula (R-4-2):

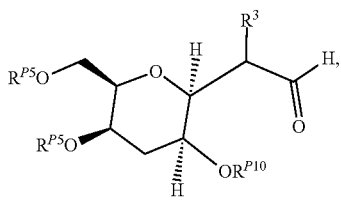

(R-4-2)

or a salt thereof, the method comprising reducing a compound of Formula (R-4-1):

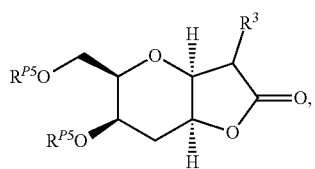

(R-4-1)

or a salt thereof, wherein:

$R^3$ is hydrogen, halogen, or optionally substituted alkyl; and each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

In certain embodiments, the method of preparing a compound of Formula (R-4-2), or a salt thereof, comprises the steps of:

(a) reducing a compound of Formula (R-4-1):

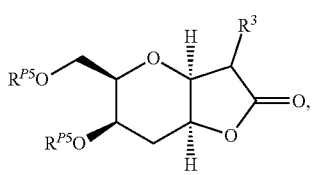

(R-4-1)

or a salt thereof, to yield a compound of Formula (R-4-1A):

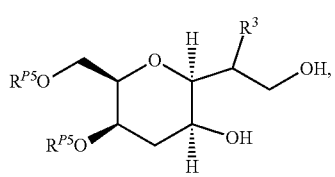

(R-4-1A)

or a salt thereof;

(b) protecting a compound of Formula (R-4-1), or a salt thereof, to yield a compound of Formula (R-4-1B):

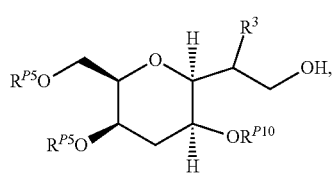

(R-4-1B)

or a salt thereof; and (c) oxidizing the compound of Formula (R-4-1B), or a salt thereof, to yield a compound of Formula (R-4-2), or a salt thereof.

The step of reducing a compound of (R-4-2), or a salt thereof, reduces the lactone of the compound. In certain embodiments, the step of reducing is carried out in the presence of a hydride (i.e., H⁻) source. Any hydride source known in the art may be used in this transformation. Examples of hydride sources are provided herein. In certain embodiments, the hydride source is lithium borohydride (LiBH$_4$). In certain embodiments, the step of oxidizing (i.e., step (c)) involves a Swern oxidation.

In certain embodiments, the step of reducing is carried out in the presence of LiBH$_4$. In certain embodiments, the reaction is carried out in a solvent such as diethyl ether. In certain embodiments, the reaction is carried out at approximately 0° C. For example, in certain embodiments, the reaction is carried out under the following conditions: LiBH$_4$ in diethyl ether at 0° C.

In certain embodiments, two $R^{P5}$ are joined with the intervening atoms to form a ring of the formula:

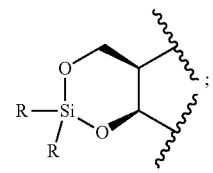

and $R^{P10}$ is a silyl protecting group. In certain embodiments, two $R^{P5}$ are joined with the intervening atoms to form a ring of the formula:

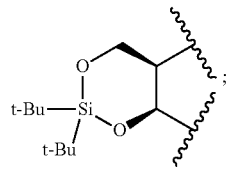 [SMILES: *[C@@H]1CO[Si](C(C)(C)C)(C(C)(C)C)O[C@@H]1*]

and $R^{P10}$ is TES.

Also provided herein is an alternative method of preparing a compound of Formula (R-4-2), or a salt thereof, comprising:

(a) a step of reducing a compound of Formula (R-4-1):

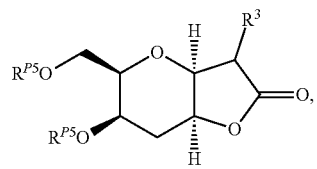
(R-4-1)

or a salt thereof, to yield a compound of Formula (R-4-2):

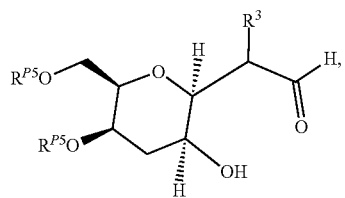
(R-4-2A)

or a salt thereof;

(b) a step of olefinating the compound of Formula (R-4-2A), or a salt thereof, to yield a compound of Formula (R-4-2B):

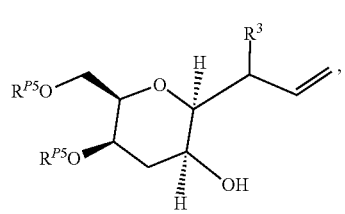
(R-4-2B)

or a salt thereof;

(c) a step of protecting the compound of Formula (R-4-2B), or salt thereof, to yield a compound of Formula (R-4-2C):

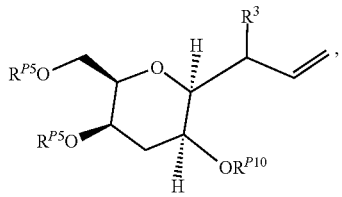
(R-4-2C)

or a salt thereof; and (d) a step of oxidizing a compound of Formula (R-4-2C), or a salt thereof, to yield a compound of Formula (R-4-2):

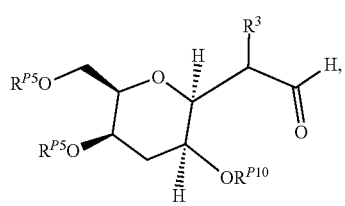
(R-4-2)

or a salt thereof, wherein:

$R^3$ is hydrogen, halogen, or optionally substituted alkyl; and each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

In certain embodiments, the method comprises:

(a) a step of reducing a compound of Formula (E-R-19):

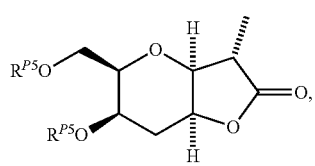
(E-R-19)

or a salt thereof, to yield a compound of Formula (E-R-20):

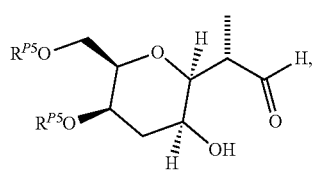
(E-R-20)

or a salt thereof;

(b) a step of olefinating the compound of Formula (E-R-20), or a salt thereof, to yield a compound of Formula (E-R-21):

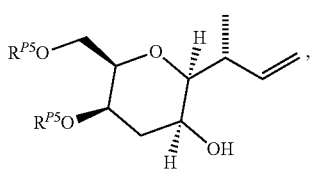

(E-R-21)

or a salt thereof;

(c) a step of protecting the compound of Formula (E-R-21), or salt thereof, to yield a compound of Formula (E-R-22):

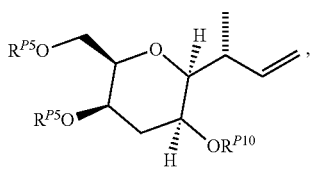

(E-R-22)

or a salt thereof; and (d) a step of oxidizing a compound of Formula (E-R-22), or a salt thereof, to yield a compound of Formula (E-R-17):

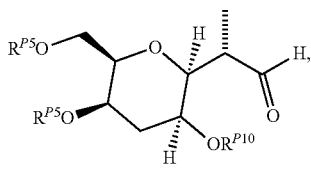

(E-R-17)

or a salt thereof, wherein:

each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

In certain embodiments, the step of reducing a compound of Formula (R-4-1), (E-R-19), or a salt thereof (i.e., step (a)), is carried out in the presence of a hydride source. Examples of hydride sources are provided herein. In certain embodiments, the hydride source is lithium borohydride (LiBH$_4$). In certain embodiments, the hydride source is diisobutylaluminum hydride (DIBAL). In certain embodiments, the reaction is carried out in a solvent (e.g., toluene). In certain embodiments, the reaction is carried out in the presence of DIBAL in toluene. In certain embodiments, the reaction is carried out at a temperature ranging from approximately room temperature to approximately −78° C. to approximately 0° C. In certain embodiments, the reaction is carried out under the following conditions: approximately 1.3 equivalents of DIBAL in toluene at from −78 to −60° C. (e.g., for less than 1 hour).

In certain embodiments, the step of olefinating a compound of Formula (R-4-2A), (E-R-20), or a salt thereof (i.e., step (b)), is carried out in the presence of an olefinating reagent and a base. In certain embodiments, the olefinating reagent is Ph$_3$PCH$_3$Br. In certain embodiments, the base is an alkoxide. In certain embodiments, the base is t-BuOK. In certain embodiments, the step of olefinating is carried out in the presence of Ph$_3$PCH$_3$Br and t-BuOK. In certain embodiments, the reaction is carried out in a solvent (e.g., THF). In certain embodiments, the reaction is carried out at a temperature ranging from approximately 0° C. to approximately room temperature. In certain embodiments, the step of olefinating is carried out under the following conditions: 4 equivalents Ph$_3$PCH$_3$Br, 3 equivalents t-BuOK, in THF at from 0 to 10° C. (e.g., for less than 1 hour).

In certain embodiments, $R^{P10}$ is a silyl protecting group; and the step (c) of protecting is carried out in the presence of a silylating reagent and an amine base. In certain embodiments, $R^{P10}$ is TES; and the silylating reagent is TESOTf. In certain embodiments, the amine base is triethylamine (TEA). In certain embodiments, the step of protecting is carried out in the presence of TESOTf and TEA. In certain embodiments, the reaction is carried out at a temperature ranging from approximately 0° C. to approximately room temperature. In certain embodiments, the step of protecting is carried out in the presence of TESOTf and TEA in THF at from 0 to 10° C. (e.g., for less than 1 hour).

In certain embodiments, the step of oxidizing a compound of Formula (R-4-2C), (E-R-22), or a salt thereof, is a Johnson-Lemieux oxidative cleavage. For example, in certain embodiments, the reaction is carried out in the presence of osmium tetroxide (OsO$_4$) or K$_2$OsO$_4$; and N-Methylmorpholine N-oxide (NMO). In certain embodiments, the reaction is carried out in the presence of sodium periodate (NaIO$_4$) or lead acetate Pb(OAc)$_4$. In certain embodiments, the reaction is carried out in the presence of osmium tetroxide (OsO$_4$) and N-Methylmorpholine N-oxide (NMO), followed by sodium periodate (NaIO$_4$). In certain embodiments, the step of oxidizing is carried out in the presence of THF, acetone, and/or water. In certain embodiments, the reaction is carried out at a temperature ranging from approximately 0° C. to approximately 50° C. For example, in certain embodiments, the step of oxidizing is carried out under the following conditions: 25 equivalents OsO$_4$ and 3 equivalents NMO in THF/acetone/water at room temperature (e.g., for 19 hours), followed by the addition of 3 equivalents NaIO$_4$ at room temperature (e.g., for less than 1 hour).

Preparation of Left Halves

As described herein, preparation of halichondrin natural products and analogs thereof may comprise a coupling of a "left half" fragment with a "right half" fragment. Methods useful in the preparation of right half building blocks are provided above. In another aspect, the present invention provides "left hand" building blocks, and methods useful in their preparation.

Preparation of Left Halves of Halichondrins

Provided herein are methods useful in the preparation of "left half" building blocks of halichondrins and analogs thereof. For example, left halves of compounds in the halichondrin series (e.g., halichondrin A, B, C, and analogs thereof) may be prepared as shown in Scheme 4A. For example, a left half building block of Formula (L-2-14) can be prepared by thiolation of a compound of Formula (L-5-17), which can be prepared by cyclizing a compound of Formula (L-5-16B). To this end, a compound of Formula (L-5-16B) can be prepared by cyclization of a compound of Formula (L-5-16A), which can be prepared from an intermediate of Formula (L-5-15) via oxidation and olefination. As also shown in Scheme 4A, an intermediate of Formula (L-5-15) can be prepared by rearrangement of a compound of Formula (L-5-14). A compound of Formula (L-5-14) can be prepared by coupling a compound of Formula (L-5-12) with a compound of Formula (L-5-5). A compound of Formula (L-5-12) can be prepared by epoxidation of a compound of Formula (L-5-11), which may be prepared by coupling a compound of Formula (L-5-10) with a compound of Formula (L-5-9).

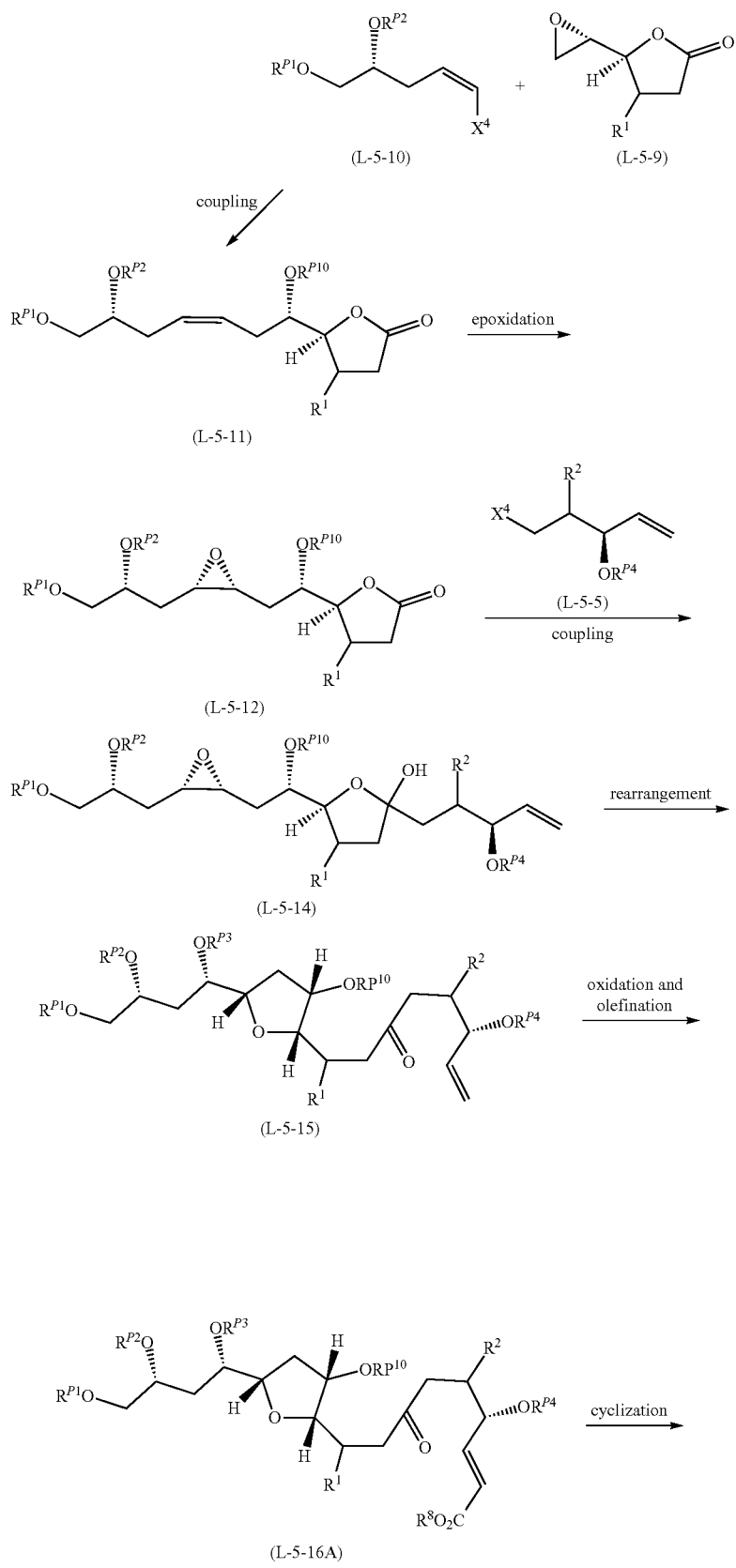

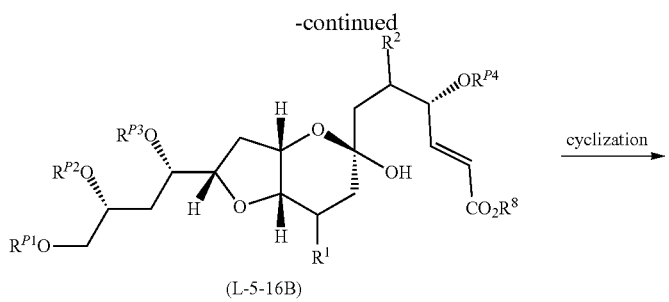

(L-5-16B)

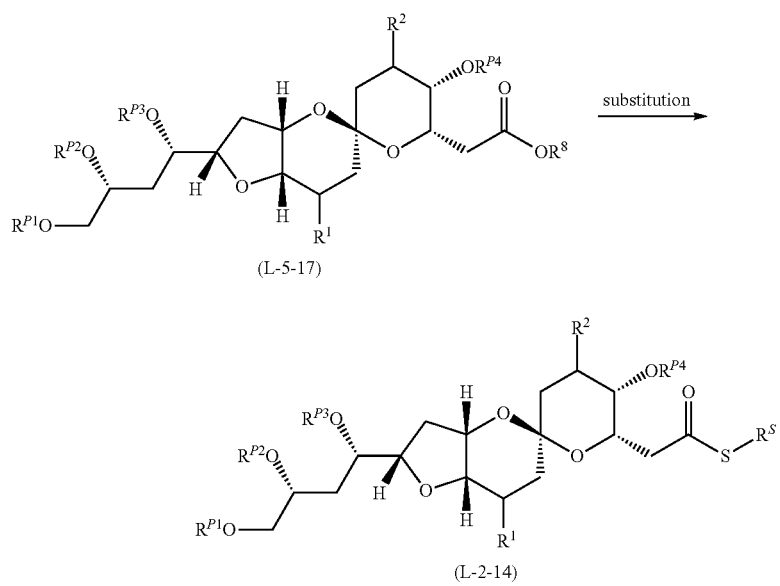

(L-5-17)

(L-2-14)

As shown in Scheme 4A, provided herein is a method of preparing a compound of Formula (L-2-14):

(L-2-14)

or a salt thereof, the method comprising a step of reacting a compound of Formula (L-5-17):

(L-5-17)

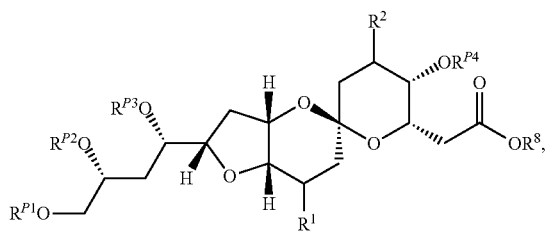

or a salt thereof, in the presence of a thiolating agent; wherein:

$R^S$ is optionally substituted alkyl, optionally substituted carbocyclyl, optionally substituted aryl, optionally substituted heterocyclyl, or optionally substituted heteroaryl;

$R^1$ and $R^2$ are independently hydrogen, halogen, or optionally substituted alkyl;

$R^{P1}$, $R^{P2}$, $R^{P3}$, and $R^{P4}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

As described herein, the step of forming a compound of Formula (L-2-14) comprises reacting a compound of Formula (L-5-17) in the presence of a thiolating agent. Any thiolating agent known in the art may be used to this end. In certain embodiments, the thiolating agent is a disulfide. In certain embodiments, the thiolating agent is of the formula $(R^S S)_2$. In certain embodiments, the thiolating agent is of the formula $(pyridine-S)_2$. In certain embodiments, the thiolating agent is:

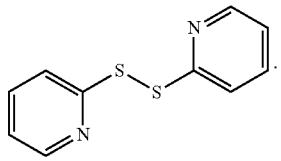

(Py-S)₂

In certain embodiments, the step of thiolating a compound of Formula (L-5-17) is carried out in the presence of one of more additional reagents. In certain embodiments, the step of thiolating is carried out in the presence of a phosphine reagent (e.g., triphenylphosphine (Ph₃P)).

In certain embodiments, the step of thiolating is carried out in the presence of a disulfide and a phosphine. In certain embodiments, the reaction is carried out in the presence of (Py-S)₂ and Ph₃P. In certain embodiments, the reaction is carried out in a solvent such as CH₂Cl₂. In certain embodiments, the reaction is carried out at a temperature ranging from approximately 0° C. to approximately 50° C. In certain embodiments, the reaction is carried out at room temperature. For example, in certain embodiments, the step of thiolating is carried out under the following conditions: 1.4 equivalents of (Py-S)₂, 1.2 equivalents of Ph₃P, in CH₂Cl₂ at room temperature (e.g., for 10-20 hours).

In certain embodiments, the method of thiolating a compound of Formula (L-5-17), or a salt thereof, comprises the steps of:

(a) deprotecting a compound of Formula (L-5-17), or a salt thereof, to yield a compound of Formula (L-5-17B):

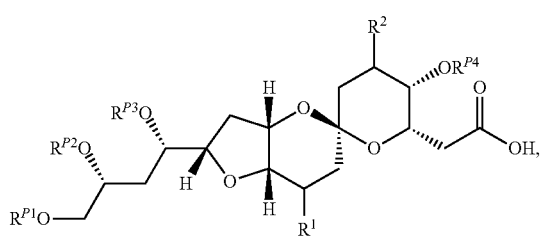

(L-5-17B)

or a salt thereof; and (b) thiolating a compound of Formula (L-5-17B), or a salt thereof, to yield a compound of Formula (L-2-14), or a salt thereof.

In certain embodiments, $R^{P1}$, $R^{P2}$, $R^{P3}$, and $R^{P4}$ are silyl protecting groups. In certain embodiments, $R^{P1}$ and $R^{P2}$ are TBS; and $R^{P3}$ and $R^{P4}$ are TES.

As also shown in Scheme 4A, provided herein is a method of preparing a compound of Formula (L-5-17):

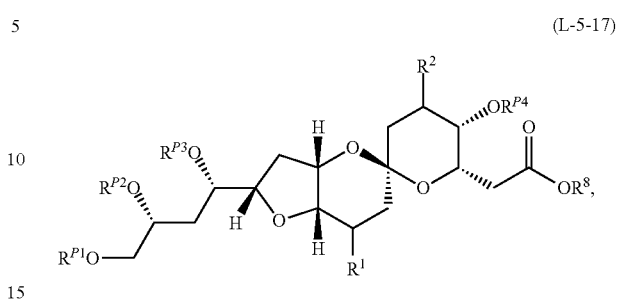

(L-5-17)

or a salt thereof, the method comprising a step of cyclizing a compound of Formula (L-5-16B):

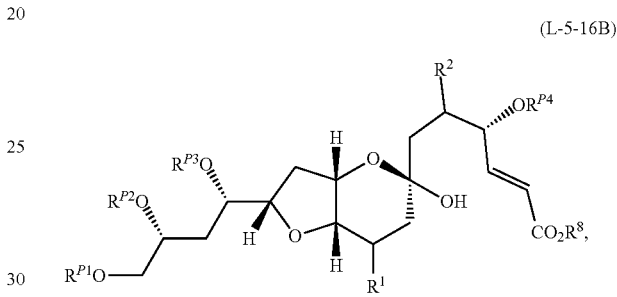

(L-5-16B)

or a salt thereof; wherein:

$R^1$ and $R^2$ are independently hydrogen, halogen, or optionally substituted alkyl;

$R^{P1}$, $R^{P2}$, $R^{P3}$, and $R^{P4}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (7-5-16B) is carried out in the presence of a base. In certain embodiments, the base is a nitrogen base. In certain embodiments, the base is an amine or amide base. In certain embodiments, the base is an amidine or guanidine base. In certain embodiments, the base is an amidine base (e.g., 1,8-diazabicyclo(5.4.0)undec-7-ene (DBU)). In certain embodiments, the step of cyclizing is carried out in the presence of an acid. In certain embodiments, the acid is a Lewis acid. In certain embodiments, the acid is a Brønsted acid.

In certain embodiments, the step of cyclizing is carried out in the presence of a lithium salt (e.g., LiBr, LiCl). The step of cyclizing may be carried out in the presence of one or more additional reagents. In certain embodiments, the step of cyclizing is carried out in the presence of $R^8$—OAc. In certain embodiments, the step of cyclizing is carried out in the presence of BnOAc.

In certain embodiments, the step of cyclizing is carried out in the presence of a lithium salt, and a base. In certain embodiments, the step of cyclizing is carried out in the presence of LiBr and DBU. In certain embodiments, the reaction is carried out in a solvent such as MeCN. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 10 equivalents LiBr, 5 equivalents DBU, and 10 equivalents BnOAc in MeCN at room temperature (e.g., for 10-20 hours).

In certain embodiments, $R^{P1}$, $R^{P2}$, and $R^{P3}$ are silyl protecting groups; and $R^{P4}$ and $R^{P8}$ are optionally substituted benzyl. In certain embodiments, $R^{P1}$ and $R^{P2}$ are TBS; $R^{P3}$ is TES; $R^{P4}$ is MPM; and $R^8$ is benzyl.

In certain embodiments, the compound of Formula (L-5-17), or a salt thereof, is deprotected to remove the group $R^{P4}$ yield a compound of Formula (L-5-17C):

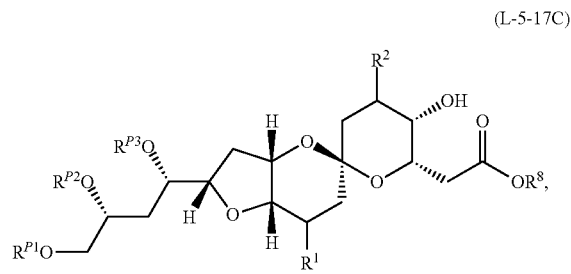

(L-5-17C)

or a salt thereof; and optionally re-protecting (i.e., to switch the group R from, e.g., a benzyl protecting group (e.g., MPM) to a silyl protecting group (e.g., trialkylsilyl such as triethylsilyl).

Provided herein is a method of preparing a compound of Formula (L-5-16B):

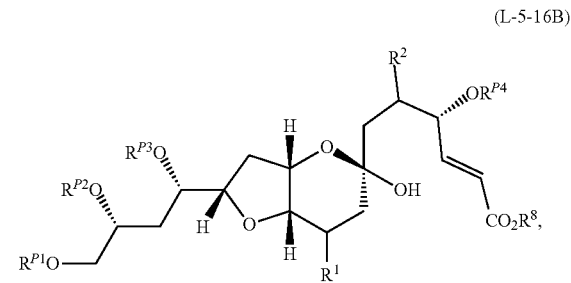

(L-5-16B)

or a salt thereof, the method comprising the steps of:
(a) cyclizing a compound of Formula (L-5-15):

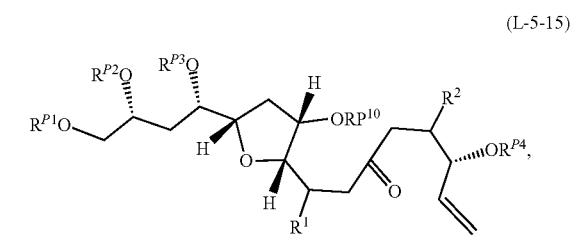

(L-5-15)

or a salt thereof, to give a compound of Formula (L-5-15B):

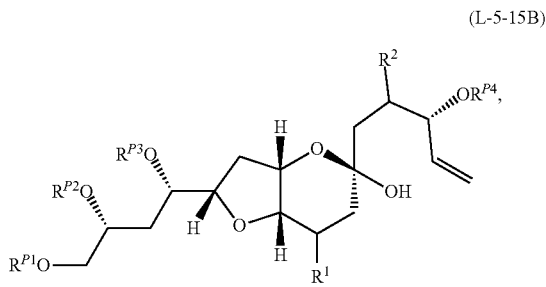

(L-5-15B)

or a salt thereof; and (b) reacting the compound of Formula (L-5-15B), or a salt thereof, in the presence of an olefin and an olefin metathesis catalyst to yield a compound of Formula (L-5-16B), wherein:

$R^1$ and $R^2$ are independently hydrogen, halogen, or optionally substituted alkyl; and $R^{P1}$, $R^{P2}$, $R^{P3}$, $R^{P4}$, and $R^{P10}$ are independently hydrogen, optionally substituted alkyl, optionally substituted acyl, or an oxygen protecting group.

In certain embodiments, the olefin is of the formula:

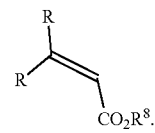

Furthermore, any olefin metathesis catalyst known in the art may be used in the metathesis reaction to furnish a compound of Formula (L-5-16B).

In certain embodiments, $R^{P1}$, $R^{P2}$, $R^{P10}$, and $R^{P3}$ are silyl protecting groups; and $R^{P4}$ is optionally substituted benzyl. In certain embodiments, $R^{P1}$ and $R^{P2}$ are TBS; $R^{P3}$ is TES; $R^{P4}$ is MPM; and $R^{P10}$ is TES.

Provided herein is a method of preparing a compound of Formula (L-5-16B):

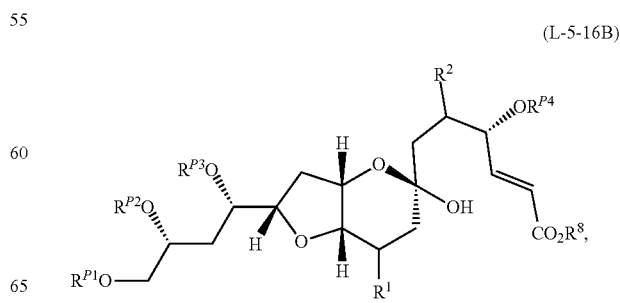

(L-5-16B)

or a salt thereof, the method comprising a step of cyclizing a compound of Formula (L-5-16A):

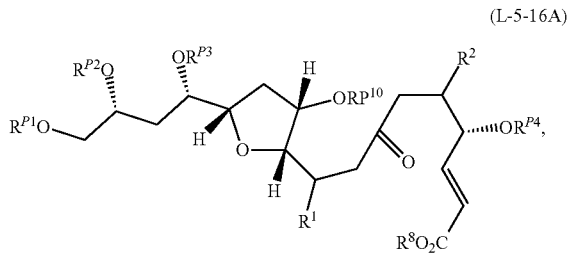
(L-5-16A)

or a salt thereof, wherein:

$R^1$ and $R^2$ are independently hydrogen, halogen, or optionally substituted alkyl;

$R^{P1}$, $R^{P2}$, $R^{P3}$, $R^{P4}$, and $R^{P10}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (L-5-16A), or a salt thereof, is carried out in the presence of a base. In certain embodiment, the step of cyclizing is carried out in the presence of an acid (e.g., Lewis acid or Brønsted acid). In certain embodiments, the acid is a phosphoric acid. In certain embodiments, the acid is diphenylphosphate ((PhO)$_2$P(=O)OH). In certain embodiments, the acid is present in catalytic, stoichiometric, or excess amount relative to the compound of Formula (L-5-16A). In certain embodiments, the acid is present in catalytic amount (e.g., approximately 5 mol %).

In certain embodiments, the step of cyclizing is carried out in the presence of diphenylphosphate. In certain embodiments, the step of cyclizing is carried out in a solvent such as THF, or a mixture of THF and H$_2$O. In certain embodiments, the reaction is carried out at a temperature ranging from approximately 0° C. to approximately 50° C. In certain embodiments, the reaction is carried out at around room temperature. For example, in certain embodiments, the reaction is carried out under the following conditions: 5 mol % diphenylphosphate in THF-H$_2$O at room temperature (e.g., for approximately 24 hours).

Also provided herein is a method of preparing a compound of Formula (L-5-16A):

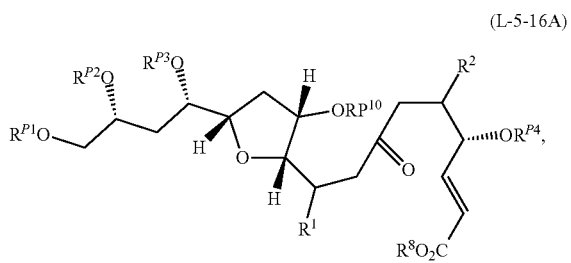
(L-5-16A)

or a salt thereof, the method comprising the steps of:
(a) oxidizing a compound of Formula (L-5-15):

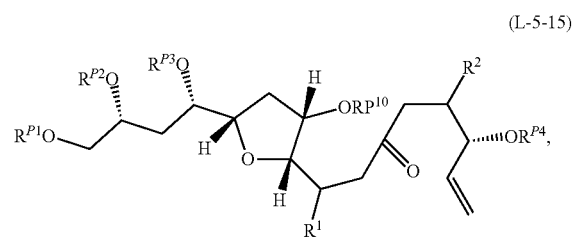
(L-5-15)

or a salt thereof, to yield a compound of Formula (L-5-15B) or (L-5-15BB):

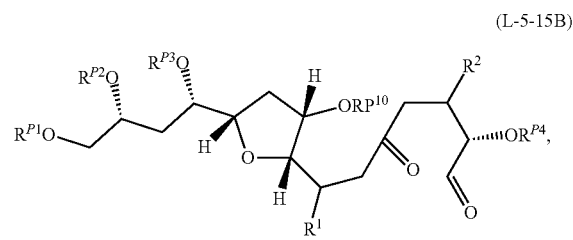
(L-5-15B)

(L-5-15BB)

or a salt thereof; and
(b) reacting the compound of Formula (L-5-15B) or (L-5-15BB), or a salt thereof, in the presence of a olefination reagent, to yield a compound of Formula (L-5-15C):

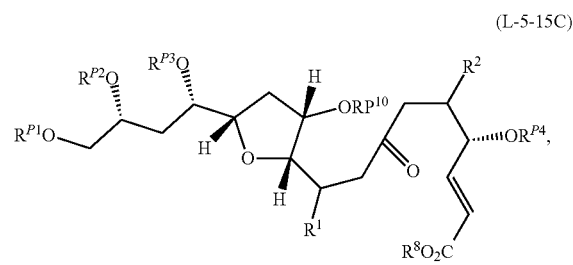
(L-5-15C)

or a salt thereof, wherein:

$R^1$ and $R^2$ are independently hydrogen, halogen, or optionally substituted alkyl;

$R^{P1}$, $R^{P2}$, $R^{P3}$, $R^{P4}$, and $R^{P10}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

The reaction in step (a) above is an oxidative cleavage; the reaction in step (b) is an olefination reaction. In certain embodiments, the oxidative cleavage is carried out via ozonolysis (e.g., in the presence of O₃). In certain embodiments, the cleavage is carried out in the presence of one or more reagents capable of dihydroxylating a double bond (e.g., osmium tetroxide (OsO₄), N-methylmorpholine N-oxide (NMMO)), followed by a transition metal (e.g., a lead complex such as Pb(OAc)₄). In certain embodiments, the double bond is dihydroxylated by treatment with OsO₄, NMMO, and water. In certain embodiments, the reaction is carried out in the presence of a solvent such as acetone. In certain embodiments, the reaction is carried out at a temperature ranging from approximately 0° C. to approximately 50° C. In certain embodiments, the reaction is carried out at room temperature. For example, in certain embodiments, the double bond is dihydroxylated under the following conditions: 10 mol % OsO₄, 2 equivalents NMMO, and water, in acetone at room temperature (e.g., for 20-25 hours). The resulting compound is then treated, in certain embodiments, with Pb(OAc)₄ and K₂CO₃ to yield the aldehyde or hemiacetal. For example, in certain embodiments, this step is carried out under the following conditions: 1.2 equivalents Pb(OAc)₄, 3 equivalents K₂CO₃, in CH₂Cl₂ at room temperature (e.g., for approximately 1 hour).

In certain embodiments, the olefination is carried out in the presence of a Wittig or Horner-Wadsworth Emmons reagent. In certain embodiments, the olefination is carried out in the presence of a reagent of the formula: (RO)₂P(O)CH₂CO₂R⁸. In certain embodiments, the reagent is of the formula: (MeO)₂P(O)CH₂CO₂R⁸ (e.g., (MeO)₂P(O)CH₂CO₂Bn). In certain embodiments, the olefination is carried out in the presence of a base (e.g., a phosphate salt such as K₃PO₄).

In certain embodiments, the olefination is carried out in the presence of an olefination reagent of the formula: (RO)₂P(O)CH₂CO₂R⁸, and a base. In certain embodiments, the olefination is carried out in the presence of (MeO)₂P(O)CH₂CO₂Bn and K₃PO₄. In certain embodiments, the reaction is carried out in a solvent such as toluene. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 4 equivalents (MeO)₂P(O)CH₂CO₂Bn, 3 equivalents K₃PO₄, in toluene at room temperature (e.g., for about 20-25 hours).

In certain embodiments, $R^{P1}$, $R^{P2}$, $R^{P3}$, and $R^{P10}$ are silyl protecting groups; and $R^{P4}$ and $R^8$ are optionally substituted benzyl. In certain embodiments, $R^{P1}$ and $R^{P2}$ are TBS; $R^{P3}$ and $R^{P10}$ are TES; $R^{P4}$ is MPM; and $R^8$ is benzyl.

Provided herein is a method of preparing a compound of Formula (L-5-15):

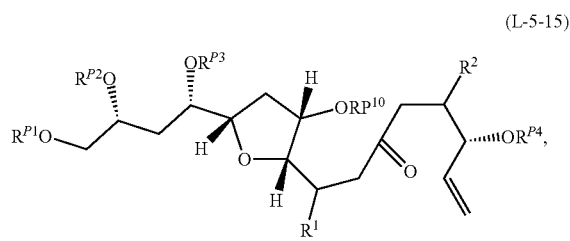

(L-5-15)

or a salt thereof, the method comprising a step of reacting a compound of Formula (L-5-14):

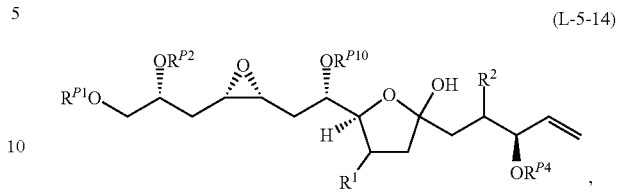

(L-5-14)

or a salt thereof, in the presence of an acid or a base, wherein:

$R^1$ and $R^2$ are independently hydrogen, halogen, or optionally substituted alkyl; and $R^{P1}$, $R^{P2}$, $R^{P3}$, $R^{P4}$, and $R^{P10}$ are independently hydrogen, optionally substituted alkyl, optionally substituted acyl, or an oxygen protecting group.

As described above, the method of forming a compound of Formula (L-5-15), or a salt thereof, involves reacting a step of reacting a compound of Formula (L-5-14), or a salt thereof, in the presence of an acid or a base. In certain embodiments, an acid is used. The acid may be a Lewis acid or a Brønsted acid. In certain embodiments, the acid is a Brønsted acid. In certain embodiments, the acid is a phosphoric acid (e.g., phosphoric acid, diphenylphosphate). In certain embodiments, the acid is diphenylphosphate ((PhO)₂P(=O)OH). In certain embodiments, the reaction is carried out in a solvent such as toluene. In certain embodiments, the reaction is carried out at a temperature ranging from approximately 0° C. to approximately 50° C. In certain embodiments, the reaction is carried out from approximately 0° C. to room temperature. For example, in certain embodiments, the reaction is carried out under the following conditions: 5 mol % (PhO)₂P(=O)OH in toluene from 0° C. to room temperature (e.g., over 10-15 hours).

In certain embodiments, the compound of Formula (L-5-15) is of the Formula (L-5-15A):

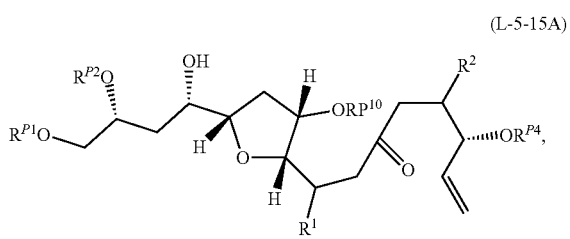

(L-5-15A)

or a salt thereof, and the method further comprises a step of protecting the compound of Formula (L-5-15A), or a salt thereof, to yield a compound of Formula (L-5-15) (e.g., to install the group $R^{P3}$, wherein the group $R^{P3}$ is an oxygen protecting group).

In certain embodiments, $R^{P1}$, $R^{P2}$, and $R^{P10}$ are silyl protecting groups; and $R^{P4}$ is optionally substituted benzyl. In certain embodiments, $R^{P1}$ and $R^{P2}$ are TBS; $R^{P10}$ is TES; and $R^{P4}$ is MPM.

As shown in Scheme 4A, also provided herein is a method of preparing a compound of Formula (L-5-14):

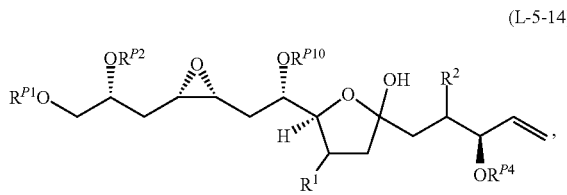
(L-5-14)

or a salt thereof, the method comprising a step of coupling a compound of Formula (L-5-12):

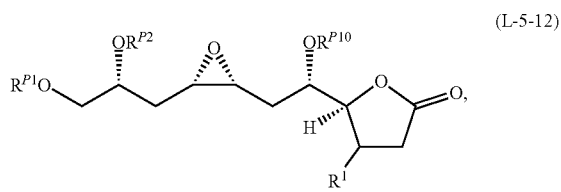
(L-5-12)

or a salt thereof, with a compound of Formula (L-5-5):

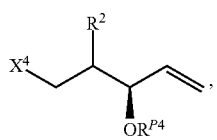
(L-5-5)

or a salt thereof, wherein:

$X^4$ is halogen or a leaving group;

$R^1$ and $R^2$ are independently hydrogen, halogen, or optionally substituted alkyl; and $R^{P1}$, $R^{P2}$, $R^{P4}$, and $R^{P10}$ are independently hydrogen, optionally substituted alkyl, optionally substituted acyl, or an oxygen protecting group.

In certain embodiments, the coupling of a compound of Formula (L-5-12) with a compound of Formula (L-5-5) is carried out in the presence of an organometallic reagent (e.g., to covert $X^4$ to a metal for addition to the compound of Formula (L-5-12)). In certain embodiments, the organometallic reagent is a lithium reagent (e.g., to convert the compound of the Formula (L-5-5) to a compound of the formula:

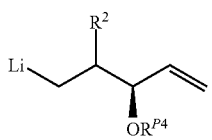

for addition to the compound of Formula (L-5-12)). In certain embodiments, lithium reagent is an organolithium (e.g., n-butyllithium, tert-butyllithium, sec-butyllithium). In certain embodiments, the lithium reagent is LiHMDS or LDA. In certain embodiments, the reaction is carried out in the presence of tert-butyllithium. In certain embodiments, the reaction is performed in a solvent such as THF. In certain embodiments, the reaction is carried out at a temperature ranging from approximately −78° C. to approximately 0° C. In certain embodiments, the reaction is carried out at −78° C. to room temperature. For example, in certain embodiments, the reaction is carried out with 2.6 equivalents of tert-butyllithium in THF from −78° C. to room temperature (e.g., over less than 1 hour).

In certain embodiments, $R^{P1}$, $R^{P2}$, and $R^{P10}$ are silyl protecting groups; and $R^{P4}$ is optionally substituted benzyl. In certain embodiments, $R^{P1}$ and $R^{P2}$ are TBS; $R^{P10}$ is TES; and $R^{P4}$ is MPM.

Also provided herein is a method of preparing a compound of Formula (L-5-12):

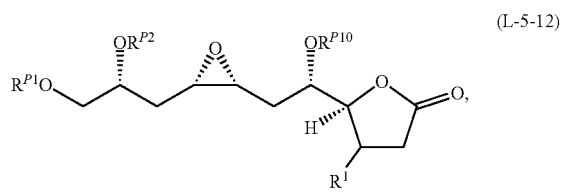
(L-5-12)

or a salt thereof, the method comprising a step of epoxidizing a compound of Formula (L-5-11):

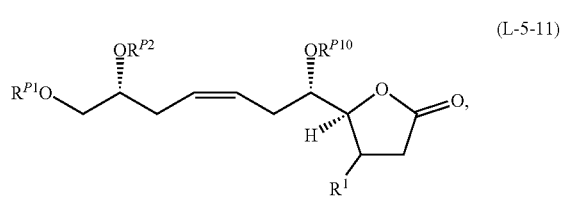
(L-5-11)

or a salt thereof, wherein:

$R^1$ is hydrogen, halogen, or optionally substituted alkyl; and $R^{P1}$, $R^{P2}$, and $R^{P10}$ are independently hydrogen, optionally substituted alkyl, optionally substituted acyl, or an oxygen protecting group.

Any epoxidation reagent may be used in the step of epoxidizing described above. In certain embodiments, the epoxidation reagent is a peracid (e.g., m-CPBA). In certain embodiments, the epoxidation reagent is an organometallic reagent. In certain embodiments, the epoxidation reagent is a titanium reagent (e.g., Ti(Oi-Pr)$_4$). In certain embodiments, the epoxidation reagent is a vanadium reagent (e.g., VO(TMHD)$_2$). In certain embodiments, the epoxidation is a Sharpless epoxidation. In certain embodiments, the step of epoxidizing is carried out in the presence of one or more additional reagents. In certain embodiments, epoxidation is carried out in the presence of a peroxide (e.g., t-BuOOH).

In certain embodiments, the step of epoxidizing is carried out in the presence of a vanadium reagent and a peroxide. In certain embodiments, the reaction is carried out in the presence of VO(TMHD)$_2$ and t-BuOOH. In certain embodiments, the reaction is carried out in a solvent such as toluene. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 5 mol % VO(TMHD)$_2$ and 2 equivalents t-BuOOH in toluene at room temperature (e.g., for 1-10 hours).

In certain embodiments, $R^{P1}$, $R^{P2}$, and $R^{P10}$ are silyl protecting groups; and $R^{P4}$ is optionally substituted benzyl. In certain embodiments, $R^{P1}$ and $R^{P2}$ are TBS; and $R^{P10}$ is TES.

Also provided herein is a method of preparing a compound of Formula (L-5-11):

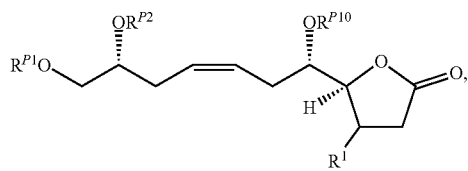

or a salt thereof, the method comprising a step of coupling a compound of Formula (L-5-10):

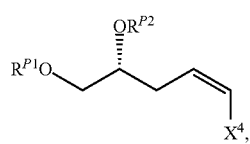

or a salt thereof, with a compound of Formula (L-5-9):

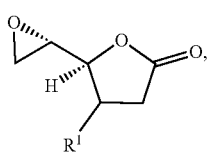

or a salt thereof, wherein:

X$^4$ is halogen or a leaving group;

R$^1$ is hydrogen, halogen, or optionally substituted alkyl; and

R$^{P1}$, R$^{P2}$, and R$^{P10}$ are independently hydrogen, optionally substituted alkyl, optionally substituted acyl, or an oxygen protecting group.

In certain embodiments, the coupling of a compound of Formula (L-5-10) with a compound of Formula (L-5-9) is carried out in the presence of a metal or organometallic reagent (e.g., to covert X$^4$ to a metal for addition to the compound of Formula (L-5-9)). In certain embodiments, the reaction is carried out in the presence of copper. In certain embodiments, the copper is a copper complex or copper salt. In a particular embodiment, the copper source is Li(thienyl-CuCN). In certain embodiments, the reaction is carried out in the presence of a lithium reagent. In certain embodiments, lithium reagent is an organolithium (e.g., n-butyllithium, tert-butyllithium, sec-butyllithium). In certain embodiments, the lithium reagent is LiHMDS or LDA. In certain embodiments, the reactions is carried out in the presence of a lithium reagent and a copper reagent (e.g., to convert the compound of the Formula (L-5-10) to a compound of the formula:

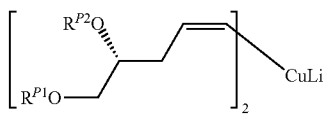

for addition to the compound of Formula (L-5-9)). The reaction may also be carried out in the presence of a Lewis acid (e.g., BF$_3$.Et$_2$O).

In certain embodiments, the step of coupling is carried out in the presence of a copper source, an organometallic, and a Lewis acid. In certain embodiments, the reaction is carried out in the presence of Li(thienylCuCN), n-butyllithium, and BF$_3$.Et$_2$O. In certain embodiments, the reaction is carried out in a solvent such as Et$_2$O. In certain embodiments, the reaction is carried out at a temperature ranging from approximately −78° C. to approximately 0° C. In certain embodiments, the reaction is carried out at a temperature ranging from approximately −78° C. to approximately room temperature. In certain embodiments, the reaction is carried out at around −78° C. For example, in certain embodiments, the reaction is carried out under the following conditions: 2 equivalents Li(thienylCuCN), 1.75 equivalents n-butyllithium, and 1.6 equivalents BF$_3$.Et$_2$O, in Et$_2$O at −78° C. (e.g., for 1 hour).

In certain embodiments, R$^{P1}$ and R$^{P2}$ are silyl protecting groups; In certain embodiments, R$^{P1}$ and R$^{P2}$ are TBS.

Preparation of Left Halves of Homohalichondrins

Also provided herein are "left hand" building blocks of homohalichondrins (e.g., homohalichondrin A, B, C), and analogs thereof, such as compounds of Formula (L-2-16). Methods useful in the preparation of left hand building blocks of homohalichondrins (e.g., compounds of Formula (L-2-16)) are outlined in Scheme 4B. For instance, a compound of Formula (L-2-16) can be prepared by thiolating a compound of Formula (L-5-26), which can be prepared via cyclization of a compound of Formula (L-5-25C). To this end, a compound of Formula (L-5-25C) can be prepared by oxidation and olefination of a compound of Formula (L-5-25A). As also shown in Scheme 4B, coupling of a compound of Formula (L-5-24) with a compound of Formula (L-5-5) can provide a compound of Formula (L-5-25A). Furthermore, a compound of Formula (L-5-24) can be prepared by hydroboration, oxidation, and cyclization of a compound of Formula (L-5-23A), which can be prepared by epoxidizing the internal olefin of a compound of Formula (L-5-22), followed by cyclization. A compound of Formula (L-5-22) can be prepared by reducing a compound of Formula (L-5-21B), which may be prepare by reduction and olefination of a nitrile of Formula (L-5-21A). The nitrile can be prepared by reduction and olefination of a compound of Formula (L-5-3), followed by substitution of a compound of Formula (L-5-20) (i.e., to convert the group —OR$^{P7}$ to —CN).

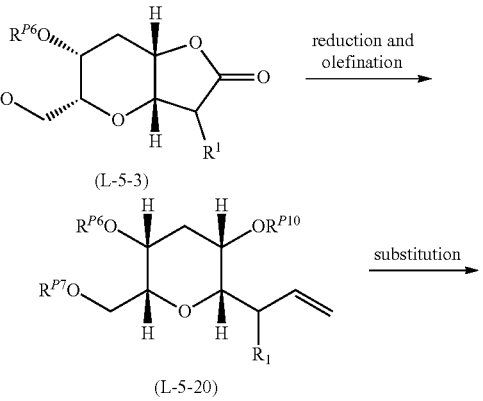

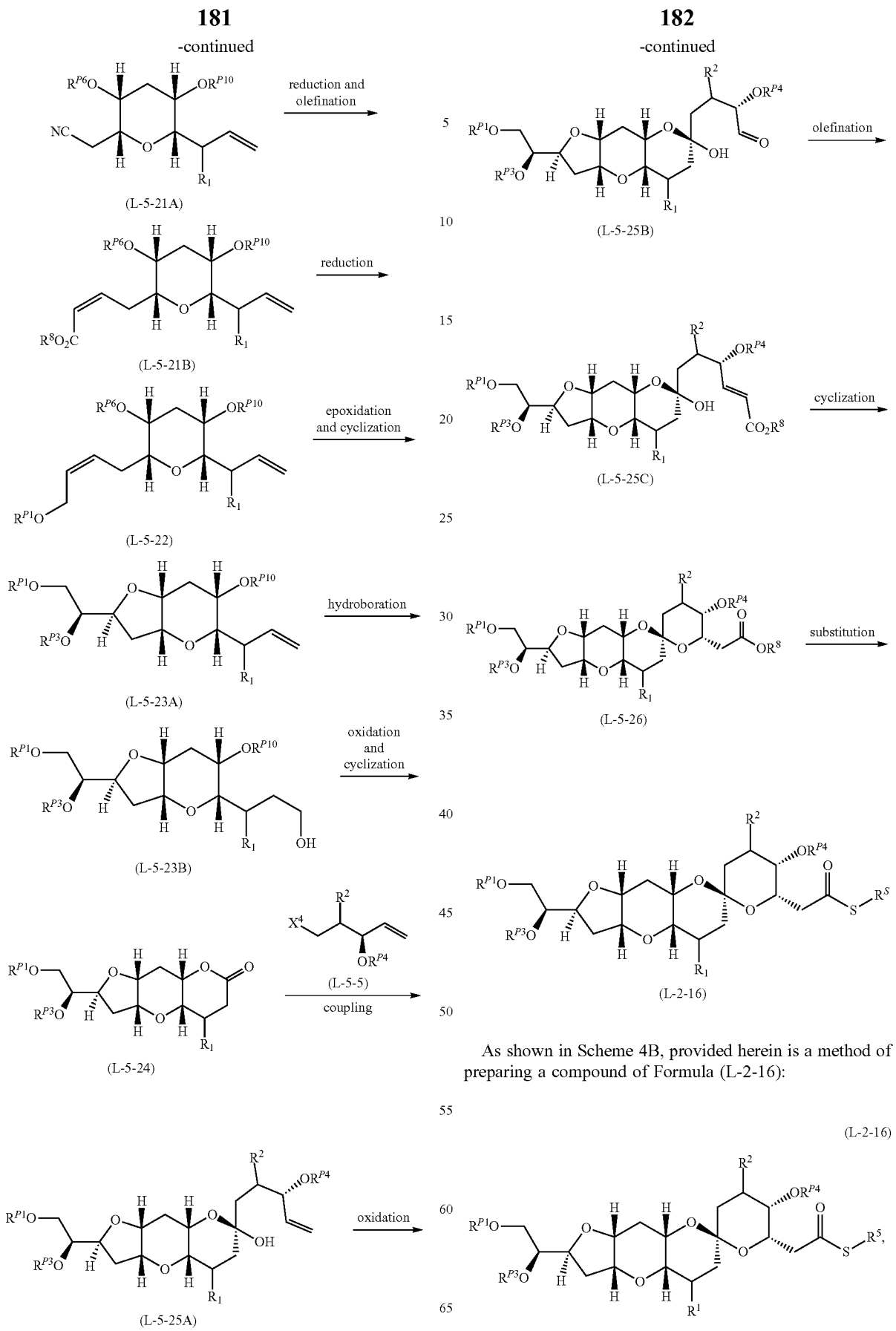
As shown in Scheme 4B, provided herein is a method of preparing a compound of Formula (L-2-16):

or a salt thereof, the method comprising a step of reacting a compound of Formula (L-5-26):

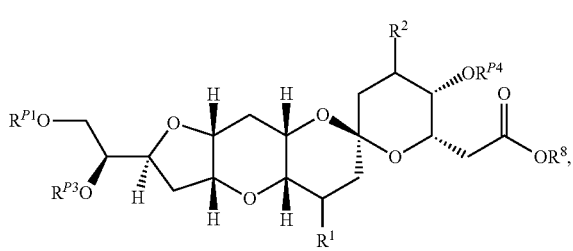

(L-5-26)

or a salt thereof, in the presence of a thiolating agent; wherein:

R$^S$ is optionally substituted alkyl, optionally substituted carbocyclyl, optionally substituted aryl, optionally substituted heterocyclyl, or optionally substituted heteroaryl;

R$^1$ and R$^2$ are independently hydrogen, halogen, or optionally substituted alkyl;

R$^{P1}$, R$^{P3}$, and R$^{P4}$ are each independently hydrogen, optionally substituted alkyl, optionally substituted acyl, or an oxygen protecting group; and R$^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

As described herein, the step of forming a compound of Formula (L-2-16) comprises reacting a compound of Formula (L-5-26) in the presence of a thiolating agent. Any thiolating agent known in the art may be used to this end. In certain embodiments, the thiolating agent is a disulfide. In certain embodiments, the thiolating agent is of the formula (R$^S$S)$_2$. In certain embodiments, the thiolating agent is of the formula (pyridine-S)$_2$. In certain embodiments, the thiolating agent is:

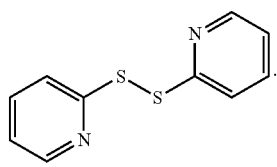 [SMILES: c1ccc(SSc2ccccn2)nc1]

In certain embodiments, the step of thiolating a compound of Formula (L-5-26) is carried out in the presence of one of more additional reagents. In certain embodiments, the step of thiolating is carried out in the presence of a phosphine reagent (e.g., triphenylphosphine (Ph$_3$P)).

In certain embodiments, the step of thiolating is carried out in the presence of a disulfide and a phosphine. In certain embodiments, the reaction is carried out in the presence of (Py-S)$_2$ and Ph$_3$P. In certain embodiments, the reaction is carried out in a solvent such as toluene. In certain embodiments, the reaction is carried out at a temperature ranging from approximately 0° C. to approximately 50° C. In certain embodiments, the reaction is carried out at room temperature. For example, in certain embodiments, the step of thiolating is carried out under the following conditions: 1.2 equivalents of (Py-S)$_2$, 3 equivalents of Ph$_3$P, in toluene at room temperature (e.g., for 10-20 hours).

In certain embodiments, the method of thiolating a compound of Formula (L-5-26), or a salt thereof, comprises the steps of:

(a) deprotecting a compound of Formula (L-5-26), or a salt thereof, to yield a compound of Formula (L-5-26B):

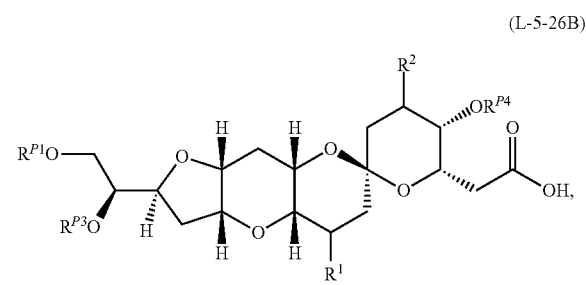

(L-5-26B)

or a salt thereof; and (b) thiolating a compound of Formula (L-5-26B), or a salt thereof, to yield a compound of Formula (L-2-6), or a salt thereof.

In certain embodiments, R$^1$, R$^{P3}$, and R$^{P4}$ are silyl protecting groups. In certain embodiments, R$^1$ is TBS; and R$^{P3}$ and R$^{P4}$ are TES.

As also shown in Scheme 4B, provided herein is a method of preparing a compound of Formula (L-5-26):

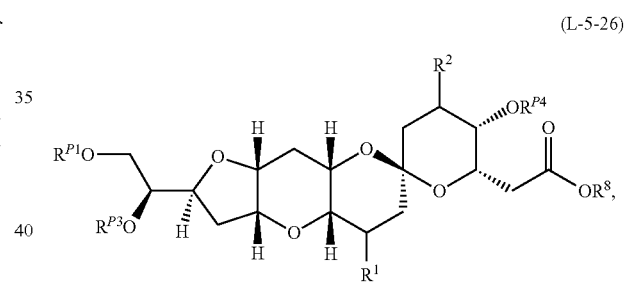

(L-5-26)

or a salt thereof, the method comprising a step of cyclizing a compound of Formula (L-5-25C):

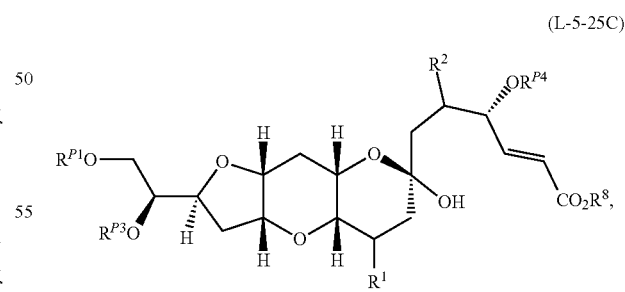

(L-5-25C)

or a salt thereof; wherein:

R$^1$ and R$^2$ are independently hydrogen, halogen, or optionally substituted alkyl;

R$^{P1}$, R$^{P3}$, and R$^{P4}$ are each independently hydrogen, optionally substituted alkyl, optionally substituted acyl, or an oxygen protecting group; and R$^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (7-5-25C) is carried out in the presence of a base. In certain embodiments, the base is a nitrogen base. In certain embodiments, the base is an amidine, guanidine base. In certain embodiments, the base is an amine or amide base. In certain embodiments, the base is an amidine base (e.g., 1,8-diazabicyclo(5.4.0)undec-7-ene (DBU)). In certain embodiments, the step of cyclizing is carried out in the presence of an acid. In certain embodiments, the acid is a Lewis acid. In certain embodiments, the step of cyclizing is carried out in the presence of a lithium salt (e.g., LiBr, LiCl). The step of cyclizing may be carried out in the presence of one or more additional reagents. In certain embodiments, the step of cyclizing is carried out in the presence of $R^8$—OAc. In certain embodiments, the step of cyclizing is carried out in the presence of BnOAc.

In certain embodiments, the step of cyclizing is carried out in the presence of a lithium salt, and a base. In certain embodiments, the step of cyclizing is carried out in the presence of LiBr and DBU. In certain embodiments, the reaction is carried out in a solvent such as MeCN. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 10 equivalents LiBr and 20 equivalents DBU in MeCN at room temperature (e.g., for 10-20 hours).

In certain embodiments, $R^{P1}$ and $R^{P3}$ are silyl protecting groups; $R^{P4}$ is optionally substituted benzyl; and $R^8$ is optionally substituted benzyl. In certain embodiments, $R^{P1}$ is TBS; $R^{P3}$ is TES; $R^{P4}$ is MPM; and $R^8$ is benzyl.

In certain embodiments, the compound of Formula (L-5-26), or a salt thereof, is deprotected to remove the group $R^{P4}$ yield a compound of Formula (L-5-26B):

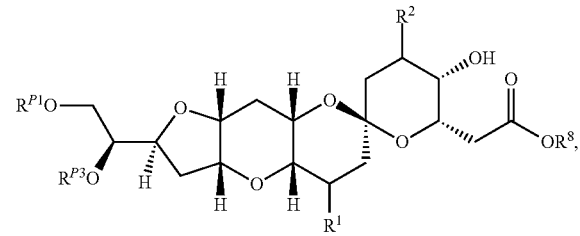

(L-5-26B)

or a salt thereof; and optionally re-protected (i.e., to switch the group $R^{P4}$ from, e.g., a benzyl protecting group (e.g., MPM) to a silyl protecting group (e.g., trialkylsilyl such as triethylsilyl).

Also provided herein is a method of preparing a compound of Formula (L-5-25C):

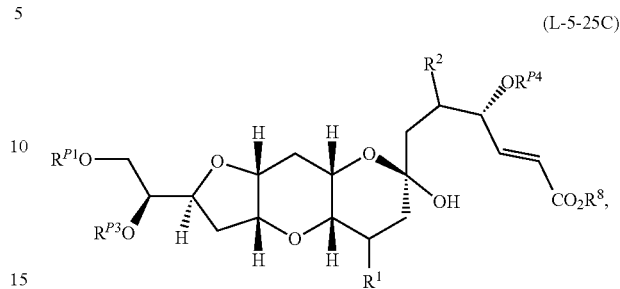

(L-5-25C)

or a salt thereof, the method comprising a step of reacting a compound of Formula (L-5-25A):

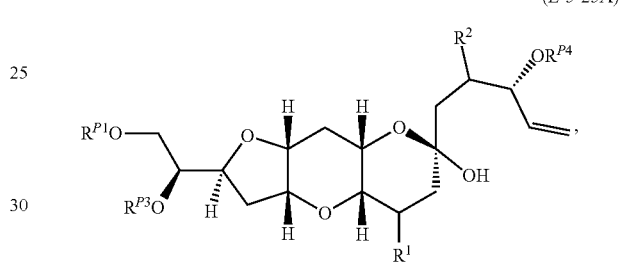

(L-5-25A)

or a salt thereof, in the presence of an olefin and an olefin metathesis catalyst; wherein:

$R^1$ and $R^2$ are independently hydrogen, halogen, or optionally substituted alkyl;

$R^{P1}$, $R^{P3}$, and $R^{P4}$ are each independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the olefin is of the formula:

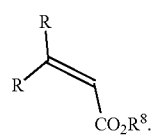

Further, any olefin metathesis known in the art may be used in the metathesis reaction to furnish a compound of Formula (L-5-25C).

Also provided herein is an alternative method of preparing a compound of Formula (L-5-25C):

(L-5-25C)

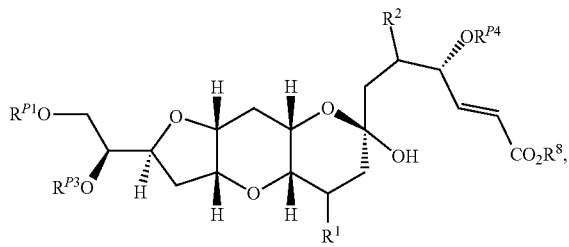

or a salt thereof, the method comprising the steps of:
(a) oxidizing a compound of Formula (L-5-25A):

(L-5-25A)

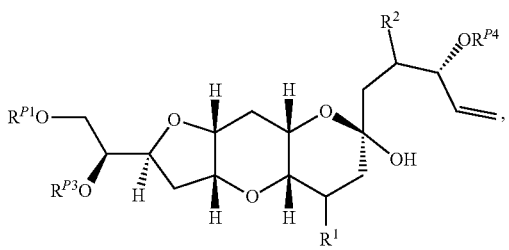

or a salt thereof, to yield a compound of Formula (L-5-25B) or (L-5-25BB):

(L-5-25B)

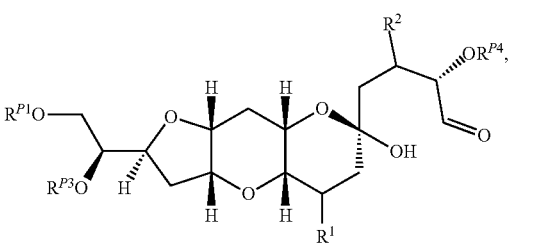

(L-5-25BB)

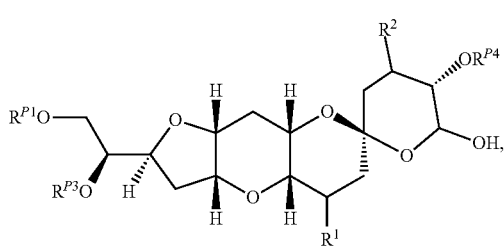

or a salt thereof, and
(c) reacting the compound of Formula (L-5-25B) or (L-5-25BB), or a salt thereof, in the presence of a olefination reagent, to yield a compound of Formula (L-5-25C), or a salt thereof.

The reaction in step (a) above is an oxidative cleavage; the reaction in step (b) is an olefination reaction. In certain embodiments, the oxidative cleavage is carried out via ozonolysis (e.g., in the presence of $O_3$). In certain embodiments, the cleavage is carried out in the presence of reagents capable of dihydroxylating a double bond (e.g., osmium tetroxide ($OsO_4$), N-methylmorpholine N-oxide (NMMO)), followed by a transition metal (e.g., a lead complex such as $Pb(OAc)_4$).

In certain embodiments, the double bond is dihydroxylated by treatment with $OsO_4$, NMMO, and water. In certain embodiments, the reaction is carried out in the presence of a solvent such as acetone. In certain embodiments, the reaction is carried out at a temperature ranging from approximately 0° C. to approximately 50° C. In certain embodiments, the reaction is carried out at room temperature. For example, in certain embodiments, the double bond is dihydroxylated under the following conditions: 10 mol % $OsO_4$, 2 equivalents NMMO, and water, in acetone at room temperature (e.g., for 1-5 hours). The resulting compound is then treated, in certain embodiments, with $Pb(OAc)_4$ and $K_2CO_3$ to yield the aldehyde or hemiacetal. For example, in certain embodiments, this step is carried out under the following conditions: 1.5 equivalents $Pb(OAc)_4$, 10 equivalents $K_2CO_3$, in $CH_2Cl_2$ at room temperature (e.g., for under 1 hour).

In certain embodiments, the olefination is carried out in the presence of a Wittig or Horner-Wadsworth Emmons reagent. In certain embodiments, the olefination is carried out in the presence of a reagent of the formula: $(RO)_2P(O)CH_2CO_2R^8$. In certain embodiments, the reagent is of the formula: $(MeO)_2P(O)CH_2CO_2R^8$ (e.g., $(MeO)_2P(O)CH_2CO_2Bn$). In certain embodiments, the olefination is carried out in the presence of a base (e.g., a phosphate salt such as $K_3PO_4$, or a hydride such as NaH).

In certain embodiments, the olefination is carried out in the presence of an olefination reagent of the formula: $(RO)_2P(O)CH_2CO_2R^8$, and a base. In certain embodiments, the olefination is carried out in the presence of $(MeO)_2P(O)CH_2CO_2Bn$ and NaH. In certain embodiments, the reaction is carried out in a solvent such as THF. In certain embodiments, the reaction is carried out at a temperature ranging from approximately −78° C. to approximately room temperature. In certain embodiments, the reaction is carried out at 0° C. For example, in certain embodiments, the reaction is carried out under the following conditions: 5 equivalents $(MeO)_2P(O)CH_2CO_2Bn$, 4 equivalents NaH, in THF at 0° C. (e.g., for about 1-5 hours).

In certain embodiments, $R^{P1}$ and $R^{P3}$ are silyl protecting groups; $R^{P4}$ is optionally substituted benzyl; and $R^8$ is optionally substituted benzyl. In certain embodiments, $R^{P1}$ is TBS; $R^{P3}$ is TES; $R^{P4}$ is MPM; and $R^8$ is benzyl.

Also provided herein is a method of preparing a compound of Formula (L-5-25A):

(L-5-25A)

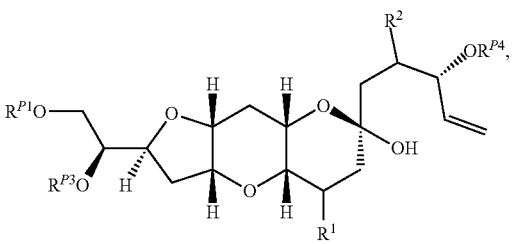

or a salt thereof, the method comprising a step of coupling a compound of Formula (L-5-24):

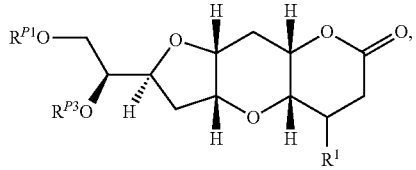
(L-5-24)

or a salt thereof, with a compound of Formula (L-5-5):

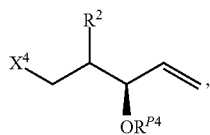
(L-5-5)

or a salt thereof, wherein:
X$^4$ is halogen or a leaving group;
R$^1$ and R$^2$ are independently hydrogen, halogen, or optionally substituted alkyl;
R$^{P1}$, R$^{P3}$, and R$^{P4}$ are each independently hydrogen, optionally substituted alkyl, optionally substituted acyl, or an oxygen protecting group; and
R$^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the coupling of a compound of Formula (L-5-24) with a compound of Formula (L-5-5) is carried out in the presence of an organometallic reagent (e.g., to covert X$^4$ to a metal for addition to the compound of Formula (L-5-24)). In certain embodiments, the organometallic reagent is a lithium reagent (e.g., to convert the compound

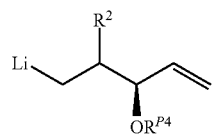

of the Formula (L-5-5) to a compound of the formula: OR$^{P4}$ for addition to the compound of Formula (L-5-24)). In certain embodiments, lithium reagent is an organolithium (e.g., n-butyllithium, tert-butyllithium, sec-butyllithium). In certain embodiments, the lithium reagent is LiHMDS or LDA.

In certain embodiments, the reaction is carried out in the presence of tert-butyllithium. In certain embodiments, the reaction is performed in a solvent such as THF. In certain embodiments, the reaction is carried out at a temperature ranging from approximately −78° C. to approximately room temperature. In certain embodiments, the reaction is carried out at approximately −78° C. For example, in certain embodiments, the reaction is carried out with 2.5 equivalents of tert-butyllithium in THF at −78° C. (e.g., over less than 1 hour).

In certain embodiments, R$^{P1}$ and R$^{P3}$ are silyl protecting groups; and R$^{P4}$ is optionally substituted benzyl. In certain embodiments, R$^1$ is TBS; R$^{P3}$ is TES; and R$^{P4}$ is MPM.

Provided herein is a method of preparing a compound of Formula (L-5-24):

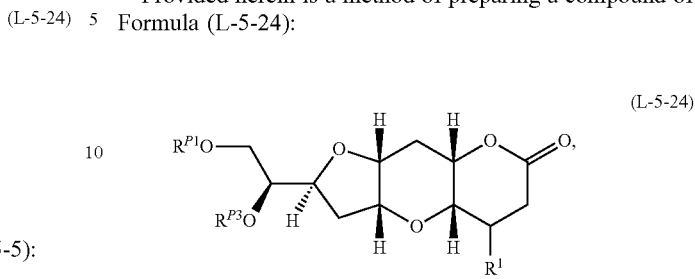
(L-5-24)

or a salt thereof, the method comprising the steps of:
(a) oxidizing a compound of Formula (L-5-23B):

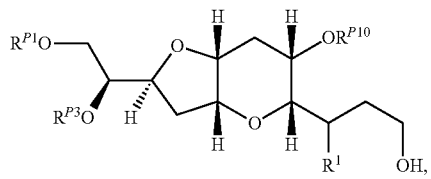
(L-5-23B)

or a salt thereof, to yield a compound of Formula (L-5-23C):

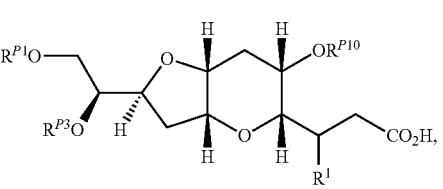
(L-5-23C)

or a salt thereof; and
(b) cyclizing a compound of Formula (L-5-23C), or a salt thereof, to yield a compound of Formula (L-5-24), or a salt thereof; wherein:
R$^1$ is hydrogen, halogen, or optionally substituted alkyl; and
R$^{P1}$, R$^{P3}$, and R$^{P10}$ are each independently hydrogen, optionally substituted alkyl, optionally substituted acyl, or an oxygen protecting group.

The step of oxidizing a compound of Formula (L-5-23B) is carried out in the presence of an oxidant. In certain embodiments, the oxidant is a hypervalent iodine reagent. In certain embodiments, the oxidant is a periodinane (e.g., Dess-Martin periodinane). In certain embodiments, the oxidant is (Diacetoxyiodo)benzene (PhI(OAc)$_2$). In certain embodiments, the oxidation is carried out in the presence of one or more addition reagents. In certain embodiments, the oxidation is carried out in the presence of (2,2,6,6-tetramethylpiperidin-1-yl)oxyl (TEMPO). In certain embodiments, the oxidation is carried out in the presence of TEMPO and hypervalent iodine. In certain embodiments, the oxidation in step (a) and the cyclization in step (b) are carried out in the same step, or in subsequent steps. In certain embodiments, the cyclization in step (b) is carried out in a separate step, and in the presence of an acid (e.g., Lewis acid or Brønsted acid) or a base.

In certain embodiments, the step of oxidizing is carried out in the presence of PhI(OAc)$_2$ and TEMPO. In certain embodiments, the step of oxidizing is carried out in a solvent such as CH$_2$Cl$_2$. In certain embodiments, the reaction is carried out at a temperature ranging from approximately 0° C. to approximately 50° C. In certain embodiments, the step of oxidizing is carried out at room temperature. For example, in certain embodiments, the reaction is carried out under the following conditions: 20 mol % TEMPO, 3 equivalents PhI(OAc)$_2$, in CH$_2$Cl$_2$ at room temperature (e.g., over 24-48 hours).

In certain embodiments, R$^{P1}$ and R$^{P3}$ are silyl protecting groups; and R$^{P10}$ is hydrogen. In certain embodiments, R$^{P1}$ is TBS; R$^{P3}$ is TES; and R$^{P10}$ is hydrogen.

Provided herein is a method of preparing a compound of Formula (L-5-23B):

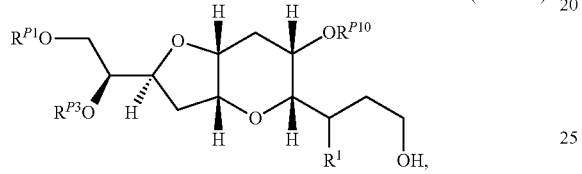

(L-5-23B)

or a salt thereof, the method comprising a step of hydrating a compound of Formula (L-5-23A):

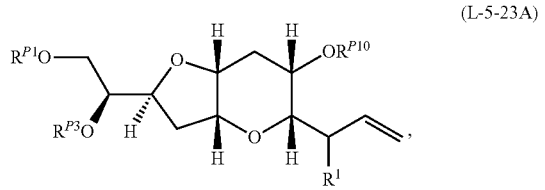

(L-5-23A)

or a salt thereof; wherein:

R$^1$ is hydrogen, halogen, or optionally substituted alkyl; and

R$^{P1}$, R$^{P3}$, and R$^{P10}$ are each independently hydrogen, optionally substituted alkyl, optionally substituted acyl, or an oxygen protecting group.

In certain embodiments, the step of hydrating the compound of Formula (L-5-23A) is a hydroboration reaction. Any reagents or conditions to effect hydroboration may be used. For example, the reaction can be carried out in the presence of a borane (e.g., BH$_3$ or 9-BBN), followed by a peroxide (e.g., H$_2$O$_2$) or a perborate (e.g., sodium perborate (NaBO$_3$)). In certain embodiments, the reaction is carried out in the presence of 9-BBN. In certain embodiments, the reaction involves addition of NaBO$_3$·H$_2$O.

In certain embodiments, the step of hydrating is carried out in the presence of 9-BBN, followed by NaBO$_3$·H$_2$O. In certain embodiments, the reaction is carried out in a solvent such as THF. In certain embodiments, the reaction is carried out at 0° C. to room temperature. In certain embodiments, the reaction is carried out under the following conditions: 3 equivalents 9-BBN in THF, from 0° C. to room temperature (e.g., over 1 hour) followed by the addition of aqueous NaBO$_3$·H$_2$O.

In certain embodiments, R$^{P1}$ and R$^{P3}$ are silyl protecting groups; and R$^{P10}$ is hydrogen. In certain embodiments, R$^{P1}$ is TBS; R$^{P3}$ is TES; and R$^{P10}$ is hydrogen.

Provided herein is a method of preparing a compound of Formula (L-5-23A):

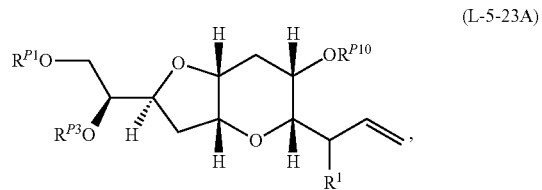

(L-5-23A)

or a salt thereof, the method comprising the steps of:

(a) epoxidizing a compound of Formula (L-5-22):

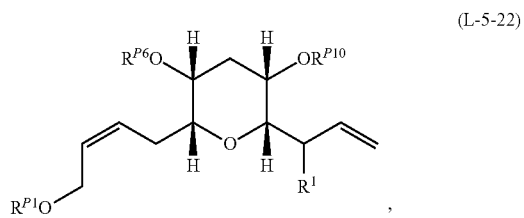

(L-5-22)

or a salt thereof, to yield a compound of Formula (L-5-22A):

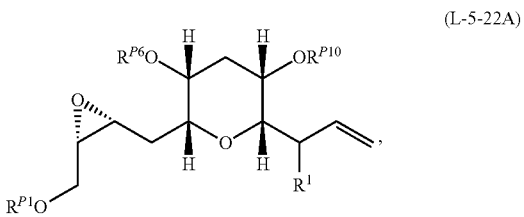

(L-5-22A)

or a salt thereof; and (b) cyclizing a compound of Formula (L-5-22A), or a salt thereof, to yield a compound of Formula (L-5-23A), or a salt thereof.

Any epoxidation reagent may be used in the step of epoxidizing described above. In certain embodiments, the epoxidation reagent is a peracid (e.g., m-CPBA). In certain embodiments, the epoxidation reagent is an organometallic reagent. In certain embodiments, the epoxidation reagent is a titanium reagent (e.g., Ti(Oi-Pr)$_4$). In certain embodiments, the epoxidation reagent is a vanadium reagent (e.g., VO(TMHD)$_2$). In certain embodiments, the epoxidation is a Sharpless epoxidation. In certain embodiments, the epoxidation is an asymmetric epoxidation (e.g., Sharpless asymmetric epoxidation). In certain embodiments, the epoxidation is carried out in the presence of one or more chiral ligands (e.g., (+)- or (−)-DET, (+)- or (−)-DIPT; wherein DET=diethyltartrate and DIPT=diisopropyltartrate). In certain embodiments, the step of epoxidizing is carried out in the presence of one or more additional reagents. In certain embodiments, epoxidation is carried out in the presence of a peroxide (e.g., t-BuOOH).

In certain embodiments, the step of epoxidizing is carried out in the presence of a titanium complex, a tartrate ligand, and a peroxide. In certain embodiments, the reaction is carried out in the presence of Ti(Oi-Pr)$_4$, (+)-DET, and t-BuOOH. In certain embodiments, the reaction is carried out in the presence of molecular sieves. In certain embodiments, the reaction is carried out in the presence of a solvent such as $CH_2Cl_2$. In certain embodiments, the reaction is carried out at a temperature ranging from approximately −78° C. to approximately room temperature. In certain embodiments, the reaction is carried out at around −10° C. For example, in certain embodiments, the reaction is carried out under the following conditions: 15 mol % $Ti(Oi-Pr)_4$, 20 mol % (+)-DET, 1.5 equivalents t-BuOOH, and 4A molecular sieves in $CH_2Cl_2$ at −10° C. (e.g., for 10-20 hours).

In certain embodiments, $R^{P6}$ and $R^{P10}$ are silyl protecting groups; and $R^{P1}$ is hydrogen. In certain embodiments, $R^{P6}$ and $R^{P10}$ are TBS; and $R^{P1}$ is hydrogen. In certain embodiments, $R^{P6}$ is deprotected before the step of cyclizing a compound of Formula (L-5-22A).

In certain embodiments, the epoxidation/cyclization provides a compound of Formula (L-5-22B):

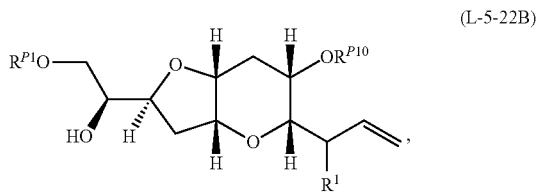
(L-5-22B)

or a salt thereof, which can then be protected to yield a compound of Formula (L-5-23A), or a salt thereof (e.g., to install the group $R^{P3}$; wherein $R^{P3}$ is an oxygen protecting group).

As shown in Scheme 4B, provided herein is a method of preparing a compound of Formula (L-5-22):

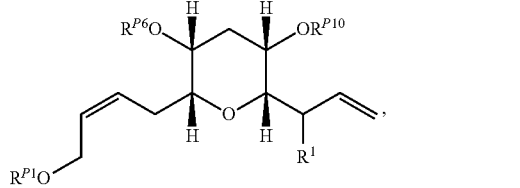
(L-5-22)

or a salt thereof, the method comprising a step of reducing a compound of Formula (L-5-21B):

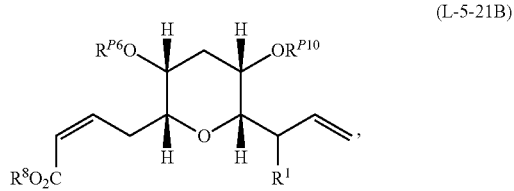
(L-5-21B)

or a salt thereof; wherein:
R¹ is hydrogen, halogen, or optionally substituted alkyl;
$R^{P1}$, $R^{P6}$, and $R^{P10}$ are each independently hydrogen, optionally substituted alkyl, optionally substituted acyl, or an oxygen protecting group; and
R⁸ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

The step of reducing a compound of (L-5-21B), or a salt thereof, converts the $—CO_2R^8$ moiety to an $—OR^{P1}$ group (i.e., —OH). In certain embodiments, the step of reducing is carried out in the presence of a hydride (i.e., H⁻) source. Any hydride source known in the art may be used in this transformation. Examples of hydride sources include, but are not limited to, lithium aluminum hydride, sodium borohydride, lithium borohydride, and diisobutylaluminum hydride. In certain embodiments, the hydride source is diisobutylaluminum hydride (DIBAL).

In certain embodiments, the step of reducing is carried out in the presence of DIBAL. In certain embodiments, the reaction is carried out in a solvent (e.g., THF). In certain embodiments, the reaction is carried out at below room temperature. In certain embodiments, the reaction is carried out at a temperature ranging from approximately −78° C. to approximately room temperature. In certain embodiments, the reaction is carried out at around −78° C. For example, in certain embodiments, the reaction is carried out under the following conditions: 4 equivalents of DIBAL in THF at −78° C. (e.g., for under 1 hour).

In certain embodiments, $R^{P6}$ and $R^{P10}$ are silyl protecting groups; and R⁸ is optionally substituted alkyl. In certain embodiments, $R^{P6}$ and $R^{P10}$ are TBS; and R⁸ is methyl.

In certain embodiments, the compound of Formula (L-5-22) is of Formula (L-5-22-C):

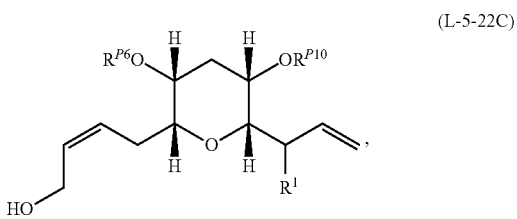
(L-5-22C)

or a salt thereof.

Also provided herein is a method of preparing a compound of Formula (L-5-21B):

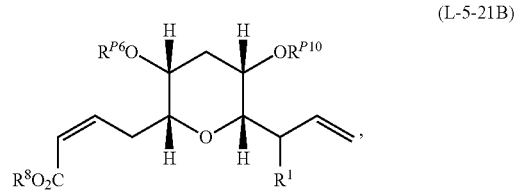
(L-5-21B)

or a salt thereof, the method comprising the steps of:
(a) reducing a compound of Formula (L-5-21A):

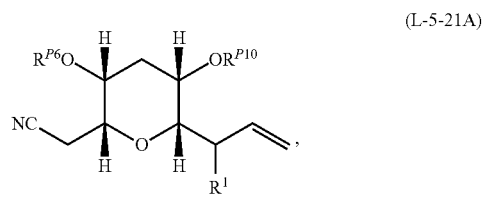
(L-5-21A)

or a salt thereof, to yield a compound of Formula (L-5-21C):

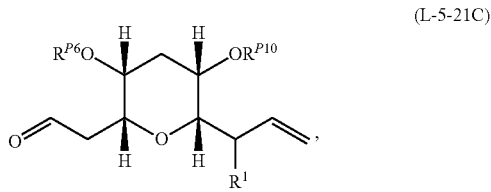

or a salt thereof; and (b) reacting a compound of Formula (L-5-21C), or a salt thereof, in the presence of an olefinating reagent to yield a compound of Formula (L-5-21B), or a salt thereof.

The step of reducing a compound of (L-5-21A), or a salt thereof (i.e., step (a) above), converts the —CN moiety to an aldehyde group (i.e., —CHO). In certain embodiments, the step of reducing is carried out in the presence of a hydride (i.e., H) source. Any hydride source known in the art may be used in this transformation. Examples of hydride sources include, but are not limited to, lithium aluminum hydride, sodium borohydride, lithium borohydride, and diisobutylaluminum hydride. In certain embodiments, the hydride source is diisobutylaluminum hydride (DIBAL). The step of reducing may optionally comprise reducing the —CN moiety to an alcohol, followed by oxidation of the resulting alcohol to an aldehyde to yield a compound of Formula (L-5-21C), or a salt thereof.

In certain embodiments, the step of reducing is carried out in the presence of DIBAL. In certain embodiments, the reaction is carried out in a solvent (e.g., hexanes, $CH_2Cl_2$). In certain embodiments, the reaction is carried out at below room temperature. In certain embodiments, the reaction is carried out at a temperature ranging from approximately −78° C. to approximately room temperature. In certain embodiments, the reaction is carried out at around −78° C. For example, in certain embodiments, the reaction is carried out under the following conditions: 1.1 equivalents of DIBAL in hexanes-$CH_2Cl_2$ at −78° C. (e.g., for under 1 hour).

In certain embodiments, the olefination of a compound of Formula (L-5-21C), or a salt thereof (i.e., step (b) above), is carried out in the presence of a Wittig or Horner-Wadsworth Emmons reagent. In certain embodiments, the olefination is carried out in the presence of a reagent of the formula: $(RO)_2P(O)CH_2CO_2R^8$. In certain embodiments, the reagent is of the formula: $(MeO)_2P(O)CH_2CO_2R^8$ (e.g., $(MeO)_2P(O)CH_2CO_2Bn$). In certain embodiments, the reagent is of the formula: $(CF_3CH_2O)_2P(O)CH_2CO_2R^8$ (e.g., $(CF_3CH_2O)_2P(O)CH_2CO_2Me$). In certain embodiments, the olefination is carried out in the presence of a base. In certain embodiments, the base is a phosphate salt such as $K_3PO_4$. In certain embodiments, the base is an amide base. In certain embodiments, the base is a diisopropyl amide base (e.g., LDA). In certain embodiments, the base is a hexamethyldisilazide base (e.g., LiHMDS, NaHMDS, KHMDS). In certain embodiments, the olefination is carried out in the presence of one or more additional reagents. In certain embodiments, the olefination is carried out in the presence of a crown ether (e.g., 18-crown-6).

In certain embodiments, the olefination is carried out in the presence of a reagent of the formula $(RO)_2P(O)CH_2CO_2R^8$, a base. In certain embodiments, the reaction is carried out in the presence of $(CF_3CH_2O)_2P(O)CH_2CO_2Me$ and KHMDS. In certain embodiments, 18-crown-6 is pres-ent. In certain embodiments, the reaction is carried out in a solvent (e.g., THF). In certain embodiments, the reaction is carried out at a temperature ranging from approximately −78° C. to approximately room temperature. In certain embodiments, the reaction is carried out at −78° C. For example, in certain embodiments, the reaction is carried out under the following conditions: 1.5 equivalents $(CF_3CH_2O)_2P(O)CH_2CO_2Me$, 1.5 equivalents KHMDS, 8 equivalents 18-crown-6, in THF at −78° C. (e.g., for under 1 hour).

In certain embodiments, $R^{P6}$ and $R^{P10}$ are silyl protecting groups; and $R^8$ is optionally substituted alkyl. In certain embodiments, $R^{P6}$ and $R^{P10}$ are TBS; and $R^8$ is methyl.

Also provided herein is a method of preparing a compound of Formula (L-5-21A):

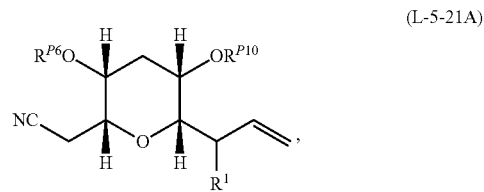

or a salt thereof, the method comprising reacting a compound of Formula (L-5-20):

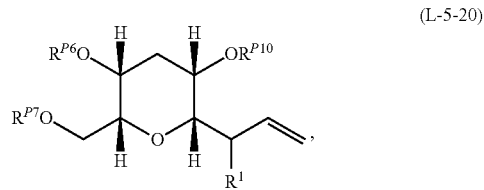

or a salt thereof, in the presence of cyanide; wherein:

$R^1$ is hydrogen, halogen, or optionally substituted alkyl; $R^{P6}$, $R^{P7}$ and $R^{P10}$ are each independently hydrogen, optionally substituted alkyl, optionally substituted acyl, or an oxygen protecting group; and wherein —$OR^{P7}$ is a leaving group.

The method of preparing a compound of Formula (L-5-21A), or a salt thereof, comprises reacting a compound of Formula (L-5-20), or a salt thereof, in the presence of cyanide. In certain embodiments, the cyanide is a cyanide salt (e.g., NaCN, KCN, LiCN). In certain embodiments, the cyanide salt is sodium cyanide (NaCN). The reaction may be carried out in the presence of one or more additional reagents (e.g., a crown ether). In certain embodiments, the reaction is carried out in the presence of NaCN, in a solvent such as DMSO. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 20 equivalents NaCN in DMSO at room temperature (e.g., for 1 hour).

In certain embodiments, $R^{P6}$ and $R^{P10}$ are silyl protecting groups. In certain embodiments, $R^{P6}$ and $R^{P10}$ are TBS.

Preparation of Left Halves of Norhalichondrins

Provided herein are method of preparing "left half" building blocks of compounds in the norhalichondrin series (e.g., norhalichondrin A, B, C, and analogs thereof). For example, as shown in Scheme 4C, left half building blocks of Formula (L-2-15) can be prepared by converting the ester group (i.e., —CO$_2$R$^8$) of a compound of Formula (L-5-32) to a thioester moiety (i.e., —C(O)SR$^S$). To this end, a compound of Formula (L-5-32) can be prepared by oxidizing a compound of Formula (L-5-31), which can be prepared by cyclizing a compound of Formula (L-5-30). A compound of Formula (L-5-30) can be prepared via oxidative cleavage and olefination of a compound of Formula (L-5-28), which can be obtained by coupling a compound of Formula (L-5-27) with a compound of Formula (L-5-5). A compound of Formula (L-5-27) can be obtained from an intermediate of Formula (L-5-21A), as described herein.

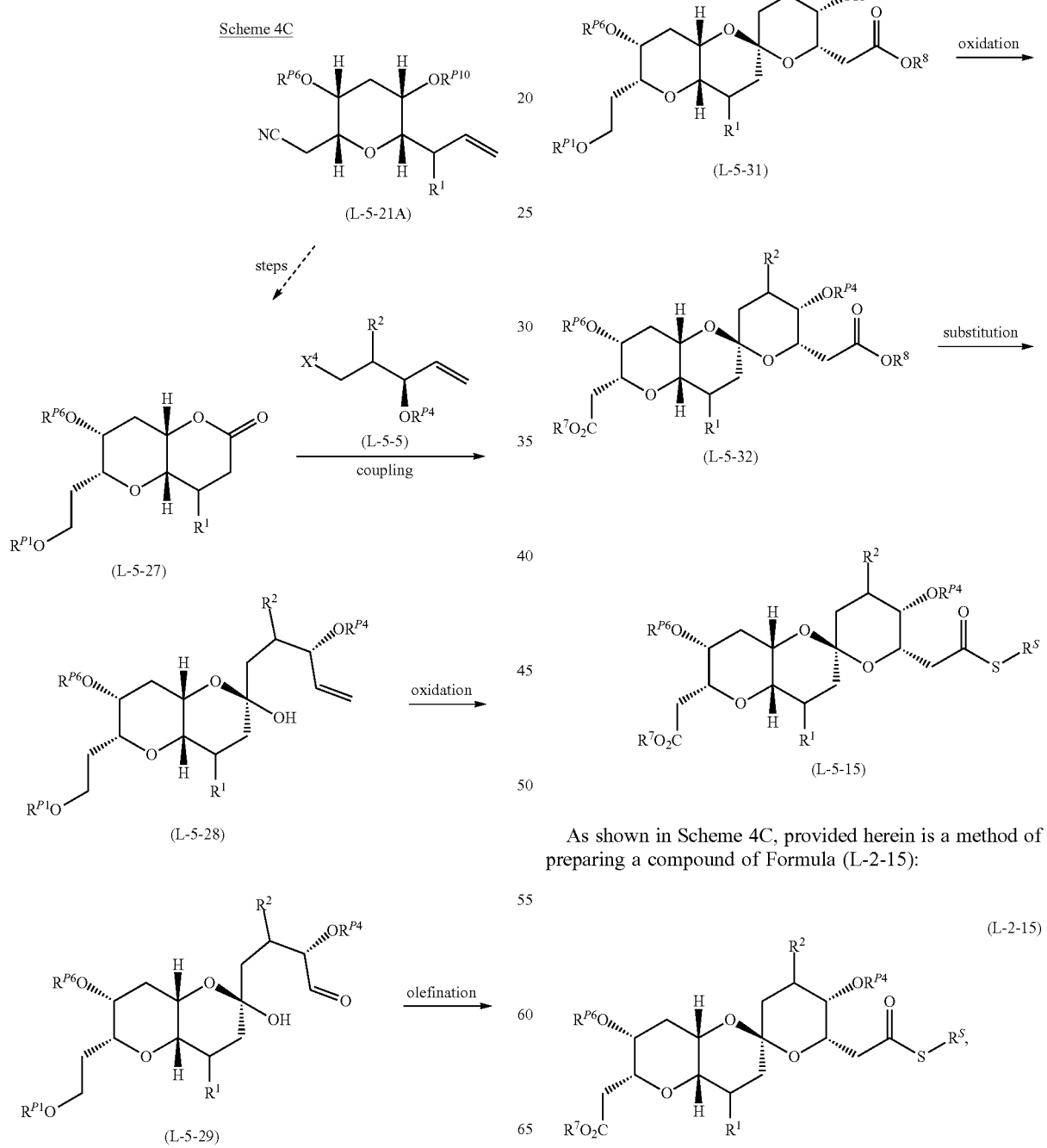

As shown in Scheme 4C, provided herein is a method of preparing a compound of Formula (L-2-15):

or a salt thereof, the method comprising a step of reacting a compound of Formula (L-5-32):

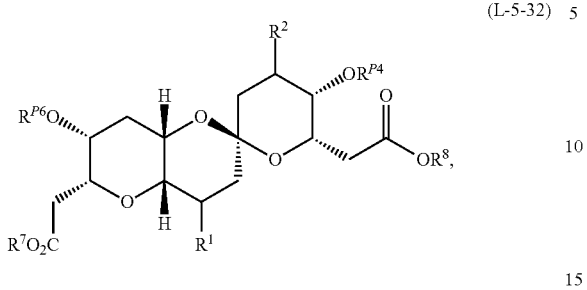

(L-5-32)

or a salt thereof, in the presence of a thiolating agent; wherein:

$R^S$ is optionally substituted alkyl, optionally substituted carbocyclyl, optionally substituted aryl, optionally substituted heterocyclyl, or optionally substituted heteroaryl;

$R^1$ and $R^2$ are independently hydrogen, halogen, or optionally substituted alkyl;

each instance of $R^{P4}$ and $R^{P6}$ are independently hydrogen, optionally substituted alkyl, optionally substituted acyl, or an oxygen protecting group; and $R^7$ and $R^8$ are independently hydrogen, optionally substituted alkyl, optionally substituted carbocyclyl, optionally substituted aryl, optionally substituted heterocyclyl, or optionally substituted heteroaryl.

As described herein, the step of forming a compound of Formula (L-2-15) comprises reacting a compound of Formula (L-5-32) in the presence of a thiolating agent. Any thiolating agent known in the art may be used to this end. In certain embodiments, the thiolating agent is a disulfide. In certain embodiments, the thiolating agent is of the formula $(R^S S)_2$. In certain embodiments, the thiolating agent is of the formula (pyridine-S)$_2$. In certain embodiments, the thiolating agent is:

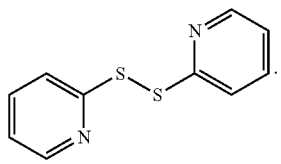

In certain embodiments, the step of thiolating a compound of Formula (L-5-32) is carried out in the presence of one of more additional reagents. In certain embodiments, the step of thiolating is carried out in the presence of a phosphine reagent (e.g., triphenylphosphine (Ph$_3$P)).

In certain embodiments, the step of thiolating is carried out in the presence of a disulfide and a phosphine. In certain embodiments, the reaction is carried out in the presence of (Py-S)$_2$ and Ph$_3$P. In certain embodiments, the reaction is carried out in a solvent such as toluene or CH$_2$Cl$_2$. In certain embodiments, the reaction is carried out at a temperature ranging from approximately 0° C. to approximately 50° C. In certain embodiments, the reaction is carried out at room temperature. For example, in certain embodiments, the step of thiolating is carried out under the following conditions: 1.4 equivalents of (Py-S)$_2$, 1.2 equivalents of Ph$_3$P, in toluene at room temperature (e.g., for 10-20 hours).

In certain embodiments, the method of thiolating a compound of Formula (L-5-32), or a salt thereof, comprises the steps of:

(a) deprotecting a compound of Formula (L-5-32), or a salt thereof, to yield a compound of Formula (L-5-32B):

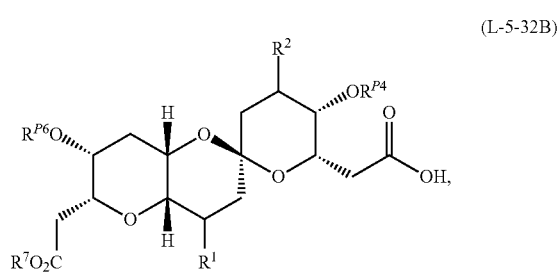

(L-5-32B)

or a salt thereof; and (b) thiolating a compound of Formula (L-5-32B), or a salt thereof, to yield a compound of Formula (L-2-15), or a salt thereof.

In certain embodiments, $R^7$ is optionally substituted alkyl; and $R^{P6}$ and $R^{P4}$ are silyl protecting groups. In certain embodiments, $R^7$ is optionally substituted alkyl; $R^{P6}$ and $R^{P4}$ are TES.

Also provided herein is a method of preparing a compound of Formula (L-5-32):

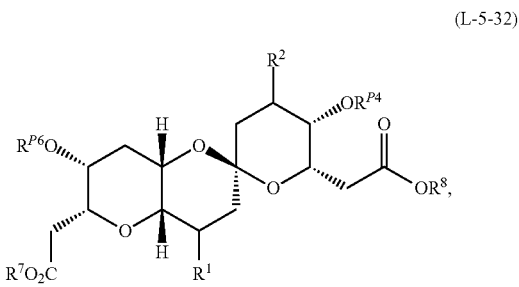

(L-5-32)

or a salt thereof, the method comprising oxidizing a compound of Formula (L-5-31):

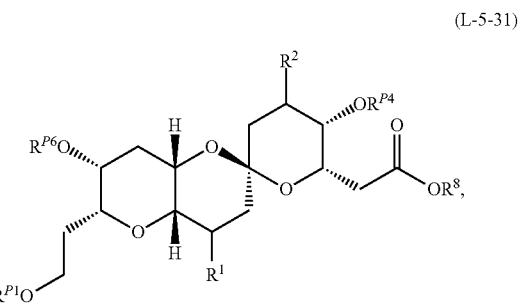

(L-5-31)

or a salt thereof; wherein:

$R^1$ and $R^2$ are independently hydrogen, halogen, or optionally substituted alkyl;

$R^{P1}$, $R^{P4}$, and $R^{P6}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method of preparing a compound of Formula (L-5-32), or a salt thereof, comprises the steps of:

(a) Oxidizing a compound of Formula (L-5-31B):

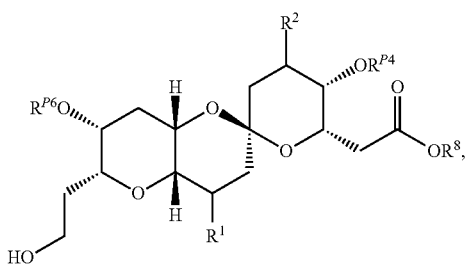

(L-5-31B)

or a salt thereof, to yield a compound of Formula (L-5-32C):

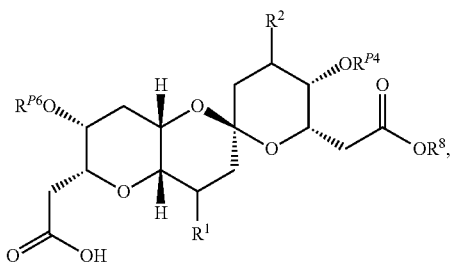

(L-5-32C)

or a salt thereof; and (b) protecting a compound of Formula (L-5-32C), or a salt thereof, to yield a compound of Formula (L-5-32), or a salt thereof.

Any method can be used in the step of oxidizing a compound of Formula (L-5-31) or (L-5-31B). In certain embodiments, the oxidation is carried out in the presence of a periodinane (e.g., Dess-Martin periodinane (DMP)). In certain embodiments, the oxidation involves a Swern oxidation. In certain embodiments, the oxidation is carried out in the presence of a chromium reagent (e.g., pyridinium chlorochromate (PCC)). In certain embodiments, the step of oxidizing involves a Pinnick oxidation, e.g., treatment of the reaction mixture with a chlorite (e.g., sodium chlorite (NaClO$_2$)). In certain embodiments, the oxidation involves carrying out the reaction in the presence of a periodinane (e.g., DMP) followed by a chlorite (e.g., NaClO$_2$). In certain embodiments, the oxidation is carried out in the presence of DMP and NaHCO$_3$ in a solvent (e.g., CH$_2$Cl$_2$), followed by NaClO$_2$ and NaH$_2$PO$_4$ in a solvent (e.g., t-BuOH/H$_2$O). In certain embodiments, the reactions are carried out at a temperature ranging from approximately 0° C. to approximately 50° C. In certain embodiments, the reactions are carried out at around room temperature. For example, in certain embodiments, the reaction is carried out under the following conditions: (a) 2 equivalents DMP, 10 equivalents NaHCO$_3$ in CH$_2$Cl$_2$ at room temperature (e.g., for under 1 hour); followed by (b) 3 equivalents NaClO$_2$, 4 equivalents NaH$_2$PO$_4$, with 2-methyl-2-butene in t-BuOH and water at room temperature (e.g., for under 1 hour).

In certain embodiments, the step of protecting a compound of Formula (L-5-32C) involves treating the compound with an alkylating agent. In certain embodiments, the alkylating agent is an alkyl halide or a reagent of the structure: alkyl-leaving group. In certain embodiments, the alkylating agent is a methyl transfer reagent (e.g., diazomethane, trimethylsilyldiazomethane (TMSCH$_2$N$_2$)).

In certain embodiments, the step of protecting is carried out in the presence of TMSCH$_2$N$_2$. In certain embodiments, the reaction is carried out in a solvent (e.g., benzene/MeOH). In certain embodiments, the reaction is carried out at a temperature ranging from approximately 0° C. to approximately 50° C. In certain embodiments, the reaction is carried out at around room temperature. For example, in certain embodiments, the reaction is carried out under the following conditions: 3 equivalents TMSCH$_2$N$_2$ in benzene/MeOH at room temperature (e.g., for 5 min).

In certain embodiments, R$^7$ is optionally substituted alkyl; and R$^{P6}$ is a silyl protecting group; R$^{P4}$ is optionally substituted benzyl; and R$^8$ is optionally substituted benzyl. In certain embodiments, R$^7$ is methyl; R$^{P6}$ is TES; R$^{P4}$ is MPM; and R$^8$ is benzyl.

In certain embodiments, the compound of Formula (L-5-32), or a salt thereof, is deprotected to remove the group R$^{P4}$ yield a compound of Formula (L-5-32D):

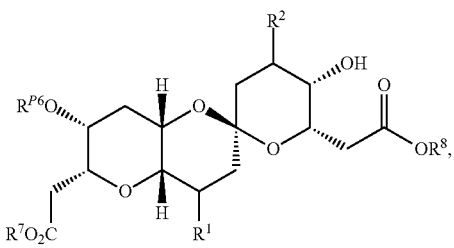

(L-5-32D)

or a salt thereof; and optionally re-protected (i.e., to switch the group R$^{P4}$ from, e.g., a benzyl protecting group (e.g., MPM) to a silyl protecting group (e.g., trialkylsilyl such as triethylsilyl).

As shown in Scheme 4C, provided herein is a method of preparing a compound of Formula (L-5-31):

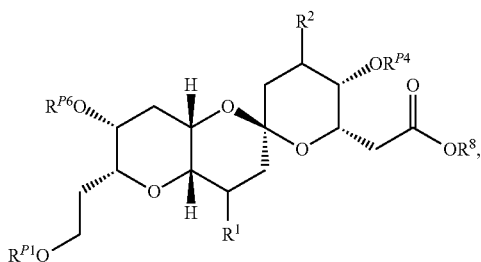

(L-5-31)

or a salt thereof, the method comprising a step of cyclizing a compound of Formula (L-5-32A):

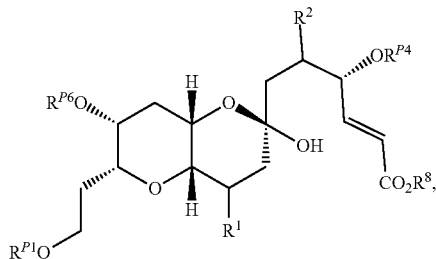
(L-5-30)

or a salt thereof; wherein:

$R^1$ and $R^2$ are independently hydrogen, halogen, or optionally substituted alkyl;

$R^{P1}$, $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (7-5-30) is carried out in the presence of a base. In certain embodiments, the base is a nitrogen base. In certain embodiments, the base is an amidine or guanidine base. In certain embodiments, the base is an amine or an amide. In certain embodiments, the base is an amidine base (e.g., 1,8-diazabicyclo(5.4.0)undec-7-ene (DBU)). In certain embodiments, the step of cyclizing is carried out in the presence of an acid. In certain embodiments, the acid is a Lewis acid. In certain embodiments, the step of cyclizing is carried out in the presence of a lithium salt (e.g., LiBr, LiCl). The step of cyclizing may be carried out in the presence of one or more additional reagents. In certain embodiments, the step of cyclizing is carried out in the presence of BnOAc.

In certain embodiments, the step of cyclizing is carried out in the presence of a lithium salt, and a base. In certain embodiments, the step of cyclizing is carried out in the presence of LiBr and DBU. In certain embodiments, the reaction is carried out in a solvent such as MeCN. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 10 equivalents LiBr, 5 equivalents DBU, and 2 equivalents BnOAc in MeCN at room temperature (e.g., for 10-20 hours).

In certain embodiments, $R^{P1}$ is a silyl; and $R^{P6}$ is a silyl protecting group; $R^{P4}$ is optionally substituted benzyl; and $R^8$ is optionally substituted benzyl. In certain embodiments, $R^{P1}$ is TES; $R^{P6}$ is TES; $R^{P4}$ is MPM; and $R^8$ is benzyl.

Also provided herein is a method of preparing a compound of Formula (L-5-30):

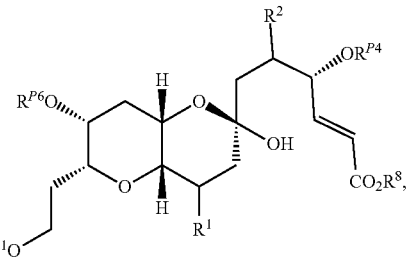
(L-5-30)

or a salt thereof, the method comprising a step of reacting a compound of Formula (L-5-28):

(L-5-28)

or a salt thereof, in the presence of an olefin and an olefin metathesis catalyst; wherein:

$R^1$ and $R^2$ are independently hydrogen, halogen, or optionally substituted alkyl; and $R^{P1}$, $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the olefin is of the formula:

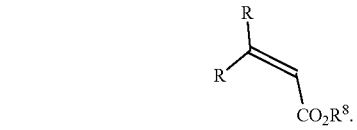

Further, any olefin metathesis known in the art may be used in the metathesis reaction to furnish a compound of Formula (L-5-30).

Also provided herein is an alternative method of preparing a compound of Formula (L-5-30):

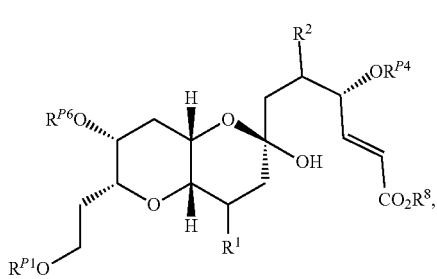
(L-5-30)

or a salt thereof, the method comprising the steps of:
 (a) oxidizing a compound of Formula (L-5-28):

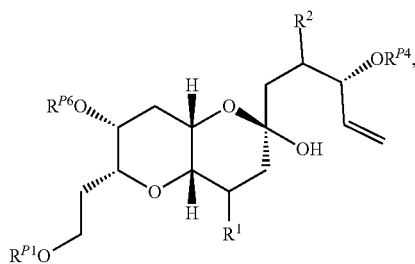

(L-5-28)

or a salt thereof, to yield a compound of Formula (L-5-29) or (L-5-29B):

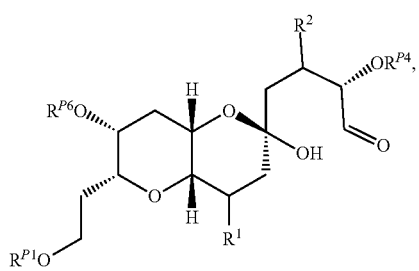

(L-5-29)

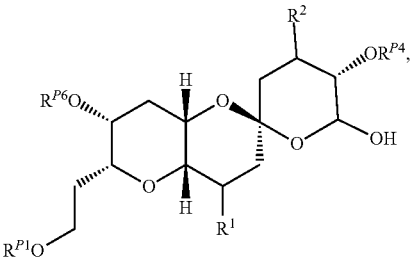

(L-5-29B)

or a salt thereof; and
 (b) reacting the compound of Formula (L-5-29) or (L-5-29B), or a salt thereof, in the presence of a olefination reagent, to yield a compound of Formula (L-5-30), or a salt thereof. The reaction in step (a) above is an oxidative cleavage; the reaction in step (b) is an olefination reaction. In certain embodiments, the oxidative cleavage is carried out via ozonolysis (e.g., in the presence of $O_3$). In certain embodiments, the cleavage is carried out in the presence of reagents capable of dihydroxylating a double bond (e.g., osmium tetroxide ($OsO_4$), N-methylmorpholine N-oxide (NMMO)), followed by a transition metal (e.g., a lead complex such as $Pb(OAc)_4$).

In certain embodiments, the double bond is dihydroxylated by treatment with $OsO_4$, NMMO, and water. In certain embodiments, the reaction is carried out in the presence of a solvent such as acetone. In certain embodiments, the reaction is carried out at a temperature ranging from approximately 0° C. to approximately 50° C. In certain embodiments, the reaction is carried out at room temperature. For example, in certain embodiments, the double bond is dihydroxylated under the following conditions: 5 mol % $OsO_4$, 2 equivalents NMMO, and water, in acetone at room temperature (e.g., for 10-20 hours). The resulting compound is then treated, in certain embodiments, with $Pb(OAc)_4$ and $K_2CO_3$ to yield the aldehyde or hemiacetal. For example, in certain embodiments, this step is carried out under the following conditions: 2 equivalents $Pb(OAc)_4$, 10 equivalents $K_2CO_3$, in $CH_2Cl_2$ at room temperature (e.g., for under 1 hour).

In certain embodiments, the olefination is carried out in the presence of a Wittig or Horner-Wadsworth Emmons reagent. In certain embodiments, the olefination is carried out in the presence of a reagent of the formula: $(RO)_2P(O)CH_2CO_2R^8$. In certain embodiments, the reagent is of the formula: $(MeO)_2P(O)CH_2CO_2R^8$ (e.g., $(MeO)_2P(O)CH_2CO_2Bn$). In certain embodiments, the olefination is carried out in the presence of a base (e.g., a phosphate salt such as $K_3PO_4$).

In certain embodiments, the olefination is carried out in the presence of an olefination reagent of the formula: $(RO)_2P(O)CH_2CO_2R^8$, and a base. In certain embodiments, the olefination is carried out in the presence of $(MeO)_2P(O)CH_2CO_2Bn$ and $K_3PO_4$. In certain embodiments, the reaction is carried out in a solvent such as toluene. In certain embodiments, the reaction is carried out at a temperature ranging from approximately 0° C. to approximately 50° C. In certain embodiments, the reaction is carried out at room temperature. For example, in certain embodiments, the reaction is carried out under the following conditions: 4 equivalents $(MeO)_2P(O)CH_2CO_2Bn$, 3 equivalents $K_3PO_4$, in a solvent at room temperature (e.g., for 24-48 hours).

In certain embodiments, $R^{P1}$ is a silyl; and $R^{P6}$ is a silyl protecting group; $R^{P4}$ is optionally substituted benzyl; and $R^8$ is optionally substituted benzyl. In certain embodiments, $R^{P1}$ is TES; $R^{P6}$ is TES; $R^{P4}$ is MPM; and $R^8$ is benzyl.

Also provided herein is a method of preparing a compound of Formula (L-5-28):

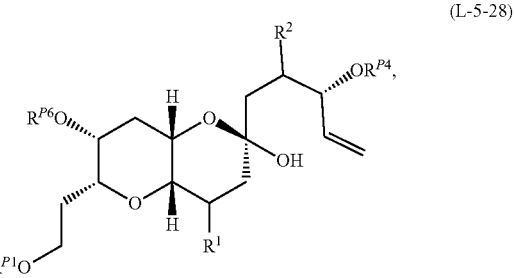

(L-5-28)

or a salt thereof, the method comprising a step of coupling a compound of Formula (L-5-27):

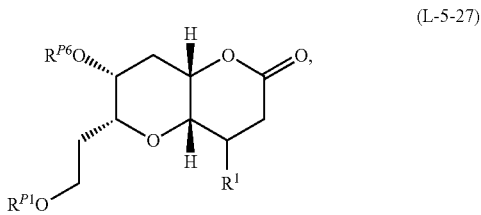

(L-5-27)

or a salt thereof, with a compound of Formula (L-5-5):

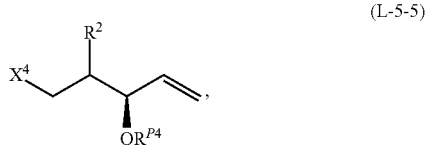

(L-5-5)

or a salt thereof, wherein:

$X^4$ is halogen or a leaving group;

$R^1$ and $R^2$ are independently hydrogen, halogen, or optionally substituted alkyl; and each instance of $R^{P1}$, $R^{P4}$, and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the coupling of a compound of Formula (L-5-4) with a compound of Formula (L-5-5) is carried out in the presence of an organometallic reagent (e.g., to covert $X^4$ to a metal for addition to the compound of Formula (L-5-4)). In certain embodiments, the organometallic reagent is a lithium reagent (e.g., to convert the compound of the Formula (L-5-5) to a compound of the formula:

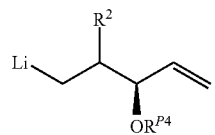

for addition to the compound of Formula (L-5-4)). In certain embodiments, lithium reagent is an organolithium (e.g., n-butyllithium, tert-butyllithium, sec-butyllithium). In certain embodiments, the lithium reagent is LiHMDS or LDA.

In certain embodiments, the reaction is carried out in the presence of tert-butyllithium. In certain embodiments, the reaction is performed in a solvent such as toluene, THF, $Et_2O$, or a combination thereof. In certain embodiments, the reaction is carried out at a temperature ranging from approximately −78° C. to approximately room temperature. In certain embodiments, the reaction is carried out at −78° C. For example, in certain embodiments, the reaction is carried out with 2.2 equivalents of tert-butyllithium in toluene and $Et_2O$ at −78° C. (e.g., for less than 1 hour).

In certain embodiments, $R^{P1}$ is a silyl; and $R^{P6}$ is a silyl protecting group; $R^{P4}$ is optionally substituted benzyl; and $R^8$ is optionally substituted benzyl. In certain embodiments, $R^{P1}$ is TES; $R^{P6}$ is TES; $R^{P4}$ is MPM; and $R^8$ is benzyl.

Preparation Left Halves of Halichondrin Analogs

Provided herein are methods useful in the preparation of "left half" building blocks of other halichondrin analogs (e.g., compounds of Formula (H3-2-1)). For example, as shown in Scheme 4D, left half building blocks of Formula (L-2-6) can be prepared by converting the ester group (i.e., —$CO_2R^8$) of a compound of Formula (L-5-7B) to a thioester moiety (i.e., —C(O)$SR^S$). A compound of Formula (L-5-7B) can be prepared by cyclizing a compound of Formula (L-5-7A), which may be prepared by oxidative cleavage and olefination of a compound of Formula (L-5-6A). A compound of Formula (L-5-6A) can be prepared by coupling a compound of Formula (L-5-4) with a compound of Formula (L-5-5). As also shown in scheme 4D, a compound of Formula (L-5-4) can be prepared via homologation of a lactone of Formula (L-5-3).

Scheme 4D

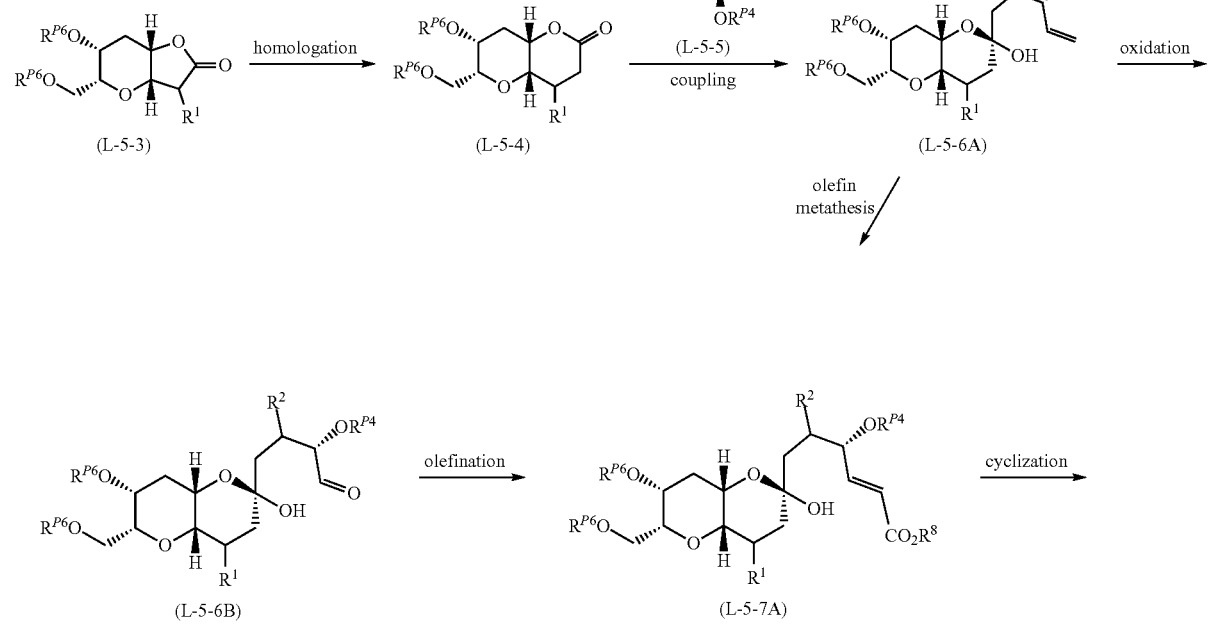

-continued

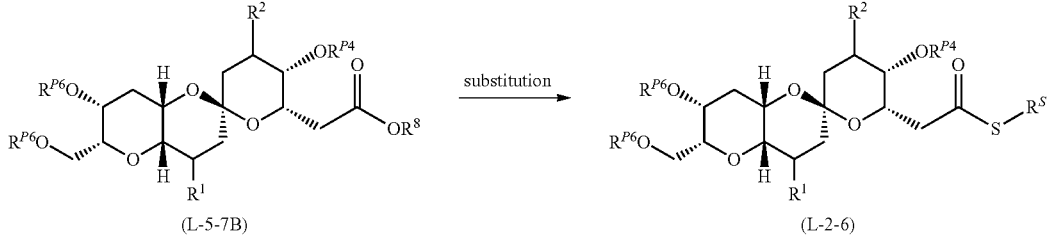

As shown in Scheme 4D, provided herein is a method of preparing a compound of Formula (L-2-6):

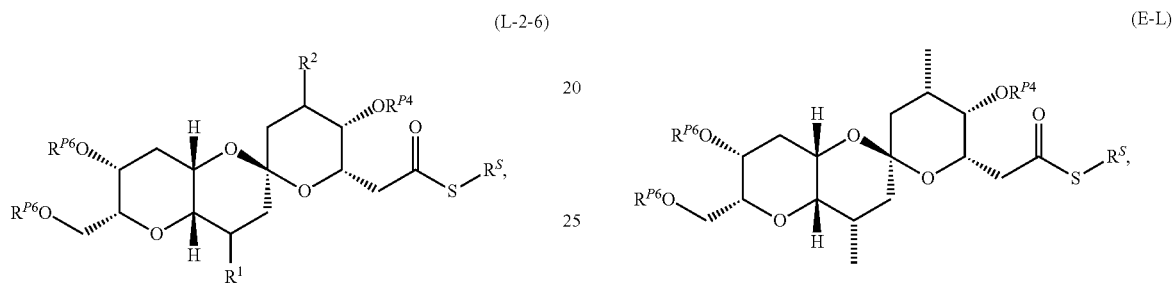

or a salt thereof, the method comprising a step of reacting a compound of Formula (L-5-7B):

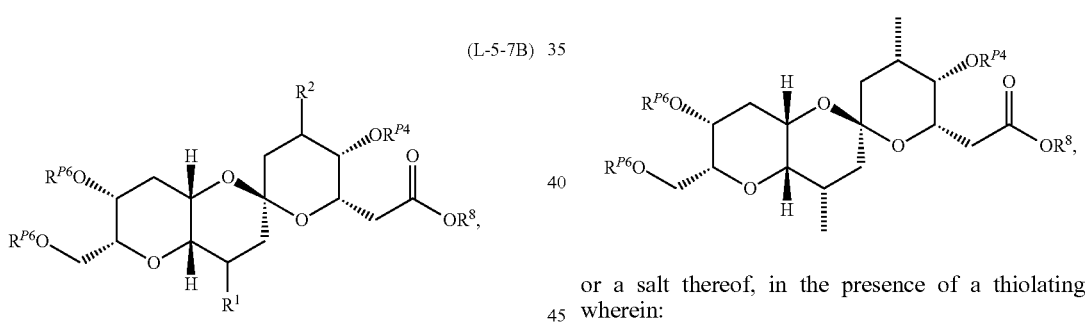

or a salt thereof, in the presence of a thiolating agent; wherein:

$R^S$ is optionally substituted alkyl, optionally substituted carbocyclyl, optionally substituted aryl, optionally substituted heterocyclyl, or optionally substituted heteroaryl;

$R^1$ and $R^2$ are independently hydrogen, halogen, or optionally substituted alkyl;

each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method is a method of preparing a compound of Formula (E-L):

(E-L)

or a salt thereof, the method comprising a step of reacting a compound of Formula (E-L-1):

(E-L-1)

or a salt thereof, in the presence of a thiolating agent; wherein:

$R^S$ is optionally substituted alkyl, optionally substituted carbocyclyl, optionally substituted aryl, optionally substituted heterocyclyl, or optionally substituted heteroaryl;

each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

As described herein, the step of forming a compound of Formula (L-2-6), (E-L), or a salt thereof, comprises reacting a compound of Formula (L-5-7B), (E-L-1), or a salt thereof, in the presence of a thiolating agent. Any thiolating agent known in the art may be used to this end. In certain embodiments, the thiolating agent is a disulfide. In certain embodiments, the thiolating agent is of the formula $(R^S S)_2$. In certain embodiments, the thiolating agent is of the formula $(pyridine-S)_2$. In certain embodiments, the thiolating agent is:

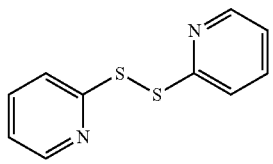 [SMILES: c1ccc(SSc2ccccn2)nc1]

(2,2'-dipyridyl sulfide). In certain embodiments, the thiolating reagent is present in stoichiometric or excess amounts (e.g., 1-2 equivalents)

In certain embodiments, the step of thiolating is carried out in the presence of one of more additional reagents. In certain embodiments, the step of thiolating is carried out in the presence of a phosphine reagent. In certain embodiments, the phosphine is a trialkyl phosphine. In certain embodiments, the phosphine is a triaryl phosphine. In certain embodiments, the phosphine is PPh$_3$. In certain embodiments, the phosphine is polymer-bound PPh$_3$. In certain embodiments, the phosphine is present in stoichiometric or excess amounts (e.g., 1-3 equivalents).

In certain embodiments, the step of thiolating is carried out in the presence of a disulfide and a phosphine. In certain embodiments, the reaction is carried out in the presence of 2,2'-dipyridyl sulfide and Ph$_3$P. In certain embodiments, the reaction is carried out in a solvent. In certain embodiments, the solvent is DCM. In certain embodiments, the solvent is acetonitrile. In certain embodiments, the reaction is carried out at from 0° C. to room temperature. In certain embodiments, the reaction is carried out at a temperature ranging from approximately 0° C. to approximately 50° C. In certain embodiments, the reaction is carried out at room temperature. In certain embodiments, the reaction is carried out in the presence of 2,2'-dipyridyl sulfide and Ph$_3$P in MeCN at from 0° C. to room temperature.

For example, in certain embodiments, the step of thiolating is carried out under the following conditions: 1.4 equivalents of 2,2'-dipyridyl sulfide, 1.2 equivalents of Ph$_3$P, in DCM at room temperature (e.g., for 10-20 hours). For example, in certain embodiments, the step of thiolating is carried out under the following conditions: 1.2 equivalents of 2,2'-dipyridyl sulfide, 2.3 equivalents of Ph$_3$P, in MeCN at from 0° C. to room temperature (e.g., for 10-20 hours).

In certain embodiments, two $R^{P6}$ are joined with the intervening atoms to form a ring of the formula:

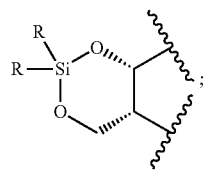

and $R^{P4}$ is a silyl protecting group. In certain embodiments, two $R^{P6}$ are joined with the intervening atoms to form a ring of the formula:

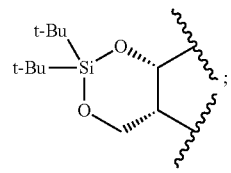 [SMILES: *[C@@H]1CO[Si](C(C)(C)C)(C(C)(C)C)O[C@@H]1*]

and $R^{P4}$ is TES.

In certain embodiments, the method of thiolating a compound of Formula (L-5-7B), or a salt thereof, comprises:

(a) a step of deprotecting a compound of Formula (L-5-7B), or a salt thereof, under conditions sufficient to remove the $R^{P4}$ and $R^8$ groups, to yield a compound of Formula (L-5-7C):

(L-5-7C)

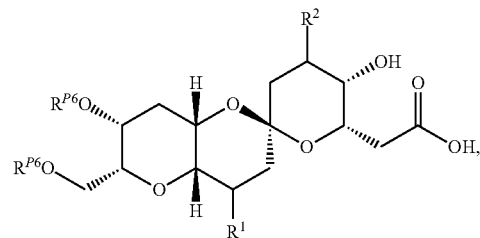

or a salt thereof; and (b) a step of protecting a compound of Formula (L-5-7C), or a salt thereof, to yield a compound of Formula (L-5-7D):

(E-L-3)

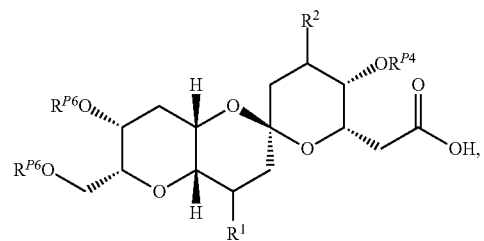

or a salt thereof.

In certain embodiments, the method comprises:

(a) a step of deprotecting a compound of Formula (E-L-1), or a salt thereof, under conditions sufficient to remove the $R^{P4}$ and $R^8$ groups, to yield a compound of Formula (E-L-3):

(E-L-3)

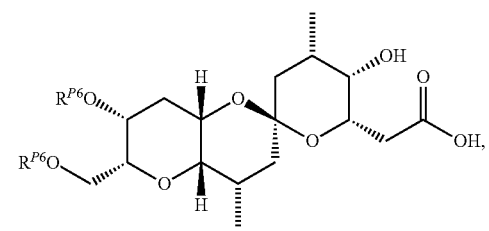

or a salt thereof; and (b) a step of protecting a compound of Formula (E-L-3), or a salt thereof, to yield a compound of Formula (E-L-4):

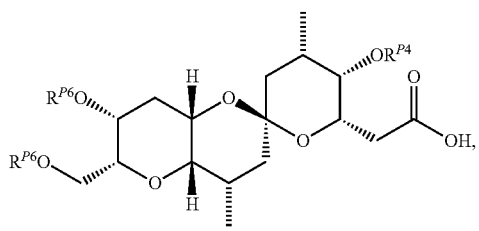

(E-L-4)

or a salt thereof.

In certain embodiments, with respect to the compounds of Formula (L-5-7B), (E-L-1), or a salt thereof, $R^{P4}$ and $R^8$ are optionally substituted benzyl protecting groups; and the step of deprotecting (i.e., step (a)) is carried out in the presence of H$_2$ and Pd/C. In certain embodiments, $R^{P4}$ is MPM and $R^8$ is benzyl (Bn); and the step of deprotecting is carried out in the presence of H$_2$ and Pd/C. In certain embodiments, the step of deprotecting is carried out in the presence of H$_2$ and Pd/C in i-PrOAc.

In certain embodiments, with respect to the compound of Formula (E-L-4), (L-5-7D), or salt thereof, $R^{P4}$ is a silyl protecting group; and the step of protecting (i.e., step (b)) is carried out in the presence of a silylating agent and base. In certain embodiments, $R^{P4}$ is TES; and the silylating reagent is TESCl. In certain embodiments, the base is imidazole. In certain embodiments, the step of protecting is carried out in the presence of TESCl and imidazole. In certain embodiments, the step of protecting is carried out in the presence of TESCl and imidazole in DMF.

In certain embodiments, the compounds of Formulae (E-L-4), (L-5-7D), or salts thereof, are purified by silica gel chromatography and/or purification.

As also shown in Scheme 4D, provided herein is a method of preparing a compound of Formula (L-5-7B):

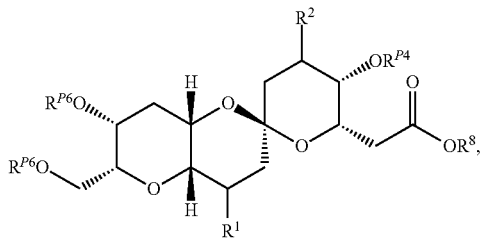

(L-5-7B)

or a salt thereof, the method comprising cyclizing a compound of Formula (L-5-7A):

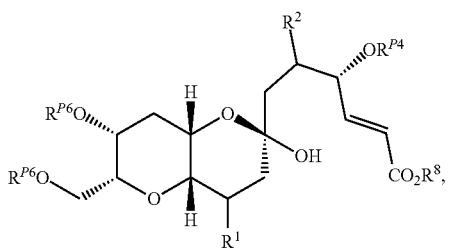

(L-5-7A)

or a salt thereof; wherein:

$R^1$ and $R^2$ are independently hydrogen, halogen, or optionally substituted alkyl;

each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the method comprises cyclizing a compound of Formula (E-L-2):

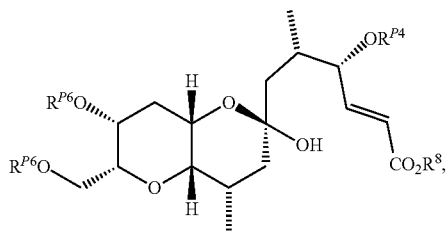

(E-L-2)

or a salt thereof, to yield a compound of Formula (E-L-1):

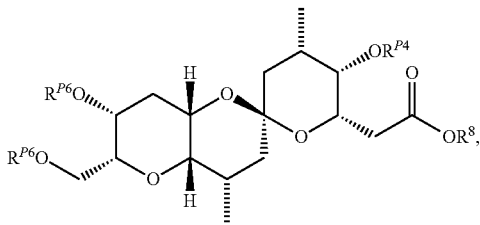

(E-L-1)

or a salt thereof, wherein:

each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the step of cyclizing a compound of Formula (7-5-7A), (E-L-2), or a salt thereof, is carried out in the presence of a base. In certain embodiments, the base is a nitrogen base. In certain embodiments, the base is an amidine, guanidine base. In certain embodiments, the base is an amine or amide base. In certain embodiments, the base is an amidine base (e.g., 1,8-diazabicyclo(5.4.0)undec-7-ene (DBU)). In certain embodiments, the base is DBU. In certain embodiments, the base is used in an excess amount.

In certain embodiments, the step of cyclizing is carried out in the presence of an acid. In certain embodiments, the acid is a Lewis acid.

In certain embodiments, the step of cyclizing is carried out in the presence of a lithium salt (e.g., LiBr, LiCl). In certain embodiments, the reaction is carried out in the presence of LiBr. In certain embodiments, the base is used in an excess amount.

The step of cyclizing may be carried out in the presence of one or more additional reagents. In certain embodiments, the step of cyclizing is carried out in the presence of a reagent of the formula: $R^8OAc$. In certain embodiments, the step of cyclizing is carried out in the presence of BnOAc. In certain embodiments, the reagent is present in an excess amount.

In certain embodiments, the reaction is carried out in a solvent. In certain embodiments, the solvent is MeCN. In certain embodiments, the reaction is carried out at a temperature ranging from approximately 0° C. to approximately 50° C. In certain embodiments, the reaction is carried out at room temperature. In certain embodiments, the reaction is carried out at around 30° C.

In certain embodiments, the step of cyclizing is carried out in the presence of a lithium salt and a base. In certain embodiments, the step of cyclizing is carried out in the presence of LiBr and DBU. In certain embodiments, the step of cyclizing is carried out in the presence of LiBr, DBU, and $R^8OAc$. In certain embodiments, the step of cyclizing is carried out in the presence of LiBr, DBU, and BnOAc. In certain embodiments, the step of cyclizing is carried out in the presence of LiBr, DBU, and BnOAc in MeCN from room temperature to around 30° C.

For example, in certain embodiments, the reaction is carried out under the following conditions: 10 equivalents LiBr, 5 equivalents DBU, and 10 equivalents BnOAc in MeCN at room temperature (e.g., for 10-20 hours). For example, in certain embodiments, the reaction is carried out under the following conditions: 10 equivalents LiBr, 5 equivalents DBU, and 5 equivalents BnOAc in MeCN at room temperature to around 30° C. (e.g., for around 24 hours).

In certain embodiments, two $R^{P6}$ are joined with the intervening atoms to form a ring of the formula:

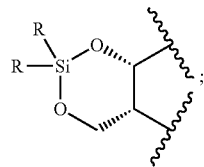

and $R^{P4}$ and $R^{P8}$ are optionally substituted benzyl groups. In certain embodiments, two $R^{P6}$ are joined with the intervening atoms to form a ring of the formula:

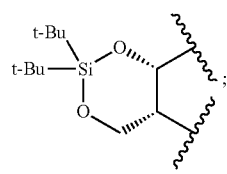

$R^{P4}$ is MPM; and $R^{P8}$ is benzyl.

In certain embodiments, the compound of Formula (L-5-7B), or a salt thereof, is deprotected to remove the group $R^{P4}$ yield a compound of Formula (L-5-7D):

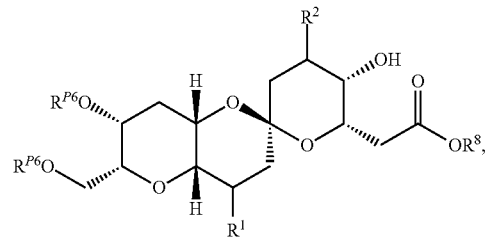

(L-5-7D)

or a salt thereof; and optionally re-protected (i.e., to switch the group $R^{P4}$ from, e.g., a benzyl protecting group (e.g., MPM) to a silyl protecting group (e.g., trialkylsilyl such as triethylsilyl).

Also provided herein is a method of preparing a compound of Formula (L-5-7A):

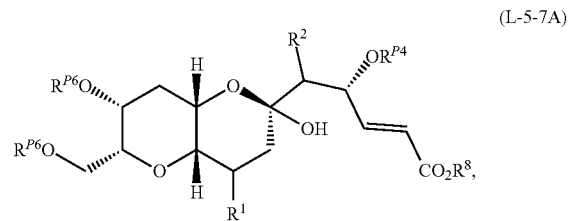

(L-5-7A)

or a salt thereof, the method comprising a step of reacting a compound of Formula (L-5-6A):

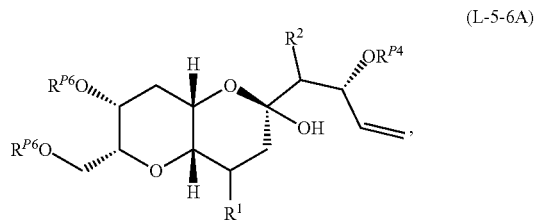

(L-5-6A)

or a salt thereof, in the presence of an olefin and an olefin metathesis catalyst; wherein:

$R^1$ and $R^2$ are independently hydrogen, halogen, or optionally substituted alkyl; each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the olefin is of the formula:

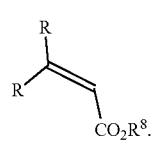

Further, any olefin metathesis known in the art may be used in the metathesis reaction to furnish a compound of Formula (L-5-7A).

Also provided herein is an alternative method of preparing a compound of Formula (L-5-7A):

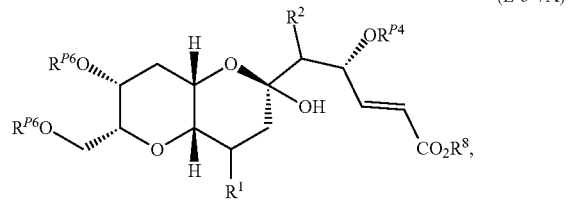

(L-5-7A)

or a salt thereof, the method comprising the steps of:
(a) oxidizing a compound of Formula (L-5-6A):

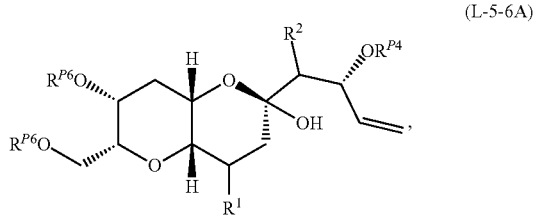

(L-5-6A)

or a salt thereof, to yield a compound of Formula (L-5-6B) and/or (L-5-6BB):

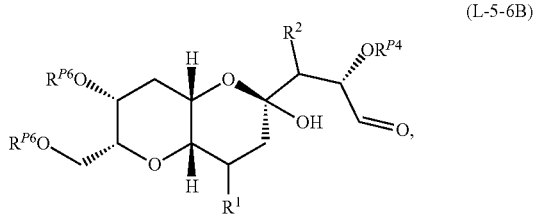

(L-5-6B)

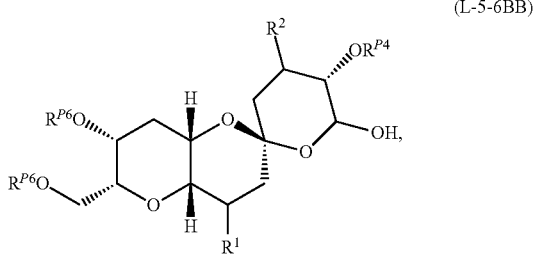

(L-5-6BB)

or a salt thereof; and
(b) reacting the compound of Formula (L-5-6B) and/or (L-5-6BB), or a salt thereof, in the presence of a olefination reagent, to yield a compound of Formula (L-5-7A), or a salt thereof.

In certain embodiments, the method comprises the steps of:
(a) oxidizing a compound of Formula (E-L-5):

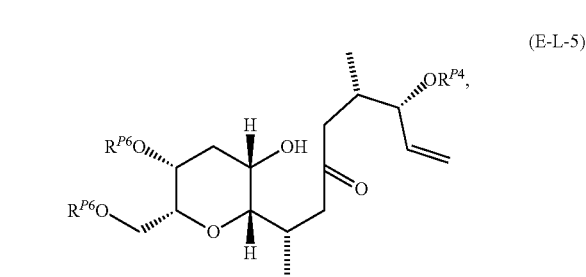

(E-L-5)

or a salt thereof, to yield a compound of Formula (E-L-6):

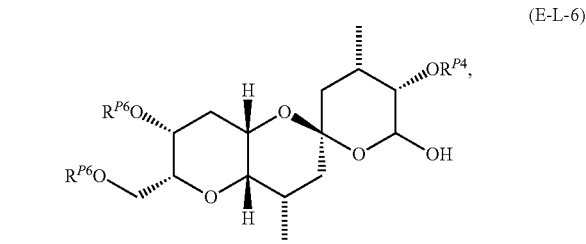

(E-L-6)

or a salt thereof; and
(b) reacting the compound of Formula (E-L-6), or a salt thereof, in the presence of a olefination reagent, to yield a compound of Formula (E-L-2):

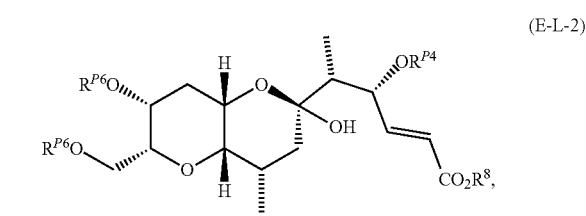

(E-L-2)

or a salt thereof, wherein:
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

The oxidation of a compound of Formula (L-5-6A), (E-L-5), or a salt thereof (i.e., step (a)) above is an oxidative cleavage. In certain embodiments, the oxidative cleavage is carried out via ozonolysis (e.g., in the presence of $O_3$). In certain embodiments, the oxidizing cleavage is a Johnson-Lemieux oxidative cleavage. For example, In certain embodiments, the cleavage is carried out in the presence of reagents capable of dihydroxylating a double bond (e.g., osmium tetroxide ($OsO_4$) and N-methylmorpholine N-oxide (NMO); or potassium osmate (VI) dehydrate ($K_2OsO_4$) and NMO), followed by a transition metal (e.g., a lead complex such as Pb(OAc)$_4$). In certain embodiments, the cleavage is carried out in the presence of reagents capable of dihydroxylating a double bond (e.g., osmium tetroxide (OsO$_4$) and N-methylmorpholine N-oxide (NMO); or potassium osmate (VI) dehydrate (K$_2$OsO$_4$) and NMO), followed by sodium periodate (NaIO$_4$).

In certain embodiments, the double bond is dihydroxylated by treatment with OsO$_4$, NMO, and water. In certain embodiments, the reaction is carried out in the presence of a solvent such as acetone. In certain embodiments, the reaction is carried out at a temperature ranging from approximately 0° C. to approximately 50° C. In certain embodiments, the reaction is carried out at room temperature. For example, in certain embodiments, the double bond is dihydroxylated under the following conditions: 10 mol % OsO$_4$, 2 equivalents NMO, and water, in acetone at room temperature (e.g., for 20-25 hours). The resulting compound is then treated, in certain embodiments, with Pb(OAc)$_4$ and K$_2$CO$_3$ to yield the aldehyde and/or hemiacetal. For example, in certain embodiments, this step is carried out under the following conditions: 1.2 equivalents Pb(OAc)$_4$, 3 equivalents K$_2$CO$_3$, in CH$_2$Cl$_2$ at room temperature (e.g., for approximately 1 hour).

In certain embodiments, the step of oxidizing is carried out in the presence of osmium tetroxide (OsO$_4$) or potassium osmate (VI) dehydrate (K$_2$OsO$_4$), and NMO; followed by NaIO$_4$. In certain embodiments, the step of oxidizing is carried out in the presence of potassium osmate (VI) dehydrate (K$_2$OsO$_4$) and NMO, followed by NaIO$_4$. In certain embodiments, the reaction is carried out in a solvent. In certain embodiments, the reaction is carried out in acetone and water. In certain embodiments, the reaction is carried out at a temperature ranging from approximately 0° C. to approximately 50° C. In certain embodiments, the reaction is carried out at around room temperature. In certain embodiments, the reaction is carried out in the presence of K$_2$OsO$_4$ and NMO, followed by NaIO$_4$, in acetone and water, at around room temperature. For example, in certain embodiments, the reaction is carried out under the following conditions: K$_2$OsO$_4$.2H$_2$O and NMO, followed by NaIO$_4$, in acetone and water, at around room temperature.

In certain embodiments, the olefination in step (b) is carried out in the presence of a Wittig or Horner-Wadsworth Emmons reagent. In certain embodiments, the olefination is carried out in the presence of a reagent of the formula: (RO)$_2$P(O)CH$_2$CO$_2$R$^8$. In certain embodiments, the reagent is of the formula: (MeO)$_2$P(O)CH$_2$CO$_2$R$^8$ (e.g., (MeO)$_2$P(O)CH$_2$CO$_2$Bn). In certain embodiments, the olefination is carried out in the presence of a base (e.g., a phosphate salt such as K$_3$PO$_4$).

In certain embodiments, the olefination is carried out in the presence of an olefination reagent of the formula: (RO)$_2$P(O)CH$_2$CO$_2$R$^8$, and a base. In certain embodiments, the olefination is carried out in the presence of (MeO)$_2$P(O)CH$_2$CO$_2$Bn and K$_3$PO$_4$. In certain embodiments, the reaction is carried out in a solvent such as toluene. In certain embodiments, the reaction is carried out at a temperature ranging from approximately 0° C. to approximately 50° C. In certain embodiments, the reaction is carried out at room temperature. In certain embodiments, the reaction is carried out at around 30° C. In certain embodiments, the olefination is carried out in the presence of (MeO)$_2$P(O)CH$_2$CO$_2$Bn and K$_3$PO$_4$, in toluene at around 30° C. For example, in certain embodiments, the reaction is carried out under the following conditions: 4 equivalents (MeO)$_2$P(O)CH$_2$CO$_2$Bn, 3 equivalents K$_3$PO$_4$ at room temperature (e.g., for about 20-25 hours). For example, in certain embodiments, the reaction is carried out under the following conditions: 5 equivalents (MeO)$_2$P(O)CH$_2$CO$_2$Bn, 4 equivalents K$_3$PO$_4$ at around 30° C. (e.g., for about 1-3 days).

In certain embodiments, two R$^{P6}$ are joined with the intervening atoms to form a ring of the formula

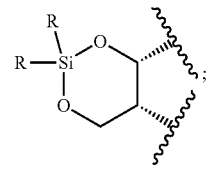

and R$^{P4}$ and R$^{P8}$ are optionally substituted benzyl groups. In certain embodiments, two R$^{P6}$ are joined with the intervening atoms to form a ring of the formula:

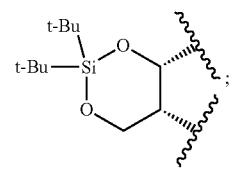 [SMILES: *[C@@H]1CO[Si](C(C)(C)C)(C(C)(C)C)O[C@@H]1*]

R$^{P4}$ is MPM; and R$^{P8}$ is benzyl.

Also provided herein is a method of preparing a compound of Formula (L-5-6A):

(L-5-6A)

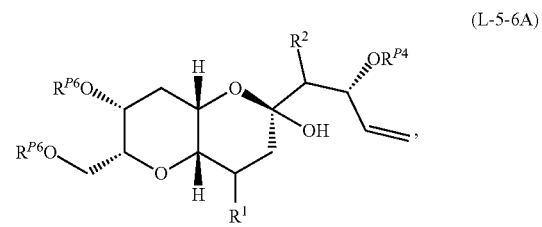

or a salt thereof, the method comprising a step of coupling a compound of Formula (L-5-4):

(L-5-4)

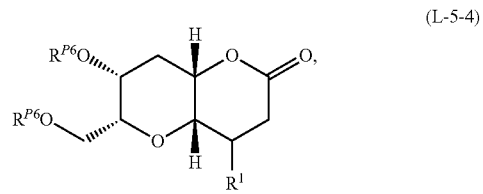

or a salt thereof, with a compound of Formula (L-5-5):

(L-5-5)

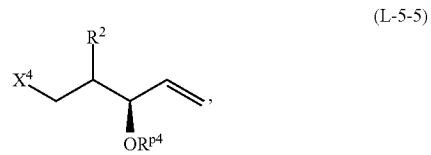

or a salt thereof, wherein:

X⁴ is halogen or a leaving group;

R¹ and R² are independently hydrogen, halogen, or optionally substituted alkyl; and each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the method comprises comprising a step of coupling a compound of Formula (E-L-7):

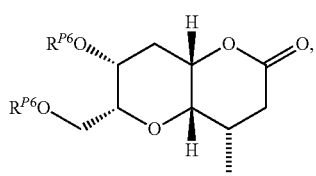

(L-5-7)

or a salt thereof, with a compound of Formula (E-L-8):

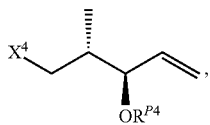

(E-L-8)

or a salt thereof, to yield a compound of Formula (E-L-5):

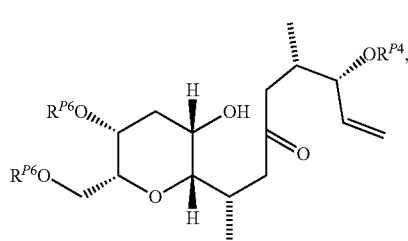

(E-L-5)

or a salt thereof; wherein:

X⁴ is halogen or a leaving group; and each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the coupling of a compound of Formula (L-5-4) with a compound of Formula (L-5-5) (or a compound of the formula (E-L-7) and (E-L-8)) is carried out in the presence of an organometallic reagent (e.g., to covert X⁴ to a metal for addition to the compound of Formula (L-5-4) or (E-L-7)). In certain embodiments, the organometallic reagent is a lithium reagent (e.g., to convert the compound of the Formula (L-5-5) to a compound of the formula:

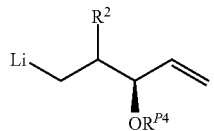

for addition to the compound of Formula (L-5-4); e.g., to convert the compound of the Formula (E-L-8) to a compound of the formula:

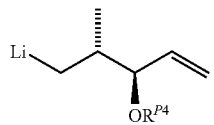

for addition to the compound of Formula (E-L-7)). In certain embodiments, lithium reagent is an organolithium (e.g., n-butyllithium, tert-butyllithium, sec-butyllithium). In certain embodiments, the lithium reagent is LiHMDS or LDA. In certain embodiments, the lithium reagent is sec-butyllithium.

In certain embodiments, the reaction is carried out in the presence of tert-butyllithium. In certain embodiments, the reaction is performed in a solvent such as THF. In certain embodiments, the reaction is carried out at a temperature ranging from approximately −78° C. to approximately room temperature. In certain embodiments, the reaction is carried out at a temperature ranging from approximately −78° C. to approximately 0° C. For example, in certain embodiments, the reaction is carried out with 2.6 equivalents of tert-butyllithium in THF from −78° C. to room temperature (e.g., over less than 1 hour).

In certain embodiments, the reaction is carried out in the presence of sec-butyllithium. In certain embodiments, the reaction is performed in THF. In certain embodiments, the reaction is carried out at a temperature ranging from approximately −78° C. to approximately room temperature. In certain embodiments, the reaction is carried out at a temperature ranging from approximately −78° C. to approximately 0° C. In certain embodiments, the reaction is carried out with sec-butyllithium in THF at around −78° C. to room temperature. For example, in certain embodiments, the reaction is carried out with about 2 equivalents of sec-butyllithium in THF from −78° C. to room temperature (e.g., over less than 1 hour).

In certain embodiments, two $R^{P6}$ are joined with the intervening atoms to form a ring of the formula:

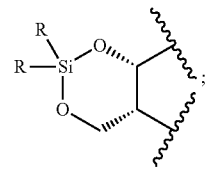

and $R^{P4}$ is optionally substituted benzyl. In certain embodiments, two $R^{P6}$ are joined with the intervening atoms to form a ring of the formula:

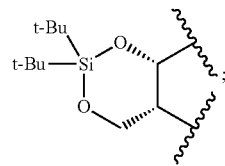

and $R^{P4}$ is MPM.

As shown in Scheme 4D, provided herein is a method of preparing a compound of Formula (L-5-4) from a compound of Formula (L-5-3). In certain embodiments, the method comprises the steps of:

(a) reducing a compound of Formula (L-5-3):

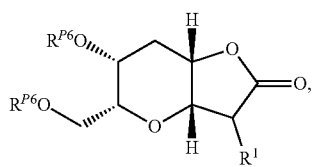

(L-5-3)

or a salt thereof, to yield a compound of Formula (L-5-3A):

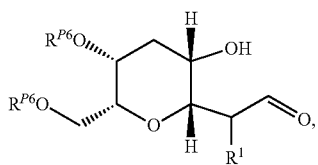

(L-5-3A)

or a salt thereof;

(b) olefinating a compound of Formula (L-5-3A), or a salt thereof, to yield a compound of Formula (L-5-3B):

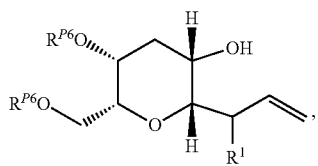

(L-5-3B)

or a salt thereof;

(c) hydrating a compound of Formula (L-5-3B), or a salt thereof, to yield a compound of Formula (L-5-3C):

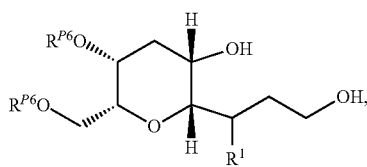

(L-5-3C)

or a salt thereof; and (d) oxidizing and cyclizing a compound of Formula (L-5-3C), or a salt thereof, to yield a compound of Formula L-5-4):

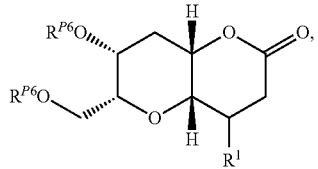

(L-5-4)

or a salt thereof.

The step of reducing in step (a) above may be carried out in the presence of a hydride source. In certain embodiments, the hydride source is DIBAL. In certain embodiments, the step of olefination in step (b) above may be carried out in the presence of an olefination reagent (e.g., MePPh$_3$Br). In certain embodiments, the step of olefination is carried out in the presence of a base (e.g., an alkoxide such as t-BuOK). In certain embodiments, the step of hydrating in step (c) above is a hydroboration reaction. In certain embodiments, the step of hydroboration involves treatment with 9-BBN followed by NaBO$_3$·H$_2$O. The steps of oxidizing and cyclizing in step (d) above may be carried out in the same step or subsequent steps. The step of oxidizing may be carried out in the presence of any oxidizing agents. In certain embodiments, the step of oxidizing is carried out in the presence of TEMPO and PhI(OAc)$_2$. In certain embodiments, the step of oxidizing is carried out in the presence of NaHCO$_3$.

In certain embodiments, two $R^{P6}$ are joined with the intervening atoms to form a ring of the formula:

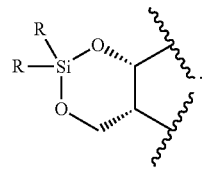

In certain embodiments, two $R^{P6}$ are joined with the intervening atoms to form a ring of the formula:

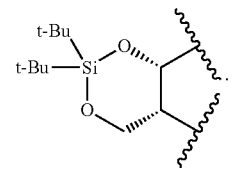 [SMILES: *[C@@H]1CO[Si](C(C)(C)C)(C(C)(C)C)O[C@@H]1*]

General Reaction Parameters

The following embodiments apply to all synthetic methods described above and herein.

The reactions provided and described herein may involve one or more reagents. In certain embodiments, a reagent may be present in a catalytic amount. In certain embodiments, a catalytic amount is from 0-1 mol %, 0-5 mol %, 0-10 mol %, 1-5 mol %, 1-10 mol %, 5-10 mol %, 10-20 mol %, 20-30 mol %, 30-40 mol %, 40-50 mol %, 50-60 mol %, 60-70 mol %, 70-80 mol %, 80-90 mol %, or 90-99 mol %. In certain embodiments, a reagent may be present in a stoichiometric amount (i.e., about 1 equivalent). In certain embodiments, a reagent may be present in excess amount (i.e., greater than 1 equivalent). In certain embodiments, the excess amount is about 1.1, 1.2, 1.3, 1.4, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, or 20 equivalents. In certain embodiments, the excess amount is from about 1.1-2, 2-3, 3-4, 4-5, 1.1-5, 5-10, 10-15, 15-20, or 10-20 equivalents. In certain embodiments, the excess amount is greater than 20 equivalents.

A reaction described herein may be carried out at any temperature. In certain embodiments, a reaction is carried out at or around room temperature (rt) (21° C. or 70° F.). In certain embodiments, a reaction is carried out at below room temperature (e.g., from −100° C. to 21° C.). In certain embodiments, a reaction is carried out at or around −78° C. In certain embodiments, a reaction is carried out at or around −10° C. In certain embodiments, a reaction is carried out at around 0° C. In certain embodiments, a reaction is carried out at above room temperature. In certain embodiment, a reaction is carried out at 30, 40, 50, 60, 70, 80, 110, 120, 130, 140, or 150° C. In certain embodiments, a reaction is carried out at above 150° C.

A reaction described herein may be carried out in a solvent, or a mixture of solvents (i.e., cosolvents). Solvents can be polar or non-polar, protic or aprotic. Any solvent may be used in the reactions described herein, and the reactions are not limited to particular solvents or combinations of solvents. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, p-xylene.

A reaction described herein may be carried out over any amount of time. In certain embodiments, a reaction is allowed to run for seconds, minutes, hours, or days.

Methods described herein can be used to prepare compounds in any chemical yield. In certain embodiments, a compound is produced in from 1-10%, 10-20% 20-30%, 30-40%, 40-50%, 50-60%, 60-70%, 70-80%, 80-90%, or 90-100% yield. In certain embodiments, the yield is the percent yield after one synthetic step. In certain embodiments, the yield is the percent yield after more than one synthetic step (e.g., 2, 3, 4, or 5 synthetic steps).

Methods described herein may further comprise one or more purification steps. For example, in certain embodiments, a compound produced by a method described herein may be purified by chromatography, extraction, filtration, precipitation, crystallization, or any other method known in the art. In certain embodiments, a compound or mixture is carried forward to the next synthetic step without purification (i.e., crude).

The synthetic method provided herein can be carried out on any scale (i.e., to yield any amount of product). In certain embodiments, the methods are applicable to small-scale synthesis or larger-scale process manufacture. In certain embodiments, a reaction provided herein is carried out to yield less than 1 g of product. In certain embodiments, a reaction provided herein is carried out to yield greater than 1 g, 2 g, 5 g, 10 g, 15 g, 20 g, 25 g, 30 g, 40 g, 50 g, 100 g, 200 g, 500 g, or 1 kg of product.

Compounds

The present invention also provides novel compounds. The compounds are useful in the preparation of halichondrins, analogs thereof, and intermediates thereto. In certain embodiments, the compounds provided herein are useful in the synthesis of compounds of Formula (H3-A), such as Compound (1), or intermediates thereto.

Provided herein are compounds of Formula (H3-N3):

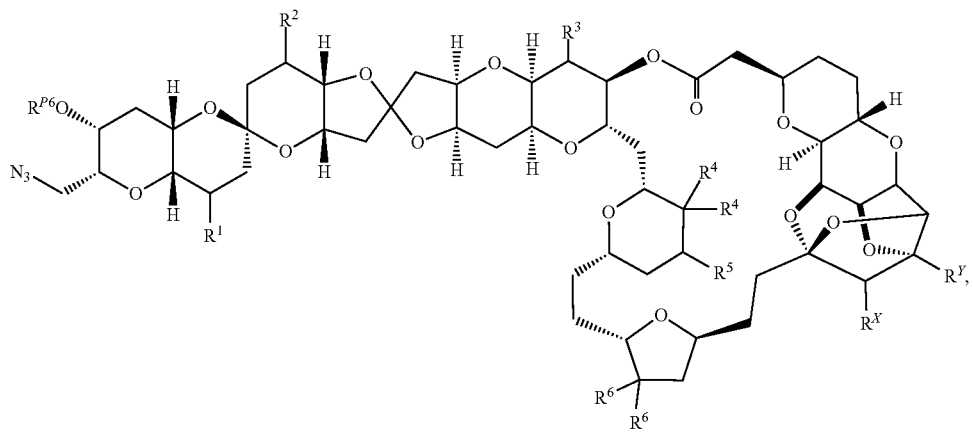

(H3-N3)

and salts thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

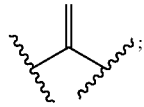

each instance of $R^6$ is independently hydrogen, halogen, or optionally substituted alkyl, or two $R^6$ groups are taken together to form:

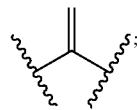 [SMILES: *C(*)=C]

$R^{P6}$ is hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the following formula:

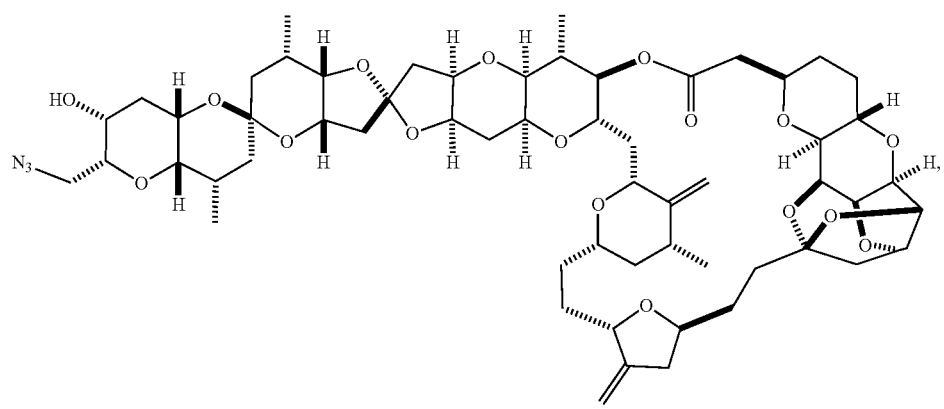

Compound (B)

or a salt thereof.

Provided herein are compounds of Formula (H3-L):

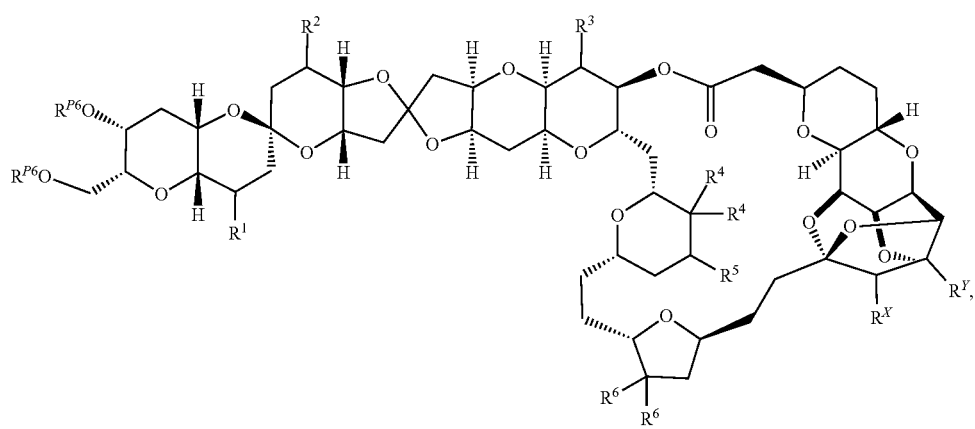

(H3-L)

and salts thereof, wherein:

$R^L$ is optionally substituted sulfonyl, optionally substituted sulfinyl, optionally substituted phosphoryl, or optionally substituted acyl;

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

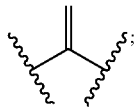 [SMILES: *C(*)=C]

each instance of $R^6$ is independently hydrogen, halogen, or optionally substituted alkyl, or two $R^6$ groups are taken together to form:

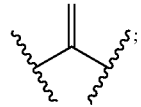 [SMILES: *C(*)=C]

$R^{P6}$ is hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the formula:

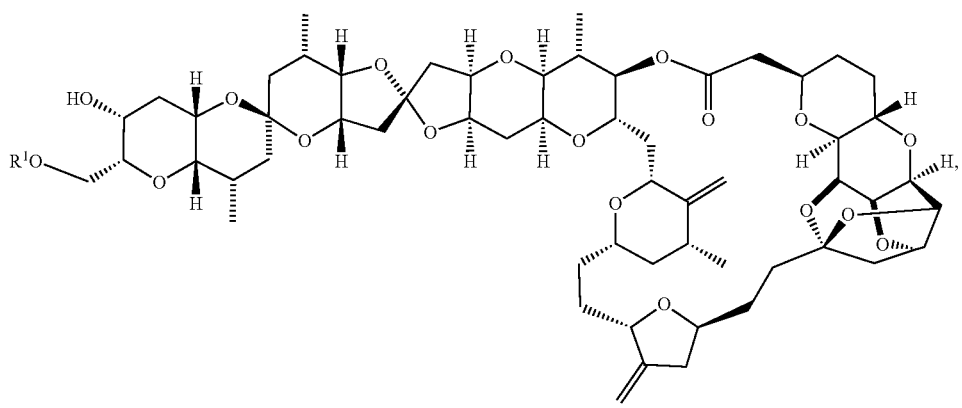

Compound (A)

or a salt thereof, wherein:

$R^1$ is optionally substituted sulfonyl, optionally substituted sulfinyl, optionally substituted phosphoryl, or optionally substituted acyl.

Provided herein are compounds of Formula (H-2-II):

(H-2-II)

and salts thereof, wherein:

R¹, R², R³, and R⁵ are each independently hydrogen, halogen, or optionally substituted alkyl;

each instance of R⁴ is independently hydrogen, halogen, or optionally substituted alkyl, or two R⁴ groups are taken together to form:

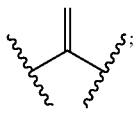

each instance of R⁶ is independently hydrogen, halogen, or optionally substituted alkyl, or two R⁶ groups are taken together to form:

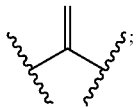

$R^{P1}$, $R^{P2}$, $R^{P3}$, $R^4$, and $R^{P5}$ are each independently hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

Provided herein are compounds of Formula (L-2-14):

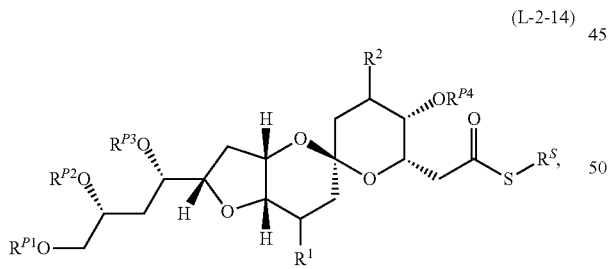

(L-2-14)

and salts thereof, wherein:

$R^S$ is optionally substituted alkyl, optionally substituted carbocyclyl, optionally substituted aryl, optionally substituted heterocyclyl, or optionally substituted heteroaryl;

R¹ and R² are each independently hydrogen, halogen, or optionally substituted alkyl; and $R^{P1}$, $R^{P2}$, $R^{P3}$, and $R^{P4}$ are each independently hydrogen, optionally substituted alkyl, optionally substituted acyl, or an oxygen protecting group.

Provided herein are compounds of Formula (R-2-I):

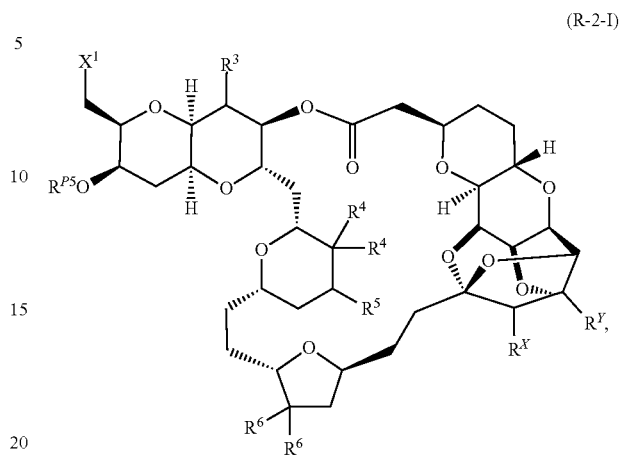

(R-2-I)

and salts thereof, wherein:

X¹ is halogen or a leaving group;

R³ and R⁵ are each independently hydrogen, halogen, or optionally substituted alkyl;

each instance of R⁴ is independently hydrogen, halogen, or optionally substituted alkyl, or two R⁴ groups are taken together to form:

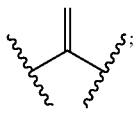

each instance of R⁶ is independently hydrogen, halogen, or optionally substituted alkyl, or two R⁶ groups are taken together to form:

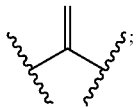

$R^{P5}$ is hydrogen, optionally substituted alkyl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of Formula (E-R):

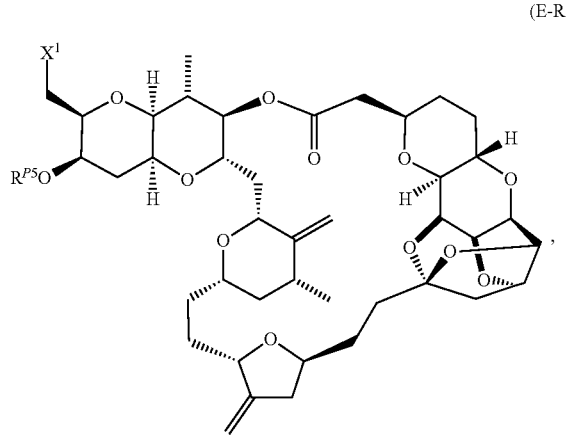
(E-R)

or a salt thereof, wherein:

$X^1$ is halogen or a leaving group; and $R^{P5}$ is hydrogen, optionally substituted alkyl, optionally substituted acyl, or an oxygen protecting group.

Provided herein are compounds of Formula (HH-2-II):

each instance of $R^6$ is independently hydrogen, halogen, or optionally substituted alkyl, or two $R^6$ groups are taken together to form:

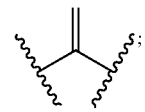 [SMILES: *C(*)=C]

$R^{P1}$, $R^{P3}$, $R^{P4}$, and $R^{P5}$ are each independently hydrogen, optionally substituted alkyl, optionally substituted acyl, or an oxygen protecting group;

$R^X$ is hydrogen or —$OR^X$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

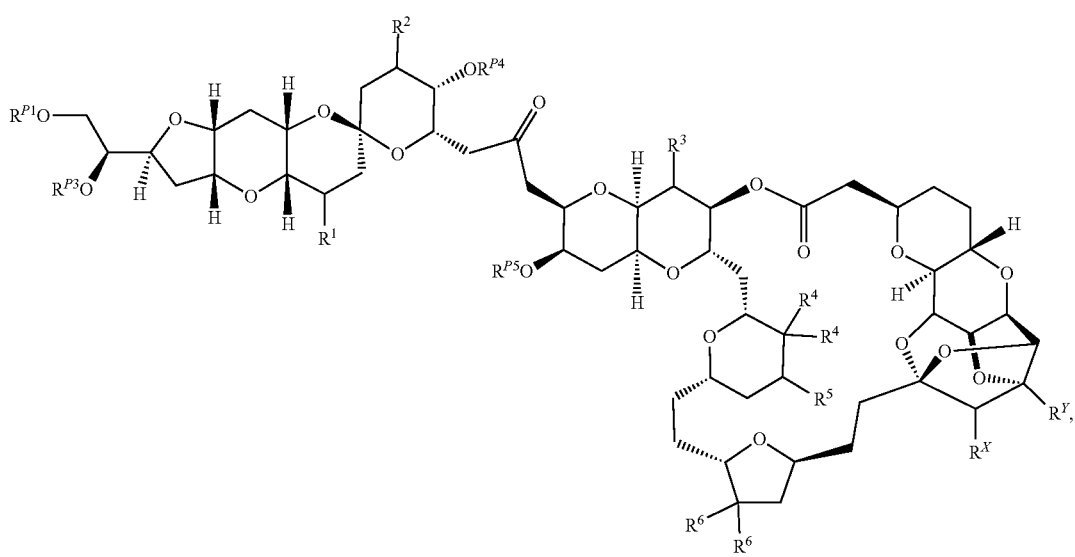
(HH-2-II)

and salts thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

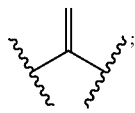 [SMILES: *C(*)=C]

Provided herein are compounds of Formula (L-2-16):

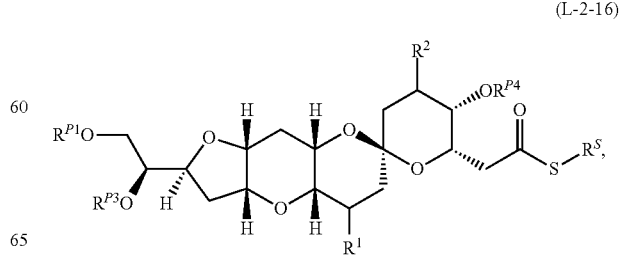
(L-2-16)

and salts thereof, wherein:

R$^S$ is optionally substituted alkyl, optionally substituted carbocyclyl, optionally substituted aryl, optionally substituted heterocyclyl, or optionally substituted heteroaryl;

R$^1$ and R$^2$ are independently hydrogen, halogen, or optionally substituted alkyl;

R$^{P1}$, R$^{P3}$ and R$^{P4}$ are independently hydrogen, optionally substituted alkyl, optionally substituted acyl, or an oxygen protecting group;

R$^X$ is hydrogen or —OR$^X$, wherein R$^{Xa}$ is hydrogen, optionally substituted alkyl, optionally substituted acyl, or an oxygen protecting group; and R$^Y$ is hydrogen or —OR$^{Ya}$, wherein R$^{Ya}$ is hydrogen, optionally substituted alkyl, optionally substituted acyl, or an oxygen protecting group;

optionally wherein R$^{Xa}$ and R$^{Ya}$ are joined together with their intervening atoms to form optionally substituted heterocyclyl.

Provided herein are compounds of Formula (NH-2-II):

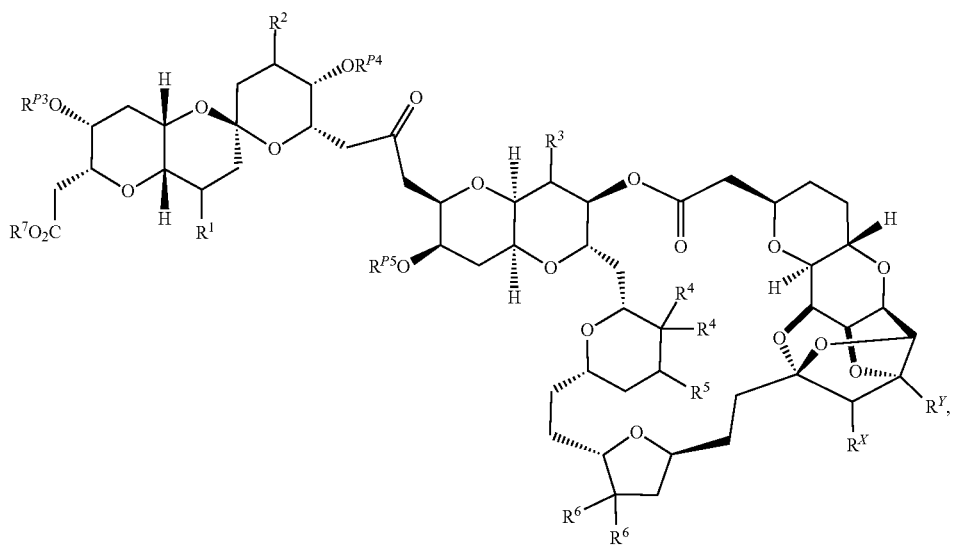

(NH-2-II)

and salts thereof, wherein:

R$^1$, R$^2$, R$^3$, and R$^5$ are each independently hydrogen, halogen, or optionally substituted alkyl;

each instance of R$^4$ is independently hydrogen, halogen, or optionally substituted alkyl, or two R$^4$ groups are taken together to form:

each instance of R$^6$ is independently hydrogen, halogen, or optionally substituted alkyl, or two R$^6$ groups are taken together to form:

R$^{P3}$, R$^{P4}$, and R$^{P5}$ are each independently hydrogen, optionally substituted alkyl, optionally substituted acyl, or an oxygen protecting group;

R$^7$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

R$^X$ is hydrogen or —OR$^{Xa}$, wherein R$^{Xa}$ is hydrogen, optionally substituted alkyl, optionally substituted acyl, or an oxygen protecting group; and R$^Y$ is hydrogen or —OR$^{Ya}$, wherein R$^{Ya}$ is hydrogen, optionally substituted alkyl, optionally substituted acyl, or an oxygen protecting group;

optionally wherein R$^{Xa}$ and R$^{Ya}$ are joined together with their intervening atoms to form optionally substituted heterocyclyl.

Provided herein are compounds of Formula (L-2-15):

(L-2-15)

and salts thereof, wherein:

$R^S$ is optionally substituted alkyl, optionally substituted carbocyclyl, optionally substituted aryl, optionally substituted heterocyclyl, or optionally substituted heteroaryl;

$R^1$ and $R^2$ are independently hydrogen, halogen, or optionally substituted alkyl;

$R^{P3}$ and $R^{P4}$ are independently hydrogen, optionally substituted alkyl, optionally substituted acyl, or an oxygen protecting group;

$R^7$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (H3-2-I):

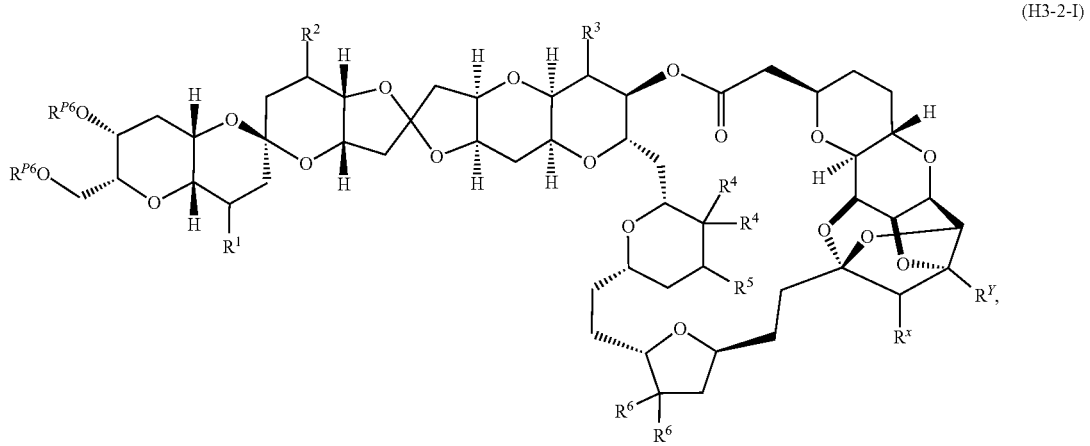

(H3-2-I)

and salts thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

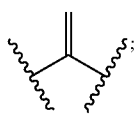 [SMILES: *C(*)=C]

each instance of $R^6$ is independently hydrogen, halogen, or optionally substituted alkyl, or two $R^6$ groups are taken together to form:

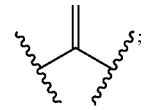 [SMILES: *C(*)=C]

each instance of $R^{P6}$ is independently hydrogen, optionally substituted alkyl, optionally substituted acyl, or an oxygen protecting group; optionally wherein two $R^{P6}$ are joined with the intervening atoms to form optionally substituted heterocyclyl;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the formula:

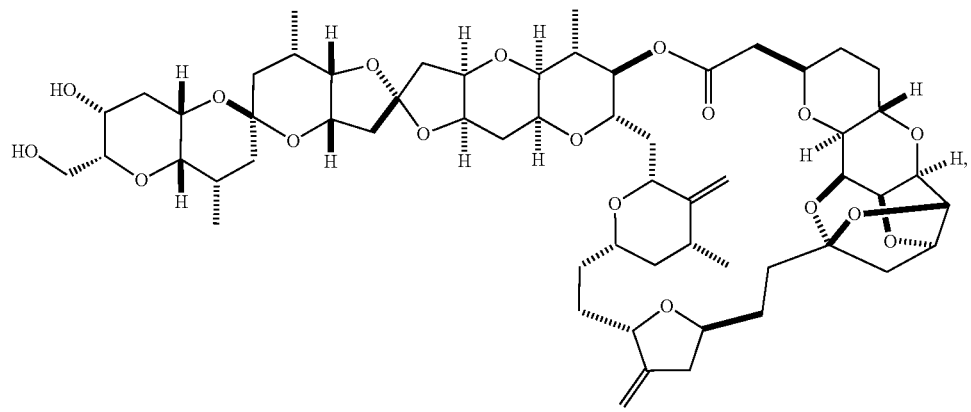

Compound (2)

or a salt thereof.

Provided herein are compounds of Formula (H3-2-II):

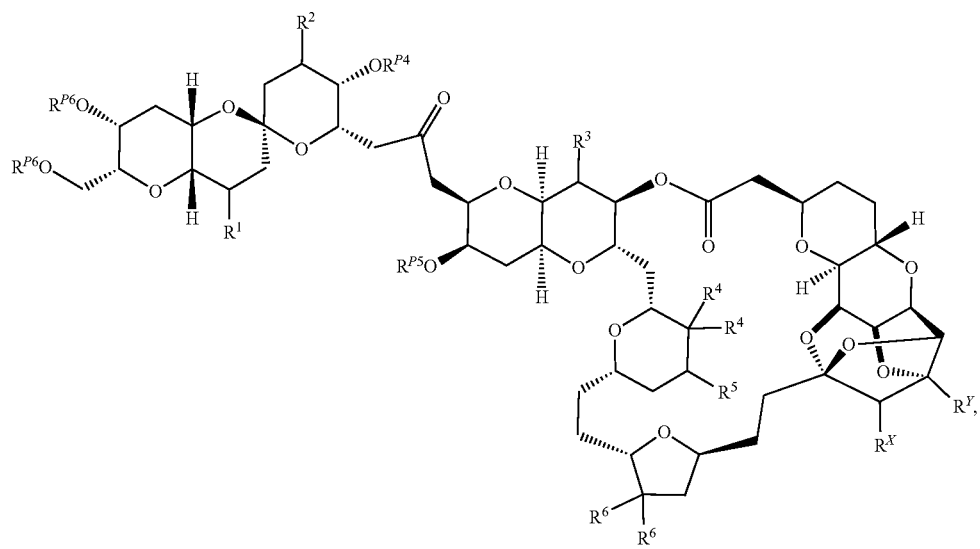

(H3-2-II)

and salts thereof, wherein:

$R^1$, $R^2$, $R^3$, and $R^5$ are each independently hydrogen, halogen, or optionally substituted alkyl;

each instance of $R^4$ is independently hydrogen, halogen, or optionally substituted alkyl, or two $R^4$ groups are taken together to form:

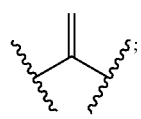 [SMILES: *C(*)=C]

each instance of $R^6$ is independently hydrogen, halogen, or optionally substituted alkyl, or two $R^6$ groups are taken together to form:

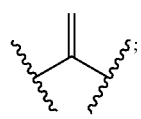 [SMILES: *C(*)=C]

$R^{P4}$, $R^{P5}$, and $R^{P6}$ are each independently hydrogen, optionally substituted alkyl, optionally substituted acyl, or an oxygen protecting group; optionally wherein two $R^{P6}$ are joined with the intervening atoms to form optionally substituted heterocyclyl;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the Formula (E-1):

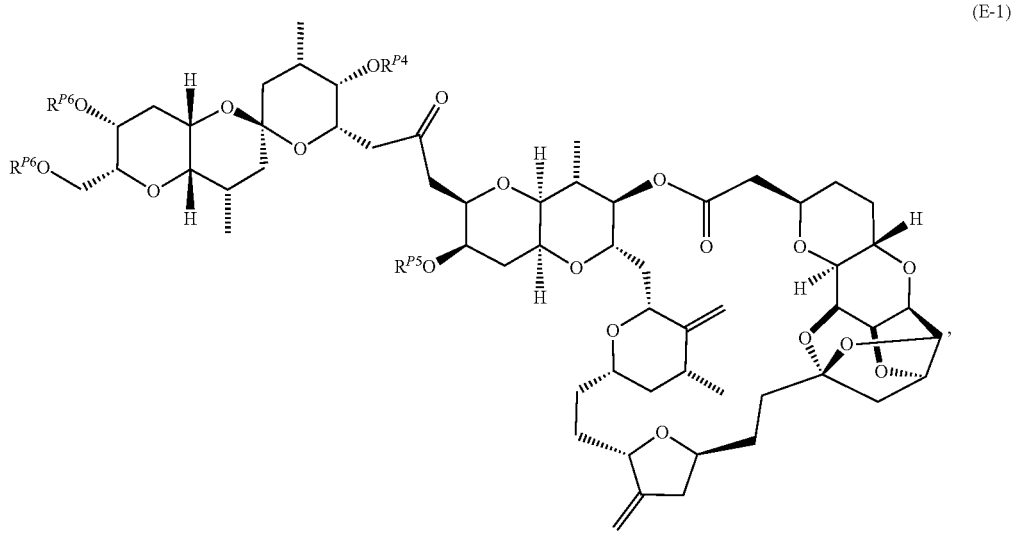

(E-1)

or a salt thereof, wherein:

$R^{P4}$, $R^{P5}$, and $R^{P6}$ are each independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the compound is of the formula:

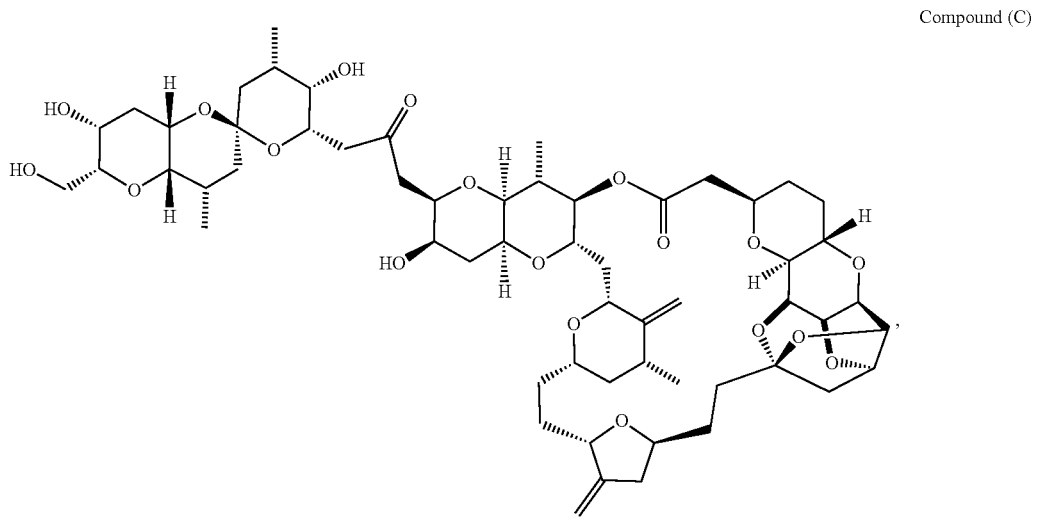 [SMILES: C=C1C[C@@H]2CC[C@@]34C[C@H]5O[C@H]6[C@@H](O3)[C@H]3O[C@H](CC[C@@H]3O[C@H]6C5O4)CC(=O)O[C@@H]3[C@@H](C)[C@@H]4O[C@H](CC(=O)C[C@@H]5O[C@@]6(C[C@H](C)[C@@H]5O)C[C@H](C)[C@@H]5O[C@H](CO)[C@H](O)C[C@@H]5O6)[C@H](O)C[C@@H]4O[C@H]3C[C@H]3O[C@@H](CC[C@@H]1O2)C[C@@H](C)C3=C]

Compound (C)

or a salt thereof.

Provided herein are compounds of Formula (L-2-6):

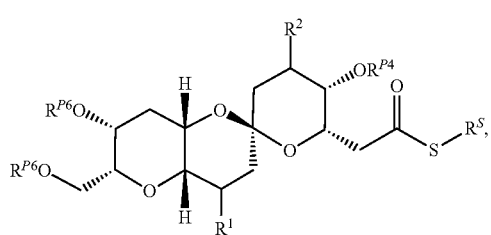
(L-2-6)

and salts thereof, wherein:

$R^S$ is optionally substituted alkyl, optionally substituted carbocyclyl, optionally substituted aryl, optionally substituted heterocyclyl, or optionally substituted heteroaryl;

$R^1$ and $R^2$ are independently hydrogen, halogen, or optionally substituted alkyl; and $R^{P4}$ and $R^{P6}$ are each independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the compound is of Formula (E-L):

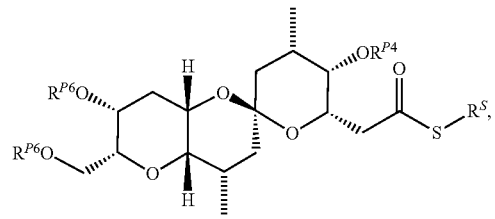
(E-L)

or a salt thereof, wherein:

$R^S$ is optionally substituted alkyl, optionally substituted carbocyclyl, optionally substituted aryl, optionally substituted heterocyclyl, or optionally substituted heteroaryl; each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the compound is of the formula:

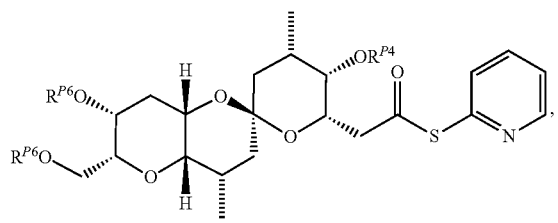

or a salt thereof.

Provided herein are compounds of Formula (R-4-11B):

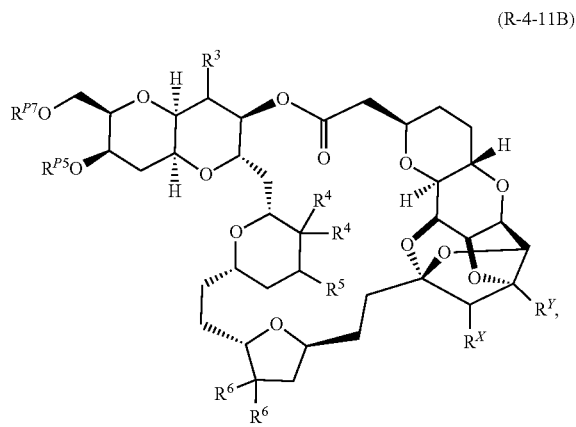
(R-4-11B)

and salts thereof, wherein:

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

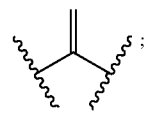 [SMILES: *C(*)=C];

each instance of $R^6$ is independently hydrogen, halogen, or optionally substituted alkyl, or two $R^6$ groups are taken together to form:

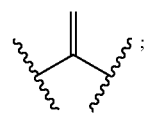;

$R^{P5}$ and $R^{P7}$ are each independently hydrogen, optionally substituted alkyl, optionally substituted acyl, or an oxygen protecting group;

$R^{P7}$ is optionally substituted sulfonyl, optionally substituted sulfinyl, optionally substituted phosphoryl, optionally substituted acyl, or an oxygen protecting group;

optionally wherein $R^{P5}$ and $R^{P7}$ are joined with the intervening atoms to form optionally substituted heterocyclyl;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the Formula (E-R-1):

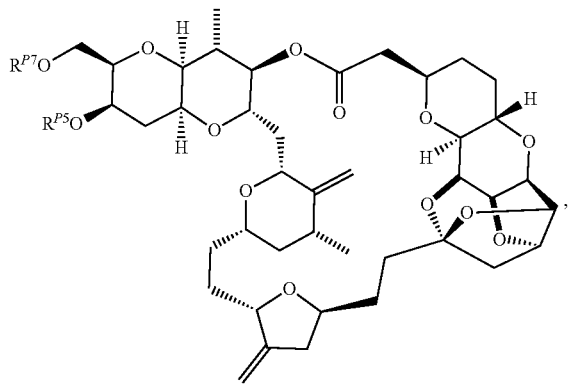

(E-R-1)

or a salt thereof, wherein:

$R^{P5}$ is hydrogen, optionally substituted alkyl, optionally substituted acyl, or an oxygen protecting group; and $R^{P7}$ is optionally substituted sulfonyl, optionally substituted sulfinyl, optionally substituted phosphoryl, optionally substituted acyl, or an oxygen protecting group; and optionally wherein $R^{P5}$ and $R^{P7}$ are joined with the intervening atoms to form optionally substituted heterocyclyl.

Provided herein are compounds of Formula (R-4-11A):

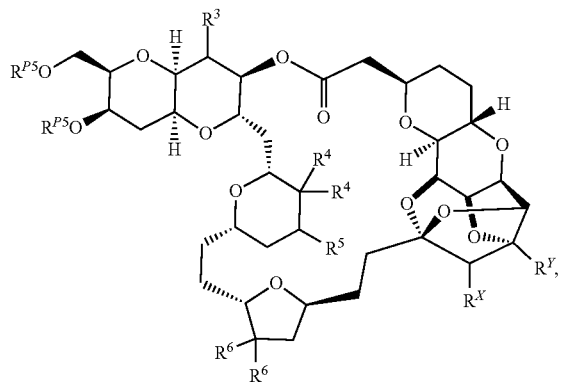

(R-4-11A)

and salts thereof, wherein:

$R^3$ and $R^5$ are each independently hydrogen, halogen, or optionally substituted alkyl;

each instance of $R^4$ is independently hydrogen, halogen, optionally substituted alkyl, or two $R^4$ groups are taken together to form:

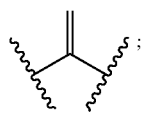

;

each instance of $R^6$ is independently hydrogen, halogen, optionally substituted alkyl, or two $R^6$ groups are taken together to form:

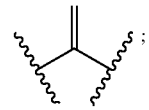

;

each instance of $R^{P5}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the Formula (E-R-2):

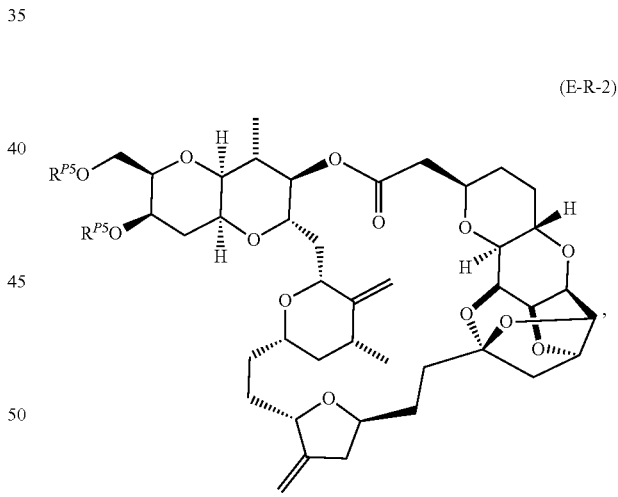

(E-R-2)

or a salt thereof, wherein:

each instance of $R^{P5}$ is hydrogen, optionally substituted alkyl, optionally substituted acyl, or an oxygen protecting group; optionally wherein two $R^{P5}$ groups are joined together with the intervening atoms to form optionally substituted heterocyclyl ring.

Provided herein are compounds of Formula (R-4-10):

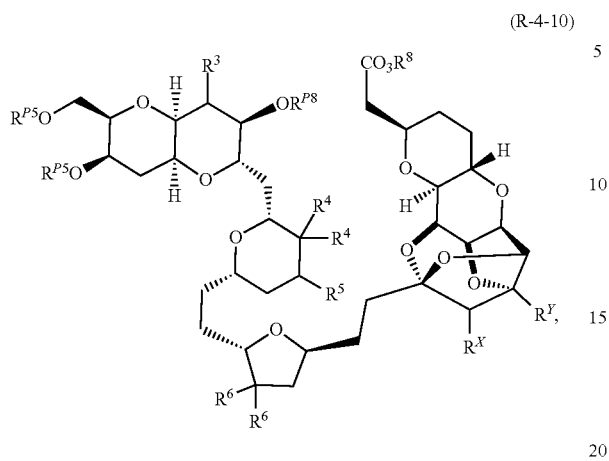

(R-4-10)

and salts thereof, wherein:

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

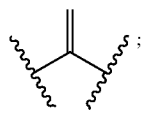 [SMILES: *C(*)=C]

each instance of $R^6$ is independently hydrogen, halogen, or optionally substituted alkyl, or two $R^6$ groups are taken together to form:

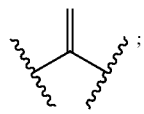 [SMILES: *C(*)=C]

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring;

$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the Formula (E-R-7):

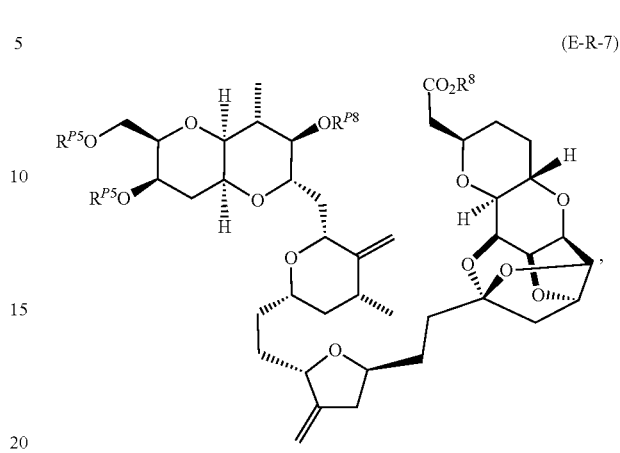

(E-R-7)

or a salt thereof, wherein:

each instance of $R^{P5}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (R-4-8):

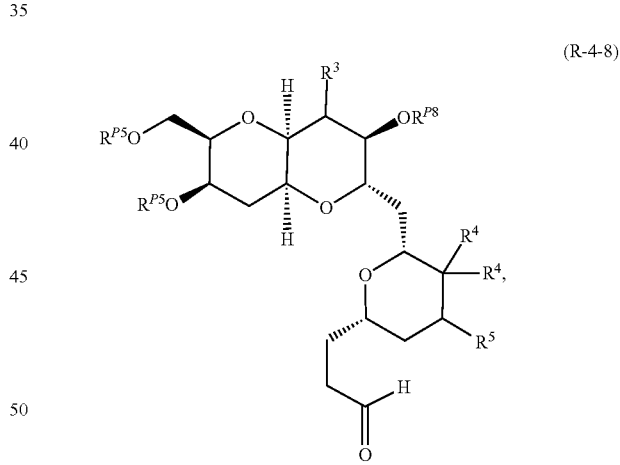

(R-4-8)

and salts thereof, wherein:

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

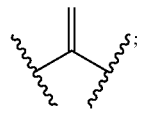 [SMILES: *C(*)=C]

and each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

In certain embodiments, the compound is of the Formula (E-R-4):

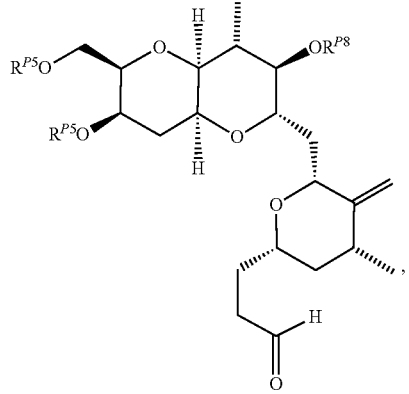

(E-R-4)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

Provided herein are compounds of Formula (R-4-9):

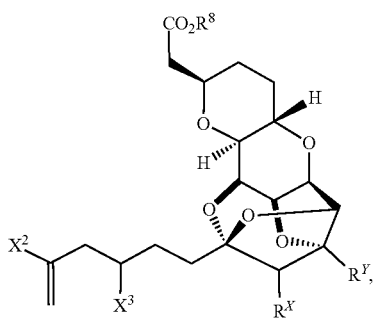

(R-4-9)

and salts thereof, wherein:

$X^3$ and $X^2$ are each independently halogen or a leaving group;

$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

Provided herein are compounds of Formula (R-4-10B):

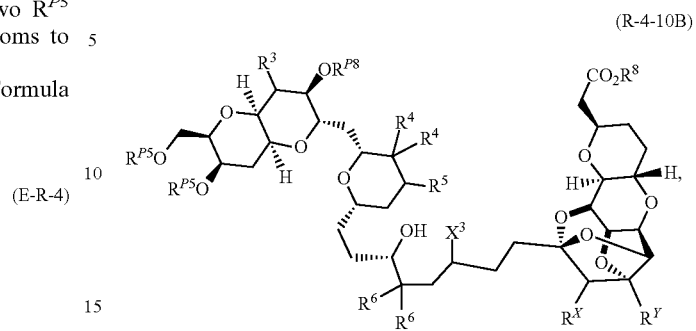

(R-4-10B)

and salts thereof, wherein:

$X^3$ is halogen or a leaving group;

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

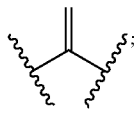 [SMILES: *C(*)=C]

each instance of $R^6$ is independently hydrogen, halogen, or optionally substituted alkyl, or two $R^6$ groups are taken together to form:

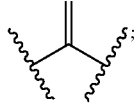 [SMILES: *C(*)=C]

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring;

$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group;

$R^X$ is hydrogen or —$OR^{Xa}$, wherein $R^{Xa}$ is hydrogen, optionally substituted alkyl, optionally substituted acyl, or an oxygen protecting group; and $R^Y$ is hydrogen or —$OR^{Ya}$, wherein $R^{Ya}$ is hydrogen, optionally substituted alkyl, optionally substituted acyl, or an oxygen protecting group;

optionally wherein $R^{Xa}$ and $R^{Ya}$ are joined together with their intervening atoms to form optionally substituted heterocyclyl.

In certain embodiments, the compound is of the Formula (E-R-6):

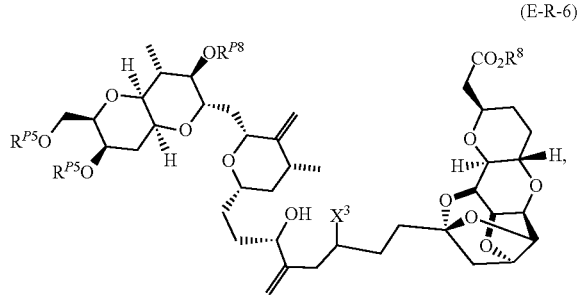

(E-R-6)

or a salt thereof, wherein:

$X^3$ is halogen or a leaving group;

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (R-4-7):

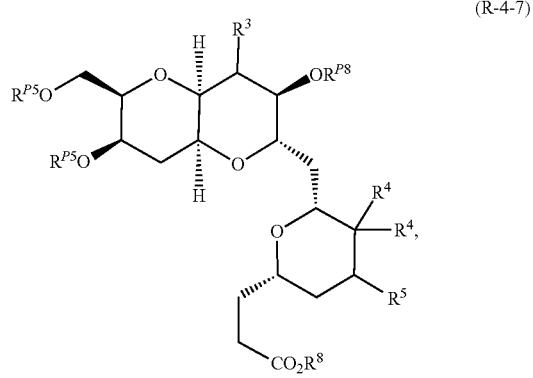

(R-4-7)

and salts thereof, wherein:

$R^3$ and $R^5$ are each independently hydrogen, halogen, or optionally substituted alkyl;

each instance of $R^4$ is independently hydrogen, halogen, optionally substituted alkyl, or two $R^4$ groups are taken together to form:

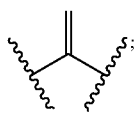 [SMILES: *C(*)=C]

;

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of the Formula (E-R-8):

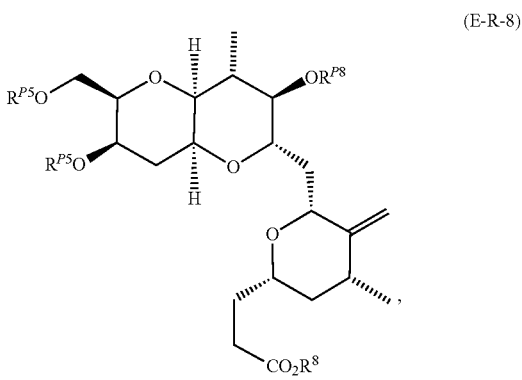

(E-R-8)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (R-4-5B):

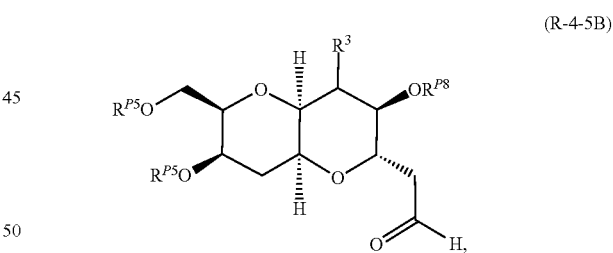

(R-4-5B)

and salts thereof, wherein:

$R^3$ is hydrogen, halogen, or optionally substituted alkyl;

each instance of $R^{P5}$ and $R^{P8}$ are independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of the Formula (E-R-9):

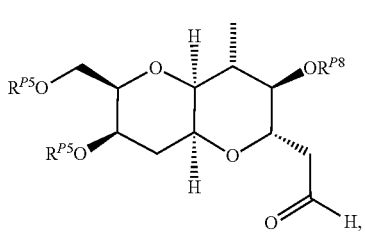

(E-R-9)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

Provided herein are compounds of Formula (R-4-7A):

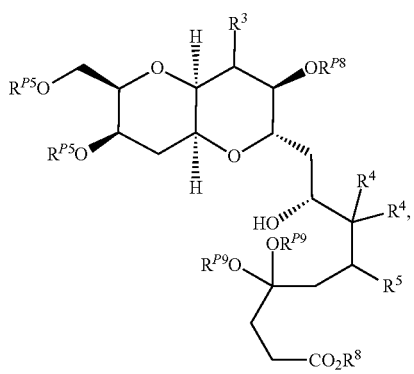

(R-4-7A)

and salts thereof; wherein:

$R^3$ and $R^5$ are each independently hydrogen, halogen, or optionally substituted alkyl;

each instance of $R^4$ is independently hydrogen, halogen, or optionally substituted alkyl, or two $R^4$ groups are taken together to form:

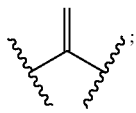

each instance of $R^{P5}$, $R^{P8}$, and $R^{P9}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and optionally wherein two $R^{P9}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of the Formula (E-R-11):

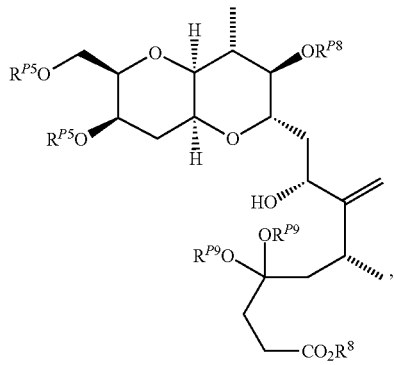

(E-R-11)

or a salt thereof, wherein:

each instance of $R^{P5}$, $R^{P8}$, and $R^{P9}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; optionally wherein two $R^{P9}$ groups are joined together with the intervening atoms to form an optionally substituted heterocyclyl ring.

Provided herein are compounds of Formula (R-4-5A):

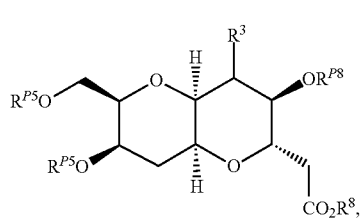

(R-4-5A)

and salts thereof, wherein:

$R^3$ is hydrogen, halogen, or optionally substituted alkyl;

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of Formula (E-R-15):

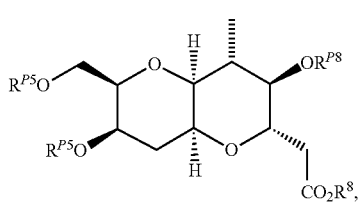

(E-R-15)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (R-4-4):

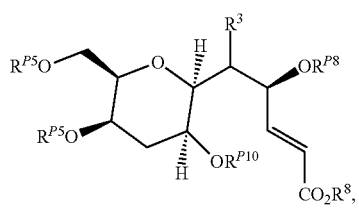

(R-4-4)

and salts thereof, wherein:

$R^3$ is hydrogen, halogen, or optionally substituted alkyl;

each instance of $R^{P5}$, $R^{P8}$, and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of Formula (E-R-16):

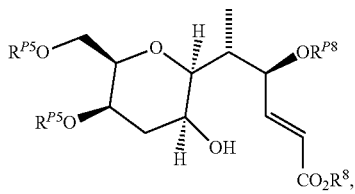

(E-R-16)

or a salt thereof, wherein:

each instance of $R^{P5}$ and $R^{P8}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (R-4-2):

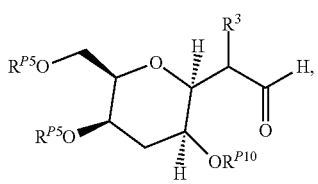

(R-4-2)

and salts thereof, wherein:

$R^3$ is hydrogen, halogen, or optionally substituted alkyl; and each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

In certain embodiments, the compound is of Formula (E-R-17):

(E-R-17)

or a salt thereof, wherein:

each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

Provided herein are compounds of Formula (R-4-1):

(R-4-1)

and salts thereof, wherein:

$R^3$ is hydrogen, halogen, or optionally substituted alkyl; and $R^{P5}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

In certain embodiments, the compound is of Formula (E-R-19):

(E-R-19)

or a salt thereof, wherein:

each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

Provided herein are compounds of the compound of Formula (E-R-22):

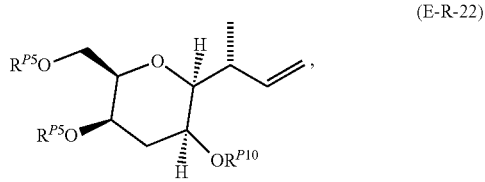

(E-R-22)

and salts thereof, wherein:

each instance of $R^{P5}$ and $R^{P10}$ is independently hydrogen, optionally substituted alkyl, optionally substituted acyl, or an oxygen protecting group; optionally wherein two $R^{P5}$ groups are joined together with the intervening atoms to form an optionally substituted heterocyclyl ring.

Provided herein are compounds of Formula (L-5-17):

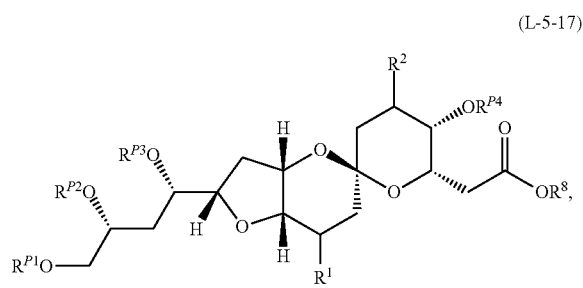

(L-5-17)

and salts thereof, wherein:

$R^1$ and $R^2$ are independently hydrogen, halogen, or optionally substituted alkyl;

$R^{P1}$, $R^{P2}$, $R^{P3}$, and $R^{P4}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, or optionally substituted heteroaryl, optionally substituted acyl, or an oxygen protecting group.

Also provided herein are compounds of Formula (L-5-16B):

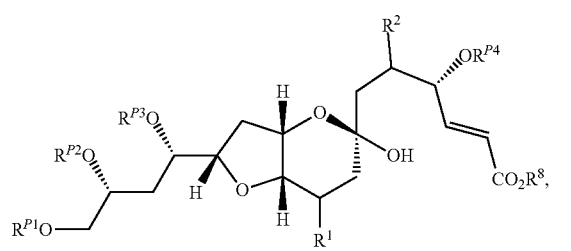

(L-5-16B)

and salts thereof; wherein:

$R^1$ and $R^2$ are independently hydrogen, halogen, or optionally substituted alkyl;

$R^{P1}$, $R^{P2}$, $R^{P3}$, and $R^{P4}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, or optionally substituted heteroaryl, optionally substituted acyl, or an oxygen protecting group.

Provided herein are compounds of Formula (L-5-16A):

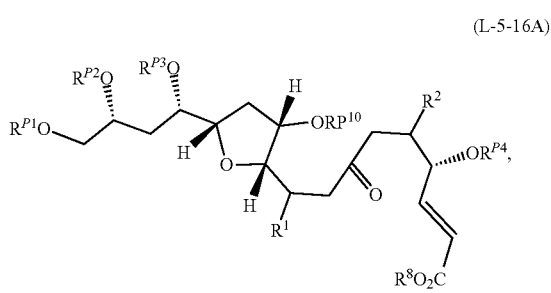

(L-5-16A)

and salts thereof, wherein:

$R^1$ and $R^2$ are independently hydrogen, halogen, or optionally substituted alkyl;

$R^{P1}$, $R^{P2}$, $R^{P3}$, $R^{P4}$, and $R^{P10}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, or optionally substituted heteroaryl, optionally substituted acyl, or an oxygen protecting group.

Provided herein are compounds of Formula (L-5-15):

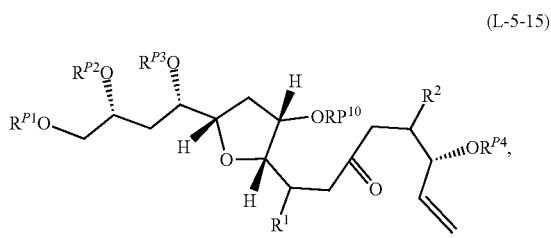

(L-5-15)

and salts thereof, wherein:

$R^1$ and $R^2$ are independently hydrogen, halogen, or optionally substituted alkyl; and $R^{P1}$, $R^{P2}$, $R^{P3}$, $R^{P4}$, and $R^{P10}$ are independently hydrogen, optionally substituted alkyl, optionally substituted acyl, or an oxygen protecting group.

Also provided herein are compounds of Formula (L-5-14):

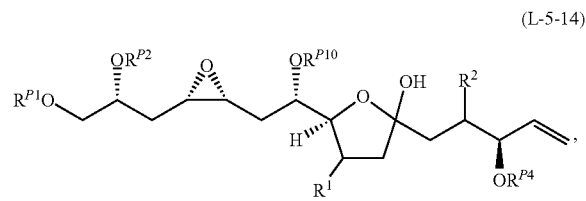

(L-5-14)

and salts thereof, in the presence of an acid, wherein:
R$^1$ and R$^2$ are independently hydrogen, halogen, or optionally substituted alkyl; and
R$^{P1}$, R$^{P2}$, R$^{P4}$, and R$^{P10}$ are independently hydrogen, optionally substituted alkyl, optionally substituted acyl, or an oxygen protecting group.

Provided herein are compounds of Formula (L-5-12):

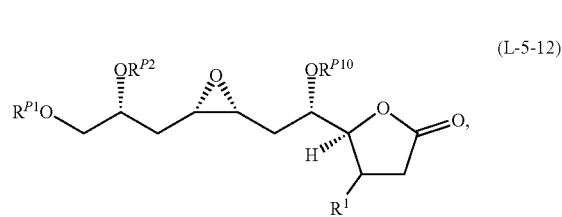

(L-5-12)

and salts thereof, wherein:
R$^1$ and R$^2$ are independently hydrogen, halogen, or optionally substituted alkyl; and
R$^{P1}$, R$^{P2}$, and R$^{P10}$ are independently hydrogen, optionally substituted alkyl, optionally substituted acyl, or an oxygen protecting group.

Provided herein are compounds of Formula (L-5-11):

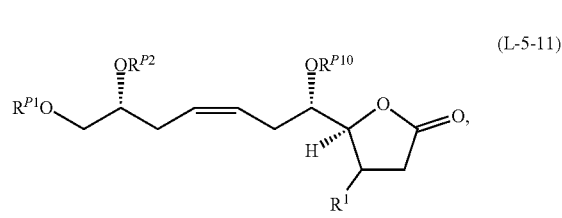

(L-5-11)

and salts thereof, wherein:
R$^1$ is hydrogen, halogen, or optionally substituted alkyl; and
R$^{P1}$, R$^{P2}$, and R$^{P10}$ are independently hydrogen, optionally substituted alkyl, optionally substituted acyl, or an oxygen protecting group.

Also provided herein are compounds of Formula (L-5-26):

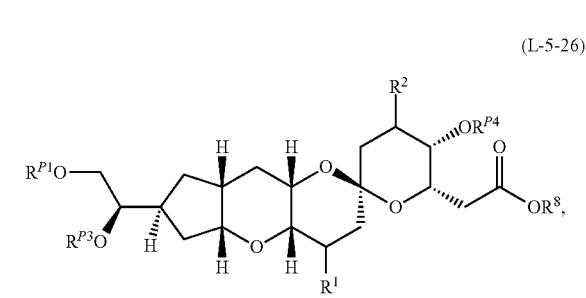

(L-5-26)

and salts thereof; wherein:
R$^1$ and R$^2$ are independently hydrogen, halogen, or optionally substituted alkyl;
R$^{P1}$, R$^{P3}$, and R$^{P4}$ are each independently hydrogen, optionally substituted alkyl, optionally substituted acyl, or an oxygen protecting group; and
R$^8$ is hydrogen, optionally substituted alkyl, optionally substituted carbocyclyl, optionally substituted aryl, optionally substituted heterocyclyl, or optionally substituted heteroaryl, optionally substituted acyl, or an oxygen protecting group.

Also provided herein are compounds of Formula (L-5-25C):

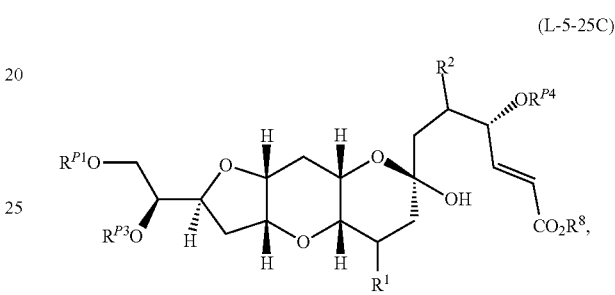

(L-5-25C)

and salts thereof; wherein:
R$^1$ and R$^2$ are independently hydrogen, halogen, or optionally substituted alkyl;
R$^{P1}$, R$^{P3}$, and R$^{P4}$ are each independently hydrogen, optionally substituted alkyl, optionally substituted acyl, or an oxygen protecting group; and
R$^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Also provided herein are compounds of Formula (L-5-25A):

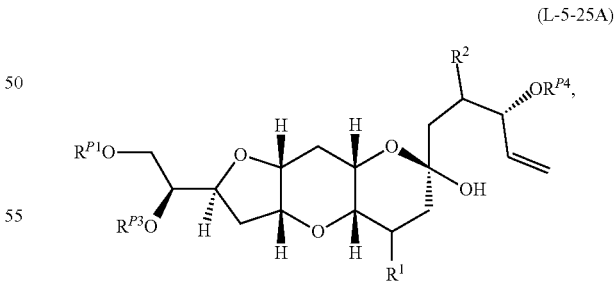

(L-5-25A)

and salts thereof, wherein:
R$^1$ and R$^2$ are independently hydrogen, halogen, or optionally substituted alkyl; and
R$^{P1}$, R$^{P3}$, and R$^{P4}$ are each independently hydrogen, optionally substituted alkyl, optionally substituted acyl, or an oxygen protecting group.

Provided herein are compounds of Formula (L-5-24):

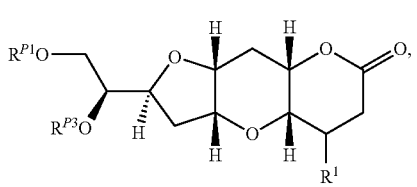
(L-5-24)

and salts thereof, wherein:
R¹ is hydrogen, halogen, or optionally substituted alkyl; and
$R^{P1}$ and $R^{P3}$ are each independently hydrogen, optionally substituted alkyl, optionally substituted acyl, or an oxygen protecting group.

Provided herein are compounds of Formula (L-5-23B):

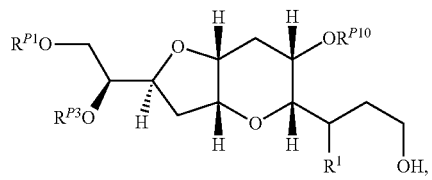
(L-5-23B)

and salts thereof, wherein:
R¹ is hydrogen, halogen, or optionally substituted alkyl; and
$R^{P1}$, $R^{P3}$, and $R^{P10}$ are each independently hydrogen, optionally substituted alkyl, optionally substituted acyl, or an oxygen protecting group.

Also provided herein are compound of Formula (L-5-23C):

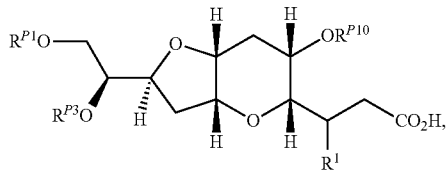
(L-5-23C)

and salts thereof; wherein:
R¹ is hydrogen, halogen, or optionally substituted alkyl; and
$R^{P1}$, $R^{P3}$, and $R^{P10}$ are each independently hydrogen, optionally substituted alkyl, optionally substituted acyl, or an oxygen protecting group.

Provided herein are compounds of Formula (L-5-23A):

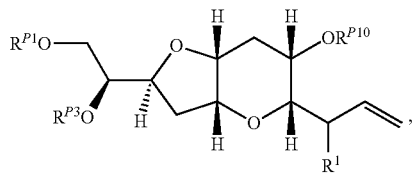
(L-5-23A)

and salts thereof; wherein:
R¹ is hydrogen, halogen, or optionally substituted alkyl; and
$R^{P1}$, $R^{P3}$, and $R^{P10}$ are each independently hydrogen, optionally substituted alkyl, optionally substituted acyl, or an oxygen protecting group.

Provided herein are compounds of Formula (L-5-22):

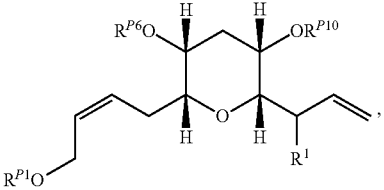
(L-5-22)

and salts thereof; wherein:
R¹ is hydrogen, halogen, or optionally substituted alkyl; and
$R^{P1}$, $R^{P3}$, and $R^{P10}$ are each independently hydrogen, optionally substituted alkyl, optionally substituted acyl, or an oxygen protecting group.

Also provided herein are compounds of Formula (L-5-22A):

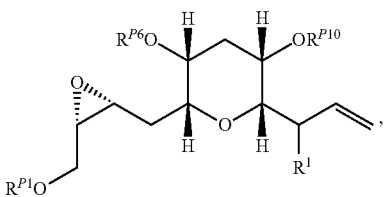
(L-5-22A)

and salt thereof; wherein:
R¹ is hydrogen, halogen, or optionally substituted alkyl; and
$R^{P1}$, $R^{P3}$, and $R^{P10}$ are each independently hydrogen, optionally substituted alkyl, optionally substituted acyl, or an oxygen protecting group.

Provided herein are compounds of Formula (L-5-21B):

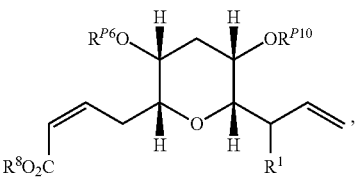
(L-5-21B)

and salts thereof; wherein:
R¹ is hydrogen, halogen, or optionally substituted alkyl;
$R^{P1}$, $R^{P6}$, and $R^{P10}$ are each independently hydrogen, optionally substituted alkyl, optionally substituted acyl, or an oxygen protecting group; and
R⁸ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (L-5-21A):

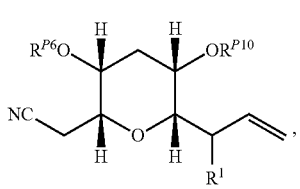
(L-5-21A)

and salts thereof; wherein:

$R^1$ is hydrogen, halogen, or optionally substituted alkyl; and $R^{P6}$ and $R^{P10}$ are each independently hydrogen, optionally substituted alkyl, optionally substituted acyl, or an oxygen protecting group.

Provided herein are compounds of Formula (L-5-32):

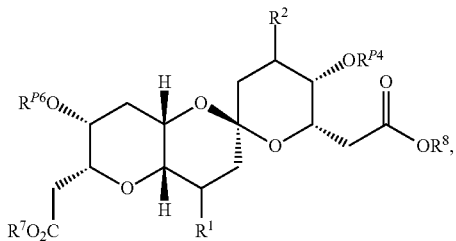
(L-5-32)

and salts thereof; wherein:

$R^1$ and $R^2$ are independently hydrogen, halogen, or optionally substituted alkyl;

each instance of $R^{P4}$ and $R^{P6}$ are independently hydrogen, optionally substituted alkyl, optionally substituted acyl, or an oxygen protecting group; and $R^7$ and $R^8$ are independently hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Also provided herein are compounds of Formula (L-5-31):

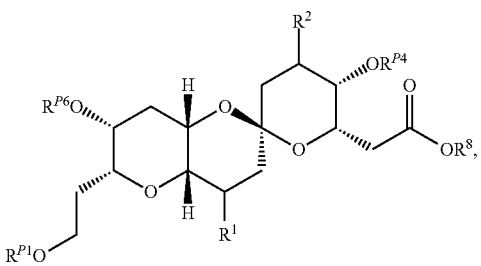
(L-5-31)

and salts thereof; wherein:

$R^1$ and $R^2$ are independently hydrogen, halogen, or optionally substituted alkyl;

$R^{P1}$, $R^{P4}$, and $R^{P6}$ are independently hydrogen, optionally substituted alkyl, optionally substituted acyl, or an oxygen protecting group; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Also provided herein are compounds of Formula (L-5-32A):

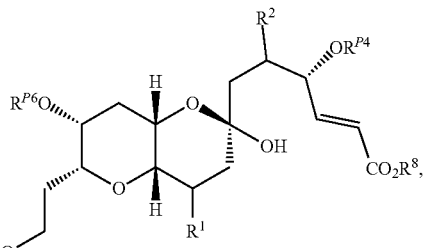
(L-5-30)

and salts thereof; wherein:

$R^1$ and $R^2$ are independently hydrogen, halogen, or optionally substituted alkyl;

$R^{P1}$, $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Also provided herein are compounds of Formula (L-5-28):

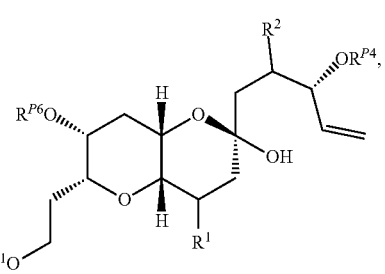
(L-5-28)

and salts thereof, wherein:

$R^1$ and $R^2$ are independently hydrogen, halogen, or optionally substituted alkyl; and $R^{P1}$, $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

Provided herein are compounds of Formula (L-5-27):

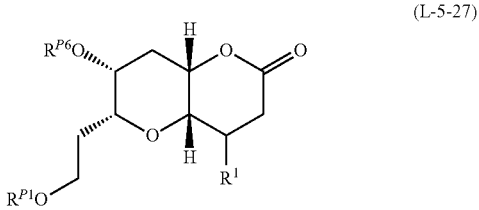

(L-5-27)

and salts thereof, wherein:
R¹ and R² are independently hydrogen, halogen, or optionally substituted alkyl; and
each instance of $R^{P4}$ and $R^{P6}$ are independently hydrogen, optionally substituted alkyl, optionally substituted acyl, or an oxygen protecting group.

Provided herein are compounds of Formula (L-5-7B):

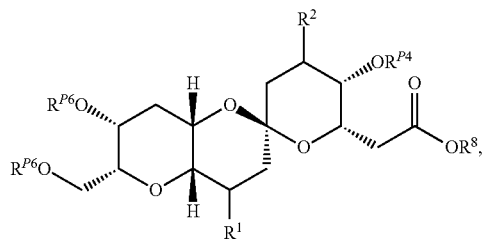

(L-5-7B)

and salts thereof; wherein:
R¹ and R² are independently hydrogen, halogen, or optionally substituted alkyl;
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and
$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of Formula (E-L-1):

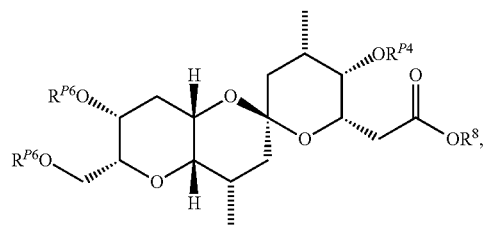

(E-L-1)

or a salt thereof, wherein:
$R^S$ is optionally substituted alkyl, optionally substituted carbocyclyl, optionally substituted aryl, optionally substituted heterocyclyl, or optionally substituted heteroaryl;
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and
$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Also provided herein are compounds of Formula (L-5-7A):

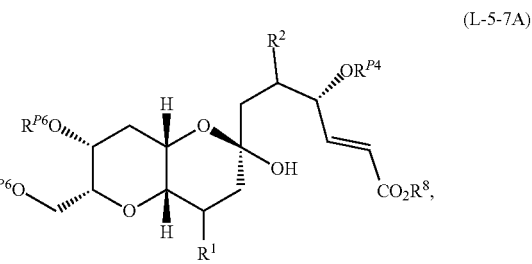

(L-5-7A)

and salts thereof; wherein:
R¹ and R² are independently hydrogen, halogen, or optionally substituted alkyl;
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and
$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

In certain embodiments, the compound is of Formula (E-L-2):

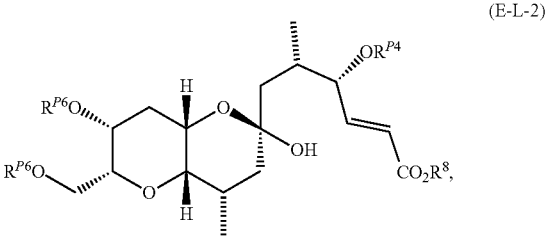

(E-L-2)

or a salt thereof, wherein:
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and
$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (E-L-6):

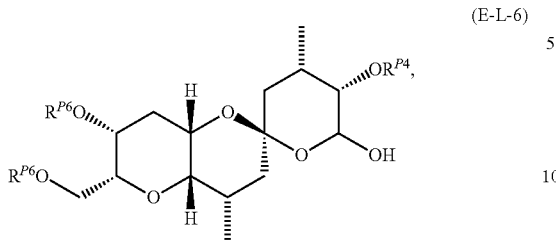

(E-L-6)

or a salt thereof, wherein:
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl; and $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group.

Provided herein are compounds of Formula (L-5-6A):

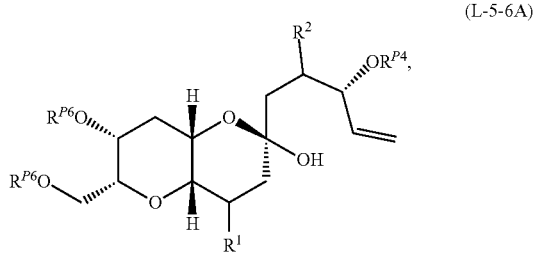

(L-5-6A)

and salts thereof; wherein:
$R^1$ and $R^2$ are independently hydrogen, halogen, or optionally substituted alkyl; and
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the compound is of Formula (E-L-5):

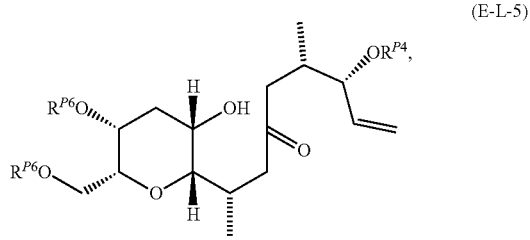

(E-L-5)

or a salt thereof, wherein:
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

Also provided herein are compounds of Formula (L-5-4):

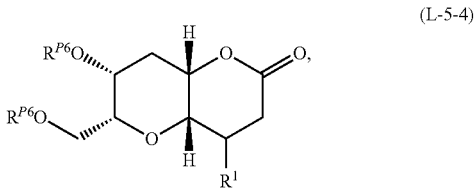

(L-5-4)

and salts thereof, wherein:
$R^1$ is independently hydrogen, halogen, or optionally substituted alkyl; and
each $R^{P6}$ is independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, the compound is of Formula (E-L-7):

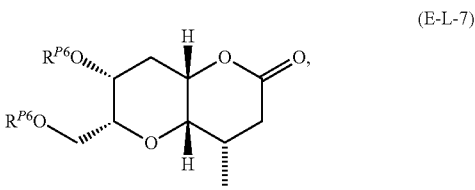

(E-L-7)

or a salt thereof, wherein:
each instance of $R^{P4}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

Group $R^L$, $X^L$

In certain embodiments, $R^L$ is optionally substituted sulfonyl, optionally substituted sulfinyl, optionally substituted phosphoryl, or optionally substituted acyl. In certain embodiments, $R^L$ is optionally substituted sulfonyl. In certain embodiments, $R^L$ is optionally substituted sulfinyl. In certain embodiments, $R^L$ is optionally substituted phosphoryl. In certain embodiments, $R^L$ is optionally substituted acyl. In certain embodiments, $R^L$ is —SO$_2$— alkyl. In certain embodiments, $R^L$ is mesyl (—SO$_2$CH$_3$; "Ms"). In certain embodiments, $R^L$ is —SO$_2$-aryl. In certain embodiments, $R^L$ is —SO$_2$Ph. In certain embodiments, $R^L$ is p-toluenesulfonyl (—SO$_2$C$_6$H$_4$p-CH$_3$; "tosyl" or "Ts"). In certain embodiments, $R^L$ is trifluoromethanesulfonyl (—SO$_2$CF$_3$; "triflyl" or "Tf"). In certain embodiments, $R^L$ is p-bromobenzenesulfonyl (—SO$_2$C$_6$H$_4$p-Br; "brosyl" or "Bs"), In certain embodiments, $R^L$ is nonafluorobutanesulfonyl (—OSO$_2$(CF$_2$)$_3$CF$_3$; "Nf"). In certain embodiments, $R^L$ is 2- or 4-nitrobenzenesulfonyl (—SO$_2$C$_6$H$_4$p-NO$_2$ or —SO$_2$C$_6$H$_4$o-NO$_2$; "nosyl" or "Ns"). In certain embodiments, $R^L$ is 2,2,2-trifluoroethyl-1-sulfonyl. In certain embodiments, $R^L$ is 5-(dimethylamino)naphthalene-1-sulfonyl ("dansyl" or "Ds").

As defined herein, $X^L$ is halogen or a leaving group. As defined herein, in certain embodiments, $X^L$ is halogen. In certain embodiments, $X^L$ is —Cl. In certain embodiments, $X^L$ is —Br. In certain embodiments, $X^L$ is —I.

Group $R^S$

As defined herein, $R^S$ is optionally substituted alkyl, optionally substituted carbocyclyl, optionally substituted aryl, optionally substituted heterocyclyl, or optionally substituted heteroaryl. In certain embodiments, $R^S$ is optionally substituted alkyl. In certain embodiments, $R^S$ is optionally substituted $C_{1-6}$ alkyl. In certain embodiments, $R^S$ is unsubstituted $C_{1-6}$ alkyl. In certain embodiments, $R^S$ is selected from the group consisting of methyl, ethyl, n-propyl, iso-propyl, n-butyl, iso-butyl, sec-butyl, and tert-butyl. In certain embodiments, $R^S$ is optionally substituted carbocyclyl. In certain embodiments, $R^S$ is optionally substituted aryl. In certain embodiments, $R^S$ is optionally substituted heterocyclyl. In certain embodiments, $R^S$ is optionally substituted heteroaryl. In certain embodiments, $R^S$ is optionally substituted 6-membered heteroaryl. In certain embodiments, $R^S$ is optionally substituted 6-membered heteroaryl comprising 1, 2, or 3 nitrogen atoms. In certain embodiments, $R^S$ is optionally substituted pyridyl. In certain embodiments, $R^S$ is unsubstituted pyridyl (Py). In certain embodiments, $R^S$ is optionally substituted 2-pyridyl. In certain embodiments, $R^S$ is unsubstituted 2-pyridyl (2-Py). In certain embodiments, $R^S$ is selected from the group consisting of:

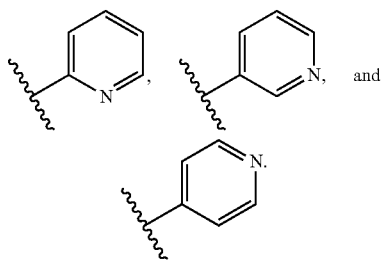

In certain embodiments, $R^S$ is

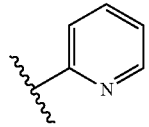 [SMILES: *c1ccccn1]

(abbreviated herein as "2-Py" or "Py").

Groups $X^1$, $X^2$, $X^3$, and $X^4$

As defined herein, $X^1$ is halogen or a leaving group. In certain embodiments, $X^1$ is a halogen. In certain embodiments, $X^1$ is —Cl (i.e., chloride). In certain embodiments, $X^1$ is —Br (i.e., bromide). In certain embodiments, $X^1$ is —I (i.e., iodide). In certain embodiments, $X^1$ is —F (i.e., fluoride). In certain embodiments, $X^1$ is a leaving group.

As defined herein, $X^2$ is halogen or a leaving group. In certain embodiments, $X^2$ is a halogen. In certain embodiments, $X^2$ is —Cl. In certain embodiments, $X^2$ is —Br. In certain embodiments, $X^2$ is —I. In certain embodiments, $X^2$ is —F. In certain embodiments, $X^2$ is a leaving group.

As defined herein, $X^3$ is halogen or a leaving group. In certain embodiments, $X^3$ is a halogen. In certain embodiments, $X^3$ is —Cl. In certain embodiments, $X^3$ is —Br. In certain embodiments, $X^3$ is —I. In certain embodiments, $X^3$ is —F. In certain embodiments, $X^3$ is a leaving group.

As defined herein, $X^4$ is halogen or a leaving group. In certain embodiments, $X^4$ is a halogen. In certain embodiments, $X^4$ is —Cl. In certain embodiments, $X^4$ is —Br. In certain embodiments, $X^4$ is —I. In certain embodiments, $X^4$ is —F. In certain embodiments, $X^4$ is a leaving group.

Groups $R^1$, $R^2$, $R^3$, $R^4$, $R^5$, and $R^6$

As defined herein, $R^1$ is hydrogen, halogen, or optionally substituted alky. In certain embodiments, $R^1$ is hydrogen. In certain embodiments, $R^1$ is halogen. In certain embodiments, $R^1$ is optionally substituted alkyl. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-3}$ alkyl. In certain embodiments, $R^1$ is unsubstituted $C_{1-3}$ alkyl. In certain embodiments, $R^1$ is selected from the group consisting of methyl, ethyl, n-propyl, iso-propyl, n-butyl, iso-butyl, sec-butyl, and tert-butyl. In certain embodiments, $R^1$ is methyl.

As defined herein, $R^2$ is hydrogen, halogen, or optionally substituted alky. In certain embodiments, $R^2$ is hydrogen. In certain embodiments, $R^2$ is halogen. In certain embodiments, $R^2$ is optionally substituted alkyl. In certain embodiments, $R^2$ is optionally substituted $C_{1-6}$ alkyl. In certain embodiments, $R^2$ is unsubstituted $C_{1-6}$ alkyl. In certain embodiments, $R^2$ is optionally substituted $C_{1-3}$ alkyl. In certain embodiments, $R^2$ is unsubstituted $C_{1-3}$ alkyl. In certain embodiments, $R^2$ is selected from the group consisting of methyl, ethyl, n-propyl, iso-propyl, n-butyl, iso-butyl, sec-butyl, and tert-butyl. In certain embodiments, $R^2$ is methyl.

As defined herein, $R^3$ is hydrogen, halogen, or optionally substituted alky. In certain embodiments, $R^3$ is hydrogen. In certain embodiments, $R^3$ is halogen. In certain embodiments, $R^3$ is optionally substituted alkyl. In certain embodiments, $R^3$ is optionally substituted $C_{1-6}$ alkyl. In certain embodiments, $R^3$ is unsubstituted $C_{1-6}$ alkyl. In certain embodiments, $R^3$ is optionally substituted $C_{1-3}$ alkyl. In certain embodiments, $R^3$ is unsubstituted $C_{1-3}$ alkyl. In certain embodiments, $R^3$ is selected from the group consisting of methyl, ethyl, n-propyl, iso-propyl, n-butyl, iso-butyl, sec-butyl, and tert-butyl. In certain embodiments, $R^3$ is methyl.

As defined herein, each instance of $R^4$ is independently hydrogen, halogen, or optionally substituted alkyl; and optionally two $R^4$ groups are taken together to form:

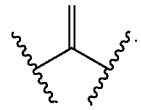 [SMILES: *C(*)=C]

In certain embodiments, $R^4$ is hydrogen. In certain embodiments, $R^4$ is halogen. In certain embodiments, $R^4$ is optionally substituted alkyl. In certain embodiments, $R^4$ is optionally substituted $C_{1-6}$ alkyl. In certain embodiments, $R^4$ is unsubstituted $C_{1-6}$ alkyl. In certain embodiments, $R^4$ is optionally substituted $C_{1-3}$ alkyl. In certain embodiments, $R^4$ is unsubstituted $C_{1-3}$ alkyl. In certain embodiments, $R^4$ is selected from the group consisting of methyl, ethyl, n-propyl, iso-propyl, n-butyl, iso-butyl, sec-butyl, and tert-butyl. In certain embodiments, $R^4$ is methyl. In certain embodiments, two $R^4$ groups are taken together to form:

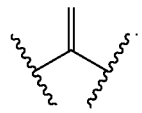

As define herein, $R^5$ is hydrogen, halogen, or optionally substituted alky. In certain embodiments, $R^5$ is hydrogen. In certain embodiments, $R^5$ is halogen. In certain embodiments, $R^3$ is optionally substituted alkyl. In certain embodiments, $R^5$ is optionally substituted $C_{1-6}$ alkyl. In certain embodiments, $R^5$ is unsubstituted $C_{1-6}$ alkyl. In certain embodiments, $R^5$ is optionally substituted $C_{1-3}$ alkyl. In certain embodiments, $R^5$ is unsubstituted $C_{1-3}$ alkyl. In certain embodiments, $R^5$ is selected from the group consisting of methyl, ethyl, n-propyl, iso-propyl, n-butyl, iso-butyl, sec-butyl, and tert-butyl. In certain embodiments, $R^5$ is methyl.

As defined herein, each instance of $R^6$ is independently hydrogen, halogen, or optionally substituted alkyl; and optionally two $R^6$ groups are taken together to form:

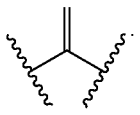 [SMILES: *C(*)=C]

In certain embodiments, $R^6$ is hydrogen. In certain embodiments, $R^6$ is halogen. In certain embodiments, $R^6$ is optionally substituted alkyl. In certain embodiments, $R^6$ is optionally substituted $C_{1-6}$ alkyl. In certain embodiments, $R^6$ is unsubstituted $C_{1-6}$ alkyl. In certain embodiments, $R^6$ is optionally substituted $C_{1-3}$ alkyl. In certain embodiments, $R^6$ is unsubstituted $C_{1-3}$ alkyl. In certain embodiments, $R^6$ is selected from the group consisting of methyl, ethyl, n-propyl, iso-propyl, n-butyl, iso-butyl, sec-butyl, and tert-butyl. In certain embodiments, $R^6$ is methyl. In certain embodiments, two $R^6$ groups are taken together to form:

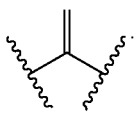

Groups $R^7$ and $R^8$

As defined herein, $R^7$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group. In certain embodiments, $R^7$ is hydrogen. In certain embodiments, $R^7$ is optionally substituted alkyl. In certain embodiments, In certain embodiments, $R^7$ is optionally substituted $C_{1-6}$ alkyl. In certain embodiments, $R^7$ is unsubstituted $C_{1-6}$ alkyl. In certain embodiments, $R^7$ is optionally substituted $C_{1-3}$ alkyl. In certain embodiments, $R^7$ is unsubstituted $C_{1-3}$ alkyl. In certain embodiments, $R^7$ is selected from the group consisting of methyl, ethyl, n-propyl, iso-propyl, n-butyl, iso-butyl, sec-butyl, and tert-butyl. In certain embodiments, $R^7$ is methyl. In certain embodiments, $R^7$ is ethyl. In certain embodiments, $R^7$ is optionally substituted carbocyclyl. In certain embodiments, $R^7$ is optionally substituted aryl. In certain embodiments, $R^7$ is optionally substituted heterocyclyl. In certain embodiments, $R^7$ is optionally substituted heteroaryl. In certain embodiments, $R^7$ is optionally substituted acyl. In certain embodiments, $R^7$ is an oxygen protecting group. In certain embodiments, $R^7$ is an optionally substituted benzyl protecting group. In certain embodiments, $R^7$ is benzyl (—$CH_2Ph$; "Bn").

As defined herein, $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group. In certain embodiments, $R^8$ is hydrogen. In certain embodiments, $R^8$ is optionally substituted alkyl. In certain embodiments, In certain embodiments, $R^8$ is optionally substituted $C_{1-6}$ alkyl. In certain embodiments, $R^8$ is unsubstituted $C_{1-6}$ alkyl. In certain embodiments, $R^8$ is optionally substituted $C_{1-3}$ alkyl. In certain embodiments, $R^8$ is unsubstituted $C_{1-3}$ alkyl. In certain embodiments, $R^8$ is selected from the group consisting of methyl, ethyl, n-propyl, iso-propyl, n-butyl, iso-butyl, sec-butyl, and tert-butyl. In certain embodiments, $R^8$ is methyl. In certain embodiments, $R^8$ is ethyl. In certain embodiments, $R^8$ is optionally substituted carbocyclyl. In certain embodiments, $R^8$ is optionally substituted aryl. In certain embodiments, $R^8$ is optionally substituted heterocyclyl. In certain embodiments, $R^8$ is optionally substituted heteroaryl. In certain embodiments, $R^8$ is optionally substituted acyl. In certain embodiments, $R^8$ is an oxygen protecting group. In certain embodiments, $R^8$ is an optionally substituted benzyl protecting group. In certain embodiments, $R^8$ is benzyl (—$CH_2Ph$; "Bn").

Groups $R^X$ and $R^Y$

As defined herein, $R^X$ is hydrogen or —$OR^X$. In certain embodiments, $R^X$ is hydrogen. In certain embodiments, $R^X$ is —$OR^{Xa}$.

As generally defined herein, $R^{Xa}$ is hydrogen, optionally substituted alkyl, optionally substituted acyl, or an oxygen protecting group. In certain embodiments, $R^{Xa}$ is hydrogen. In certain embodiments, $R^{Xa}$ is optionally substituted alkyl. In certain embodiments, $R^{Xa}$ is optionally substituted acyl. In certain embodiments, $R^{Xa}$ is or an oxygen protecting group. In certain embodiments, $R^{Xa}$ is optionally substituted allyl. In certain embodiments, $R^{Xa}$ is

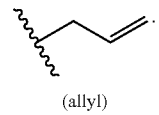

(allyl)

As defined herein, $R^Y$ is hydrogen or —$OR^{Ya}$. In certain embodiments, $R^Y$ is hydrogen. In certain embodiments, $R^Y$ is —$OR^{Ya}$.

As generally defined herein, $R^{Ya}$ is hydrogen, optionally substituted alkyl, optionally substituted acyl, or an oxygen protecting group. In certain embodiments, $R^{Ya}$ is hydrogen. In certain embodiments, $R^{Ya}$ is optionally substituted alkyl. In certain embodiments, $R^{Ya}$ is optionally substituted acyl. In certain embodiments, $R^{Ya}$ is or an oxygen protecting group. In certain embodiments, $R^{Ya}$ is optionally substituted allyl. In certain embodiments, $R^{Ya}$ is

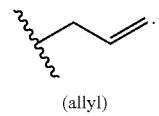 [SMILES: *CC=C]

(allyl)

In certain embodiments, $R^{Xa}$ and $R^{Ya}$ are joined together with their intervening atoms to form optionally substituted heterocyclyl. In certain embodiments, $R^{Xa}$ and $R^{Ya}$ are joined together with their intervening atoms to form optionally substituted 5-membered heterocyclyl. In certain embodiments, $R^{Xa}$ and $R^{Ya}$ are joined together with their intervening atoms to form optionally substituted 1,3-dioxolane ring. In certain embodiments, $R^{Xa}$ and $R^{Ya}$ are joined together with their intervening atoms to form the following:

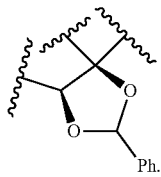

In certain embodiments, $R^{Xa}$ and $R^{Ya}$ are joined together with their intervening atoms to form the following:

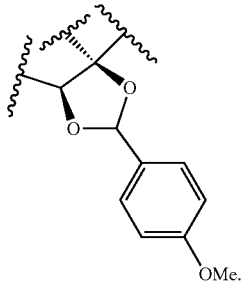

Groups $R^{P1}$, $R^{P2}$, $R^{P3}$, $R^{P4}$, $R^{P5}$, $R^{P6}$, $R^{P7}$, $R^{P8}$, $R^{P9}$, and $R^{P10}$ As defined herein, $R^{P1}$ is hydrogen, optionally substituted alkyl, optionally substituted acyl, or an oxygen protecting group. In certain embodiments, $R^{P1}$ is hydrogen. In certain embodiments, $R^{P1}$ is optionally substituted alkyl. In certain embodiments, In certain embodiments, $R^{P1}$ is optionally substituted $C_{1-6}$ alkyl. In certain embodiments, $R^{P1}$ is unsubstituted $C_{1-6}$ alkyl. In certain embodiments, $R^{P1}$ is optionally substituted $C_{1-3}$ alkyl. In certain embodiments, $R^{P1}$ is unsubstituted $C_{1-3}$ alkyl. In certain embodiments, $R^{P1}$ is selected from the group consisting of methyl, ethyl, n-propyl, iso-propyl, n-butyl, iso-butyl, sec-butyl, and tert-butyl. In certain embodiments, $R^{P1}$ is optionally substituted acyl. In certain embodiments, $R^{P1}$ is an oxygen protecting group. In certain embodiments, $R^{P1}$ is optionally substituted allyl. In certain embodiments, $R^{P1}$ is allyl. In certain embodiments, $R^{P1}$ is optionally substituted silyl. In certain embodiments, $R^{P1}$ is trialkylsilyl. In certain embodiments, $R^{P1}$ is triethylsilyl (—SiEt$_3$; "TES"). In certain embodiments, $R^{P1}$ is trimethylsilyl (—SiMe$_3$; "TMS"). In certain embodiments, $R^{P1}$ is tert-butyl dimethylsilyl (—Sit-BuMe$_2$; "TBS"). In certain embodiments, $R^{P1}$ is tert-butyl diphenylsilyl (—Sit-BuPh$_2$; "TBDPS"). In certain embodiments, $R^{P1}$ is an optionally substituted benzyl protecting group. In certain embodiments, $R^{P1}$ is benzyl (—CH$_2$Ph; "Bn"). In certain embodiments, $R^{P1}$ is a methoxybenzyl protecting group. In certain embodiments, $R^{P1}$ is para-methoxybenzyl:

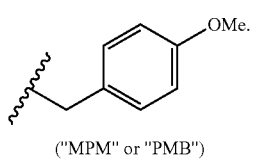 [SMILES: *Cc1ccc(OC)cc1]

("MPM" or "PMB")

In certain embodiments, $R^{P1}$ and $R^{P2}$ are joined with the intervening atoms to form optionally substituted heterocyclyl.

As defined herein, $R^{P2}$ is hydrogen, optionally substituted alkyl, optionally substituted acyl, or an oxygen protecting group. In certain embodiments, $R^{P2}$ is hydrogen. In certain embodiments, $R^{P2}$ is optionally substituted alkyl. In certain embodiments, $R^{P2}$ is optionally substituted $C_{1-6}$ alkyl. In certain embodiments, $R^{P2}$ is unsubstituted $C_{1-6}$ alkyl. In certain embodiments, $R^{P2}$ is optionally substituted $C_{1-3}$ alkyl. In certain embodiments, $R^{P2}$ is unsubstituted $C_{1-3}$ alkyl. In certain embodiments, $R^{P2}$ is selected from the group consisting of methyl, ethyl, n-propyl, iso-propyl, n-butyl, iso-butyl, sec-butyl, and tert-butyl. In certain embodiments, $R^{P2}$ is optionally substituted acyl. In certain embodiments, $R^{P2}$ is an oxygen protecting group. In certain embodiments, $R^{P2}$ is optionally substituted allyl. In certain embodiments, $R^{P2}$ is allyl. In certain embodiments, $R^{P2}$ is optionally substituted silyl. In certain embodiments, $R^{P2}$ is trialkylsilyl. In certain embodiments, $R^{P2}$ is triethylsilyl (—SiEt$_3$; "TES"). In certain embodiments, $R^{P2}$ is trimethylsilyl (—SiMe$_3$; "TMS"). In certain embodiments, $R^{P2}$ is tert-butyl dimethylsilyl (—Sit-BuMe$_2$; "TBS"). In certain embodiments, $R^{P2}$ is tert-butyl diphenylsilyl (—Sit-BuPh$_2$; "TBDPS"). In certain embodiments, $R^{P2}$ is an optionally substituted benzyl protecting group. In certain embodiments, $R^{P2}$ is benzyl (—CH$_2$Ph; "Bn"). In certain embodiments, $R^{P2}$ is a methoxybenzyl protecting group. In certain embodiments, $R^{P2}$ is para-methoxybenzyl:

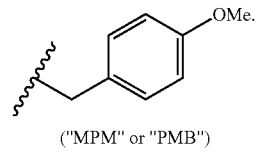 [SMILES: *Cc1ccc(OC)cc1]

("MPM" or "PMB")

In certain embodiments, $R^{P3}$ and $R^{P3}$ are joined with the intervening atoms to form optionally substituted heterocyclyl.

As defined herein, $R^{P3}$ is hydrogen, optionally substituted alkyl, optionally substituted acyl, or an oxygen protecting group. In certain embodiments, $R^{P3}$ is hydrogen. In certain embodiments, $R^{P3}$ is optionally substituted alkyl. In certain embodiments, $R^{P3}$ is optionally substituted $C_{1-6}$ alkyl. In certain embodiments, $R^{P3}$ is unsubstituted $C_{1-6}$ alkyl. In certain embodiments, $R^{P3}$ is optionally substituted $C_{1-3}$ alkyl. In certain embodiments, $R^{P3}$ is unsubstituted $C_{1-3}$ alkyl. In certain embodiments, $R^{P3}$ is selected from the group consisting of methyl, ethyl, n-propyl, iso-propyl, n-butyl, iso-butyl, sec-butyl, and tert-butyl. In certain embodiments, $R^{P3}$ is optionally substituted acyl. In certain embodiments, $R^{P3}$ is an oxygen protecting group. In certain embodiments, $R^{P3}$ is optionally substituted allyl. In certain embodiments, $R^{P3}$ is allyl. In certain embodiments, $R^{P3}$ is optionally substituted silyl. In certain embodiments, $R^{P3}$ is trialkylsilyl. In certain embodiments, $R^{P3}$ is triethylsilyl (—SiEt$_3$; "TES"). In certain embodiments, $R^{P3}$ is trimethylsilyl (—SiMe$_3$; "TMS"). In certain embodiments, $R^{P3}$ is tert-butyl dimethylsilyl (—Sit-BuMe$_2$; "TBS"). In certain embodiments, $R^{P3}$ is tert-butyl diphenylsilyl (—Sit-BuPh$_2$; "TBDPS"). In certain embodiments, $R^{P3}$ is an optionally substituted benzyl protecting group. In certain embodiments, $R^{P3}$ is benzyl (—CH$_2$Ph; "Bn"). In certain embodiments, $R^{P3}$ is a methoxybenzyl protecting group. In certain embodiments, $R^{P3}$ is para-methoxybenzyl:

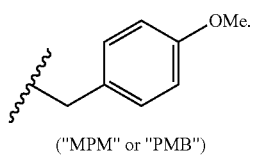 [SMILES: *Cc1ccc(OC)cc1]

("MPM" or "PMB")

As defined herein, $R^{P4}$ is hydrogen, optionally substituted alkyl, optionally substituted acyl, or an oxygen protecting group. In certain embodiments, $R^{P4}$ is hydrogen. In certain embodiments, $R^{P4}$ is optionally substituted alkyl. In certain embodiments, $R^{P4}$ is optionally substituted $C_{1-6}$ alkyl. In certain embodiments, $R^{P4}$ is unsubstituted $C_{1-6}$ alkyl. In certain embodiments, $R^{P4}$ is optionally substituted $C_{1-3}$ alkyl. In certain embodiments, $R^{P4}$ is unsubstituted $C_{1-3}$ alkyl. In certain embodiments, $R^{P4}$ is selected from the group consisting of methyl, ethyl, n-propyl, iso-propyl, n-butyl, iso-butyl, sec-butyl, and tert-butyl. In certain embodiments, $R^{P4}$ is optionally substituted acyl. In certain embodiments, $R^{P4}$ is an oxygen protecting group. In certain embodiments, $R^{P4}$ is optionally substituted allyl. In certain embodiments, $R^{P4}$ is allyl. In certain embodiments, $R^{P4}$ is optionally substituted silyl. In certain embodiments, $R^{P4}$ is trialkylsilyl. In certain embodiments, $R^{P4}$ is triethylsilyl (—SiEt$_3$; "TES"). In certain embodiments, $R^{P4}$ is trimethylsilyl (—SiMe$_3$; "TMS"). In certain embodiments, $R^{P4}$ is tert-butyl dimethylsilyl (—Sit-BuMe$_2$; "TBS"). In certain embodiments, $R^{P4}$ is tert-butyl diphenylsilyl (—Sit-BuPh$_2$; "TBDPS"). In certain embodiments, $R^{P4}$ is an optionally substituted benzyl protecting group. In certain embodiments, $R^{P4}$ is benzyl (—CH$_2$Ph; "Bn"). In certain embodiments, $R^{P4}$ is a methoxybenzyl protecting group. In certain embodiments, $R^{P4}$ is para-methoxybenzyl:

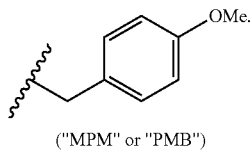 [SMILES: *Cc1ccc(OC)cc1]

("MPM" or "PMB")

As defined herein, $R^{P5}$ is hydrogen, optionally substituted alkyl, optionally substituted acyl, or an oxygen protecting group; optionally wherein two $R^{P5}$ are joined with the intervening atoms to form optionally substituted heterocyclyl. In certain embodiments, $R^{P5}$ is hydrogen. In certain embodiments, $R^{P5}$ is optionally substituted alkyl. In certain embodiments, $R^{P5}$ is optionally substituted $C_{1-6}$ alkyl. In certain embodiments, $R^{P5}$ is unsubstituted $C_{1-6}$ alkyl. In certain embodiments, $R^{P5}$ is optionally substituted $C_{1-3}$ alkyl. In certain embodiments, $R^{P5}$ is unsubstituted $C_{1-3}$ alkyl. In certain embodiments, $R^{P5}$ is selected from the group consisting of methyl, ethyl, n-propyl, iso-propyl, n-butyl, iso-butyl, sec-butyl, and tert-butyl. In certain embodiments, $R^{P5}$ is optionally substituted acyl. In certain embodiments, $R^{P5}$ is an oxygen protecting group. In certain embodiments, $R^{P5}$ is optionally substituted allyl. In certain embodiments, $R^{P5}$ is allyl. In certain embodiments, $R^{P5}$ is optionally substituted silyl. In certain embodiments, $R^{P5}$ is trialkylsilyl. In certain embodiments, $R^{P5}$ is triethylsilyl (—SiEt$_3$; "TES"). In certain embodiments, $R^{P5}$ is trimethylsilyl (—SiMe$_3$; "TMS"). In certain embodiments, $R^{P5}$ is tert-butyl dimethylsilyl (—Sit-BuMe$_2$; "TBS"). In certain embodiments, $R^{P5}$ is tert-butyl diphenylsilyl (—Sit-BuPh$_2$; "TBDPS"). In certain embodiments, $R^{P5}$ is an optionally substituted benzyl protecting group. In certain embodiments, $R^{P5}$ is benzyl (—CH$_2$Ph; "Bn"). In certain embodiments, $R^{P5}$ is a methoxybenzyl protecting group. In certain embodiments, $R^{P5}$ is para-methoxybenzyl:

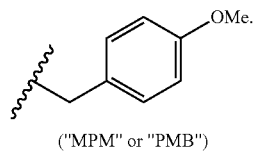 [SMILES: *Cc1ccc(OC)cc1]

("MPM" or "PMB")

In certain embodiments, two $R^{P5}$ are joined with the intervening atoms to form optionally substituted heterocyclyl. In certain embodiments, two $R^{P5}$ are joined with the intervening atoms to form optionally substituted six-membered heterocyclyl. In certain embodiments, two $R^{P5}$ are joined with the intervening atoms to form a ring of the formula:

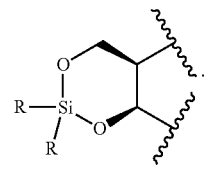

In certain embodiments, two $R^{P5}$ are joined with the intervening atoms to form a ring of the formula:

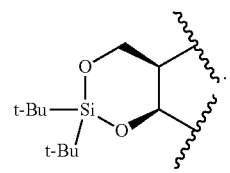 [SMILES: *[C@@H]1CO[Si](C(C)(C)C)(C(C)(C)C)O[C@@H]1*]

In certain embodiments, two $R^{P5}$ are joined with the intervening atoms to form a ring of the formula:

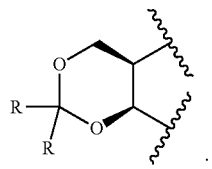

In certain embodiments, two $R^{P5}$ are joined with the intervening atoms to form a ring of the formula:

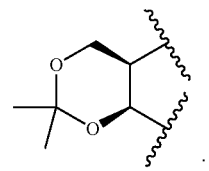 [SMILES: *[C@@H]1COC(C)(C)O[C@@H]1*]

As defined herein, $R^{P6}$ is hydrogen, optionally substituted alkyl, optionally substituted acyl, or an oxygen protecting group; optionally wherein two $R^{P6}$ are joined with the intervening atoms to form optionally substituted heterocyclyl. In certain embodiments, $R^{P6}$ is hydrogen. In certain embodiments, $R^{P6}$ is optionally substituted alkyl. In certain embodiments, $R^{P6}$ is optionally substituted $C_{1-6}$ alkyl. In certain embodiments, $R^{P6}$ is unsubstituted $C_{1-6}$ alkyl. In certain embodiments, $R^{P6}$ is optionally substituted $C_{1-3}$ alkyl. In certain embodiments, $R^{P6}$ is unsubstituted $C_{1-3}$ alkyl. In certain embodiments, $R^{P6}$ is selected from the group consisting of methyl, ethyl, n-propyl, iso-propyl, n-butyl, iso-butyl, sec-butyl, and tert-butyl. In certain embodiments, $R^{P6}$ is optionally substituted acyl. In certain embodiments, $R^{P6}$ is an oxygen protecting group. In certain embodiments, $R^{P6}$ is optionally substituted allyl. In certain embodiments, $R^{P6}$ is allyl. In certain embodiments, $R^{P6}$ is optionally substituted silyl. In certain embodiments, $R^{P6}$ is trialkylsilyl. In certain embodiments, $R^{P6}$ is triethylsilyl (—SiEt$_3$; "TES"). In certain embodiments, $R^{P6}$ is trimethylsilyl (—SiMe$_3$; "TMS"). In certain embodiments, $R^{P6}$ is tert-butyl dimethylsilyl (—Sit-BuMe$_2$; "TBS"). In certain embodiments, $R^{P6}$ is tert-butyl diphenylsilyl (—Sit-BuPh$_2$; "TBDPS"). In certain embodiments, $R^{P6}$ is an optionally substituted benzyl protecting group. In certain embodiments, $R^{P6}$ is benzyl (—CH$_2$Ph; "Bn"). In certain embodiments, $R^{P6}$ is a methoxybenzyl protecting group. In certain embodiments, $R^{P6}$ is para-methoxybenzyl:

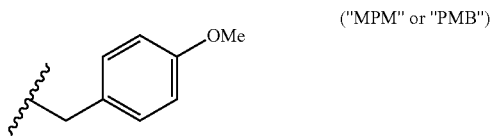 [SMILES: *Cc1ccc(OC)cc1]

("MPM" or "PMB")

In certain embodiments, two $R^{P6}$ are joined with the intervening atoms to form optionally substituted heterocyclyl. In certain embodiments, two $R^{P6}$ are joined with the intervening atoms to form optionally substituted six-membered heterocyclyl. In certain embodiments, two $R^{P6}$ are joined with the intervening atoms to form a ring of the formula:

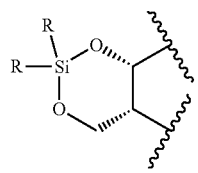

In certain embodiments, two $R^{P6}$ are joined with the intervening atoms to form a ring of the formula:

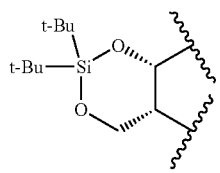

As defined herein, in certain embodiments, $R^{P7}$ is hydrogen, optionally substituted alkyl, optionally substituted acyl, or an oxygen protecting group. In other embodiments, $R^{P7}$ is optionally substituted sulfonyl, optionally substituted sulfinyl, optionally substituted phosphoryl, optionally substituted acyl, or an oxygen protecting group. In certain embodiments, $R^{P7}$ is optionally substituted sulfonyl. In certain embodiments, $R^{P7}$ is mesyl (—SO$_2$CH$_3$; "Ms"). In certain embodiments, $R^{P7}$ is tosyl (C—SO$_2$C$_6$H$_4$p-CH$_3$; "Ts"). In certain embodiments, $R^{P7}$ is triflyl (—SO$_2$CF$_3$; "Tf"). In certain embodiments, $R^{P7}$ is optionally substituted sulfinyl. In certain embodiments, $R^{P7}$ is optionally substituted phosphoryl. In certain embodiments, $R^{P7}$ is optionally substituted acyl.

In certain embodiments, $R^{P7}$ is hydrogen. In certain embodiments, $R^{P7}$ is optionally substituted alkyl. In certain embodiments, $R^{P7}$ is optionally substituted $C_{1-6}$ alkyl. In certain embodiments, $R^{P7}$ is unsubstituted $C_{1-6}$ alkyl. In certain embodiments, $R^{P7}$ is optionally substituted $C_{1-3}$ alkyl. In certain embodiments, $R^{P7}$ is unsubstituted $C_{1-3}$ alkyl. In certain embodiments, $R^{P7}$ is selected from the group consisting of methyl, ethyl, n-propyl, iso-propyl, n-butyl, iso-butyl, sec-butyl, and tert-butyl. In certain embodiments, $R^{P7}$ is optionally substituted acyl. In certain embodiments, $R^{P7}$ is an oxygen protecting group. In certain embodiments, $R^{P7}$ is optionally substituted allyl. In certain embodiments, $R^{P7}$ is allyl. In certain embodiments, $R^{P7}$ is optionally substituted silyl. In certain embodiments, $R^{P7}$ is trialkylsilyl. In certain embodiments, $R^{P7}$ is triethylsilyl (—SiEt$_3$; "TES"). In certain embodiments, $R^{P7}$ is trimethylsilyl (—SiMe$_3$; "TMS"). In certain embodiments, $R^{P7}$ is tert-butyl dimethylsilyl (—Sit-BuMe$_2$; "TBS"). In certain embodiments, $R^{P7}$ is tert-butyl diphenylsilyl (—Sit-BuPh$_2$; "TBDPS"). In certain embodiments, $R^{P7}$ is an optionally substituted benzyl protecting group. In certain embodiments, $R^{P7}$ is benzyl (—CH$_2$Ph; "Bn"). In certain embodiments, $R^{P7}$ is a methoxybenzyl protecting group. In certain embodiments, $R^{P7}$ is para-methoxybenzyl:

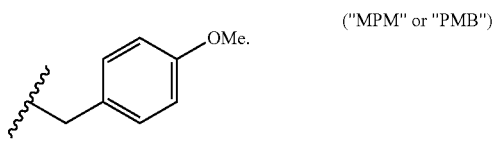 [SMILES: *Cc1ccc(OC)cc1]

("MPM" or "PMB")

As defined herein, $R^{P8}$ is hydrogen, optionally substituted alkyl, optionally substituted acyl, or an oxygen protecting group. In certain embodiments, $R^{P8}$ is hydrogen. In certain embodiments, $R^{P8}$ is optionally substituted alkyl. In certain embodiments, $R^{P8}$ is optionally substituted $C_{1-6}$ alkyl. In certain embodiments, $R^{P8}$ is unsubstituted $C_{1-6}$ alkyl. In certain embodiments, $R^{P8}$ is optionally substituted $C_{1-3}$ alkyl. In certain embodiments, $R^{P8}$ is unsubstituted $C_{1-3}$ alkyl. In certain embodiments, $R^{P8}$ is selected from the group consisting of methyl, ethyl, n-propyl, iso-propyl, n-butyl, iso-butyl, sec-butyl, and tert-butyl. In certain embodiments, $R^{P8}$ is optionally substituted acyl. In certain embodiments, $R^{P8}$ is an oxygen protecting group. In certain embodiments, $R^{P8}$ is optionally substituted allyl. In certain embodiments, $R^{P8}$ is allyl. In certain embodiments, $R^{P8}$ is optionally substituted silyl. In certain embodiments, $R^{P8}$ is trialkylsilyl. In certain embodiments, $R^{P8}$ is triethylsilyl (—SiEt$_3$; "TES"). In certain embodiments, $R^{P8}$ is trimethylsilyl (—SiMe$_3$; "TMS"). In certain embodiments, $R^{P8}$ is tert-butyl dimethylsilyl (—Sit-BuMe$_2$; "TBS"). In certain embodiments, $R^{P8}$ is tert-butyl diphenylsilyl (—Sit-BuPh$_2$; "TBDPS"). In certain embodiments, $R^{P8}$ is an optionally substituted benzyl protecting group. In certain embodiments, $R^{P8}$ is benzyl (—CH$_2$Ph; "Bn"). In certain embodiments, $R^{P8}$ is a methoxybenzyl protecting group. In certain embodiments, $R^{P8}$ is para-methoxybenzyl:

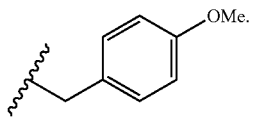

("MPM" or "PMB")

As defined herein, $R^{P9}$ is hydrogen, optionally substituted alkyl, optionally substituted acyl, or an oxygen protecting group. In certain embodiments, $R^{P9}$ is hydrogen. In certain embodiments, $R^{P9}$ is optionally substituted alkyl. In certain embodiments, $R^{P9}$ is optionally substituted $C_{1-6}$ alkyl. In certain embodiments, $R^{P9}$ is unsubstituted $C_{1-6}$ alkyl. In certain embodiments, $R^{P9}$ is optionally substituted $C_{1-3}$ alkyl. In certain embodiments, $R^{P9}$ is unsubstituted $C_{1-3}$ alkyl. In certain embodiments, $R^{P9}$ is selected from the group consisting of methyl, ethyl, n-propyl, iso-propyl, n-butyl, iso-butyl, sec-butyl, and tert-butyl. In certain embodiments, $R^{P9}$ is optionally substituted acyl. In certain embodiments, $R^{P9}$ is an oxygen protecting group. In certain embodiments, $R^{P9}$ is optionally substituted allyl. In certain embodiments, $R^{P9}$ is allyl. In certain embodiments, $R^{P9}$ is optionally substituted silyl. In certain embodiments, $R^{P9}$ is trialkylsilyl. In certain embodiments, $R^{P9}$ is triethylsilyl (—SiEt$_3$; "TES"). In certain embodiments, $R^{P9}$ is trimethylsilyl (—SiMe$_3$; "TMS"). In certain embodiments, $R^{P9}$ is tert-butyl dimethylsilyl (—Sit-BuMe$_2$; "TBS"). In certain embodiments, $R^{P9}$ is tert-butyl diphenylsilyl (—Sit-BuPh$_2$; "TBDPS"). In certain embodiments, $R^{P9}$ is an optionally substituted benzyl protecting group. In certain embodiments, $R^{P9}$ is benzyl (—CH$_2$Ph; "Bn"). In certain embodiments, $R^{P9}$ is a methoxybenzyl protecting group. In certain embodiments, $R^{P9}$ is para-methoxybenzyl:

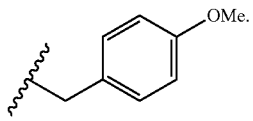

("MPM" or "PMB")

In certain embodiments, two $R^{P9}$ are joined together with the intervening atoms to form optionally substituted heterocyclyl. In certain embodiments, two $R^{P9}$ are joined together to form

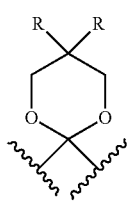

In certain embodiments, two $R^{P9}$ are joined together to form

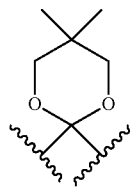

As defined herein, $R^{P10}$ is hydrogen, optionally substituted alkyl, optionally substituted acyl, or an oxygen protecting group. In certain embodiments, $R^{P10}$ is hydrogen. In certain embodiments, $R^{P10}$ is optionally substituted alkyl. In certain embodiments, $R^{P10}$ is optionally substituted $C_{1-6}$ alkyl. In certain embodiments, $R^{P10}$ is unsubstituted $C_{1-6}$ alkyl. In certain embodiments, $R^{P10}$ is optionally substituted $C_{1-3}$ alkyl. In certain embodiments, $R^{P10}$ is unsubstituted $C_{1-3}$ alkyl. In certain embodiments, $R^{P10}$ is selected from the group consisting of methyl, ethyl, n-propyl, iso-propyl, n-butyl, iso-butyl, sec-butyl, and tert-butyl. In certain embodiments, $R^{P10}$ is optionally substituted acyl. In certain embodiments, $R^{P10}$ is an oxygen protecting group. In certain embodiments, $R^{P10}$ is optionally substituted allyl. In certain embodiments, $R^{P10}$ is allyl. In certain embodiments, $R^{P10}$ is optionally substituted silyl. In certain embodiments, $R^{P10}$ is trialkylsilyl. In certain embodiments, $R^{P10}$ is triethylsilyl (—SiEt$_3$; "TES"). In certain embodiments, $R^{P10}$ is trimethylsilyl (—SiMe$_3$; "TMS"). In certain embodiments, $R^{P10}$ is tert-butyl dimethylsilyl (—Sit-BuMe$_2$; "TBS"). In certain embodiments, $R^{P10}$ is tert-butyl diphenylsilyl (—Sit-BuPh$_2$; "TBDPS"). In certain embodiments, $R^{P10}$ is an optionally substituted benzyl protecting group. In certain embodiments, $R^{P^\circ 0}$ is benzyl (—CH$_2$Ph; "Bn"). In certain embodiments, $R^{P10}$ is a methoxybenzyl protecting group. In certain embodiments, $R^{P10}$ is para-methoxybenzyl:

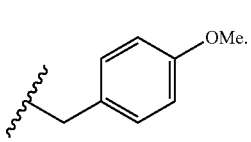

("MPM" or "PMB")

Group R

As generally defined herein, R is hydrogen or optionally substituted alkyl. In certain embodiments, R is hydrogen. In certain embodiments, R is optionally substituted alkyl. In certain embodiments, R is optionally substituted $C_{1-6}$ alkyl. In certain embodiments, R is unsubstituted $C_{1-6}$ alkyl. In certain embodiments, R is optionally substituted $C_{1-3}$ alkyl. In certain embodiments, R is unsubstituted $C_{1-3}$ alkyl. In certain embodiments, R is selected from the group consisting of methyl, ethyl, n-propyl, iso-propyl, n-butyl, iso-butyl, sec-butyl, and tert-butyl.

EXAMPLES

Zr/Ni-Mediated Ketolization Reactions

Figure 1:
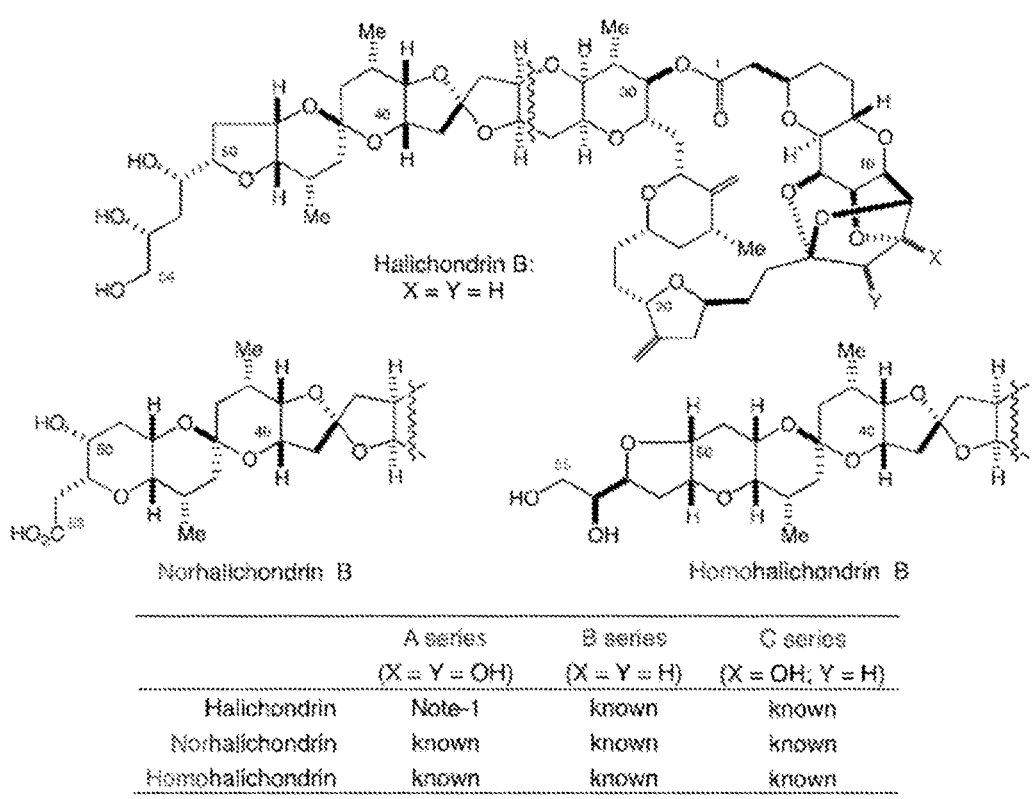
FIG. 1 shows the structures of halichondrin A, B, and C; homohalichondrin A, B, and C; and norhalichondrin A, B, and C.
Figure 2A:
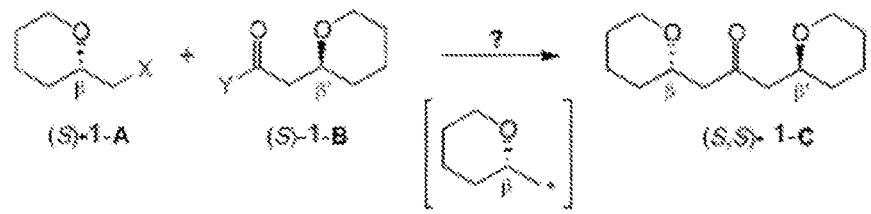
FIG. 2A shows an example of a Ni/Zr-mediated ketolization.

The structure (S,S)-1-C can be prepared directly via a coupling of (S)-1-A with (S)-1-B (FIG. 2A). Although appealing, sequence presents challenges. For example, anion-based ketone syntheses might be problematic, because of the presence of an O—R group at the β- and β'-positions. The "umpolung" concept, represented by dithiane chemistry, is the historical solution for this type of problem (see, e.g., For a review, for example see: Seebach, D. *Angew. Chem. Int. Ed.* 1979, 18, 239; Corey, E. J.; Seeback, D. *Angew. Chem. Int. Ed,* 1965, 4, 1077; Seebach, D.; Corey, E. J. *J. Org. Chem.* 1975, 40, 231). Indeed, dithiane-based ketone synthesis has successfully been applied to a synthesis of complex natural products (For a review, see, e.g., Yus, M.; Najera, C.; Foubelo, F. *Tetrahedron,* 2003, 59, 6147; Smith, III. A. S.; Adams, C. M.; *Acc. Chem. Rev.* 2004, 37, 365). Nevertheless, a direct ketone synthesis was developed which can be used in the synthesis of ketones, including complex molecules. The best chance of achieving this goal would be a radical-based, preferably one-pot, ketone synthesis. A related Zn/Pd-mediated one-pot ketone synthesis was reported (see, e.g., Lee, J. H.; Kishi, Y. *J. Am. Chem. Soc.* 2016, 138, 7178).

Figure 2B:
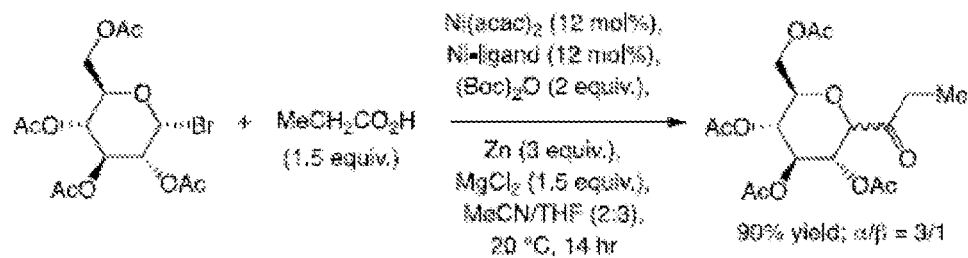
FIG. 2B shows an example of a Ni-catalyzed ketone coupling.
Figure 2C:
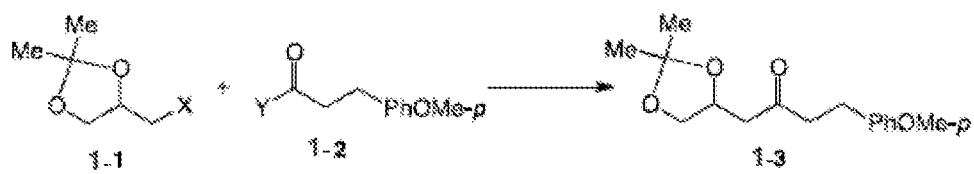
FIG. 2C shows feasibility studies under three variations of Ni-mediated one-pot ketone coupling.

Recently, Weix, Gong, Reisman, and others extensively studied Ni-mediated one-pot ketone synthesis, pioneered by Mukaiyama in 1981 (see, e.g., Onaka, M.; Matsuoka, Y.; Mukaiyama, T. *Chem. Lett.* 1981, 531; Wotal, A. C.; Weix, D. J. *Org. Lett.* 2012, 14, 1476; Wotal, A. C.; Ribson, R. D.; Weix, D. J. *Organometallics* 2014, 33, 5874; Wu, F.; Lu, W.; Qian, Q.; Ren, Q.; Gong, H. *Org. Lett.* 2012, 14, 3044; Zhao, C.; Jia, X.; Wang, X.; Gong, H. *J. Am. Chem. Soc.* 2014, 136, 17645 and references cited therein; Cherney, A. H.; Kadunce, N. T.; Reisman, S. E. *J. Am. Chem. Soc.* 2013, 135, 7442). Among a wide range of substrates reported, one specific example given by Gong and coworkers suggested a possibility that Ni-mediated one-pot ketone synthesis might meet with our need (FIG. 2B). The substrates shown in FIG. 2C were arbitrarily chosen for this study. The arbitrarily chosen substrates were tested under these three conditions, thereby demonstrating the feasibility of proposed coupling, e.g., via Weix and Reisman protocols. At the same time, it became evident that serious improvements were required successfully to use the Ni-mediated one-pot ketone synthesis at a late-stage coupling in a convergent synthesis of complex molecules.

More than 15 ligands were first tested to solubilize $NiCl_2$, thereby showing 4,4'-di-tert-butyl-2,2'-bipyrine (dtbbpy) to give the best result. Noteworhily, $NiBr_2$.(dtbbpy) complex gave a better coupling efficiency than $NiCl_2$.(dtbbpy) complex (see, e.g., Lu, Z.; Fu, G. C. *Angew. Chem. Int. Ed.* 2010, 49, 6676; Serrano, E.; Martin, R. *Angew. Chem. Int. Ed.* 2016, 55, 11207; Zhang, X.; MacMillan, D. W. C. *J. Am. Chem. Soc.* 2016, 138, 13862).

Among the activated forms of carboxylic acid studied, 2-thiopyridine ester, originally reported by Mukaiyama, was found most effective for the coupling. 2-Thiopyridine ester was originally used for their seminal work of macrolactonization by Corey and Nicolaou (see, e.g., Corey, E. J.; Nicolaou, K. C. *J Am. Chem. Soc.* 1974, 96, 5614) and by Nicolaou Gerlack and Thalmann (see, e.g., Gerlach, H.; Thalmann, A. *Helv. Chim. Acta* 1974, 57, 2661). Mn (powder) and Zn (powder) were found to be effective reducing-metals.

Among many solvent-systems tested, 1,3-dimethyl-2-imdazolidione (DMI) was found best. A 5:1 mixture of DMI and EtOAc was a good solvent system, when a substrate(s) exhibited a poor solubility in DMI. As expected, better coupling yields were obtained at higher concentration, typical concentration being in the range of C=0.1~0.5 M. While studying additive effects, it was discovered that addition of one equivalent $Cp_2ZrCl_2$ dramatically enhanced the coupling rate; the coupling completed within minutes to hours with $Cp_2ZrCl_2$, compared with overnight to days without $Cp_2ZrCl_2$. In addition, by-product formation via a (I→SPy)-displacement was eliminated or suppressed by addition of $Cp_2ZrCl_2$.

Figure 3A:
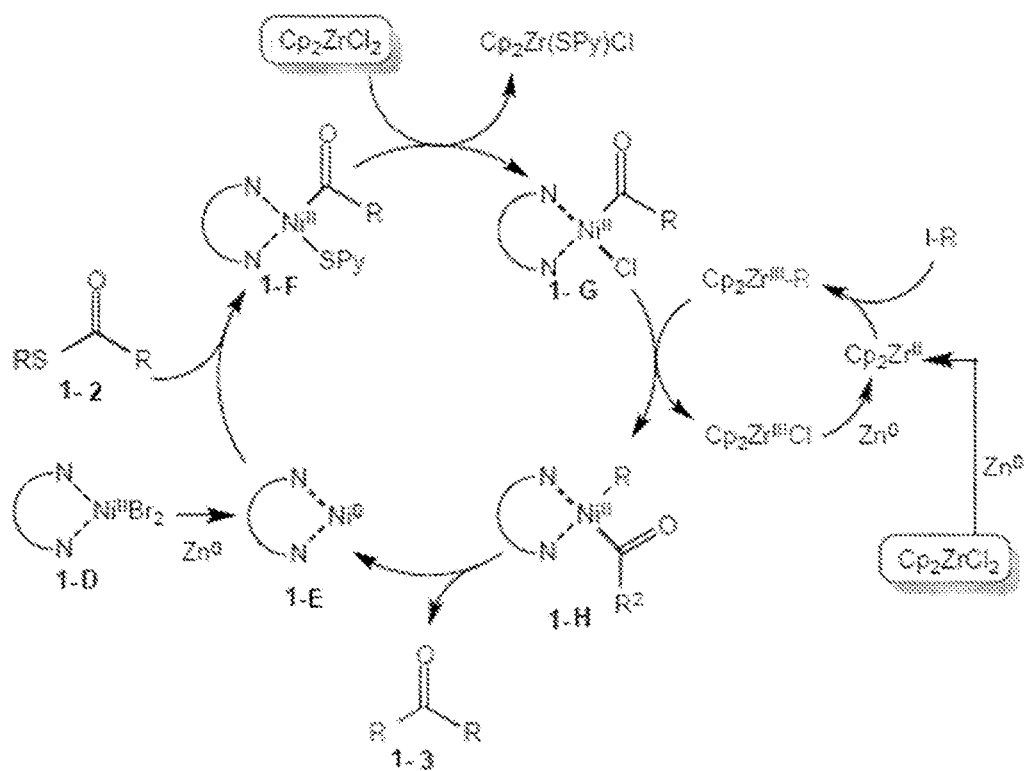
FIG. 3A shows proposed catalytic cycles for the Ni/Zr-mediated ketolization provided herein.

The observed, dramatic rate-acceleration indicated that $Cp_2ZrCl_2$ was involved in the rate-limiting step of catalytic reaction. Two different catalytic cycles had been proposed for the Ni-mediated one-pot ketone synthesis, i.e., (1) the catalytic cycle involving a $(L)Ni(alkyl)_2$ intermediate and (2) the catalytic cycle of sequential reduction. However, in order to explain the observed results, a new mechanism is proposed, consisting of Ni-catalytic cycle, Zr-catalytic cycle, and Zr→Ni transmetallation (FIG. 3A). The Ni-catalytic cycle starts with Ni(II)→Ni(0) reduction by Zn, followed by its oxidative addition to 2-thiopyridine ester, i.e., 2-D→2-E→2-F. Because of the strong Zr—SR bond, it is possible that $Cp_2ZrCl_2$ and/or a Zr-salt could accelerate the step from 2-F to 2-G, thereby resulting in the dramatic rate-acceleration. On the other hand, a second catalytic cycle involving $Cp_2ZrCl_2$; Zn-reduction of $CpzZrCl_2$ to form a low-valent Zr-species could be operative. According to the seminal work by Schwartz, such a low-valent Zr-species readily activates an alkyl iodide, i.e., $Cp_2ZrCl_2 \rightarrow Cp_2Zr \rightarrow Cp_2Zr$—R (see, e.g., Williams, G. M.; Gell, K. I.; Schwartz, J. *J. Am. Chem. Soc.* 1980, 102, 3660; Williams, G. M.; Schwartz, J. *J. Am. Chem. Soc.* 1982, 104, 1122). Then, the Ni- and Zr-catalytic cycles are coupled with Zr/Ni-transmetallation, to yield 2-H (For transmetallation from alkenyl-Zr→alkenyl-Ni, see, e.g., Negishi, E., Van Horn, D. E. *J. Am. Chem. Soc.* 1977, 99, 3168; Loots, M. J., Schwartz, J. *J. Am. Chem. Soc.* 1977, 99, 8045). Overall, $CpzZrCl_2$ plays critical dual roles in this scheme. To differentiate the previous Ni-mediated method, this transformation as Zr/Ni-mediated ketone synthesis.

Related to the mechanism proposed, several commonly known thiol-scavengers were tested, observing only insignificant effect on the acceleration of coupling rate, thereby supporting the proposed dual roles of $Cp_2ZrCl_2$. As noted, the dramatic coupling-rate acceleration of coupling-rate by addition of $Cp_2ZrCl_2$ indicated its involvement in the rate-limiting step. Although there is no experimental support, it is possible that the rate-limiting step is likely 1-F→1-G. Thus, alkyl iodide participates only after the rate-limiting step, which could explain the reason why the Zr/Ni-mediated ketone synthesis is uniquely different from the Zn/Pd- and Fe/Cu-mediated ketone syntheses. As noted, the coupling-rate acceleration by addition of $Cp_2ZrCl_2$ indicates its involvement in the rate-limiting step. Therefore, the rate-limiting step is likely 1-E→1-F. Thus, alkyl iodide participates only after the rate-limiting step, which could explain the reason why the Zr/Ni-mediated one-pot ketone synthesis is uniquely different from other Zn/Pd- and Fe/Cu-mediated ketone syntheses.

Figure 3B:
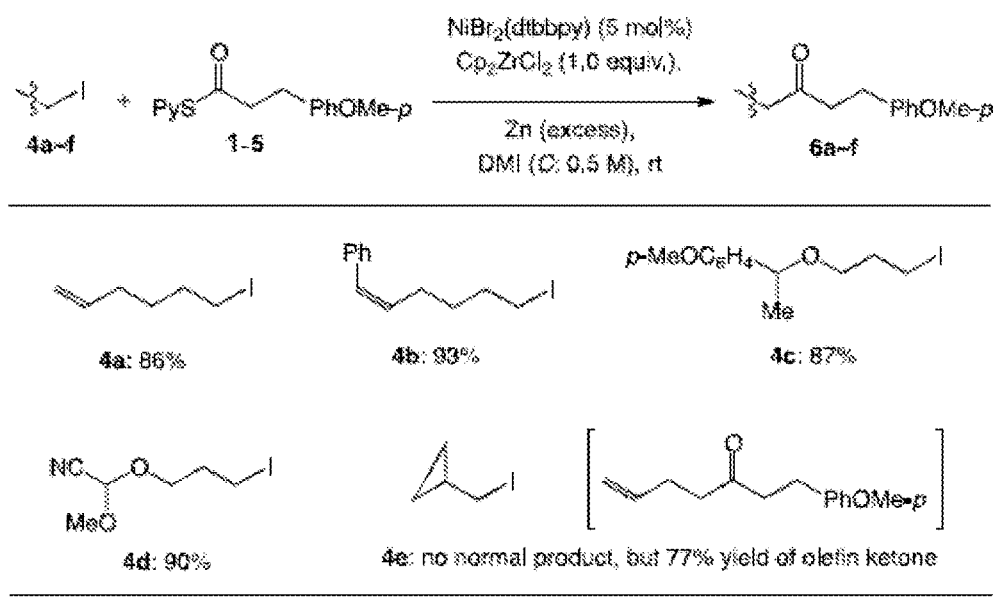
FIG. 3B shows exemplary coupling with common radical probes.

The behavior of common radical probes were tested (FIG. 3B). The observation on 4e showed the radical nature of coupling reaction. On the other hand, 4a~d gave the normal ketones, thereby suggesting that a radical intermediate was involved only in a very short time-scale (for the reactivity and stability-instability of β-alkoxyalkyl-Zr(IV)-species, see, e.g., Buchwald, S. L.; Nielsen, R. B.; Dewan, J. C. *Organometallics* 1988, 7, 2324; Wipf, P.; Smitrovich, J. H. *J. Org. Chem.* 1991, 56, 6494).

Figure 4:
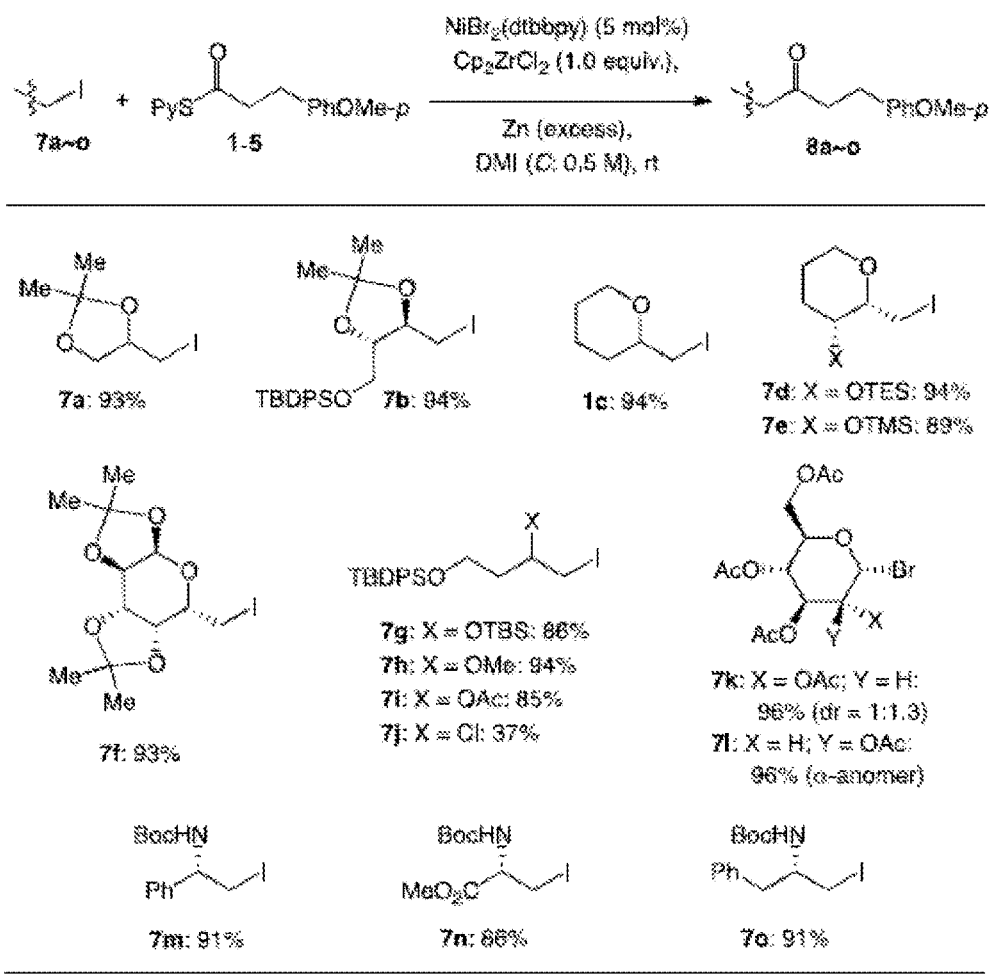
FIG. 4 shows one-pot ketone coupling with nucleophiles bearing a ca-OR and other functional groups. Reaction conditions: 1-5 (1.0 equiv.), 1-7 (1.2 equiv.), $NiBr_2 \cdot (dtbbpy)$ (5 mol %).

In order to establish exemplary optimum conditions, the effect of molar ratio of 1-1 (X=I) and 1-2 (Y=SPy) on the coupling efficiency were studied under the condition of $NiBr_2$(dtbbpy) (5 mol %), $Cp_2ZrCl_2$ (1.0 equiv.), Zn (excess) in DMI (C: 0.5 M) at rt, to give the following results: 89% isolated yield for 1-1:1-2=1.5:1.0, 89% for 1-1:1-2=1.2:1.0, 85% for 1-1:1-2=1.1:1.0, 83% for 1-1:1-2=1.0:1.0, 75% for 1-1:1-2=0.8:1.0. Considering all of these observations, the conditions were chosen as: NiBr$_2$(dtbbpy) (5 mol %), Cp$_2$ZrCl$_2$ (1 equiv.), Mn or Zn (excess) in DMI or 5:1 DMI-EtOAc (C: 0.5~0.1 M) at ~20° C., with (1.2:1.0)-molar ratio of nucleophile and electrophile for further studies. However, based on the molecular size and complexity of coupling partners, the molar ratio could accordingly be adjusted without any noticeable drawback. FIG. 4 summarizes the substrates bearing an OR or relevant group at the a-position. The new method gave the expected products in excellent yields.

Figure 5A:
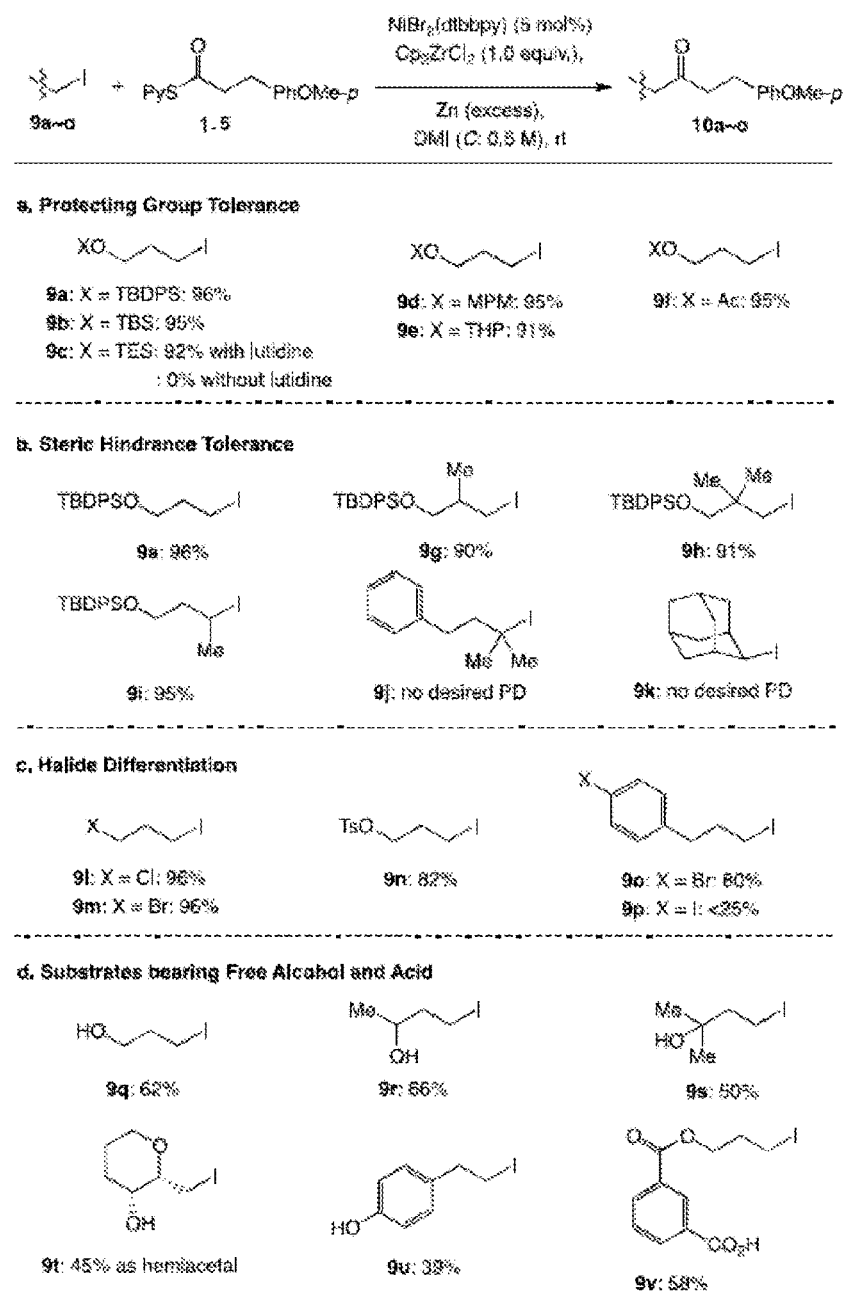
FIG. 5A shows examples of Ni/Zr-ketolization reaction.

FIG. 5A summarizes further examples. Common protecting groups were tolerated well (a, FIG. 5A). The coupling was effective for mono- and di-methylated substrates at the β-position, as well as mono-methylated substrate at the α-position, but not effective for dimethylated substrate at the α-position or admantyl substrate (b, FIG. 5A). This method allows one to selectively to activate, and couple, an alkyl iodide over an alkyl bromide or chloride, as well as an aryl bromide (c, FIG. 5A). As mentioned, this reaction exhibited a radical nature, thereby suggesting the possibility that it might be effective for substrates bearing a free hydroxyl and/or acidic group. Indeed, the coupling with these substrates gave the desired products, but further improvements were obviously required for practical uses (d, FIG. 5A).

Figure 5B:
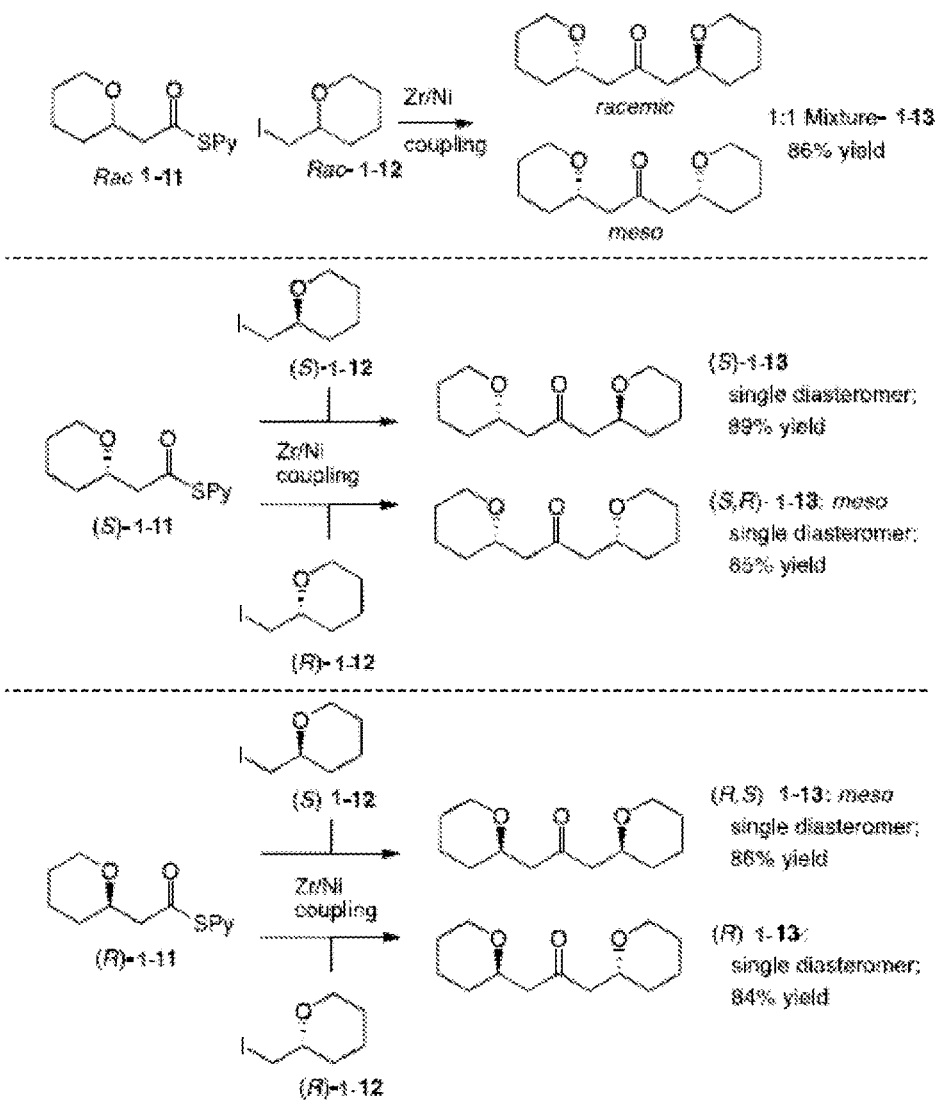
FIG. 5B shows a further example.
Figure 5C:
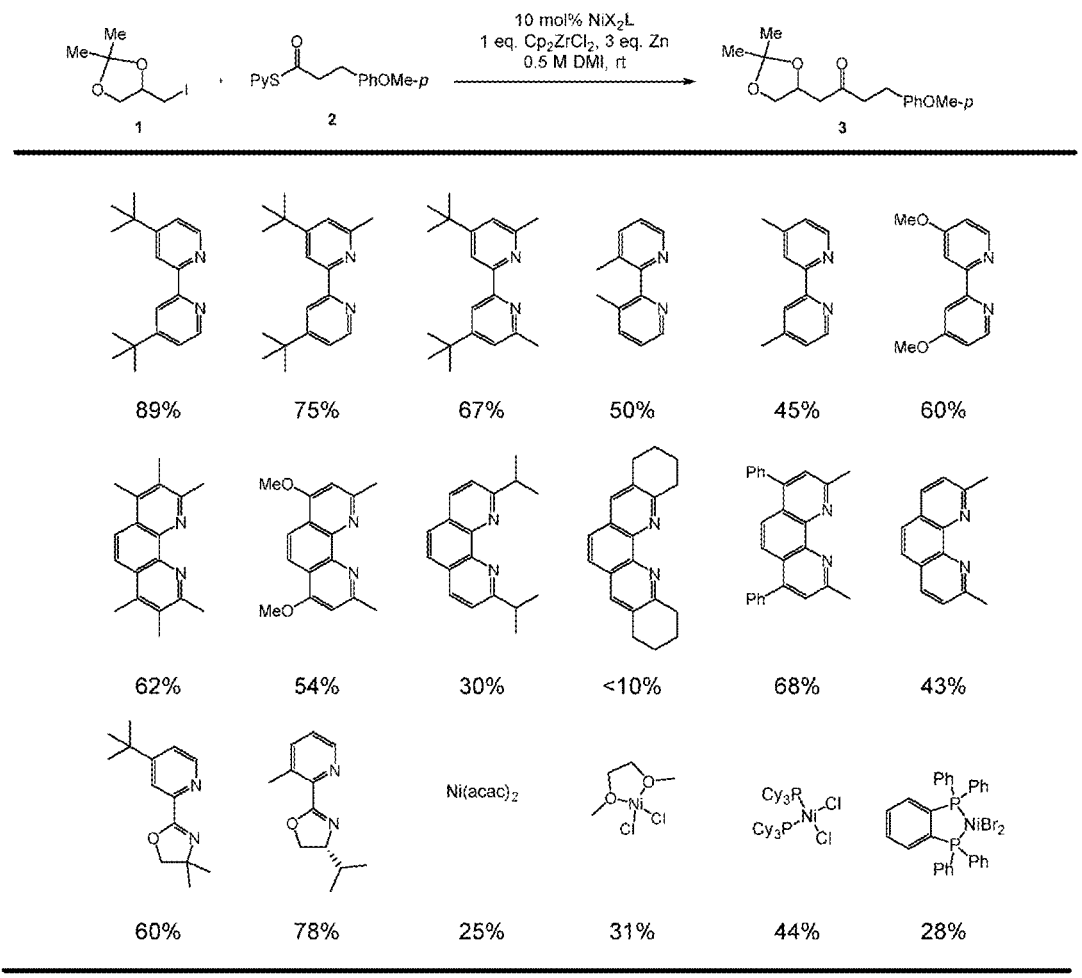
FIG. 5C shows results of nickel ligand screening experiments.
Figure 5D:
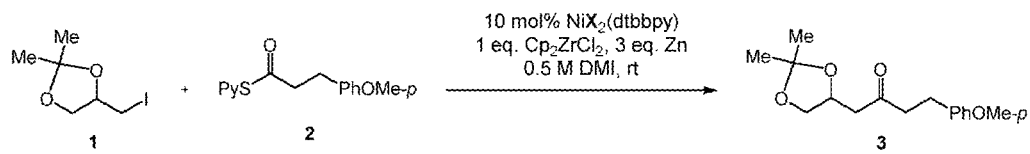
FIG. 5D shows NiBr$_2$, NiCl$_2$, and NiI$_2$ comparison experiments.
Figure 5E:
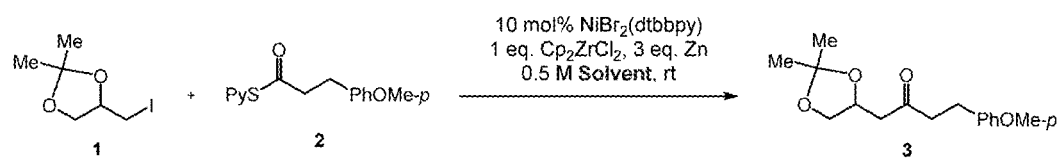
FIG. 5E shows the results of solvent screening experiments.
Figure 5F:
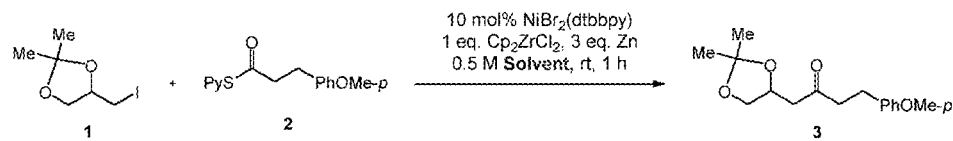
FIG. 5F shows the results of co-solvent screening experiments.
Figure 5G:
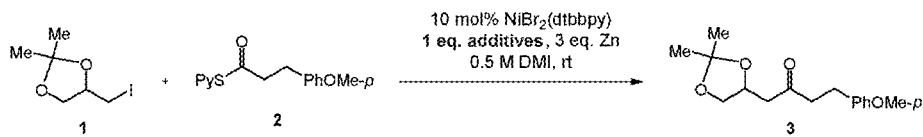
FIG. 5G shows additive screening experiments.
Figure 5H:
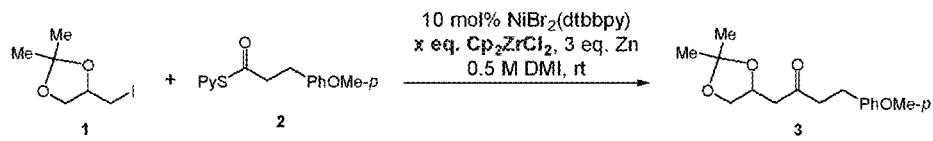
FIG. 5H shows screening of zirconium equivalents.
Figure 5I:
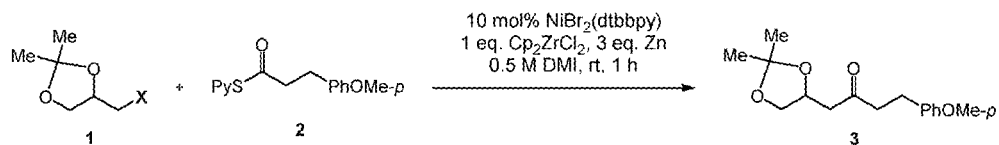
FIG. 5I shows studies with various electrophiles.
Figure 5J:
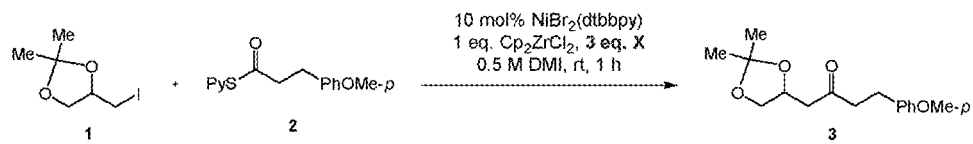
FIG. 5J shows reducing reagent screening experiments.
Figure 5K:
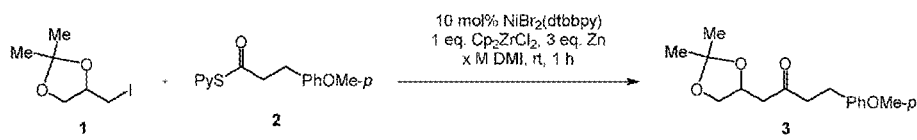
FIG. 5K shows concentration studies.
Figure 5L:
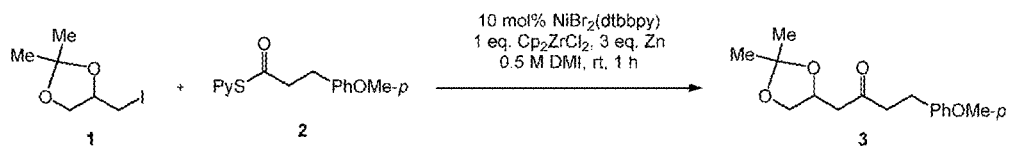
FIG. 5L shows substrate ratio experiments.
Figure 6:
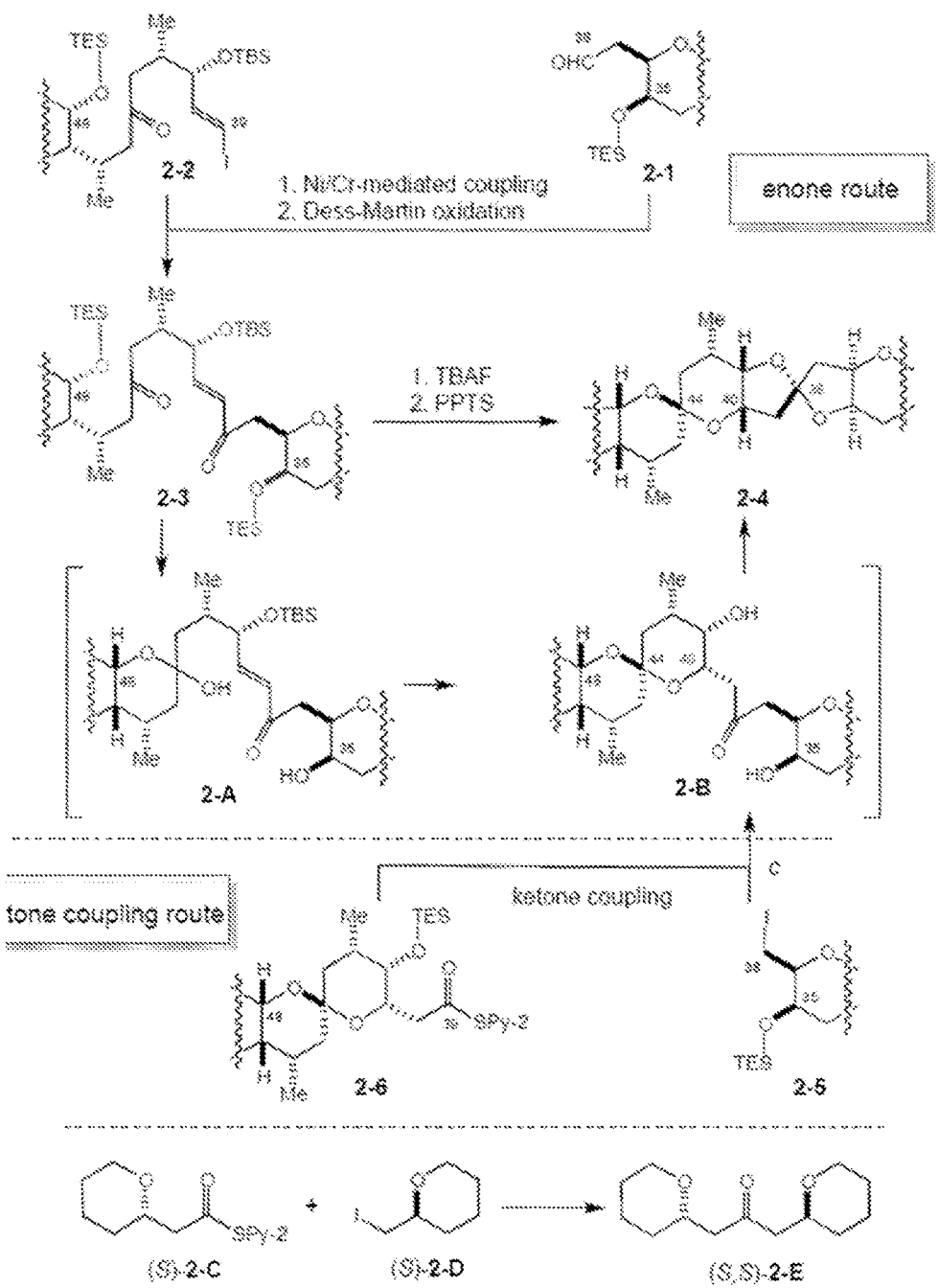
FIG. 6 shows potential routes to halichondrins and analogs thereof.

Finally, in order to demonstrate the applicability of the Zr/Ni-mediated one-pot ketone synthesis to the structure motif given in FIG. 2, we studied the coupling of (S)-1-11 with (S)-1-12 and (R)-1-12 and obtained expected products (S,S)-1-13 and (S,R)-1-13, respectively (FIG. 5B). During the coupling, the stereochemical purity of products, as well as starting materials, could be lost, for example, via retro-oxy-Michael/oxy-Michael process. Experimentally, it was found that (S,S)-1-13 and (S,R)-1-13 gave virtually identical $^1$H NMR spectra, but exhibited a very similar but distinctly different $^{13}$C NMR spectra. With use of $^{13}$C NMR spectra, the stereochemical purity of (S,S)-1-13 and (S,R)-1-13 was studied, thereby demonstrating that no stereochemistry scrambling took place in the ketone coupling.

A new Zr/Ni-mediated one-pot ketone synthesis was reported, where Cp$_2$ZrCl$_2$ dramatically accelerated the coupling rate and, at the same time, suppressed by-product formation via a (I→SPy)-displacement. Unlike Zn/Pd- and Fe/Cu-mediated one-pot ketone syntheses, the new method was found effective for the nucleophiles bearing an OR or relevant group at α-position. A mechanism, consisting of Ni-catalytic cycle, Zr-catalytic cycle, and Zr→Ni transmetallation, was proposed, where Cp$_2$ZrCl$_2$ was suggested to play critical dual roles. The newly developed Zr/Ni-mediated method gives a realistic hope of incorporating one-pot ketone at the late-stage in a convergent synthesis of complex molecules.

Experimental Procedures for Ni/Zr-Mediated Ketolization Reactions

Solvents and reagents are commercial grade and were used as supplied, unless otherwise noted. Reactions involving air or moisture sensitive reagents or intermediates were performed under an inert atmosphere of nitrogen or argon in glassware that was oven dried. Analytical thin layer chromatography (TLC) was performed with E. Merck pre-coated TLC plates, silica gel 60F-254, layer thickness 0.25 mm. TLC plates were visualized by staining with AMCAN (ammonium molybdate/cerium ammonium nitrate), potassium permanganate, orp-anisaldehyde. Flash chromatography separations were performed on E. Merck Silica Gel 60 (40-63 μm), Kanto Chemical Silica Gel 60N (spherical, neutral, 40-50 μm), or Wako Pure Chemical Industry Wako-gel 50NH$_2$ (38-63 μm). Medium pressure column chromatography was performed with YAMAZEN Smart Flash. NMR spectra were recorded on a Varian Inova 600 MHz or Varian Inova 500 MHz. Chemical shifts were reported in parts per million (ppm). The residual solvent peak was used as an internal reference (for $^1$H NMR spectra: 7.26 ppm in CDCl$_3$, 7.16 ppm in C$_6$D$_6$, 3.31 ppm in CD$_3$OD, and 5.33 in CD$_2$Cl$_2$; for $^{13}$C NMR: 77.0 ppm in CDCl$_3$, 128.0 ppm in C$_6$D$_6$, 49.0 ppm in CD$_3$OD, and 53.8 ppm in CD$_2$Cl$_2$). Coupling constants (J) are reported in Hz and the splitting abbreviations used are: s for singlet, d for doublet, t for triplet, q for quartet, m for multiplet, and br for broad. Optical rotations were measured at 20° C. using Perkin-Elmer 241 polarimeter. IR spectra were recorded on Bruker Alpha FT-IR spectrometer. Electrospray ionization experiments were performed on Micromass Inc., Platform II Atmospheric Pressure Ionization Mass Spectrometer.

A General Procedure for Ni/Zr-Mediated Coupling Reactions

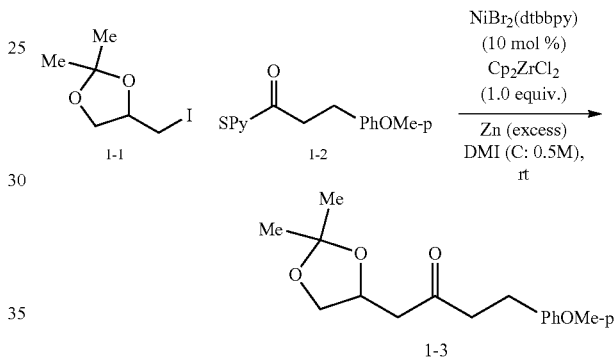

In a glove box, to a solution of iodide 1-1 (29.1 mg, 0.12 mmol, 1.2 eq.) and thioester 1-2 (27.3 mg, 0.10 mmol, 1.0 eq) in DMI (0.2 mL, Sigma-aldrich, 99.5%) were added Cp$_2$ZrCl$_2$ (29.3 mg, 0.10 mmol, 1.0 eq. Sigma-aldrich, 98%), Zn powder (19.6 mg, 0.3 mmol, 3.0 eq. Sigma-aldrich, used without any activation), and NiBr$_2$-dtbbpy (4.8 mg, 0.01 mmol, 10 mol %, preparation see page 8) at room temperature. After being stirred at the same temperature for mins to hrs (monitored by TLC), the reaction mixture was removed from glove box and diluted with EtOAc and sat. NaHCO$_3$ aq. The organic layer was separated and the aqueous layer was extracted with ethyl acetate. The combined organic layer was dried over Na$_2$SO$_4$, filtered, and concentrated under reduced pressure. The obtained crude material was purified by flash column chromatography on silica gel to give 1-3 as colorless oil.

Experimental Procedures for the Reactions Outlined in FIG. 3B

In a glove box, to a solution of iodide 4a-e (0.24 mmol, 1.2 eq.) and thioester 1-5 (54.6 mg, 0.20 mmol, 1.0 eq.) in either DMI (0.4 mL, sigma aldrich, 99.5%) or DMI/EtOAc (0.334 mL/0.066 mL) were added Cp$_2$ZrCl$_2$ (58.5 mg, 0.20 mmol, 1.0 eq. Sigma-aldrich, 98%), Zn powder (39.2 mg, 0.6 mmol, 3.0 eq. Sigma-aldrich, used without any activation), and NiBr$_2$.dtbbpy (9.7 mg, 0.02 mmol, 10 mol %, preparation see page 8) at room temperature. After being stirred at the same temperature for 10 min to 1 h (monitored by TLC), the reaction mixture was removed from glove box and diluted with EtOAc and sat. NaHCO$_3$ aq. The organic layer was separated and the aqueous layer was extracted with ethyl acetate. The combined organic layer was dried over Na$_2$SO$_4$, filtered, and concentrated under reduced pressure. The obtained crude material was purified by flash column chromatography on silica gel to give 4a-d, S1 as colorless oils. Note: DMI or DMI/EtOAc depending on the solubilities f substrates was used as solvent.

1-(4-methoxyphenyl)non-8-en-3-one (6a)

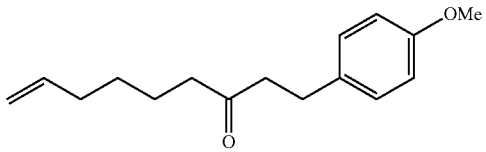 [SMILES: C=CCCCCC(=O)CCc1ccc(OC)cc1]

42.1 mg (0.171 mmol, 86%); IR (film) 2930, 2856, 1712, 1612, 1513, 1463, 1300, 1246, 1178, 1109, 1037, 910, 831 cm$^{-1}$; $^1$H NMR (600 MHz, CDCl$_3$) δ=7.09 (d, J=8.4 Hz, 2H), 6.82 (d, J=8.4 Hz, 2H), 5.81-5.74 (m, 1H), 4.99 (dd, J=17.4, 1.7 Hz, 1H), 4.94 (dd, J=10.2, 1.7 Hz, 1H), 3.78 (s, 3H), 2.83 (t, J=7.8 Hz, 2H), 2.69 (t, J=7.8 Hz, 2H), 2.38 (t, J=7.2 Hz, 2H), 2.03 (q, J=7.2 Hz, 2H), 1.60-1.54 (m, 2H), 1.38-1.32 (m, 2H); $^{13}$C NMR (126 MHz, CDCl$_3$) δ=210.5, 158.1, 138.6, 133.3, 129.4, 114.8, 114.0, 55.4, 44.7, 43.0, 33.6, 29.1, 28.6, 23.4; HRMS (ESI) m/z calc. for C$_{16}$H$_{23}$O$_2$ [M+H]$^+$ 247.1708; found 247.1693.

(Z)-1-(4-methoxyphenyl)-9-phenylnon-8-en-3-one (6b)

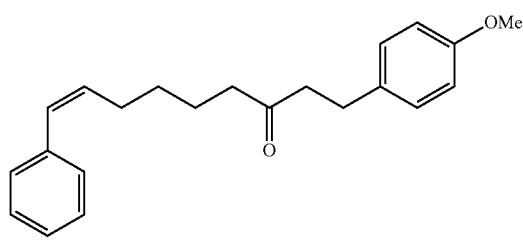 [SMILES: COc1ccc(CCC(=O)CCCC/C=C\c2ccccc2)cc1]

59.8 mg, (0.186 mmol, 93%); IR (film) 2931, 2859, 1712, 1612, 1513, 1594, 1463, 1447, 1408, 1373, 1300, 1246, 1178, 1101, 1036, 826, 771, 700 cm$^{-1}$; $^1$H NMR (600 MHz, CDCl$_3$) δ=7.32 (t, J=7.8 Hz, 2H), 7.25 (d, J=7.8 Hz, 2H), 7.22 (t, J=7.8 Hz, 1H), 7.09 (d, J=9.0 Hz, 2H), 6.82 (d, J=9.0 Hz, 2H), 6.42 (d, J=11.4 Hz, 1H), 5.65-5.60 (m, 1H), 3.78 (s, 3H), 2.82 (t, J=7.2 Hz, 2H), 2.66 (t, J=8.4 Hz, 2H), 2.35 (t, J=7.8 Hz, 2H), 2.32 (qd, J=7.2 Hz, 2.0 Hz, 2H), 1.62-1.56 (m, 2H), 1.44-1.38 (m, 2H); $^{13}$C NMR (126 MHz, CDCl$_3$) δ=210.4, 158.1, 137.8, 133.3, 132.6, 129.4, 129.3, 128.9, 128.3, 126.6, 114.0, 55.4, 44.7, 42.9, 29.5, 29.1, 28.4, 23.5; HRMS (ESI) m/z calc. for C$_{22}$H$_{26}$NaO$_2$ [M+Na]$^+$ 345.1825; found 345.1830.

1-(4-methoxyphenyl)-6-(1-(4-methoxyphenyl)ethoxy)hexan-3-one (6c)

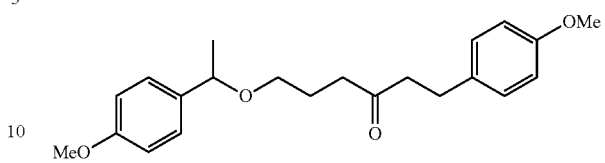

61.6 mg, (0.173 mmol, 87%); IR (film) 2953, 2932, 2836, 1712, 1612, 1512, 1464, 1442, 1369, 1301, 1287, 1245, 1177, 1099, 1035, 832 cm$^{-1}$; $^1$H NMR (600 MHz, CDCl$_3$) δ=7.20 (d, J=8.4 Hz, 2H), 7.08 (d, J=8.4 Hz, 2H), 6.87 (d, J=8.4 Hz, 2H), 6.82 (d, J=8.4 Hz, 2H), 4.29 (q, J=6.6 Hz, 1H), 3.80 (s, 3H), 3.78 (s, 3H), 3.28-3.20 (m, 2H), 2.83-2.78 (m, 2H), 2.70-2.66 (m, 2H), 2.50-2.39 (m, 2H), 1.84-1.77 (m, 2H), 1.39 (d, J=6.6 Hz, 3H); $^{13}$C NMR (126 MHz, CDCl$_3$) δ=210.1, 159.0, 158.0, 136.1, 133.3, 129.3, 127.5, 114.0, 113.9, 77.5, 67.4, 55.4, 44.7, 39.9, 29.0, 24.2, 24.1; HRMS (ESI) m/z calc. for C$_{22}$H$_{28}$NaO$_4$ [M+Na]$^+$ 379.1880; found 379.1885.

2-methoxy-9-(4-methoxyphenyl)-7-oxononanenitrile (6d)

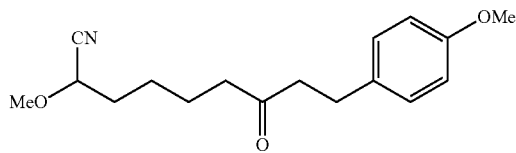 [SMILES: COc1ccc(CCC(=O)CCCCC(C#N)OC)cc1]

52.3 mg (0.180 mmol, 90%); IR (film) 2937, 2868, 2834, 1711, 1612, 1513, 1463, 1410, 1372, 1300, 1246, 1179, 1113, 1073, 1035, 829 cm$^{-1}$; $^1$H NMR (600 MHz, CDCl$_3$) δ=7.09 (d, J=8.4 Hz, 2H), 6.82 (d, J=8.4 Hz, 2H), 4.02 (t, J=7.2 Hz, 1H), 3.78 (s, 3H), 3.47 (s, 3H), 2.83 (t, J=7.8 Hz, 2H), 2.69 (t, J=7.8 Hz, 2H), 2.39 (t, J=7.8 Hz, 2H), 1.81 (q, J=7.2 Hz, 2H), 1.62-1.56 (m, 2H), 1.47-1.41 (m, 2H); $^{13}$C NMR (126 MHz, CDCl$_3$) δ=209.8, 158.1, 133.2, 129.4, 118.1, 114.0, 70.5, 58.1, 55.4, 44.7, 42.7, 33.3, 29.1, 24.4, 23.0; HRMS (ESI) m/z calc. for C$_{17}$H$_{24}$NO$_3$ [M+H]$^+$ 290.1751; found 290.1760.

1-(4-methoxyphenyl)hept-6-en-3-one (S1, the Product from 4e)

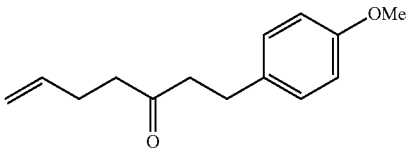 [SMILES: C=CCCC(=O)CCc1ccc(OC)cc1]

33.8 mg (0.155 mmol, 77%)IR (film) 2926, 1753, 1612, 1513, 1442, 1365, 1301, 1246, 1178, 1109, 1036, 911, 829 cm$^{-1}$; $^1$H NMR (500 MHz, CDCl$_3$) δ=7.09 (d, J=8.5 Hz, 2H), 6.82 (d, J=8.5 Hz, 2H), 5.83-5.73 (m, 1H), 5.01 (dd, J=17.5 Hz, 1.4 Hz, 1H), 4.97 (dd, J=10.0 Hz, 1.4 Hz, 1H), 3.78 (s, 3H), 2.84 (t, J=7.5 Hz, 2H), 2.70 (t, J=7.5 Hz, 2H), 2.48 (t, J=7.5 Hz, 2H), 2.31 (q, J=7.5 Hz, 2H); $^{13}$C NMR (126 MHz, C$_6$D$_6$) δ=207.1, 158.6, 137.6, 133.6, 129.6, 115.0, 114.2, 54.7, 44.5, 41.8, 29.1, 28.0; HRMS (ESI) m/z calc. for C$_{14}$H$_{19}$O$_2$[M+H]$^+$ 219.1380; found 219.1374.

Experimental Details for the Reactions Outlined in FIG. 4

In a glove box, to a solution of iodide 7a-m (0.24 mmol, 1.2 eq.) and thioester 1-5 (54.6 mg, 0.20 mmol, 1.0 eq.) in either DMI (0.4 mL, sigma aldrich, 99.5%) or DMI/EtOAc (0.334 mL/0.066 mL) were added Cp$_2$ZrCl$_2$ (58.5 mg, 0.20 mmol, 1.0 eq. Sigma-aldrich, 98%), Zn powder (39.2 mg, 0.6 mmol, 3.0 eq. Sigma-aldrich, used without any activation), and NiBr$_2$.dtbbpy (9.7 mg, 0.02 mmol, 10 mol %, preparation see page 8) at room temperature. After being stirred at the same temperature for 10 min to 2 hr (monitored by TLC), the reaction mixture was removed from glove box and diluted with EtOAc and sat. NaHCO$_3$ aq. The organic layer was separated and the aqueous layer was extracted with ethyl acetate. The combined organic layer was dried over Na$_2$SO$_4$, filtered, and concentrated under reduced pressure. The obtained crude material was purified by flash column chromatography on silica gel to give 8a-m as colorless oils or white amorphous solids. Note 1: DMI or DMI/EtOAc depending on the solubilities of substrates was used as the solvent. Note 2: 2.0 eq. of lutidine was added before addition of Cp$_2$ZrCl$_2$ for the syntheses of 8d and 8e.

1-(2,2-dimethyl-1,3-dioxolan-4-yl)-4-(4-methoxyphenyl)butan-2-one (8a)

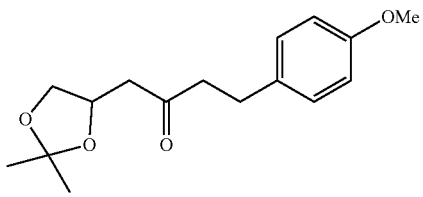 [SMILES: COc1ccc(CCC(=O)CC2COC(C)(C)O2)cc1]

51.7 mg (0.186 mmol, 93%); IR (film) 3035, 2988, 2935, 1711, 1612, 1513, 1478, 1370, 1246, 1178, 1058, 1036, 829, 669 cm$^{-1}$; $^1$H NMR (500 MHz, CDCl$_3$) δ=7.09 (d, J=8.5 Hz, 2H), 6.81 (d, J=8.5 Hz, 2H), 4.44 (quin, J=6.0H, 1H), 4.15 (dd, J=8.5 Hz, 8.0 Hz, 1H), 3.77 (s, 3H), 3.50 (dd, J=8.5 Hz, 8.0 Hz, 1H), 2.88-2.80 (m, 3H), 2.76-2.71 (m, 2H), 2.52 (dd, J=16.5 Hz, 7.0 Hz, 1H) 1.38 (s, 3H), 1.33 (s, 3H); $^{13}$C NMR (126 MHz, CDCl$_3$) δ=207.8, 158.0, 132.8, 129.2, 113.9, 108.8, 71.7, 69.4, 55.2, 47.2, 45.2, 28.7, 26.9, 25.5; HRMS (ESI) m/z calc. for C$_{16}$H$_{22}$NaO$_4$ [M+Na]$^+$301.1410; found 301.1425.

1-((4S,5S)-5-(((tert-butyldiphenylsilyl)oxy)methyl)-2,2-dimethyl-1,3-dioxolan-4-yl)-4-(4-methoxyphenyl)butan-2-one (8b)

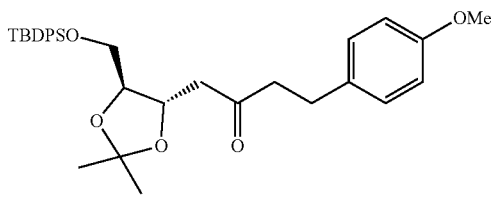

102.3 mg (0.187 mg, 94%); [α]$_D^{22}$=−8.9 (c 1.8, CHCl$_3$); IR (film) 2985, 2955, 2932, 2898, 2858, 1716, 1612, 1513, 1472, 1463, 1428, 1379, 1370, 1301, 1247, 1177, 1112, 1981, 1037, 998, 823, 787, 742, 704, 603, 505, 490 cm$^{-1}$; $^1$H NMR (500 MHz, CDCl$_3$) δ=7.69-7.64 (m, 4H), 7.45-7.35 (m, 6H), 7.10 (d, J=8.5 Hz, 2H), 6.82 (d, J=8.5 Hz, 2H), 4.42-4.37 (m, 1H), 3.84-3.71 (m, 3H), 3.78 (s, 3H), 2.85 (t, J=8.0 Hz, 2H), 2.77-2.73 (m, 2H), 2.69-2.65 (m, 2H), 1.38 (s, 3H), 1.37 (s, 3H), 1.06 (s, 9H); $^{13}$C NMR (126 MHz, CDCl$_3$) δ=207.4, 158.2, 135.8, 133.3, 133.2, 130.0, 129.5, 128.0, 114.1, 109.4, 80.6, 74.8, 64.3, 55.5, 46.7, 45.5, 28.8, 27.4, 27.1, 27.0, 19.4; HRMS (ESI) m/z calc. for C$_{33}$H$_{43}$O$_5$Si [M+H]$^+$ 547.2874; found 547.2869.

4-(4-methoxyphenyl)-1-(tetrahydro-2H-pyran-2-yl)butan-2-one (8c)

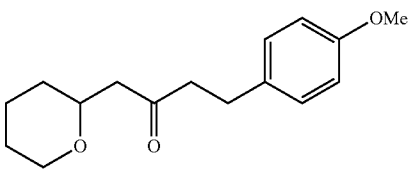 [SMILES: COc1ccc(CCC(=O)CC2CCCCO2)cc1]

49.1 mg (0.188 mg, 94%); IR (film) 2934, 2849, 1712, 1612, 1513, 1441, 1300, 1246, 1178, 1087, 1043, 828 cm$^{-1}$; H NMR (600 MHz, CDCl$_3$) δ=7.09 (d, J=8.4 Hz, 2H), 6.81 (d, J=8.4 Hz, 2H), 3.91 (d, J=11.4 Hz, 1H), 3.78 (s, 3H), 3.77-3.72 (m, 1H), 3.41 (t, J=10.8 Hz, 1H), 2.83 (t, J=7.8 Hz, 2H), 2.74 (q, J=5.4 Hz, 2H), 2.64 (dd, J=15.6 Hz, 7.8 Hz, 1H), 2.36 (dd, J=15.6 Hz, 5.2 Hz, 1H), 1.80 (d, J=5.2 Hz, 1H), 1.58 (d, J=12.6 Hz, 1H), 1.53-1.46 (m, 3H), 1.29-1.21 (m, 1H); $^{13}$C NMR (126 MHz, CDCl$_3$) δ=210.2, 158.1, 135.7, 133.9, 133.3, 129.8, 129.3, 127.8, 114.0, 63.1, 55.4, 44.7, 39.5, 29.1, 27.0, 26.7, 19.3; HRMS (ESI) m/z calc. for C$_{16}$H$_{23}$O$_3$[M+H]$^+$263.1642; found 263.1649.

4-(4-methoxyphenyl)-1-((2R,3R)-3-((triethylsilyl)oxy)tetrahydro-2H-pyran-2-yl)butan-2-one (8d)

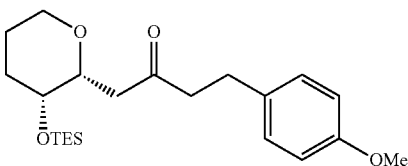

73.4 mg (0.187 mg, 94%); [α]$_D^{22}$=−11.8 (c 1.0, CHCl$_3$); IR (film) 2953, 2915, 2875, 1714, 1612, 1513, 1463, 1300, 1246, 1178, 1098, 1071, 1023, 828, 743 cm$^{-1}$; $^1$H NMR (500 MHz, CDCl$_3$) δ=7.09 (d, J=8.4 Hz, 2H), 6.81 (d, J=8.4 Hz, 2H), 3.89 (d, J=14.3 Hz, 1H), 3.81 (ddd, J=7.8, 7.5, 2.5 Hz, 1H), 3.78 (s, 3H), 3.71 (s, 1H), 3.43 (td, J=14.4, 2.5 Hz, 1H), 2.85-2.67 (m, 5H), 2.44 (dd, J=19.8, 6.6 Hz, 1H), 1.96 (m, 1H), 1.81 (m, 1H), 1.71-1.63 (m, 1H), 1.32 (d, J=15.5 Hz, 1H), 0.95 (t, J=9.6 Hz, 9H), 0.59 (q, J=9.6 Hz, 6H); $^{13}$C NMR (126 MHz, CDCl$_3$) δ 208.9, 158.0, 133.3, 129.4, 114.1, 76.2, 67.9, 67.5, 55.4, 45.8, 45.2, 31.3, 28.8, 20.6, 7.1, 5.1; HRMS (ESI) m/z calc. for C$_{22}$H$_{37}$O$_4$Si [M+H]$^+$ 393.2461; found. 393.2449.

289

4-(4-methoxyphenyl)-1-((2R,3R)-3-((trimethylsilyl)oxy)tetrahydro-2H-pyran-2-yl)butan-2-one (8e)

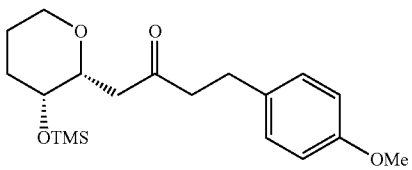

61.9 mg (0.177 mg, 89%); $[\alpha]_D^{22}$=−15.8 (c 1.0, CHCl$_3$); IR (film) 2952, 2852, 2839 1713, 1612, 1513, 1441, 1409, 1300, 1247, 1178, 1137, 1098, 1071, 1023, 840, 763 cm$^{-1}$; $^1$H NMR (500 MHz, C$_6$D$_6$) δ=6.93 (d, J=8.4 Hz, 2H), 6.81 (d, J=8.4 Hz, 2H), 3.77 (ddd, J=6.0, 5.8, 1.5 Hz, 1H), 3.72 (d, J=10.2 Hz, 1H), 3.44 (s, 1H), 3.27 (s, 3H), 3.16 (ddd, J=11.2, 10.8, 1.5 Hz, 1H), 2.81 (m, 2H), 2.71 (dd, J=15.0, 9.0 Hz, 1H), 2.52-2.46 (m, 1H), 2.44-2.38 (m, 1H), 2.26 (dd, J=15.0, 5.1 Hz, 1H), 1.90 (m, 1H), 1.53 (d, J=12.6 Hz, 1H), 1.26 (m, 1H), 0.87 (d, J=12.6 Hz, 1H), 0.00 (s, 9H); $^{13}$C NMR (126 MHz, C$_6$D$_6$) δ207.3, 158.6, 133.5, 129.7, 114.3, 76.3, 67.7, 67.5, 54.7, 45.8, 45.4, 31.3, 29.0, 20.6, 0.2; HRMS (ESI) m/z calc. for C$_{19}$H$_{31}$O$_4$Si [M+H]$^+$ 351.1992; found 351.1978.

4-(4-methoxyphenyl)-1-((3aR,5R,5aS,8aS,8bR)-2,2,7,7-tetramethyltetrahydro-5H-bis([1,3]dioxolo)[4,5-b:4',5'-d]pyran-5-yl)butan-2-one (8f)

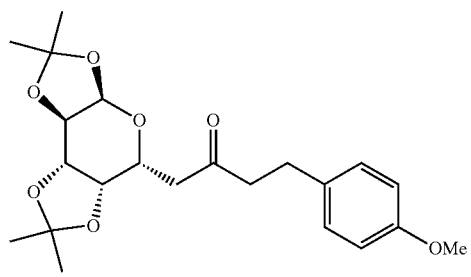 [SMILES: COc1ccc(CCC(=O)C[C@H]2O[C@@H]3OC(C)(C)O[C@@H]3[C@H]3OC(C)(C)O[C@H]32)cc1]

75.7 mg (0.186 mmol, 93%); $[\alpha]_D^{22}$=−10.7 (c 1.0, CHCl$_3$); IR (film) 2987, 2935, 1713, 1612, 1513, 1465, 1382, 1456, 1382, 1372, 1246, 1211, 1178, 1099, 1066, 1037, 1000, 861, 547 cm$^{-1}$; $^1$H NMR (600 MHz, CDCl$_3$) δ=7.09 (d, J=7.8 Hz, 2H), 6.81 (d, J=7.8 Hz, 2H), 5.46 (d J=4.7 Hz, 1H), 4.60 (dd J=7.2, 2.5 Hz, 1H), 4.33-4.28 (m, 2H), 4.18 (d J=7.2 Hz, 1H), 3.77 (s, 3H), 2.85 (dd, J=6.4, 6.0 Hz, 2H), 2.82-2.73 (m, 3H), 2.65 (dd, J=17.2, 5.0 Hz, 1H), 1.58 (s, 3H), 1.44 (s, 3H), 1.33 (s, 6H); $^{13}$C NMR (151 MHz, CDCl$_3$) δ=207.8, 158.1, 133.2, 129.4, 114.1, 109.3, 108.9, 96.5, 72.6, 70.9, 70.5, 64.2, 55.4, 45.4, 43.6, 28.7, 26.2, 25.2, 24.6; HRMS (ESI) m/z calc. for C$_{22}$H$_{31}$O$_7$[M+H]$^+$ 407.2064; found 407.2050.

290

5-((tert-butyldimethylsilyl)oxy)-7-((tert-butyldiphenylsilyl)oxy)-1-(4-methoxyphenyl)heptan-3-one (8g)

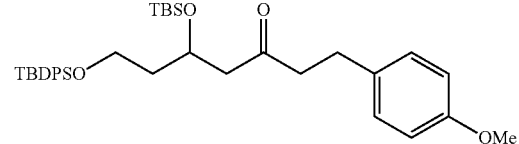

103.4 mg, (0.171 mmol, 86%); IR (film) 2955, 2930, 2893, 2856, 1716, 1513, 1472, 1428, 1361, 1248, 1178, 1111, 1084, 1038, 836, 776, 739, 702, 615, 505 cm$^{-1}$; $^1$H NMR (600 MHz, CDCl$_3$) δ=7.68-7.65 (m, 4H), 7.45-7.35 (m, 6H), 7.09 (d, J=7.8 Hz, 2H), 6.82 (d, J=7.8 Hz, 2H), 4.42-4.37 (m, 1H), 3.78 (s, 3H), 3.71 (t, J=6.0 Hz, 2H), 2.85-2.79 (m, 1H), 2.72-2.68 (m, 1H), 2.60 (dd, J=15.6 Hz, 6.6 Hz, 1H), 2.49 (dd, J=15.6 Hz, 4.8 Hz, 1H), 1.78-1.65 (m, 2H), 1.06 (s, 9H), 0.83 (s, 9H), 0.03 (s, 3H), 0.01 (s, 3H); $^{13}$C NMR (151 MHz, CDCl$_3$) δ=209.0, 158.0, 135.72, 135.69, 133.87, 133.84, 133.3, 129.75, 129.73, 129.3, 127.8, 114.0, 66.7, 60.5, 55.4, 50.5, 46.5, 40.3, 28.7, 27.0, 26.0, 19.3, 19.1, −4.5, −4.6; HRMS (ESI) m/z calc. for C$_{36}$H$_{53}$O$_4$Si$_2$ [M+H]$^+$ 605.3477; found 605.3464.

7-((tert-butyldiphenylsilyl)oxy)-5-methoxy-1-(4-methoxyphenyl)heptan-3-one (8h)

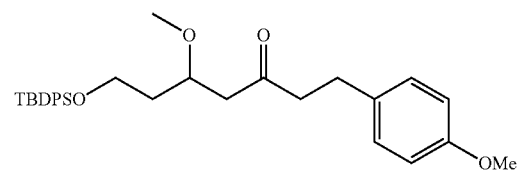

94.8 mg (0.188 mmol, 94%); IR (film) 2931, 2896, 2835, 1715, 1612, 1513, 1471, 1464, 1428, 1362, 1300, 1247, 1178, 1111, 1087, 1037, 823, 738, 703, 688, 622, 615, 505, 490, 429 cm$^{-1}$; $^1$H NMR (600 MHz, C$_6$D$_6$) δ=7.81-7.77 (m, 4H), 7.26-7.22 (m, 6H), 6.98 (d, J=8.5 Hz, 2H), 6.77 (d, J=8.5 Hz, 2H), 3.99-3.93 (m, 1H), 3.86-3.80 (m, 1H), 3.76-3.70 (m, 1H), 3.33 (s, 3H), 3.10 (s, 3H), 2.82 (t, J=8.0 Hz, 2H), 2.44-2.36 (m, 3H), 2.13 (dd, J=15.5 Hz, 4.8 Hz, 1H), 1.73-1.67 (m, 2H), 1.18 (s, 9H); $^{13}$C NMR (126 MHz, C$_6$D$_6$) δ=207.3, 159.0, 136.4, 134.6, 134.0, 130.4, 130.0, 128.5, 114.0, 75.0, 61.1, 57.2, 55.1, 48.1, 46.1, 37.5, 29.4, 27.5, 17.8; HRMS (ESI) m/z calc. for C$_{31}$H$_{40}$NaO$_4$Si [M+Na]$^+$ 527.2588; found 527.2593.

1-((tert-butyldiphenylsilyl)oxy)-7-(4-methoxyphenyl)-5-oxoheptan-3-yl acetate (8i)

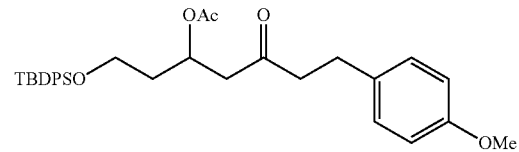

90.0 mg (0.169 mmol, 85%); IR (film) 2956, 2931, 2857, 1738, 1716, 1513, 1428, 1363, 1244, 1179, 1111, 1036, 824, 739, 704, 614, 505 cm$^{-1}$; $^1$H NMR (600 MHz, C$_6$D$_6$) δ=7.79-7.74 (m, 4H), 7.26-7.21 (m, 6H), 6.98 (d, J=7.8 Hz, 2H), 6.77 (d, J=7.8 Hz, 2H), 5.67-5.62 (m, 1H), 3.73-3.64 (m, 2H), 3.32 (s, 3H), 2.79 (t, J=7.2 Hz, 2H), 2.46 (dd, J=16.2 Hz, 6.6 Hz, 1H), 2.42-2.35 (m, 1H), 2.33-2.26 (m, 1H), 2.22 (dd, J=16.2 Hz, 6.6 Hz, 2H), 1.86-1.79 (m, 1H), 1.78-1.72 (m, 1H), 1.62 (s, 3H), 1.18 (s, 9H); $^{13}$C NMR (126 MHz, C$_6$D$_6$) δ=205.8, 170.0, 159.0, 136.4, 134.4, 133.8, 130.4, 130.0, 128.5, 114.6, 68.4, 60.8, 55.2, 47.7, 45.4, 37.4, 29.4, 27.4, 21.0, 19.8; HRMS (ESI) m/z calc. for C$_{32}$H$_{40}$NaO$_5$Si [M+Na]$^+$ 555.2537; found 555.2533.

((S)-7-((tert-butyldimethylsilyl)oxy)-5-chloro-1-(4-methoxyphenyl)heptan-3-one (8j)

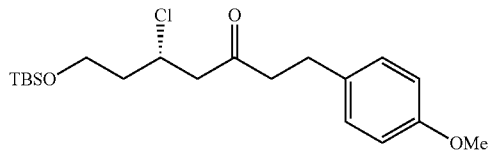 [SMILES: COc1ccc(CCC(=O)C[C@@H](Cl)CCO[Si](C)(C)C(C)(C)C)cc1]

28.4 mg (0.074 mmol, 37%); [α]$_D^{22}$=−11.6 (c 0.5, CHCl$_3$) IR (film) 2954, 2928, 2856, 1738, 1716, 1612, 1513, 1463, 1300, 1247, 1178, 1123, 1038, 838, 779 cm$^{-1}$; $^1$H NMR (600 MHz, CDCl$_3$) δ=6.10 (d, J=7.8 Hz, 2H), 6.82 (d, J=7.8 Hz, 2H), 3.88 (m, 1H), 3.78 (s, 3H), 3.77 (dd, J=10.2, 5.1 Hz, 1H), 3.67 (dd, J=10.2, 6.6 Hz, 1H), 2.85 (t, J=7.2 Hz, 2H), 2.72 (t, J=7.2 Hz, 2H), 2.68-2.55 (m, 2H), 2.25-2.19 (m, 1H), 1.83-1.77 (m, 1H), 0.89 (s, 9H), 0.07 (s, 6H); $^{13}$C NMR (126 MHz, C$_6$D$_6$) δ=209.3, 158.2, 133.1, 129.4, 114.1, 67.4, 62.2, 55.4, 44.8, 39.5, 29.1, 28.3, 26.0, 18.5, −5.9, −5.3; HRMS (ESI) m/z calc. for C$_{20}$H$_{34}$ClO$_3$Si [M+H]$^+$ 385.1960; found 385.1943.

R)-(5-(4-methoxyphenyl)-3-oxo-1-phenylpentyl) carbamate (8k)

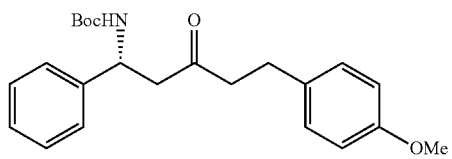 [SMILES: COc1ccc(CCC(=O)C[C@@H](NC(=O)OC(C)(C)C)c2ccccc2)cc1]

69.6 mg (0.182 mmol, 91%); [α]$_D^{22}$=+14.7 (c 0.3, CHCl$_3$); IR (film) 3376, 2979, 2932, 1707, 1612, 1513, 1455, 1366, 1247, 1175, 1037, 819, 701 cm$^{-1}$; $^1$H NMR (600 MHz, CDCl$_3$) δ=7.33-7.29 (m, 2H), 7.27-7.22 (m, 3H), 7.00 (d, J=8.4 Hz, 2H), 6.78 (d, J=8.4 Hz, 2H), 5.46 (brs, 1H), 5.07 (brs, 1H), 3.78 (s, 3H), 3.00 (brs, 1H), 2.85 (dd, J=17.4 Hz, 4.3 Hz, 1H), 2.73 (t, J=7.8 Hz, 2H), 2.69-2.62 (m, 1H), 2.59-2.52 (m, 1H), 1.41 (s, 9H); $^{13}$C NMR (126 MHz, CDCl$_3$) δ=208.5, 158.1, 155.3, 141.7, 132.9, 129.3, 128.8, 127.5, 126.4, 114.0, 79.5, 55.4, 51.3, 48.8, 45.4, 28.7, 28.5; HRMS (ESI) m/z calc. for C$_{23}$H$_{29}$NNaO$_4$ [M+Na]$^+$ 406.1989; found 406.1980.

methyl (R)-2-((tert-butoxycarbonyl)amino)-6-(4-methoxyphenyl)-4-oxohexanoate (81)

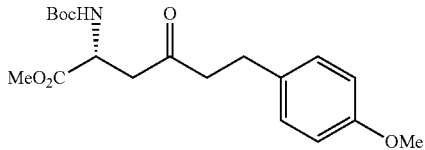 [SMILES: COC(=O)[C@@H](CC(=O)CCc1ccc(OC)cc1)NC(=O)OC(C)(C)C]

62.8 mg (0.172 mmol, 86%); [α]$_D^{22}$=+19.0 (c 0.8, CHCl$_3$); IR (film) 3383, 2974, 2953, 2932, 1749, 1713, 1612, 1513, 1454, 1439, 1367, 1342, 1299, 1247, 1165, 1110, 1088, 1034, 830 cm$^{-1}$; $^1$H NMR (600 MHz, C$_6$D$_6$) δ=6.83 (d, J=8.4 Hz, 2H), 6.74 (d, J=8.4 Hz, 2H), 5.63 (brs, 1H), 4.62 (brs, 1H), 3.32 (s, 3H), 3.27 (s, 3H), 2.70 (d, J=19.2 Hz, 1H), 2.61 (q, J=6.6 Hz, 2H), 2.50 (d, J=19.2 Hz, 1H) 2.16-2.06 (m, 2H), 1.42 (s, 9H); $^{13}$C NMR (126 MHz, C$_6$D$_6$) δ=207.7, 172.2, 159.0, 156.0, 133.4, 129.9, 114.6, 79.9, 55.1, 52.4, 50.4, 44.9, 44.7, 29.2, 28.7; HRMS (ESI) m/z calc. for C$_{19}$H$_{27}$NNaO$_6$ [M+Na]$^+$ 388.1731; found 388.1740.

tert-butyl (S)-(6-(4-methoxyphenyl)-4-oxo-1-phenylhexan-2-yl)carbamate (8m)

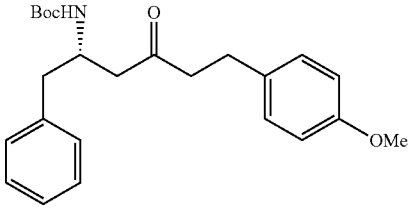 [SMILES: COc1ccc(CCC(=O)C[C@H](Cc2ccccc2)NC(=O)OC(C)(C)C)cc1]

71.9 mg (0.181 mmol, 91%); [α]$_D^{22}$=−5.7 (c 1.1, CHCl$_3$); IR (film) 3360, 2977, 2931, 1708, 1612, 1513, 1455, 1391, 1366, 1301, 1247, 1174, 1109, 1077, 1037, 824, 778, 702 cm$^{-1}$; $^1$H NMR (600 MHz, CDCl$_3$) δ=7.29-7.25 (m, 2H), 7.21 (t, J=7.2 Hz, 1H), 7.10 (d, J=7.2 Hz, 2H), 7.08 (d, J=9.0 Hz, 2H), 6.82 (d, J=9.0 Hz, 2H), 5.04 (brs, 1H), 4.11 (brs, 1H), 3.78 (s, 3H), 2.91 (brs, 1H), 2.84-2.75 (m, 3H), 2.71-2.58 (m, 2H), 2.54 (d, J=4.9 Hz, 2H), 1.40 (s, 9H); $^{13}$C NMR (126 MHz, CDCl$_3$) δ=209.5, 158.1, 155.4, 138.2, 132.9, 129.4, 129.3, 128.7, 126.7, 114.1, 79.5, 55.4, 48.9, 45.6, 45.1, 40.4, 28.8, 28.5; HRMS (ESI) m/z calc. for C$_{24}$H$_{32}$NO$_4$ [M+H]$^+$ 398.2331; found 398.2326.

Experimental Procedures for the Reactions Outlined in FIG. 5A

In a glove box, to a solution of iodide 9a-u (0.24 mmol, 1.2 eq.) and thioester 1-5 (54.6 mg, 0.20 mmol, 1.0 eq.) in either DMI (0.4 mL, sigma aldrich, 99.5%) or DMI/EtOAc (0.334 mL/0.066 mL) were added Cp$_2$ZrCl$_2$ (58.5 mg, 0.20 mmol, 1.0 eq. Sigma-aldrich, 98%), Zn powder (39.2 mg, 0.6 mmol, 3.0 eq. Sigma-aldrich, used without any activation), and NiBr$_2$ dtbbpy (9.7 mg, 0.02 mmol, 10 mol %, preparation see page 8) at room temperature. After being stirred at the same temperature for 10 min to 3 hr (monitored by TLC), the reaction mixture was removed from glove box and diluted with EtOAc and sat. NaHCO$_3$ aq. The organic layer was separated and the aqueous layer was extracted with ethyl acetate. The combined organic layer was dried over Na$_2$SO$_4$, filtered, and concentrated under reduced pressure. The obtained crude material was purified by flash column chromatography on silica gel to give 10a-u as colorless oils or white amorphous solids. Note 1: DMI or DMI/EtOAc depending on the solubilities of substrates was used as the solvent. Note 2: 2.0 eq. of lutidine was added before addition of Cp$_2$ZrCl$_2$ for the syntheses of 10c. Note 3: 1.5 eq. of iodide 9p-u, and 1.5 eq. of Cp$_2$ZrCl$_2$ were used during syntheses of 10p-u.

6-((tert-butyldiphenylsilyl)oxy)-1-(4-methoxyphenyl)hexan-3-one (10a)

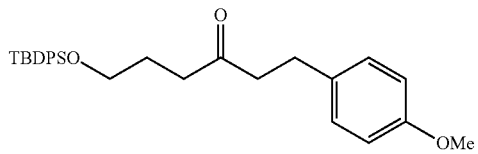

87.9 mg (0.191 mmol, 96%); IR (film) 2952, 2931, 2834, 1714, 1513, 1247, 1036, 975, 823, 688, 613, 487 cm$^{-1}$; $^1$H NMR (600 MHz, CDCl$_3$) δ=7.66-7.64 (m, 4H), 7.44-7.36 (m, 6H), 7.09 (d, J=9.0 Hz, 2H), 6.82 (d, J=9.0 Hz, 2H), 3.78 (s, 3H), 3.66 (t, J=5.9 Hz, 2H), 2.83 (t, J=7.2 Hz, 2H), 2.69 (t, J=7.8 Hz, 2H), 2.51 (t, J=7.2 Hz, 2H), 1.85-1.80 (m, 2H), 1.05 (s, 9H); $^{13}$C NMR (151 MHz, CDCl$_3$) δ=210.2, 158.1, 135.7, 133.9, 133.3, 129.8, 129.3, 127.8, 114.0, 63.1, 55.4, 44.7, 39.5, 29.1, 27.0, 26.7, 19.3; HRMS (ESI) m/z calc. for C$_{29}$H$_{37}$O$_3$Si [M+H]$^+$ 461.2506; found 461.2508.

6-((tert-butyldimethylsilyl)oxy)-1-(4-methoxyphenyl)hexan-3-one (10b)

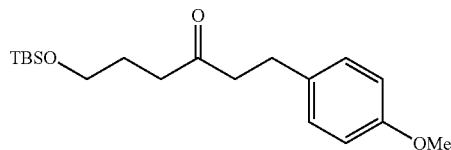 [SMILES: COc1ccc(CCC(=O)CCCO[Si](C)(C)C(C)(C)C)cc1]

63.8 mg (0.190 mmol, 95%); IR (film) 2954, 2929, 2857, 1715, 1513, 1247, 1097, 1038, 835, 776 cm$^{-1}$; $^1$H NMR (600 MHz, CDCl$_3$) δ=7.09 (d, J=9.0 Hz, 2H), 6.82 (d, J=9.0 Hz, 2H), 3.78 (s, 3H), 3.59 (t, J=6.0 Hz, 2H), 2.84 (t, J=7.2 Hz, 2H), 2.71 (t, J=7.8 Hz, 2H), 246 (t, J=7.2 Hz, 2H), 1.79-1.74 (m, 2H), 0.88 (s, 9H), 0.03 (s, 6H); $^{13}$C NMR (151 MHz, CDCl$_3$) δ=210.3, 158.1, 133.3, 129.4, 114.0, 62.3, 55.4, 44.8, 39.5, 29.1, 26.9, 26.1, 18.4, −5.2; HRMS (ESI) m/z calc. for C$_{19}$H$_{33}$O$_3$Si [M+H]$^+$ 337.2193; found 337.2186.

1-(4-methoxyphenyl)-6-((triethylsilyl)oxy)hexan-3-one (10c)

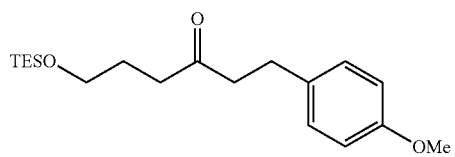

61.5 mg (0.183 mmol, 92%); IR (film) 2953, 2876, 2835, 1715, 1612, 1513, 1464, 1247, 1178, 1095, 1038, 1005, 826, 808, 743 cm$^{-1}$; $^1$H NMR (600 MHz, C$_6$D$_6$) δ=6.97 (d, J=8.4 Hz, 2H), 6.77 (d, J=8.4 Hz, 2H), 3.47 (t, J=5.9 Hz, 2H), 3.33 (s, 3H), 2.80 (t, J=7.8 Hz, 2H), 2.31 (t, J=7.8 Hz, 2H), 2.15 (t, J=7.2 Hz, 2H), 1.80-1.75 (m, 2H), 0.99 (t, J=7.2 Hz, 9H), 0.58 (q, J=7.2 Hz, 6H); $^{13}$C NMR (151 MHz, C$_6$D$_6$) δ=208.3, 159.0, 134.0, 130.0, 114.6, 62.4, 55.1, 44.9, 39.5, 29.6, 27.6, 7.5, 5.2; HRMS (ESI) m/z calc. for C$_{19}$H$_{33}$O$_3$Si [M+H]$^+$ 337.2193; found 337.2186.

6-((4-methoxybenzyl)oxy)-1-(4-methoxyphenyl)hexan-3-one (10d)

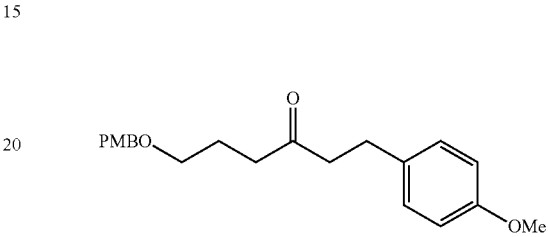

64.9 mg (0.190 mmol, 95%); IR (film) 2932, 2855, 2835, 1711, 1612, 1585, 1512, 1464, 1441, 1363, 1301, 1245, 1177, 1095, 1034, 819 cm$^{-1}$; $^1$H NMR 7.23 (d, J=9.0 Hz, 2H), 7.08 (d, J=9.0 Hz, 2H), 6.87 (d, J=9.0 Hz, 2H), 6.81 (d, J=9.0 Hz, 2H), 4.39 (s, 2H), 3.80 (s, 3H), 3.78 (s, 3H), 3.43 (t, J=6.0 Hz, 2H), 2.82 (t, J=7.2 Hz, 2H), 2.68 (t, J=7.2 Hz, 2H), 2.48 (t, J=7.2 Hz, 2H), 1.89-1.84 (m, 2H); $^{13}$C NMR (126 MHz, CDCl$_3$) δ=210.1, 159.3, 158.1, 133.3, 130.6, 129.39, 129.36, 114.0, 113.9, 72.6, 69.1, 55.40, 55.39, 44.7, 39.8, 29.0, 24.0; HRMS (ESI) m/z calc. for C$_{21}$H$_{26}$NaO$_4$ [M+Na]$^+$ 365.1723; found 365.1724.

1-(4-methoxyphenyl)-6-((tetrahydro-2H-pyran-2-yl)oxy)hexan-3-one (10e)

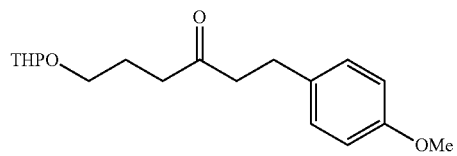

55.4 mg (0.181 mmol, 91%); IR (film) 2940, 2870, 1712, 1612, 1513, 1442, 1331, 1246, 1179, 1076, 1034, 991, 815 cm$^{-1}$; $^1$H NMR (600 MHz, CDCl$_3$) δ=7.09 (d, J=9.0 Hz, 2H), 6.81 (d, J=9.0 Hz, 2H), 4.53 (s, 1H), 3.82 (t, J=9.6 Hz, 1H), 3.78 (s, 3H), 3.71 (q, J=6.0 Hz, 1H), 3.48 (t, J=5.0 Hz, 1H), 3.38 (q, J=6.0 Hz, 1H), 2.84 (t, J=7.8 Hz, 2H), 2.72 (t, J=7.8 Hz, 2H), 2.54-2.44 (m, 2H), 1.89-1.83 (m, 2H), 1.80 (d, J=8.4 Hz, 1H), 1.71-1.65 (m, 1H), 1.58-1.48 (m, 4H); $^{13}$C NMR (151 MHz, CDCl$_3$) δ=209.9, 157.9, 133.2, 129.2, 113.9, 76.8, 66.5, 62.4, 55.2, 44.6, 39.8, 30.7, 28.9, 25.4, 23.9, 19.7; HRMS (ESI) m/z calc. for C$_{18}$H$_{26}$NaO$_4$ [M+Na]$^+$ 329.1723; found 329.1722.

6-(4-methoxyphenyl)-4-oxohexyl acetate (10f)

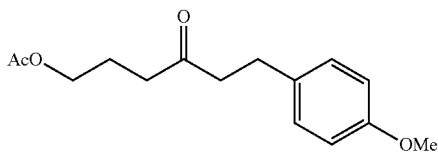 [SMILES: COc1ccc(CCC(=O)CCCOC(C)=O)cc1]

49.9 mg (0.189 mmol, 95%); IR (film) 2959, 2935, 1734, 1711, 1512, 1364, 1238, 1177, 1109, 1034, 761 cm$^{-1}$; $^1$H NMR (600 MHz, CDCl$_3$) δ=7.09 (d, J=9.0 Hz, 2H), 6.81 (d, J=9.0 Hz, 2H), 4.03 (t, J=6.6 Hz, 2H), 3.77 (s, 3H), 2.84 (t, J=7.2 Hz, 2H), 2.70 (t, J=7.2 Hz, 2H), 2.45 (t, J=7.2 Hz, 2H), 2.02 (s, 3H), 1.92-1.86 (m, 2H); $^{13}$C NMR (151 MHz, CDCl$_3$) δ=209.2, 171.2, 158.1, 133.1, 129.4, 114.0, 63.7, 55.4, 44.7, 39.3, 29.0, 22.7, 21.0; HRMS (ESI) m/z calc. for C$_{15}$H$_{21}$O$_4$[M+H]$^+$ 265.1434; found 265.1433.

6-((tert-butyldiphenylsilyl)oxy)-1-(4-methoxyphenyl)-5-methylhexan-3-one (10g)

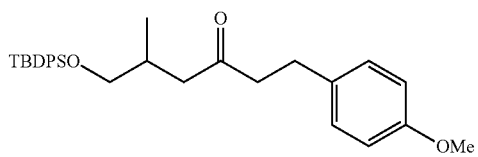

85.4 mg (0.180 mmol, 90%); IR (film) 2959, 2931, 2857, 1713, 1513, 1463, 1442, 1247, 1178, 1111, 1037, 824, 741, 702, 614, 506 cm$^{-1}$; $^1$H NMR (600 MHz, CDCl$_3$) δ=7.66-7.63 (m, 4H), 7.44-7.41 (m, 2H), 7.40-7.36 (m, 4H), 7.09 (d, J=9.0 Hz, 2H), 6.82 (d, J=9.0 Hz, 2H), 3.78 (s, 3H), 3.52 (dd, J=9.6 Hz, 5.2 Hz, 1H), 3.43 (dd, J=10.2 Hz, 6.6 Hz, 1H), 2.82 (t, J=8.4 Hz, 2H), 2.68 (td, J=7.8 Hz, 2.0 Hz, 2H), 2.63 (dd, J=16.2 Hz, 5.2 Hz, 1H), 2.28-2.22 (m, 1H), 2.18 (dd, J=16.2 Hz, 16.0 Hz, 1H), 1.05 (s, 9H), 0.88 (d, J=6.6 Hz, 3H); $^{13}$C NMR (126 MHz, CDCl$_3$) δ=209.9, 157.9, 135.6, 133.7, 133.2, 129.6, 129.2, 127.7, 113.9, 68.3, 55.3, 46.8, 45.1, 32.0, 28.9, 26.9, 19.3, 16.8; HRMS (ESI) m/z calc. for C$_{30}$H$_{39}$O$_3$Si [M+H]$^+$ 475.2663; found 475.2654.

6-((tert-butyldiphenylsilyl)oxy)-1-(4-methoxyphenyl)-5,5-dimethylhexan-3-one (10h)

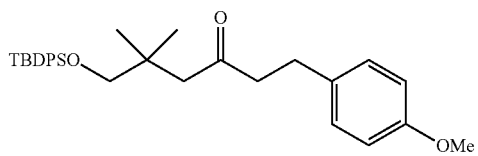

88.4 mg (0.181 mmol, 91%); IR (film) 2958, 2858, 1711, 1512, 1264, 1178, 907, 825, 731, 703, 650, 436 cm$^{-1}$; $^1$H NMR (600 MHz, CDCl$_3$) δ=7.64-7.62 (m, 4H), 7.44-7.41 (m, 2H), 7.39-7.36 (m, 4H), 7.09 (d, J=9.0 Hz, 2H), 6.82 (d, J=9.0 Hz, 2H), 3.78 (s, 3H), 3.39 (s, 2H), 2.79 (t, J=7.8 Hz, 2H), 2.68 (t, J=7.8 Hz, 2H), 2.42 (s, 2H), 1.06 (s, 9H), 0.97 (s, 6H); $^{13}$C NMR (126 MHz, CDCl$_3$) δ=210.2, 158.0, 135.8, 133.8, 133.4, 129.8, 129.4, 127.8, 114.0, 72.2, 55.4, 50.2, 46.9, 36.3, 29.0, 27.1, 24.5, 19.6; HRMS (ESI) m/z calc. for C$_{31}$H$_{41}$O$_3$Si [M+H]$^+$ 489.2819; found 489.2832.

6-((tert-butyldiphenylsilyl)oxy)-1-(4-methoxyphenyl)-4-methylhexan-3-one (10i)

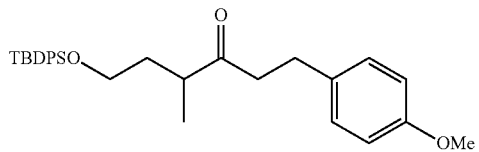

90.1 mg (0.190 mmol, 95%); IR (film) 2959, 2931, 2857, 1710, 1612, 1513, 1463, 1247, 1178, 1111, 1038, 823, 740, 703, 614, 519 cm$^{-1}$; $^1$H NMR (600 MHz, CDCl$_3$) δ=7.66-7.64 (m, 4H), 7.45-7.41 (m, 2H), 7.40-7.37 (m, 4H), 7.09 (d, J=9.0 Hz, 2H), 6.82 (d, J=9.0 Hz, 2H), 3.79 (s, 3H), 3.65 (t, J=6.6 Hz, 2H), 2.84-2.70 (m, 5H), 1.97-1.90 (m, 1H), 1.53-1.47 (m, 1H), 1.06 (s, 9H), 1.02 (d, J=7.2 Hz, 3H); $^{13}$C NMR (126 MHz, CDCl$_3$) δ=213.6, 157.9, 135.6, 133.7, 133.4, 129.7, 129.3, 127.7, 113.9, 61.6, 55.3, 43.1, 42.9, 35.3, 28.9, 26.9, 19.2, 16.2; HRMS (ESI) m/z calc. for C$_{30}$H$_{39}$O$_3$Si [M+H]$^+$ 475.2663; found 475.2657.

6-chloro-1-(4-methoxyphenyl)hexan-3-one (10l)

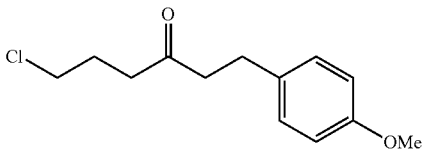 [SMILES: COc1ccc(CCC(=O)CCCCl)cc1]

46.0 mg (0.192 mmol, 96%); IR (film) 2932, 2836, 1712, 1612, 1513, 1442, 1374, 1300, 1245, 1178, 1091, 1034, 829, 546 cm$^{-1}$; $^1$H NMR (600 MHz, CDCl$_3$) δ=7.10 (d, J=8.4 Hz, 2H), 6.82 (d, J=8.4 Hz, 2H), 3.78 (s, 3H), 3.55 (t, J=6.6 Hz, 2H), 2.85 (t, J=7.8 Hz, 2H), 2.72 (t, J=7.8 Hz, 2H), 2.58 (t, J=7.8 Hz, 2H), 2.05-2.00 (m, 2H); $^{13}$C NMR (126 MHz, CDCl$_3$) δ=209.1, 158.2, 133.0, 129.4, 114.1, 55.4, 44.8, 44.6, 29.7, 29.1, 26.4; HRMS (ESI) m/z calc. for C$_{13}$H$_{18}$ClO$_2$ [M+H]$^+$ 241.0990; found 241.0998.

6-bromo-1-(4-methoxyphenyl)hexan-3-one (10m)

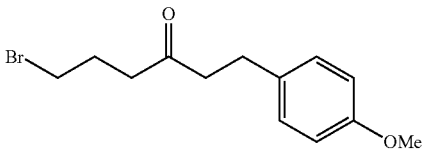

54.3 mg (0.191 mmol, 96%); IR (film) 2933, 2835, 1712, 1611, 1512, 1441, 1409, 1372, 1300, 1245, 1178, 1035, 828, 555 cm$^{-1}$; $^1$H NMR (600 MHz, CDCl$_3$) δ=7.09 (d, J=8.4 Hz, 2H), 6.82 (d, J=8.4 Hz, 2H), 3.78 (s, 3H), 3.42 (t, J=6.6 Hz, 2H), 2.85 (t, J=7.8 Hz, 2H), 2.72 (t, J=7.8 Hz, 2H), 2.58 (t, J=7.8 Hz, 2H), 2.13-2.08 (m, 2H); $^{13}$C NMR (126 MHz, CDCl$_3$) δ=209.0, 158.1, 133.0, 129.4, 114.1, 55.4, 44.8, 40.9, 33.4, 29.1, 26.4; HRMS (ESI) m/z calc. for $C_{13}H_{18}BrO_2$ [M+H]$^+$ 285.0485; found 285.0476.

6-(4-methoxyphenyl)-4-oxohexyl 4-methylbenzenesulfonate (10n)

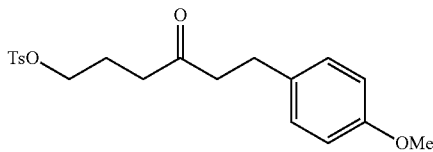 [SMILES: COc1ccc(CCC(=O)CCCOS(=O)(=O)c2ccc(C)cc2)cc1]

61.7 mg (0.164 mmol, 82%); IR (film) 2960, 2936, 1714, 1612, 1513, 1465, 1455, 1443, 1416, 1359, 1302, 1246, 1189, 1175, 1098, 1037, 1037, 1019, 963, 931, 921, 903, 830, 814, 795, 664, 543 cm$^{-1}$; $^1$H NMR (600 MHz, $C_6D_6$) δ=7.72 (d, J=8.4 Hz, 2H), 6.94 (d, J=8.4 Hz, 2H), 6.79 (d, J=8.4 Hz, 2H), 6.69 (d, J=8.4 Hz, 2H), 3.79 (t, J=6.6 Hz, 2H), 3.34 (s, 3H), 2.70 (t, J=7.2 Hz, 2H), 2.14 (t, J=7.2 Hz, 2H), 1.85 (t, J=6.6 Hz, 2H), 1.82 (s, 3H), 1.59-1.54 (m, 2H); $^{13}$C NMR (126 MHz, $C_6D_6$) δ=207.4, 159.0, 144.6, 134.7, 133.8, 130.2, 129.9, 114.6, 70.0, 55.2, 55.1, 44.7, 38.3, 29.5, 23.5, 21.5; HRMS (ESI) m/z calc. for $C_{20}H_{24}NaO_5S$ [M+Na]$^+$ 399.1237; found 399.1221.

6-(4-bromophenyl)-1-(4-methoxyphenyl)hexan-3-one (10o)

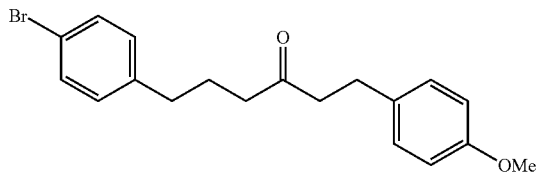 [SMILES: COc1ccc(CCC(=O)CCCc2ccc(Br)cc2)cc1]

57.6 mg (0.160 mmol, 82%); IR (film) 2934, 1712, 1612, 1512, 1488, 1454, 1404, 1370, 1300, 1246, 1178, 1109, 1035, 1011, 824, 518 cm$^{-1}$; $^1$H NMR (600 MHz, CDCl$_3$) δ=7.38 (d, J=8.4 Hz, 2H), 7.08 (d, J=8.4 Hz, 2H), 7.00 (d, J=8.4 Hz, 2H), 6.81 (d, J=8.4 Hz, 2H), 3.78 (s, 3H), 2.82 (t, J=8.4 Hz, 2H), 2.66 (t, J=8.4 Hz, 2H), 2.53 (t, J=7.2 Hz, 2H), 2.36 (t, J=7.2 Hz, 2H), 1.88-1.82 (m, 2H); $^{13}$C NMR (151 MHz, CDCl$_3$) δ=209.9, 158.1, 140.7, 133.2, 131.5, 130.3, 129.4, 119.8, 114.0, 55.4, 44.7, 42.1, 34.5, 29.0, 25.0; HRMS (ESI) m/z calc. for $C_{19}H_{21}BrNaO_2$ [M+Na]$^+$ 383.0617; found 383.0608.

6-hydroxy-1-(4-methoxyphenyl)hexan-3-one (10p)

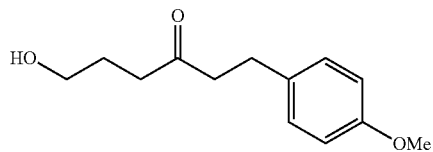

27.3 mg (0.123 mmol, 62%); IR (film) 3523-3306 (br), 2918, 1708, 1612, 1513, 1299, 1246, 1179, 1107, 1066, 848 cm$^{-1}$; $^1$H NMR (600 MHz, CDCl$_3$) δ=7.10 (d, J=8.4 Hz, 2H), 6.82 (d, J=8.4 Hz, 2H), 3.78 (s, 3H), 3.63 (t, J=6.6 Hz, 2H), 2.85 (t, J=6.6 Hz, 2H), 2.73 (t, J=6.6 Hz, 2H), 2.53 (t, J=6.6 Hz, 2H), 1.85-1.80 (m, 2H); $^{13}$C NMR (126 MHz, CDCl$_3$) δ=210.9, 158.1, 133.1, 129.3, 114.1, 62.5, 55.4, 44.8, 39.9, 29.1, 26.5; HRMS (ESI) m/z calc. for $C_{13}H_{17}O_2$ [M+H−H$_2$O]$^+$ 205.1223; found 205.1223. Note: Exists as a mixture of ketone and hemiacetal (30:1).

6-hydroxy-1-(4-methoxyphenyl)heptan-3-one (10q)

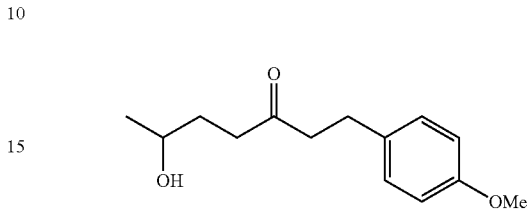

30.9 mg (0.131 mmol, 66%); IR (film) 3513-3300 (br), 2916, 1705, 1610, 1513, 1299, 1246, 1179, 1107, 1100, 1087, 845 cm$^{-1}$; $^1$H NMR (600 MHz, CDCl$_3$) δ=7.10 (d, J=8.4 Hz, 2H), 6.82 (d, J=8.4 Hz, 2H), 3.78 (s, 3H), 3.78-3.76 (m, 1H), 2.87-2.80 (m, 2H), 2.77-2.68 (m, 2H), 2.58-2.49 (m, 2H), 1.65-1.55 (m, 2H), 1.18 (d, J=5.2 Hz, 3H); $^{13}$C NMR (126 MHz, CDCl$_3$) δ=211.1, 158.0, 133.4, 129.3, 114.1, 67.6, 55.4, 44.8, 39.5, 32.7 29.1, 23.9; HRMS (ESI) m/z calc. for $C_{14}H_{20}O_3$ [M+H]$^+$ 237.1491; found 237.1485. Note: Exists as a mixture of ketone and hemiacetal (20:1).

6-hydroxy-1-(4-methoxyphenyl)-6-methylheptan-3-one (10r)

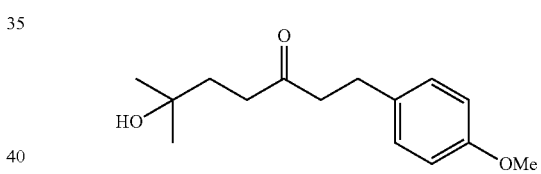

24.8 mg (0.099 mmol, 50%); IR (film) 3550-3450 (br), 2966, 2928, 1708, 1611, 1512, 1464, 1366, 1300. 1244, 1177, 1138, 1035, 822 cm$^{-1}$; $^1$H NMR (500 MHz, CDCl$_3$) (only peaks of the ketone in the mixture are shown) δ=7.09 (d, J=8.4 Hz, 2H), 6.82 (d, J=8.4 Hz, 2H), 3.78 (s, 3H), 2.84 (t, J=9.6 Hz, 2H), 2.74 (t, J=9.6 Hz, 2H), 2.52 (t, J=9.6 Hz, 2H), 1.74 (t J=9.6 Hz, 2H), 1.19 (s, 6H); $^{13}$C NMR (126 MHz, CDCl$_3$) (all peaks of the mixture are shown) δ=210.9, 133.0, 129.2, 129.1, 113.9, 113.8, 70.1, 55.3, 44.8, 43.2, 38.0, 37.2, 36.6, 36.2, 30.4, 30.0, 29.4, 29.0 HRMS (ESI) m/z calc. for $C_{15}H_{23}O_3$ [M+H]$^+$ 251.1647; found 251.1639. Note: Exists as a mixture of ketone and hemiacetal (2.5:1).

1-((2R,3R)-3-hydroxytetrahydro-2H-pyran-2-yl)-4-(4-methoxyphenyl)butan-2-one (10s)

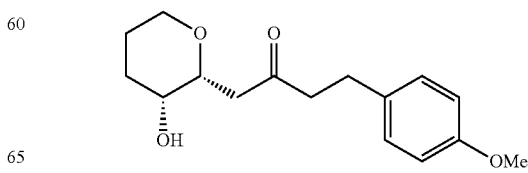

25.3 mg (0.091 mmol); ¹H NMR shows complex mixtures which are considered as a mixture of the ketone and two hemiacetal isomers. ¹H NMR of 10s is shown in Part 8 of this supporting information. In order to confirm the structure, 10s was subject to TESOTf (1.2 eq.) and 2,6-lutidine (1.5 eq.) in dichloromethane. The expected 8e was isolated as the major product for 87% yield.

7-((tert-butyldiphenylsilyl)oxy)-5-hydroxy-1-(4-methoxyphenyl)heptan-3-one (10t)

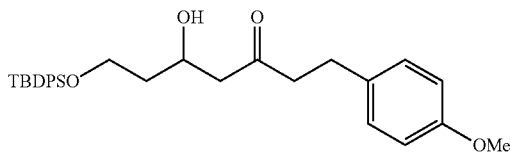

40.7 mg (0.083 mmol, 42%); IR (film) 3489 (br), 2930, 2857, 1711, 1612, 1513, 1471, 1428, 1301, 1247, 1178, 1111, 1038, 823, 739, 703, 689, 617, 504 cm⁻¹; ¹H NMR (600 MHz, C$_6$D$_6$) δ=7.80-7.75 (m, 4H), 7.25-7.20 (m, 6H), 6.95 (d, J=9.0 Hz, 2H), 6.78 (d, J=9.0 Hz, 2H), 4.33-4.27 (m, 1H), 3.88-3.83 (m, 1H), 3.80-3.76 (m, 1H), 3.32 (s, 3H), 3.28 (d, J=2.9 Hz, 1H), 2.77-2.73 (m, 2H), 2.27 (t, J=7.8 Hz, 2H), 2.19 (dd, J=16.8 Hz, 9.0 Hz, 1H), 2.02 (dd, J=16.8 Hz, 3.4 Hz, 2H), 1.68-1.61 (m, 1H), 1.52-1.46 (m, 1H), 1.16 (s, 9H); ¹³C NMR (126 MHz, C$_6$D$_6$) δ=209.7, 159.0, 136.4, 134.3, 133.8, 130.4, 130.0, 114.6, 110.8, 110.7, 66.6, 62.5, 55.2, 50.1, 45.7, 39.6, 29.3, 27.5, 19.7; HRMS (ESI) m/z calc. for C$_{30}$H$_{39}$O$_4$Si [M+H]⁺ 491.2612; found 491.2604.

3-(((6-(4-methoxyphenyl)-4-oxohexyl)oxy)carbonyl)benzoic acid (10u)

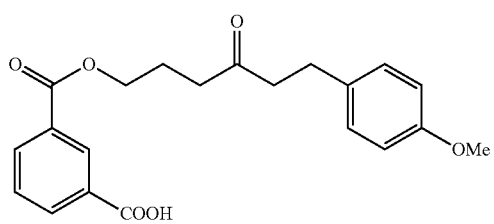 [SMILES: COc1ccc(CCC(=O)CCCOC(=O)c2cccc(C(=O)O)c2)cc1]

42.9 mg (0.116 mmol, 58%); IR (film) 2951, 2905, 2834, 1721, 1610, 1508, 1483, 14691, 1280, 1170, 1105, 1087, 845, 721 cm⁻¹; ¹H NMR (600 MHz, CDCl$_3$) δ=8.73 (s, 1H), 8.30 (d, J=5.6 Hz, 1H), 8.26 (d, J=5.6 Hz, 1H), 7.59 (t, J=5.6 Hz, 1H), 7.08 (d, J=8.4 Hz, 2H), 6.80 (d, J=8.4 Hz, 2H), 4.35 (t, J=6.6 Hz, 2H), 3.75 (s, 3H), 2.86 (t, J=7.8 Hz, 2H), 2.73 (t, J=7.8 Hz, 2H), 2.56 (t, J=6.6 Hz, 2H), 2.07 (m, 2H); ¹³C NMR (126 MHz, CDCl$_3$) δ=209.2, 170.8, 165.8, 158.4, 134.8, 134.5, 133.0, 131.4, 131.0, 129.8, 129.4, 128.9, 114.0, 64.8, 55.4, 44.8, 39.4, 29.3, 22.9; HRMS (ESI) m/z calc. for C$_{21}$H$_{22}$NaO$_6$ [M+Na]⁺393.1314; found 393.1303.

Experimental Procedures for the Reactions Outlined in FIG. 5B

In a glove box, to a solution of iodide 1-12 (27.1 mg, 0.12 mmol, 1.2 eq.) and thioester 1-11 (23.7 mg, 0.10 mmol, 1.0 eq.) in DMI (0.2 mL, Sigma-aldrich, 99.5%) were added Cp$_2$ZrCl$_2$ (29.3 mg, 0.10 mmol, 1.0 eq. Sigma-aldrich, 98%), Zn powder (19.6 mg, 0.3 mmol, 3.0 eq. Sigma-aldrich, used without any activation), and NiBr$_2$.dtbbpy (4.8 mg, 0.01 mmol, 10 mol %, preparation see page 8) at room temperature. After being stirred at the same temperature for 40 mins (monitored by TLC), the reaction mixture was removed from glove box and diluted with EtOAc and sat. NaHCO$_3$ aq. The organic layer was separated and the aqueous layer was extracted with ethyl acetate. The combined organic layer was dried over Na$_2$SO$_4$, filtered, and concentrated under reduced pressure. The obtained crude material was purified by flash column chromatography on silica gel to give 1-13 as a colorless oil.

1,3-bis(tetrahydro-2H-pyran-2-yl)propan-2-one (1:1 mixture-1-13)

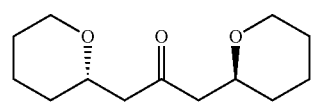

Racemic

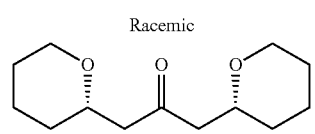

Meso 19.4 mg (0.086 mmol, 86%); IR (film) 2933, 2487, 1713, 1440, 1378, 1356, 1203, 1175, 1088 cm⁻¹; ¹H NMR (600 MHz, CDCl$_3$) δ=3.91 (d, J=9.2 Hz, 2H), 3.79-3.73 (m, 2H), 3.43 (dd, J=11.2, 10.8 Hz, 2H), 2.67 (dd, J=14.8, 5.8 Hz, 2H), 2.44 (dd, J=14.8, 5.8 Hz, 2H), 1.80 (d, J=7.2 Hz, 2H), 1.62-1.58 (m, 3H), 1.52-1.46 (m, 5H), 1.30-1.21 (m, 2H); ¹³C NMR (126 MHz, CDCl$_3$) δ=207.7, 74.1, 68.7, 50.6, 50.4, 31.9, 25.9, 23.5 HRMS (ESI) m/z calc. for C$_{13}$H$_{22}$NaO$_3$ [M+Na]⁺ 249.1467; found 249.1460.

1,3-bis((S)-tetrahydro-2H-pyran-2-yl)propan-2-one [(S)-1-13]

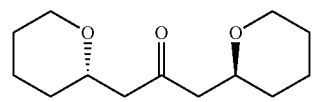 [SMILES: O=C(C[C@@H]1CCCCO1)C[C@@H]1CCCCO1]

20.2 mg (0.089 mmol, 89%); [α]$_D^{22}$=−7.3 (c 0.74, CHCl$_3$); ¹H NMR (600 MHz, CDCl$_3$) δ=3.91 (d, J=9.2 Hz, 2H), 3.79-3.73 (m, 2H), 3.43 (dd, J=11.2, 10.8 Hz, 2H), 2.67 (dd, J=14.8, 5.8 Hz, 2H), 2.44 (dd, J=14.8, 5.8 Hz, 2H), 1.80 (d, J=7.2 Hz, 2H), 1.62-1.58 (m, 3H), 1.52-1.46 (m, 5H), 1.30-1.21 (m, 2H); ¹³C NMR (126 MHz, CDCl$_3$) δ=207.7, 74.1, 68.7, 50.6, 31.9, 25.9, 23.5 ppm; HRMS (ESI) m/z calc. for C$_{13}$H$_{22}$NaO$_3$ [M+Na]⁺ 249.1467; found 249.1463.

1-((R)-tetrahydro-2H-pyran-2-yl)-3-((S)-tetrahydro-2H-pyran-2-yl)propan-2-one[(S,R)-1-13]

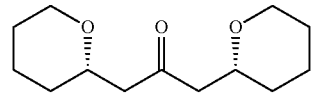 [SMILES: O=C(C[C@H]1CCCCO1)C[C@@H]1CCCCO1]

19.2 mg (0.085 mmol, 85%) from (S)-1-11; 19.4 mg (0.086 mmol, 86%) from (R)-1-11. $^1$H NMR (600 MHz, CDCl$_3$) δ=3.91 (d, J=9.2 Hz, 2H), 3.79-3.73 (m, 2H), 3.43 (dd, J=11.2, 10.8 Hz, 2H), 2.67 (dd, J=14.8, 5.8 Hz, 2H), 2.44 (dd, J=14.8, 5.8 Hz, 2H), 1.80 (d, J=7.2 Hz, 2H), 1.62-1.58 (m, 3H), 1.52-1.46 (m, 5H), 1.30-1.21 (m, 2H); $^{13}$C NMR (126 MHz, CDCl$_3$) δ=207.7, 74.1, 68.7, 50.4, 31.9, 25.9, 23.5 ppm; HRMS (ESI) m/z calc. for C$_{13}$H$_{22}$NaO$_3$ [M+Na]$^+$ 249.1467; found 249.1463.

1,3-bis((R)-tetrahydro-2H-pyran-2-yl)propan-2-one [(R)-1-13]

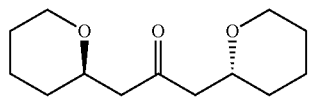 [SMILES: O=C(C[C@H]1CCCCO1)C[C@H]1CCCCO1]

19.0 mg (0.084 mmol, 84%); [α]$_D^{22}$=+7.6 (c 0.77, CHCl$_3$); $^1$H NMR (600 MHz, CDCl$_3$) δ=3.91 (d, J=9.2 Hz, 2H), 3.79-3.73 (m, 2H), 3.43 (dd, J=11.2, 10.8 Hz, 2H), 2.67 (dd, J=14.8, 5.8 Hz, 2H), 2.44 (dd, J=14.8, 5.8 Hz, 2H), 1.80 (d, J=7.2 Hz, 2H), 1.62-1.58 (m, 3H), 1.52-1.46 (m, 5H), 1.30-1.21 (m, 2H); $^{13}$C NMR (126 MHz, CDCl$_3$) δ=207.7, 74.1, 68.7, 50.6, 31.9, 25.9, 23.5 ppm; HRMS (ESI) m/z calc. for C$_{13}$H$_{22}$NaO$_3$ [M+Na]$^+$249.1467; found 249.1455.

Synthesis of Halichondrins and Analogs

Figure 7:
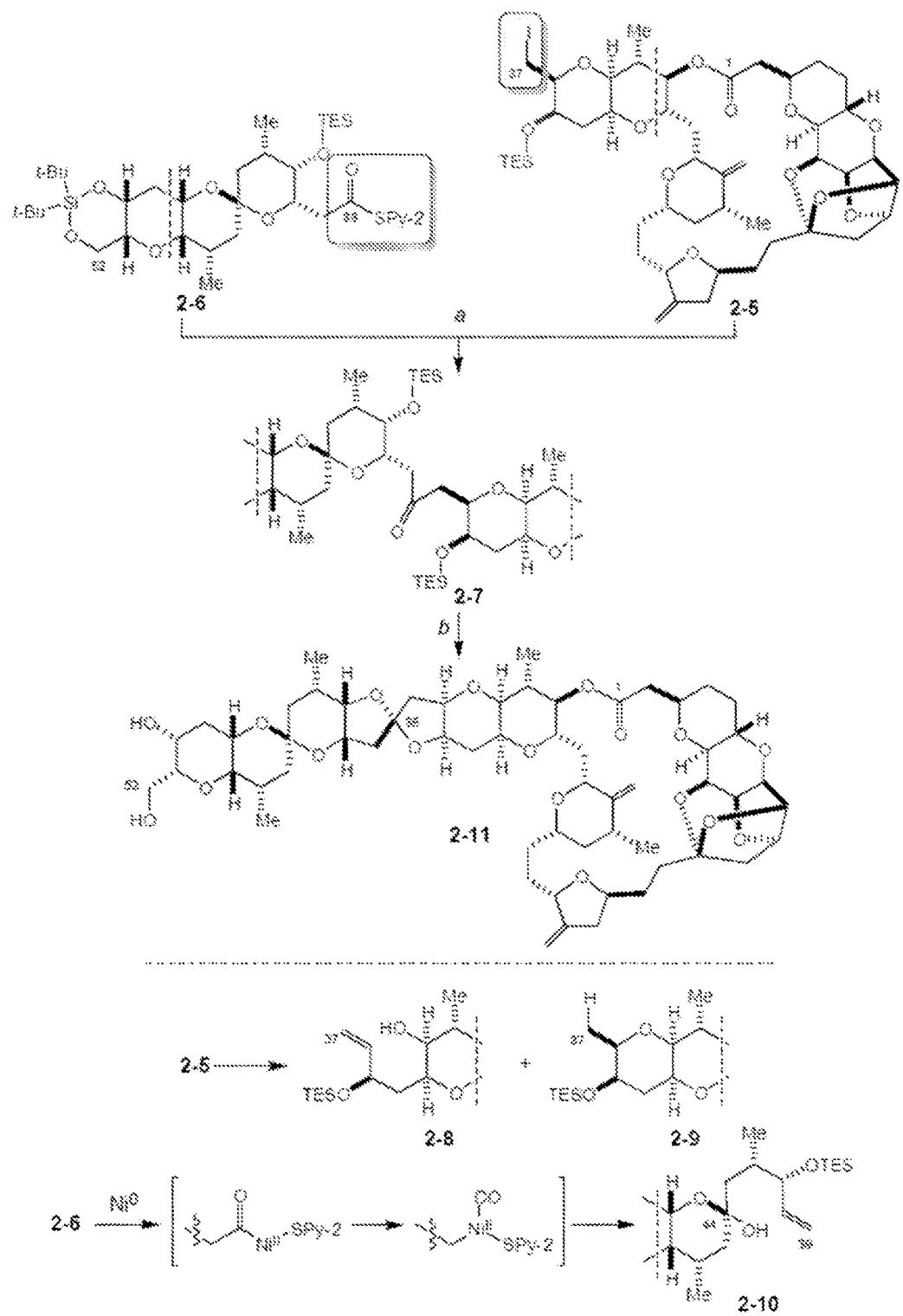
FIG. 7 shows the Ni/Zr-ketolization provided herein applied to the synthesis of a halichondrin analog. Reagents and conditions: (a) 2-5 (1.0 equiv.), 2-6 (1.3 equiv.), NiBr$_2$.(dtbbpy) (30 mol %), Cp$_2$ZrCl$_2$ (3 equiv.), (t-Bu)$_2$(Me)Py (4 equiv.), Zn (6 equiv.) in 5:1 DMI-EtOAc (C 0.1 M), rt. (b) HF.Py (20 equiv.), THF, followed by TBAF (4 equiv.), pivalic acid (2 equiv.), DMF, rt. (c) PPTS (5 equiv.), CH$_2$Cl$_2$, –20° C., 2 hr. Abbreviation: TES=Et$_3$Si—; SPy-2: 2-thiopyridine; DMI: 1,3-dimethyl-2-imidazolidinone; TBAF: tetrabutylammonium fluoride; PPTS: pyridinium p-toluenesulfonate.

A unified, efficient, and scalable synthesis of halichondrins, with use of Zr/Ni-mediated one-pot ketone synthesis as the final coupling reaction has been developed. In a previous synthesis, the key intermediate for construction of the [6,6] and [5,5] spiroketals was enone 2-3, which was synthesized via a Ni/Cr-mediated coupling of 2-1 with 2-2 in an excellent overall yield (FIG. 7). The best combination of protecting groups at C35, C41, and C48 was recently identified to be TES, TBS, and TES, respectively. During this transformation, three chiral centers were introduced at C38, C40, and C44, cf., 2-3→2-A→2-B→2-4. Based on the synthetic work of calcimycin, the desired stereochemistry should be preferentially formed under a basic condition (see, e.g., Negri, D. P.; Kishi, Y. *Tetrahedron Lett.*, 1987, 28, 1063). Indeed, this approach worked nicely for a synthesis of halichondrins A-Cs. However, an alternative route for the final transformation was desired.

Ketone 2-B is available via an alternative, well-defined route. The Zr/Ni-mediated one-pot ketone synthesis showed a potential to meet these needs; specifically, this method was proved effective for coupling of (S)-2-C+(S)-2-D→(Σ,Σ)-2-E. The requisite ketone 2-B could be synthesized from iodide 2-5 and 2-thiopyridine ester 2-6. Ketone 2-B could also be obtained via coupling at the C38-C39 bond, but we focused on the former route because of the overall synthetic efficiency of 2-5. The feasibility of this disconnection was demonstrated with use of the combination of CH$_2$I at C40 with C(=O)SPy at C38. Py=2-pyridyl.

Being encouraged with the successful ((S)-2-C+(S)-2-D→(2,4)-2-E)-coupling, the feasibility study for the proposed synthesis began. For this study, the right half 2-5 of halichondrin Bs was chosen. The C35-protecting group was selected for two reasons, i.e., (1) the rate of ketone coupling with 2-5 was significantly faster than that with the corresponding C35-TBS substrate and (2) deprotection of the C35-TES group in the following step was noticeably faster than that of the corresponding C35-TBS substrate. On the other hand, the left half 2-6 was chosen, because of its availability in a larger quantity at the time of preliminary study. The C41-protecting group was chosen primarily for the ease of deprotection.

The desired product 2-7 was obtained in the first attempt under the conditions used for ((S)-2-C+(S)-2-D→(Σ,Σ)-2-E)-coupling. Conditions were then optimized for this case. First, Cp$_2$ZrCl$_2$ was important to accelerate the ketone coupling and, at the same time, suppress by-product formation via a (I→SPy)-displacement at C37. Second, a 5:1 mixture of DMI and EtOAc was found to be the best solvent. Third, the coupling proceeded well at 0.1 M concentration, although a higher concentration, for example 0.4 M, was better. Fourth, both Zn and Mn metals were effective. Fifth, 2,6-di-tert-butyl-4-methylpyridine was used to avoid partial deprotection of the TES groups during the reaction and/or workup. Lastly, as expected, the coupling efficiency depended on the molar ratio of 2-5 and 2-6, for example 84% yield with 2-5:2-6=1.0:1.3; 62% with 1.0:1.0; 71% with 1.0:1.2.

Considering all these factors, the coupling condition specified in FIG. 7 is shown as an example procedure. For all the couplings, the molar ratio of 2-5:2-6=1.0:1.3 was used, considering the molecular size and complexity of 2-5 vs. 2-6. Under this condition, the ketone coupling was carried out in 0.5-1.0 g scales, to furnish the desired product 2-7 in 80-90% yields.

In this coupling, three by-products were isolated in very small amounts (~3% yields). Spectroscopic analysis ($^1$H NMR, MS) suggested these by-products to be 2-8, 2-9, and 2-10, respectively. The first two by-products were derived from 2-5, formation of which was not surprising in light of the results discussed in the method-development work. The third by-product 2-10 was obviously derived from 2-6, which was, as speculated, formed via a Ni-mediated decarbonylation, the transformation depicted in FIG. 7.

Ketone 2-7 also served for a model study on the second stage of synthesis, i.e., deprotection of the silyl groups, followed by acid-catalyzed [5,5]-spiroketal formation. As expected, the C50/C52-dioxasilinane group in 2-7 was readily removed on a treatment with HF.Py, to give the corresponding diol. A treatment of the resultant C49/C52-diol with TBAF (4 equiv.) buffered with pivalic acid (2 equiv.) gave the completely deprotected product within 6 hours, thereby confirming the ease of deprotection of the two TES group at C35 and C41. This transformation was also done in one step, i.e., treatment directly with TBAF, buffered with pivalic acid.

The completely desilylated product was treated with an acid, to furnish 2-11; namely, PPTS in CH$_2$Cl$_2$ at room temperature gave a ~5:1 mixture of 2-11 and its C38-epi-11, which were separated by revere phase, medium-pressure column chromatography, to furnish 2-11 (67% overall yield from 2-5) and C38-epi-2-11 (13% overall yield from 2-5). With the method previously reported, C38-epi-2-11 was isomerized to give additional 2-11 (9% isolated yield), thereby making the overall yield of 2-11 from 5 76%. The structure of 2-11 was concluded from spectroscopic analysis; $^1$H and $^{13}$C NMR spectra were found beautifully to correspond to those of norhalichondrin B.

The results given in the previous section made a convincing case that the Zr/Ni-mediated one-pot ketone synthesis should lead to the development of a unified synthesis of the halichondrin class of natural products, and analogs thereof. To demonstrate experimentally, three types of right- and left-halves were prepared, respectively (FIG. 8A). Combinations of these right- and left-halves should give all the nine halichondrins (FIG. 8B).

The first stage in this approach was to apply Zr/Ni-mediated one-pot ketone synthesis for each combination. The ketone coupling was conducted under the previously defined condition, to furnish the expected products in 80-90% isolated yields. All the ketones were isolated by medium-pressured column chromatography (neutral silica gel) and fully characterized. The results were virtually identical with those found for 2-5+2-6→2-7, including coupling rates, isolated yields, and detected by-products. For example, the (2-5+2-14)-coupling was carried out in a 200 mg scale of 2-5, to give the expected, desired ketone in 88% isolated yield, along with three by-products 2-8, 2-9, and one corresponding to 2-11 in small amounts (~3%). Noteworthily, the C12 allyl group of halichondrins-C was found intact in the time-scale of ketone synthesis.

The second stage was deprotection of the silyl protecting groups, followed by [5,5]-spiroketal formation under acidic conditions. Halichondrin-B synthesis was first studied, where deprotection of the silyl groups and formation of the [5,5]-spiroketal were effected with TBAF buffered with pivalic acid in DMF and then PPTS in $CH_2Cl_2$, to give a ~5:1 mixture of halichondrin B and its C38-epimer. Reverse-phase medium-pressure column chromatography was adopted for separation/isolation, to furnish halichondrin B and C38-epimer in an excellent overall yield; for example, 200 mg of 2-5 gave 133 mg (68%) and 25 mg (13%) of halichondrin B and C38-epi-halichondrin B, respectively. With the method previously reported, C38-epi-halichondrin B was isomerized to give additional 17 mg halichondrin B (9% isolated yield). Thus, the overall yield of halichondrin B was 77% from 2-5. Spectroscopic comparison (HR-MS, $^1$H and $^{13}$C NMR) confirmed that halichondrin B was identical to the authentic sample. The reproducibility of overall transformation was excellent and no potential issue was noticed for scaling.

Similarly, the synthesis of halichondrin A (2-12+2-14→2-20) was carried out. In this series, an additional step was required to remove the C12/C13 anisylidene, i.e., PPTS treatment in a mixture of isopropanol and 2,2-dimethyl-1,3-propandiol. During the acid-treatment, the ratio of halichondrin A and its C38-epimer changed from ~5:1 down to ~3:1. As before, C38-epimer was isomerized, furnishing halichondrin A in 61% total yield from 2-12. Spectroscopic comparison confirmed that halichondrin A was identical to the authentic sample.

The synthesis of halichondrin C (2-13+2-14→2-23) was also carried out. In this series, an additional step was required to remove the allyl group at C12, which was uneventfully achieved with the method used in the previous synthesis. Synthetic halichondrin C and C38-epimer were isolated in 55% and 11% yields, respectively. Spectroscopic comparison confirmed that halichondrin C was identical to the authentic sample. Noteworthily, attempted TMSOTf-induced isomerization in $CH_2Cl_2$ did not give halichondrin C. This phenomenon was observed for all the members in the halichondrin-C sub-group, but not for any member of other sub-groups, thereby indicating that the reason for the unsuccessful isomerization was due to the chemical property of halichondrin-C polycycle. Spectroscopic analysis of a product formed during the attempted reaction suggested a rearrangement of the halichondrin-C polycycle to a C12 ketal.

Synthesis in the norhalichondrin series proceeded equally well, although an extra step was required to hydrolyze the methyl ester at C53, which was achieved under the condition used in the previous work. It should be noted that, for synthesis of norhalichondrin C, base-induced hydrolysis of the methyl ester was done before deprotection of the ally group, because of the base-instability of halichondrin-C polycycle. Spectroscopic comparison established that norhalichondrins A-C thus obtained were identical to the authentic samples.

Lastly, the ketone route was applied to the homohalichondrin series. It is noteworthy that the previous enone route was not effective for a synthesis of homohalichondrins; it was successful only for homohalichondrin A, but with a very low efficiency (5% isolated yield). To our delight, the new synthetic route was found effective for a total synthesis of all the homohalichondrins; the overall efficiency in the homohalichondrin series was comparable to that in the halichondrin and norhalichondrin series. For instance, 100 mg 2-5 furnished 72 mg homohalichondrin B (75% overall yield). Spectroscopic comparison (HR-MS, $^1$H and $^{13}$C NMR) confirmed that homohalichondrins A-C were identical to the authentic samples. The reproducibility of overall transformation was excellent and no potential issue was noticed for scaling.

In summary, a unified, efficient, and scalable synthesis of the halichondrin class of natural products was completed. Newly developed Zr/Ni-mediated one-pot ketone synthesis was used for coupling of right halves with left halves, where $Cp_2ZrCl_2$ was found crucial to accelerate the coupling rate and, at the same time, suppress by-product formation. Halichondrins were obtained from these ketones basically in two operations, i.e., desilylation and then [5,5]-spiroketal formation. Notably, the new synthetic route was successfully applied for a total synthesis of all the homohalichondrins. All the halichondrins thus synthesized were isolated as crystalline solids. We succeeded in growing a single crystal for an X-ray analysis for some of them; thus far, the analysis completed for halichondrin C, which was the first successful X-ray analysis of intact halichondrin. To demonstrate the scalability, halichondrin B was chosen, where 150 mg of halichondrin B (77% yield) was obtained from 200 mg of the right half 2-5.

Experimental Procedures for the Synthesis of Halichondrins and Analogs
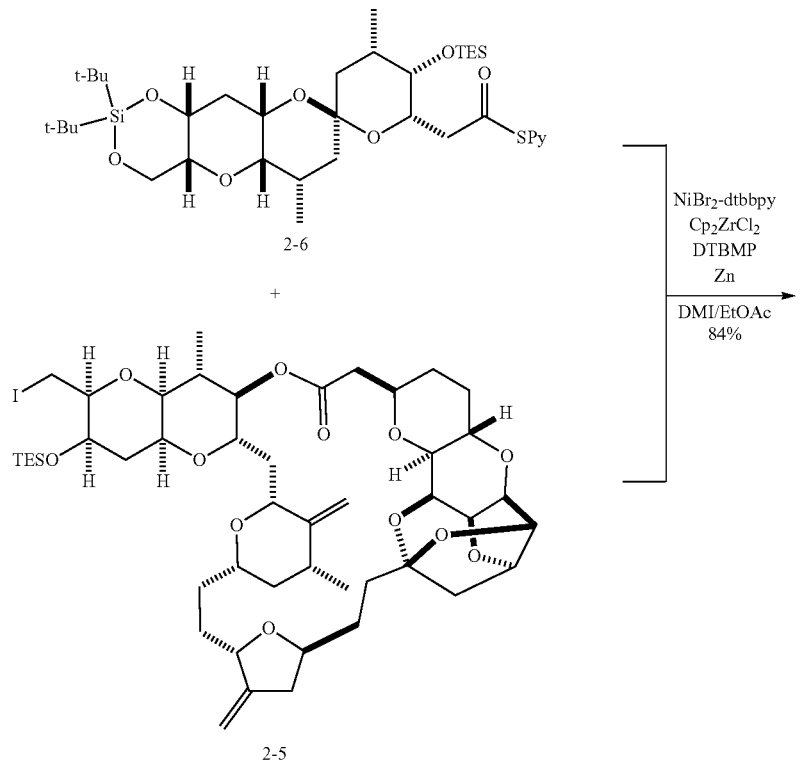
2-6
2-5
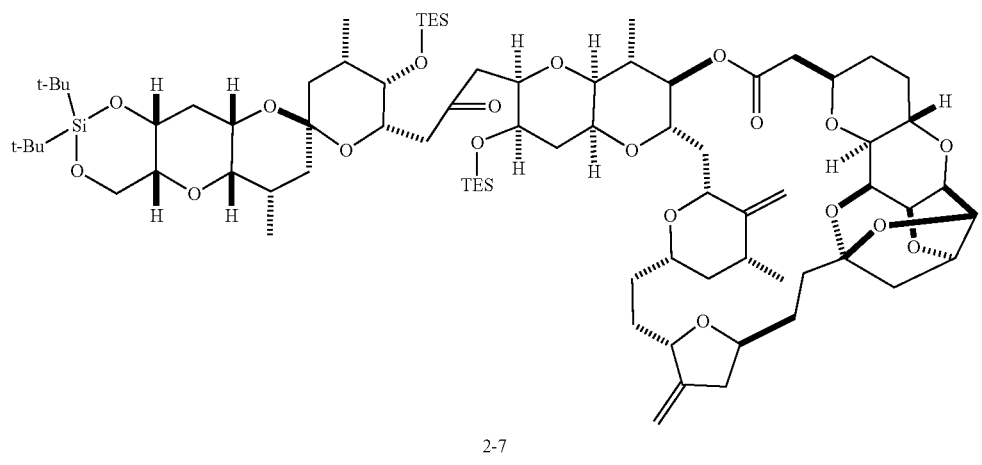
2-7

In a glove box, to a mixture of 2-5 (41.6 mg, 0.0424 mmol, 1 eq.), 2-6 (39 mg, 0.0551 mol, 1.3 eq.), DTBMP (21.8 mg, 0.106 mmol, 2.5 eq.), Zn (16.6 mg, 0.254 mmol, 6 eq.), and $Cp_2ZrCl_2$ (24.8 mg, 0.0848 mmol, 2 eq.) were added 5:1 mixture of DMI-EtOAc (0.2 mL) and $NiBr_2$-dtbbpy (7.2 mg, 0.0148 mmol, 35 mol %) at room temperature. After being stirred for 1.5 h at the same temperature, the reaction was removed from the glove box and quenched with sat. $NaHCO_3$ aq. The organic layer was separated and the aqueous layer was extracted with $Et_2O$. The combined organic layer was dried over $Na_2SO_4$, filtered, and concentrated under reduced pressure. The residue was purified by YAMAZEN purification system with neutral silica gel to give 2-7 (51.7 mg, 0.0356 mmol, 84%) as a colorless amorphous solid. (2-7): $[\alpha]^{20}_D$ −59.7 (c 1.0, $CHCl_3$). $^1H$ NMR (600 MHz, $C_6D_6$) δ: 5.20 (1H, s), 5.10 (1H, s), 4.92 (1H, s), 4.84-4.74 (3H, m), 4.68 (1H, d, J=10.6 Hz), 4.52 (1H, ddd, J=10.0, 10.0, 4.1 Hz), 4.35 (1H, m), 4.27 (1H, m), 4.21 (1H, d, J=12.3 Hz), 4.17-4.06 (4H, m), 4.03-3.94 (4H, m), 3.89 (1H, dd, J=6.5, 4.7 Hz), 3.84-3.70 (3H, m), 3.64 (1H, dd, J=6.5, 4.1 Hz), 3.45 (1H, ddd, J=4.7, 4.7, 4.7 Hz), 3.33 (1H, s), 3.19 (1H, dd, J=16.4, 10.0 Hz), 3.14 (1H, dd, J=5.3, 4.1 Hz), 3.07-2.95 (3H, m), 2.84-2.72 (3H, m), 2.61 (1H, dd, J=9.4, 1.8 Hz), 2.45-2.02 (15H, m), 2.02-1.90 (2H, m), 1.83 (1H, m), 1.79-1.66 (6H, m), 1.59 (1H, ddd, J=14.1, 4.7, 4.7 Hz), 1.56-1.37 (6H, m), 1.37-1.27 (10H, m), 1.17 (3H, d, J=7.0 Hz), 1.13 (9H, s), 1.10-1.02 (22H, m), 1.00 (3H, d, J=6.5 Hz), 0.96 (3H, d, J=6.5 Hz), 0.72-0.62 (12H, m) ppm. $^{13}C$ NMR (125 MHz, $C_6D_6$) δ: 206.9, 171.3, 153.0, 152.7, 110.0, 15.0, 103.7, 97.2, 82.4, 81.0, 78.3, 78.0, 77.8, 77.7, 77.6, 76.9, 76.2, 75.5, 74.8, 74.7 (×2), 74.2, 74.0, 73.8, 73.2, 70.4, 69.3, 68.6, 68.5, 67.3, 66.0, 64.7, 63.8, 48.6, 46.7, 46.3, 43.9, 41.3, 39.5, 39.2, 38.5, 37.7, 36.8, 36.6, 36.3, 35.5, 35.3, 32.5, 31.1, 30.7, 30.6, 30.4, 29.5, 29.1, 27.9, 27.7, 23.4, 21.0, 18.6, 18.1, 17.4, 16.4, 7.5, 7.3, 6.0, 5.3 ppm. IR (film): 2955, 2933, 2875, 1723, 1371, 1133, 1097, 1084, 1017 $cm^{-1}$. HRMS (ESI) m/z: $[M+Na]^+$ calcd for $C_{78}H_{128}NaO_{19}Si_3$, 1475.8250; found, 1475.8251.

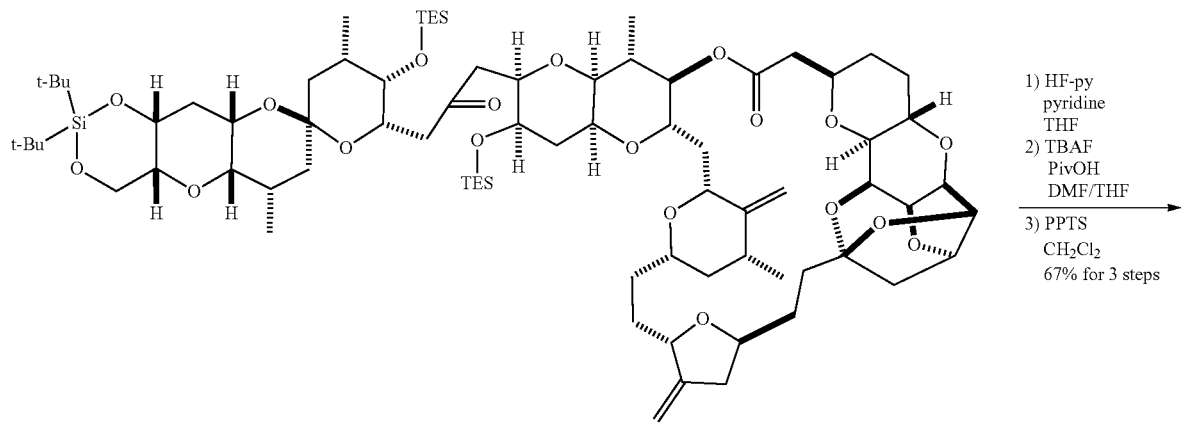

2-7

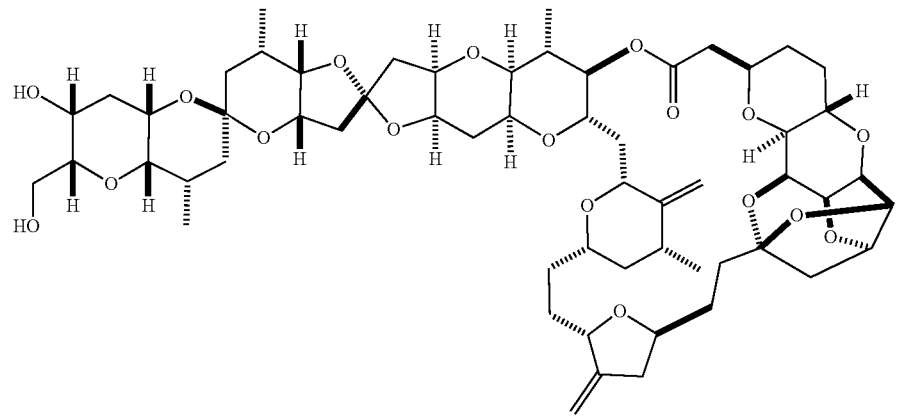

2-11

To a stirred solution of 2-7 (108 mg, 0.0743 mmol, 1 equiv.) in dry THF (7.5 mL, 0.01M) in a plastic tube was added pyridine-buffered pyridinium hydrofluoride solution (0.16 mL, 20 equiv.; freshly prepared from 0.20 mL of pyridinium hydrofluoride available from Aldrich, 0.60 mL of pyridine) at 0° C. After being stirred for 2 hours at the same temperature, the reaction was quenched with sat. aq. $NaHCO_3$ until gas evolution stopped. The aqueous layer was extracted with EtOAc. The combined organic phase was washed with brine, dried over $Na_2SO_4$, and concentrated under reduced pressure. The crude material was used for the next step without further purification. To a stirred solution of crude diol (calculated as 0.0743 mmol, 1 equiv.) in DMF (3.7 mL, 0.02M) was added the buffered TBAF solution (0.37 mL, 5 equiv., freshly prepared by 0.74 mL TBAF solution (1 M in THF) and 38 mg PivOH at room temperature. After being stirred for 4 h at the same temperature, $CaCO_3$ (2.0 g) and DOWEX 50WX8-400 (2.0 g) were added. After being stirred for 1 h at room temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of the crude tetraol (calculated as 0.0743 mmol, 1 eq.) in $CH_2Cl_2$ (3.7 mL, 0.02M) was added PPTS (93.3 mg, 0.371 mmol, 5 equiv.) at room temperature. After being stirred for 2.5 h at the same temperature, the reaction mixture was directly subjected to column chromatography on amino silica gel (100% EtOAc, then 9% MeOH in EtOAc) to give a crude 2-11 with its C38 epimer. The mixture was purified by YAMAZEN purification system with ODS column (Rf gradient: 10% MeCN in $H_2O$ to 100% MeCN) to give 2-11 (53.1 mg, 0.0498 mmol, 67% for 3 steps) as a white solid and C38-epi-2-11 (10.2 mg, 0.0096 mmol, 13% for 3 steps) as a white solid. (2-11): $[\alpha]^{20}_D$ −62.0 (c 0.30, MeOH). $^1$H NMR (600 MHz, $CD_3OD$) δ: 5.06 (1H, s), 5.02 (1H, s), 4.88 (1H, s), 4.81 (1H, s), 4.70 (1H, dd, J=4.5, 4.5 Hz), 4.63 (1H, dd, J=7.8, 4.8 Hz), 4.60 (1H, dd, J=4.2, 4.2 Hz), 4.45 (1H, d, J=12.6 Hz), 4.33 (1H, ddd, J=9.6, 9.6, 4.2 Hz), 4.30 (1H, m), 4.25-4.23 (1H, m), 4.18 (1H, dd, J=6.6, 4.8 Hz), 4.13-4.06 (4H, m), 3.99 (1H, d, J=2.4 Hz), 3.90-3.86 (2H, m), 3.81 (1H, s), 3.72-3.69 (3H, m), 3.61 (1H, d, J=10.8 Hz), 3.41 (1H, dd, J=6.0, 6.6 Hz), 3.22 (1H, ddd, J=6.6, 4.8, 4.8 Hz), 2.98 (1H, dd, J=10.4, 1.5 Hz), 2.82-2.79 (1H, m), 2.56 (1H, dd, J=17.4, 3.6 Hz), 2.45 (1H, dd, J=17.4, 1.8 Hz), 2.40 (1H, dd, J=13.2, 6.0 Hz), 2.38-2.25 (6H, m), 2.22-2.16 (3H, m), 2.11-1.97 (9H, m), 1.94-1.90 (3H, m), 1.86-1.80 (3H, m), 1.74-1.67 (3H, m), 1.60 (1H, ddd, J=12.0, 12.0, 6.0 Hz), 1.51-1.29 (9H, m), 1.11 (3H, d, J=7.8 Hz), 1.06 (3H, d, J=7.8 Hz), 1.05-0.99 (1H, m), 0.95 (3H, d, J=7.2 Hz), 0.94 (3H, d, J=7.2 Hz) ppm. $^{13}$C NMR (125 MHz, $CD_3OD$) δ: 172.8, 153.3, 153.2, 114.8, 111.2, 105.7, 104.7, 98.6, 83.8, 82.4, 81.4, 80.6, 79.1, 78.0, 78.0, 77.9, 77.3, 77.3, 77.2, 76.3, 76.1, 75.8, 75.3, 75.0, 75.0, 74.9, 73.8, 72.7, 69.6, 68.5, 66.3, 65.7, 63.2, 49.4, 45.5, 44.9, 44.8, 41.2, 39.7, 38.2, 38.1, 37.8, 37.4, 37.2, 35.8, 35.4, 33.0, 31.8, 31.2, 31.0, 30.8, 30.1, 29.4, 27.3, 18.4, 18.1, 17.4, 15.8 ppm. FTIR (film): 3476, 2956, 2918, 2850, 1733, 1668, 1589, 1433, 1207, 1134, 1097, 1021 cm$^{-1}$. HRMS (ESI) m/z: [M+Na]$^+$ calcd for $C_{58}H_{82}O_{18}Na$, 1089.5393; found, 1089.5378.

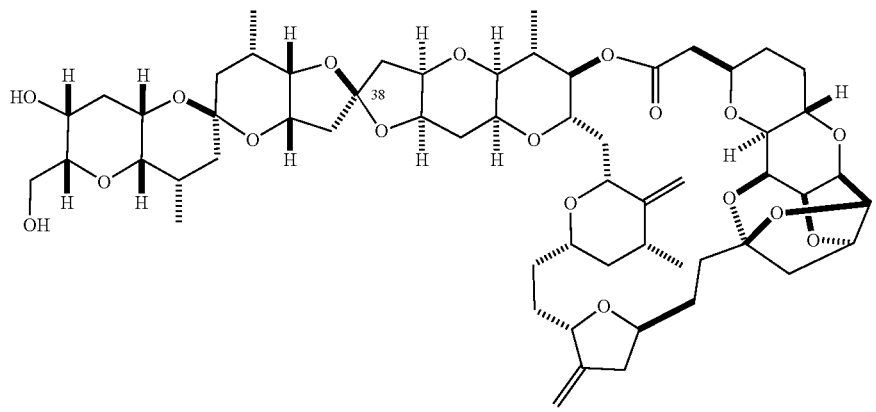

C38-epi-2-11

C38-Epi-2-11:

$[\alpha]^{20}_D$ −68.3 (c 0.20, MeOH). $^1$H NMR (600 MHz, $CD_3OD$) δ: 5.04 (1H, s), 5.00 (1H, s), 4.87 (1H, s), 4.80 (1H, s), 4.72 (1H, dd, J=12.0, 7.2 Hz), 4.70 (1H, dd, J=6.0, 5.4 Hz), 4.60 (1H, dd, J=5.4, 5.4 Hz), 4.43 (1H, d, J=12.0 Hz), 4.36 (1H, ddd, J=12.0, 12.0, 4.8 Hz), 4.27 (1H, m), 4.18-4.05 (6H, m), 4.10 (1H, dd, J=5.4, 1.8 Hz), 3.91-3.84 (3H, m), 3.78 (1H, s), 3.70-3.60 (4H, m), 3.57 (1H, d, J=13.8 Hz), 3.42 (1H, dd, J=7.8, 6.6 Hz), 3.33 (1H, d, J=2.4 Hz), 3.32-3.31 (2H, m), 3.16 (1H, dd, J=10.6, 7.6 Hz), 2.99 (1H, d, J=11.4 Hz), 2.84-2.79 (1H, m), 2.55 (1H, dd, J=20.7, 10.5 Hz), 2.45 (1H, dd, J=20.7, 2.4 Hz), 2.35-1.90 (20H, m), 1.86-1.70 (3H, m), 1.74-1.51 (5H, m), 1.51-1.29 (9H, m), 1.10 (3H, d, J=7.8 Hz), 1.03 (3H, d, J=8.4 Hz), 1.05-0.99 (1H, m), 1.01 (3H, d, J=7.8 Hz), 1.00 (3H, d, J=7.8 Hz) ppm. $^{13}$C NMR (125 MHz, $CD_3OD$) δ: 172.8, 153.3, 152.8, 115.6, 111.3, 105.1, 104.7, 98.4, 83.8, 82.4, 81.5, 79.8, 79.2, 79.0, 78.9, 78.4, 77.9, 77.9, 77.0, 76.5, 76.1, 76.1, 76.0, 75.2, 75.2, 75.0, 74.7, 73.2, 73.2, 69.5, 68.5, 68.3, 66.3, 63.2, 49.5, 45.5, 45.0, 44.8, 41.2, 39.6, 38.7, 38.2, 38.2, 37.5, 37.4, 37.2, 35.4, 35.3, 34.6, 33.3, 31.8, 31.3, 31.0, 30.7, 30.1, 29.2, 27.0, 18.4, 18.3, 17.4, 15.2 ppm. FTIR (film): 3465, 2960, 2918, 2850, 1735, 1668, 1590, 1433, 1210, 1134, 1097, 1022 cm$^{-1}$. HRMS (ESI) m/z: [M+Na]$^+$ calcd for $C_{58}H_{82}O_{18}Na$, 1089.5393; found, 1089.5367. C38-epi-2-11 was epimerized to 2-11 by the following procedure:

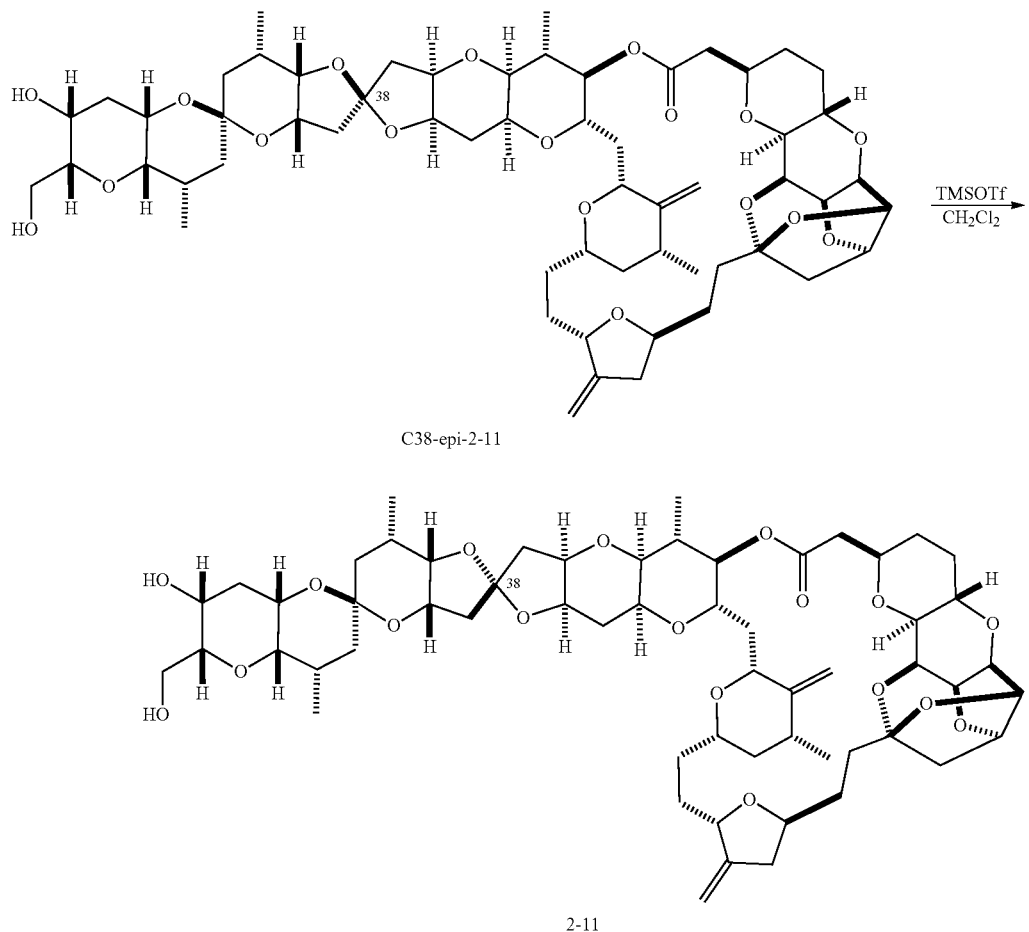

C38-epi-2-11

2-11

To a solution of C38-epi-2-11 (10.1 mg, 0.0095 mmol, 1 eq.) in $CH_2Cl_2$ (4.7 mL) was added TMSOTf (95 μL, 0.525 mmol, excess) at −78° C. After being stirred for 15 min at the same temperature, the reaction was quenched with sat. $NaHCO_3$ aq. After being stirred for 1 h at 0° C., the organic layer was separated and the aqueous layer was extracted with $CH_2Cl_2$. The combined organic layer was dried over $Na_2SO_4$, filtered, and concentrated under reduced pressure. The crude material was purified by YAMAZEN purification system with ODS column (Rf gradient: 10% MeCN in $H_2O$ to 100% MeCN) to give 2-11 (6.9 mg, 0.0065 mmol, 68%) as a white solid.

An exemplary reaction sequence converting Compound (2) to Compound (1) is shown below in Scheme 3. Exemplary experimental procedures are provided below.

Scheme 3

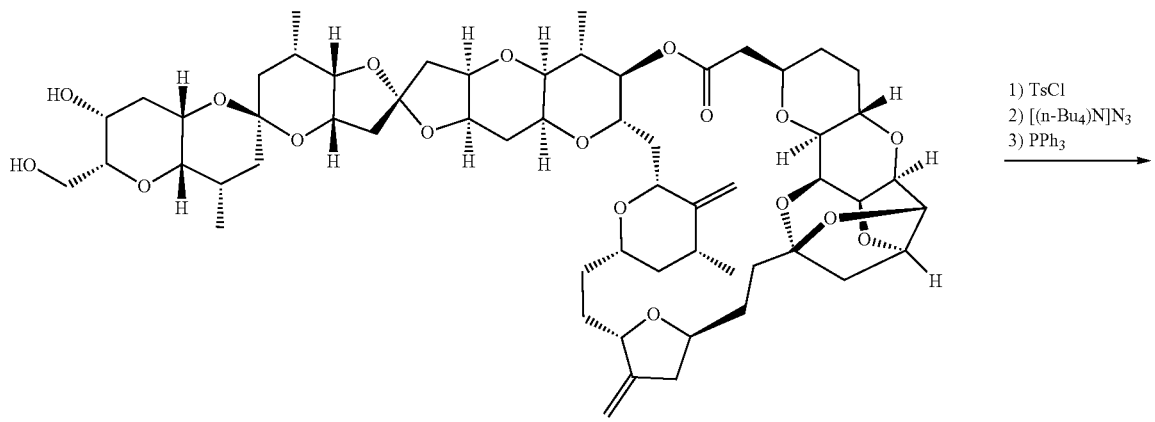

1) TsCl
2) [(n-Bu₄)N]N₃
3) PPh₃

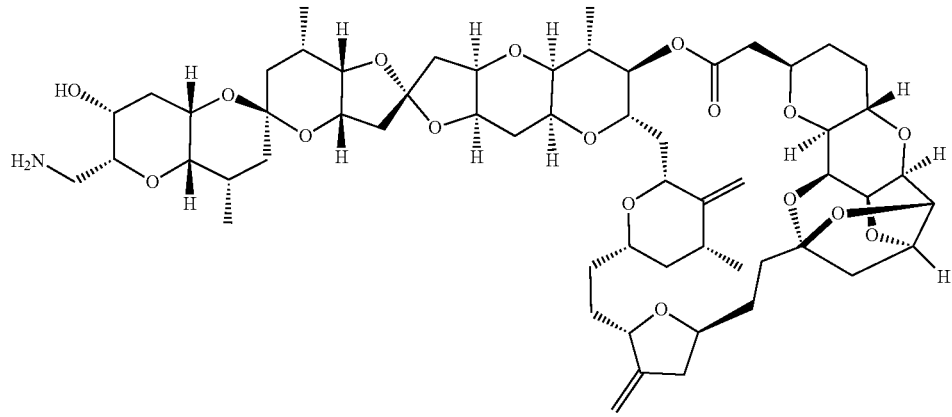
Halichondrin B (17)
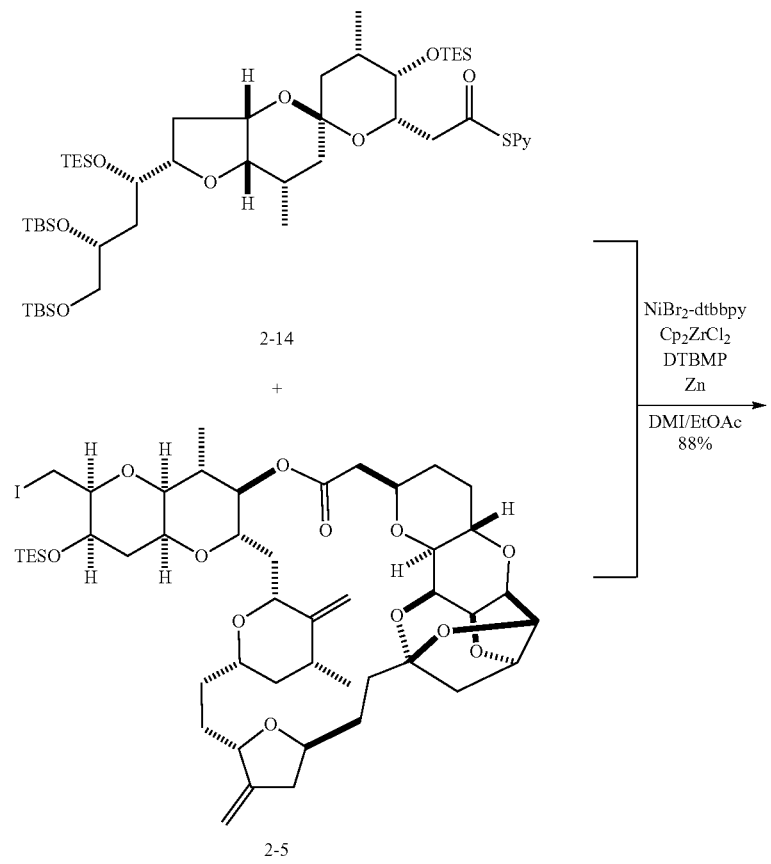

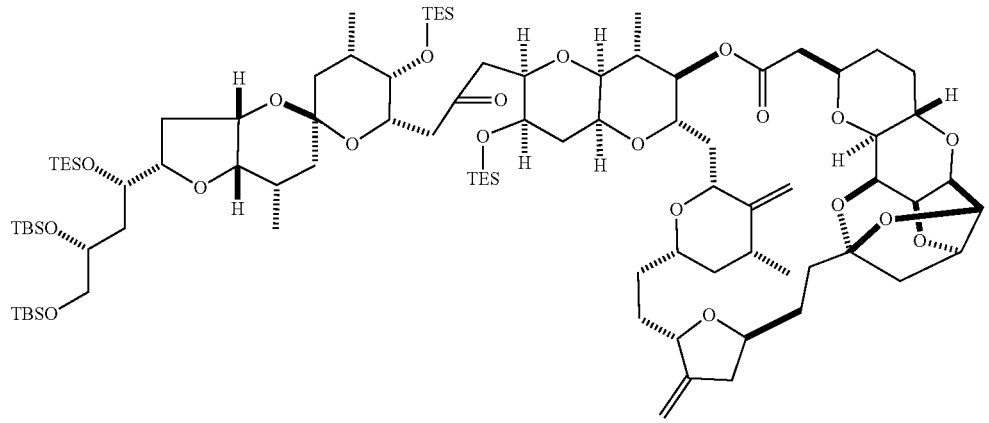

2-S-1

In a glove box, to a solution of iodide 2-5 (200 mg, 0.203 mmol, 1 eq.) and thioester 2-14 (252.5 mg, 0.264 mmol, 1.3 equiv.) in DMI (1.7 mL) and EtOAc (0.34 mL) were added DTBMP (167 mg, 0.816 mmol, 4 eq.), Zn powder (80.0 mg, 1.22 mmol, 6 eq.), $Cp_2ZrCl_2$ (178.4 mg, 0.612 mmol, 3 eq.), and $NiBr_2$-dtbbpy (29.7 mg, 0.062 mmol, 30 mol %) at room temperature. After being stirred for 1.5 h at the same temperature, the reaction mixture was removed from glove box and diluted with EtOAc and sat. $NaHCO_3$ aq. The organic layer was separated and the aqueous layer was extracted with EtOAc. The combined organic layer was dried over $Na_2SO_4$, filtered, and concentrated under reduced pressure. The obtained crude material was purified by YAMAZEN purification system on neutral silica gel to give ketone 2-S-1 (303 mg, 0.178 mmol, 88%) as a white amorphous solid. (2-S-1): $[\alpha]^{20}_D$ −58.3 (c 1.20, $CHCl_3$). $^1H$ NMR (600 MHz, $C_6D_6$) δ: 5.21 (1H, s), 5.11 (1H, s), 4.94 (1H, s), 4.85 (1H, d, J=7.2 Hz), 4.81-4.78 (2H, m), 4.69 (1H, d, J=10.2 Hz), 4.54-4.51 (2H, m), 4.36 (1H, d, J=7.8 Hz), 4.27 (1H, s), 4.24 (1H, m), 4.18-4.13 (2H, m), 4.10-4.07 (2H, m), 3.93-3.88 (2H, m), 3.83-3.81 (3H, m), 3.78-3.75 (2H, m), 3.63 (1H, dd, J=6.0, 4.2 Hz), 3.44 (2H, m), 3.33 (1H, s), 3.19 (1H, dd, J=16.2, 10.2 Hz), 3.16 (1H, d, J=5.4 Hz), 3.11-3.02 (2H, m), 2.78 (1H, dd, J=16.8, 7.2 Hz), 2.60 (1H, d, J=9.6 Hz), 2.49-2.43 (1H, m), 2.41-2.31 (5H, m), 2.28-2.24 (3H, m), 2.19-1.96 (10H, m), 1.93 (1H, d, J=13.2 Hz), 1.87-1.64 (7H, m), 1.61 (1H, ddd, J=15.0, 4.8, 4.8 Hz), 1.56-1.43 (7H, m), 1.40 (1H, dd, J=13.2, 4.8 Hz), 1.33 (1H, dd, J=9.6, 9.6 Hz), 1.18 (3H, d, J=6.6 Hz), 1.15 (3H, d, J=7.2 Hz), 1.12-1.04 (27H, m), 1.10 (9H, s), 1.04 (9H, s), 1.00 (3H, d, J=6.6 Hz), 0.96 (3H, d, J=6.0 Hz), 0.78 (6H, q, J=8.0 Hz), 0.69-0.65 (12H, m), 0.28 (6H, s), 0.150 (3H, s), 0.148 (3H, s) ppm. $^{13}C$ NMR (125 MHz, $C_6D_6$) δ: 206.8, 171.3, 153.0, 152.7, 110.0, 104.9, 103.8, 97.0, 82.4, 81.5, 81.0, 80.4, 78.4, 78.1, 77.6, 76.9, 75.5, 74.9, 74.7, 74.1, 74.0, 73.8, 72.9, 72.0, 71.8, 71.5, 70.5, 69.9, 68.4, 68.3, 65.9, 64.6, 48.6, 46.8, 46.3, 43.9, 41.3, 39.5, 39.3, 38.5, 38.2, 37.8, 36.4, 35.5, 35.4, 35.3, 32.5, 31.3, 30.7, 30.6, 29.0, 26.6, 26.3 (×6), 26.3 (×6), 18.7, 18.6, 18.5, 18.4, 18.1, 16.4, 7.4 (×6), 7.4 (×6), 7.3 (×6), 6.0 (×3), 5.7 (×3), 5.3 (×3), −4.0, −4.2, −5.1, −5.2 ppm. FTIR (film): 3450, 2936, 2864, 1734, 1642, 1547, 1147, 1112, 1055, 1021, 997 $cm^{-1}$. HRMS (ESI) m/z: $[M+Na]^+$ calcd for $C_{90}H_{158}O_{20}Si_5Na$, 1722.0085; found, 1722.0061.

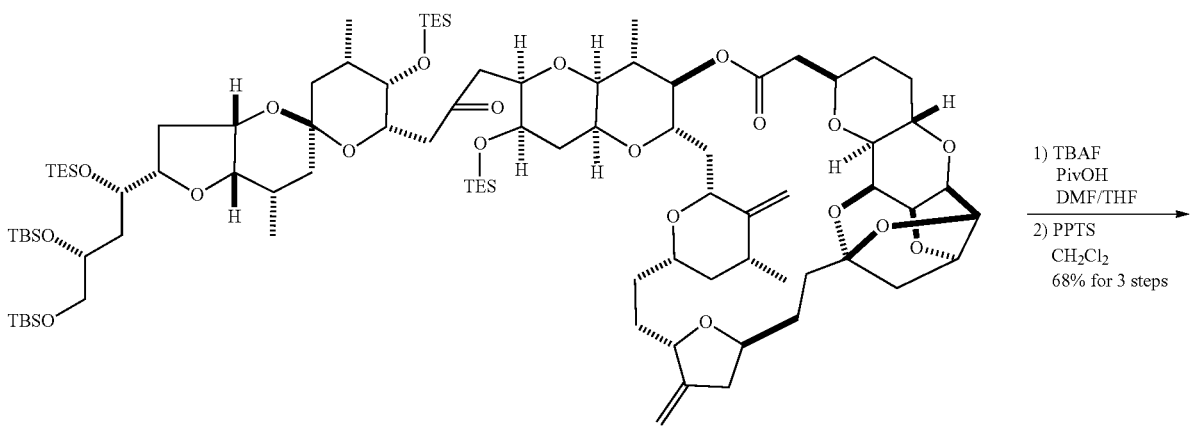

2-S-2

1) TBAF
PivOH
DMF/THF

2) PPTS
$CH_2Cl_2$

68% for 3 steps

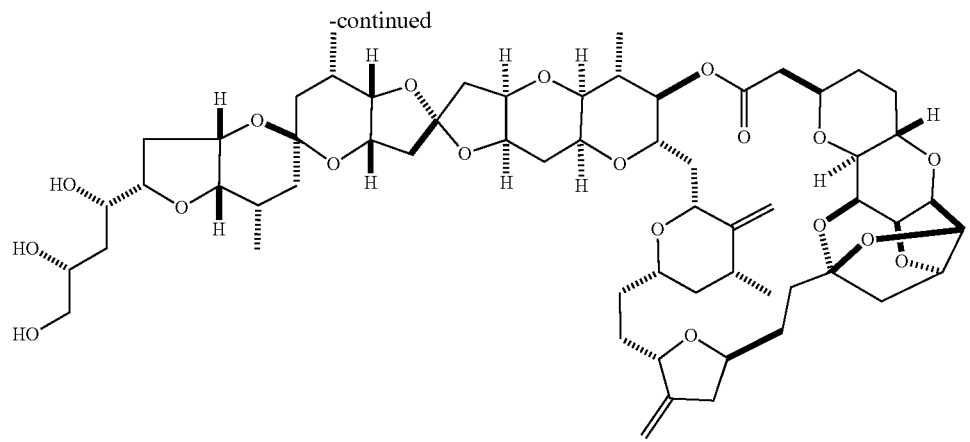

2-17

A buffered TBAF solution was prepared by mixing TBAF solution (TCI #T1125; 3.52 mL of 1 M in THF, 3.52 mmol, 10 eq.) and PivOH (180 mg, 1.76 mmol, 5 eq.). To a stirred solution of 2-S-1 (303 mg, 0.178 mmol, 1 equiv.) in DMF (8.8 mL) was added the buffered TBAF solution at room temperature. After being stirred for 4 h at the same temperature, $CaCO_3$ (6.0 g) and DOWEX 50WX8-400 (6.0 g) were added. After being stirred for 2 h at room temperature, the resulted mixture was diluted with EtOAc and filtered through a pad of Celite. The filter cake was washed with EtOAc thoroughly. The filtrate was concentrated under reduced pressure to give a crude material, which was used in the next step without further purification. To a stirred solution of the crude material (calculated as 0.178 mmol, 1 eq.) in $CH_2Cl_2$ (17.6 mL) was added PPTS (221.8 mg, 0.882 mmol, 5 eq.) at room temperature. After being stirred for 4 h at the same temperature, the reaction mixture was directly subjected to column chromatography on amino silica gel (100% EtOAc, then 9% MeOH in EtOAc) to give a crude 2-17 with its C38 epimer. The mixture was purified by YAMAZEN purification system with ODS column (Rf gradient: 10% MeCN in $H_2O$ to 100% MeCN) to give halichondrin B 17 (133.0 mg, 0.120 mmol, 68% for 2 steps) as a white crystalline solid and C38-epi-17 (25.0 mg, 0.0225 mmol, 13% for 2 steps) as a white solid. Halichondrin B (17): $[\alpha]^{20}_D$ −62.3 (c 1.00, MeOH). MP: 164-166° C. (recrystallized from Hexanes-$CH_2Cl_2$). $^1$H NMR (600 MHz, $CD_3OD$) δ: 5.07 (1H, d, J=1.8 Hz), 5.02 (1H, d, J=1.8 Hz), 4.89 (1H, s), 4.81 (1H, s), 4.70 (1H, dd, J=4.8, 3.6 Hz), 4.63 (1H, dd, J=7.2, 4.8 Hz), 4.60 (1H, dd, J=4.2, 4.2 Hz), 4.45 (1H, d, J=10.8 Hz), 4.33 (1H, ddd, J=9.6, 9.6, 4.2 Hz), 4.30 (1H, m), 4.25-4.23 (1H, m), 4.18 (1H, dd, J=6.6, 4.2 Hz), 4.13-4.05 (6H, m), 3.99 (1H, ddd, J=9.6, 4.8, 4.8 Hz), 3.90-3.85 (3H, m), 3.71 (1H, dd, J=10.2, 10.2 Hz), 3.70 (1H, m), 3.61 (1H, d, J=7.6 Hz), 3.56 (1H, s), 3.53 (1H, dd, J=10.4, 4.2 Hz), 3.47 (1H, dd, J=10.8, 6.0 Hz), 3.22 (1H, dd, J=6.6, 4.8 Hz), 2.98 (1H, dd, J=9.6, 2.4 Hz), 2.82-2.78 (1H, m), 2.56 (1H, dd, J=17.4, 9.6 Hz), 2.45 (1H, dd, J=17.4, 2.4 Hz), 2.39 (1H, dd, J=13.8, 5.7 Hz), 2.38-2.22 (7H, m), 2.22-2.16 (2H, m), 2.09-1.97 (7H, m), 1.86-1.81 (3H, m), 1.77-1.67 (4H, m), 1.62-1.58 (2H, m), 1.57-1.29 (9H, m), 1.10 (3H, d, J=6.6 Hz), 1.06 (3H, d, J=6.6 Hz), 1.05-0.99 (1H, m), 1.02 (3H, d, J=6.6 Hz), 0.97 (3H, d, J=6.6 Hz) ppm. $^{13}$C NMR (125 MHz, $CD_3OD$) δ: 172.8, 153.3, 153.2, 114.8, 111.3, 105.7, 104.8, 98.4, 83.8, 82.4, 81.3, 81.3, 80.7, 79.1, 78.1, 77.9, 77.4, 77.2, 76.3, 76.1, 75.8, 75.4, 75.0, 75.0, 74.9, 73.7, 73.3, 73.1, 73.0, 71.6, 69.6, 67.2, 65.7, 49.4, 45.5, 44.9, 44.9, 41.2, 39.7, 37.9, 37.9, 37.8, 37.5, 37.5, 37.2, 36.3, 35.8, 33.0, 31.8, 31.3, 31.0, 30.8, 29.4, 27.1, 27.1, 18.4, 18.3, 18.1, 15.8 ppm. FTIR (film): 3460, 2936, 2864, 1736, 1642, 1557, 1167, 1122, 1105, 1054, 1041, 1021, 997 $cm^{-1}$. HRMS (ESI) m/z: $[M+Na]^+$ calcd for $C_{60}H_{86}O_{19}Na$, 1133.5656; found, 1133.5651.

C38-epi-17

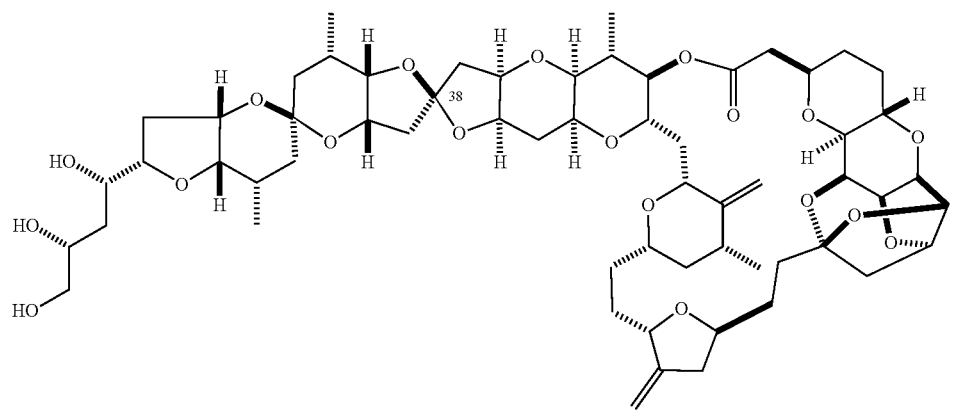

C38-Epi-Halichondrin B:

[α]$^{20}_D$ −66.0 (c 1.00, MeOH). $^1$H NMR (600 MHz, CD$_3$OD) δ: 5.04 (1H, s), 5.00 (1H, s), 4.87 (1H, s), 4.81 (1H, s), 4.72 (1H, dd, J=10.2, 6.6 Hz), 4.70 (1H, dd, J=4.2, 4.2 Hz), 4.60 (1H, dd, J=4.8, 4.8 Hz), 4.43 (1H, d, J=10.8 Hz), 4.37 (1H, ddd, J=12.0, 12.0, 4.8 Hz), 4.27 (1H, m), 4.19-4.06 (8H, m), 3.99 (1H, ddd, J=9.6, 5.4, 4.2 Hz), 3.91-3.82 (4H, m), 3.78 (1H, ddd, J=14.4 4.8, 4.2 Hz), 3.64-3.56 (3H, m), 3.53 (1H, dd, J=11.4, 4.5 Hz), 3.46 (1H, dd, J=11.4, 6.0 Hz), 3.34 (2H, m), 3.17 (1H, dd, J=8.7, 6.3 Hz), 2.99 (1H, dd, J=9.6, 1.8 Hz), 2.84-2.79 (1H, m), 2.55 (1H, dd, J=16.8, 8.4 Hz), 2.47 (1H, dd, J=16.8, 2.4 Hz), 2.35-1.93 (20H, m), 1.86-1.82 (2H, m), 1.79-1.70 (5H, m), 1.67-1.33 (12H, m), 1.10 (3H, d, J=6.6 Hz), 1.04 (3H, d, J=8.4 Hz), 1.05-0.99 (1H, m), 1.02 (3H, d, J=7.8 Hz), 1.00 (3H, d, J=6.6 Hz) ppm. $^{13}$C NMR (125 MHz, CD$_3$OD) δ: 172.8, 153.3, 152.8, 115.5, 111.3, 105.1, 104.7, 98.2, 83.8, 82.4, 81.3, 81.1, 79.9, 79.2, 78.9, 78.9, 78.4, 77.9, 77.9, 76.5, 76.1, 76.1, 76.0, 75.2, 75.2, 74.7, 73.5, 73.3, 73.1, 73.0, 71.7, 69.5, 68.2, 67.1, 49.9, 45.6, 45.0, 44.7, 41.2, 39.6, 38.3, 38.2, 38.1, 37.5, 37.5, 37.2, 36.2, 35.4, 33.3, 31.8, 31.3, 30.9, 30.5, 30.2, 29.3, 27.1, 26.8, 18.4, 18.3, 15.2 ppm. FTIR (film): 3460, 2936, 2864, 1736, 1642, 1557, 1167, 1122, 1105, 1054, 1041, 1021, 997 cm$^{-1}$. HRMS (ESI) m/z: [M+Na]$^+$ calcd for C$_{60}$H$_{86}$O$_{19}$Na, 1133.5656; found, 1133.5651. C38-epi-17 was epimerized to halichondrin B (17) by the following procedure:

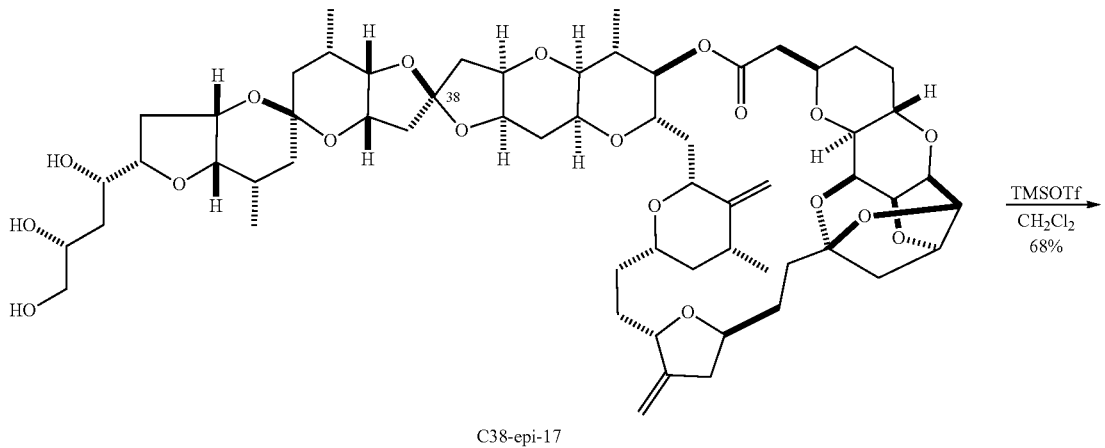

C38-epi-17

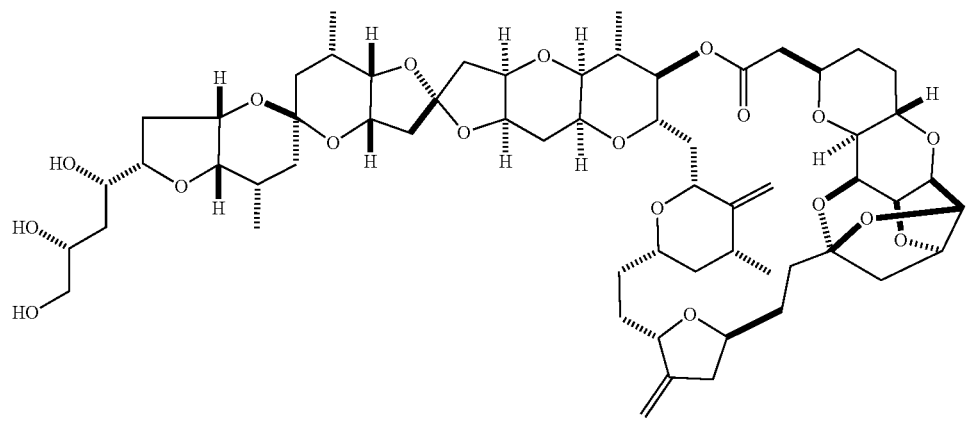

17

To a solution of C38-epi-17 (25.0 mg, 0.0225 mmol, 1 eq.) in CH$_2$Cl$_2$ (11.2 mL) was added TMSOTf (0.225 mL, 0.719 mmol, excess) at −78° C. After being stirred for 15 min, the reaction was quenched with sat. NaHCO$_3$ aq. After being stirred for 1 h at 0° C., the organic layer was separated and the aqueous layer was extracted with CH$_2$Cl$_2$. The combined organic layer was dried over Na$_2$SO$_4$, filtered, and concentrated under reduced pressure. The crude material was purified by YAMAZEN purification system with ODS column (Rf gradient: 10% MeCN in H$_2$O to 100% MeCN) to give halichondrin B (17) (17.1 mg, 0.0154 mmol, 68%) as a colorless solid.

Norhalichondrin B (18)

0.612 mmol, 6 eq.), Cp$_2$ZrCl$_2$ (89.4 mg, 0.306 mmol, 3 eq.), and NiBr$_2$-dtbbpy (14.9 mg, 0.0306 mmol, 30 mol %) at room temperature. After being stirred for 1.5 h at the same temperature, the reaction mixture was removed from glove box and diluted with Et$_2$O and sat. NaHCO$_3$ aq. The organic layer was separated and the aqueous layer was extracted with Et$_2$O. The combined organic layer was dried over Na$_2$SO$_4$, filtered, and concentrated under reduced pressure. The obtained crude material was purified by flash column chromatography on neutral silica gel (0%, 15%, 25% EtOAc in Hexanes) to give ketone 2-S-2 (125.7 mg, 0.0856 mmol, 84%) as a colorless amorphous solid. (2-S-2): [ ]$^{20}_D$ −68.4 (c 1.00, CHCl$_3$). $^1$H NMR (600 MHz, C$_6$D$_6$) δ: 5.21 (1H, s),

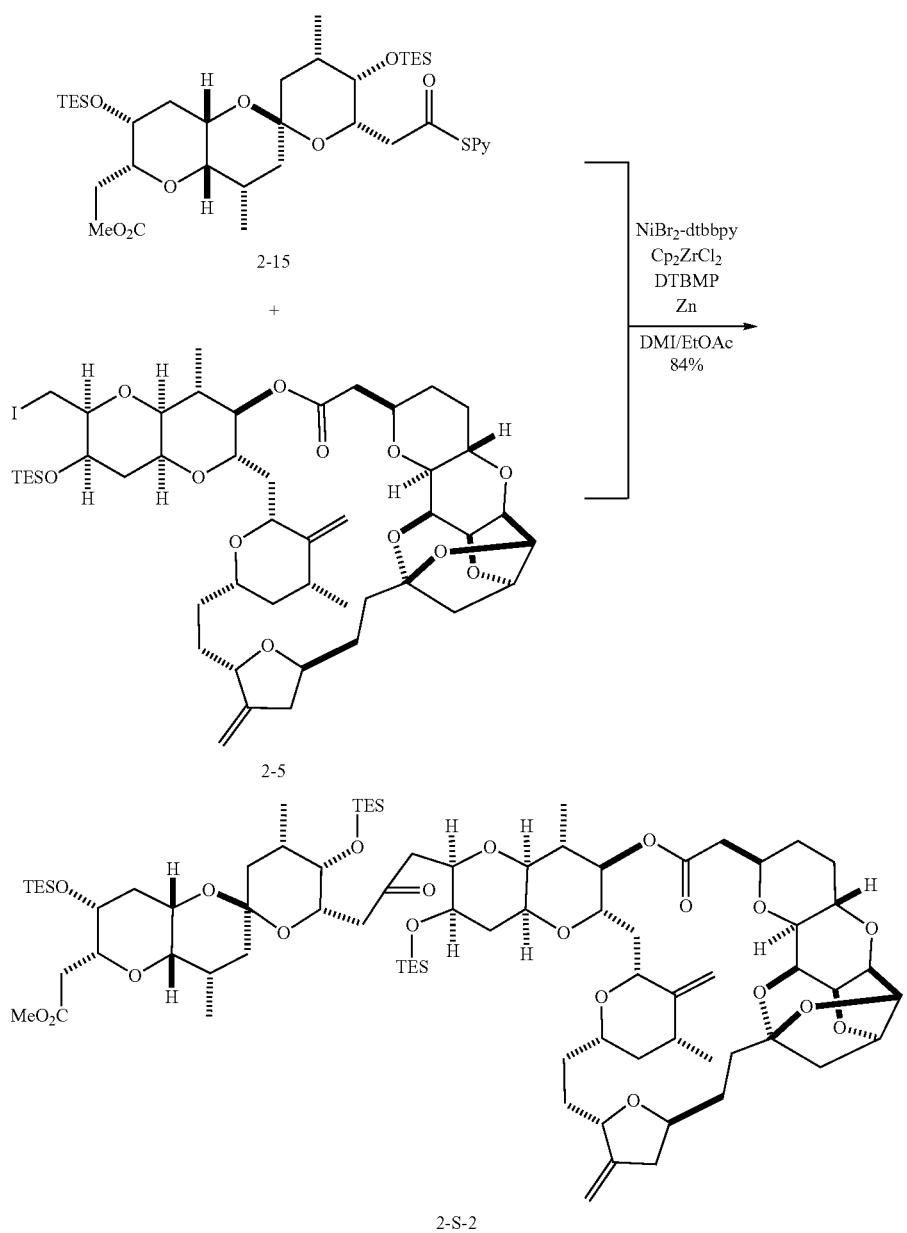

In a glove box, to a solution of iodide 2-5 (100 mg, 0.102 mmol, 1 eq.) and thioester 2-16 (95.5 mg, 0.132 mmol, 1.3 eq.) in DMI (0.85 mL) and EtOAc (0.17 mL) were added DTBMP (83.8 mg, 0.408 mmol, 4 eq.), Zn powder (40.0 mg, 5.11 (1H, s), 4.94 (1H, s), 4.85 (1H, t, J=6.6 Hz), 4.81-4.77 (2H, m), 4.69 (1H, d, J=10.2 Hz), 4.52 (1H, ddd, J=9.8, 9.8, 4.2 Hz), 4.36 (1H, d, J=9.6 Hz), 4.27 (1H, s), 4.14 (1H, dd, J=4.2, 4.2 Hz), 4.11-4.06 (2H, m), 4.03-3.97 (3H, m), 3.89

(1H, dd, J=5.7, 5.7 Hz), 3.84-3.72 (4H, m), 3.78-3.68 (5H, m), 3.64 (1H, dd, J=6.3, 3.9 Hz), 3.59 (1H, brs), 3.45 (1H, q, J=4.0 Hz), 3.38 (3H, s), 3.37 (1H, s), 3.20-3.14 (2H, m), 3.13 (1H, s), 3.07 (1H, dd, J=17.8, 6.0 Hz), 2.99 (1H, dd, J=17.8, 6.0 Hz), 2.84 (1H, dd, J=14.4, 7.8 Hz), 2.81-2.75 (2H, m), 2.61 (1H, d, J=10.2 Hz), 2.58 (1H, dd, J=14.8, 5.4 Hz), 2.42-2.21 (7H, m), 2.21-2.06 (5H, m), 1.99 (1H, dd, J=12.6, 12.6 Hz), 1.93 (1H, d, J=13.2 Hz), 1.89-1.82 (1H, m), 1.79-1.64 (3H, m), 1.62-1.30 (9H, m), 1.18 (3H, d, J=6.6 Hz), 1.12-1.04 (31H, m), 1.01 (3H, d, J=6.6 Hz), 0.98 (3H, d, J=6.6 Hz), 0.70-0.61 (18H, m) ppm. $^{13}$C NMR (125 MHz, $C_6D_6$) δ: 206.9, 171.7, 171.3, 153.0, 152.6, 110.0, 104.9, 103.7, 96.9, 82.4, 81.0, 78.3, 78.0, 77.7, 77.2, 76.9, 76.5, 76.1, 75.5, 74.8, 74.70, 74.67, 74.1, 74.0, 73.8, 73.0, 70.3, 69.6, 68.4, 65.9, 65.7, 64.6, 64.5, 50.9, 48.6, 46.8, 46.3, 43.9, 41.3, 39.5, 39.3, 38.6, 37.5, 36.3, 35.5, 35.4, 32.5, 31.1, 31.0, 30.7, 30.6, 29.2, 29.0, 26.2, 18.6, 18.1, 17.2, 16.4, 7.4, 7.28, 7.25, 6.0, 5.4, 5.3 ppm; FTIR (film): 2954, 2921, 2876, 1737, 1458, 1436, 1372, 1287, 1262, 1239, 1207, 1187, 1154, 1073, 740, 728 cm$^{-1}$. HRMS (ESI) m/z: [M+Na]$^+$ calcd for $C_{78}H_{128}O_{20}Si_3Na$, 1491.8204; found, 1491.8181.

A buffered TBAF solution was prepared by mixing TBAF solution (TCI #T1125; 0.86 mL of 1 M in THF, 0.86 mmol, 10 eq.) and PivOH (43.9 mg, 0.430 mmol, 5 eq.). To a stirred solution of ketone 2-S-2 (125.7 mg, 0.0856 mmol, 1 eq.) in DMF (4.3 mL) was added the buffered TBAF solution at room temperature. After being stirred for 6 h at the same temperature, $CaCO_3$ (2.4 g) and DOWEX 50WX8-400 (2.4 g) were added after diluting with 10 mL EtOAc. After being stirred for 1 h at room temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of the crude tetraol (calculated as 0.0856 mmol, 1 eq.) in $CH_2Cl_2$ (8.5 mL) was added PPTS (86.4 mg, 0.344 mmol, 4 eq.) at room temperature. After being stirred for 1 h at the same temperature, the reaction mixture was directly subjected to column chromatography on amino silica gel ($CH_2Cl_2$ then 25%, 50%, 75%, then 100% EtOAc in Hexanes then 2% MeOH in EtOAc) to give a crude Norhalichondrin B methyl ester with its C38

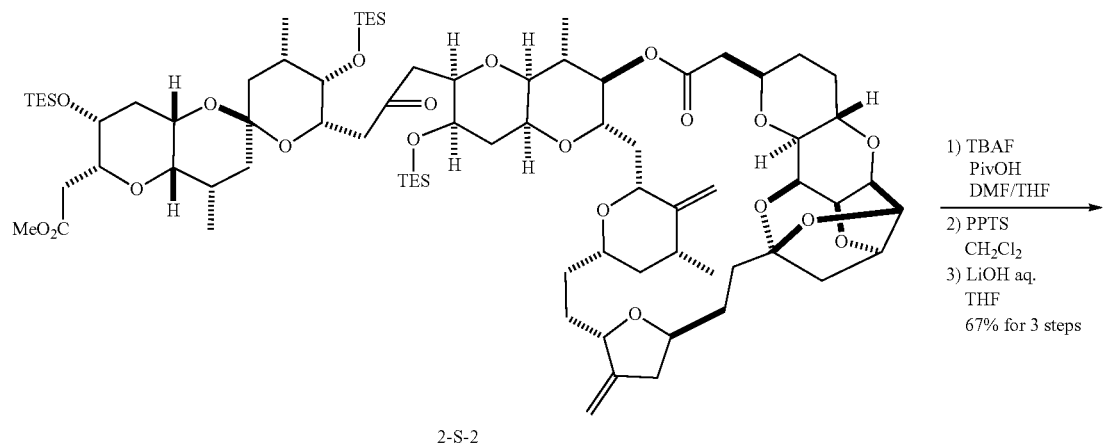

2-S-2

1) TBAF
   PivOH
   DMF/THF
2) PPTS
   $CH_2Cl_2$
3) LiOH aq.
   THF
67% for 3 steps

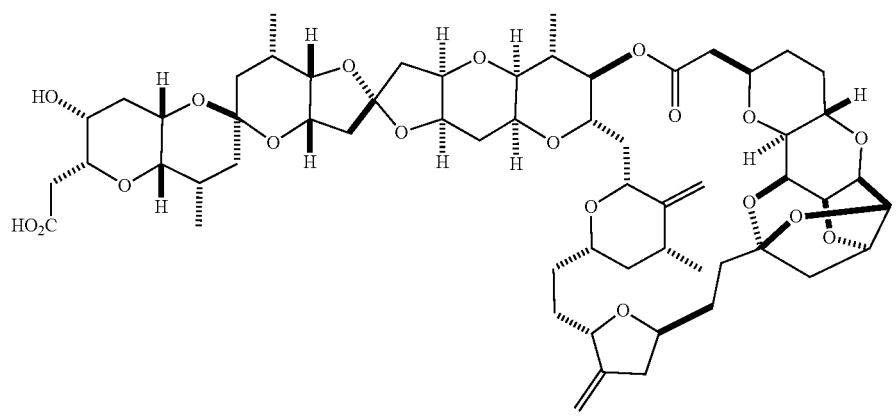

epimer. The compound was used in the next step after concentration without further purification.

To a stirred solution of the crude methyl ester (calculated as 0.0856 mmol, 1 eq.) in THF (10 mL) was added 1M LiOH aq. (3.3 mL) at room temperature.[3] After being stirred for 2 h at the same temperature, the reaction mixture was diluted with 6.6 mL of water. The THF was then removed from the mixture by evaporator. After the reaction was cooled down to 0° C., 1 M HCl aq. (3.3 mL) was added and the reaction mixture was allowed for further 2 min stirring. The resulting mixture was extracted by EtOAc. The combined organic layer was dried over $Na_2SO_4$, filtered, and concentrated under reduced pressure. The resulting mixture was purified by YAMAZEN purification system with ODS column (Rf gradient: 10% MeCN in $H_2O$ to 100% MeCN) to give Norhalichondrin B (18) (62.4 mg, 0.0570 mmol, 67% for 3 steps) as a colorless solid and 38-epi-Norhalichondrin B (C38-epi-18) (8.4 mg, 0.0077 mmol, 9% for 3 steps) as a colorless solid. Norhalichondrin B (18): $[\alpha]^{20}_D$ −54.6 (c 1.00, MeOH). $^1$H NMR (600 MHz, $CD_3OD$) δ: 5.06 (1H, d, J=1.5 Hz), 5.01 (1H, d, J=1.5 Hz), 4.88 (1H, s), 4.81 (1H, d, J=1.5 Hz), 4.70 (1H, t, J=4.0 Hz), 4.63 (1H, dd, J=7.8, 4.7 Hz), 4.60 (1H, t, J=4.0 Hz), 4.45 (1H, d, J=9.6 Hz), 4.32 (1H, td, J=10.2, 4.6 Hz), 4.31-4.29 (1H, m), 4.24 (1H, ddd, J=11.2, 4.2, 1.8 Hz), 4.18 (1H, dd, J=6.6, 4.8 Hz), 4.14-4.09 (3H, m), 4.07 (1H, dd, J=9.6, 9.3 Hz), 3.99 (1H, dd, J=5.8, 2.4 Hz), 3.91-3.85 (2H, m), 3.82-3.78 (2H, m), 3.74-3.69 (2H, m), 3.61 (1H, d, J=10.4 Hz), 3.59-3.56 (1H, m), 3.30 (1H, m), 3.22 (1H, dd, J=6.6, 5.1 Hz), 2.98 (1H, dd, J=9.6, 1.8 Hz), 2.81 (1H, ddd, J=16.0, 8.0, 2.1 Hz), 2.59 (1H, dd, J=15.0, 7.8 Hz), 2.57-2.52 (2H, m), 2.45 (1H, dd, J=17.6, 1.8 Hz), 2.40 (1H, dd, J=13.2, 6.2 Hz), 2.34-2.32 (2H, m), 2.32-2.24 (4H, m), 2.21-2.15 (3H, m), 2.13-1.93 (8H, m), 1.87-1.79 (2H, m), 1.76-1.71 (3H, m), 1.70-1.66 (5H, m), 1.64-1.57 (1H, m), 1.56-1.47 (4H, m), 1.46-1.29 (5H, m), 1.10 (3H, d, J=6.6 Hz), 1.06 (3H, d, J=7.0 Hz), 1.02 (1H, d, J=12.0 Hz), 0.98 (3H, d, J=7.2 Hz), 0.95 (3H, d, J=7.2 Hz) ppm. $^{13}$C NMR (150 MHz, $CD_3OD$) δ: 172.8 (2C), 153.3, 153.2, 114.7, 111.2, 105.6, 104.8, 98.5, 83.8, 82.4, 80.6, 79.0, 78.1, 77.90, 77.85, 77.76, 77.4, 77.23, 77.18, 76.3, 76.1, 75.8, 75.4, 75.02, 74.98, 74.9, 73.7, 72.7, 69.6, 68.0, 67.8, 65.8, 49.4, 45.4, 44.9, 44.7, 41.2, 39.8, 38.22, 38.20, 38.0, 37.8, 37.5, 37.2, 35.7, 35.5, 33.0, 31.8, 31.3, 31.0, 30.8, 30.0, 29.4, 27.3, 18.4, 18.1, 17.3, 15.8 ppm. FTIR (film): 3480, 2926, 2873, 2853, 1736, 1676, 1565, 1395, 1334, 1265, 1207, 1188, 1152, 1134, 1118, 1086, 1072, 1045, 1020, 996 cm$^{-1}$. HRMS (ESI) m/z: [M+Na]$^+$ calcd for $C_{59}H_{82}O_{19}Na$, 117.5348; found 1117.5292.

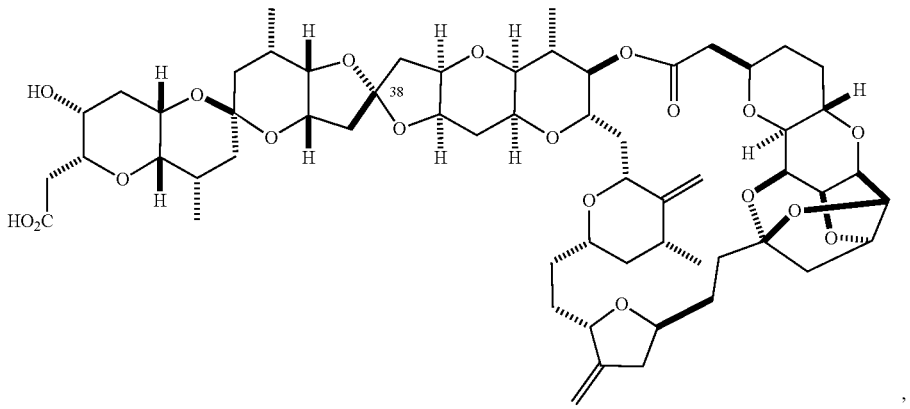

C38-epi-18

38-Epi-Norhalichondrin B (C38-Epi-18):
$[\alpha]^{20}_D$ −69.7 (c 0.400, MeOH). $^1$H NMR (600 MHz, $CD_3OD$) δ: 5.04 (1H, d, J=1.5 Hz), 4.96 (1H, d, J=1.5 Hz), 4.87 (1H, d, J=1.5 Hz), 4.80 (1H, s), 4.74-4.68 (2H, m), 4.60 (1H, t, J=4.5 Hz), 4.43 (1H, d, J=9.6 Hz), 4.37 (1H, td, J=10.2, 4.6 Hz), 4.30-4.25 (1H, m), 4.20-4.04 (4H, m), 4.01 (1H, dd, J=5.8, 2.4 Hz), 3.91-3.83 (2H, m), 3.80 (1H, t, J=7.8 Hz), 3.75 (1H, brs), 3.65-3.55 (2H, m), 3.34 (1H, m), 3.17 (1H, dd, J=6.6, 5.0 Hz), 2.99 (1H, dd, J=9.6, 1.8 Hz), 2.82 (1H, ddd, J=16.0, 8.0, 2.1 Hz), 2.63-2.51 (2H, m), 2.48 (1H, dd, J=15.0, 7.8 Hz), 2.36-2.24 (4H, m), 2.23-2.13 (4H, m), 2.13-1.92 (5H, m), 2.47 (1H, dd, J=17.6, 1.8 Hz), 2.40 (1H, dd, J=13.2, 6.2 Hz), 2.34-2.32 (2H, m), 2.32-2.24 (4H, m), 2.21-2.15 (2H, m), 2.13-1.93 (6H, m), 1.82 (1H, td, J=12.0, 2.0 Hz), 1.77 (1H, d, J=12.0 Hz), 1.72 (1H, d, J=12.0 Hz), 1.69-1.60 (2H, m), 1.59-1.47 (3H, m), 1.47-1.34 (4H, m), 1.10 (3H, d, J=6.6 Hz), 1.06 (1H, d, J=12.0 Hz), 1.04 (3H, d, J=7.0 Hz), 1.00 (3H, d, J=7.2 Hz), 0.97 (3H, d, J=7.2 Hz) ppm. $^{13}$C NMR (150 MHz, $CD_3OD$) δ: 172.9 (2C), 153.3, 152.9, 115.6, 111.4, 105.1, 104.7, 98.4, 83.8, 82.4, 79.9, 79.2, 79.0, 78.4, 78.0, 77.9, 77.1, 76.5, 76.1, 76.0, 75.2, 74.8, 73.3, 73.2, 69.5, 68.3, 68.0, 67.9, 45.6, 45.0, 44.7, 41.2, 38.9, 38.7, 38.3, 38.2, 37.5, 37.2, 35.5, 33.3, 31.8, 31.3, 31.0, 30.2, 30.0, 29.3, 27.0, 18.4, 18.3, 17.4, 15.2 ppm. FTIR (film): HRMS (ESI) m/z: [M+Na]$^+$ calcd for $C_{59}H_{82}O_{19}Na$, 117.5348; found 1117.5292. C38-epi-18 was epimerized to Norhalichondrin B (18) by the following procedure:

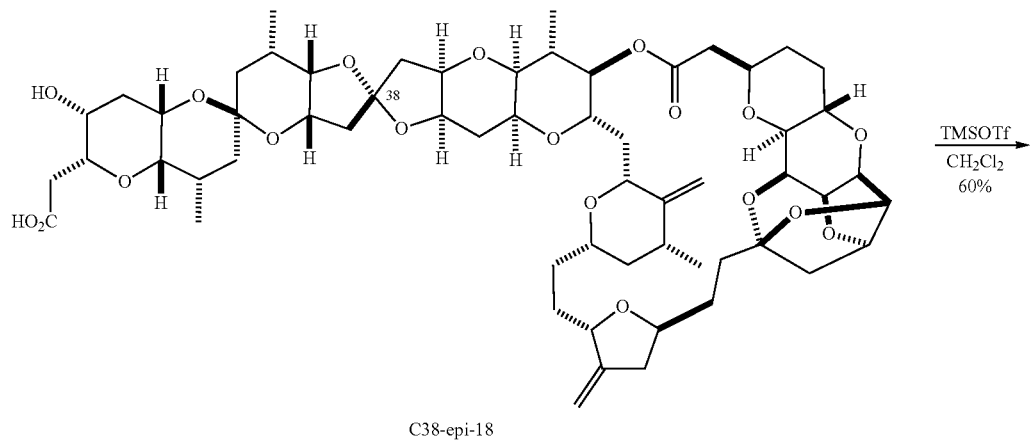

C38-epi-18

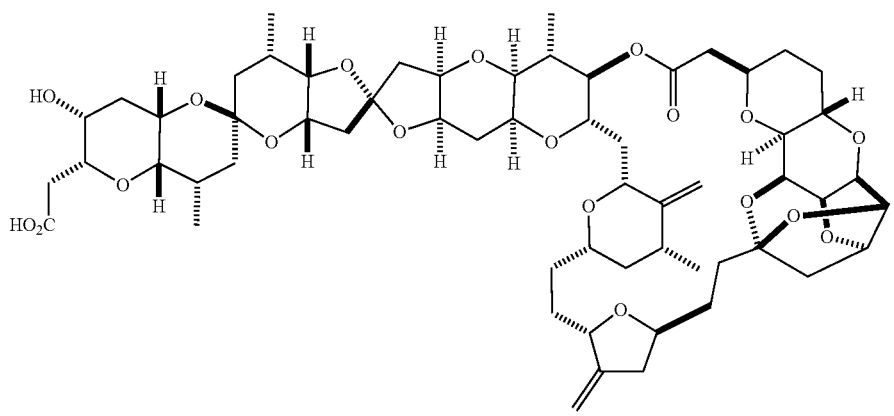

18

To a solution of C38-epi-18 (8.4 mg, 0.0077 mmol, 1 eq.) in $CH_2Cl_2$ (3 mL) was added TMSOTf (0.07 mL, 0.385 mmol, excess) at −78° C. After being stirred for 15 min at the same temperature, the reaction was quenched with sat. $NaHCO_3$ aq. After being stirred for 1 h at 0° C., the organic layer was separated and the aqueous layer was extracted with $CH_2Cl_2$. The combined organic layer was dried over $Na_2SO_4$, filtered, and concentrated under reduced pressure. The crude material was purified by YAMAZEN purification system with ODS column (Rf gradient: 10% MeCN in $H_2O$ to 100% MeCN) to give Norhalichondrin B (18) (5.0 mg, 0.0046 mmol, 60%) as a colorless solid.

Homohalichondrin B (19)

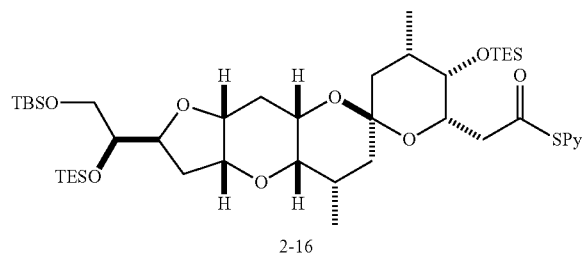

2-16

+

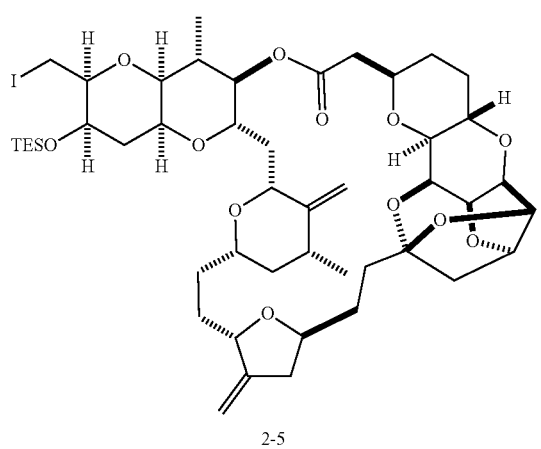

2-5

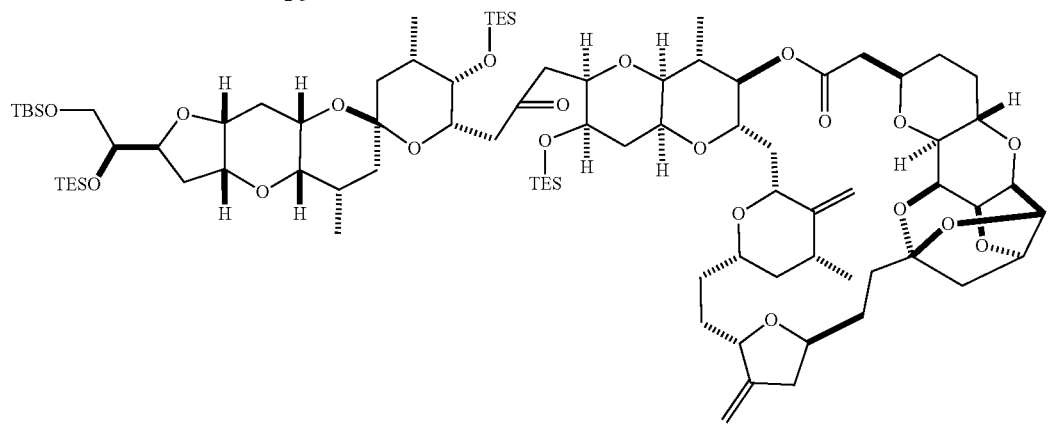

2-S-3

In a glove box, to a solution of iodide 2-5 (103 mg, 0.105 mmol, 1 eq.) and thioester 2-16 (113 mg, 0.132 mmol, 1.3 eq.) in DMI (0.85 mL) and EtOAc (0.17 mL) were added DTBMP (83.8 mg, 0.408 mmol, 4 eq.), Zn powder (40.0 mg, 0.612 mmol, 6 eq.), Cp$_2$ZrCl$_2$ (89.4 mg, 0.306 mmol, 3 eq.), and NiBr$_2$-dtbbpy (14.9 mg, 0.0306 mmol, 30 mol %) at room temperature. After being stirred for 1.5 h at the same temperature, the reaction mixture was removed from glove box and diluted with Et$_2$O and sat. NaHCO$_3$ aq. The organic layer was separated and the aqueous layer was extracted with Et$_2$O. The combined organic layer was dried over Na$_2$SO$_4$, filtered, and concentrated under reduced pressure. The obtained crude material was purified by flash column chromatography on neutral silica gel (0%, 9%, 17% EtOAc in Hexanes) to give ketone 2-S-3 (137 mg, 0.0857 mmol, 82%) as a colorless amorphous solid. In a preliminary study, the coupling reaction of iodide 5 (25.0 mg, 0.0254 mmol) and thioester 16 (30.0 mg, 0.0352 mmol) gave desired ketone (35.7 mg 0.0223 mmol) in 88% yield. (2-S-3): $[\alpha]^{20}_D$ −50.8 (c 1.00, CHCl$_3$). $^1$H NMR (600 MHz, C$_6$D$_6$) δ: 5.21 (1H, s), 5.11 (1H, s), 4.93 (1H, s), 4.85-4.78 (3H, m), 4.69 (1H, d, J=10.2 Hz), 4.52 (1H, ddd, J=9.8, 9.8, 4.2 Hz), 4.47 (1H, ddd, J=10.4, 5.3, 5.3 Hz), 4.34 (1H, d, J=9.6 Hz), 4.27 (1H, s), 4.14 (1H, dd, J=4.2, 4.2 Hz), 4.11-4.07 (2H, m), 4.02-4.00 (3H, m), 3.89 (1H, dd, J=5.7, 5.7 Hz), 3.84-3.80 (3H, m), 3.78-3.68 (5H, m), 3.64 (1H, dd, J=6.3, 3.9 Hz), 3.45 (1H, d, J=3.6 Hz), 3.29 (1H, s), 3.20-3.16 (2H, m), 3.06 (1H, dd, J=17.6, 5.7 Hz), 3.01 (1H, dd, J=17.6, 6.9 Hz), 2.93 (1H, s), 2.80 (1H, d, J=7.8 Hz), 2.77 (1H, d, J=7.2 Hz), 2.61 (1H, d, J=10.2 Hz), 2.46 (1H, d, J=15.0 Hz), 2.39-2.22 (9H, m), 2.20-2.05 (6H, m), 1.98 (1H, dd, J=12.6, 12.6 Hz), 1.93 (1H, d, J=13.2 Hz), 1.87-1.84 (2H, m), 1.75-1.65 (4H, m), 1.62-1.30 (11H, m), 1.18 (3H, d, J=6.6 Hz), 1.12-1.04 (30H, m), 1.04-1.03 (12H, m), 0.96 (3H, d, J=6.6 Hz), 0.77 (6H, q, J=8.0 Hz), 0.69-0.64 (12H, m), 0.14 (3H, s), 0.13 (3H, s) ppm. $^{13}$C NMR (125 MHz, C$_6$D$_6$) δ: 206.7, 171.3, 153.0, 152.6, 110.0, 104.9, 103.7, 96.9, 82.4, 81.0, 79.1, 78.3, 78.0, 77.9, 77.7, 76.9, 76.8, 76.1, 75.5, 74.8, 74.7, 74.2, 74.1, 74.0, 73.8, 73.6, 73.0, 70.4, 69.3, 68.4, 66.1, 65.9, 64.7, 63.7, 48.6, 46.8, 46.3, 43.9, 41.3, 39.5, 39.3, 38.6, 37.7, 37.6, 36.5, 36.3, 35.5, 35.3, 32.5, 31.6, 31.1, 30.7, 30.65, 30.60, 29.5, 29.0, 26.2, 18.7, 18.6, 18.1, 17.6, 16.4, 7.5, 7.34, 7.28, 6.0, 5.7, 5.3, −5.1, −5.3 ppm. FTIR (film): 2953, 2927, 2875, 1720, 1459, 1086, 1015, 834, 725 cm$^{-1}$. HRMS (ESI) m/z: [M+Na]$^+$ calcd for C$_{85}$H$_{144}$O$_{20}$Si$_4$Na, 1619.9220; found, 1619.9298.

halichondrin B with its C38 epimer. The mixture was purified by YAMAZEN purification system with ODS column (Rf gradient: 10% MeCN in H$_2$O to 100% MeCN) to give Homohalichondrin B (19) (63.8 mg, 0.0568 mmol, 66% for 2 steps) as a colorless solid and 38-epi-Homohalichondrin B (C38-epi-19) (14.4 mg, 0.0.0128 mmol, 15% for 2 steps) as a colorless solid. Homohalichondrin B (19): [α]$^{20}_D$ −43.7 (c 1.02, MeOH). $^1$H NMR (600 MHz, CD$_3$OD) δ: 5.06 (1H, s), 5.01 (1H, s), 4.88 (1H, s), 4.81 (1H, s), 4.70 (1H, dd, J=4.5, 4.5 Hz), 4.63 (1H, dd, J=7.8, 4.8 Hz), 4.60 (1H, dd, J=4.5, 4.5 Hz), 4.45 (1H, d, J=10.8 Hz), 4.33 (1H, ddd, J=9.6, 9.6, 4.2 Hz), 4.30 (1H, s), 4.25-4.21 (2H, m), 4.18 (1H, dd, J=5.7, 5.7 Hz), 4.06-4.13 (4H, m), 4.02 (1H, s), 3.95 (1H, s), 3.87-3.88 (3H, m), 3.71 (1H, dd, J=10.2,

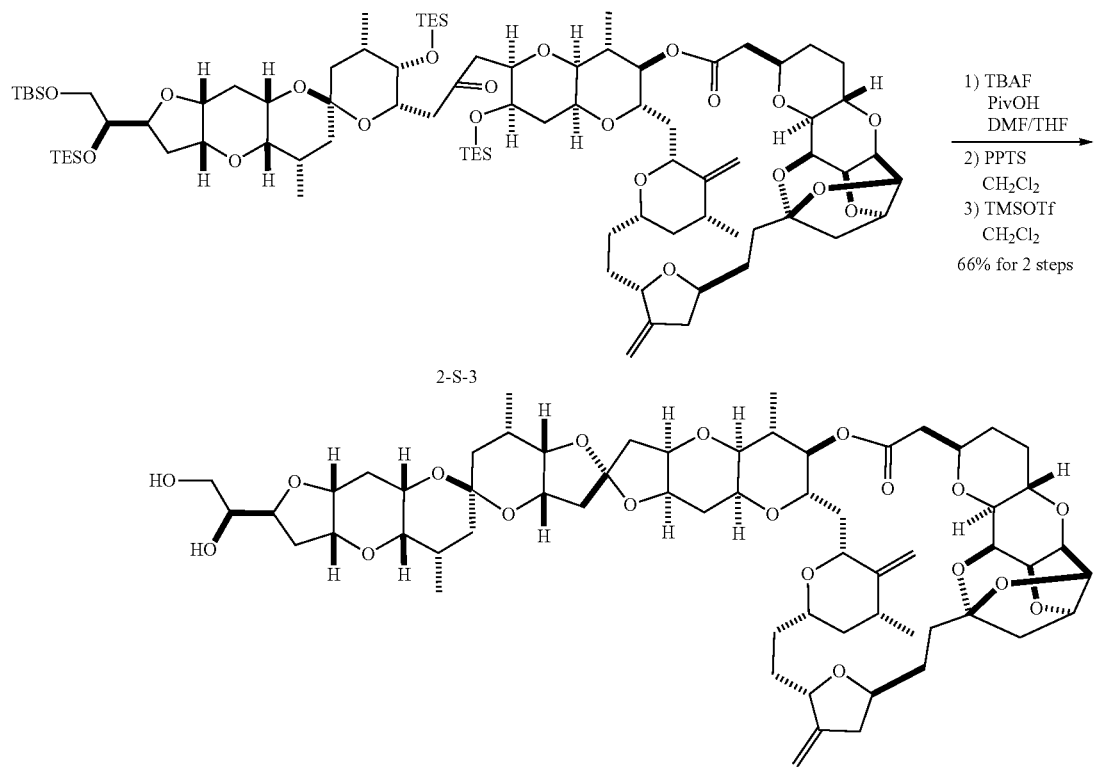

A buffered TBAF solution was prepared by mixing TBAF solution (TCI #T1125; 0.86 mL of 1 M in THF, 0.86 mmol, 10 eq.) and PivOH (43.9 mg, 0.430 mmol, 5 eq.). To a stirred solution of ketone 2-S-3 (137 mg, 0.0857 mmol, 1 eq.) in DMF (4.3 mL) was added the buffered TBAF solution at room temperature. After being stirred for 7 h at the same temperature, CaCO$_3$ (2.4 g) and DOWEX 50WX8-400 (2.4 g) were added. After being stirred for 1 h at room temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of the crude tetraol (calculated as 0.0857 mmol, 1 eq.) in CH$_2$Cl$_2$ (8.6 mL) was added PPTS (108 mg, 0.430 mmol, 5 eq.) at room temperature. After being stirred for 1 h at the same temperature, the reaction mixture was directly subjected to column chromatography on amino silica gel (CH$_2$Cl$_2$ then 25%, 50%, 75%, then 100% EtOAc in Hexanes then 2% MeOH in EtOAc) to give a crude Homo- 10.2 Hz), 3.66 (1H, s), 3.61 (1H, d, J=10.8 Hz), 3.55-3.60 (3H, m), 3.50 (1H, ddd, J=5.4, 5.4, 5.4 Hz), 3.21 (1H, dd, J=5.7, 5.7 Hz), 3.12 (1H, s), 2.98 (1H, d, J=10.2 Hz), 2.80 (1H, dd, J=9.0, 6.6 Hz), 2.56 (1H, dd, J=17.4, 9.6 Hz), 2.45 (1H, d, J=17.4 Hz), 2.39 (1H, dd, J=13.2, 5.4 Hz), 2.38-2.24 (6H, m), 2.22-2.13 (4H, m), 2.09-1.97 (9H, m), 1.90 (1H, ddd, J=15.6, 4.2, 4.2 Hz), 1.80-1.84 (2H, m), 1.74-1.67 (3H, m), 1.60 (1H, ddd, J=12.0, 12.0, 6.0 Hz), 1.51-1.29 (9H, m), 1.10 (3H, d, J=6.6 Hz), 1.05 (3H, d, J=7.2 Hz), 1.05-0.99 (1H, m), 0.95 (3H, d, J=6.6 Hz), 0.94 (3H, d, J=5.4 Hz) ppm. $^{13}$C NMR (125 MHz, CDCl$_3$) δ: 171.2, 151.8, 151.6, 112.4, 110.1, 104.4, 104.1, 96.6, 82.2, 81.1, 79.8, 78.4, 77.7, 77.6, 76.6, 76.29, 76.25, 75.4, 75.3, 75.1, 74.9, 74.8, 74.4, 73.9, 73.7, 73.5, 72.8, 71.9, 71.2, 70.8, 68.2, 66.7, 65.7, 63.7, 48.4, 43.4, 42.5, 40.4, 38.7, 37.3, 37.0, 36.92, 36.87, 36.6, 36.0, 34.4, 32.1, 31.4, 30.7, 30.1, 29.4, 29.0, 28.9, 28.2, 25.8, 18.0, 17.8, 17.1, 15.0 ppm. FTIR (film): 3460, 2926, 2874, 1736, 1652, 1567, 1187, 1132, 1105, 1074, 1041, 1021, 997 cm$^{-1}$. HRMS (ESI) m/z: [M+Na]$^+$ calcd for C$_{61}$H$_{86}$O$_{19}$Na, 1145.5656; found, 1145.5770.

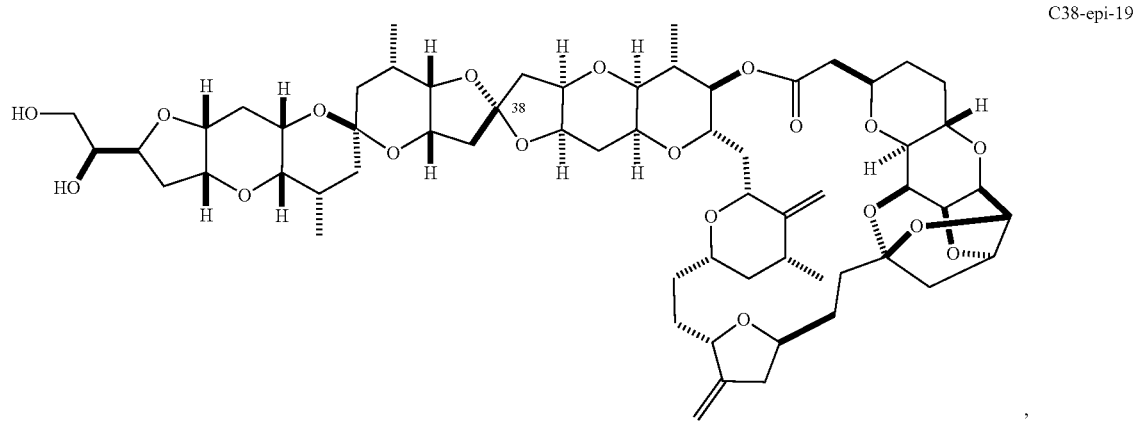

C38-epi-19

38-Epi-Homohalichondrin B (C38-Epi-19):

$[\alpha]^{20}_D$ −86.6 (c 0.860, MeOH). $^1$H NMR (600 MHz, CD$_3$OD) δ: 5.04 (1H, d, J=1.8 Hz), 4.96 (1H, d, J=1.8 Hz), 4.87 (1H, s), 4.80 (1H, s), 4.72 (1H, dd, J=10.2, 6.6 Hz), 4.70 (1H, dd, J=4.2, 4.2 Hz), 4.60 (1H, dd, J=4.5, 4.5 Hz), 4.44 (1H, d, J=10.8 Hz), 4.37 (1H, ddd, J=10.2, 10.2, 4.2 Hz), 4.28 (1H, d, J=2.4 Hz), 4.23 (1H, ddd, J=9.6, 4.8, 4.8 Hz), 4.19-4.05 (6H, m), 4.02 (1H, s), 3.98 (1H, dd, J=4.8, 1.8 Hz), 3.91-3.85 (3H, m), 3.81 (1H, s), 3.63 (1H, dd, J=10.5, 10.5 Hz), 3.59-3.56 (3H, m), 3.54 (1H, d, J=2.4 Hz), 3.51-3.47 (1H, m), 3.17 (1H, dd, J=8.4, 6.0 Hz), 3.15 (1H, s), 2.99 (1H, dd, J=9.6, 1.2 Hz), 2.83-2.79 (1H, m), 2.56 (1H, dd, J=17.0, 8.7 Hz), 2.47 (1H, dd, J=17.0, 2.4 Hz), 2.35-1.93 (21H, m), 1.91 (1H, ddd, J=15.6, 4.5, 4.5 Hz), 1.83 (1H, ddd, J=11.1, 11.1, 2.4 Hz), 1.77 (1H, d, J=13.2 Hz), 1.71 (1H, dd, 13.2, 2.4 Hz), 1.68-1.60 (2H, m), 1.58-1.54 (1H, m), 1.50-1.33 (7H, m), 1.29 (1H, dd, J=12.6, 4.2 Hz), 1.10 (3H, d, J=7.2 Hz), 1.05-0.98 (1H, m), 1.004 (3H, d, J=7.2 Hz), 0.995 (3H, d, J=6.6 Hz), 0.96 (3H, d, J=7.2 Hz) ppm. $^{13}$C NMR (125 MHz, CD$_3$OD) δ: 172.9, 153.3, 152.8, 115.6, 111.3, 105.1, 104.7, 98.0, 83.8, 82.4, 80.2, 79.8, 79.2, 78.9, 78.5, 78.4, 77.9, 77.8, 76.5, 76.12, 76.09, 76.0, 75.7, 75.2, 75.1, 74.8, 74.4, 73.2, 72.9, 69.5, 68.3, 65.3, 65.1, 45.6, 45.0, 44.7, 41.2, 39.6, 38.6, 38.2, 38.1, 37.5, 37.2, 35.4, 33.3, 31.9, 31.8, 31.3, 30.9, 30.19, 30.16, 29.3, 26.8, 18.4, 17.7, 15.2 μm. FTIR (film): 3487, 2925, 2872, 1737, 1188, 1119, 1074, 1019, 996, 896, 735 cm$^{-1}$. HRMS (ESI) m/z: [M+Na]$^+$ calcd for C$_{61}$H$_{86}$O$_{19}$Na, 1145.5656; found, 1145.5631. C38-epi-19 was epimerized to Homohalichondrin B (19) by the following procedure:

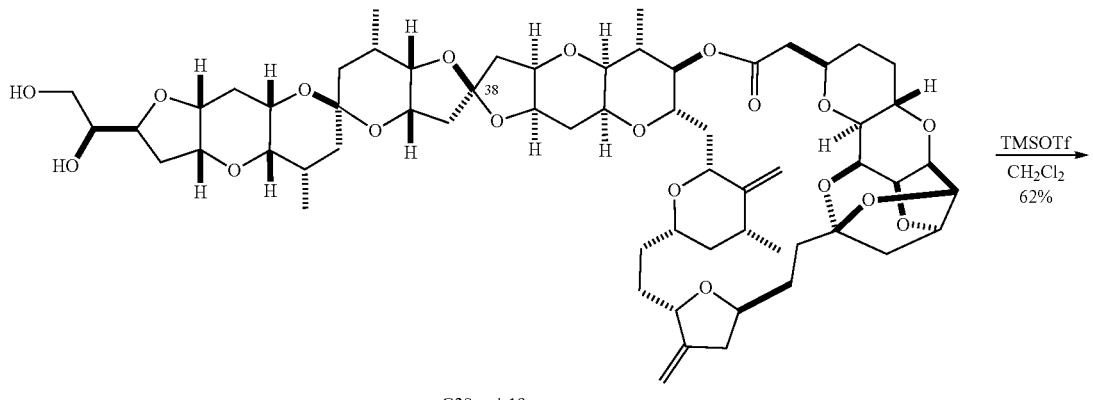

C38-epi-19

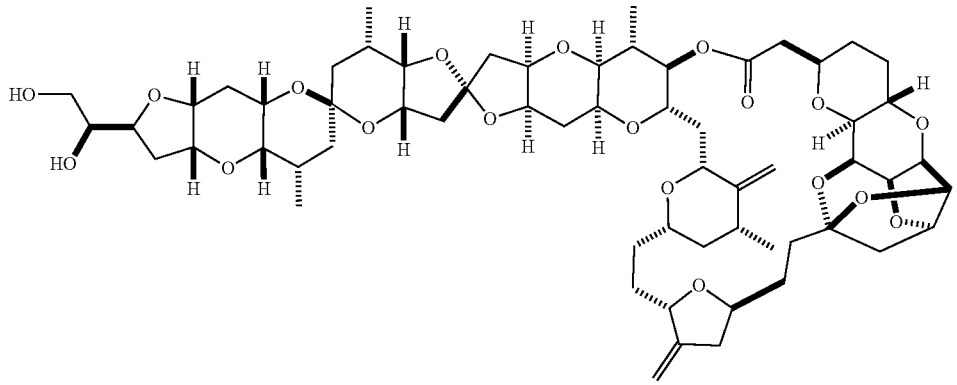

19

To a solution of C38-epi-19 (14.4 mg, 0.0128 mmol, 1 eq.) in CH$_2$Cl$_2$ (6.4 mL) was added TMSOTf (0.13 mL, 0.719 mmol, excess) at −78° C. After being stirred for 15 min at the same temperature, the reaction was quenched with sat. NaHCO$_3$ aq. After being stirred for 1 h at 0° C., the organic layer was separated and the aqueous layer was extracted with CH$_2$Cl$_2$. The combined organic layer was dried over Na$_2$SO$_4$, filtered, and concentrated under reduced pressure. The crude material was purified by YAMAZEN purification system with ODS column (Rf gradient: 10% MeCN in H$_2$O to 100% MeCN) to give Homohalichondrin B (19) (8.9 mg, 0.00792 mmol, 62%) as a colorless solid. Halichondrin A (20)

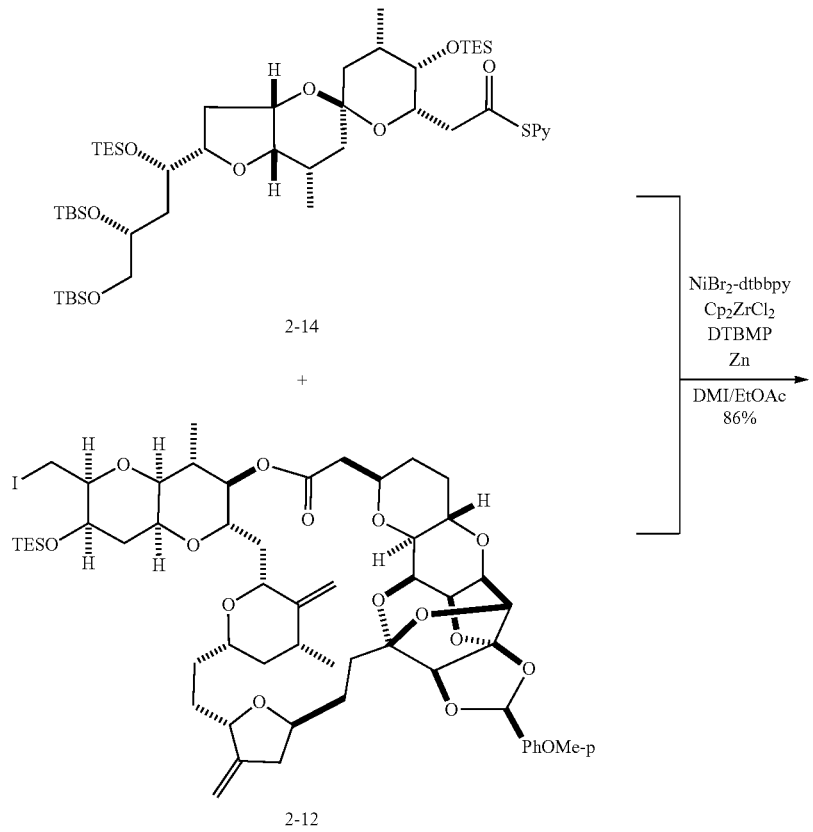

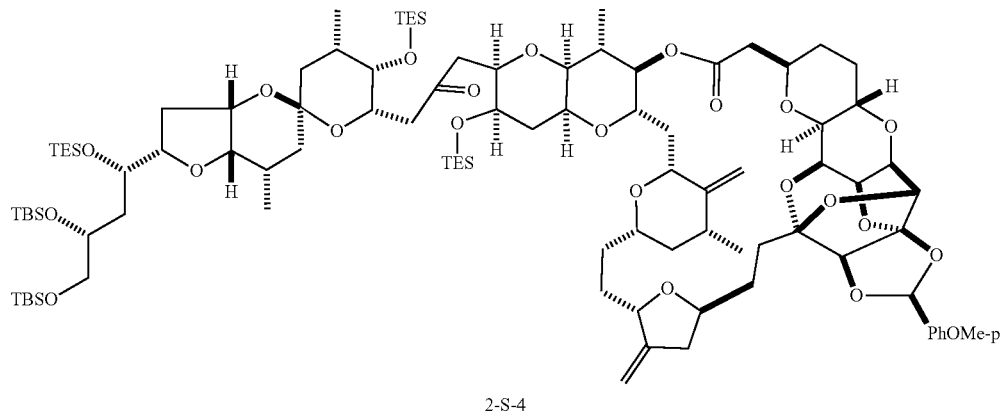

2-S-4

In a glove box, to a solution of iodide 2-12 (100.0 mg, 0.0883 mmol, 1 eq.) and thioester 2-14 (109.5 mg, 0.115 mmol, 1.3 eq.) in DMI (0.75 mL) and EtOAc (0.15 mL) were added DTBMP (72.5 mg, 0.353 mmol, 4 eq.), Zn powder (34.6 mg, 0.529 mmol, 6 eq.), $Cp_2ZrCl_2$ (77.4 mg, 0.265 mmol, 3 eq.), and $NiBr_2$-dtbbpy (12.9 mg, 0.027 mmol, 30 mol %) at room temperature. After being stirred for 1.5 h at the same temperature, the reaction mixture was removed from glove box and diluted with EtOAc and sat. $NaHCO_3$ aq. The organic layer was separated and the aqueous layer was extracted with EtOAc. The combined organic layer was dried over $Na_2SO_4$, filtered, and concentrated under reduced pressure. The obtained crude material was purified by YAMAZEN purification system on neutral silica gel (0%, 9%, then 20% EtOAc in Hexanes) to give ketone 2-S-4 (140.0 mg, 0.0756 mmol, 86%) as a colorless amorphous solid. (2-S-4): $[\alpha]^{20}_D$ −64.8 (c 1.00, $CHCl_3$). $^1H$ NMR (600 MHz, $C_6D_6$) δ: 7.35 (2H, d, J=8.4 Hz), 6.72 (2H, d, J=8.4 Hz), 6.07 (1H, s), 5.19 (1H, s), 5.08 (1H, s), 4.94 (1H, s), 4.84-4.79 (3H, m), 4.66 (1H, d, J=10.8 Hz), 4.51-4.46 (2H, m), 4.39 (1H, br s), 4.35 (1H, dd, J=5.4, 1.2 Hz), 4.33 (1H, dd, J=8.4, 1.2 Hz), 4.23-4.21 (1H, m), 4.14-4.11 (1H, m), 3.83-3.80 (3H, m), 4.05 (1H, s), 4.03-3.95 (4H, m), 3.91-3.87 (1H, m), 3.82-3.79 (3H, m), 3.76-3.71 (3H, m), 3.46 (1H, dd, J=8.4, 4.8 Hz), 3.41 (1H, s), 3.31 (1H, s), 3.24 (3H, s), 3.18-3.13 (2H, m), 3.07-2.99 (2H, m), 2.76 (1H, dd, J=16.8, 4.8 Hz), 2.74-2.70 (1H, m), 2.52 (1H, d, J=9.6 Hz), 2.47-2.41 (1H, m), 2.37-2.29 (6H, m), 2.27-2.18 (5H, m), 2.13-1.92 (11H, m), 1.83-1.46 (12H, m), 1.38-1.27 (1H, m), 1.18 (3H, d, J=6.6 Hz), 1.12 (3H, d, J=7.2 Hz), 1.09 (9H, t, J=7.2 Hz), 1.08 (9H, s), 1.07-1.03 (21H, m), 1.02 (9H, s), 0.94 (3H, d, J=7.2 Hz), 0.76 (6H, q, J=7.8 Hz), 0.69-0.64 (12H, m), 0.26 (6H, s), 0.13 (3H, s), 0.13 (3H, s) ppm. $^{13}C$ NMR (125 MHz, $C_6D_6$) δ206.7, 171.1, 161.4, 152.9, 152.7, 119.0, 114.1, 109.3, 109.0, 105.0, 103.8, 97.0, 90.2, 83.8, 81.5, 80.3, 78.4, 78.1, 77.9, 76.0, 76.0, 75.5, 74.8, 74.7, 74.2, 74.0, 73.6, 72.9, 72.0, 71.8, 71.5, 70.1, 69.8, 68.3, 68.3, 65.9, 64.6, 54.8, 46.8, 46.2, 44.0, 41.3, 39.5, 38.7, 38.2, 37.7, 36.4, 35.4, 35.4, 32.4, 31.0, 30.9, 30.7, 30.3, 27.6, 26.6, 26.3 (×6), 26.3 (×6), 18.7, 18.6, 18.5, 18.4, 18.1, 16.4, 7.4 (×6), 7.3 (×6), 7.3 (×3), 7.3 (×3), 6.0 (×6), 5.7 (×6), 5.3 (×6) ppm. FTIR (film): 2955, 2917, 2876, 1736, 1648, 1519, 1253, 1096, 1032, 1009, 851 $cm^{-1}$. HRMS (ESI) m/z: $[M+Na]^+$ calcd for $C_{98}H_{164}O_{23}Si_5Na$, 1849.0510; found, 1849.0490.

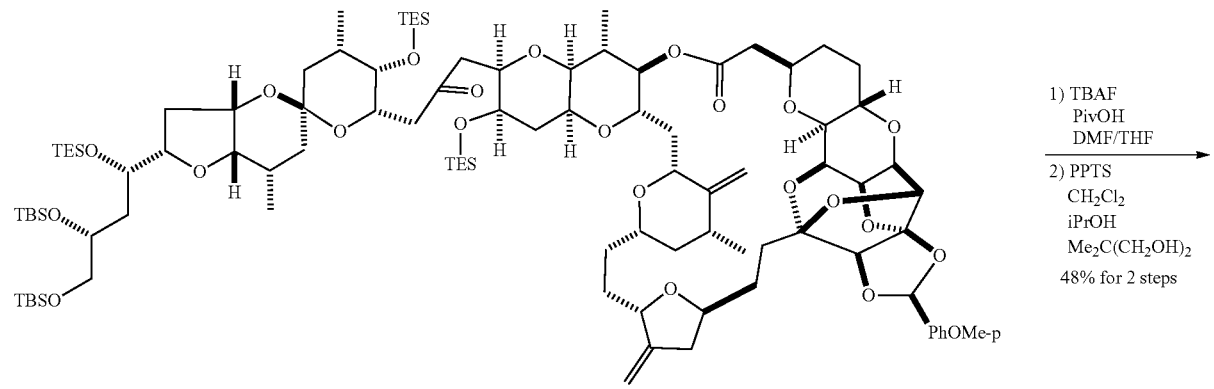

2-S-5

1) TBAF
PivOH
DMF/THF

2) PPTS
$CH_2Cl_2$
iPrOH
$Me_2C(CH_2OH)_2$

48% for 2 steps

-continued

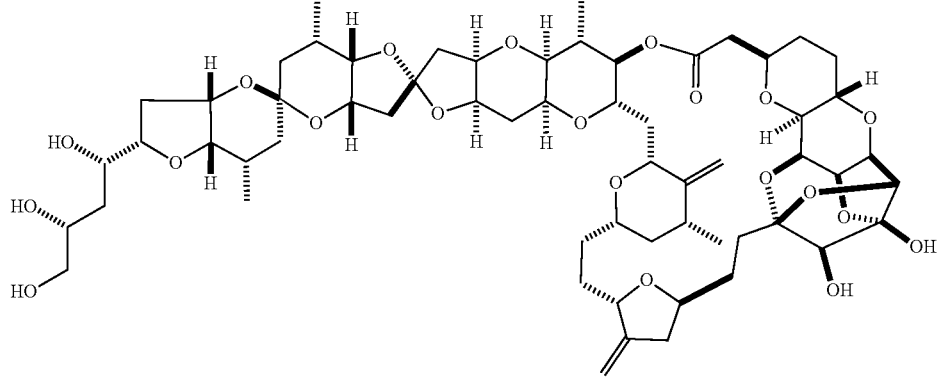

20

To a stirred solution of 2-S-5 (138 mg, 0.0735 mmol, 1 equiv.) in DMF (3.7 mL, 0.02M) was added the buffered TBAF solution (0.74 mL, 10 equiv., freshly prepared by 1.48 mL TBAF solution (1 M in THF) and 75 mg PivOH) at room temperature. After being stirred for 3 h at the same temperature, $CaCO_3$ (3.0 g) and DOWEX 50WX8-400 (3.0 g) were added.[1] After being stirred for 2 h at room temperature, the resulted mixture was diluted with EtOAc and filtered through a pad of Celite. The filter cake was washed with EtOAc thoroughly. The filtrate was concentrated under reduced pressure to give a crude material, which was used in the next step without further purification. To a stirred solution of the crude material (calculated as 0.0735 mmol, 1 eq.) in $CH_2Cl_2$ (3.7 mL, 0.02M) was added PPTS (184.6 mg, 0.735 mmol, 10 equiv.) at room temperature. After being stirred for 1.5 h at the same temperature, TLC analysis indicated the disappearance of starting material. iPrOH (1.2 mL) and additional PPTS (184.6 mg, 0.735 mmol, 10 eq.) were added to the resulted solution at the same temperature. After being stirred for 20 h, the reaction mixture was directly subjected to column chromatography on amino silica gel ($CH_2Cl_2$ then 100% EtOAc then 16% MeOH in EtOAc) to give a crude halichondrin A with its C-38 epimer. The mixture was purified by YAMAZEN purification system with ODS column (Rf gradient: 10% MeCN in $H_2O$ to 50% MeCN in $H_2O$) to give halichondrin A (20) (40.0 mg, 0.035 mmol, 48% for 3 steps) as a white crystalline solid and 38-epi-halichondrin A (C38-epi-20) (13.5 mg, 0.0118 mmol, 16% for 3 steps) as a white solid. Halichondrin A (20): $[\alpha]^{20}_D$ −73.2 (c 0.11, MeOH). MP: 168-170° C. (recrystallized from Hexanes-$CH_2Cl_2$) $^1$H NMR (600 MHz, $CD_3OD$) δ: 5.08 (1H, s), 5.03 (1H, s), 4.88 (1H, s), 4.82 (1H, s), 4.62 (1H, dd, J=7.2, 4.2 Hz), 4.45 (1H, d, J=11.2 Hz), 4.37 (1H, dd, J=4.8, 3.0 Hz), 4.32 (1H, ddd, J=10.0, 10.0, 4.2 Hz), 4.32-4.28 (2H, m), 4.25 (1H, ddd, J=11.2, 4.4, 2.4 Hz), 4.20 (1H, dd, J=3.2, 2.1 Hz), 4.14-4.07 (4H, m), 4.05 (1H, ddd, J=2.4, 2.4, 2.4 Hz), 3.99 (1H, ddd, J=9.6, 4.8, 4.2 Hz), 3.91-3.84 (3H, m), 3.78 (1H, ddd, J=8.8, 4.8, 4.4 Hz), 3.75-3.70 (1H, m), 3.69 (1H, dd, J=2.3, 2.3 Hz), 3.61 (1H, d, J=11.7 Hz), 3.56 (1H, dd, J=2.3, 1.8 Hz), 3.53 (1H, s), 3.53 (1H, dd, J=11.2, 4.7, Hz), 3.47 (1H, dd, J=11.2, 6.5 Hz), 3.22 (1H, dd, J=6.5, 4.7 Hz), 2.94 (1H, dd, J=10.0, 2.3 Hz), 2.82 (1H, dddd, J=15.8, 7.6, 4.7, 2.9 Hz), 2.57 (1H, dd, J=17.9, 9.7 Hz), 2.45 (1H, dd, J=17.9, 1.8 Hz), 2.40 (1H, dd, J=13.2, 6.2 Hz), 2.36-2.24 (8H, m), 2.20-2.13 (1H, m), 2.10-1.97 (6H, m), 1.92-1.79 (4H, m), 1.78-1.67 (4H, m), 1.60 (1H, ddd, J=14.2, 8.4, 8.4 Hz), 1.56-1.42 (4H, m), 1.42-1.28 (5H, m), 1.10 (3H, d, J=6.5 Hz), 1.06 (3H, d, J=7.6 Hz), 1.02 (3H, d, J=7.0 Hz), 1.04-0.98 (1H, m), 0.97 (3H, d, J=7.0 Hz) ppm. $^{13}$C NMR (125 MHz, $^{12}CD_3OD$) δ 172.8, 153.3, 153.1, 114.8, 113.4, 112.9, 105.7, 104.8, 98.4, 85.5, 82.3, 81.3, 81.2, 80.8, 79.0, 78.0, 77.9, 77.6, 77.4, 76.3, 76.0, 75.8, 75.5, 75.2, 75.1, 75.1, 73.8, 73.7, 73.3, 73.1, 73.0, 71.6, 69.6, 67.2, 65.6, 45.6, 45.0, 44.9, 41.1, 39.8, 37.9, 37.9, 37.8, 37.5, 37.5, 37.2, 36.3, 33.0, 31.8, 31.3, 31.3, 30.9, 30.8, 28.4, 27.1, 27.1, 18.4, 18.3, 18.1, 15.9 ppm. FTIR (film): 3429, 2925, 2872, 1736, 1454, 1372, 1269, 1191, 1129, 1109, 1073, 1020, 753 $cm^{-1}$. HRMS (ESI) m/z: $[M+H]^+$ calcd for $C_{60}H_{87}O_{21}$, 1143.5734; found, 1143.5720.

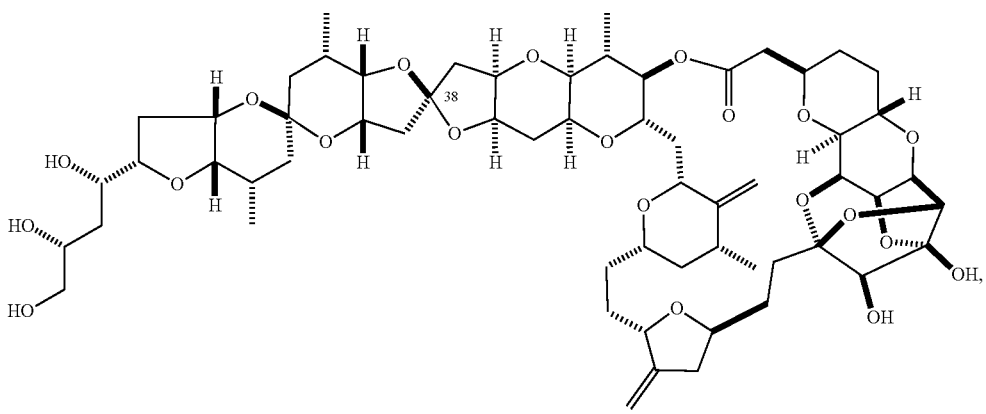

C38-epi-20

38-Epi-Halichondrin A (C38-Epi-20):

$[\alpha]^{20}_D$ −74.3 (c 0.50, MeOH). $^1$H NMR (600 MHz, CD$_3$OD) δ: 5.04 (1H, s), 4.96 (1H, s), 4.87 (1H, s), 4.81 (1H, s), 4.72 (1H, dd, J=10.2, 6.6 Hz), 4.43 (1H, d, J=10.2 Hz), 4.38-4.31 (4H, m), 4.37 (1H, ddd, J=12.0, 12.0, 4.8 Hz), 4.20 (1H, m), 4.18-4.06 (7H, m), 3.99 (1H, ddd, J=9.6, 5.4, 4.2 Hz), 3.91-3.83 (4H, m), 3.78 (1H, ddd, J=14.4 4.8, 4.2 Hz), 3.64 (1H, d, J=9.6 Hz), 3.59-3.56 (2H, m), 3.53 (1H, dd, J=10.8, 4.5 Hz), 3.47 (1H, dd, J=11.4, 6.0 Hz), 3.17 (1H, dd, J=9.0, 6.6 Hz), 2.95 (1H, dd, J=9.6, 1.8 Hz), 2.86-2.80 (1H, m), 2.56 (1H, dd, J=17.4, 9.6 Hz), 2.47 (1H, dd, J=17.4, 2.4 Hz), 2.36-2.18 (9H, m), 2.12-2.07 (3H, m), 2.04-1.96 (4H, m), 1.88-1.81 (3H, m), 1.77-1.73 (2H, m), 1.69-1.65 (2H, m), 1.62-1.34 (10H, m), 1.09 (3H, d, J=6.6 Hz), 1.04 (3H, d, J=8.4 Hz), 1.05-0.99 (1H, m), 1.02 (3H, d, J=7.8 Hz), 1.00 (3H, d, J=6.6 Hz) ppm. $^{13}$C NMR (125 MHz, CD$_3$OD) δ: 172.9, 153.3, 152.8, 115.6, 113.3, 113.0, 105.1, 104.7, 98.3, 85.5, 82.4, 81.3, 81.1, 80.0, 79.1, 78.9, 78.9, 78.5, 77.9, 76.7, 76.1, 76.0, 75.9, 75.5, 75.3, 74.8, 73.9, 73.5, 73.3, 73.2, 73.2, 71.7, 69.5, 68.3, 67.2, 45.6, 44.9, 44.8, 41.2, 39.7, 38.3, 38.3, 38.1, 37.5, 37.5, 37.2, 36.2, 33.3, 31.8, 31.3, 31.0, 30.9, 29.9, 28.3, 27.1, 26.8, 18.4, 18.3, 18.3, 15.2 ppm. FTIR (film): 3439, 2925, 2872, 1736, 1454, 1372, 1279, 1192, 1119, 1073, 1020, 753 cm$^{-1}$. HRMS (ESI) m/z: [M+H]$^+$ calcd for C$_{60}$H$_{87}$O$_{21}$, 1143.5734; found, 1143.5721. C38-epi-20 was epimerized to Halichondrin A (20) by the following procedure:

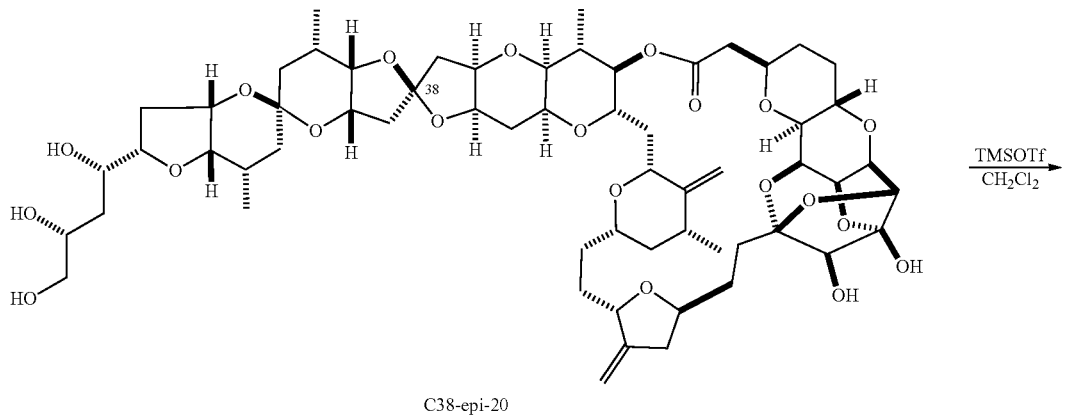

C38-epi-20

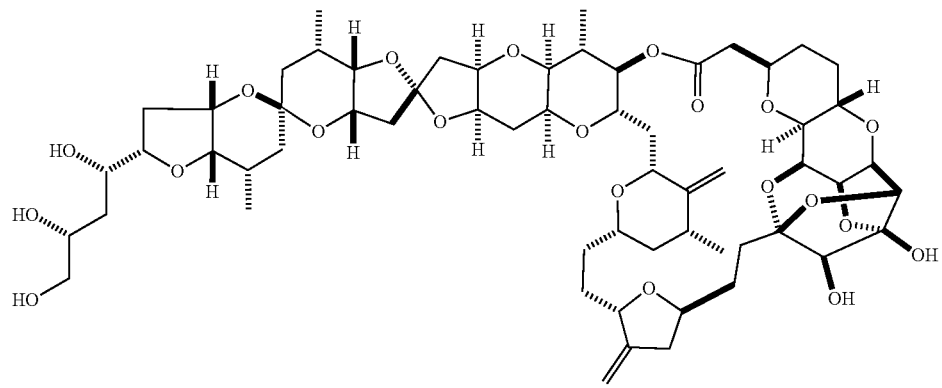

20

To a stirred solution of C38-epi-20 (13.0 mg, 0.0114 mmol, 1 eq.) in CH$_2$Cl$_2$ (5.7 mL) was added TMSOTf (0.114 mL, 0.631 mmol, excess) at −78° C. After being stirred for 15 min, the reaction was quenched with sat. NaHCO$_3$ aq. After being stirred for 1 h at 0° C., the organic layer was separated and the aqueous layer was extracted with CH$_2$Cl$_2$. The combined organic layer was dried over Na$_2$SO$_4$, filtered, and concentrated under reduced pressure. The crude material was purified by YAMAZEN purification system with ODS column (Rf gradient: 10% MeCN in H$_2$O to 50% MeCN in H$_2$O) to give halichondrin A (20) (11.3 mg, 0.00988 mmol, 86%) as a white solid.

Norhalichondrin A (21)

temperature. After being stirred for 1.5 h at the same temperature, the reaction mixture was removed from glove box and diluted with Et$_2$O and sat. NaHCO$_3$ aq. The organic layer was separated and the aqueous layer was extracted with Et$_2$O. The combined organic layer was dried over Na$_2$SO$_4$, filtered, and concentrated under reduced pressure. The obtained crude material was purified by flash column chromatography on neutral silica gel (0%, 15%, 25% EtOAc in Hexanes) to give ketone 2-S-5 (68.4 mg, 0.0423 mmol, 87%) as a colorless amorphous solid. 2-S-5: $[\alpha]^{20}_D$ −61.5 (c 1.00, CHCl$_3$). $^1$H NMR (600 MHz, C$_6$D$_6$) δ: 7.36 (2H, d, J=8.4 Hz), 6.73 (2H, d, J=8.4 Hz), 6.08 (1H, s), 5.22 (1H, s), 5.11 (1H, s), 4.96 (1H, s), 4.84-4.80 (3H, m), 4.69 (1H, d,

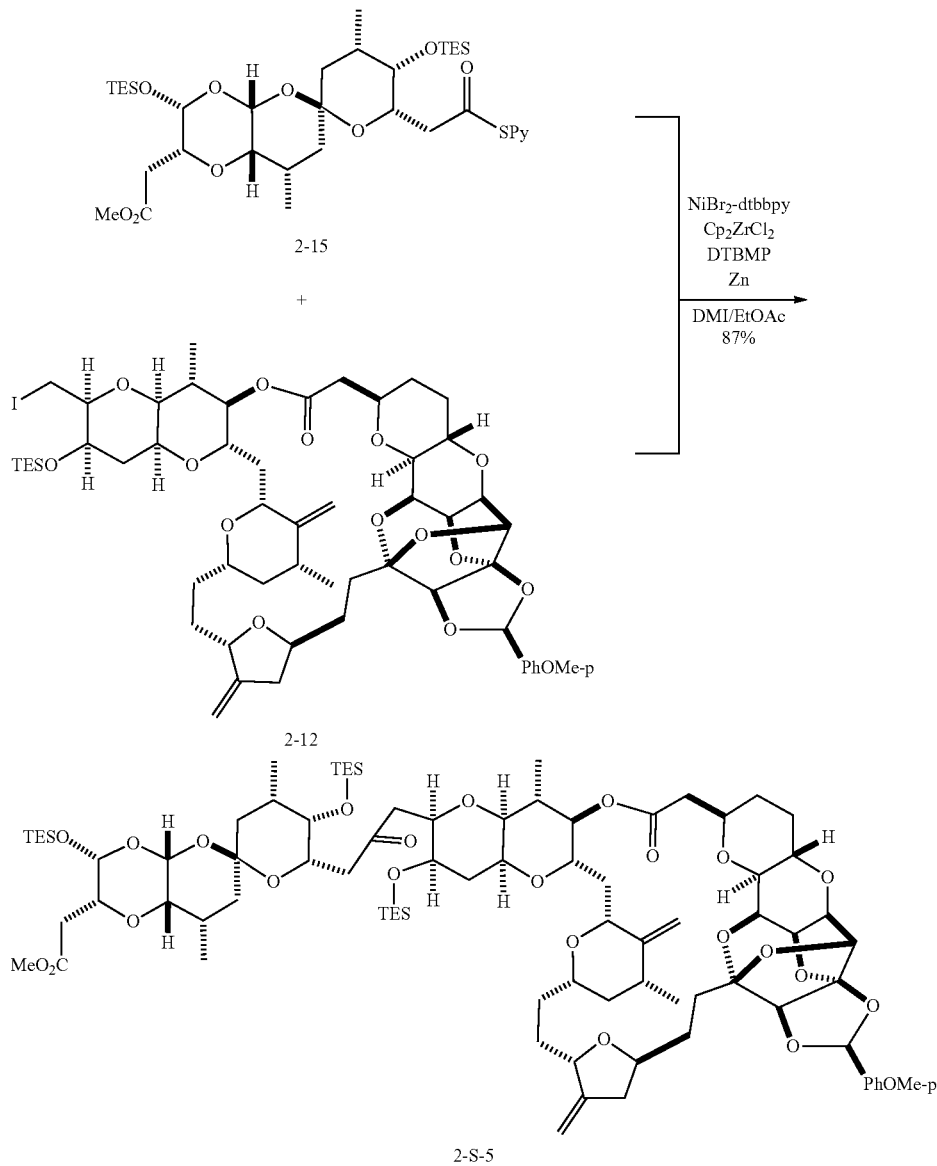

In a glove box, to a solution of iodide 2-5 (55 mg, 0.0487 mmol, 1 eq.) and thioester 2-16 (45.9 mg, 0.0634 mmol, 1.3 eq.) in DMI (0.4 mL) and EtOAc (0.08 mL) were added DTBMP (40 mg, 0.195 mmol, 4 eq.), Zn powder (19.0 mg, 0.292 mmol, 6 eq.), Cp$_2$ZrCl$_2$ (42.7 mg, 0.146 mmol, 3 eq.), and NiBr$_2$-dtbbpy (7.1 mg, 0.0146 mmol, 30 mol %) at room J=10.2 Hz), 4.50 (1H, ddd, J=9.6, 9.3, 2.0 Hz), 4.41 (1H, s), 4.39-4.34 (2H, m), 4.06 (1H, s), 4.05-3.96 (4H, m), 3.84-3.77 (2H, m), 3.77-3.70 (3H, m), 3.58 (1H, s), 3.45 (1H, dd, J=8.4, 4.2 Hz), 3.37 (3H, s), 3.35 (1H, s), 3.22 (3H, s), 3.20-3.14 (1H, m), 3.11 (1H, s), 3.07 (1H, dd, J=17.4, 5.7 Hz), 2.99 (1H, dd, J=17.4, 6.9 Hz), 2.84 (1H, dd, J=14.4, 7.2

Hz), 2.78 (1H, dd, J=14.8, 7.2 Hz), 2.76-2.70 (1H, m), 2.57 (1H, dd, J=15.0, 5.4 Hz), 2.53 (1H, d, J=9.6 Hz), 2.43-2.20 (10H, m), 2.16-2.06 (5H, m), 2.06-2.01 (1H, m), 1.98 (1H, dd, J=12.0, 12.0 Hz), 1.87-1.80 (1H, m), 1.78-1.63 (4H, m), 1.62-1.44 (7H, m), 1.38-1.30 (3H, m), 1.20 (3H, d, J=7.2 Hz), 1.13-1.02 (34H, m), 0.98 (3H, d, J=7.2 Hz), 0.71-0.60 (18H, m) ppm. $^{13}$C NMR (150 MHz, $C_6D_6$) δ: 206.9, 171.8, 171.2, 161.4, 153.0, 152.6, 128.8, 128.7, 119.0, 114.1, 109.3, 109.0, 105.1, 103.8, 96.9, 90.2, 83.8, 78.3, 78.1, 78.0, 77.2, 76.5, 76.1, 76.0, 75.5, 74.8, 74.7, 74.2, 74.0, 73.8, 73.6, 73.0, 70.1, 69.5, 68.4, 65.9, 65.7, 64.6, 64.5, 54.8, 50.9, 46.9, 46.3, 44.0, 41.3, 39.50, 38.7, 37.5, 37.2, 36.4, 36.3, 35.5, 32.4, 31.1, 31.0, 30.9, 30.3, 30.2, 29.2, 27.6, 18.6, 18.2, 17.3, 16.5, 7.5, 7.3, 7.2, 6.0, 5.4, 5.3 ppm. FTIR (film): 2953, 2934, 2876, 2104, 1738, 1518, 1458, 1373, 1304, 1154, 1090, 1033, 1014, 855, 830, 740 cm$^{-1}$. HRMS (ESI) m/z: [M+Na]$^+$ calcd for $C_{86}H_{134}O_{23}Si_3Na$, 1641.8521; found, 1641.8591.

temperature, $CaCO_3$ (1.0 g) and DOWEX 50WX8-400 (1.0 g) were added after diluting with 5 mL EtOAc. After being stirred for 1 h at room temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of the crude tetraol (calculated as 0.0364 mmol, 1 eq.) in $CH_2Cl_2$ (8.5 mL) was added PPTS (36.8 mg, 0.146 mmol, 4 eq.) at room temperature. After 1 h, TLC analysis indicated the disappearance of starting material. iPrOH (0.4 mL) and additional PPTS (46.0 mg, 0.183 mmol, 5 eq.) were added to the resulted solution at the same temperature. After being stirred for 12 h at the same temperature, the reaction mixture was directly subjected to column chromatography on amino silica gel ($CH_2Cl_2$ then 25%, 50%, 75%, then 100% EtOAc in Hexanes then 2% MeOH in EtOAc) to give a crude Norh-

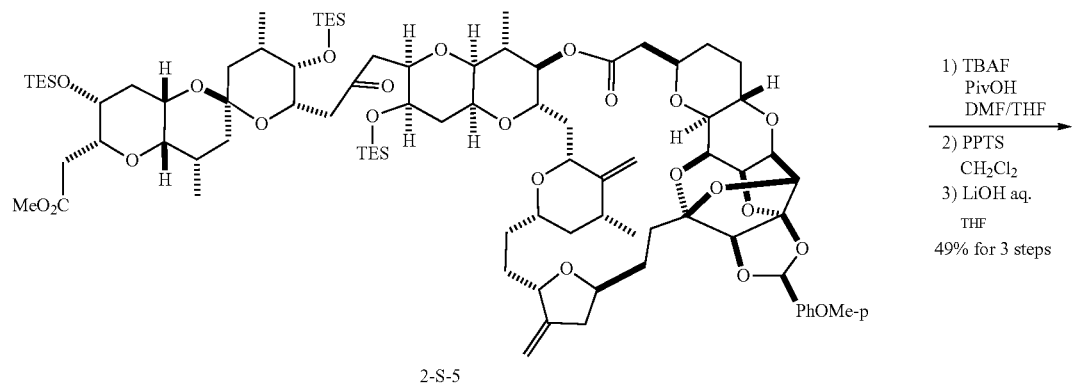

2-S-5

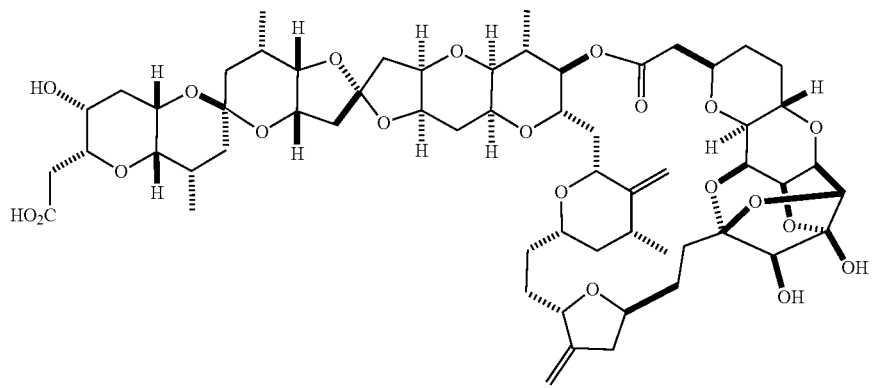

21

A buffered TBAF solution was prepared by mixing TBAF solution (TCI #T1125; 0.37 mL of 1 M in THF, 0.37 mmol, 10 eq.) and PivOH (18.5 mg, 0.182 mmol, 5 eq.). To a stirred solution of ketone 2-S-5 (59 mg, 0.0364 mmol, 1 eq.) in DMF (2.0 mL) was added the buffered TBAF solution at room temperature. After being stirred for 6 h at the same alichondrin A methyl ester with its C38 epimer. The compound was used in the next step after concentration without further purification. To a stirred solution of the crude methyl ester (calculated as 0.0364 mmol, 1 eq.) in THF (5 mL) was added 1M LiOH aq. (1.5 mL) at room temperature.$^3$ After being stirred for 2 h at the same temperature, the reaction mixture was diluted with water (3 mL). The THF was then removed from the mixture by evaporator. After the reaction was cooled down to 0° C., 1 M HCl aq. (1.5 mL) was added and the reaction mixture was allowed for further 2 min stirring. The resulting mixture was extracted with EtOAc. The combined organic layer was dried over $Na_2SO_4$, filtered, and concentrated under reduced pressure. The resulting mixture was purified by YAMAZEN purification system with ODS column (Rf gradient: 10% MeCN in $H_2O$ to 100% MeCN) to give Norhalichondrin A (21) (20.2 mg, 0.0179 mmol, 49% for 3 steps) as a colorless solid and 38-epi-Norhalichondrin A (C38-epi-21) (9.8 mg, 0.0087 mmol, 24% for 3 steps) as a colorless solid. Norhalichondrin A (21) $[\alpha]^{20}_D$ −70.3 (c 0.37, MeOH) $^1$H NMR (600 MHz, $CD_3OD$) δ: 5.06 (1H, s), 5.02 (1H, s), 4.88 (1H, s), 4.81 (1H, s), 4.62 (1H, dd, J=7.3, 4.7 Hz), 4.45 (1H, d, J=9.6 Hz), 4.39-4.35 (1H, m), 4.35-4.29 (3H, m), 4.25 (1H, ddd, J=11.2, 4.2, 1.8 Hz), 4.21 (1H, dd, J=3.2, 2.4 Hz), 4.13-4.07 (3H, m), 3.98 (1H, d, J=2.1 Hz), 3.91-3.86 (2H, m), 3.82-3.76 (2H, m), 3.74-3.69 (2H, m), 3.63-3.58 (2H, m), 3.53 (1H, s), 3.33-3.28 (1H, m), 3.22 (1H, dd, J=6.6, 4.7 Hz), 2.93 (1H, dd, J=9.6, 1.8 Hz), 2.83 (1H, ddd, J=16.0, 8.0, 2.1 Hz), 2.58 (1H, dd, J=16.2, 9.6 Hz), 2.53-2.47 (2H, brs), 2.44 (1H, dd, J=17.6, 1.8 Hz), 2.39 (1H, dd, J=13.2, 6.2 Hz), 2.36-2.23 (6H, m), 2.20-2.12 (2H, m), 2.11-1.99 (6H, m), 1.94 (1H, ddd, J=14.8, 3.0, 3.0 Hz), 1.90-1.79 (2H, m), 1.76-1.66 (3H, m), 1.57-1.47 (4H, m), 1.43-1.31 (7H, m), 1.10 (3H, d, J=6.6 Hz), 1.06 (3H, d, J=7.0 Hz), 1.04-1.03 (1H, m), 0.98 (3H, d, J=7.2 Hz), 0.96 (3H, d, J=7.2 Hz) ppm. $^{13}$C NMR (150 MHz, $CD_3OD$) δ: 172.8 (2C), 153.3, 153.2, 114.8, 113.4, 112.9, 105.7, 104.8, 98.5, 85.5, 82.3, 80.7, 79.0, 78.8, 78.0 (2C), 77.6, 77.4, 77.3, 76.3, 76.0, 75.8, 75.5, 75.3, 75.1 (2C), 73.8, 73.7, 72.7, 69.6, 68.1, 68.0, 65.7, 45.5, 44.9 (2C), 41.1, 39.8, 38.2, 38.1, 37.8, 37.5, 37.1, 35.7, 33.0, 31.8, 31.34, 31.30, 30.8 (2C), 30.7, 30.1, 28.4, 27.3, 18.4, 18.1, 17.4, 15.8 ppm. FTIR (film): 3458, 2927, 2873, 1750, 1579, 1410, 1269, 1195, 1074, 1019, 991, 967 cm$^{-1}$. HRMS (ESI) m/z: [M+Na]$^+$ calcd for $C_{59}H_{82}O_{21}Na$, 1149.5246; found, 1149.5189.

38-Epi-Norhalichondrin A (C38-Epi-21):

$[\alpha]^{20}_D$ −83.8 (c 0.277, MeOH) δ: 5.05 (1H, s), 4.96 (1H, s), 4.87 (1H, s), 4.80 (1H, s), 4.62 (1H, dd, J=9.6, 6.6 Hz), 4.43 (1H, d, J=9.6 Hz), 4.39-4.33 (2H, m), 4.32-4.29 (2H, m), 4.20 (1H, t, J=3.2 Hz), 4.17-4.05 (4H, m), 4.00 (1H, dd, J=5.4, 2.1 Hz), 3.93-3.83 (4H, m), 3.79 (1H, t, J=6.4 Hz), 3.75-3.73 (1H, m), 3.67-3.56 (2H, m), 3.52 (1H, s), 3.34-3.32 (1H, m), 3.17 (1H, dd, J=9.6, 6.0 Hz), 2.94 (1H, dd, J=9.6, 1.8 Hz), 2.83 (1H, ddd, J=16.0, 8.0, 2.1 Hz), 2.56 (1H, dd, J=16.2, 9.6 Hz), 2.53-2.47 (2H, brs), 2.47 (1H, dd, J=17.6, 1.8 Hz), 2.35 (1H, d, J=15.6 Hz), 2.33-2.17 (6H, m), 2.14-2.06 (4H, m), 2.05-1.95 (4H, m), 1.92-1.80 (m, 3H), 1.77-1.64 (3H, m), 1.59-1.46 (4H, m), 1.43-1.31 (7H, m), 1.09 (3H, d, J=6.6 Hz), 1.03 (3H, d, J=7.0 Hz), 1.01-0.99 (1H, m), 0.99 (3H, d, J=7.2 Hz), 0.98 (3H, d, J=7.2 Hz). $^{13}$C NMR (125 MHz, $CD_3OD$) 172.9 (2C), 153.4, 152.7, 115.6, 113.4, 113.0, 105.2, 104.7, 98.4, 85.5, 82.4, 79.9, 79.1, 79.0, 78.9, 78.8, 78.6, 78.0, 77.0, 76.7, 76.1, 75.9, 75.8, 75.6, 75.3, 74.8, 74.0, 73.3, 73.2, 69.5, 68.4, 68.2, 68.0, 65.9, 45.5, 44.9, 44.8, 41.2, 39.7, 38.6, 38.2, 38.1, 37.5, 37.2, 35.7, 33.2, 31.8, 31.3, 31.0, 30.9, 30.1, 29.9, 27.0, 18.4, 18.3, 17.5, 15.1 ppm. FTIR (film): 3500 (br), 2927, 2873, 1736, 1579, 1191, 1075, 1020, 1009, 882, 756 cm$^{-1}$. HRMS (ESI) m/z: [M+Na]$^+$ calcd for $C_{59}H_{82}O_{21}Na$, 1149.5246; found, 1149.5156. C38-epi-21 was epimerized to Norhalichondrin A (21) by the following procedure:

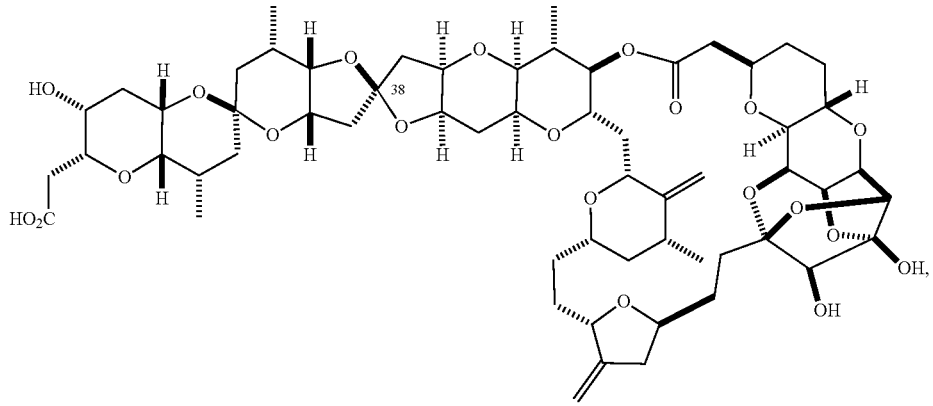

C38-epi-21

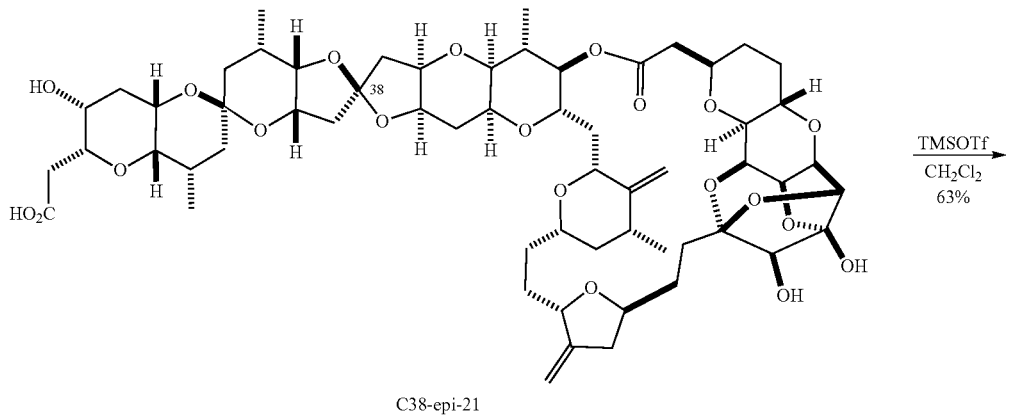

C38-epi-21

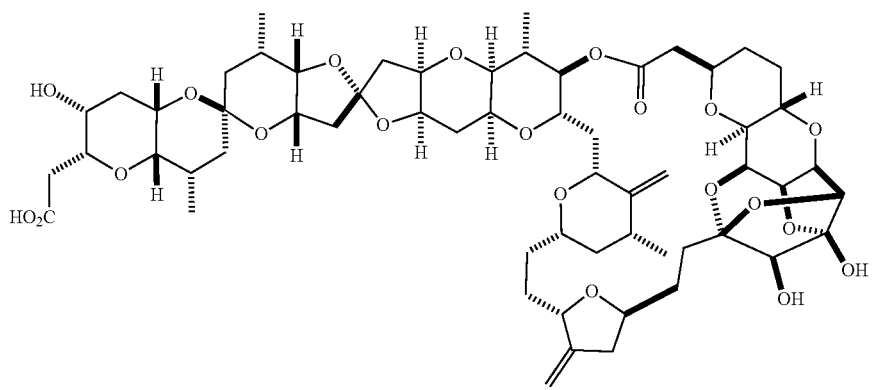

21

To a solution of C38-epi-21 (9.8 mg, 0.0087 mmol, 1 eq.) in $CH_2Cl_2$ (3.5 mL) was added TMSOTf (0.11 mL, 0.435 mmol, excess) at −78° C. After being stirred for 15 min, the reaction was quenched with sat. $NaHCO_3$ aq. After being stirred for 1 h at 0° C., the organic layer was separated and the aqueous layer was extracted with $CH_2Cl_2$. The combined organic layer was dried over $Na_2SO_4$, filtered, and concentrated under reduced pressure. The crude material was purified by YAMAZEN purification system with ODS column (Rf gradient: 10% MeCN in $H_2O$ to 100% MeCN) to give Norhalichondrin B (21) (6.2 mg, 0.0055 mmol, 63%) as a colorless solid.

Homohalichondrin A (22)

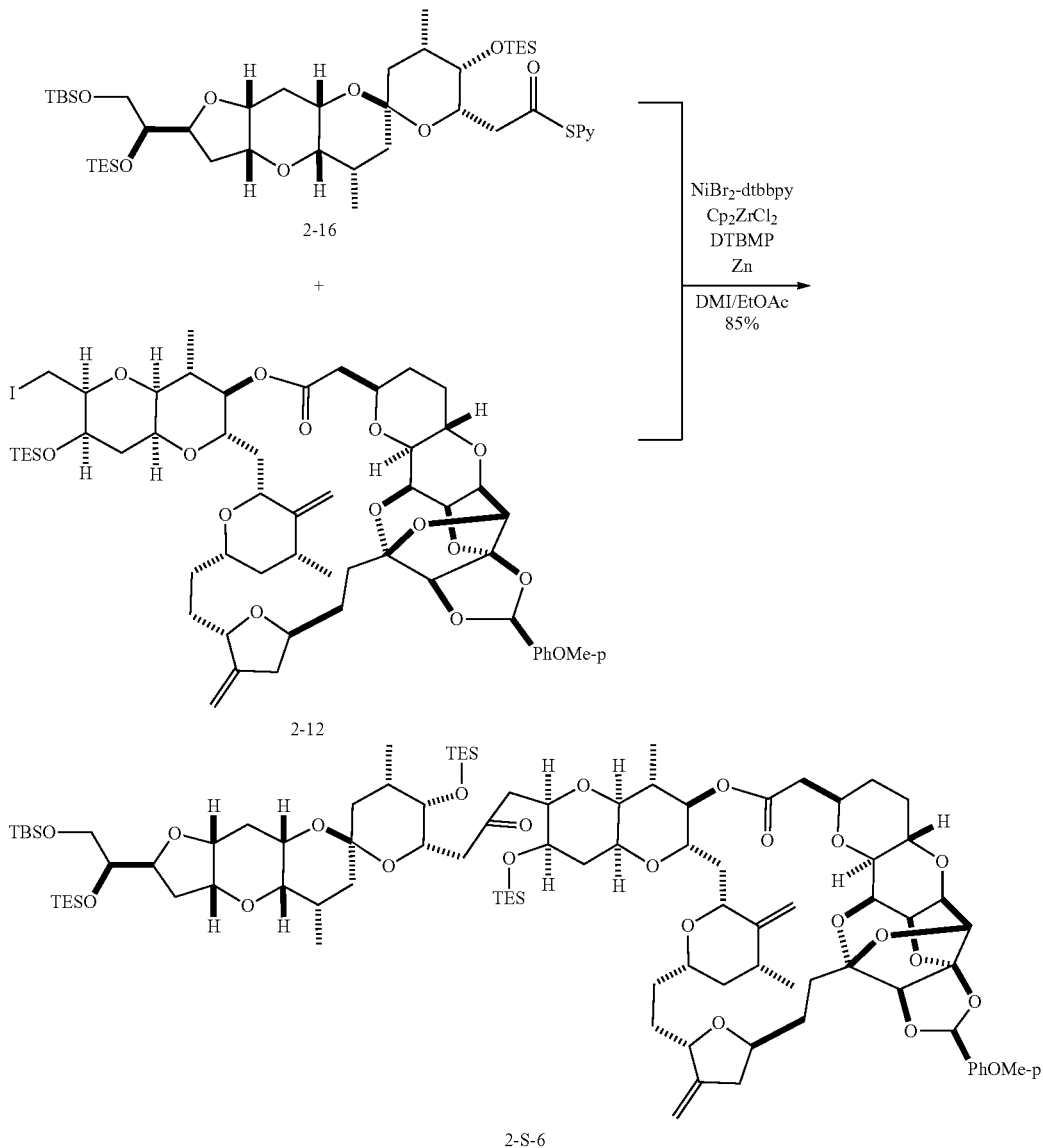

2-S-6

In a glove box, to a solution of iodide 2-12 (57.0 mg, 0.0503 mmol, 1 eq.) and thioester 2-16 (55.7 mg, 0.0653 mmol, 1.3 eq.) in DMI (0.42 mL) and EtOAc (80 μL) were added DTBMP (41.3 mg, 0.201 mmol, 4 eq.), Zn powder (19.7 mg, 0.301 mmol, 6 eq.), Cp$_2$ZrCl$_2$ (44.1 mg, 0.151 mmol, 3 eq.), and NiBr$_2$-dtbbpy (7.3 mg, 0.0150 mmol, 30 mol %) at room temperature. After being stirred for 2 h at the same temperature, the reaction mixture was removed from glove box and diluted with Et$_2$O and sat. NaHCO$_3$ aq. The organic layer was separated and the aqueous layer was extracted with Et$_2$O. The combined organic layer was dried over Na$_2$SO$_4$, filtered, and concentrated under reduced pressure. The obtained crude material was purified by flash column chromatography on neutral silica gel (0%, 9%, then 16% EtOAc in Hexanes) to give ketone 2-S-6 (74.8 mg, 0.0428 mmol, 85%) as a colorless amorphous solid. 2-S-6: $[i]^{20}_D$ −73.0 (c 1.07, CHCl$_3$). $^1$H NMR (600 MHz, C$_6$D$_6$) δ: 7.36 (2H, d, J=8.4 Hz), 6.73 (2H, d, J=8.4 Hz), 6.08 (1H, s), 5.22 (1H, s), 5.11 (1H, s), 4.96 (1H, s), 4.84-4.80 (3H, m), 4.69 (1H, d, J=10.2 Hz), 4.52-4.46 (2H, m), 4.41 (1H, s), 4.37 (1H, dd, J=4.8, 1.2 Hz), 4.35 (1H, d, J=10.2 Hz), 4.06-3.97 (5H, m), 3.83-3.80 (3H, m), 3.78-3.69 (69H, m), 3.67 (1H, s), 3.47 (1H, dd, J=8.4, 4.2 Hz), 3.28 (1H, s), 3.22 (3H, s), 3.19-3.15 (2H, m), 3.06 (1H, dd, J=17.4, 5.7 Hz), 3.00 (1H, dd, J=17.4, 6.9 Hz), 2.92 (1H, d, J=1.8 Hz), 2.79 (1H, dd, J=17.1, 7.5 Hz), 2.77-2.73 (1H, m), 2.53 (1H, d, J=9.6 Hz), 2.47 (1H, d, J=15.6 Hz), 2.42-2.21 (10H, m), 2.15-2.03 (6H, m), 1.98 (1H, dd, J=12.0, 12.0 Hz), 1.87-1.82 (2H, m), 1.76-1.67 (4H, m), 1.61-1.47 (6H, m), 1.38-1.27 (3H, m), 1.20 (3H, d, J=7.8 Hz), 1.11 (9H, t, J=8.1 Hz), 1.09 (3H, d, J=6.6 Hz), 1.06-1.04 (21H, m), 1.00 (9H, s), 0.96 (3H, d, J=6.0 Hz), 0.77 (6H, q, J=7.8 Hz), 0.70-0.65 (12H, m), 0.14 (3H, s), 0.13 (3H, s) ppm. $^{13}$C NMR (125 MHz, C$_6$D$_6$) δ: 206.7, 171.1, 161.4, 153.0, 152.7, 128.73, 128.69, 119.0, 114.1, 109.3, 109.0, 105.1, 103.8, 96.9, 90.2, 83.8, 79.1, 78.4, 78.1, 77.99, 77.96, 76.8, 76.1, 76.0, 75.5, 74.8, 74.7, 74.2, 74.0, 73.8, 73.6, 73.1, 70.1, 69.3, 68.4, 66.2, 65.9, 64.6, 63.8, 54.8, 46.9, 46.3, 44.0, 41.3, 39.50, 39.45, 38.7, 37.7, 37.6, 36.5, 36.4, 35.5, 32.4, 31.6, 31.1, 30.9, 30.7, 30.3, 30.2, 29.6, 27.7, 26.2, 18.7, 18.2, 17.6, 16.5, 7.5, 7.4, 7.3, 6.0, 5.7, 5.3, −5.1, −5.3 ppm. FTIR (film): 2953, 2927, 2875, 2104, 1724, 1615, 1518, 1459, 1373, 1306, 1251, 1092, 1032, 1010, 833, 742 cm$^{-1}$. HRMS (ESI) m/z: [M+Na]$^+$ calcd for $C_{93}H_{150}O_{23}Si_4Na$, 1769.9537; found, 1769.9316.

Hexanes then 4% MeOH in EtOAc) to give a crude Homohalichondrin A with its C-38 epimer. The mixture was purified by YAMAZEN purification system with ODS column (Rf gradient: 10% MeCN in $H_2O$ to 100% MeCN) to give Homohalichondrin A (22) (27.2 mg, 0.0235 mmol, 55% for 2 steps) as a colorless solid and 38-epi-Homohalichondrin A (C38-epi-22) (10.7 mg, 0.00926 mmol, 22% for 2 steps) as a colorless solid. Homohalichondrin A (22): $[\alpha]^{20}_D$ −80.3 (c 1.22, MeOH). $^1$H NMR (600 MHz, $CD_3OD$) δ:

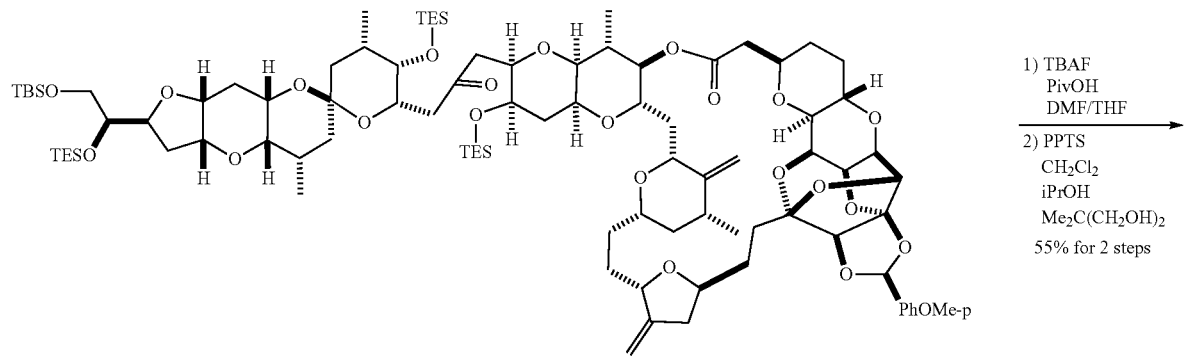

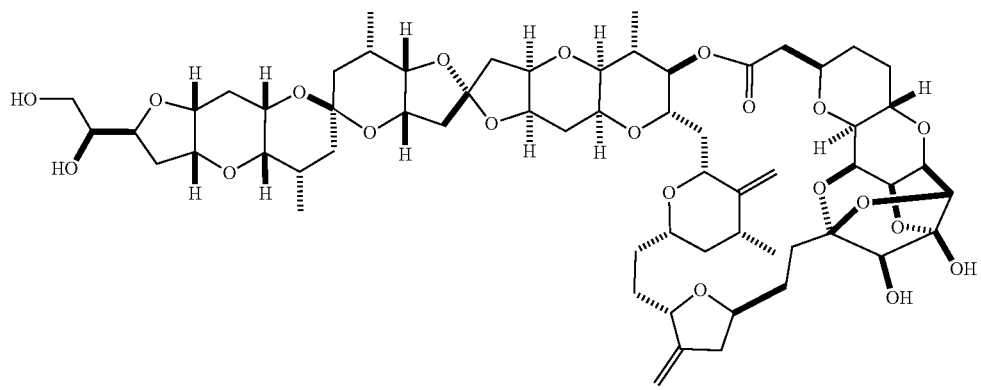

A buffered TBAF solution was prepared by mixing TBAF solution (TCI #T1125; 0.43 mL of 1 M in THF, 0.43 mmol, 10 eq.) and PivOH (22.0 mg, 0.215 mmol, 5 eq.). To a solution of ketone S-6 (74.8 mg, 0.0428 mmol, 1 eq.) in DMF (2.1 mL) was added the buffered TBAF solution at room temperature. After being stirred for 7 h at the same temperature, $CaCO_3$ (1.5 g) and DOWEX 50WX8-400 (1.5 g) were added. After being stirred for 1 h at the same temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of above tetraol (calculated as 0.0428 mmol, 1 eq.) in $CH_2Cl_2$ (2.1 mL) was added PPTS (53.8 mg, 0.214 mmol, 5 eq.) at room temperature. After 1 h, TLC analysis indicated the disappearance of starting material. iPrOH (0.43 mL) and additional PPTS (53.8 mg, 0.214 mmol, 5 eq.) were added to the resulted solution at the same temperature. After being stirred for 18 h, the reaction mixture was directly subjected to column chromatography on amino silica gel ($CH_2Cl_2$ then 25%, 50%, 75%, then 100% EtOAc in 5.07 (1H, s), 5.01 (1H, s), 4.88 (1H, s), 4.81 (1H, s), 4.63 (1H, dd, J=7.8, 4.8 Hz), 4.44 (1H, d, J=4.8 Hz), 4.37 (1H, s), 4.34-4.31 (3H, m), 4.25-4.22 (2H, m), 4.21 (1H, dd, J=2.7, 2.7 Hz), 4.11-4.08 (3H, m), 4.03 (1H, s), 3.95 (1H, s), 3.89-3.87 (3H, m), 3.71 (1H, dd, J=10.2, 10.2 Hz), 3.66 (1H, s), 3.61-3.57 (4H, m), 3.53 (1H, s), 3.50 (1H, dd, J=9.6, 4.8 Hz), 3.22 (1H, dd, J=6.0, 6.0 Hz), 3.12 (1H, s), 2.94 (1H, d, J=10.2 Hz), 2.82 (1H, dd, J=15.9, 5.7 Hz), 2.57 (1H, dd, J=17.3, 9.3 Hz), 2.45 (1H, d, J=17.3 Hz), 2.39 (1H, dd, J=13.5, 5.7 Hz), 2.38-2.24 (6H, m), 2.20-2.14 (3H, m), 2.09-1.98 (8H, m), 1.91-1.81 (4H, m), 1.74-1.68 (3H, m), 1.51-1.32 (9H, m), 1.10 (3H, d, J=6.6 Hz), 1.05 (3H, d, J=7.2 Hz), 1.05-0.99 (1H, m), 0.95 (3H, d, J=6.6 Hz), 0.94 (3H, d, J=6.0 Hz) ppm. $^{13}$C NMR (125 MHz, $^{12}CD_3OD$) δ: 172.8, 153.2, 153.0, 114.7, 113.3, 112.9, 105.7, 104.8, 98.1, 85.5, 82.3, 81.0, 79.8, 79.0, 78.4, 78.1, 77.9, 77.5, 76.3, 75.9, 75.8, 75.7, 75.5, 75.3, 74.5, 73.8, 73.7, 72.3, 69.6, 65.8, 65.2, 65.1, 49.9, 45.5, 44.9, 44.8, 41.1, 39.8, 38.1, 38.0, 37.8, 37.4, 37.23, 37.15, 33.0, 32.0, 31.8, 31.3, 30.8, 30.7, 30.1, 28.4, 27.1, 18.4, 18.2, 17.7 ppm. FTIR (film): 3398, 2927, 2873, 1736, 1372, 1269, 1187, 1129, 1074, 1020, 902, 753 cm$^{-1}$. HRMS (ESI) m/z: [M+NH$_4$]$^+$ calcd for $C_{61}H_{90}NO_{21}$, 1172.6000; found, 1172.5982.

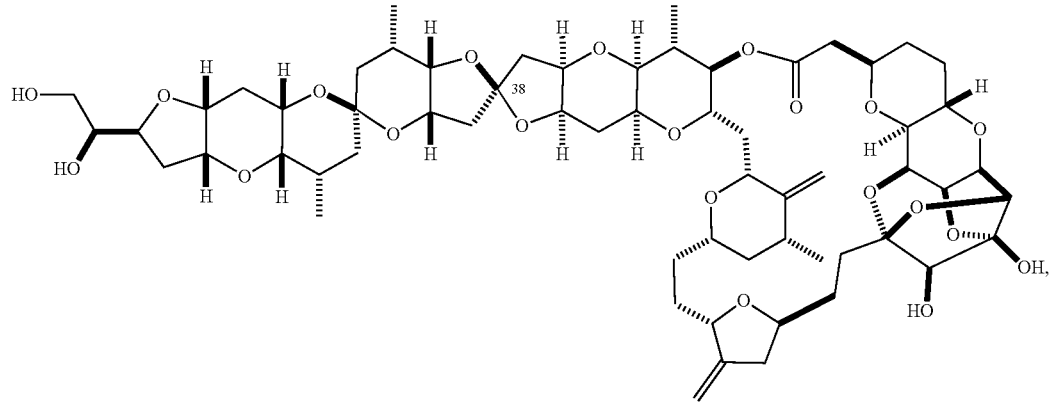

38-Epi-Homohalichondrin A (C38-Epi-22):

$[\alpha]^{20}_D$ −92.3 (c 0.573, MeOH). $^1$H NMR (600 MHz, CD$_3$OD) δ: 5.04 (1H, d, J=1.8 Hz), 4.96 (1H, d, J=1.8 Hz), 4.87 (1H, s), 4.80 (1H, s), 4.72 (1H, dd, J=10.5, 6.6 Hz), 4.43 (1H, d, J=10.2 Hz), 4.37 (1H, ddd, J=9.6, 9.6, 4.2 Hz), 4.34 (1H, s), 4.32-4.30 (2H, m), 4.23 (1H, ddd, J=10.2, 5.7, 4.5 Hz), 4.20 (1H, dd, J=2.7, 2.7 Hz), 4.16-4.06 (4H, m), 4.02 (1H, s), 3.98 (1H, dd, J=4.5, 2.1 Hz), 3.91-3.84 (3H, m), 3.81 (1H, dd, J=2.4, 2.4 Hz), 3.64 (1H, dd, J=10.2, 10.2 Hz), 3.60-3.56 (3H, m), 3.54 (1H, d, J=3.0 Hz), 3.52 (1H, s), 3.51-3.47 (1H, m), 3.17 (1H, dd, J=8.4, 6.0 Hz), 3.15 (1H, d, J=1.8 Hz), 2.95 (1H, dd, J=9.6, 1.8 Hz), 2.85-2.81 (1H, m), 2.56 (1H, dd, J=17.1, 9.0 Hz), 2.47 (1H, dd, J=17.1, 2.4 Hz), 2.36-1.97 (19H, m), 1.91 (1H, ddd, J=15.9, 4.8, 4.8 Hz), 1.88-1.81 (2H, m), 1.79-1.65 (3H, m), 1.57-1.52 (1H, m), 1.47 (1H, dd, J=12.9, 12.9 Hz), 1.42-1.35 (6H, m), 1.29 (1H, dd, J=12.6, 4.8 Hz), 1.09 (3H, d, J=6.6 Hz), 1.06-0.99 (1H, m), 1.003 (3H, d, J=7.2 Hz), 0.997 (3H, d, J=6.6 Hz), 0.96 (3H, d, J=7.2 Hz) ppm. $^{13}$C NMR (125 MHz, CD$_3$OD) δ: 172.9, 153.3, 152.7, 115.6, 113.3, 113.0, 105.1, 104.7, 97.9, 85.5, 82.4, 80.2, 79.8, 79.1, 78.88, 78.86, 78.5, 78.4, 77.8, 76.7, 76.1, 75.9, 75.83, 75.76, 75.5, 75.3, 75.1, 74.8, 74.4, 73.9, 73.2, 72.9, 69.5, 68.3, 65.3, 65.1, 45.6, 45.0, 44.8, 41.2, 39.7, 38.6, 38.3, 38.1, 37.5, 37.2, 33.3, 31.9, 31.7, 31.3, 31.0, 30.9, 30.1, 29.9, 28.3, 26.8, 18.4, 17.7, 15.2 ppm. FTIR (film): 3445, 2926, 2873, 1737, 1435, 1373, 1267, 1193, 1108, 1075, 1018, 897, 736 cm$^{-1}$. HRMS (ESI) m/z: [M+Na]$^+$ calcd for C$_{61}$H$_{86}$O$_{21}$Na, 1177.5536; found, 1177.5554. C38-epi-22 was epimerized to Homohalichondrin A (22) by following procedure:

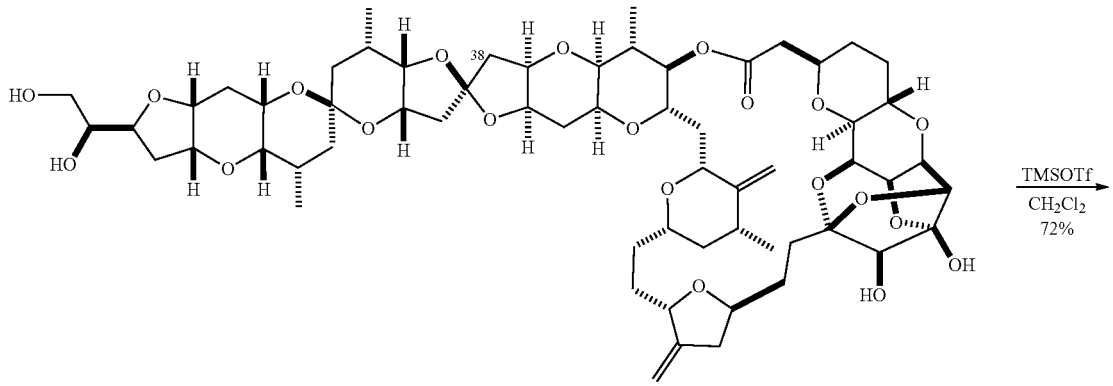

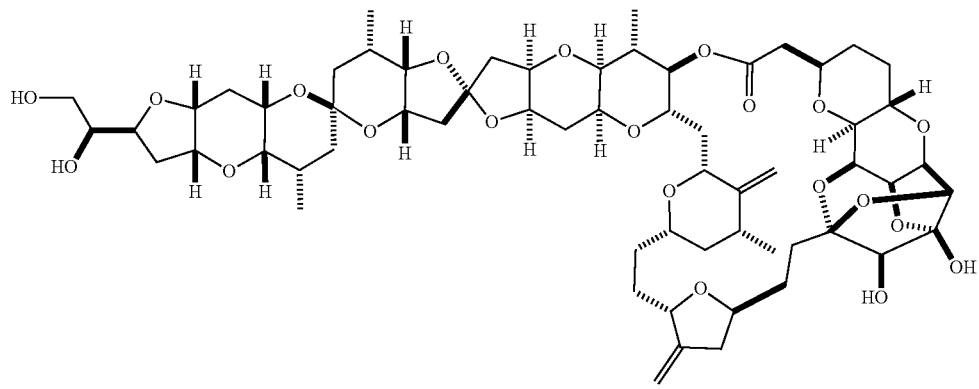

22

To a solution of C38-epi-22 (9.7 mg, 0.00840 mmol, 1 eq.) in $CH_2Cl_2$ (4.2 mL) was added TMSOTf (0.084 mL, 0.465 mmol, excess) at −78° C. After being stirred for 15 min, the reaction was quenched with sat. $NaHCO_3$ aq. After being stirred for 1 h at 0° C., the organic layer was separated and the aqueous layer was extracted with $CH_2Cl_2$. The combined organic layer was dried over $Na_2SO_4$, filtered, and concentrated under reduced pressure. The crude material was purified by YAMAZEN purification system with ODS column (Rf gradient: 10% MeCN in $H_2O$ to 100% MeCN) to give Homohalichondrin A (22) (7.0 mg, 0.00606 mmol, 72%) as a colorless solid.

Halichondrin C (23)

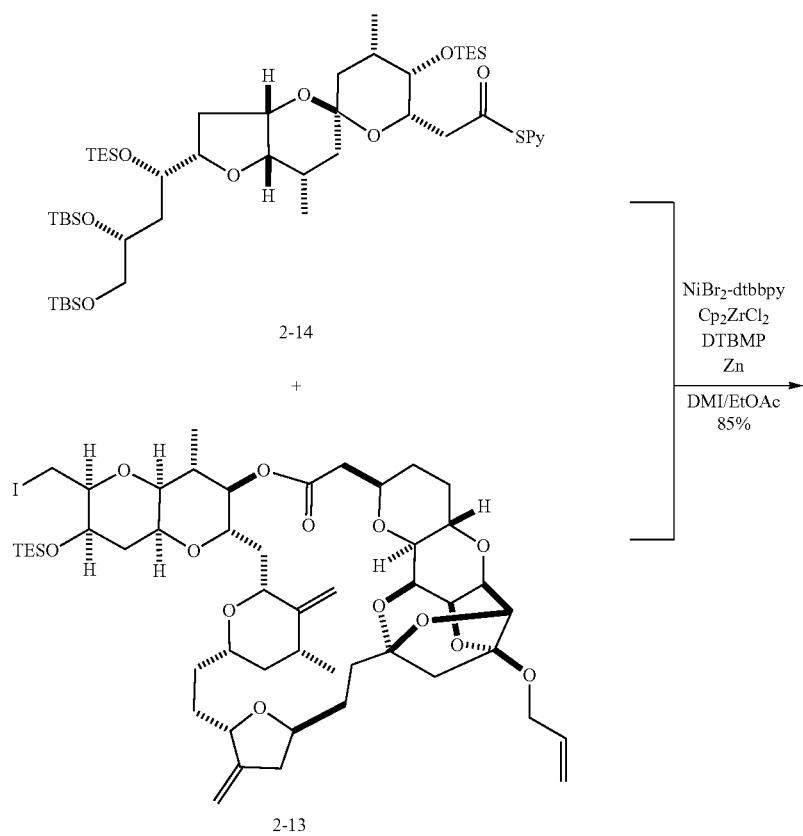

25

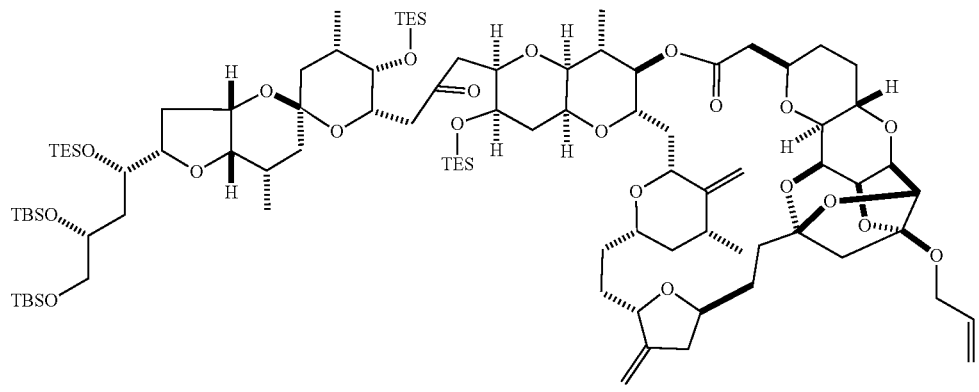

2-S-7

In a glove box, to a solution of iodide 2-13 (100 mg, 0.0962 mmol, 1 eq.) and thioester 2-14 (119 mg, 0.1246 mmol, 1.3 eq.) in DMI (0.80 mL) and EtOAc (0.16 mL) were added DTBMP (79 mg, 0.385 mmol, 4 eq.), Zn powder (37.7 mg, 0.576 mmol, 6 eq.), $Cp_2ZrCl_2$ (84.4 mg, 0.289 mmol, 3 eq.), and $NiBr_2$-dtbbpy (14.0 mg, 0.0288 mmol, 30 mol %) at room temperature. After being stirred for 1.5 h at the same temperature, the reaction mixture was removed from glove box and diluted with EtOAc and sat. $NaHCO_3$ aq. The organic layer was separated and the aqueous layer was extracted with EtOAc. The combined organic layer was dried over $Na_2SO_4$, filtered, and concentrated under reduced pressure. The obtained crude material was purified by YAMAZEN purification system on neutral silica gel (0%, 9%, then 15% EtOAc in Hexanes) to give ketone S-7 (143.2 mg, 0.0818 mmol, 85%) as a white amorphous solid. 2-S-8: $[\alpha]^{20}_D$ -59.4 (c 1.25, $CHCl_3$). $^1H$ NMR (600 MHz, $C_6D_6$) δ: 5.75 (1H, dddd, J=17.3, 10.5, 5.1, 5.1 Hz), 5.21 (1H, s), 5.15 (1H, ddd, J=17.3, 1.8, 1.8 Hz), 5.12 (1H, s), 4.97 (1H, ddd, J=10.5, 1.8, 1.8 Hz), 4.94 (1H, s), 4.85 (1H, dd, J=7.2, 7.2 Hz), 4.81-4.79 (2H, m), 4.67 (1H, d, J=10.2 Hz), 4.54-4.50 (2H, m), 4.37-4.36 (2H, m), 4.32 (1H, d, J=4.2 Hz), 4.26-4.23 (1H, m), 4.17-4.14 (1H, m), 4.11 (1H, dd, J=6.6, 4.8 Hz), 4.06-3.99 (3H, m), 3.93-3.88 (2H, m), 3.84-3.74 (7H, m), 3.70 (1H, dd, J=13.2, 6.0 Hz), 3.44-3.43 (2H, m), 3.33 (1H, s), 3.19 (1H, dd, J=17.6, 6.3 Hz), 3.16 (1H, dd, J=17.6, 6.6 Hz), 3.11-3.02 (2H, m), 2.77 (1H, dd, J=10.8, 2.4 Hz), 2.57 (1H, d, J=9.6 Hz), 2.49-2.44 (1H, m), 2.40-2.23 (9H, m), 2.18-2.02 (9H, m), 1.96 (1H, dd, J=13.8, 6.0 Hz), 1.86-1.66 (7H, m), 1.61 (1H, ddd, J=15.0, 4.8, 4.8 Hz), 1.55-1.47 (5H, m), 1.36-1.32 (3H, m), 1.19 (3H, d, J=7.2 Hz), 1.15 (3H, d, J=6.6 Hz), 1.11 (9H, t, J=8.0 Hz), 1.10 (9H, s), 1.09 (9H, t, J=8.4 Hz), 1.07 (9H, t, J=8.4 Hz), 1.04 (9H, s), 1.01 (3H, d, J=7.2 Hz), 0.96 (3H, d, J=7.2 Hz), 0.77 (6H, q, J=7.8 Hz), 0.70-0.65 (12H, m), 0.28 (6H, s), 0.15 (6H, s) ppm. $^{13}C$ NMR (125 MHz, $C_6D_6$) δ: 206.8, 171.3, 152.9, 152.6, 134.6, 116.6, 116.2, 109.3, 104.9, 103.8, 97.0, 83.3, 81.5, 80.4, 78.4, 77.9, 77.6, 75.9, 75.4, 75.1, 75.0, 75.0, 74.9, 74.7, 74.1, 74.0, 73.8, 72.8, 72.0, 71.8, 71.5, 70.4, 69.9, 68.4, 68.3, 65.9, 64.6, 51.7, 46.8, 46.3, 43.9, 41.2, 39.4, 39.3, 38.5, 38.2, 37.8, 36.4, 35.9, 35.4, 35.3, 32.5, 31.1, 30.7, 30.6, 30.5, 28.5, 26.6, 26.3 (×6), 26.3 (×6), 18.7, 18.6, 18.5, 18.4, 18.1, 16.4, 7.4 (×6), 7.4 (×6), 7.3 (×6), 6.0 (×3), 5.7 (×3), 5.3 (×3), −4.0, −4.2, −5.1, −5.2 ppm. FTIR (film): 2953, 2928, 2876, 1732, 1461, 1410, 1372, 1253, 1079, 1034, 1006, 834, 740 $cm^{-1}$. HRMS (ESI) m/z: $[M+H]^+$ calcd for $C_{93}H_{162}O_{21}Si_5Na$, 1778.0347; found, 1778.0332.

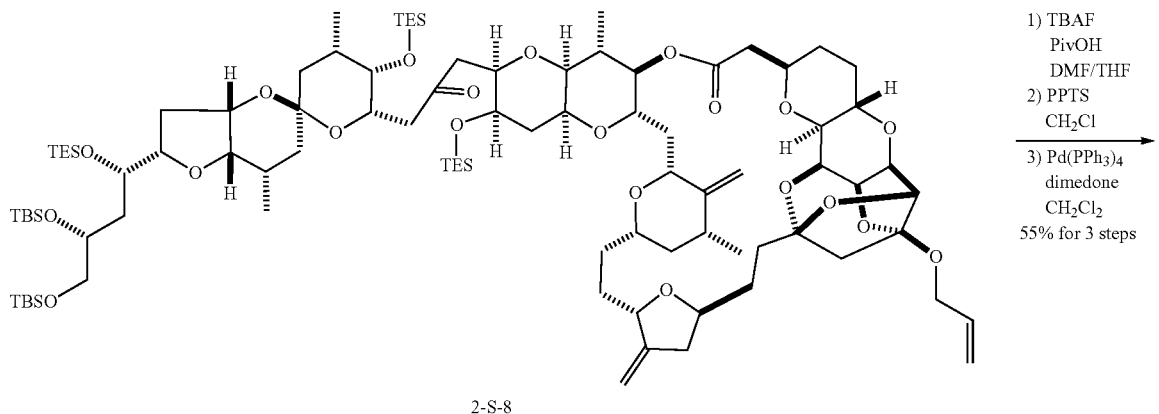

2-S-8

1) TBAF
PivOH
DMF/THF
2) PPTS
$CH_2Cl$
3) $Pd(PPh_3)_4$
dimedone
$CH_2Cl_2$
55% for 3 steps

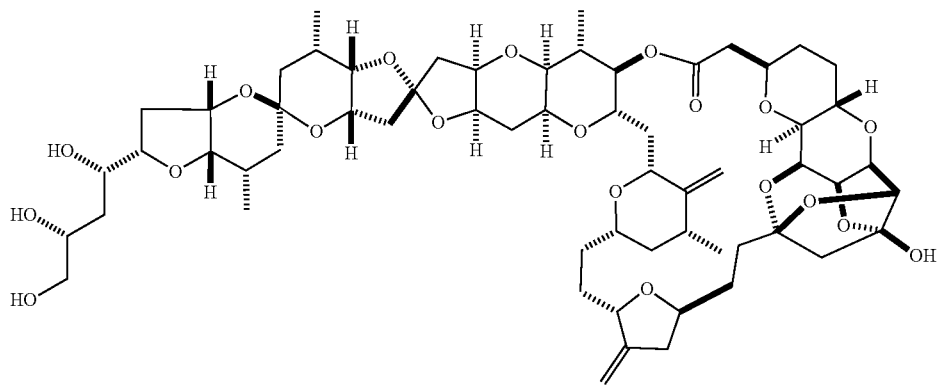

23

To a stirred solution of 2-S-8 (141 mg, 0.0803 mmol, 1 equiv.) in DMF (4.0 mL, 0.02M) was added the buffered TBAF solution (0.80 mL, 10 equiv., freshly prepared by 1.60 mL TBAF solution (1 M in THF) and 81.6 mg PivOH) at room temperature. After being stirred for 3 h at the same temperature, CaCO$_3$ (3.0 g) and DOWEX 50WX8-400 (3.0 g) were added.[1] After being stirred for 2 h at room temperature, the resulted mixture was diluted with EtOAc and filtered through a pad of Celite. The filter cake was washed with EtOAc thoroughly. The filtrate was concentrated under reduced pressure to give a crude material, which was used in the next step without further purification. To a stirred solution of above tetraol (calculated as 0.0803 mmol, 1 eq.) in CH$_2$Cl$_2$ (8 mL) was added PPTS (100 mg, 0.402 mmol, 5 eq.) at room temperature. After being stirred for 3 h at the same temperature, the reaction mixture was directly subjected to column chromatography on amino silica gel (CH$_2$Cl$_2$ then 50%, 75%, then 100% EtOAc in Hexanes then 9% MeOH in EtOAc) to give a crude spiro ketal, which was used in the next step without further purification. To a mixture of above crude spiro ketal (calculated as 0.0803 mmol, 1 eq.), dimedone (22.5 mg, 0.160 mmol, 2 equiv.), and Pd(PPh$_3$)$_4$ (9.3 mg, 0.00803 mmol, 10 mol %) was added degassed CH$_2$Cl$_2$ (8 mL) at room temperature. After being stirred for 4 h at the same temperature, the resulted solution was directly subjected to column chromatography on amino silica gel (CH$_2$Cl$_2$ then 50%, 100% EtOAc in Hexanes then 9% MeOH in EtOAc) to give a crude halichondrin C with its C-38 epimer. The mixture was purified by YAMAZEN purification system with ODS column (Rf gradient: 10% MeCN in H$_2$O to 100% MeCN) to give Halichondrin C (23) (48.1 mg, 0.0427 mmol, 55% for 3 steps) as a white crystalline solid and 38-epi-halicondrin C (C38-epi-23) (9.5 mg, 0.00843 mmol, 11% for 3 steps) as a colorless solid. Halichondrin C (23): $[\alpha]^{20}_D$ −66.8 (c 0.25, MeOH). $^1$H NMR (600 MHz, CD$_3$OD) δ: 5.07 (1H, s), 5.01 (1H, s), 4.88 (1H, s), 4.81 (1H, s), 4.62 (1H, dd, J=7.2, 4.4 Hz), 4.43 (1H, d, J=11.2 Hz), 4.42-4.38 (1H, m), 4.34-4.27 (3H, m), 4.24 (1H, ddd, J=11.2, 4.4, 2.0 Hz), 4.17 (1H, dd, J=3.8, 1.0 Hz), 4.14-4.06 (4H, m), 4.05 (1H, ddd, J=2.0, 2.0, 2.0 Hz), 3.99 (1H, ddd, J=9.4, 4.3, 4.3 Hz), 3.92-3.82 (3H, m), 3.77 (1H, ddd, J=8.4, 4.4, 4.2 Hz), 3.74-3.66 (2H, m), 3.61 (1H, d, J=11.2 Hz), 3.58-3.55 (1H, m), 3.53 (1H, dd, J=11.2, 4.4 Hz), 3.46 (1H, dd, J=11.2, 6.4 Hz), 3.22 (1H, dd, J=6.4, 4.8 Hz), 2.94 (1H, dd, J=9.8, 2.0 Hz), 2.84-2.75 (1H, m), 2.55 (1H, dd, J=17.6, 9.2 Hz), 2.45 (1H, dd, J=17.6, 2.4 Hz), 2.39 (1H, dd, J=13.2, 6.3 Hz), 2.36-2.21 (9H, m), 2.20-2.02 (5H, m), 2.01-1.94 (2H, m), 1.89-1.78 (3H, m), 1.78-1.56 (6H, m), 1.56-1.20 (11H, m), 1.10 (3H, d, J=6.3 Hz), 1.06 (3H, d, J=6.8 Hz), 1.05-0.99 (1H, m), 1.02 (3H, d, J=7.2 Hz), 0.97 (3H, d, J=6.8 Hz). $^{13}$C NMR (125 MHz, CD$_3$OD) δ: 172.8, 153.3, 153.1, 114.8, 114.2, 110.4, 105.7, 104.7, 98.4, 86.2, 81.3, 81.2, 80.8, 79.0, 78.0, 78.0, 77.4, 77.2, 76.4, 76.3, 76.1, 75.8, 75.3, 75.0, 74.9, 74.7, 73.8, 73.3, 73.1, 73.0, 71.6, 69.5, 67.2, 65.7, 53.7, 45.5, 44.9, 44.9, 41.2, 39.7, 38.0, 37.9, 37.8, 37.5, 37.5, 37.2, 36.3, 36.2, 33.0, 31.8, 31.2, 31.0, 30.8, 29.0, 27.1, 27.0, 18.4, 18.3, 18.1, 15.8. FTIR (film): 3422, 2926, 2873, 1736, 1436, 1310, 1186, 1117, 1074, 1021, 995, 910, 755 cm$^{-1}$. HRMS (ESI) m/z: [M+Na]$^+$ calcd for C$_{60}$H$_{86}$O$_{20}$Na, 1149.5605; found, 1149.5614.

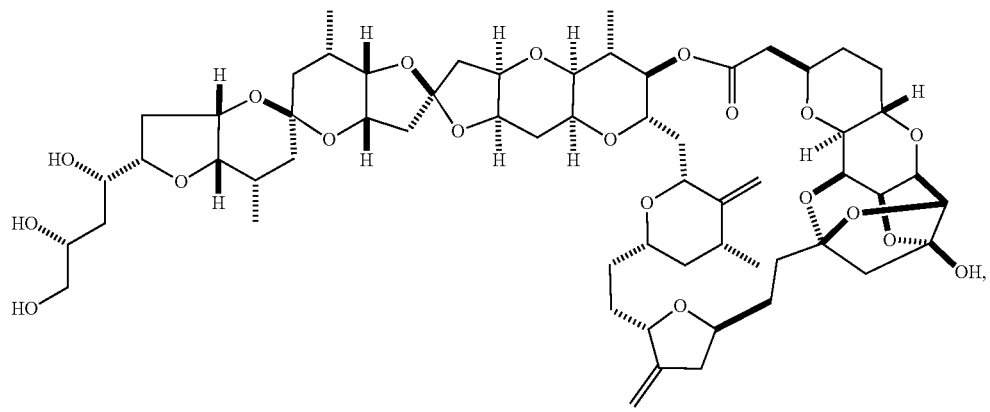
C38-epi-23
38-Epi-Halichondrin C (C38-Epi-23):
$[\alpha]^{20}_D$ −69.6 (c 0.46, MeOH). $^1$H NMR (600 MHz, CD$_3$OD) δ: 5.03 (1H, s), 4.95 (1H, s), 4.87 (1H, s), 4.81 (1H, s), 4.72 (1H, dd, J=10.2, 6.6 Hz), 4.41 (1H, d, J=11.4 Hz), 4.38-4.32 (2H, m), 4.32-4.28 (2H, m), 4.17-4.06 (6H, m), 3.99 (1H, ddd, J=9.6, 5.4, 4.2 Hz), 3.90-3.83 (4H, m), 3.78 (1H, ddd, J=14.4 4.8, 4.2 Hz), 3.63-3.56 (3H, m), 3.53 (1H, dd, J=11.6, 4.5 Hz), 3.47 (1H, dd, J=10.8, 6.0 Hz), 3.17 (1H, dd, J=9.0, 6.0 Hz), 2.95 (1H, dd, J=9.6, 1.8 Hz), 2.86-2.80 (1H, m), 2.54 (1H, dd, J=16.8, 8.4 Hz), 2.47 (1H, dd, J=16.8, 2.4 Hz), 2.34-2.08 (12H, m), 2.12-2.07 (3H, m), 2.04-1.96 (4H, m), 1.88-1.81 (2H, m), 1.79-1.29 (15H, m), 1.10 (3H, d, J=6.0 Hz), 1.04 (3H, d, J=8.4 Hz), 1.05-0.99 (1H, m), 1.02 (3H, d, J=6.6 Hz), 1.00 (3H, d, J=6.6 Hz) ppm. $^{13}$C NMR (125 MHz, CD$_3$OD) δ: 172.9, 153.3, 152.8, 115.6, 114.2, 110.5, 105.1, 104.7, 98.3, 86.2, 81.3, 81.1, 80.0, 79.2, 78.9, 78.9, 78.4, 77.9, 76.6, 76.4, 76.1, 76.0, 75.9, 75.2, 74.9, 74.8, 73.6, 73.3, 73.2, 73.1, 71.7, 69.4, 68.3, 67.2, 53.7, 45.6, 44.9, 44.7, 41.2, 39.6, 38.3, 38.3, 38.1, 37.5, 37.5, 37.2, 36.2, 36.0, 33.3, 31.7, 31.2, 30.9, 30.2, 28.9, 27.1, 26.8, 18.4, 18.3, 18.3, 15.2. ppm. FTIR (film): 3427, 2925, 2872, 1736, 1662, 1553, 1436, 1311, 1188, 1117, 1075, 1023, 996, 898, 735 cm$^{-1}$. HRMS (ESI) m/z: [M+Na]$^+$ calcd for C$_{60}$H$_{86}$O$_{20}$Na, 1149.5605; found, 1149.5618.
Norhalichondrin C (24)
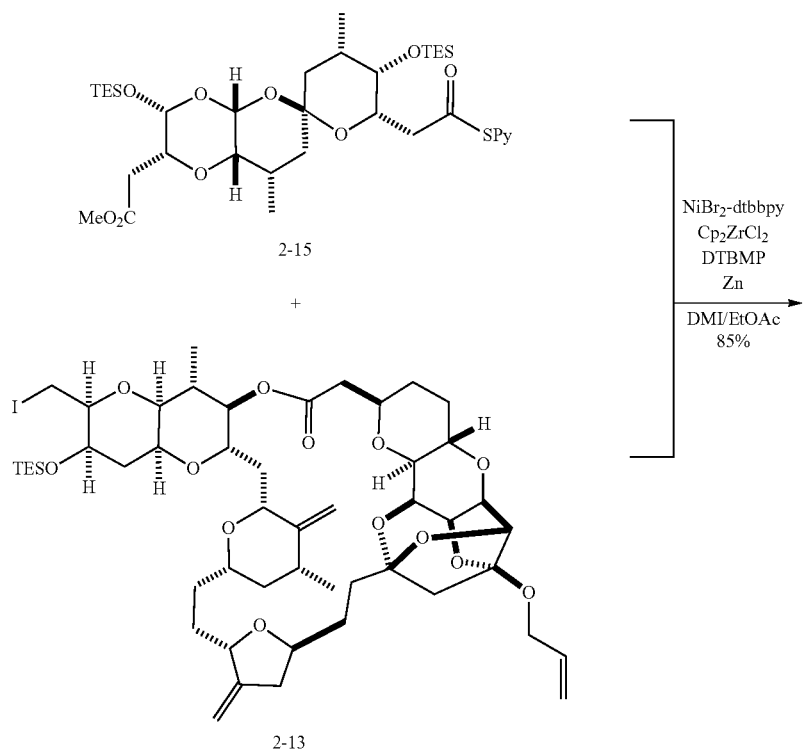

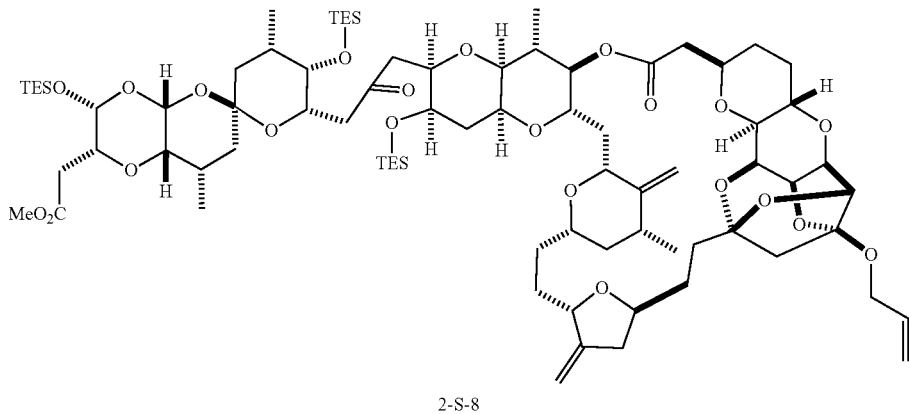

2-S-8

In a glove box, to a solution of iodide 2-13 (50 mg, 0.0482 mmol, 1 eq.) and thioester 2-15 (45.4 mg, 0.0627 mmol, 1.3 eq.) in DMI (0.4 mL) and EtOAc (0.08 mL) were added DTBMP (39.5 mg, 0.193 mmol, 4 eq.), Zn powder (18.8 mg, 0.289 mmol, 6 eq.), $Cp_2ZrCl_2$ (42.2 mg, 0.144 mmol, 3 eq.), and $NiBr_2$-dtbbpy (7.0 mg, 0.0144 mmol, 30 mol %) at room temperature. After being stirred for 1.5 h at the same temperature, the reaction mixture was removed from glove box and diluted with $Et_2O$ and sat. $NaHCO_3$ aq. The organic layer was separated and the aqueous layer was extracted with $Et_2O$. The combined organic layer was dried over $Na_2SO_4$, filtered, and concentrated under reduced pressure. The obtained crude material was purified by flash column chromatography on neutral silica gel (0%, 15%, 25% EtOAc in Hexanes) to give ketone 2-S-8 (62.4 mg, 0.0409 mmol, 85%) as a colorless amorphous solid. (S-8): $[i]^{20}_D$ −64.8 (c 1.00, $CHCl_3$). $^1H$ NMR (600 MHz, $C_6D_6$) δ: 5.75 (1H, dddd, J=17.3, 10.5, 5.1, 5.1 Hz), 5.21 (1H, s), 5.15 (1H, ddd, J=17.3, 1.8, 1.8 Hz), 5.11 (1H, s), 4.97 (1H, ddd, J=10.5, 1.8, 1.8 Hz), 4.94 (1H, s), 4.87-4.82 (1H, m), 4.82-4.77 (2H, m), 4.67 (1H, d, J=10.8 Hz), 4.52 (1H, ddd, J=10.2, 10.2, 4.8 Hz), 4.38-4.33 (2H, m), 4.32 (1H, J=4.6 Hz), 4.11 (1H, dd, J=6.9, 5.1 Hz), 4.07-3.97 (4H, m), 3.84-3.78 (4H, m), 3.77-3.68 (3H, m), 3.58 (1H, d, J=1.2 Hz), 3.43 (1H, ddd, J=4.5, 4.5, 4.5 Hz), 3.37 (4H, s), 3.36 (1H, s), 3.21-3.11 (3H, m), 2.86-2.81 (1H, m), 2.80-2.74 (2H, m), 2.59-2.54 (2H, m), 2.42-2.35 (3H, m), 2.34-2.22 (8H, m), 2.20-2.04 (7H, m), 1.97 (1H, dd, J=13.8, 13.5 Hz,), 1.87-1.80 (1H, m), 1.78-1.63 (4H, m), 1.62-1.44 (7H, m), 1.38-1.30 (2H, m), 1.19 (3H, d, J=7.2 Hz), 1.13-1.02 (31H, m), 1.01 (3H, d, J=7.2 Hz), 0.99 (3H, d, J=7.2 Hz), 0.71-0.60 (18H, m) ppm. $^{13}C$ NMR (125 MHz, $C_6D_6$) δ: 206.9, 171.8, 171.3, 152.9, 152.6, 134.6, 116.6, 116.2, 109.3, 105.0, 103.8, 96.9, 83.3, 78.3, 77.9, 77.7, 77.2, 76.5, 76.0, 75.4, 75.1, 75.0, 74.9, 74.6, 74.1, 74.0, 73.8, 73.0, 70.4, 69.6, 68.4, 66.0, 65.9, 64.6, 64.5, 51.7, 50.9, 46.8, 46.3, 43.9, 41.2, 39.5, 39.3, 38.6, 37.7, 37.2, 36.4, 36.3, 35.9, 35.4, 32.5, 31.1, 31.0, 30.7, 30.5, 29.2, 28.5, 18.6, 18.2, 17.3, 16.5, 7.5, 7.3, 7.2, 6.0, 5.4, 5.3 ppm. FTIR (film): 2953, 2913, 2876, 1737, 1458, 1372, 1337, 1312, 1280, 1208, 1186, 1155, 1119, 1085, 1072, 1035, 1012, 823, 736 $cm^{-1}$. HRMS (ESI) m/z: $[M+Na]^+$ calcd for $C_{81}H_{132}O_{21}Si_3Na$, 1547.8467; found, 1547.8524.

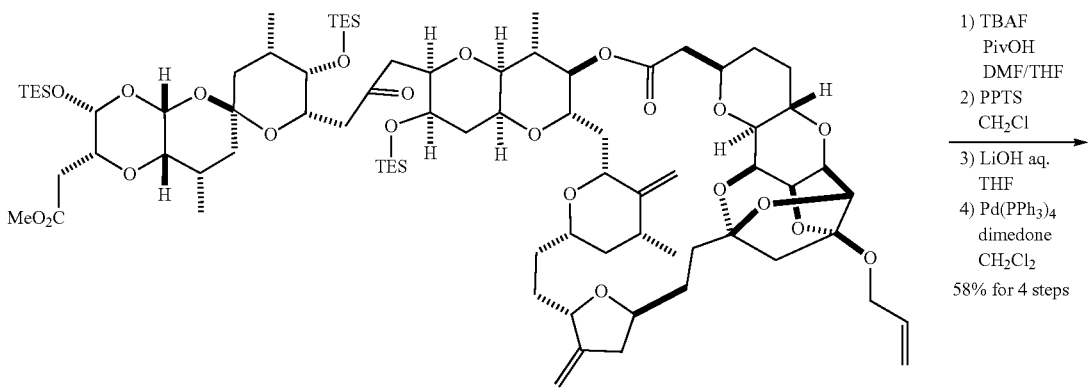

2-S-8

1) TBAF
   PivOH
   DMF/THF
2) PPTS
   $CH_2Cl$
3) LiOH aq.
   THF
4) $Pd(PPh_3)_4$
   dimedone
   $CH_2Cl_2$ 58% for 4 steps

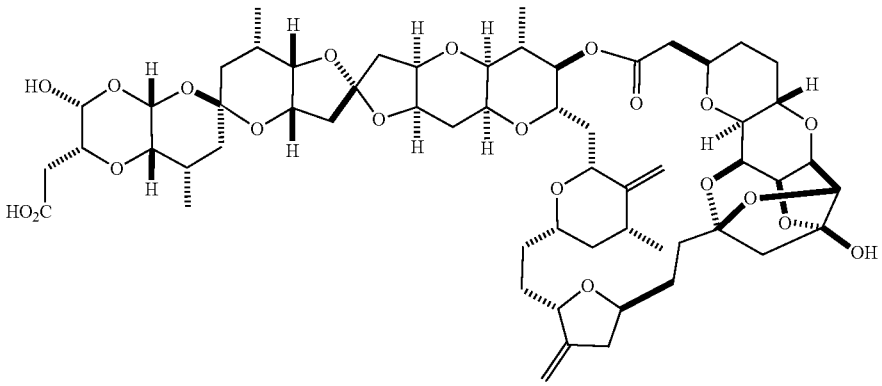

24

A buffered TBAF solution was prepared by mixing TBAF solution (TCI #T1125; 0.33 mL of 1 M in THF, 0.33 mmol, 10 eq.) and PivOH (16.7 mg, 0.164 mmol, 5 eq.). To a stirred solution of ketone 2-S-8 (50 mg, 0.0328 mmol, 1 eq.) in DMF (2.0 mL) was added the buffered TBAF solution at room temperature. After being stirred for 6 h at the same temperature, $CaCO_3$ (1.0 g) and DOWEX 50WX8-400 (1.0 g) were added after diluting with 5 mL EtOAc. After being stirred for 1 h at room temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of the crude tetraol (calculated as 0.0328 mmol, 1 eq.) in $CH_2Cl_2$ (8.5 mL) was added PPTS (33.1 mg, 0.132 mmol, 4 eq.) at room temperature. After 1 h, TLC analysis indicated the disappearance of starting material. The reaction mixture was directly subjected to column chromatography on amino silica gel ($CH_2Cl_2$ then 25%, 50%, 75%, then 100% EtOAc in Hexanes then 2% MeOH in EtOAc) to give a crude allyl protected Norhalichondrin C methyl ester with its C38 epimer. The compound was used in the next step after concentration without further purification. To a stirred solution of the crude methyl ester (calculated as 0.0328 mmol, 1 eq.) in THF (5 mL), 1.3 mL of aqueous 1M LiOH was added at room temperature. After being stirred for 1.5 h at the same temperature, the reaction mixture was diluted by 3 mL of water. The THF was then removed from the mixture by evaporator. After the reaction was cooled down to 0° C., 1.5 mL of 1 M aqueous HCl was added immediately followed by 10 mL of PH 7 aqueous buffer solution. The resulting mixture was extracted with EtOAc. The combined organic layers were dried over $Na_2SO_4$, filtered, and concentrated under reduced pressure. The resulting mixture was moved to next step without further purification.

To a mixture of above crude acid (calculated as 0.0328 mmol, 1 eq.), dimedone (9.2 mg, 0.0656 mmol, 2 eq.), and $Pd(PPh_3)_4$ (5.7 mg, 0.00492 mmol, 15 mol %) was added $CH_2Cl_2$ (4.0 mL) at room temperature. After being stirred for 3 h at the same temperature, the resulted solution was diluted with DMF (3 mL). After removal of DCM by evaporator, the mixture was purified by YAMAZEN purification system with ODS column (Rf gradient: 10% MeCN in $H_2O$ to 100% MeCN) to give Norhalichondrin C (24) (21.0 mg, 0.019 mmol, 58% for 4 steps) as a colorless solid. 38-epi-Homohalicondrin C (C38-epi-24) was decomposed while concentrating with inseparable reagent residue after ODS column. Norhalichondrin C (24): $[\alpha]^{20}_D$ −61.2 (c 0.300, MeOH)$^1$H NMR (600 MHz, $CD_3OD$) δ: 5.06 (1H, s), 5.01 (1H, s), 4.88 (1H, s), 4.81 (1H, s), 4.62 (1H, dd, J=7.2, 4.8 Hz), 4.43 (1H, d, J=10.8 Hz), 4.42-4.39 (1H, m), 4.34-4.27 (3H, m), 4.24 (1H, ddd, J=11.2, 4.2, 1.8 Hz), 4.17 (1H, dd, J=4.2 Hz), 4.11 (2H, brs), 4.09-4.05 (1H, m), 3.98 (1H, brs), 3.91-3.85 (2H, m), 3.82-3.76 (2H, m), 3.73-3.67 (2H, m), 3.62-3.57 (2H, m), 3.53 (1H, s), 3.31 (1H, m), 3.21 (1H, dd, J=6.6, 4.7 Hz), 2.94 (1H, d, J=9.6 Hz), 2.81 (1H, dd, J=15.0, 6.6 Hz), 2.55 (1H, dd, J=16.2, 9.6 Hz), 2.52-2.48 (2H, brs), 2.45 (1H, d, J=17.6), 2.39 (1H, dd, J=13.2, 6.2 Hz), 2.33 (2H, brs), 2.31-2.23 (5H, m), 2.19-1.99 (6H, m), 1.99-1.94 (2H, m), 1.92 (1H, d, J=13.2 Hz), 1.90-1.79 (2H, m), 1.76-1.63 (3H, m), 1.54-1.46 (4H, m), 1.46-1.26 (7H, m), 1.10 (3H, d, J=6.0 Hz), 1.06 (3H, d, J=6.6 Hz), 1.02 (1H, d, J=12.0 Hz), 0.98 (3H, d, J=7.2 Hz), 0.96 (3H, d, J=7.2 Hz). $^{13}$C NMR (150 MHz, $CD_3OD$) δ: 172.8 (2C), 153.3, 153.2, 114.8, 114.2, 110.4, 105.7, 104.8, 98.5, 86.2, 80.7, 80.6, 79.1, 79.0, 78.0 (2C), 77.2 (2C), 76.3 (2C), 76.0, 75.8, 75.3, 75.0, 74.9, 74.7, 73.8, 73.7, 72.7 (2C), 69.5, 68.1, 68.0, 65.7, 53.6, 45.5, 44.9, 41.1, 39.7, 38.2, 38.1, 37.8, 37.5, 37.1, 36.7, 35.7, 33.0, 31.8, 31.2, 32.0, 30.8, 30.0, 29.0, 27.3, 18.4, 18.1, 17.4, 15.8. FTIR (film): 3480, 2953, 2932, 2923, 1733, 1317, 1189, 1119, 1073, 1011, 995, 964, 914, 555 cm$^{-1}$. HRMS (ESI) m/z: [M+Na]$^+$ calcd for $C_{59}H_{82}O_{20}Na$, 1113.5297; found, 1133.5248.

Homohalichondrin C (25)

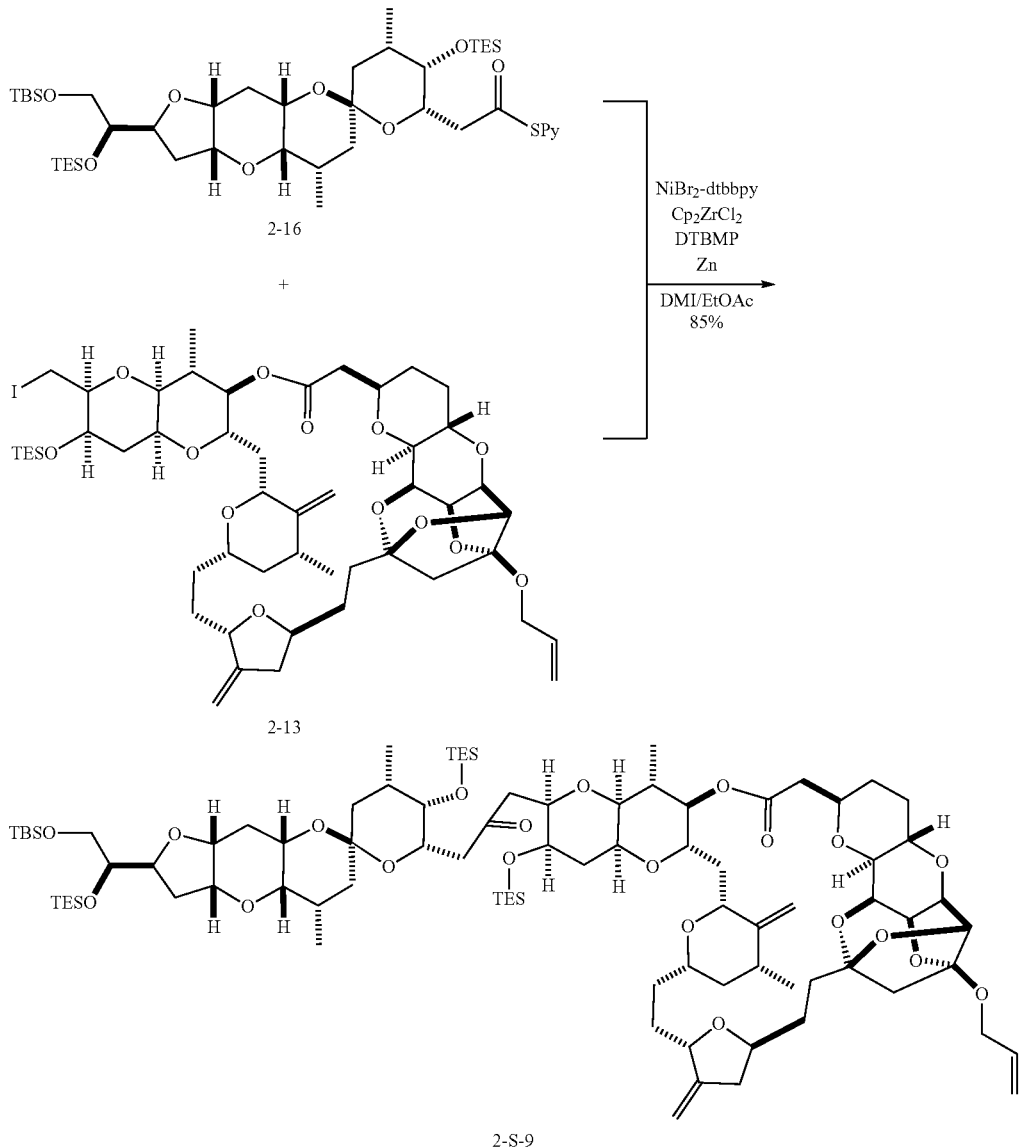

In a glove box, to a solution of iodide 2-13 (52.1 mg, 0.0501 mmol, 1 eq.) and thioester 2-16 (55.5 mg, 0.0651 mmol, 1.3 eq.) in DMI (0.40 mL) and EtOAc (80 μL) were added DTBMP (39.5 mg, 0.192 mmol, 4 eq.), Zn powder (18.9 mg, 0.289 mmol, 6 eq.), Cp$_2$ZrCl$_2$ (42.2 mg, 0.144 mmol, 3 eq.), and NiBr$_2$-dtbbpy (7.0 mg, 0.0144 mmol, 30 mol %) at room temperature. After being stirred for 4 h at the same temperature, the reaction mixture was removed from glove box and diluted with Et$_2$O and sat. NaHCO$_3$ aq. The organic layer was separated and the aqueous layer was extracted with Et$_2$O. The combined organic layer was dried over Na$_2$SO$_4$, filtered, and concentrated under reduced pressure. The obtained crude material was purified by flash column chromatography on neutral silica gel (0%, 9%, 13%, then 17% EtOAc in Hexanes) to give ketone 2-S-9 (70.5 mg, 0.0426 mmol, 85%) as a colorless amorphous solid. 2-S-9: $[\alpha]^{20}_D$ −64.0 (c 0.800, CHCl$_3$). $^1$H NMR (600 MHz, C$_6$D$_6$) δ: 5.75 (1H, dddd, J=17.3, 10.5, 5.1, 5.1 Hz), 5.21 (1H, s), 5.15 (1H, ddd, J=17.3, 1.8, 1.8 Hz), 5.12 (1H, s), 4.97 (1H, ddd, J=10.5, 1.8, 1.8 Hz), 4.94 (1H, s), 4.86-4.79 (3H, m), 4.67 (1H, d, J=10.8 Hz), 4.52 (1H, ddd, J=10.2, 10.2, 4.8 Hz), 4.48 (1H, ddd, J=10.2, 5.4, 5.4 Hz), 4.37 (1H, dd, J=3.9, 3.0 Hz), 4.35 (1H, dd, J=10.2, 1.8 Hz), 4.32 (1H, d, J=3.6 Hz), 4.11 (1H, dd, J=6.9, 5.1 Hz), 4.06-3.98 (4H, m), 3.84-3.79 (5H, m), 3.78-3.75 (2H, m), 3.73-3.67 (4H, m), 3.45 (1H, ddd, J=4.5, 4.5, 4.5 Hz), 3.28 (1H, s), 3.21-3.16 (2H, m), 3.07 (1H, dd, J=17.6, 6.3 Hz), 3.01 (1H, dd, J=17.6, 6.6 Hz), 2.93 (1H, d, J=2.4 Hz), 2.80-2.76 (2H, m), 2.57 (1H, dd, J=9.9, 2.1 Hz), 2.47 (1H, d, J=16.2 Hz), 2.40-2.23 (9H, m), 2.23-2.05 (6H, m), 1.98 (1H, dddd, J=14.1, 11.7, 4.0, 4.0 Hz), 1.89-1.82 (2H, m), 1.77-1.68 (4H, m), 1.61 (1H, ddd, J=14.4, 4.8, 4.8 Hz), 1.58 (1H, dd, J=12.9, 3.9 Hz), 1.55-1.47 (5H, m), 1.36-1.32 (3H, m), 1.19 (3H, d, J=7.8 Hz), 1.11 (9H, t, J=8.0 Hz), 1.09 (3H, d, J=6.6 Hz), 1.07 (9H, t, J=8.4 Hz), 1.05 (9H, t, J=8.4 Hz), 1.02-1.01 (12H, m), 0.96 (3H, d, J=7.2 Hz), 0.77 (6H, q, J=7.8 Hz), 0.69-0.65 (12H, m), 0.14 (3H, s), 0.13 (3H, s) ppm. $^{13}$C NMR (125 MHz, C$_6$D$_6$) δ: 206.8, 171.3, 153.0, 152.6, 134.6, 116.6, 116.2, 109.3, 104.39, 103.8, 96.9, 83.3, 79.1, 78.4, 78.0, 77.9, 77.7, 76.8, 76.0, 75.5, 75.1, 75.0, 74.9, 74.7, 74.22, 74.16, 74.1, 73.8, 73.6, 73.0, 70.4, 69.4, 68.4, 66.2, 65.9, 64.6, 63.8, 51.7, 46.8, 46.3, 43.9, 41.2, 39.5, 39.3, 38.6, 37.7, 37.6, 36.5, 36.4, 35.9, 35.3, 32.5, 31.6, 31.1, 30.72, 30.67, 30.5, 29.6, 28.6, 26.2, 18.7, 18.6, 18.1, 17.6, 16.4, 7.5, 7.4, 7.3, 6.0, 5.7, 5.3, −5.1, −5.3 ppm. FTIR (film): 2953, 2928, 2875, 1730, 1554, 1459, 1372, 1310, 1238, 1185, 1155, 1077, 1034, 1012, 834, 740 cm$^{-1}$. HRMS (ESI) m/z: [M+H]$^+$ calcd for C$_{88}$H$_{149}$O$_{21}$Si$_4$, 1653.9663; found, 1653.9702.

Hexanes then 2% MeOH in EtOAc) to give a crude spiro ketal, which was used in the next step without further purification.

To a mixture of above crude spiro ketal (calculated as 0.0426 mmol, 1 eq.), dimedone (11.9 mg, 0.0849 mmol, 2 eq.), and Pd(PPh$_3$)$_4$ (4.9 mg, 0.00424 mmol, 10 mol %) was added CH$_2$Cl$_2$ (4.3 mL) at room temperature. After being stirred for 8 h at the same temperature, the resulted solution was directly subjected to column chromatography on amino silica gel (CH$_2$Cl$_2$ then 25%, 50%, 77%, then 100% EtOAc in Hexanes then 3% MeOH in EtOAc) to give a crude Homohalichondrin C with its C-38 epimer. The mixture was

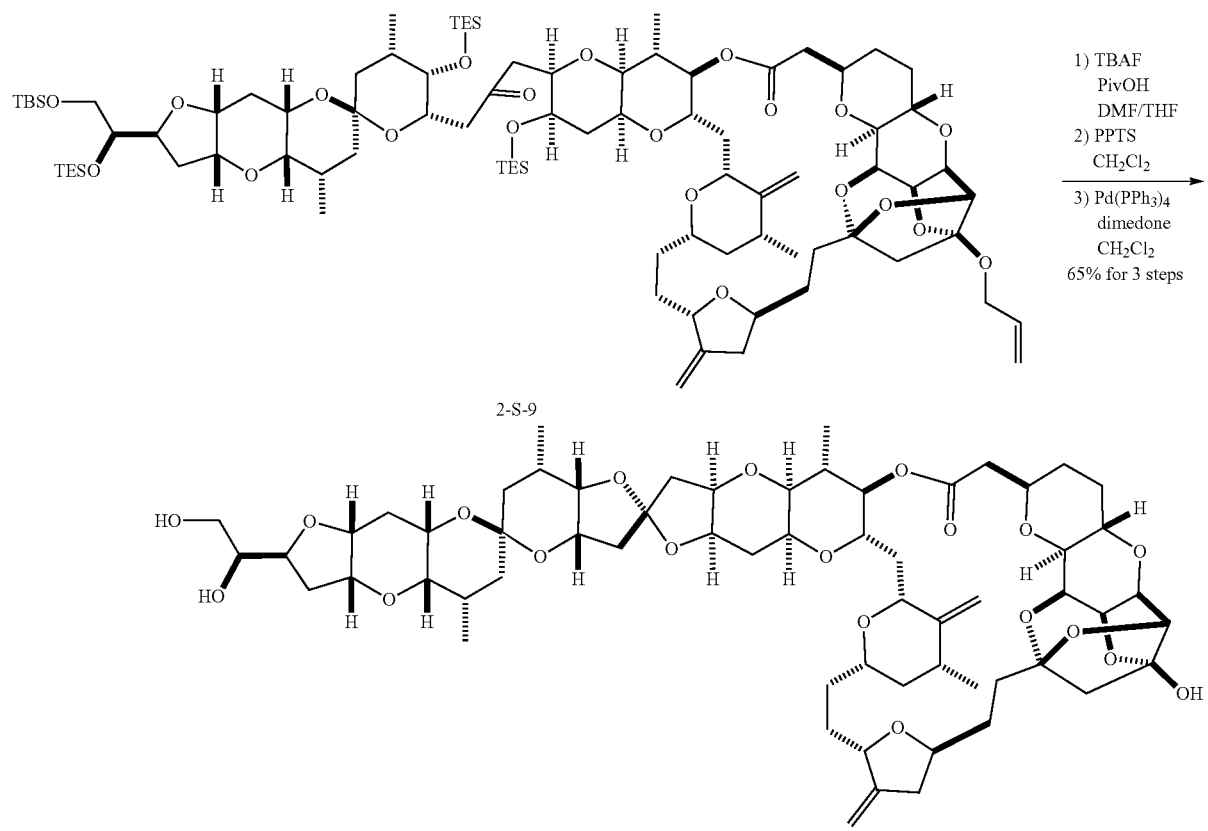

A buffered TBAF solution was prepared by mixing TBAF solution (TCI #T1125; 0.43 mL of 1 M in THF, 0.43 mmol, 10 eq.) and PivOH (22.0 mg, 0.215 mmol, 5 eq.). To a stirred solution of ketone 2-S-9 (70.5 mg, 0.0426 mmol) in DMF (2.1 mL) were added the buffered TBAF solution at room temperature. After being stirred for 8 h at the same temperature, CaCO$_3$ (1.5 g) and DOWEX 50WX8-400 (1.5 g) were added. After being stirred for 1 h at the same temperature, the resulted mixture was diluted with EtOAc and filtered through a pad of Celite. The filter cake was washed with EtOAc thoroughly. The filtrate was concentrated under reduced pressure to give a crude tetraol, which was used in the next step without further purification. To a stirred solution of above tetraol (calculated as 0.0426 mmol, 1 eq.) in CH$_2$Cl$_2$ (4.3 mL) was added PPTS (53.5 mg, 0.213 mmol, 5 eq.) at room temperature. After being stirred for 1 h at the same temperature, the reaction mixture was directly subjected to column chromatography on amino silica gel (CH$_2$Cl$_2$ then 25%, 50%, 75%, then 100% EtOAc in purified by YAMAZEN purification system with ODS column (Rf gradient: 10% MeCN in H$_2$O to 100% MeCN) to give Homohalichondrin C (25) (31.7 mg, 0.0278 mmol, 65% for 3 steps) as a colorless solid and 38-epi-Homohalicondrin C (C38-epi-25) (5.1 mg, 0.00448 mmol, 11% for 3 steps) as a colorless solid. Homohalichondrin C (25): [α]$^{20}_D$ −57.9 (c 0.53, CH$_2$Cl$_2$). $^1$H NMR (600 MHz, CD$_3$OD) δ: 5.06 (1H, d, J=1.8 Hz), 5.01 (1H, s), 4.88 (1H, s), 4.81 (1H, d, J=1.2 Hz), 4.63 (1H, dd, J=7.8, 4.8 Hz), 4.43 (1H, d, J=9.6 Hz), 4.40 (1H, s), 4.34-4.28 (3H, m), 4.25-4.22 (2H, m), 4.17 (1H, d, J=4.2 Hz), 4.13-4.09 (2H, m), 4.07 (1H, dd, J=7.8, 7.8 Hz), 4.02 (1H, s), 3.95 (1H, s), 3.90-3.86 (3H, m), 3.70 (1H, dd, J=10.5, 10.5 Hz), 3.66 (1H, dd, J=2.7, 2.7 Hz), 3.60 (1H, d, J=11.4 Hz), 3.59-3.57 (3H, m), 3.50 (1H, dd, J=10.5, 5.1 Hz), 3.21 (1H, dd, J=7.2, 4.8 Hz), 3.12 (1H, d, J=2.4 Hz), 2.95 (1H, d, J=10.2, 1.8 Hz), 2.82-2.79 (1H, m), 2.55 (1H, dd, J=17.9, 9.3 Hz), 2.45 (1H, dd, J=17.9, 2.4 Hz), 2.39 (1H, dd, J=13.2, 6.0 Hz), 2.37-2.24 (8H, m), 2.20-1.96 (11H, m), 1.90 (1H, ddd, J=15.6, 4.8, 4.8 Hz), 1.84-1.80 (2H, m), 1.74

(1H, s), 1.72 (1H, s), 1.68-1.64 (2H, m), 1.51-1.29 (9H, m), 1.10 (3H, d, J=6.0 Hz), 1.05 (3H, d, J=7.2 Hz), 1.04-0.99 (1H, m), 0.95 (3H, d, J=7.2 Hz), 0.94 (3H, d, J=6.6 Hz) ppm. $^{13}$C NMR (125 MHz, CDCl$_3$) δ: 171.2, 151.7, 151.4, 113.2, 112.4, 109.3, 104.5, 104.2, 96.6, 84.4, 79.8, 79.4, 77.6, 77.1, 76.3, 76.2, 75.3, 75.1, 74.8, 74.7, 74.4, 73.8, 73.7, 73.5, 72.8, 72.0, 71.2, 70.8, 68.1, 66.1, 65.3, 63.6, 52.4, 43.4, 42.5, 40.4, 38.7, 37.2, 36.94, 36.89, 36.8, 36.5, 36.0, 34.9, 32.0, 31.3, 30.6, 30.0, 29.4, 29.0, 28.9, 27.7, 25.8, 18.0, 17.7, 17.1, 15.0 ppm. FTIR (film): 3422, 2926, 2873, 1736, 1436, 1310, 1186, 1117, 1074, 1021, 995, 910, 755 cm$^{-1}$. HRMS (ESI) m/z: [M+Na]$^+$ calcd for C$_{61}$H$_{86}$O$_{20}$Na, 1161.5605; found, 1161.5587.

e.g., Namba, K.; Kishi, Y. *Org. Lett.* 2004, 6, 5031; Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387). Second, an oxy-Michael reaction was used to construct the tetrahydropyran ring with the desired stereochemistry at C29. The previous work suggested that this process could be achieved in a highly stereoselective manner; indeed, on treatment of 4-4 with K$_3$PO$_4$/18-Crown-6/toluene, oxy-Michael cyclization smoothly took place, to furnish the desired stereoisomer exclusively (see, e.g., Aicher, T. D.; Buszek, K. R.; Fang, F. G.; Forsyth, C. J.; Jung, S. H.; Kishi, Y.; Scola, P. M. *Tetrahedron Lett.* 1992, 33, 1549). The methyl ester was then reduced with DIBAL, to give alde-

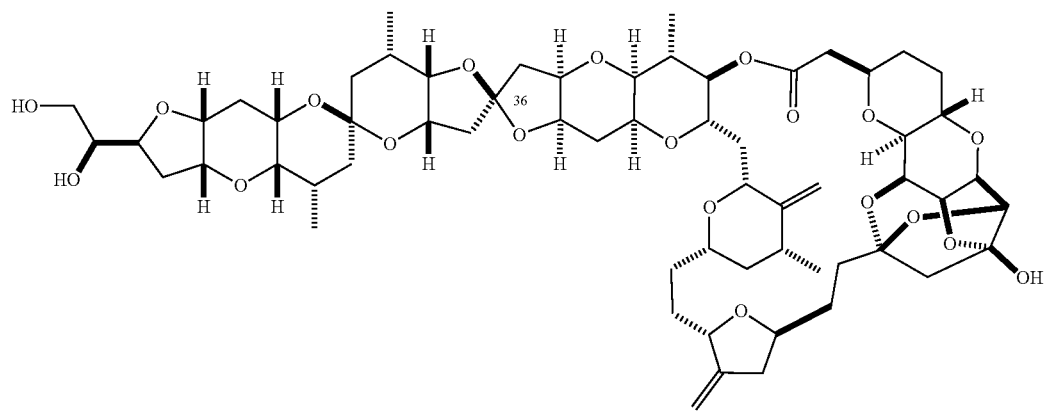

C38-epi-25

38-Epi-Homohalichondrin C (C38-Epi-25):

[α]$^{20}_D$ −88.2 (c 0.34, CH$_2$Cl$_2$). $^1$H NMR (600 MHz, CD$_3$OD) δ: 5.04 (1H, d, J=1.8 Hz), 4.95 (1H, d, J=2.4 Hz), 4.87 (1H, s), 4.81 (1H, s), 4.72 (1H, dd, J=10.2, 6.6 Hz), 4.42 (1H, d, J=10.8 Hz), 4.38 (1H, s), 4.36 (1H, ddd, J=10.4, 10.4, 4.5 Hz), 4.32-4.28 (2H, m), 4.23 (1H, ddd, J=10.1, 5.9, 4.2 Hz), 4.17-4.09 (4H, m), 4.08-4.05 (1H, m), 4.03 (1H, s), 3.98 (1H, dd, J=4.8, 1.8 Hz), 3.89-3.84 (3H, m), 3.81 (1H, dd, J=2.4, 2.4 Hz), 3.63-3.56 (4H, m), 3.54 (1H, d, J=3.0 Hz), 3.50 (1H, dd, J=10.2, 5.4 Hz), 3.17 (1H, dd, J=9.0, 6.6 Hz), 3.15 (1H, s), 2.96 (1H, dd, J=9.9, 2.1 Hz), 2.83-2.79 (1H, m), 2.54 (1H, dd, J=17.4, 8.4 Hz), 2.47 (1H, dd, J=17.4, 2.7 Hz), 2.36-1.89 (23H, m), 1.83 (1H, ddd, J=12.0, 12.0, 2.4 Hz), 1.78-1.75 (1H, m), 1.72-1.67 (2H, m), 1.64 (1H, ddd, J=12.0, 3.0, 3.0 Hz), 1.58-1.53 (1H, m), 1.49-1.28 (8H, m), 1.10 (3H, d, J=6.0 Hz), 1.05-0.98 (1H, m), 1.00 (3H, d, J=7.2 Hz), 0.998 (3H. d. J=6.6 Hz), 0.96 (3H, d, J=7.2 Hz) ppm. $^{13}$C NMR (125 MHz, CD$_3$OD) δ: 172.9, 153.3, 152.8, 115.6, 114.2, 110.5, 105.1, 104.7, 98.0, 86.2, 80.3, 79.8, 79.2, 78.9, 78.5, 78.4, 77.8, 76.6, 76.4, 76.1, 76.0, 75.9, 75.8, 75.2, 75.1, 74.9, 74.8, 74.4, 73.2, 72.9, 69.4, 68.4, 65.3, 65.1, 53.7, 45.6, 45.0, 44.8, 41.2, 39.6, 38.6, 38.3, 38.2, 37.5, 37.2, 36.0, 33.3, 31.9, 31.7, 31.2, 30.9, 30.2, 28.9, 26.8, 18.4, 17.7, 15.2 ppm. FTIR (film): 34.7, 2925, 2872, 1736, 1662, 1553, 1436, 1311, 1188, 1117, 1075, 1023, 996, 898, 735 cm$^{-1}$. HRMS (ESI) m/z: [M+Na]$^+$ calcd for C$_{61}$H$_{86}$O$_{20}$Na, 1161.5605; found, 1161.5618.

Synthesis of Right Halves

Figure 9A:
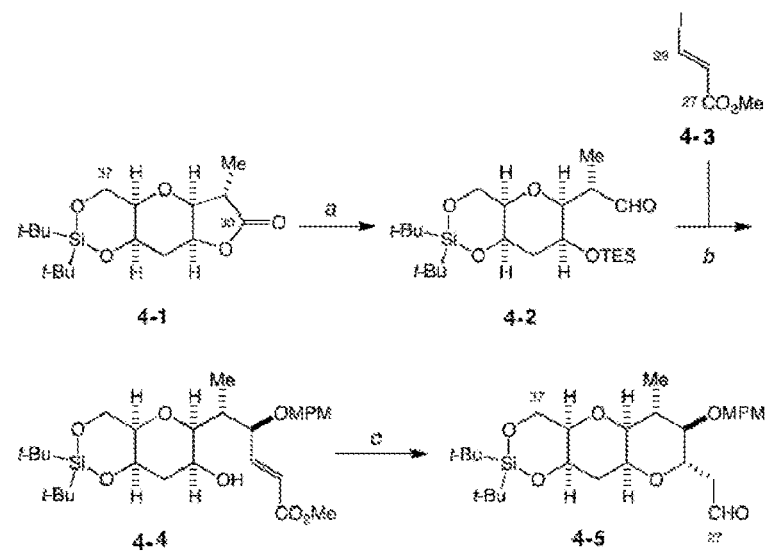
FIG. 9A shows an exemplary synthesis of the C27-C37 building block. Reagents and Conditions: a. 1. LiBH$_4$, Et$_2$O, 0° C. (~100%). 2. TES-Cl, imidazole, CH$_2$Cl$_2$, rt (~100%). 3. Swern oxidation (see, e.g., Rodriguez, A.; Nomen, M.; Spur, B. W.; Godfroid, J. J. *Tetrahedron Lett.* 1999, 40, 5161); b. 1. Cr-catalyst prepared from (S)-4-E (10 mol %), (Me)$_2$Phen-(OMe)$_2$.NiCl$_2$ (2 mol %), LiCl (2 equiv.), Mn (excess), Cp$_2$ZrCl$_2$ (1.1 equiv.), 2,6-lutidine (1 equiv.), MeCN (C 0.4 M), rt, 1 hour (93% for 2 steps; dr=19:1). 2. MPMO(=NH)CCl$_3$, La(OTf)$_3$, toluene, rt, 6 hours. 3. p-TsOH (cat.), MeOH—CH$_2$Cl$_2$, rt, 4 hours (88% for 2 steps). c. 1. K$_3$PO$_4$ (1 equiv.), 18-Crown-6 (3 equiv.), toluene (79%). 2. DIBAL, CH$_2$Cl$_2$, –78° C., 1.5 hours (94%). Abbreviation: 18-Crown-6=1,4,7,10,13,16-hexa-oxacyclooctadecane; DIBAL=diisobutylaluminium hydride; p-TsOH=p-toluenesulfonic acid.
Figure 9B:
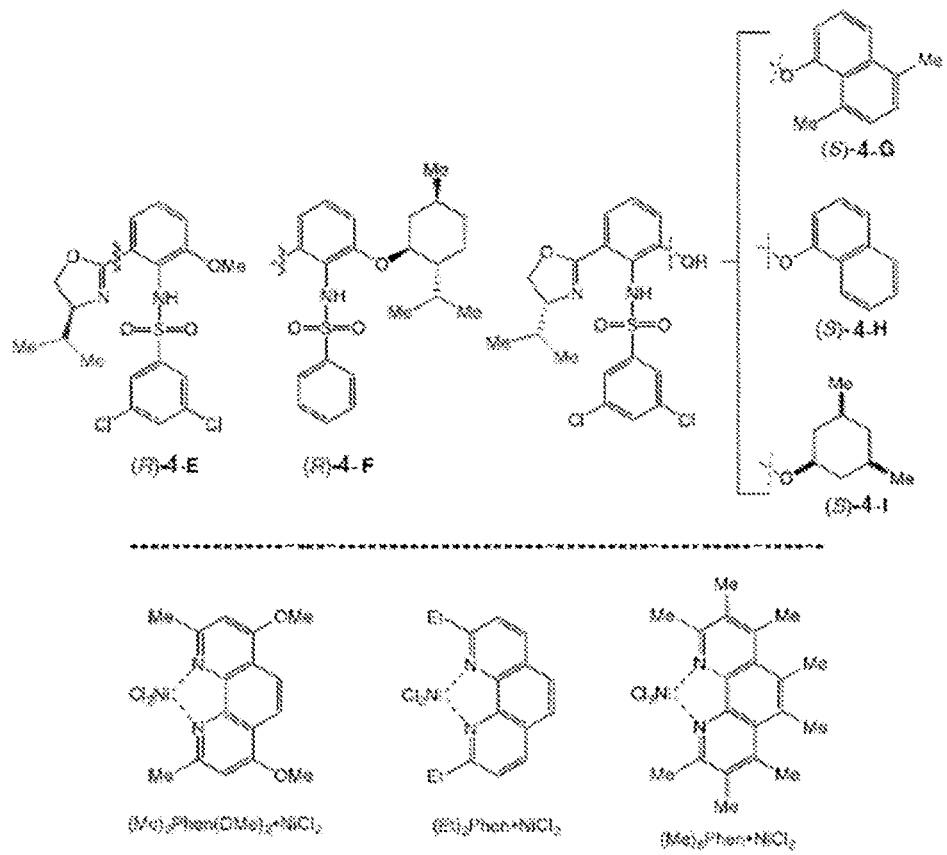
FIG. 9B shows exemplary sulfonamide ligands and nickel complexes useful in the Ni/Cr coupling reactions provided herein.

The synthesis of C27-C37 building block is summarized in FIG. 9A. First, a catalytic, asymmetric Ni/Cr-mediated reaction was used to couple aldehyde 4-2 with methyl β-iodoacrylate (4-3) in the presence of the Cr-catalyst (10 mol %) prepared from (R)-4-E (FIG. 9B), to furnish the allylic alcohol in 93% yield with 19:1 stereoselectivity (see, hyde 5, the substrate for the next catalytic, asymmetric Ni/Cr-mediated coupling reaction to form the C$_{19}$-C$_{20}$ bond.

Figure 10A:
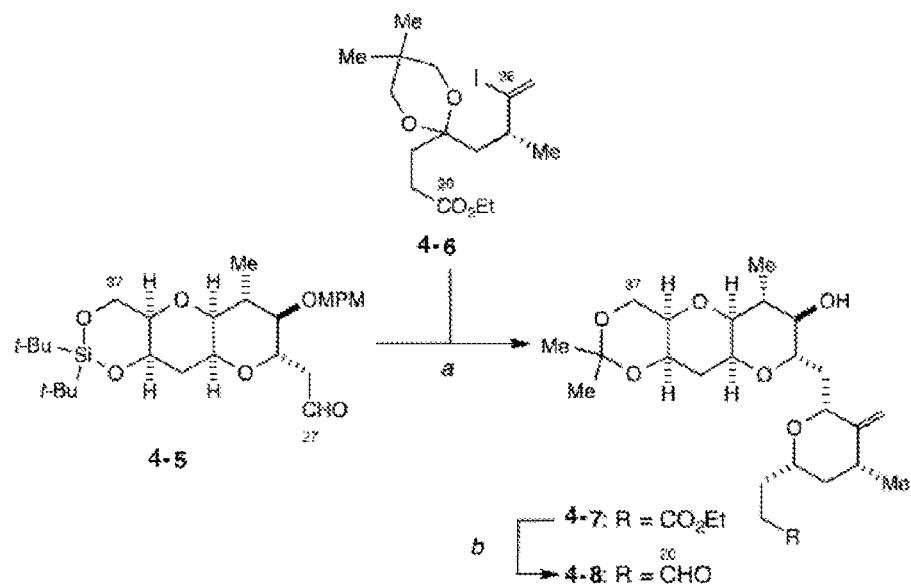
FIG. 10A shows exemplary synthesis of C20-C37 building block. Reagents and Conditions: a. 1. Cr-catalyst prepared from (R)-4-F (10 mol %), (Et)$_2$Phen.NiCl$_2$ (2 mol %), LiCl (2 equiv.), Mn (excess), Cp$_2$ZrCl$_2$ (1 equiv.), MeCN (C 0.3 M), rt, 3 hours. 2. TBAF (2 equiv.), AcOH (0.6 equiv.), THF, 0° C.→rt (79% for 2 steps). 3. TES-H (10 equiv.), TEOTf (5 equiv.), CH$_2$Cl$_2$, 0° C., 3 hours (87%). 4. 2,2-dimethoxypropane (3 equiv.), acetone, 0° C.→rt. b. DIBAL, CH$_2$Cl$_2$, –78° C., 1.5 hours (89% for 2 steps). Abbreviation: MPM=p-MeOC$_6$H$_4$CH$_2$—; TES=Et$_3$Si—.

FIG. 10A summarizes the synthesis of C20-C37 building block from 4-5. The crucial transformation in this sequence was the catalytic, asymmetric Ni/Cr-mediated coupling to introduce the chiral center at C27, followed by reductive cyclization to introduce the chiral center at C23. The overall stereochemistry-outcome of the proposed transformation deserves a comment. The stereochemistry at C27 was introduced under the influence of a chiral Cr-catalyst prepared from a chiral sulfonamide. Via the toolbox approach, (S)-4-F was identified as the best ligand for the substrates closely related to 4-6 (see, e.g., Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387). The same Cr-catalyst was found equally effective for the present case; the (4-5→4-6)-coupling was conducted in the presence of 10 mol % Cr-catalyst and 2 mol % (Et)$_2$Phen(H)$_2$.NiCl$_2$, to furnish the expected allylic alcohol with >40:1 stereoselectivity ($^1$H NMR). To facilitate $^1$H NMR analysis, the authentic sample of undesired allylic alcohol was prepared with the Cr-catalyst prepared from (R)-sulfonamide.

The next reductive cyclization was expected stereoselectively to yield the desired product, as demonstrated on the closely related substrates (see, e.g., Lewis, M. D.; Cha, J. K.; Kishi, Y. *J. Am. Chem. Soc.* 1982, 104, 4976; Dong, C.-G.; Henderson, J. A.; Kaburagi, Y.; Sasaki, T.; Kim, D.-S.; Kim, J. T.; Urabe, D.; Guo, H.; Kishi, Y. *J. Am. Chem. Soc.* 2009, 131, 15642). Nevertheless, there was a concern on the proposed transformation, because of the presence of dioxasilinane group. Experimentally, it was found that the reductive cyclization did give the desired product as the major product, but accompanied with by-products apparently derived through reactions on the dioxasilinane group. In order to avoid the complication due to the undesired side-reaction(s), the dioxasilinane group was first deprotected with TBAF-AcOH treatment and then subjected to reductive-cyclization, to furnish practically the single product. The undesired allylic alcohol was prepared via the coupling of 4-5 with 4-6 in the presence of the Cr-catalyst derived from (S)-4-A. The product at this stage was a triol, as the C30 MPM group was cleaved off during the process. With a standard procedure, the alcohols at C35 and C37 were selectively protected, to give six-membered acetonide 4-7.

Figure 10B:
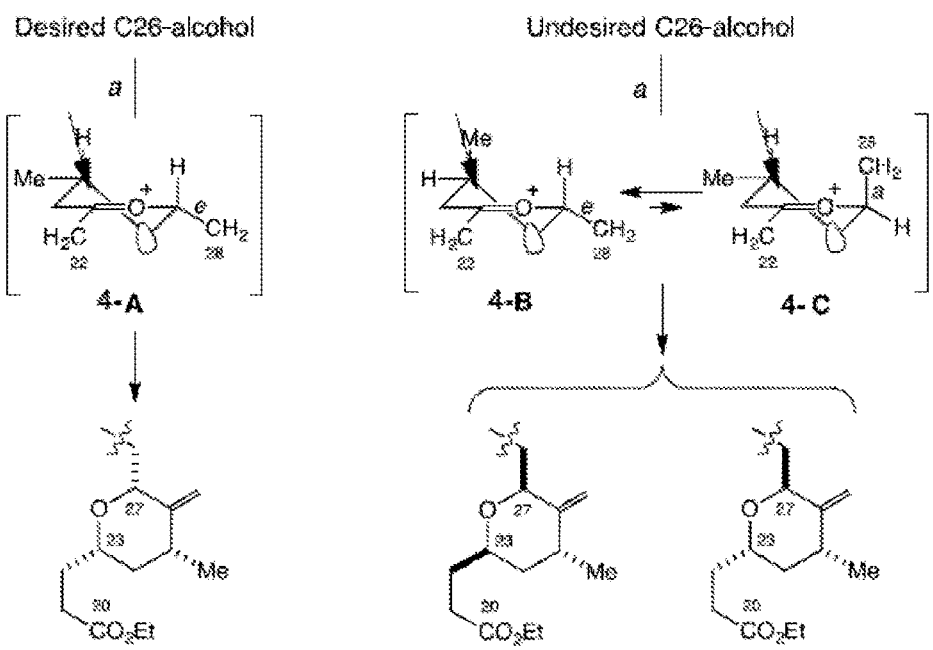
FIG. 10B shows Analysis on stereochemical course of reductive cyclization: desired and undesired series.

The observed stereochemistry-outcome was explained by a stereoelectronic effect, coupled with conformational analysis. Due to a stereoelectronic effect, the reducing-reagent approached the oxonium ion preferentially from the direction resulting in a trans-diaxial relationship between the newly formed bond and a lone pair of oxygen-electrons, the oxonium ion 4-A (FIG. 10B). For clarity, the C27-olefinic carbon is replaced with a saturated carbon in the oxonium ions 4-A-C, and the oxonium ion 4-C is shown its antipode. Similarly, the approach from the bottom-direction also met with the stereoelectronic effect. However, the top-approach was favored over the bottom-approach, because the former approach led directly to the product in chair-conformation, whereas the latter approach led to the product in boat-conformation. Apparently, there was no serious steric hindrance for the reagent to approach from the top-face. Reductive cyclization of the undesired allylic alcohol gave a 2:1 mixture of tetrahydropyrans. The observed result was again explained again by a stereoelectronic effect, coupled conformational analysis, cf, oxonium ions 4-B and 4-C in FIG. 10B. Two modes of reduction depicted on 4-B and 4-C led directly to a product in chair conformation, but both approaches suffer from the 1,3-diaxial-like interaction with either C25-Me or C29-$CH_2$ group. This analysis explained the poor stereoselectivity in reductive cyclization in the undesired allylic alcohol series. Because of the poor-selectivity observed in the reductive cyclization of undesired allylic alcohol, the overall stereoselectivity of 4-5+4-6→4-7 became higher than the stereoselectivity achieved by the catalytic, asymmetric Ni/Cr-mediated coupling. Finally, the ethyl ester in 4-7 was reduced with DIBAL, to furnish aldehyde 4-8, the synthetic intermediate for the next Ni/Cr-mediated coupling reaction to form the $C_{19}$-$C_{20}$ bond of halichondrins A-C. Notably, without protection of the C30 hydroxyl group, the DIBAL reduction smoothly and cleanly proceeded to give the desired 4-8 in 89% yield, along with ~5% of the over-reduced primary alcohol.

Figure 11:
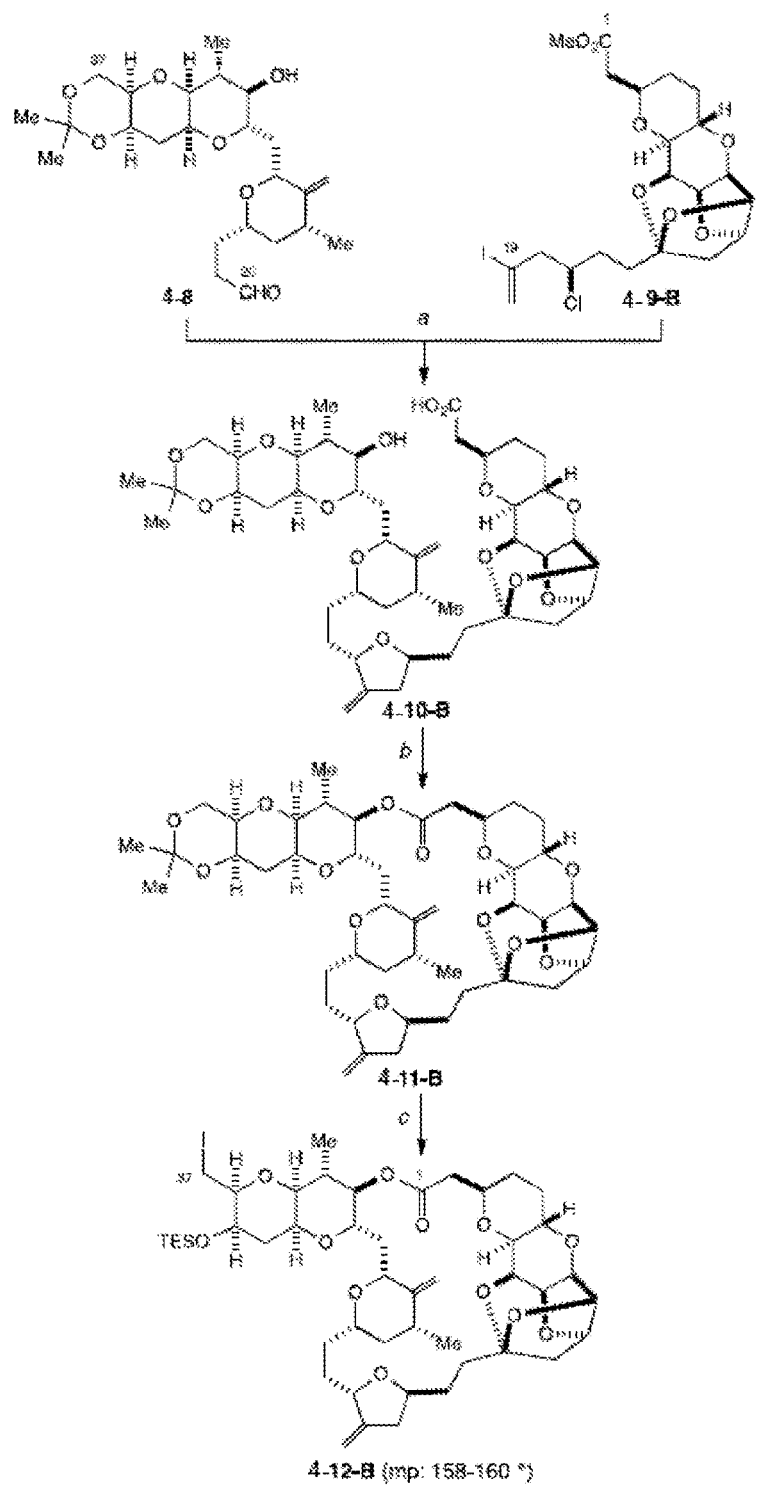
FIG. 11 shows exemplary synthesis of the C1-C37 building block in the halichondrin B series. Reagents and Conditions: a. 1. Cr-catalyst prepared from (S)-4-G (10 mol %), (Et)$_2$Phen.NiCl$_2$ (2 mol %), LiCl (2 equiv.), Mn (excess), ZrCp$_2$Cl$_2$ (2.5 equiv.), 2,6-di-t-butyl-4-methyridine (2.5 equiv.), MeCN (C 0.x M), rt, 2 hours. 2. K$_2$CO$_3$ (10 equiv.), 60° C., 16 hr, then add H$_2$O (1/10 volume of MeOH), 60° C., 3 hours. b. 2-methyl-6-nitrobenzoic anhydride (6 equiv.), 4-dimethylaminopyridine (12 equiv.), i-Pr$_2$NEt (6 equiv.), toluene, 70° C. (syringe pump; 73% for 3 steps). c. 1. p-TsOH, MeOH, rt, 1 hour. 2. Tf$_2$O (1.2 equiv.), 2,6-lutidine (5 equiv.), CH$_2$Cl$_2$, –78° C., 15 min, followed by addition of TESOTf (1.5 equiv.), –78° C.→0° C., then followed by addition of NaI (5 equiv.) in DMF, rt, 2.5 hours (94% for steps). Abbreviation: TES=Et$_3$Si—; p-TsOH=p-toluenesulfonic acid.

The $C_{19}$-$C_{20}$ bond with a catalytic, asymmetric Ni/Cr-mediated coupling of 4-8 with 4-9-B was formed (FIG. 11) (see, e.g., Yan, W.; Li, Z.; Kishi, Y. *J. Am. Chem. Soc.* 2015, 137, 6219; Li, Z.; Yan, W.; Kishi, Y. *Am. Chem. Soc.* 2015, 137, 6226). It should be noted that aldehyde 4-8 bore a free hydroxyl group at C30. There was no precedent for demonstrating that the catalytic cycle of Ni/Cr-mediated reaction could function with a substrate with a free hydroxyl group. Nevertheless, this possibility was pursued, because two synthetic steps, i.e., protection and deprotection of the C30 hydroxyl group, could be saved in this manner. In this connection, it should be noted that catalytic asymmetric Ni/Cr-mediated coupling uses $Cp_2ZrCl_2$ as the agent dissociating a product from a Cr-complex (see, e.g., Namba, K.; Kishi, Y. *Org. Lett.* 2004, 6, 5031) thereby suggesting a possibility of utilizing $Cp_2ZrCl_2$ as a masking agent for the free hydroxyl group in situ. This possibility was experimentally tested; the catalytic, asymmetric coupling of 4-8 with 4-9-B smoothly proceeded in addition of $Cp_2ZrCl_2$ (2.5 equiv.) and 2,6-di-t-butyl-4-methylpyridine (2.5 equiv.), to furnish the desired product in an excellent yield.

Being encouraged with the successful coupling of 4-8 bearing a free hydroxyl group, a coupling with the vinyl iodide bearing a free carboxylic acid at C1 was tested. Amazingly, the catalytic, asymmetric Ni/Cr-mediated coupling of 4-8 did give the desired product in ~50% yield. The coupling with 4-9-B was used for further studies.

Adopting the toolbox approach, a satisfactory sulfonamide ligand was identified. The ligand screening was conducted in the presence of Cr-catalyst, prepared from $CrCl_2$ (10 mol %), sulfonamide (13 mol %), proton scavenger (12 mol %), and $(Me)_6Phen.NiCl_2$ in MeCN at room temperature. Through this screening, three exemplary sulfonamides emerged, i.e., (S)-4-I (dr=19:1), (S)-4-G (dr=29:1), and (S)-4-H (dr=24:1). The coupling yield with these three ligands was then estimated from the overall yield of 4-8→4-11-B, i.e., 73% with (S)-4-I, 65% with (S)-4-G, and 67% with (S)-4-H. These overall yields were based on the experiments starting with 1.65 g, 250 mg, and 250 mg of 7 with (S)-4-I, (S)-4-G, and (S)-4-H, respectively. Based on this result, sulfonamide (S)-4-I was used for preparative purpose. It is noteworthy that, unlike the first and second couplings, this Ni/Cr-mediated coupling utilized the structurally complex nucleophile. Remarkably, the coupling efficiency was excellent even with use of the molar ratio 4-7:4-8=1.0:1.1.

Figure 12:
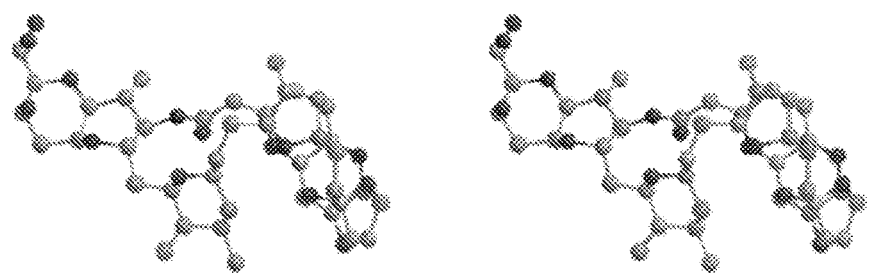
FIG. 12 shows the X-ray structure of C35/C37-Diol of 4-10-B.

The next task was an $S_N2$-cylcization of the C20 alcohol to the C 17 chloride to form the methylenetetrahydrofuran ring. Various bases cleanly achieved this five-membered-ring forming cyclization, unless there was a base-labile functional group(s) in the substrate (see, e.g., Lee, J. H.; Li, Z.; Osawa, A.; Kishi, Y. *J. Am. Chem. Soc.* 2016, 138, 16248). After the base-induced cyclization, the methyl ester at Cl was hydrolyzed with aqueous base, to furnish seco-acid 4-10-B. For example, in the halichondrin-A synthesis, this transformation was achieved in 2 separate steps, i.e., AgOTf/$Ag_2O$ in THF and LiOH in aqueous MeOH. In this work, this transformation was carried out in one-pot. The seco-acid thus obtained was subjected to macrolactonization with Shiina's reagent, to furnish crystalline C1-C37 mactrolactone acetonide 4-11-B in an excellent yield (see, e.g., Shiina, I.; Kubota, M.; Ibuka, R. *Tetrahedron Lett.* 2002, 43, 7535; Shiina, I.; Mukaiyama, T. *Chem. Lett.* 1994, 677; Shiina, I. *Bull Chem. Soc. Jpn.* 2014, 87 196). The structure of 4-11-B was confirmed via an X-ray analysis of its C35/C37-diol, i.e., the product at step c-1 (FIG. 12).

For the preparative purpose, the transformation of 4-8+4-9-B→4-10-B→11-B was carried out without purification/isolation of the intermediates. The macrolactone 4-11-B was isolated by silica gel flash-chromatography (neutral silica gel) in 73% overall yield from 4-8 in multi-gram scales.

A $^1H$ NMR analysis indicated that 4-11-B thus obtained was contaminated with ~5% of its C20-epimer, thereby showing that the overall stereoselectivity for this transformation was ~20:1. The material was carried on of this purity; namely, 4-11-B was transformed to iodide 4-12-B with 4-steps/2-pots procedure, i.e., (1) p-TsOH/MeOH—$CH_2Cl_2$, (2) $Tf_2O$/lutidine/$CH_2Cl_2$, followed by addition of TESOTf and then NaI in DMF. The product was isolated by silica gel flash-chromatography (neutral silica gel), to furnish 4-12-B in 92% overall yield. $^1H$ NMR analysis indicated that 4-12-B thus obtained was contaminated with ~5% of the C20-epimer. Although 4-12-B was crystalline, it was again difficult to remove the minor stereoisomer by recrystallization. Therefore, the minor C20 diastereomer was removed by preparative HPLC (ZORBAX SIL; 300-500 mg injection), to furnish 4-12-B (mp: 158-160° C.), which was used for the synthesis of halichondrins in the B-series.

Figure 13:
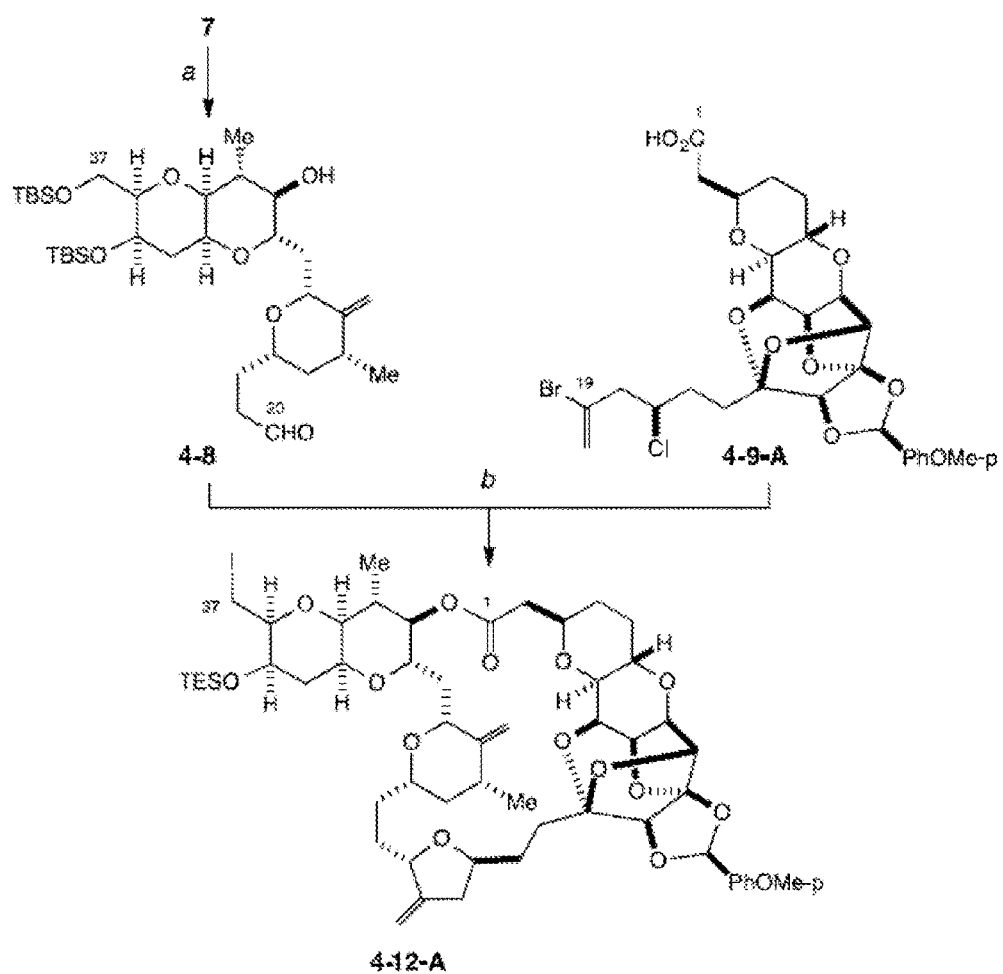
FIG. 13 shows exemplary synthesis of the C1-C37 building block in the halichondrin A series. Reagents and conditions: a. 1. Ac$_2$O, py, rt. 2. CSA, CH$_2$Cl$_2$-MeOH, rt. 3. TBSOTf, 2,6-lutidine, CH$_2$Cl$_2$, –78° C., 1 hour (92% for 3 steps). 4. DIBAL, CH$_2$Cl$_2$, –78° C., 1 hour (88%). Follow the synthetic sequence under the conditions defined in FIG. 11, except that (Me)$_6$PhenNiCl$_2$ (2 mol %) was used for the Ni/Cr-mediated coupling. The overall yield from bis-TBS-4-8 to 4-12-A was 40.8%, which was good compared with the overall yield in the halichondrin B series. Abbreviation: TBS=tBuMe$_2$Si—; CSA=camphorsulfonic acid.

FIG. 13 summarizes the synthesis of right half in the halichondrin-A series. The synthesis followed the synthetic route developed in the halichondrin B series, with two modifications. First, 4-9-A, instead of 4-9-B, was used. Second, the C35/C37-protecting group in 8 was switched to the corresponding bis-TBS before the Ni/Cr-mediated coupling reaction, because the anisylidene group in 4-9-A was acid-labile and could not survive under the aqueous acidic condition; step c-1 in FIG. 11. Once again, the minor stereoisomer that originated from the Ni/Cr-mediated coupling was removed by preparative HPLC.

Figure 14A:
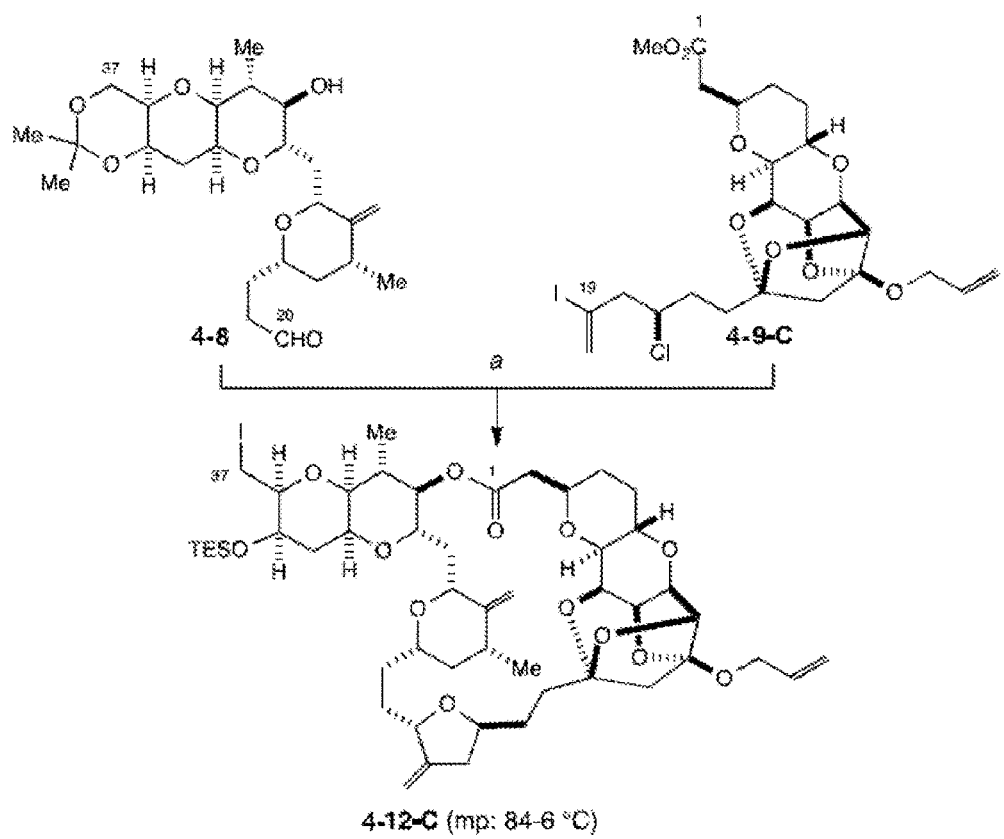
FIG. 14A shows an exemplary synthesis of the C1-C37 building block in the halichondrin-C series Reagents and conditions: a. Follow the synthetic sequence under the conditions defined in FIG. 11. The overall yield from 4-8 to 4-12-C was 54.2%, which was good compared with the overall yield in the halichondrin B series.
Figure 14B:
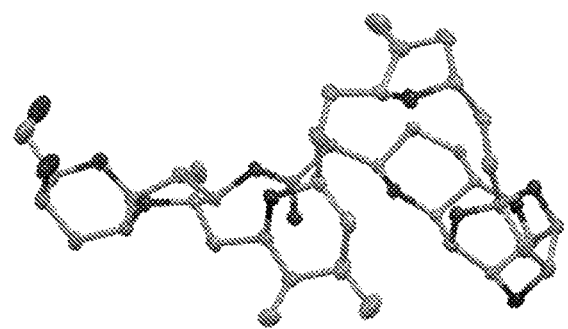
FIG. 14B shows an X-ray structure of the product.

FIG. 14 summarizes the synthesis of right half in the halichondrin C series. The synthesis followed the synthetic route developed in the halichondrin B series, except one; 4-9-C, instead of 4-9-B, was used for the Ni/Cr-mediated coupling. The synthesis proceeded without any unexpected difficulty, to furnish the right half 4-12-C(mp: 84-6° C.) in the overall efficiency very similar to that in the halichondrin B series. Once again, the minor stereoisomer that originated from the Ni/Cr-mediated coupling was removed by preparative HPLC.

In the syntheses reported, seven chiral centers were introduced at C17, C20, C23, C25, C27, C29, and C30. The availability of the authentic sample of undesired stereoisomer(s) should facilitate the analysis of purity and stereoselectivity for a given step. Among them, the chiral centers at C20, C27, and C30 were introduced under the influence of chiral Cr-catalysts derived from (R)-4-E, (R)-4-F, and (S)-4-I. Therefore, the authentic sample of undesired minor stereoisomers formed in each of catalytic, asymmetric Ni/Cr-mediated couplings was readily prepared via the coupling in the presence of (S)-4-E, (S)-4-F, and (R)-4-I. In practice, the antipode was prepared with use of the Cr-catalyst prepared from (S)-E or (R)-E for each coupling. The chiral centers at C17 and C25 originated from the chiral centers present in $C_1$-$C_{19}$ and $C_{20}$-$C_{26}$ building blocks. Thus, use of C17-epi-$C_1$-$C_{19}$ building block gave the stereoisomer at C17, whereas use of the antipode of $C_{20}$-$C_{26}$ building block gave the minor stereoisomers at C25. The stereochemistry analysis was carried out in reference to these authentic samples.

Right halves of halichondrins A-C were synthesized by coupling the common C20-C37 building block 4-8 with the $C_1$-$C_{19}$ building blocks 4-9-A, 4-9-B, and 4-9-C, respectively. Catalytic, asymmetric Ni/Cr-mediated coupling was used for three C—C bond formations. For all the cases, the stereochemistry was introduced under the influence of Cr-catalysts prepared from chiral sulfonamides, identified via the toolbox approach. For (4-2+4-3)-, (4-5+4-6)-, and (4-7+4-8)-couplings, the stereoselectivity of 19:1, >40:1, and ~20:1 was achieved by the Cr-catalysts prepared from (R)-4-E, (R)-4-F, and (S)-4-I, respectively. Unlike the first and second couplings, the third coupling utilized the structurally complex nucleophile. It was demonstrated that the coupling efficiency was excellent even with use of the molar ratio 4-8:4-9A~C=1.0:1.1. In addition, third coupling was achieved with the substrate bearing a free-hydroxyl group. The products obtained in the Ni/Cr-mediated couplings were converted to the right halves of halichondrins A-C in excellent overall yields. The right halves of halichondrins A-C (4-12A through 4-12C) were synthesized in 28, 24, and 24 steps from commercial D-galactal in 13.4%, 21.1%, and 16.7% overall yields, respectively.

Experimental Procedures for the Synthesis of Right Halves

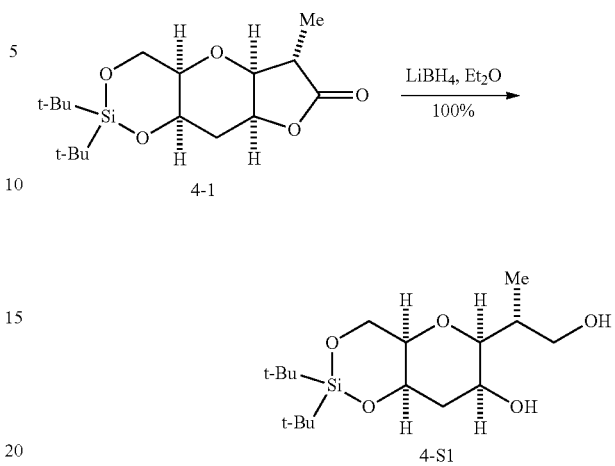

To a stirred solution of 4-1 (4.0 g, 11.7 mmol, 1 eq.) in $Et_2O$ (100 mL) was added lithium borohydride (510 mg, 23.4 mmol, 2 eq.) at 0° C. After being stirred for 8 h at room temperature, the reaction was carefully quenched with sat. $NH_4Cl$ aq. at 0° C. and stirred for 30 min. The organic layer was separated and the aqueous phase was extracted with EtOAc. The combined organic layer was washed with brine, dried over $Na_2SO_4$, and concentrated under reduced pressure. The residue was purified by flash column chromatography on silica gel (33% then 100% EtOAc in Hexanes) to give diol (4.1 g, 11.8 mmol, quantitative) as a white solid. The spectroscopic data obtained are consistent with those previously reported in our literature. See, e.g., Chen, C.-L.; Namba, K.; Kishi, Y. Org. Lett. 2009, 11, 409-412.

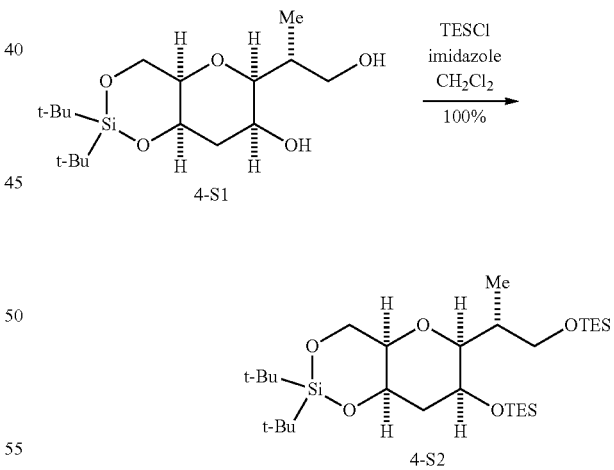

To a stirred solution of diol (4.1 g, calculated as 11.7 mmol, 1 eq.) in $CH_2Cl_2$ (57 mL) were added imidazole (4.8 g, 70.2 mmol, 6 eq.) and TESCl (5.9 mL, 35.1 mmol, 3 eq.) at room temperature. After being stirred for 12 h at the same temperature, the reaction was quenched with sat. $NaHCO_3$ aq. at 0° C. and stirred for 30 min. The organic layer was separated and the aqueous phase was extracted with hexanes/EtOAc (1:1). The combined organic layer was washed with brine, dried over $Na_2SO_4$, and concentrated under reduced pressure. The residue was purified by flash column chromatography on silica gel (0% then 3% EtOAc in Hexanes) to give bis-TES 4-S2 (6.8 g, 11.8 mmol, quantitative) as colorless oil. 4-S2: $[\alpha]^{20}_D$ +1.1 (c 1.0, CHCl$_3$). $^1$H NMR (600 MHz, CDCl$_3$) δ: 4.23 (1H, m), 4.21 (1H, dd, J=12.6, 2.4 Hz), 4.17 (1H, dd, J=12.6, 1.8 Hz), 3.77 (1H, ddd, J=4.2, 2.4, 1.8 Hz), 3.53 (1H, dd, J=10.2, 5.4 Hz), 3.50 (1H, dd, J=10.2, 5.4 Hz), 3.29 (1H, dd, J=6.6, 1.8 Hz), 3.20 (1H, brs), 2.16 (1H, ddd, J=14.4, 2.4, 2.4 Hz), 1.99 (1H, qdt, J=7.2, 6.6, 5.4 Hz), 1.74 (1H, ddd, J=14.4, 4.2, 4.2 Hz), 1.05 (9H, s), 1.03 (3H, d, J=7.2 Hz), 1.02 (9H, s), 0.98 (9H, t, J=8.4 Hz), 0.94 (9H, t, J=8.4 Hz), 0.70-0.55 (12H, m) ppm. $^{13}$C NMR (150 MHz, CDCl$_3$) δ: 81.1, 77.1, 68.2, 67.8, 65.5, 64.9, 38.8, 37.4, 27.8, 27.2, 23.3, 20.6, 13.2, 7.0, 6.8, 5.1, 4.4 ppm. FTIR (film): 2954, 2875, 1465, 1239, 1168, 1104, 1082, 1036, 1007, 927, 826, 772, 723, 649, 442 cm$^{-1}$. HRMS (ESI) m/z: [M+Na]$^+$ calcd for C$_{29}$H$_{62}$O$_5$Si$_3$Na, 597.3797; found, 597.3807.

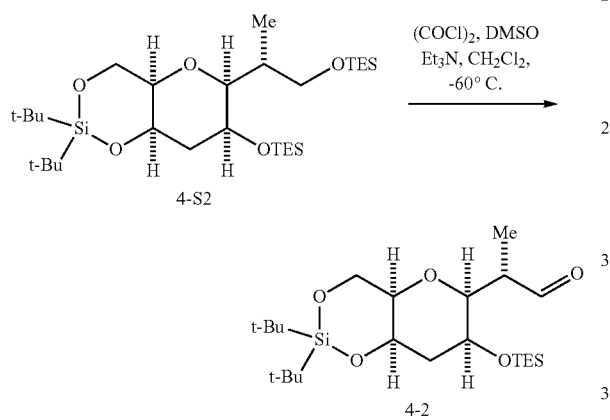

To a stirred solution of (COCl)$_2$ (7.5 mL, 88.6 mmol, 5 eq.) in CH$_2$Cl$_2$ (250 mL) was added a solution of DMSO (12.4 mL, 174 mmol, 10 eq.) in CH$_2$Cl$_2$ (10 mL) at −78° C. After being stirred for 30 min at the same temperature, a solution of 4-S2 (10.0 g, 17.4 mmol, 1 eq.) in CH$_2$Cl$_2$ (30 mL) was introduced to the reaction mixture. After being stirred for 2 h at −60° C., to the mixture was added Et$_3$N (42 mL, 305 mmol, 17 eq.) at −78° C. and warmed up to 0° C. over 30 min. After being stirred for 15 min at 0° C., the mixture was quenched with sat. NH$_4$Cl aq. The organic layer was separated and the aqueous phase was extracted with EtOAc. The combined organic layer was washed with brine, dried over Na$_2$SO$_4$, and concentrated under reduced pressure. The residue was filtrated though a pad of silica gel (hexanes/EtOAc=1:1) to give a crude aldehyde 4-2 as pale yellow oil. The obtained crude material was used in the next reaction without further purification.

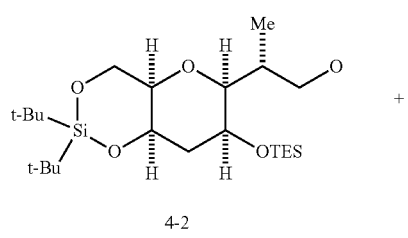

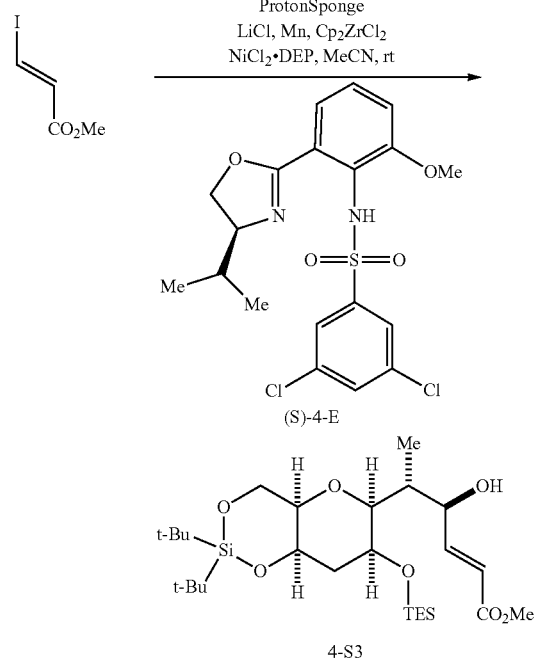

To a mixture of CrCl$_2$ (257 mg, 2.1 mmol, 12 mol %), (S)-sulfonamide ligand [i-Pr, PhCl$_2$, OMe] (1.08 g, 2.4 mmol, 14 mol %), and proton scavenger (522 mg, 2.4 mmol, 14 mol %) in a glove box was added MeCN (44 mL) and the resulting solution was stirred for 3 h at room temperature. In a separate flask, the above crude 4-2 (calculated as 17.4 mmol, 1 eq.), methyl 3-iodoacrylate (3.7 g, 17.4 mmol, 1 eq.), NiCl$_2$DMP(OMe)$_2$ (138 mg, 0.348 mmol, 2 mol %), LiCl (1.48 mg, 34.8 mmol, 2 eq.), Mn (3.8 g, 70 mmol, 4 eq.), Cp$_2$ZrCl$_2$ (5.6 g, 19.1 mmol, 1.1 eq.), and 2,6-lutidine (4.1 mL, 34.8 mmol, 2 eq.) were mixed together and the Cr-complex solution (26 mL) was transferred to the flask. Additional methyl 3-iodoacrylate (1.8 g, 8.7 mmol, 0.5 eq.) and Cr-complex solution (11 mL) were added after 30 min. After being stirred for 45 min, to the mixture was added the remained Cr-complex solution (7 mL). After being stirred for 15 min, the reaction mixture was removed from the glove box and diluted with EtOAc. After florisil was added, the resultant suspension was stirred vigorously for 1 h. The mixture was filtered through a short pad of silica gel (EtOAc). After removal of solvent under reduced pressure, the residue was purified by flash column chromatography on silica gel (3% then 25% EtOAc in Hexanes) to give allylic alcohol 4-S3 (8.8 g, 16.2 mmol, 93% for 2 steps, dr: 16:1 based on integration ratio of $^1$H NMR) as pale yellow oil. 4-S3: $[\alpha]^{20}_D$ −1.3 (c 1.0, CHCl$_3$). $^1$H NMR (600 MHz, C$_6$D$_6$) δ: 7.18 (1H, dd, J=15.6, 3.6 Hz), 6.32 (1H, dd, J=15.6, 2.4 Hz), 4.39 (1H, brs), 4.15 (1H, dd, J=12.6, 1.2 Hz), 3.94 (1H, dd, J=12.6, 2.4 Hz), 3.89 (1H, brs), 3.66 (1H, ddd, J=4.2, 2.4, 1.2 Hz), 3.43 (3H, s), 3.18 (1H, dd, J=6.6, 1.2 Hz), 2.66 (1H, brs), 2.13 (1H, qdd, J=6.6, 6.6, 1.8 Hz), 2.02 (1H, ddd, J=15.0, 2.4, 2.4 Hz), 1.99 (1H, d, J=4.2 Hz), 1.29 (1H, m), 1.28 (9H, s), 1.12 (9H, s), 1.10 (3H, d, J=6.6 Hz), 1.06-1.00 (9H, m), 0.74-0.61 (6H, m) ppm. $^{13}$C NMR (150 MHz, CDCl$_3$) δ: 166.6, 150.2, 128.3, 120.5, 82.2, 77.4, 72.1, 68.2, 67.7, 65.6, 51.1, 40.3, 38.7, 28.0, 27.6, 23.5, 20.9, 9.8, 7.3, 5.4 ppm. IR (film): 3501, 2952, 2876, 1725, 1706, 1659, 1474, 1167 cm$^{-1}$. HRMS (ESI) m/z: [M+Na]$^+$ calcd for C$_{27}$H$_{52}$O$_7$Si$_2$Na, 567.3144; found, 567.3157.

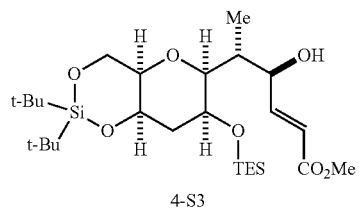

4-S3

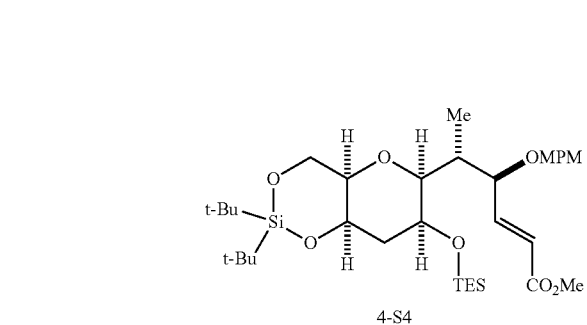

4-S4

To a stirred suspension of allylic alcohol 4-S3 (5.65 g, 10.4 mmol, 1 eq.) and La(OTf)$_3$ (640 mg, 1.1 mmol, 10 mol %) in toluene (21 mL) was added MPMOC(NH)CCl$_3$ (6.0 g, 21 mmol, 2 eq.) by syringe pump over 5.5 h. After being stirred for additional 30 min, the mixture was quenched with sat. NaHCO$_3$ aq. The organic layer was separated and the aqueous phase was extracted with EtOAc. The combined organic layer was washed with brine, dried over Na$_2$SO$_4$, and concentrated under reduced pressure. The residue was purified by flash column chromatography on silica gel (3% then 17% EtOAc in Hexanes) to give MPM ether S-3 as a partially separable mixture with reagent residues. 4-S4: [α]$^{20}_D$ +20.9 (c 1.0, CHCl$_3$). $^1$H NMR (600 MHz, CDCl$_3$) δ: 7.20 (2H, d, J=8.4 Hz), 6.89 (1H, dd, J=16.2, 6.0 Hz), 6.87 (2H, d, J=8.4 Hz), 6.03 (1H, dd, J=16.2, 1.2 Hz), 4.56 (1H, d, J=11.4 Hz), 4.20 (1H, d, J=11.4 Hz), 4.19 (1H, brs), 4.18 (1H, dd, J=12.0, 2.4 Hz), 4.11 (1H, dd, J=12.0, 1.2 Hz), 3.96 (1H, ddd, J=6.0, 2.4, 1.2 Hz), 3.80 (3H, s), 3.77 (3H, s), 3.45 (1H, ddd, J=4.2, 2.4, 1.2 Hz), 3.27 (1H, dd, J=7.2, 1.2 Hz), 3.14 (1H, brs), 2.10 (1H, dqd, J=7.2, 6.6, 2.4 Hz), 2.08 (1H, ddd, J=14.4, 2.4, 2.4 Hz), 1.61 (1H, ddd, J=14.4, 4.2, 4.2 Hz), 1.03 (9H, s), 1.01 (3H, d, J=6.6 Hz), 1.00 (9H, s), 0.98-0.94 (9H, m), 0.65-0.50 (6H, m) ppm. $^{13}$C NMR (150 MHz, CDCl$_3$) δ: 166.7, 159.3, 147.7, 130.2, 129.3, 121.4, 113.7, 80.6, 77.9, 76.9, 70.5, 68.0, 67.5, 64.9, 55.2, 51.6, 38.6, 27.7, 27.2, 23.2, 20.5, 10.3, 7.0, 5.1 ppm. IR (film): 2950, 2875, 1726, 1659, 1612, 1513, 1168 cm$^{-1}$. HRMS (ESI) m/z: [M+Na]$^+$ calcd for C$_{35}$H$_{60}$O$_8$Si$_2$Na, 687.3719; found, 687.3706.

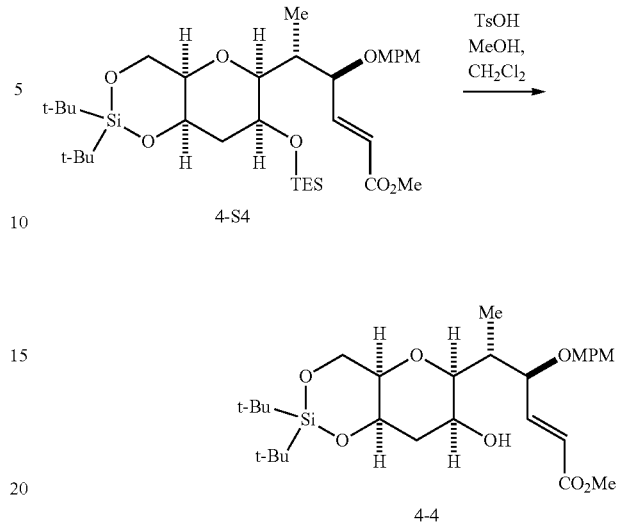

4-S4

4-4

This selective deprotection of TES ether could be accomplished by following two different procedures. Selective deprotection with TsOH.H$_2$O: To a stirred solution of the above MPM-ether 4-S4 (calculated as 10.4 mmol, 1 eq.) in CH$_2$Cl$_2$ (20 mL) and MeOH (10 mL) was added TsOH.H$_2$O (10 mg, 0.0525 mmol, 0.5 mol %) at room temperature. After being stirred for 30 min at the same temperature, additional TsOH.H$_2$O (20×3 mg, 0.450 mmol, 3 mol %) was added every 30 min, and the resultant mixture was stirred for 4 h. The reaction mixture was quenched with sat. NaHCO$_3$ aq. The organic layer was separated and the aqueous layer was extracted with EtOAc. The combined organic layer was washed with brine, dried over Na$_2$SO$_4$, and concentrated under reduced pressure. The residue was purified by flash column chromatography on silica gel (3% then 33% EtOAc in Hexanes) to give secondary alcohol 4-4 (5.04 g, 9.15 mmol, 88% for 2 steps) as colorless oil, which is contaminated with a small amount of reagent residue. Selective deprotection with HFIP: A solution of the above MPM-ether 4-S4 (~6 g) in 1,1,1,3,3,3-hexafluoro-2-propanol (40 mL) and H$_2$O (4 mL) was stirred for 10 h at room temperature. The reaction mixture was concentrated and the resultant residue was purified by flash column chromatography on silica gel (3% then 33% EtOAc in Hexanes) to give secondary alcohol 4-4 (4.2 g, 7.63 mmol, ca. 79% in 2 steps) as colorless oil. 4-4: [α]20D+18.8 (c 1.0, CHCl$_3$). $^1$H NMR (600 MHz, CDCl$_3$) δ: 7.20 (2H, d, J=12.0 Hz), 6.95 (1H, dd, J=16.2, 4.8 Hz), 6.86 (2H, d, J=12.0 Hz), 6.07 (1H, dd, J=16.2, 1.2 Hz), 4.54 (1H, d, J=12.0 Hz), 4.35 (1H, dd, J=3.0, 3.0 Hz), 4.22 (1H, dd, J=12.6, 3.0 Hz), 4.19 (1H, d, J=12.0 Hz), 4.18 (1H, m), 4.16 (1H, dd, J=12.6, 1.2 Hz), 3.80 (3H, s), 3.76 (3H, s), 3.53 (1H, d, J=10.8 Hz), 3.45 (1H, ddd, J=10.8, 3.0, 3.0 Hz), 3.27 (1H, brs), 3.24 (1H, d, J=8.4 Hz), 2.19 (1H, ddd, J=14.4, 3.0, 3.0 Hz), 2.14 (1H, dqd, J=8.4, 6.6, 2.4 Hz), 1.57 (1H, ddd, J=14.4, 3.0, 3.0 Hz), 1.03 (9H, s), 1.02 (3H, d, J=6.6 Hz), 1.02 (9H, s) ppm. $^{13}$C NMR (150 MHz, CDCl$_3$) δ: 166.7, 159.3, 148.1, 130.2, 129.4, 121.6, 113.8, 82.1, 77.1, 76.6, 70.6, 69.3, 68.6, 64.4, 55.3, 51.6, 38.3, 36.7, 27.7, 27.2, 23.1, 20.3, 10.9 ppm. IR (film): 3538, 2938, 2859, 1725, 1658, 1612, 1514, 1251 cm$^{-1}$. HRMS (ESI) m/z: [M+Na]$^+$ calcd for C$_{29}$H$_{46}$O$_8$SiNa, 573.2854; found, 573.2846.

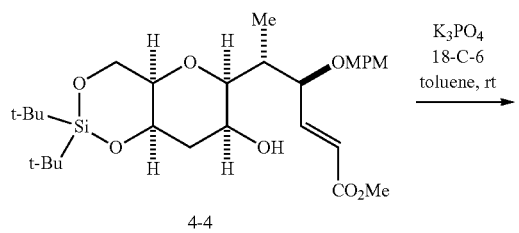

4-4

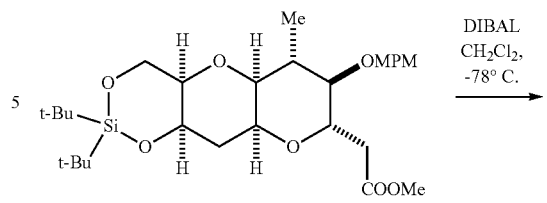

4-S5

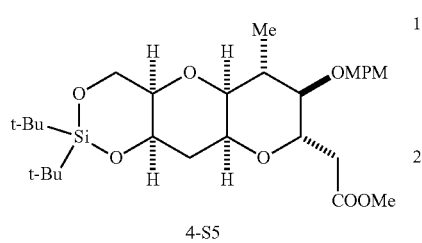

4-S5

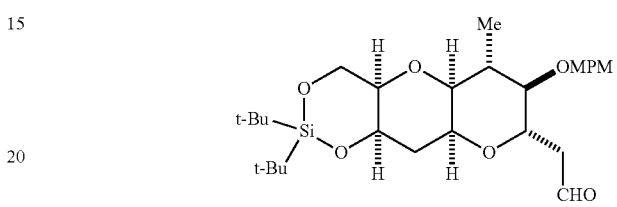

4-5

To a stirred solution of 4-4 (2.80 g, 5.08 mmol, 1 eq.) in toluene (340 mL) were added 18-crown-6 (2.69 g, 10.2 mmol, 2 eq.) and K$_3$PO$_4$ (21.6 g, 102 mmol, 20 eq.) at room temperature. After being stirred for 14 h at the same temperature, additional 18-crown-6 (671 mg, 2.54 mmol, 0.5 eq.) was added. After being stirred for 5 h at the same temperature, the reaction was quenched with sat. NH$_4$Cl aq. The organic layer was separated and the aqueous layer was extracted with EtOAc. The combined organic layer was washed with brine, dried over Na$_2$SO$_4$, filtered, and concentrated under reduced pressure. The residue was purified by flash column chromatography to give 4-S5 (2.64 g, 4.79 mmol, 94%) as colorless oil. 4-S5: $[\alpha]^{20}_D$ −25.8 (c 1.0, CHCl$_3$). $^1$H NMR (600 MHz, CDCl$_3$) δ: 7.25 (2H, d, J=8.4 Hz), 6.88 (1H, d J=8.4 Hz), 4.56 (1H, d, J=10.2 Hz), 4.45 (1H, d, J=10.2 Hz), 4.29 (1H, ddd, J=7.8, 4.2, 4.2 Hz), 4.14 (1H, dd, J=12.0, 6.0 Hz), 4.07 (1H, dd, J=12.0, 3.0 Hz), 3.98 (1H, ddd, J=9.6, 7.8, 3.6 Hz), 3.82-3.77 (4H, m), 3.66 (3H, s), 3.60 (1H, ddd, J=6.0, 4.2, 3.0 Hz), 3.40 (1H, dd, J=7.8, 4.8 Hz), 3.14 (1H, dd, J=9.6, 9.6 Hz), 2.67 (1H, dd, J=15.6, 3.6 Hz), 2.48 (1H, dd, J=15.6, 7.8 Hz), 2.11 (1H, ddd, J=13.2, 7.8, 7.8 Hz), 2.00-1.92 (2H, m), 1.21 (3H, d, J=7.2 Hz), 1.03 (9H, s), 1.01 (9H, s) ppm. $^{13}$C NMR (150 MHz, CDCl$_3$) δ: 171.6, 159.4, 129.9, 129.7, 113.9, 80.4, 78.6, 73.7, 73.0, 72.4, 68.9, 66.9, 65.1, 55.3, 51.6, 39.5, 37.8, 31.9, 27.4, 27.1, 22.2, 20.8, 16.1 ppm. IR (film): 2934, 2858, 1740, 1612, 1514, 1250 cm$^{-1}$. HRMS (ESI) m/z: [M+Na]$^+$ calcd for C$_{29}$H$_{46}$O$_8$SiNa, 573.2854; found, 573.2847.

To a stirred solution of 4-S5 (5.0 g, 9.07 mmol, 1 eq.) in toluene (100 ml) was added DIBAL solution (11.3 mL of 1M in hexanes, 11.3 mmol, 1.2 eq.) dropwise at −78° C. After being stirred for 1.5 h at the same temperature, the reaction was quenched with acetone (0.3 mL). The mixture was stirred for 15 min and sat. Rochelle's salt aq. was added. After being stirred for 3 h at room temperature, the mixture was diluted with EtOAc. The organic layer was separated and the aqueous layer was extracted with EtOAc. The combined organic layer was washed with brine, dried over Na$_2$SO$_4$, filtered, and concentrated under reduced pressure. The residue was purified by flash column chromatography on neutral silica gel (5%, 20% then 33% EtOAc in Hexanes) to give 4-5 (4.37 g, 8.49 mmol, 94%) as a colorless amorphous solid. 4-5: $[\alpha]^{20}_D$ −37.3 (c 1.0, CHCl$_3$). $^1$H NMR (600 MHz, C$_6$D$_6$) δ: 9.51 (1H, t, J=2.4 Hz), 7.21 (2H, m), 6.82 (2H, m), 4.33 (1H, d, J=10.6 Hz), 4.24 (1H, d, J=10.6 Hz), 4.17 (1H, dd, J=12.3, 3.5 Hz), 4.11 (1H, m), 3.99-3.91 (2H, m), 3.31 (3H, s), 3.26 (1H, m), 3.0 (1H, dd, J=7.0, 4.1 Hz), 2.91 (1H, m), 2.81 (1H, dd, J=10.6, 9.4 Hz), 2.40 (1H, m), 2.34 (1H, m), 2.18-2.08 (2H, m), 1.54 (1H, dt, J=14.1, 5.3 Hz), 1.24 (9H, s), 1.18 (3H, d, J=7.0 Hz), 1.13 (9H, s) ppm. $^{13}$C NMR (125 MHz, C$_6$D$_6$) δ: 200.1, 160.6, 131.2, 130.4, 114.7, 81.4, 80.8, 74.5, 74.4, 73.3, 69.1, 68.2, 66.0, 55.4, 47.9, 40.9, 34.2, 28.4, 28.1, 23.6, 21.6, 17.3 ppm. IR (film): 2933, 2857, 1725, 1514, 1250, 1078 cm$^{-1}$. HRMS (ESI) m/z: [M+Na]$^+$ calcd for C$_{28}$H$_{44}$O$_7$SiNa, 543.7272; found, 543.2750.

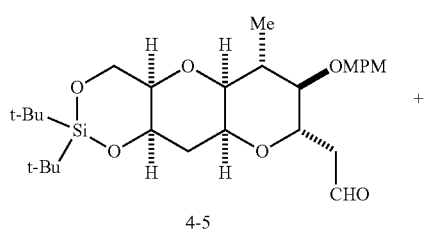

4-5

+

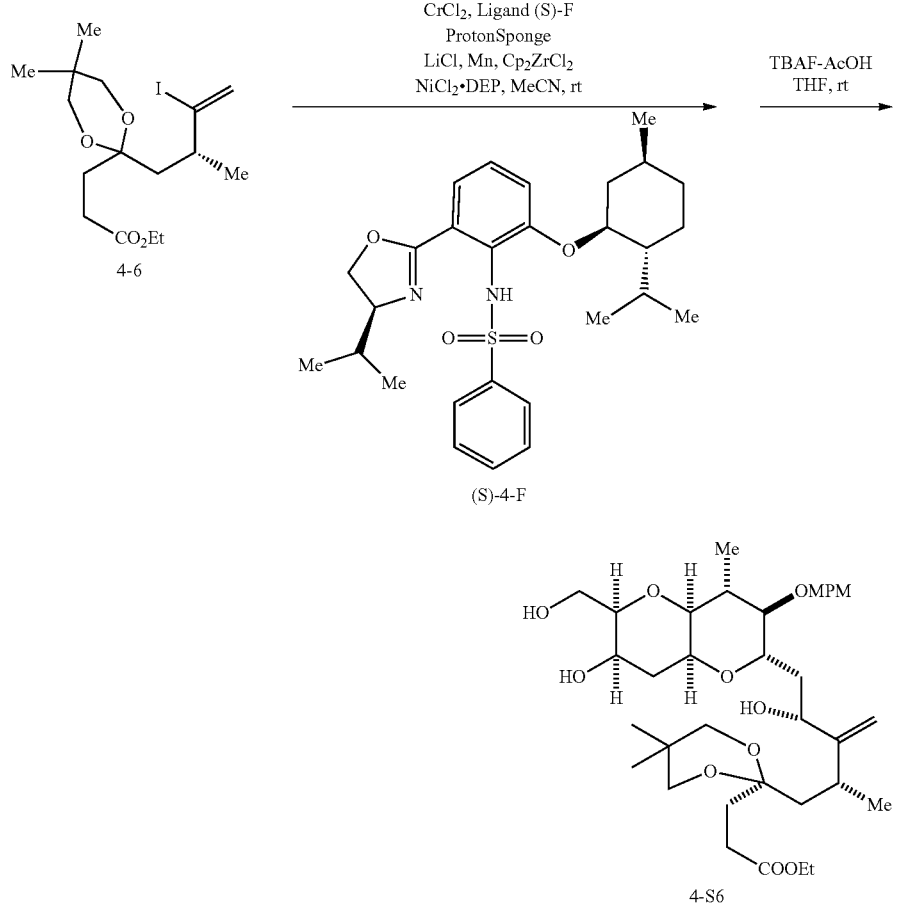

In a glove box, to a mixture of CrCl₂ (104 mg, 0.849 mmol, 10 mol %), (S)-sulfonamide ligand (465 mg, 0.934 mmol, 11 mol %), and proton scavenger (200 mg, 0.934 mmol, 11 mol %) was added MeCN (28 mL) and the resulted solution was stirred for 1 h at room temperature. In a separate flask, 4-5 (4.37 g, 8.49 mmol, 1 eq.), 4-6 (5.22 g, 12.7 mmol, 1.5 eq.), LiCl (720 mg, 17.0 mmol, 2 eq.), Mn (932 mg, 17.0 mmol, 2 eq.), Cp₂ZrCl₂ (2.48 g, 8.49 mmol, 1 eq.), and NiCl₂.DEP (331 mg, 0.849 mmol, 10 mol %) were mixed together. Then Cr complex solution was transferred to the flask, and the resulting mixture was stirred vigorously for 3 h at room temperature. The reaction mixture was removed from the glove box and diluted with EtOAc (100 mL). Aqueous potassium serinate (0.5 M, 100 mL) and sat. NaHCO₃ aq. (100 mL) were added, and the resulting mixture was stirred for 1 h. The suspension was filtered through a pad of Celite. The organic layer was separated and the aqueous layer was extracted with EtOAc. The combined organic layer washed with brine, dried over Na₂SO₄, filtered, and concentrated under reduced pressure to give a crude allylic alcohol, which was used in the next reaction without further purification. A buffered TBAF solution was prepared by mixing TBAF solution (21 ml of 1M in THF, 21.0 mmol, 2.5 eq.) and AcOH (0.608 mL, 10.6 mmol, 1.25 eq.) at room temperature. To a stirred solution of the crude alcohol (calculated as 8.49 mmol) in THF (100 mL) was added the TBAF-AcOH solution at 0° C. The reaction mixture was stirred for 1 h at the same temperature, and then quenched with sat. NH₄Cl aq. The mixture was diluted with EtOAc. The organic layer was separated and the aqueous layer was extracted with EtOAc. The combined organic layer was washed with brine, dried over Na₂SO₄, filtered, and concentrated under reduced pressure. The residue was purified by flash column chromatography on neutral silica gel (20%, 50% then 100% EtOAc in Hexanes) to give 4-S6 (4.45 g, 6.69 mmol, 79% for 2 steps) as colorless oil. 4-S6: $[\alpha]^{20}_D$ −23.9 (c 1.0, CHCl₃). ¹H NMR (600 MHz, C₆D₆) δ: 7.29 (2H, m), 6.86 (2H, m), 5.45 (1H, s), 5.01 (1H, s), 4.52 (1H, brd, J=5.9 Hz), 4.47 (1H, d, J=11.2 Hz), 4.43 (1H, m), 4.38 (1H, d, J=11.2 Hz), 4.02-3.95 (3H, m), 3.87 (2H, m), 3.57 (1H, brs), 3.43 (1H, brs), 3.37-3.30 (4H, m), 3.25 (2H, m), 3.07 (1H, m), 2.98 (1H, dd, J=7.6, 6.5 Hz), 2.93 (1H, m), 2.61 (1H, m), 2.55 (2H, t, J=7.9 Hz), 2.29 (1H, m), 2.24-2.14 (2H, m), 2.12 (1H, ddd, J=14.2, 3.2, 3.2 Hz), 2.02 (2H, m), 2.07-1.98 (2H, m), 1.90-1.80 (3H, m), 1.30 (3H, d, J=7.0 Hz), 1.18 (1H, m), 0.99 (3H, t, J=7.0 Hz), 0.89 (3H, d, J=7.6 Hz), 0.74 (3H, s), 0.69 (3H, s) ppm, ¹³C NMR (125 MHz, C₆D₆) δ: 173.7, 159.8, 159.3, 131.1, 129.5, 114.1, 107.9, 100.0, 81.0, 80.1, 79.5, 75.7, 74.5, 72.2, 70.12, 70.11, 64.8, 64.4, 63.5, 60.2, 54.8, 41.5, 38.9, 38.8, 35.2, 31.3, 30.5, 29.4, 28.9, 22.9, 22.8, 22.7, 17.8, 14.3 ppm. IR (film): 3470, 2956, 2871, 1732, 1514, 1248, 1081, 1035 cm⁻¹. HRMS (ESI) m/z: [M+Na]⁺ calcd for C₃₆H₅₆O₁₁Na, 687.3715; found, 687.3715.

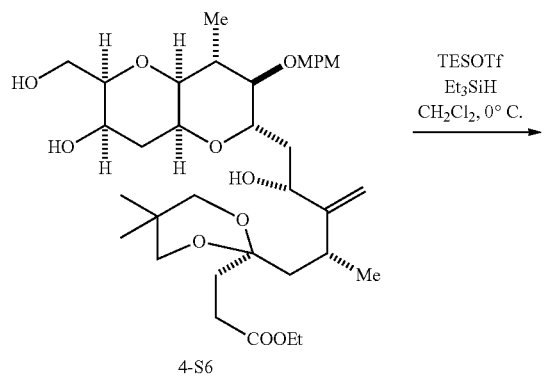

4-S6

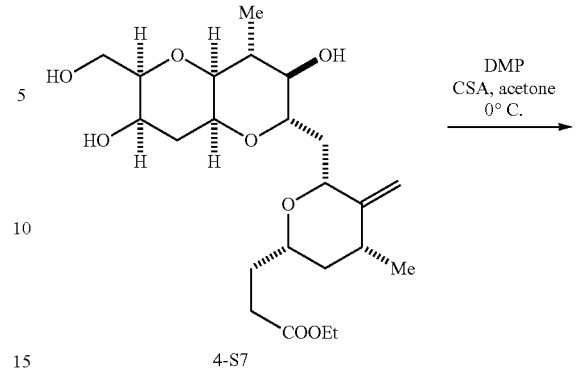

4-S7

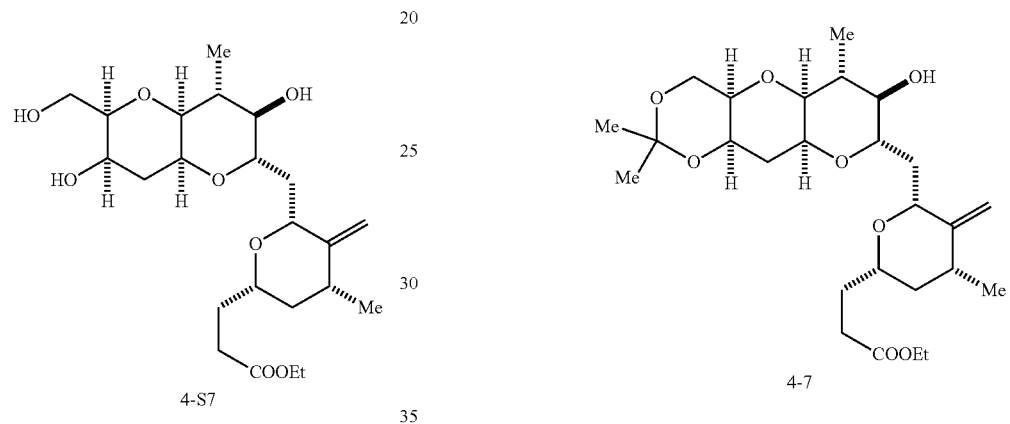

4-S7

4-7

To a stirred solution of 4-S6 (4.45 g, 6.69 mmol, 1 eq.) and TESH (10.7 mL, 66.9 mmol, 10 eq.) in CH$_2$Cl$_2$ (90 mL) was added TESOTf (7.58 mL, 33.5 mmol, 5 eq.) dropwise at 0° C. After being stirred for 3 h, the mixture was poured into sat. NaHCO$_3$ aq. The organic layer was separated and the aqueous layer was extracted with CH$_2$Cl$_2$. The combined organic layer was washed with brine, dried over Na$_2$SO$_4$, filtrated, and concentrated under reduced pressure. The residue was purified by flash column chromatography on neutral silica gel (10%, 50% then 100% EtOAc in Hexanes) to give 4-S7 (2.57 g, 5.81 mmol, 87%) as colorless oil 4-S7: $[\alpha]^{20}_D$ −29.1 (c 1.0, MeOH). $^1$H NMR (600 MHz, C$_6$D$_6$) δ: 4.77 (1H, s), 4.75 (1H, d, J=1.8 Hz), 4.39 (1H, m), 4.27-4.14 (2H, m), 4.03 (1H, m), 3.95 (1H, m), 3.88 (1H, ddd, J=11.9, 7.8, 4.4 Hz), 3.78 (1H, dd, J=8.2, 4.1 Hz), 3.57 (1H, m), 3.52 (1H, m), 3.46 (1H, ddd, J=7.5, 3.6, 3.6 Hz), 3.41 (1H, m), 3.03 (1H, dd, J=5.0 Hz), 2.91 (1H, brs), 2.88 (1H, brs), 2.44 (2H, m), 2.25 (1H, m), 2.07-1.85 (4H, m), 1.76-1.65 (2H, m), 1.31 (1H, ddd, J=12.8, 4.3, 1.8 Hz), 1.16 (1H, ddd, J=15.0, 3.1, 3.1 Hz), 1.02 (3H, t, J=7.0 Hz), 0.95-0.87 (4H, m), 0.85 (3H, d, J=7.6 Hz) (one OH proton is missing) ppm. $^{13}$C NMR (125 MHz, C$_6$D$_6$) δ: 173.5, 151.2, 104.6, 80.9, 78.6, 77.2, 76.7, 76.5, 71.0, 65.5, 63.5, 62.6, 60.3, 42.7, 38.7, 35.9, 35.0, 32.4, 31.3, 30.7, 18.0, 16.2, 14.3 ppm. IR (film): 3435, 2928, 1729, 1420, 1253, 1165, 1092, 1048, 639 cm$^{-1}$. HRMS (ESI) m/z: [M+Na]$^+$ calcd for C$_{23}$H$_{38}$O$_8$Na, 465.2459; found, 465.2460.

To a stirred solution of 4-S7 (1.83 g, 4.14 mmol, 1 eq.) and 2,2-dimethoxypropane (37.6 mL, 306 mmol, 30 eq.) in acetone (100 mL) was added CSA (236 mg, 1.02 mmol, 10 mol %) at 0° C. After being stirred for 30 min, the mixture was warmed to room temperature and stirred for 4 h. The reaction was quenched with Et$_3$N (2 mL), diluted with EtOAc and stirred for 30 min. Then the mixture was poured into sat. NaHCO$_3$ aq. The organic layer was separated and the aqueous layer was extracted with EtOAc. The combined organic layer was washed with brine, dried over Na$_2$SO$_4$, filtrated, and concentrated under reduced pressure. The residue was passed through a pad of silica gel (EtOAc) to give a crude acetonide 4-7 as colorless oil. The obtained crude material was used in the next reaction without further purification. Pure acetonide 4-7 (239 mg, 0.495 mmol) was isolated in 91% yield from diol (241 mg, 0.545 mmol). The product was obtained as colorless oil. 4-7: $[\alpha]^{20}_D$ −19.0 (c 1.05, CHCl$_3$). $^1$H NMR (600 MHz, C$_6$D$_6$) δ: 4.91 (1H, s), 4.72 (1H, s), 4.39-4.36 (1H, m), 4.09 (1H, dd, J=7.2, 4.2 Hz), 4.01-3.98 (2H, m), 3.75 (1H, dd, J=12.6, 2.4 Hz), 3.68 (1H, dd, J=7.8, 4.5 Hz), 3.63 (1H, dd, J=12.3, 2.7 Hz), 3.52 (1H, s), 3.45-3.40 (2H, m), 3.37 (1H, d, J 7.2 Hz), 3.17 (1H, dd, J=3.6, 3.6 Hz), 2.71 (1H, dd, J=5.4, 3.0 Hz), 2.47-2.44 (2H, m), 2.28-2.13 (4H, m), 1.96-1.92 (1H, m), 1.74-1.66 (2H, m), 1.48 (3H, s), 1.41 (1H, ddd, J=14.4, 4.5, 4.5 Hz), 1.32-1.30 (1H, m), 1.21 (3H, s), 1.17 (3H, d, J=7.2 Hz), 1.00 (3H, t, J=6.9 Hz), 0.94-0.87 (1H, m), 0.87 (3H, d, J=6.6 Hz) ppm. $^{13}$C NMR (125 MHz, C$_6$D$_6$) δ: 173.2, 151.3, 104.7, 98.4, 78.3, 76.7, 75.8, 73.9, 70.2, 64.1, 63.7, 62.9, 60.0, 42.9, 40.6, 36.0, 34.5, 32.8, 31.2, 30.6, 28.8, 19.7, 18.0, 16.5, 14.3 ppm. FTIR (film): 3502, 2957, 2926, 2874, 1733, 1457, 1373, 1250, 1181, 1084, 1057, 1039, 977, 906, 836 cm$^{-1}$. HRMS (ESI) m/z: [M+NH$_4$]$^+$ calcd for C$_{26}$H$_{46}$NO$_8$, 500.3218; found, 500.3248.

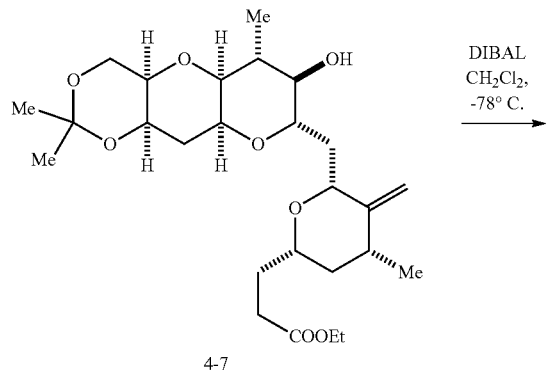

To a stirred solution of 4-7 (calculated as 10.2 mmol) in CH$_2$Cl$_2$ (200 mL) was added DIBAL (22 mL, 22.4 mmol, 2.2 eq.) dropwise at −78° C. After being stirred for 1.5 h at the same temperature, the reaction was quenched with acetone (0.30 mL) and stirred for 15 min at −78° C. Then sat. Rochelle's salt aq. was added, and the mixture was warmed to room temperature. After being stirred for 3h, the mixture was diluted with EtOAc. The organic layer was separated and the aqueous layer was extracted with EtOAc. The combined organic layer was washed with brine, dried over Na$_2$SO$_4$, filtrated, and concentrated under reduced pressure. The residue was combined with another crude material (ca. 400 mg) and purified by flash column chromatography on neutral silica gel (5%, 20% then 33% EtOAc in Hexanes) to give aldehyde 4-8 (4.1 g, 82-90% for 2 steps) as a colorless amorphous solid. One batch reaction: To a solution of 4-7 (206 mg, 0.427 mmol, 1 eq.) in CH$_2$Cl$_2$ (8.5 mL) was added DIBAL (0.94 mL of 1.0 M in Hexanes, 0.939 mmol, 2.2 eq.) dropwise at −78° C. After being stirred for 50 min at the same temperature, the reaction was quenched with acetone (0.30 mL) and MeOH (0.30 mL). Then 20% Rochelle's salt aq. was added, and the mixture was stirred for 2 h at room temperature. The organic layer was separated and the aqueous layer was extracted with EtOAc. The combined organic layer was washed with brine, dried over Na$_2$SO$_4$, filtrated, and concentrated under reduced pressure. The residue was purified by flash column chromatography on neutral silica gel (5%, 20% then 33% EtOAc in Hexanes) to give 4-8 (167 mg, 0.381 mmol, 89%) as a colorless amorphous solid. 4-8: [α]$^{20}_D$ −17.3 (c 1.0, CHCl$_3$). $^1$H NMR (600 MHz, C$_6$D$_6$) δ: 9.46 (1H, t, J=1.5 Hz), 4.92 (1H, s), 4.73 (1H, d, J=1.8 Hz), 4.41 (1H, dd, J=5.9 Hz), 4.02 (1H, dd, J=7.6, 4.7 Hz), 3.74 (1H, dd, J=12.3, 2.9 Hz), 3.66 (1H, dd, J=7.6, 4.1 Hz), 3.60 (1H, dd, J=12.3, 3.5 Hz), 3.48 (1H, m), 3.39 (1H, m), 3.32 (1H, m), 3.27 (1H, m), 3.12 (1H, dd, J=3.5, 3.5 Hz), 2.64 (1H, m), 2.34-2.11 (6H, m), 1.91 (1H, m), 1.53-1.45 (4H, m), 1.38 (1H, ddd, J=14.1, 4.7, 4.7 Hz), 1.24 (1H, ddd, J=12.6, 4.4, 2.3 Hz), 1.19 (3H, s), 1.11 (3H, d, J=7.6 Hz), 0.89 (3H, d, J=6.5 Hz), 0.86 (1H, dd, J=24.6, 12.3 Hz) ppm. $^{13}$C NMR (125 MHz, C$_6$D$_6$) δ: 201.0, 151.2, 104.8, 98.4, 78.2, 76.6, 75.9, 74.2, 73.8, 70.2, 63.9, 63.2, 63.0, 42.9, 40.38, 40.36, 36.0, 34.5, 33.0, 29.0, 28.4, 19.5, 18.0, 16.4 ppm. IR (film): 3506, 2923, 2852, 1723, 1374, 1112, 1086, 908 cm$^{-1}$. HRMS (ESI) m/z: [M+Na]$^+$ calcd for C$_{24}$H$_{38}$O$_7$Na, 461.2510; found, 461.2512.

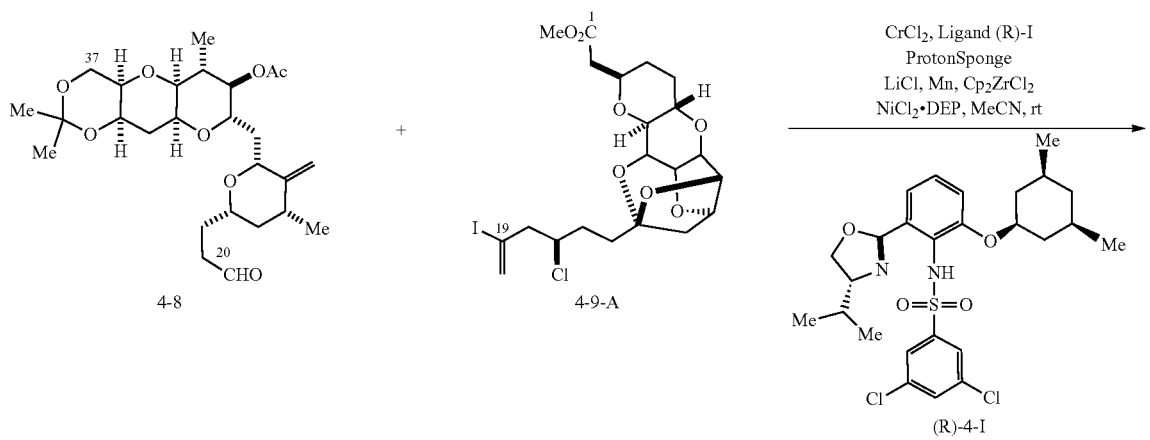

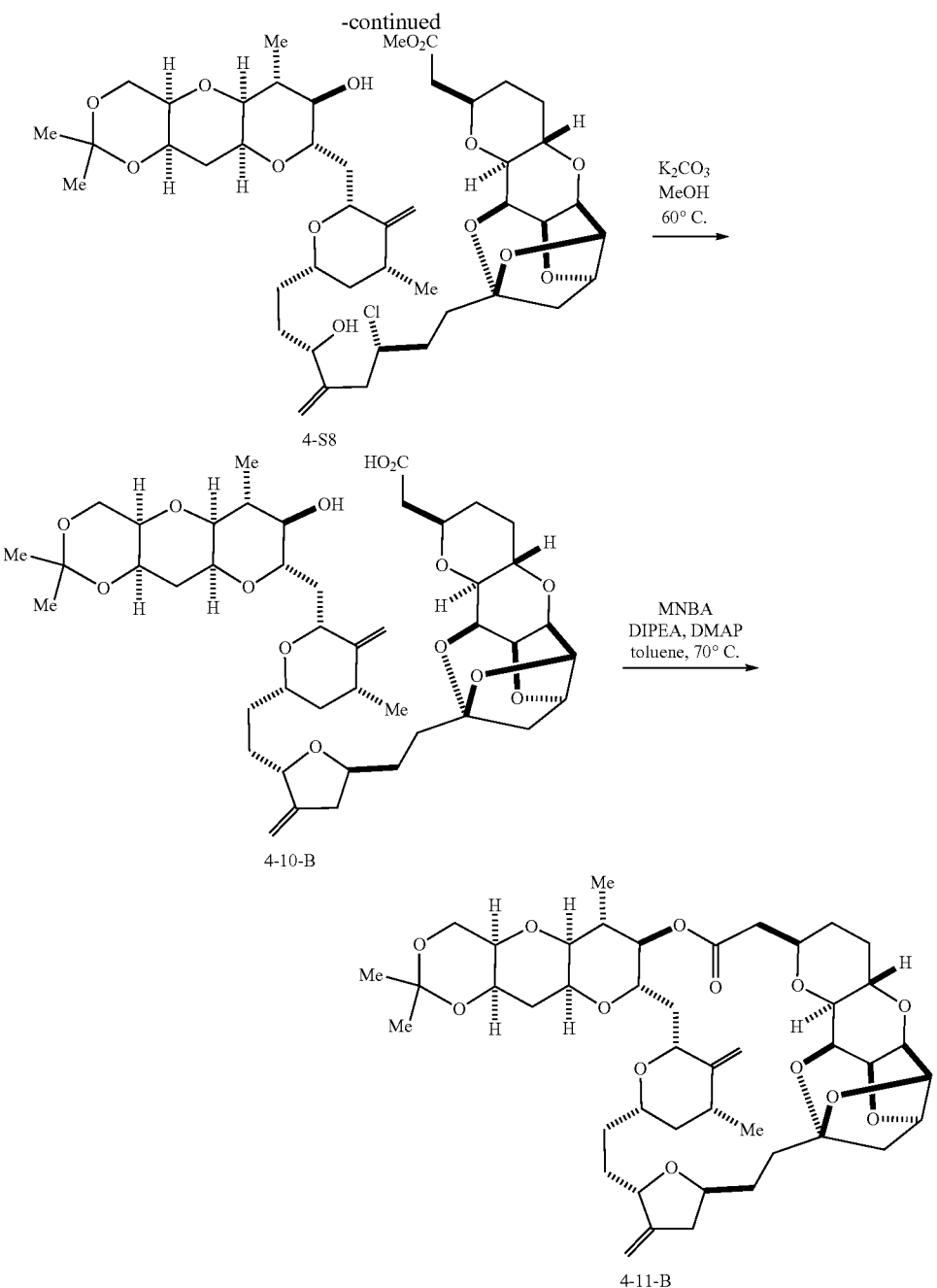

In a glove box, to a mixture of CrCl$_2$ (46.2 mg, 0.376 mmol, 10 mol %), (R)-sulfonamide ligand (264 mg, 0.491 mmol, 13 mol %), and proton scavenger (97 mg, 0.453 mmol, 12 mol %) was added MeCN (9.4 mL) and the resulting solution was stirred for 1 h at room temperature. In a separate flask, 4-8 (1.65 g, 3.76 mmol, 1 eq.), 4-9-B (2.30 g, 4.14 mmol, 1.1 eq.), DTBMP (1.93 g, 9.40 mmol, 2.5 eq.), LiCl (319 mg, 7.52 mmol, 2 eq.), Mn (826 mg, 15.0 mmol, 4 eq.), Cp$_2$ZrCl$_2$ (2.75 g, 9.40 mmol, 2.5 eq.), and NiCl$_2$.DEP (27.5 mg, 0.0752 mmol, 2 mol %) were mixed and then the solution of Cr complex was transferred to this flask. After being stirred for 1 h at room temperature, the reaction was removed from the glove box and diluted with EtOAc (15 mL). Potassium serinate aq. (0.5M, 15 mL) and sat. NaHCO$_3$ aq. (15 mL) were added. After being stirred for 1 h, the resulting suspension was filtered through a pad of Celite. The organic layer was separated and the aqueous layer was extracted with EtOAc and washed with brine. The combined organic layer was dried over Na$_2$SO$_4$, filtered, and concentrated under reduced pressure to give a crude diol, which was used in the next reaction without further purification. To a stirred solution of the crude diol (calculated as 3.76 mmol, 1 eq.) in MeOH (75 mL) was added K$_2$CO$_3$ (5.2 g, 37.6 mmol, 10 eq.). The reaction was heated to 60° C. and stirred for 15 h. Then H$_2$O (7.5 mL) was added. After being stirred for additional 3 h at the same temperature, the mixture was cooled to room temperature, filtered through a pad of Celite, and concentrated under reduced pressure. To the residue were added EtOAc, sat. NH₄Cl aq., and brine. The organic layer was separated and the aqueous phase was extracted with EtOAc. The combined organic layer was dried over Na₂SO₄, filtrated, and concentrated under reduced pressure to give a crude seco acid 10-B, which was used in the next reaction without further purification. The macrolactonization was tested under Shiina's condition and Yamaguchi's condition. Shiina macrolactonization: To a stirred solution of MNBA (7.8 g, 22.6 mmol, 6 eq.) in toluene (2.5 L) was added DMAP (5.5 g, 45.1 mmol, 12 eq.) at 70° C. A solution of the crude 4-10-B (calculated as 3.76 mmol, 1 eq.) and DIPEA (3.9 mL, 22.6 mmol, 6 eq.) in toluene (200 mL) was added to the MNBA solution via a syringe pump over 15 h. After completion of addition, the syringe was rinsed with toluene (40 mL). After being stirred for additional 30 min, the reaction was cooled to room temperature and concentrated under reduced pressure. The residue was dissolved in CH₂Cl₂ and washed with 0.5 M HCl and sat. NaHCO₃ aq., successively. The organic layer was dried over Na₂SO₄, filtrated, and concentrated under reduced pressure. The residue was purified by flash column chromatography on neutral silica gel (13%, 25%, 33%, 50%, 67%, then 100% EtOAc in Hexanes) to give 4-11-B (2.19 g, 2.74 mmol, 73% for 3 steps) as a colorless solid. The obtained product was a mixture of diastereomer at C-20 stereocenter (dr=19:1, determined by ¹H NMR) Yamaguchi macroloctonization: To a stirred solution of the crude 4-10-B (calculated as 0.456 mmol) in THF (4.6 mL) were added NEt₃ (0.159 mL, 1.14 mmol, 2.5 eq.) and 2,4,6-trichlorobenzoyl chloride (139 mg, 0.57 mmol, 1.25 eq.). The mixture was stirred for 2 h, and then filtered through a pad of Celite, which was washed with toluene (35.4 mL). In a separate flask, DMAP (334 mg, 2.74 mmol, 6 eq.) was dissolved in toluene (290 mL, 1.6 mM) at 80° C. The solution of mixed anhydride was transferred into DMAP solution via a syringe pump over 13 h. The reaction was cooled to room temperature and quenched with sat. NaHCO₃ aq. The organic layer was separated and the aqueous layer was extracted with EtOAc. The combined organic layer was dried over Na₂SO₄, filtered, and concentrated. The residue was purified by flash column chromatography on neutral silica gel (13%, 25%, 33%, 50%, 67%, then 100% EtOAc in Hexanes) to give 4-11-B (124 mg, 0.155 mmol, 34% for 3 steps) as a colorless solid. 4-11-B: [α]²⁰_D –72.5 (c 1.09, CHCl₃). MP: 188-189° C. (recrystallized from CH₂Cl₂-EtOAc). ¹H NMR (600 MHz, C₆D₆) δ: 5.22 (1H, brs), 5.08 (1H, d, J=1.8 Hz), 5.00 (1H, ddd, J=10.6, 7.6, 2.9 Hz), 4.94 (1H, s), 4.82 (1H, dd, J=7.6, 5.3 Hz), 4.76 (1H, brs), 4.68 (1H, brd, J=10.0 Hz), 4.55 (1H, ddd, J=10.3, 10.3, 4.1 Hz), 4.30 (1H, dd, J=4.1, 1.8 Hz), 4.17-4.07 (3H, m), 3.98 (1H, m), 3.90 (1H, dd, J=6.5, 4.7 Hz), 3.85 (1H, brd, J=10.6 Hz), 3.81 (1H, dd, J=11.7, 4.1 Hz), 3.73 (1H, m), 3.69 (1H, dd, J=12.0, 3.8 Hz), 3.65 (1H, dd, J=6.5, 4.1 Hz), 3.58-3.50 (2H, m), 3.05 (1H, dd, J=3.3, 3.3 Hz), 2.85 (1H, dd, J=16.4, 7.0 Hz), 2.76 (1H, m), 2.72 (1H, m), 2.62 (1H, dd, J=9.4, 1.8 Hz), 2.50-2.36 (3H, m), 2.34-2.22 (3H, m), 2.22-2.03 (5H, m), 1.97-1.85 (3H, m), 1.72 (1H, dddd, J=9.8, 9.8, 9.8, 4.7 Hz), 1.62-1.27 (11H, m), 1.26-1.21 (6H, m), 1.06 (1H, dd, J 23.5, 12.3 Hz), 0.97 (3H, d, J=6.5 Hz) ppm. ¹³C NMR (125 MHz, C₆D₆) δ: 171.3, 152.9, 152.7, 110.0, 105.0, 103.8, 98.7, 82.3, 81.0, 78.2, 78.1, 77.3, 76.9, 76.4, 76.1, 75.1, 74.7, 74.3 (×2), 74.0, 70.4, 69.9, 68.5, 64.1, 63.9, 62.4, 48.5, 43.8, 41.5, 39.4, 39.3, 38.8, 36.3, 35.6, 32.5, 32.4, 31.11, 31.09, 30.62, 29.3, 28.5, 20.3, 18.1, 16.4 ppm. IR (film): 2923, 2869, 1725, 1188, 1118, 1086, 755 cm⁻¹. HRMS (ESI) m/z: [M+Na]⁺ calcd for C₄₄H₆₂O₁₃Na, 821.4083; found, 821.4084.

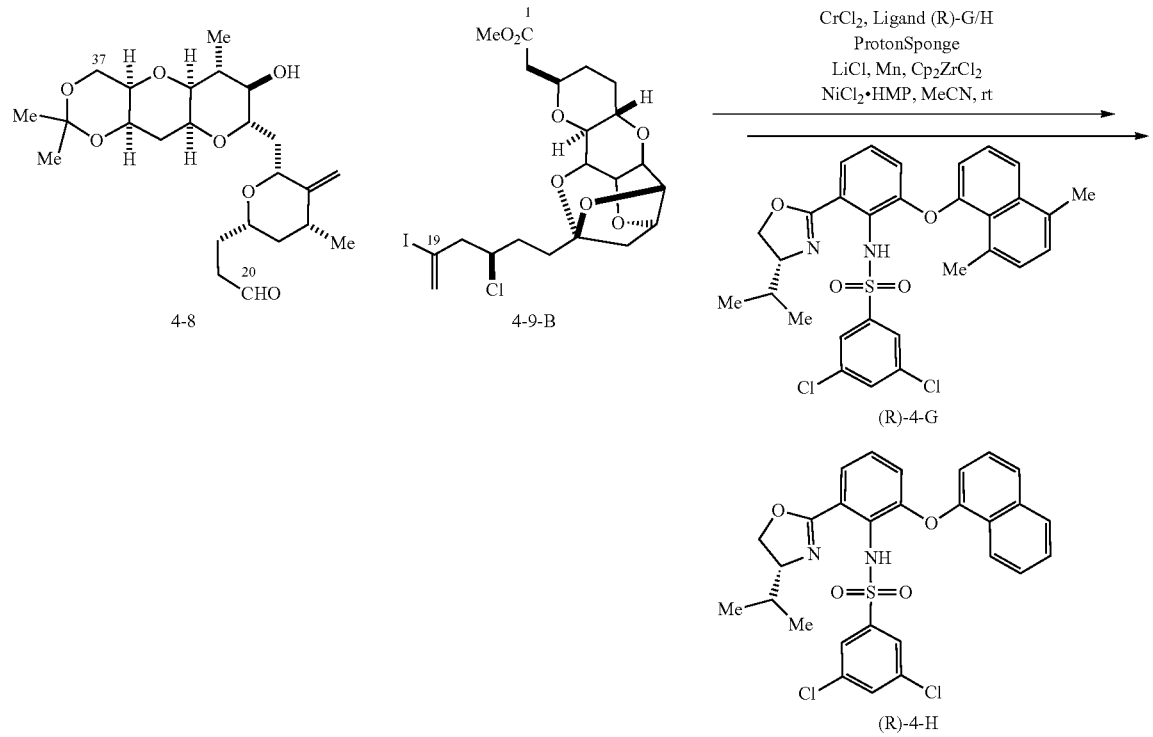

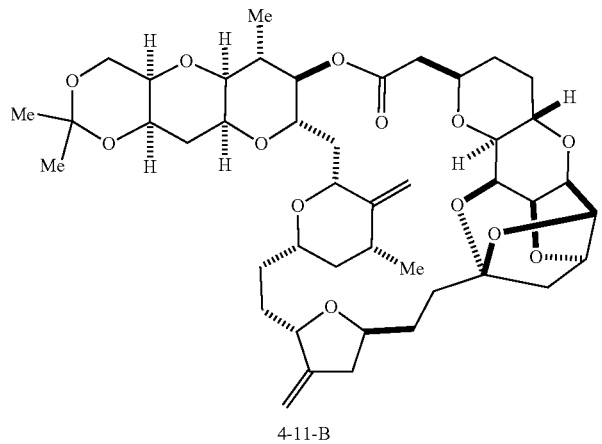

4-11-B

Ni/Cr-Mediated coupling of 4-8 with 4-9-B in the presence of Cr-catalyst prepared from (R)-4-G and (R)-4-H was carried out as follows: In a glove box, to a mixture of $CrCl_2$ (7.0 mg, 10 mol %), sulfonamide (R)-G (43.2 mg, 13 mol %), proton scavenger (14.7 mg, 12 mol %) and LiCl (24.1 mg, 0.57 mmol, 1.0 eq) was added MeCN (1.4 mL, 0.4 M) and stirred for 1 h at r.t. In a separate flask, 4-8 (250 mg, 0.57 mmol, 1.0 eq), 4-9-B (350 mg, 0.63 mmol, 1.1 eq), DTBMP (290 mg, 1.43 mmol, 2.5 eq), Mn (125 mg, 2.28 mmol, 4.0 eq) and $Cp_2ZrCl_2$ (0.42 g, 1.43 mmol, 2.5 eq) were mixed, and the solution of Cr complex was then transferred to this flask. After being stirred for 1 min, $HMP·NiCl_2$ (2.2 mg, 1 mol %; doped in LiCl) was added. Additional $HMP·NiCl_2$ (2.2 mg, 1 mol %; doped in LiCl) was added after 1 and 2 h, respectively. The reaction mixture was stirred for 3 h total at r.t. The reaction was removed from the glove box and diluted with EtOAc (10 mL). Aqueous potassium serinate (0.5 M, 3 mL) and saturated aqueous $NaHCO_3$ (3 mL) were added. After being stirred for 1 h, the resulting suspension was filtered through a pad of celite. The filtrate was extracted with EtOAc, washed with sat. NaCl, dried over $Na_2SO_4$, filtered, and concentrated. With use of the procedure given for the coupling with sulfonamide (R)-4-G, the crude product was converted to macrolactone 4-11-B; thus, 296 mg 4-11-B (65% overall yield; dr=29:1) was obtained from 250 mg 4-8.

The Ni/Cr-mediated coupling with the Cr-catalyst prepared from (R)-4-H was carried out with use of the same procedure; 305 mg 4-11-B (67% overall yield; dr=24:1) was obtained from 250 mg 4-8.

Sulfonamides (R)-4-G, (R)-4-H, and (R)-4-I were synthesized via the general scheme shown below. As an example, the synthesis of (R)-4-G is given below.

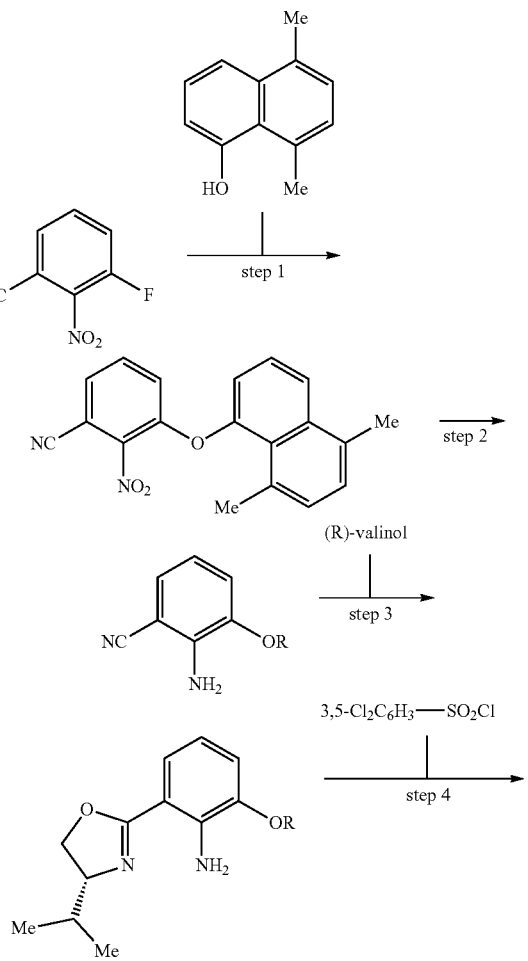

-continued

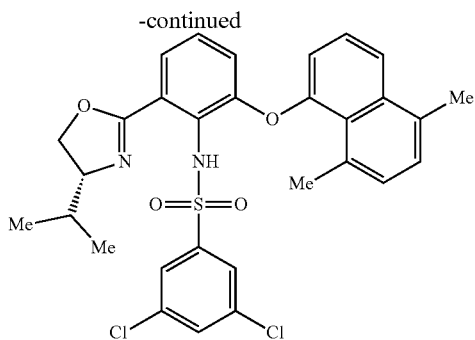

Step 1: To a slurry of NaH (5.56 g, 60% in mineral oil, 140 mmol, 3.0 eq) in anhydrous THF (100 mL) was added 5,8-dimethylnapthol (8.00 g, 46.5 mmol, 1.0 eq) at 0° C. with stirring for 1 h. Then 3-fluoro-2-nitrobenzonitrile (8.50 g, 51.2 mmol, 1.1 eq) was dissolved in THF (50 mL) added via syringe. The reaction was allowed to warm to room temperature and stirred for 3 h at room temperature before quenched with water at 0° C. The organic solvent (THF) was removed in vacuo and the slurry was extracted with EtOAc (2×100 ml). The combined organic layers were washed with brine, water, dried over $Na_2SO_4$ and filtered. The solvent was removed in vacuo to afford 16.1 g of crude product which was purified with column chromatography using EtOAc:Hexanes (10:90) to afford pure red solid (12.20 g, 38.4 mmol, 82%). $^1$H NMR (600 MHz, $CDCl_3$) δ: 7.96 (1H, dd, J=8.5, 1.1 Hz), 7.48 (1H, dd, J=8.4, 7.5 Hz), 7.46-7.40 (2H, m), 7.30-7.24 (1H, m), 7.19 (1H, d, J=7.1 Hz), 7.08 (1H, dd, J=7.5, 1.1 Hz), 6.97-6.91 (1H, m), 2.69 (3H, s), 2.66 (3H, s) ppm. $^{13}$C NMR (125 MHz, $CDCl_3$) δ: 151.6, 151.5, 142.3, 135.6, 132.7, 130.9, 129.7, 127.7, 126.7, 126.5, 125.3, 123.5, 122.8, 117.6, 113.6, 108.0, 23.6, 20.1 ppm. IR (neat) v 2963, 2929, 2242, 1599, 1573, 1442, 1357, 1263, 1135, 997, 908, 824, 793, 750, 729 $cm^{-1}$. HRMS (ESI) calcd. for $C_{19}H_{14}N_2O_3Na$ [M+Na]+: 341.0897, found 341.0903.

Step 2: To a solution of the above adduct (12.20 g, 38.4 mmol, 1.0 eq) in anhydrous EtOAc (150 mL) was added AcOH (17.5 ml, 307 mmol, 8.0 eq) followed by Pd/C (0.61 g, 5.8 mmol, 0.015 eq). A hydrogen balloon was attached. After the reaction was stirred for 4 h, the slurry was filtered through celite, and a mixture of brine and sat. $NaHCO_3$ (1:1) was added to filtrate, extracted carefully with EtOAc (2×50 ml) and the organic solvent was removed in vacuo and crude product was purified by column chromatography using EtOAc:Hexanes (5:95) to afford pure yellow solid (9.69 g, 33.6 mmol, 88% yield). $^1$H NMR (600 MHz, $CDCl_3$) δ: 7.85 (1H, dd, J=8.5, 1.2 Hz), 7.43 (1H, dd, J=8.5, 7.5 Hz), 7.28-7.23 (1H, m), 7.18 (1H, dd, J=7.1, 1.0 Hz), 7.13 (1H, dd, J=7.9, 1.4 Hz), 6.96 (1H, dd, J=7.6, 1.1 Hz), 6.67 (1H, dd, J=8.0, 1.4 Hz), 6.59 (1H, t, J=7.9 Hz), 4.74 (1H, s), 2.75 (3H, s), 2.68 (3H, s). $^{13}$C NMR (125 MHz, $CDCl_3$) δ: 153.3, 145.5, 141.7, 135.6, 132.5, 131.7, 129.1, 127.4, 126.6, 126.0, 125.4, 121.7, 120.9, 117.8, 117.3, 115.9, 96.7, 23.9, 20.1. IR (neat) v 3477, 3366, 2963, 2930, 2218, 1621, 1481, 1232, 1140, 969, 824, 750, 731 $cm^{-1}$.

Step 3: To a solution of the above product (9.60 g, 33.3 mmol, 1.0 eq) in anhydrous chlorobenzene (80 mL) was added to $ZnCl_2$ (9.09 g, 66.7 mmol, 2.0 eq) and (R)-valinol (6.9 g, 66.7 mmol, 2.0 eq) at room temperature. The solution was heated to reflux for 30 h and quenched with water. The slurry was treated with $NH_4OH$ (50 mL) with stirring for 30 min and extracted with EtOAc (3×50 mL). The combined organic layers were washed with brine and water, dried over $Na_2SO_4$ and filtered. The solvent was removed in vacuo and the crude product was purified by column chromatography using EtOAc:Hexanes (15:85) to afford pure light yellow solid (10.43 g, 27.9 mmol, 84%). $[α]_D^{20}$ −22.9 (c=1.0, $CHCl_3$). $^1$H NMR (600 MHz, $CDCl_3$) δ: 7.78 (1H, dd, J=8.5, 1.1 Hz), 7.51 (1H, dd, J=8.1, 1.5 Hz), 7.39 (1H, t, J=8.0 Hz), 7.25 (1H, dd, J=7.1, 0.9 Hz), 7.18 (1H, dd, J=7.2, 1.1 Hz), 6.97-6.92 (1H, m), 6.72 (1H, dd, J=7.8, 1.4 Hz), 6.56 (2H, t, J=7.9 Hz), 6.51 (1H, s), 4.38 (1H, dd, J=9.5, 8.2 Hz), 4.15 (1H, ddd, J=9.5, 8.1, 6.8 Hz), 4.05 (1H, t, J=8.1 Hz), 2.87 (3H, s), 2.68 (3H, s), 1.89-1.78 (1H, m, J=6.6 Hz), 1.08 (3H, d, J=6.7 Hz), 0.98 (3H, d, J=6.8 Hz) ppm. $^{13}$C NMR (125 MHz, $CDCl_3$) δ: 163.6, 154.8, 144.8, 140.9, 135.5, 132.4, 132.2, 128.7, 127.2, 126.5, 125.5, 124.2, 120.5, 120.1, 115.1, 114.4, 110.2, 73.1, 69.0, 33.3, 24.5, 20.2, 19.1, 18.7 ppm. IR (neat) v 3478, 3282, 2958, 1634, 1592, 1551, 1472, 1362, 1228, 1192, 1075, 981, 823, 734 $cm^{-1}$. HRMS (ESI) calcd. for $C_{24}H_{26}Cl_2N_2O_2$ [M+H]+: 375.2067, found 375.2051.

Step 4: To a solution of the above product (10.41 g, 27.8 mmol, 1.0 eq) in anhydrous pyridine (70 mL) was added 3,5-dichlorobenzenesulfonyl chloride (10.26 g, 41.8 mmol, 1.5 equiv) and DMAP (36 mg, 0.3 mmol, 0.01 eq). The solution was stirred at room temperature overnight before quenched with water. The mixture was extracted with EtOAc (2×50 ml) and combined organic layers were washed with 1N HCl (3×50 ml), brine and water. The organic layer was dried over $Na_2SO_4$ and filtered. The solvent was removed in vacuo to afford the crude product which was purified by column chromatography using EtOAc:Hexanes (15:85) to afford pure white solid (R)-4-G (12.82 g, 22.0 mmol, 83%). Recrystallization from EtOAc/Hexanes gave 10.31 g white crystals. (R)-4-G: $[α]D_2^{20}$ −12.1 (c=1.0, $CHCl_3$). mp=138-140° C. $^1$H NMR (600 MHz, $CDCl_3$) δ: 12.71 (1H, s), 7.78 (2H, s), 7.56 (4H, brs), 7.45-7.42 (2H, m), 7.19-7.14 (3H, m), 7.02 (4H, s), 7.01-6.97 (4H, m), 6.90 (2H, brs), 6.85 (2H, s), 6.80 (2H, s), 4.48 (1H, dd, J=9.6, 8.3 Hz), 4.25 (1H, brs), 4.17 (2H, t, J=8.2 Hz), 2.64 (1.3H, s), 2.37 (1.7H, s), 2.18 (3H, s), 1.92 (1H, m), 1.15 (3H, s), 1.04 (3H, s) ppm. $^{13}$C NMR (125 MHz, $CDCl_3$) δ: 163.4, 152.1, 150.7, 145.0, 135.4, 134.7, 132.2, 131.3, 130.9, 128.7, 127.0, 126.5, 125.2, 124.8, 124.6, 123.6, 123.1, 122.3, 121.7, 121.0, 118.3, 116.9, 115.9, 72.7, 70.1, 33.3, 23.2, 20.1, 18.8 ppm. IR (neat) v 3078, 2959, 2929, 1639, 1571, 1464, 1339, 1265, 1164, 1134, 989, 923, 801, 746, 669, 576 $cm^{-1}$. HRMS (ESI) calcd. for $C_{30}H_{28}Cl_2N_2O_4S$ [M+H]+: 583.1220, found 583.1233;

Using the same procedure, sulfonamides (R)-4-H and (R)-4-I were synthesized. (R)-4-H: $[α]_D$20-9.1 (c=1.0, $CHCl_3$). mp=117-119° C. $^1$H NMR (500 MHz, $CDCl_3$) δ: 12.77 (1H, s), 7.85-7.78 (1H, m), 7.67-7.59 (2H, m), 7.59-7.55 (2H, m), 7.47 (1H, ddd, J=8.2, 6.9, 1.3 Hz), 7.40-7.30 (2H, m), 7.02 (1H, t, J=8.0 Hz), 6.89-6.82 (3H, m), 4.49 (1H, dd, J=9.6, 8.3 Hz), 4.25 (1H, ddd, J=9.6, 8.1, 6.8 Hz), 4.17 (1H, t, J=8.3 Hz), 1.97-1.86 (1H, m, J=6.8 Hz), 1.15 (3H, d, J=6.7 Hz), 1.04 (3H, d, J=6.7 Hz) ppm. $^{13}$C NMR (125 MHz, $CDCl_3$) δ 163.5, 150.9, 150.2, 145.3, 134.9, 131.1, 127.7, 126.8, 126.6, 126.1, 125.7, 124.8, 124.7, 124.6, 124.3, 123.9, 121.8, 121.5, 118.4, 114.1, 72.8, 70.3, 33.4, 18.9 ppm. IR (neat) v 3076, 2959, 2929, 1639, 1571, 1465, 1389, 1339, 1268, 1165, 1134, 1078, 980, 800, 739, 580 $cm^{-1}$. HRMS (ESI) calcd. for $C_{28}H_{25}Cl_2N_2O_4S$ [M+H]+: 555.0907, found 555.0915. (R)-4-I: $[α]D^{20}$ +13.4 (c=1.0, $CHCl_3$). mp=96-98° C. $^1$HNMR (600 MHz, $CDCl_3$) δ: 12.27 (1H, brs), 7.86-7.94 (2H, m), 7.50-7.54 (1H, m), 7.43 (1H, d, J=7.8, Hz), 7.13 (1H, t, J=8.1 Hz), 7.01 (1H, d, J=8.3 Hz), 4.40-4.48 (1H, m), 4.06-4.20 (3H, m), 1.83-1.91 (1H, m), 1.79 (1H, brd, J=12.2 Hz), 1.71 (1H, br d, J=12.2 Hz), 1.55 (1H, m), 1.31-1.43 (2H, m), 1.10 (3H, d, J=6.6 Hz), 0.99 (3H, d, J=6.6 Hz), 0.85 (3H, d, J=6.8 Hz), 0.87 (3H, d, J=6.8 Hz), 0.40 (1H, q, J=12.0 Hz), 0.25 (1H, q, J=12.0 Hz), 0.20 (1H, q, J=12.0 Hz); $^{13}$C NMR (125 MHz, CDCl$_3$) δ: 163.4, 150.5, 146.3, 135.3, 131.5, 128.9, 125.2, 124.8, 120.8, 119.1, 117.2, 76.7, 72.6, 69.8, 42.9, 39.1, 39.0, 33.1, 30.4, 30.4, 22.0, 18.7, 18.6. IR (neat) ν 3079, 2951, 2926, 2869, 1638, 1571, 1467, 1337, 1269, 1165, 1014, 940, 801, 744, 606, 577 cm$^{-1}$ HRMS (ESI) m/z 539.1556 [(M+H)]+; calcd. for C$_{26}$H$_{33}$Cl$_2$N$_2$O$_4$S: 539.1533]. 5, 8-Dimethyl-1-naphthol

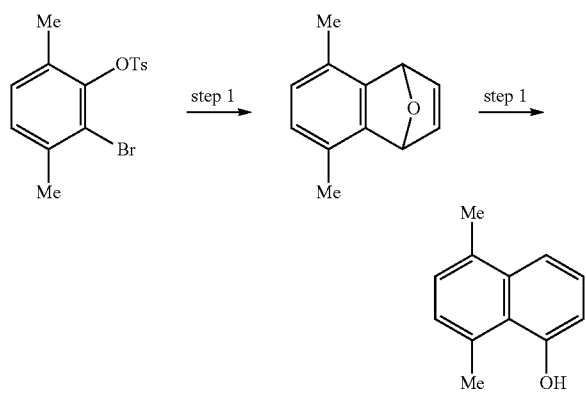

Step 1: A stirred solution of bromotosylate (see, e.g., Velder, J.; Robert, T.; Weidner, I.; Neudçrfl, J. M. *Adv. Synth. Catal.* 2008, 350, 1309) (20.0 g, 56.5 mmol, 1.0 equiv) and freshly distilled furan (34 mL, 452 mmol, 8.0 equiv) in 150 mL of THF was cooled under nitrogen to −78° C., and n-BuLi (34 mL, 84.7 mmol, 2.5 M, 1.5 equiv) was added dropwise. Stirring was continued for 10 h, during which time the solution was allowed to warm to room temperature. See, e.g., Jung, K. Y.; Koreeda, M. *J. Org. Chem.* 1989, 54, 5667. The reaction was quenched by the addition of a few drops of saturated aqueous ammonium chloride solution. The solvent was evaporated, and the resulting brownish residue was taken up in 200 mL of diethyl ether. The ethereal solution was washed with brine (100 mL) and water (100 mL), and dried over anhydrous Na$_2$SO$_4$. Evaporation of the solvent under reduced pressure, followed by purification by flash column chromatography on silica gel with ethyl acetate/hexanes (1:9) as the eluent, gave the adduct as light yellow solid (8.64 g, 50.2 mmol, 88%). $^1$H NMR (600 MHz, CDCl$_3$) δ: 7.03 (2H, dd, J=1.0, 1.0 Hz), 6.72 (2H, s), 5.8 (2H, dd, J=1.0, 1.0 Hz), 2.3 (6H, s) ppm.

Step 2: To a solution of Cu(OTf)$_2$ (0.358 g, 0.99 mmol) in anhydrous DCE (10 mL) at 4° C., the above adduct (3.41 g, 19.8 mmol) in DCE (10 mL) was added under a nitrogen atmosphere. The resulting mixture was stirred at r.t. until the reaction was complete (TLC monitoring). The mixture was then quenched by the addition of H$_2$O (20 mL), extracted with CH$_2$Cl$_2$ (50 mL) and dried over Na$_2$SO$_4$. The crude product thus obtained was purified by flash column chromatography on silica gel with methylene chloride/hexanes (2:3) as the eluent, to give the 5,8-dimethyl-1-naphthol as white crystalline solid (2.67 g, 15.5 mmol, 77%). mp=76-78° C.; $^1$H NMR (600 MHz, CDCl$_3$) δ: 7.55 (1H, dd, J=8.5, 1.1 Hz), 7.33-7.23 (1H, m), 7.17 (1H, dd, J=7.1, 1.0 Hz), 7.09 (1H, dd, J=7.1, 1.0 Hz), 6.75 (1H, dd, J=7.4, 1.1 Hz), 5.19 (1H, s), 2.92 (3H, s), 2.61 (3H, s) ppm. $^{13}$C NMR (125 MHz, CDCl$_3$) δ: 154.3, 135.5, 132.9, 131.8, 127.7, 126.9, 125.4, 123.8, 117.6, 110.2, 24.8, 20.2 ppm. IR (neat) ν 3322, 3032, 2930, 2898, 1589, 1461, 1413, 1277, 1240, 1138, 897, 737 cm$^{-1}$.

syn,syn,syn-3,5-Dimethylcyclohaxan-1-ol

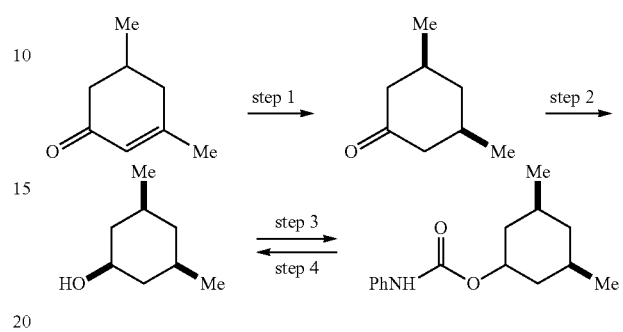

Step 1: Pd/C (wet Degussa, 5% wt %; 1.2 g, 8.46 mmol, 0.05 eq) was added to the solution of 3,5-dimethylcyclo-heeanone (21.0 g, 169 mmol, 1.0 eq) in isopropanol (210 mL). The internal atmosphere was replaced with H$_2$ (balloon). The reaction mixture was stirred under H$_2$ (balloon) at room temperature for 2 h. The crude reaction mixture was filtered through Celite pad, and the filtrate was diluted with 100 mL water. The ketone was extracted with pentane (3×150 mL). The combined organic layers were washed with water (2×100 mL), dried over Na$_2$SO$_4$, and concentrated under reduced pressure, to give 21.3 g of crude product (syn:anti ratio=33:1 by $^1$H NMR analysis). The crude product 2 was used for next step without further purification.

Step 2: To a solution of 3,5-dimethylcyclohexanone (~21.0 g, 0.17 mol, 1.0 eq) in anhydrous hexanes (315 mL) was added anhydrous isopropanol (129 mL, 1.70 mol, 10 eq), followed by sodium metal (24.4 g, 102 mmol, 6.00 eq) were added under N$_2$ atmosphere at 10° C. The resulting solution was stirred vigorously at this temperature, slowly warmed to room temperature, and stirred for another 2 h. The reaction was quenched by the addition of an aqueous HCl (100 mL, 3.0 M) at 0° C., diluted with Et$_2$O (100 mL), and the organic layer was separated. The aqueous layer was extracted by Et$_2$O (3×200 mL). Combined organic layers were dried over Na$_2$SO$_4$ and concentrated under reduced pressure to give 19.1 g of crude product (the diastereomeric ratio was >45:1 by $^1$H NMR). The product thus obtained was purified by recrystallization of its phenylurethane.

Step 3: To the solution of crude alcohol (19.1 g, 149 mmol, 1 equiv) in CH$_2$Cl$_2$ (200 mL) was added phenyl isocyanate (19.4 mL, 179 mmol, 1.2 equiv) followed by DMAP (0.98 g, 7.46 mmol, 0.05 eq). The resulting mixture was stirred at room temperature for 15 h. After completion of the reaction (by TLC), the reaction mixture was filtered through silica gel pad and concentrated under reduced pressure. The crude residue was dissolved in EtOAc and diluted with large excess of hexanes. The solution was left standing for overnight at 0° C. and white crystals were precipitated out. Crystals were collected by filtration and washed with cold hexanes to give urethane (31.22 g; 75% overall yield from 3,5-dimethylcycloheeanone; dr=ca. 200:1). m.p. 95-97° C. (ref. 106-107° C.)$^6$. $^1$H NMR (500 MHz, CDCl$_3$) δ: 7.38-7.34 (2H, m), 7.28 (2H, t, J=15 Hz), 7.05 (1H, t, J=15 Hz) 6.52 (1H, br), 4.7 (1H, m), 2.04 (1H, dd, J=3.4 Hz, 3.2 Hz), 1.63 (1H, dt, J$_1$=14 Hz, J$_2$=1.2 Hz), 1.57-1.52 (2H, m), 0.96 (2H, m), 0.94 (6H, d, J=6.6 Hz), 0.56 (1H, q, J=12 Hz). $^{13}$C NMR (125 MHz, CDCl$_3$) δ: 153.3, 138.1, 128.9, 123.2, 118.5, 73.9, 42.9, 40.2, 30.6, 22.1. IR (neat) v 3313, 2949, 2925, 1702, 1598, 1539, 1442, 1312, 1221, 1052, 751, 691 cm$^{-1}$. HRMS (ESI) m/z: (M+Na)$^+$ calculated for C$_{15}$H$_{21}$NO$_2$Na, 270.1484; found, 270.1464.

Step 4: A solution of urethane (31.2 g, 126.2 mmol) in 10% NaOH/MeOH (320 mL) was heated up to 60° C. and stirred for 18 h at this temperature. After completion of the reaction, the reaction mixture was diluted by EtOAc/hexanes (1:1) and washed with H$_2$O, 1N HCl (3×100 mL), and brine, dried and concentrated. Distillation of the crude product gave pure syn,syn,syn-3,5-dimethylcyclohaxan-1-ol (14.42 g; colorless liquid; 90% yield). $^1$H NMR (500 MHz, CDCl$_3$) δ: 3.60 (1H, m), 1.92 (2H, m), 1.58 (1H, m), 1.49-1.42 (3H, m), 0.92 (1H, d, J=7.8 Hz), 0.82 (2H, q, J=15 Hz), 0.51 (1H, q, J=15 Hz) ppm. $^{13}$C NMR (125 MHz, CDCl$_3$) δ: 70.3, 44.0, 43.1, 30.7, 22.2 ppm.

crude diol 4-S9, which was used in the next reaction without further purification. For the analytical purpose, a single crystal of the 4-S9 was obtained by vapor diffusion method (CH$_2$Cl$_2$-Et$_2$O) (See FIG. 14B). 4-S9: [α]$^{20}$$_D$ −69.5 (c 1.02, CHCl$_3$). MP: 239-241° C. (recrystallized from CH$_2$Cl$_2$-Et$_2$O). $^1$H NMR (600 MHz, CD$_2$Cl$_2$) δ: 5.03 (1H, s), 4.95 (1H, s), 4.84 (1H, s), 4.81 (1H, s), 4.66 (1H, dd, J=4.5, 4.5 Hz), 4.56 (1H, dd, J=4.5, 4.5 Hz), 2.54 (1H, dd, J=3.9, 3.9 Hz), 4.38 (1H, d, J=10.2 Hz), 4.33 (1H, d, J=10.8 Hz), 4.29 (1H, s), 4.23 (1H, ddd, J=9.9, 9.9, 4.2 Hz), 4.16 (1H, dd, J=5.7, 5.7 Hz), 4.09 (1H, dd, J=7.8, 7.8 Hz), 4.03 (1H, dd, J=6.3, 3.9 Hz), 3.87 (1H, s), 3.84-3.79 (2H, m), 3.71-3.62 (4H, m), 3.50-3.43 (2H, m), 3.64 (1H, dd, J=6.6, 4.2 Hz), 3.32 (1H, s), 2.89 (1H, dd, J=9.3, 1.5 Hz), 2.81-2.77 (1H, m), 2.51 (1H, dd, J=17.1, 9.9 Hz), 2.37 (1H, dd, J=17.1, 2.1 Hz), 2.35-2.32 (2H, m), 2.26 (1H, d, J=15.0 Hz), 2.23-2.07 (4H, m), 2.05-2.03 (1H, m), 1.96-1.91 (2H, m), 1.88-1.78 (3H, m), 1.72-1.65 (2H, m), 1.56 (1H, ddd, J=12.3, 12.3, 4.8 Hz),

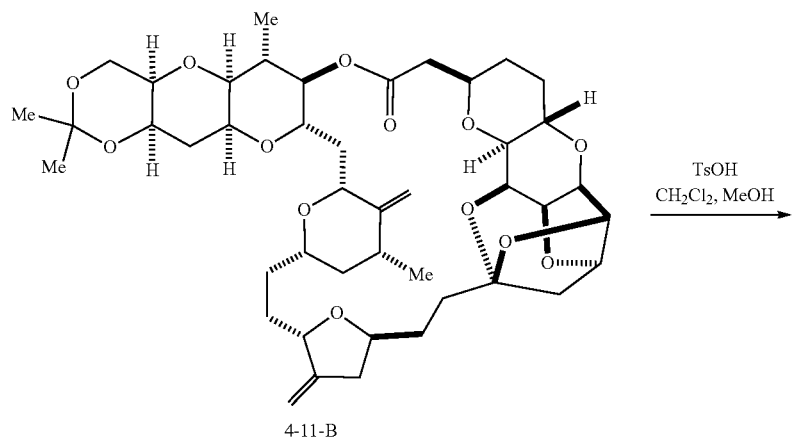

4-11-B

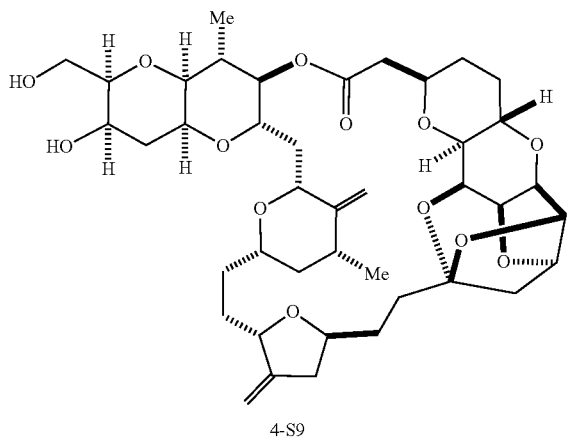

4-S9

To a stirred solution of 4-11-B (1.42 g, 1.78 mmol, 1 eq., dr=~20:1) in CH$_2$Cl$_2$ (8.9 mL) and MeOH (8.9 mL, 0.2 M) was added TsOH.H$_2$O (16.9 mg, 0.089 mmol, 5 mol %) at room temperature. After being stirred for 1 h, the reaction was quenched with Et$_3$N (0.1 mL) and concentrated under reduced pressure. The residue was dissolved in EtOAc and sat. NaHCO$_3$ aq. The organic layer was separated and the aqueous layer was extracted with EtOAc. The combined organic layer was washed with brine, dried over Na$_2$SO$_4$, filtered, and concentrated under reduced pressure to give a 1.51-1.31 (5H, m), 1.17-1.13 (1H, m), 1.15 (3H, d, J=7.2 Hz), 1.10-1.03 (1H, m), 1.10 (3H, d, J=6.6 Hz) ppm. $^{13}$C NMR (125 MHz, CD$_2$Cl$_2$) δ: 171.2, 153.2, 152.4, 110.3, 104.7, 104.4, 82.9, 81.7, 80.2, 78.1, 77.6, 77.5, 77.1, 75.9, 75.5, 74.7, 74.5, 74.4, 74.3, 73.9, 73.8, 68.9, 66.1, 64.4, 63.9, 48.8, 44.2, 41.0, 39.2, 37.1, 36.4, 35.9, 35.3, 35.2, 31.9, 31.7, 31.3, 30.8, 29.1, 18.3, 16.9 ppm. FTIR (film): 3502, 2926, 2854, 1734, 1189, 1135, 1071, 1020, 995, 753 cm$^{-1}$. HRMS (ESI) m/z: [M+NH$_4$]$^+$ calcd for C$_{41}$H$_{62}$NO$_{13}$, 776.4216; found, 776.4230.

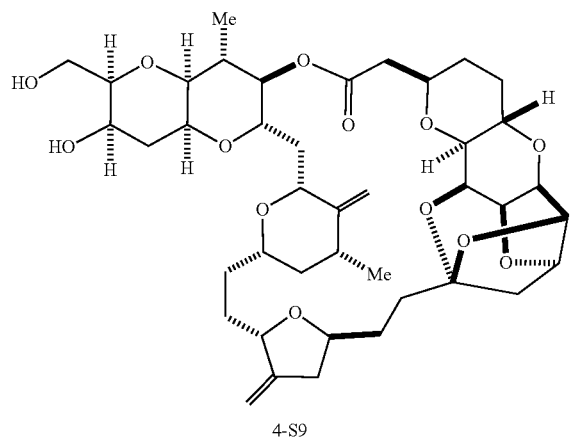

4-S9 a. Tf₂O, 2,6-lutidine, CH₂Cl₂, -78° C;
b. TESOTf, -78° C.;
c. NaI, DMF, rt.

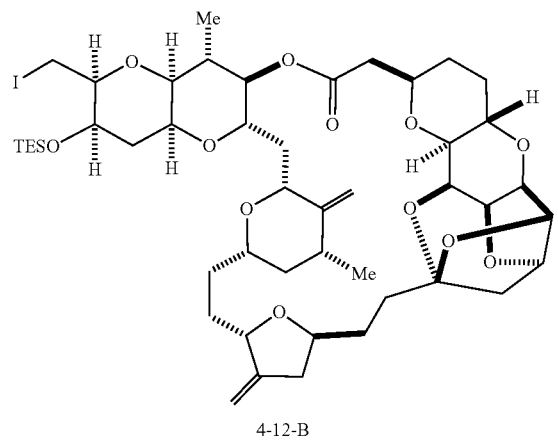

4-12-B

To a stirred solution of 4-S9 (crude, calculated as 1.78 mmol) in CH₂Cl₂ (17.8 mL) was added 2,6-lutidine (1.04 mL, 8.93 mmol, 5 eq.). The mixture was cooled to −78° C., and then Tf₂O (0.36 mL, 2.14 mmol, 1.2 eq.) was added. After being stirred for 15 min at the same temperature, TESOTf (0.60 mL, 2.65 mmol, 1.5 eq) was added. The reaction was warmed to 0° C. with ice bath. After being stirred for additional 20 min, to the reaction were added DMF (35.6 mL) and NaI (1.33 g, 8.87 mmol, 5 eq). The resulting mixture was allowed to warm to room temperature and stirred for 2.5 h. Then the reaction was quenched with sat. NaHCO₃ aq. The organic layer was separated and the aqueous layer was extracted with TBME. The combined organic layer was dried over Na₂SO₄, filtered, and concentrated under reduced pressure. The residue was purified by flash column chromatography on neutral silica gel (9%, 13%, 17%, then 25% EtOAc in Hexanes) to give iodide 4-12-B (1.64 g, 1.67 mmol, 94% for 2 steps), which was a mixture of C20-epimer (dr=~25:1), as a colorless solid. The C20-epimer was separated by HPLC purification (Column: DuPont Instruments ZORBAL SIL 21.2 mm×25 cm (880952-101), Solvent: 10% iPrOH in Hexanes, Flow rate: 10.0 mL/min., Detection: UV at 254 nm and 220 nm, $t_{R(desired)}$=19 min. $t_{R(C20\text{-}epimer)}$=25 min.). 4-12-B: $[\alpha]^{20}_D$ −33.2 (c 1.0, CHCl₃). MP: 158-160° C. (recrystallized from Hexanes-iPrOH). ¹H NMR (600 MHz, C₆D₆) δ: 5.17 (1H, s), 5.12 (1H, d, J=1.8 Hz), 4.92 (1Hm s), 4.78 (3H, m), 4.67 (1H, brd, J=10.0 Hz), 4.53 (1H, ddd, J=10.0, 10.0, 4.1 Hz), 4.27 (1H, dd, J=3.5, 1.8 Hz), 4.14 (1H, dd, J=4.7, 4.7 Hz), 4.10 (1H, dd, J=4.7, 4.7 Hz), 4.06 (1H, m), 4.00 (1H, m), 3.89 (1H, dd, J=6.5, 4.7 Hz), 3.79 (1H, d, J=11.2 Hz), 3.75-3.67 (2H, m), 3.64 (1H, dd, J=6.5, 4.1 Hz), 3.36-3.28 (3H, m), 3.20 (1H, ddd, J=6.7, 6.7, 1.8 Hz), 3.03 (1H, dd, J=4.7, 3.5 Hz), 2.78 (1H, dd, J=16.7, 7.3 Hz), 2.71 (1H, m), 2.60 (1H, dd, J=9.7, 2.1 Hz), 2.41-2.23 (5H, m), 2.23-1.90 (8H, m), 1.84 (1H, m), 1.73 (1H, m), 1.58-1.27 (8H, m), 1.17 (3H, d, J=7.0 Hz), 1.08 (1H, dd, J=24.1, 12.3 Hz), 1.02 (9H, t, J=7.9 Hz), 0.99 (3H, d, J=6.5 Hz), 0.67 (6H, q, J=8.2 Hz) ppm. ¹³C NMR (125 MHz, C₆D₆) δ: 171.4, 153.0, 152.6, 110.0, 105.0, 103.6, 82.4, 81.0, 80.0, 78.7, 78.0, 77.7, 76.9, 76.1, 75.6, 74.8, 74.7, 74.08, 74.06, 73.9, 70.1, 68.5, 64.9, 64.0, 48.6, 43.9, 41.4, 39.4, 39.3, 39.0, 36.3, 36.2, 35.5, 32.5, 31.1, 30.7, 30.6, 29.0, 18.1 16.6, 73.2, 5.7, 5.4 ppm. IR (film): 2951, 2874, 1726, 1087, 1016, 996, 907, 753 cm⁻¹. HRMS (ESI) m/z: [M+Na]⁺ calcd for C₄₇H₇₁IO₁₂SiNa, 1005.3652; found, 1005.3649.

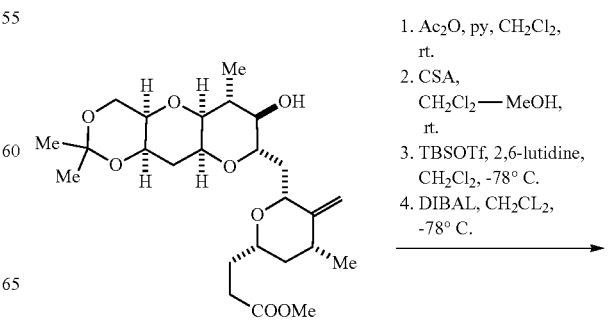

1. Ac₂O, py, CH₂Cl₂, rt.
2. CSA, CH₂Cl₂—MeOH, rt.
3. TBSOTf, 2,6-lutidine, CH₂Cl₂, -78° C.
4. DIBAL, CH₂CL₂, -78° C.

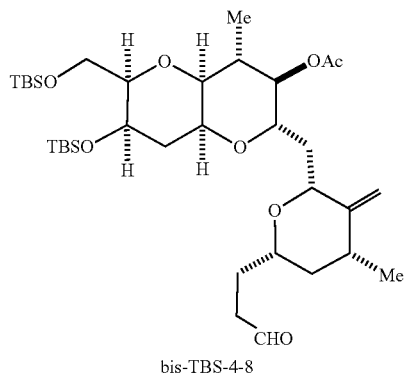

bis-TBS-4-8

To a stirred solution of alcohol (1.30 g, 2.77 mmol) in CH$_2$Cl$_2$ (26 mL) was added pyridine (1.35 mL, 16.6 mmol), acetic anhydride (0.79 mL, 8.3 mmol) at 0° C. The reaction was stirred for 1 h at room temperature, added MeOH at 0° C., and further stirred for 5 h at room temperature. Sat. NaHCO$_3$ aq. was added to the reaction and the aqueous phase was extracted with CH$_2$Cl$_2$ three times. Combined organic phases were dried over Na$_2$SO$_4$ and evaporated. The crude product was purified by flash column chromatography on silica gel (3% EtOAc in hexanes) to provide acetate (1.35 g, 2.64 mmol, 96%) as a pale oil.

To a stirred solution of acetate (1.35 g, 2.64 mmol, 1 eq.) in CH$_2$Cl$_2$ (26 mL) and MeOH (26 mL) was added CSA (30.7 mg, 0.089 mmol, 5 mol %) at room temperature. After being stirred for 3 h, the reaction was quenched with Et$_3$N (0.2 mL) and concentrated under reduced pressure. The residue was dissolved in EtOAc and sat. NaHCO$_3$ aq. The organic layer was separated and the aqueous layer was extracted with EtOAc. The combined organic layer was washed with brine, dried over Na$_2$SO$_4$, filtered, and concentrated under reduced pressure. This crude was used in the next reaction without further purification.

To a mixture of alcohol (2.644 mmol, 1 eq.) and 2,6-lutidine (2.2 mL, 18.7 mmol) in CH$_2$Cl$_2$ (30 mL) was added TBSOTf (2.15 mL, 9.3 mmol) dropwise at −78° C. and the reaction mixture was stirred for 30 min at the same temperature prior to the addition of sat. NaHCO$_3$ aq. The aqueous phase was extracted with CH$_2$Cl$_2$ twice and combined organic phases were dried over Na$_2$SO$_4$, concentrated under reduced pressure. The crude material was connected to high vacuum pump to remove remaining 2,6-lutidine. The obtained residue was purified by flash column chromatography on silica gel (10% then 20% EtOAc in hexanes) to give TBS ether (1.83 g, 99% for 2 steps) as a pale oil.

To a solution of bis-TBS ether (1.40 g, 2.0 mmol, 1 eq.) in CH$_2$Cl$_2$ (20 mL) was added DIBAL (5 mL of 1.0 M in Hexanes, 5 mmol, 2.5 eq.) dropwise at −78° C. After being stirred for 30 min at the same temperature, the reaction was quenched with acetone (0.30 mL) and MeOH (0.30 mL). Then 20% Rochelle's salt aq. was added, and the mixture was stirred for 2 h at room temperature. The organic layer was separated and the aqueous layer was extracted with EtOAc. The combined organic layer was washed with brine, dried over Na$_2$SO$_4$, filtrated, and concentrated under reduced pressure. The residue was purified by flash column chromatography on neutral silica gel (5%, 20% then 33% EtOAc in Hexanes) to give bis-TBS-4-8 (1.105 g, 1.76 mmol, 88%) as a colorless amorphous solid. bis-TBS-4-8: $[\alpha]^{20}_D$-22.4 (c=1.0, CDCl$_3$). $^1$H NMR (600 MHz, C$_6$D$_6$) δ: 9.40 (1H, br s), 4.89 (1H, br s), 4.73 (1H, br d, J=1.9 Hz), 4.29 (1H, q, J=5.6 Hz), 3.88 (1H, t, J=6.1 Hz), 3.83 (2H, d, J=6.2 Hz), 3.68 (1H, td, J=3.5, 1.6 Hz), 3.60 (1H, td, J=3.7, 2.1 Hz), 3.59-3.50 (1H, m), 3.36 (1H, t, J=5.6 Hz), 3.26 (1H, td, J=6.2, 1.7 Hz), 3.24-3.18 (1H, m), 3.05 (1H, t, J=2.4 Hz), 2.32-2.25 (1H, m), 2.17-2.05 (4H, m), 2.00 (1H, dt, J=14.6, 3.4 Hz), 1.94-1.83 (1H, m), 1.48-1.34 (2H, m), 1.27 (1H, dt, J=14.5, 3.9 Hz), 1.22-1.17 (1H, m), 1.01 (9H, s), 1.0 (3H, d, J=6.0 Hz), 0.97 (9H, s), 0.86 (3H, d, J=6.5 Hz), 0.84-0.76 (1H, m), 0.11 (3H, s), 0.10 (6H, s), 0.05 (3H, s). $^{13}$C NMR (125 MHz, C$_6$D$_6$) δ: 200.2, 150.8, 128.2, 104.4, 80.9, 78.9, 76.4, 75.7, 74.4, 72.1, 64.2, 63.4, 62.6, 42.4, 39.8, 39.4, 35.6, 35.4, 32.6, 27.9, 25.8, 25.7, 18.2, 18.1, 17.7, 16.2, −4.3, −5.2, −5.3, −5.4. IR (neat) v 3518, 2955, 2928, 2855, 1726, 1471, 1462, 1372, 1252, 1092, 836, 755 cm$^{-1}$. HRMS (ESI) calcd. for C$_{33}$H$_{63}$O$_7$Si$_2$ [M+H]$^+$: 627.4107, found 627.4108.

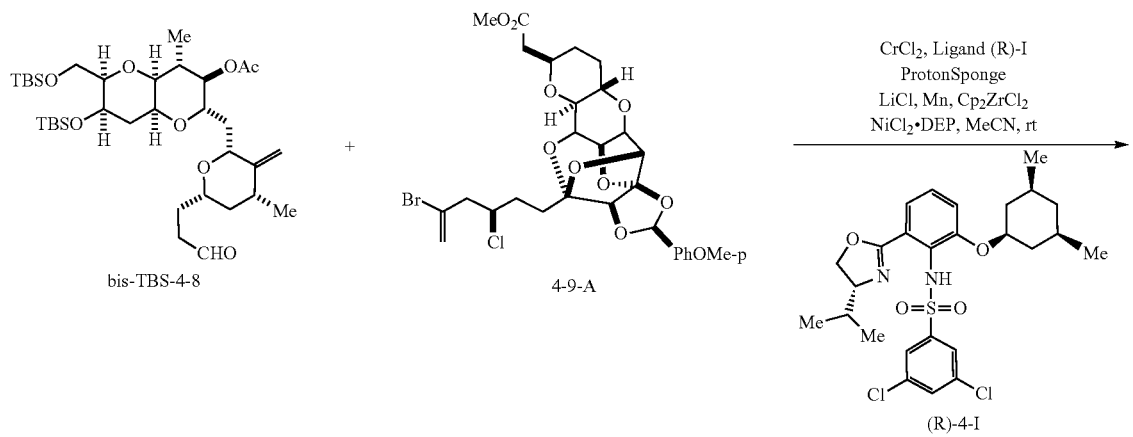

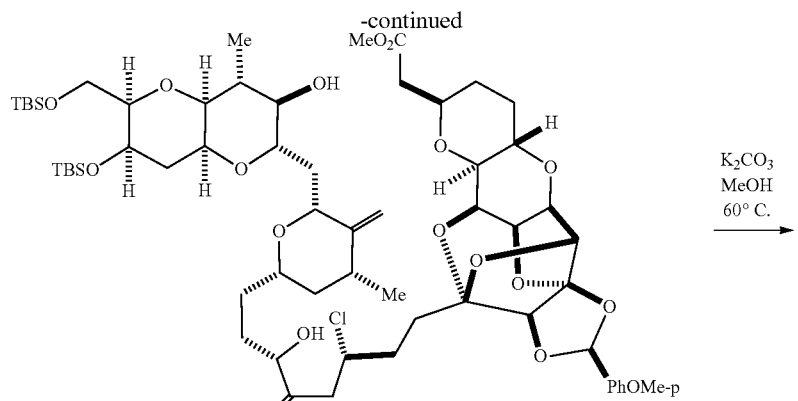

4-S9

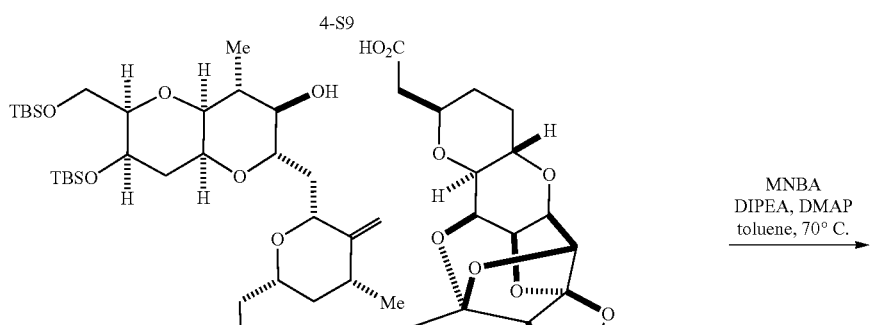

4-S10

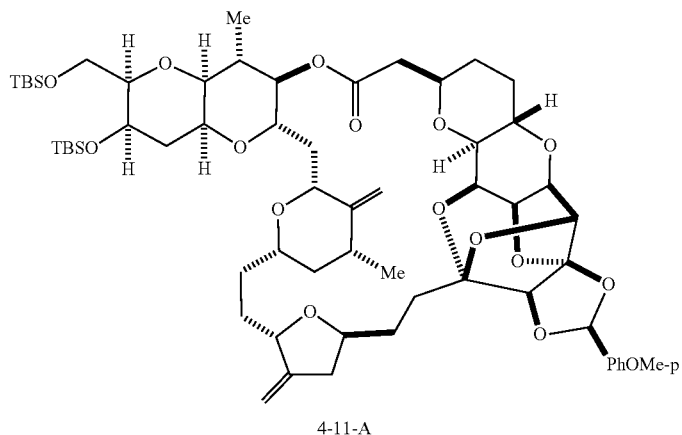

4-11-A

In a glove box, to a mixture of CrCl$_2$ (3.9 mg, 10 mol %), sulfonamide ligand (R)-I (24.1 mg, 13 mol %), proton scavenger (8.2 mg, 12 mol %) and LiCl (13.2 mg, 0.32 mmol, 1.0 eq) was added MeCN (0.8 mL, 0.4 M) and stirred for 1 h at r.t. In a separate flask, bis-TBS-4-8 (0.20 g, 0.32 mmol, 1.0 eq), 4-9-A (0.23 g, 0.35 mmol, 1.1 eq), DTBMP (0.16 g, 0.79 mmol, 2.5 eq), Mn (70.1 mg, 1.28 mmol, 4.0 eq) and Cp$_2$ZrCl$_2$ (0.23 g, 0.79 mmol, 2.5 eq) and the above Cr complex solution was transferred, and mixture was stirred for 1 min, then NiCl$_2$.HMP (1.3 mg, 2 mol %, 0.02 eq, doped in LiCl) was added. Additional NiCl$_2$.HMP (1.3 mg each, 2 mol %, 0.01 eq, twice, doped in LiCl) was added after 1 and 2 h respectively. In total the reaction mixture was stirred for 3.5 h at r.t. The reaction was removed from the glove box and diluted with EtOAc (10 mL). Aqueous potassium serinate (0.5M, 2 mL) and saturated aqueous NaHCO$_3$ (2 mL) were added. After being stirred for 1 h, the resulting suspension was filtered through a pad of celite. The filtrate was extracted with EtOAc, washed with sat. NaCl, dried over Na$_2$SO$_4$, filtered, and concentrated. Without further purification, the crude was used in next reaction.

To a solution of 4-S9 (estimated as 0.32 mmol, 1.0 eq) in MeOH (8 mL) was added K$_2$CO$_3$ (0.44 g, 3.2 mmol, 10.0 eq). The reaction was heated to 60° C. and stirred for 15 h. Then H$_2$O (0.4 mL) was added. After being stirred for additional 3 h at the same temperature, the mixture was cooled to room temperature, filtered through a pad of Celite, and concentrated. The residue was dissolved in EtOAc, sat.

NH₄Cl, and sat. NaCl. The mixture was extracted for five times with EtOAc. The combined organic layers were dried over Na₂SO₄, filtered, and concentrated. Without further purification, the crude product was used in the next reaction.

To a solution of MNBA[3] (Shiina's reagent, 0.658 g, 1.91 mmol, 6.0 eq) in hot toluene (200 mL) at 70° C. was added DMAP (0.47 g, 3.83 mmol, 12.0 eq). A solution of carboxylic acid S10 (estimated as 0.32 mmol, 1.0 eq) and DIPEA (0.66 mL, 3.83 mmol, 12.0 eq) in toluene (20 mL) was added to the reaction mixture via syringe pump over 15 h. After completion of addition, the syringe was washed with toluene (20 mL) and stirred for additional 30 min. The reaction was cooled to room temperature, and concentrated. The residue was dissolved in CH₂Cl₂ and washed with 0.5 M HCl, sat. NaHCO₃ successively. The organic layer was dried over Na₂SO₄, filtered, and concentrated. Flash chromatography (neutral SiO₂, Hexanes/EtOAc=40/1, 20/1, 5/1 then 4/1 gave white crystalline solid 4-11-A (211 mg, 0.19 mmol, 54% over 3 steps). The overall stereoselectivity (dr=25:1) was estimated from ¹H NMR spectrum of 4-11-A thus obtained.

Under the condition given on page S18, Ni/Cr-Mediated coupling of bis-TBS-4-8 with 4-9-A in the presence of Cr-catalyst prepared from (R)-4-G and (R)-4-H was carried out. Following the procedure given above, the crude coupling product was converted to the macrolactone acetonide, to determine the overall yield and stereoselectivity; sulfonamide (R)-4-H gave 58% overall yield from bis-TBS-4-8 (200-mg scale) and dr=28:1, whereas sulfonamide (R)-4-G gave 58% overall yield from bis-TBS-4-8 (200-mg scale) and dr=27:1. 11-A: [α]$^{20}_D$ −54.8 (c=1.0, CDCl₃). mp=88-89° C. ¹H NMR (600 MHz, C₆D₆) δ: 7.31 (2H, d, J=8.8 Hz), 6.68 (2H, d, J=8.7 Hz), 6.03 (1H, s), 5.11 (1H, br s), 5.02 (1H, br s), 4.89 (1H, br s), 4.76-4.71 (3H, m), 4.61 (1H, d, J=10.4 Hz), 4.44 (1H, td, J=10.5, 10.0, 4.3 Hz), 4.36 (1H, brs), 4.32 (1H, dt, J=5.3, 0.9 Hz), 3.4 (1H, q, J=3.9 Hz), 3.26 (1H, td, J=6.2, 1.9 Hz), 3.19 (3H, s), 3.09 (1H, dd, J=4.7, 3.1 Hz), 2.72 (1H, dd, J=16.8, 7.7 Hz), 2.62 (1H, ddt, J=15.5, 7.7, 2.4 Hz), 2.48 (1H, dd, J=9.5, 1.8 Hz), 2.35 (1H, dd, J=16.8, 4.4 Hz), 2.32-2.18 (6H, m), 1.97 (1H, dt, J=11.6, 3.9 Hz), 1.88 (1H, ddt, J=14.2, 11.4, 3.1 Hz), 1.77 (1H, tt, J=13.6, 3.7 Hz), 1.70-1.62 (1H, m), 1.49 (1H, dddd, J=11.9, 7.3, 5.6, 2.5 Hz), 1.43 (2H, dt, J=12.5, 2.8 Hz), 1.37 (1H, dt, J=14.6, 4.5 Hz), 1.33-1.19 (3H, m), 1.16 (3H, d, J=7.3 Hz), 1.14-1.0 (2H, M), 0.99 (9H, s), 0.98 (9H, s), 0.14 (3H, s), 0.12 (6H, s), 0.09 (3H, s) ppm. ¹³C NMR (125 MHz, C₆D₆) δ: 170.7, 161.0, 152.6, 152.4, 128.4, 128.3, 118.6, 113.7, 108.9, 108.6, 104.6, 103.4, 89.8, 83.4, 79.7, 78.0, 77.8, 77.4, 75.8, 75.6, 75.4, 74.4, 73.9, 73.6, 73.5, 73.4, 69.7, 68.0, 64.13, 64.09, 63.3, 54.4, 43.7, 40.9, 39.2, 39.0, 38.2, 36.0, 35.3, 31.9, 30.9, 30.5, 29.97, 29.9, 27.3, 26.0, 25.9, 25.8, 18.3, 17.8, 16.4, −4.3, −5.0, −5.3, −5.4 ppm. IR (neat) ν 2952, 2927, 2855, 1732, 1615, 1518, 1251, 1092, 1010, 834, 775, 756 cm⁻¹ HRMS (ESI) calcd. for C₆₁H₉₂NaO₁₆Si₂ [M+Na]⁺: 1159.7774, found 1159.7816.

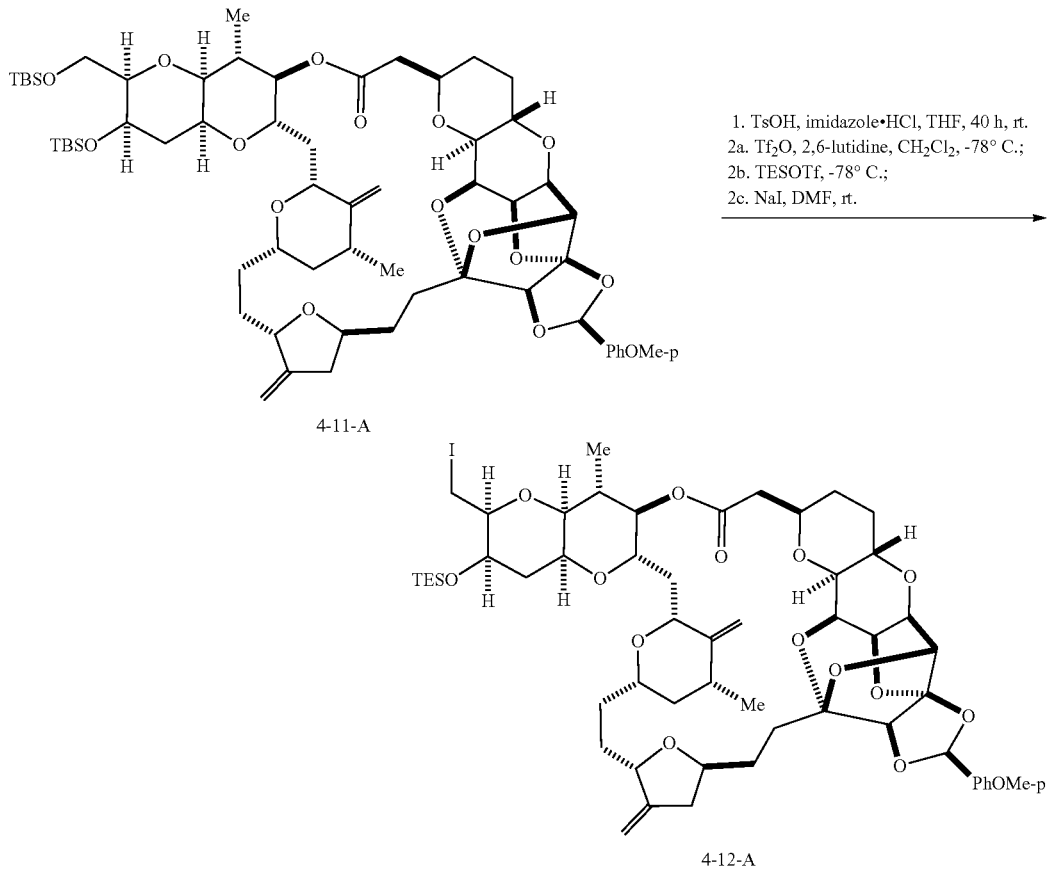

4-11-A

1. TsOH, imidazole·HCl, THF, 40 h, rt.
2a. Tf₂O, 2,6-lutidine, CH₂Cl₂, -78° C.;
2b. TESOTf, -78° C.;
2c. NaI, DMF, rt.

4-12-A

To a solution of 4-11-A (720 mg, 0.633 mmol) in THF (12.7 mL) was added TBAF solution (0.95 M in THF, buffered with 0.5 eq of imidazole-hydrochloride, 3.2 mL, 3.17 mmol) at room temperature. After stirring for 40 h at room temperature, solvent was removed by a stream of nitrogen gas and redissolved in EtOAc and water. The aqueous layer was extracted with EtOAc four times and the combined organic layer was dried over Na$_2$SO$_4$, filtered, and concentrated. Without further purification, the crude product was used in the next reaction.

To a stirred solution of crude diol (estimated as 0.633 mmol) in CH$_2$Cl$_2$ (6.3 mL) was added 2,6-lutidine (0.733 mL, 6.33 mmol, 10 eq.). The mixture was cooled to −78° C., and then added Tf$_2$O (0.13 mL, 0.760 mmol, 1.2 eq.). After being stirred for 15 min at the same temperature, TESOTf (0.23 mL, 1.01 mmol, 1.6 eq) was added. The reaction was warmed to 0° C. with ice bath. After being stirred for additional 20 min, to the reaction were added DMF (12.6 mL) and NaI (0.475 g, 3.17 mmol, 5 eq). The resulting mixture was allowed to warm to room temperature and stirred for 2.5 h. Then the reaction was quenched with sat. NaHCO$_3$ aq. The organic layer was separated and the aqueous layer was extracted with TBME. The combined organic layer was dried over Na$_2$SO$_4$, filtered, and concentrated under reduced pressure. The residue was purified by flash column chromatography on neutral silica gel (9%, 20%, 30%, then 40% EtOAc in Hexanes) to give iodide 4-12-A (595 mg, 0525 mmol, 83% for 2 steps), which was a mixture of C20-epimer (dr=~20:1), as a colorless solid. The C20-epimer was separated by HPLC purification (Column: DuPont Instruments ZORBAL SIL 21.2 mm×25 cm (880952-101), Solvent: 3% iPrOH in Hexanes, Flow rate: 10.0 mL/min., Detection: UV at 254 nm and 220 nm, tR(desired)=17 min. tR(C20-epimer)=21 min.). 4-12-A: white solid, [α]$^{20}_D$ −50.0 (c 0.65, CHCl$_3$). MP: 115-117° C. (recrystallized from H$_2$O-iPrOH). $^1$H NMR (600 MHz, C$_6$D$_6$) δ: 7.36 (2H, d, J=8.8 Hz), 6.73 (2H, d, J=8.8 Hz), 6.09 (1H, s), 5.17 (1H, s), 5.11 (1H, d, J=1.2 Hz), 4.94 (1H, s), 4.80-4.77 (3H, m), 4.66 (1H, brd, J=11.2 Hz), 4.49 (1H, ddd, J=11.2, 11.2, 4.2 Hz), 4.40 (1H, d, J=1.8 Hz), 4.37 (1H, dd, J=5.4, 1.2 Hz), 4.06 (1H, s), 4.01 (1H, dd, J=6.0, 6.0 Hz), 4.00-3.96 (2H, m), 3.79 (1H, d, J=11.4 Hz), 3.73-3.68 (3H, m), 3.36-3.28 (3H, m), 3.22 (3H, s), 3.20 (1H, ddd, J=6.6, 6.6, 1.8 Hz), 3.04 (1H, dd, J=4.2, 3.0 Hz), 2.77 (1H, dd, J=16.2, 7.8 Hz), 2.66-2.62 (1H, m), 2.51 (1H, dd, J=9.9, 1.5 Hz), 2.39-2.24 (6H, m), 2.19-1.94 (7H, m), 1.85-1.82 (1H, m), 1.76-1.71 (1H, m), 1.55-1.27 (6H, m), 1.18 (3H, d, J=7.2 Hz), 1.08 (1H, dd, J=12.6, 11.4 Hz), 1.03 (9H, t, J=7.9 Hz), 1.01 (3H, d, J=6.5 Hz), 0.70 (6H, q, J=8.2 Hz) ppm. $^{13}$C NMR (125 MHz, C$_6$D$_6$) δ: 171.2, 161.4, 153.0, 152.6, 119.0, 114.1, 109.3, 109.0, 105.1, 103.7, 90.3, 83.8, 79.8, 78.7, 78.1, 77.9, 76.0, 75.6, 74.7, 74.1, 74.0, 73.8, 73.7, 69.9, 68.4, 64.8, 64.0, 54.8, 44.0, 41.4, 39.4, 39.4, 39.0, 36.4, 36.3, 32.4, 31.1, 30.9, 30.3, 30.2, 27.6, 18.2, 16.6, 7.3 (×3), 5.7, 5.3 (×3) ppm. IR (film): 2953, 2935, 2875, 1731, 1615, 1518, 1251, 1092, 1011, 907, 831 cm$^{-1}$. HRMS (ESI) m/z: [M+Na]$^+$ calcd for C$_{55}$H$_{77}$IO$_{15}$SiNa, 1155.3969; found, 1155.3987.

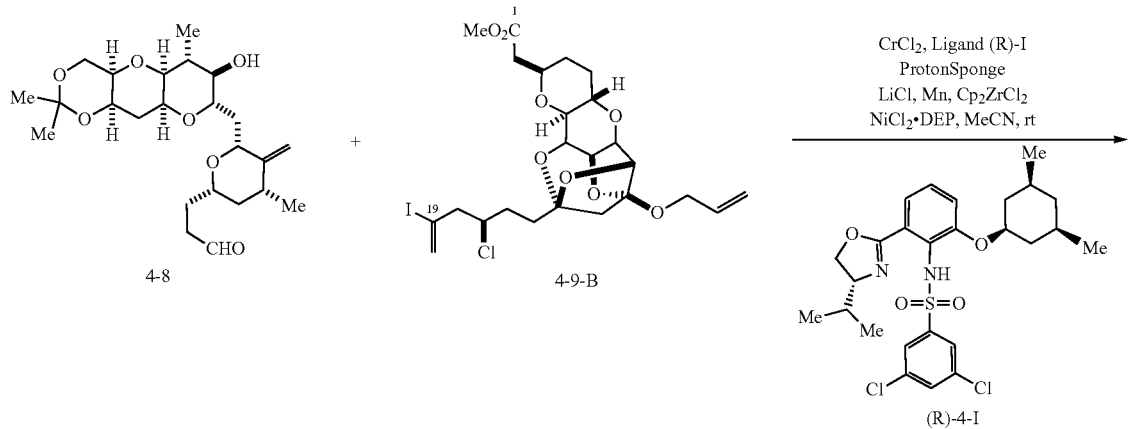

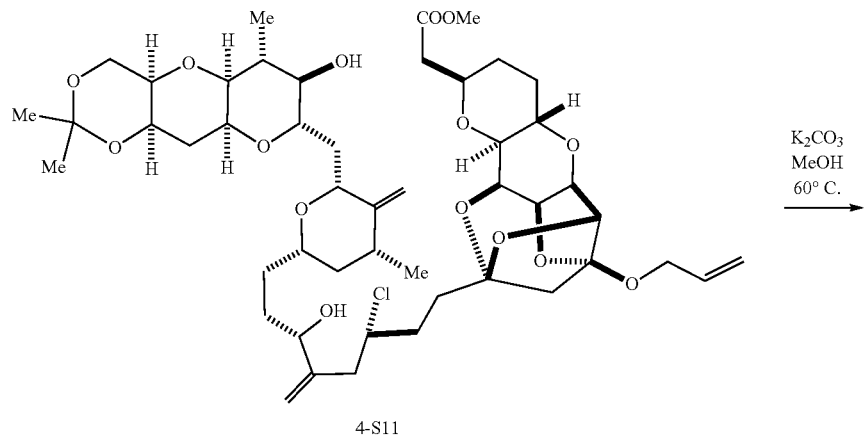

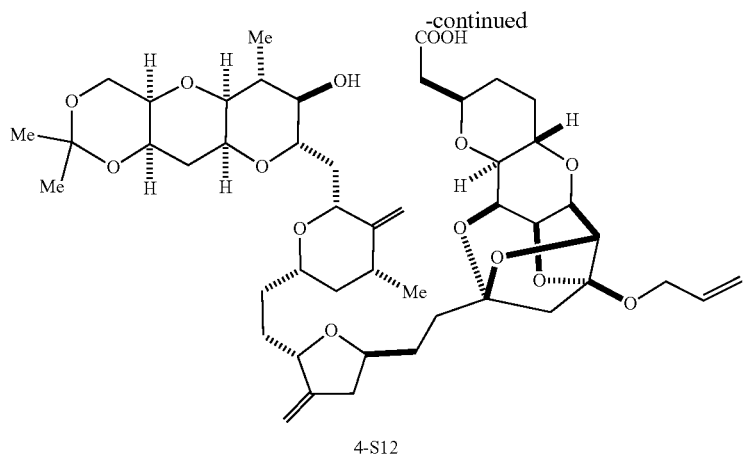

4-S12

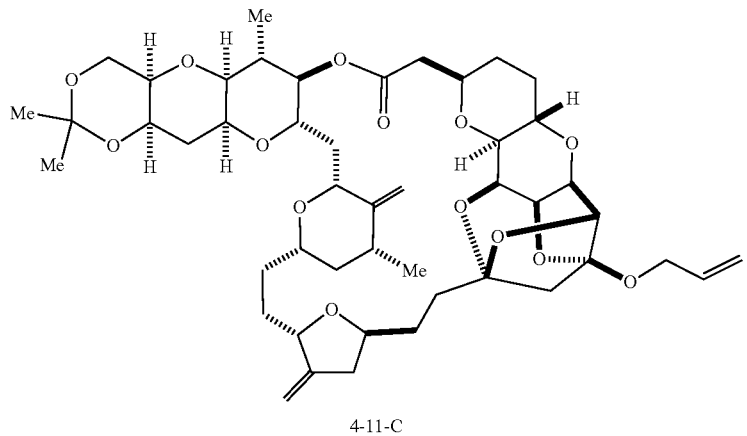

4-11-C

In a glove box, to a mixture of CrCl₂ (7.0 mg, 10 mol %), sulfonamide ligand (R)-4-I (43.2 mg, 13 mol %), proton scavenger (14.7 mg, 12 mol %) and LiCl (24.1 mg, 0.57 mmol, 1.0 eq) was added MeCN (1.4 mL, 0.4 M) and stirred for 1 h at r.t. In a separate flask, 4-8 (0.25 g, 0.57 mmol, 1.0 eq), 4-9-C(0.35 g, 0.63 mmol, 1.1 eq), DTBMP (0.29 g, 1.43 mmol, 2.5 eq), Mn (125 mg, 2.28 mmol, 4.0 eq) and Cp₂ZrCl₂ (0.42 g, 1.43 mmol, 2.5 eq) and the above Cr complex solution was transferred, and mixture was stirred for 1 min, then NiCl₂.DEP (2.2 mg, 1 mol %, 0.01 eq, doped in LiCl) was added. Additional NiCl₂.DEP (2.2 mg each, 1 mol %, 0.01 eq, twice, doped in LiCl) was added after 1 and 2 h respectively. In total the reaction mixture was stirred for 3 h at r.t. The reaction was removed from the glove box and diluted with EtOAc (10 mL). Aqueous potassium serinate (0.5M, 3 mL) and saturated aqueous NaHCO₃ (3 mL) were added. After being stirred for 1 h, the resulting suspension was filtered through a pad of celite. The filtrate was extracted with EtOAc, washed with sat. NaCl, dried over Na₂SO₄, filtered, and concentrated. Without further purification, the crude was used in next reaction.

To a solution of 4-S11 (estimated as 0.57 mmol, 1.0 eq) in MeOH (10 mL) was added K₂CO₃ (0.79 g, 5.71 mmol, 10.0 eq). The reaction was heated to 60° C. and stirred for 15 h. Then H₂O (0.6 mL) was added. After being stirred for additional 3 h at the same temperature, the mixture was cooled to room temperature, filtered through a pad of Celite, and concentrated. The residue was dissolved in EtOAc, sat. NH₄Cl, and sat. NaCl (adjust pH=~7 by adding few drops of 1N HCl). The mixture was extracted for five times with EtOAc. The combined organic layers were dried over Na₂SO₄, filtered, and concentrated. Without further purification, the crude product was used in the next reaction.

To a solution of MNBA (1.18 g, 3.43 mmol, 6.0 eq) in hot toluene (380 mL) at 70° C. was added DMAP (0.84 g, 6.85 mmol, 12.0 eq). A solution of carboxylic acid 4-S12 (estimated as 0.57 mmol, 1.0 eq) and DIPEA (1.2 mL, 6.85 mmol, 12.0 eq) in toluene (27 mL) was added to the reaction mixture via syringe pump over 15 h. After completion of addition, the syringe was washed with toluene (20 mL) and stirred for additional 30 min. The reaction was cooled to room temperature, and concentrated. The residue was dissolved in CH₂Cl₂ and washed with 0.5 M HCl, sat. NaHCO₃ successively. The organic layer was dried over Na₂SO₄, filtered, and concentrated. Flash chromatography (neutral SiO₂, Hexanes/EtOAc=7/1, 5/1, 3/1, 1/1, 1/2 then 1/3 gave white crystalline solid 4-11-C(307 mg, 0.36 mmol, 61% over 3 steps). The overall stereoselectivity (dr=17:1) was estimated from ¹H NMR spectrum of 4-11-C thus obtained. 4-11-C: $[\alpha]^{20}_D$ −52.2 (c=1.0, CDCl₃). mp=157-158° C. ¹H NMR (600 MHz, C₆D₆) δ: 5.71 (1H, ddt, J=17.3, 10.6, 5.3 Hz), 5.18 (1H, brs), 5.11 (1H, dq, J=17.3, 1.7 Hz), 5.05 (1H, q, J=2.2 Hz), 5.02-4.91 (2H, m), 4.90 (1H, s), 4.77 (1H, dd, J=7.7, 5.0 Hz), 4.72 (1H, d, J=1.8 Hz), 4.62 (1H, dt, J=10.3, 2.4 Hz), 4.54-4.47 (1H, m), 4.35 (1H, dd, J=4.2, 2.0 Hz), 4.30-4.26 (1H, m), 4.11-4.00 (2H, m), 3.94 (1H, m), 3.83-3.73 (3H, m), 3.72-3.62 (m, 3H), 3.53-3.45 (2H, m), 3.00 (1H, dd, J=5.1, 4.0 Hz), 2.80 (1H, dd, J=16.5, 7.2 Hz), 2.73-2.63 (2H, m), 2.53 (1H, dd, J=9.6, 2.1 Hz), 2.46-2.37 (2H, m), 2.29 (2H, dtdt, J=19.4, 7.2, 4.9, 2.1 Hz), 2.25-2.09

(4H, m), 2.09-1.98 (4H, m), 1.92-1.80 (2H, m), 1.75-1.62 (1H, m), 1.56-1.40 (4H, m), 1.40-1.23 (3H, m), 1.19 (5H, d, J=6.9 Hz), 1.02 (1H, td, J=12.4, 11.0 Hz), 0.93 (2H, d, J=6.4 Hz) ppm. $^{13}$C NMR (125 MHz, C$_6$D$_6$) δ: 170.9, 152.5, 152.3, 134.3, 116.3, 115.9, 108.9, 104.6, 103.4, 98.4, 82.9, 77.9, 77.6, 76.9, 75.9, 75.7, 74.7, 74.7, 73.9, 73.7, 73.6, 70.0, 69.5, 68.1, 65.6, 63.7, 63.5, 62.1, 51.3, 43.4, 41.1, 39.0, 38.9, 38.4, 35.9, 35.6, 32.2, 31.9, 30.7, 30.7, 30.1, 28.5, 28.1, 19.8, 17.8, 16.1 ppm. IR (neat) v 2925, 2867, 1729, 1373, 1311, 1186, 1118, 1073, 995, 911, 832, 756 cm$^{-1}$. HRMS (ESI) calcd. for C$_{47}$H$_{66}$NaO$_{14}$ [M+Na]$^+$: 877.4345, found 821.4353.

Under the condition given on page S18, Ni/Cr-Mediated coupling of 4-8 with 4-9-C in the presence of Cr-catalyst prepared from (R)-4-G and (R)-4-H was carried out. Following the procedure given above, the crude coupling product was converted to the macrolactone acetonide, to determine the overall yield and stereoselectivity; sulfonamide (R)-4-H gave 63% overall yield from 8 (250-mg scale) and dr=20:1, whereas sulfonamide (R)-4-G gave 63% overall yield from 4-8 (250-mg scale) and dr=21:1.

filtered, and concentrated under reduced pressure to give a crude diol, which was used in the next reaction without further purification.

To a stirred solution of crude diol (estimated as 0.819 mmol) in CH$_2$Cl$_2$ (8.2 mL) was added 2,6-lutidine (0.57 mL, 4.91 mmol, 6 eq.). The mixture was cooled to −78° C., and then added Tf$_2$O (0.18 mL, 1.1 mmol, 1.2 eq.). After being stirred for 15 min at the same temperature, TESOTf (0.30 mL, 1.31 mmol, 1.5 eq) was added. The reaction was warmed to 0° C. with ice bath. After being stirred for additional 20 min, to the reaction were added DMF (16.4 mL) and NaI (650 g, 4.43 mmol, 5 eq). The resulting mixture was allowed to warm to room temperature and stirred for 6 h. Then the reaction was quenched with sat. NaHCO$_3$ aq. The organic layer was separated and the aqueous layer was extracted with TBME. The combined organic layer was dried over Na$_2$SO$_4$, filtered, and concentrated under reduced pressure. The residue was purified by flash column chromatography on neutral silica gel (9%, 13%, 20%, then 30% EtOAc in Hexanes) to give iodide 4-12-C(689 mg, 0.663 mmol, 81% for 2 steps), which was a mixture of C20-epimer

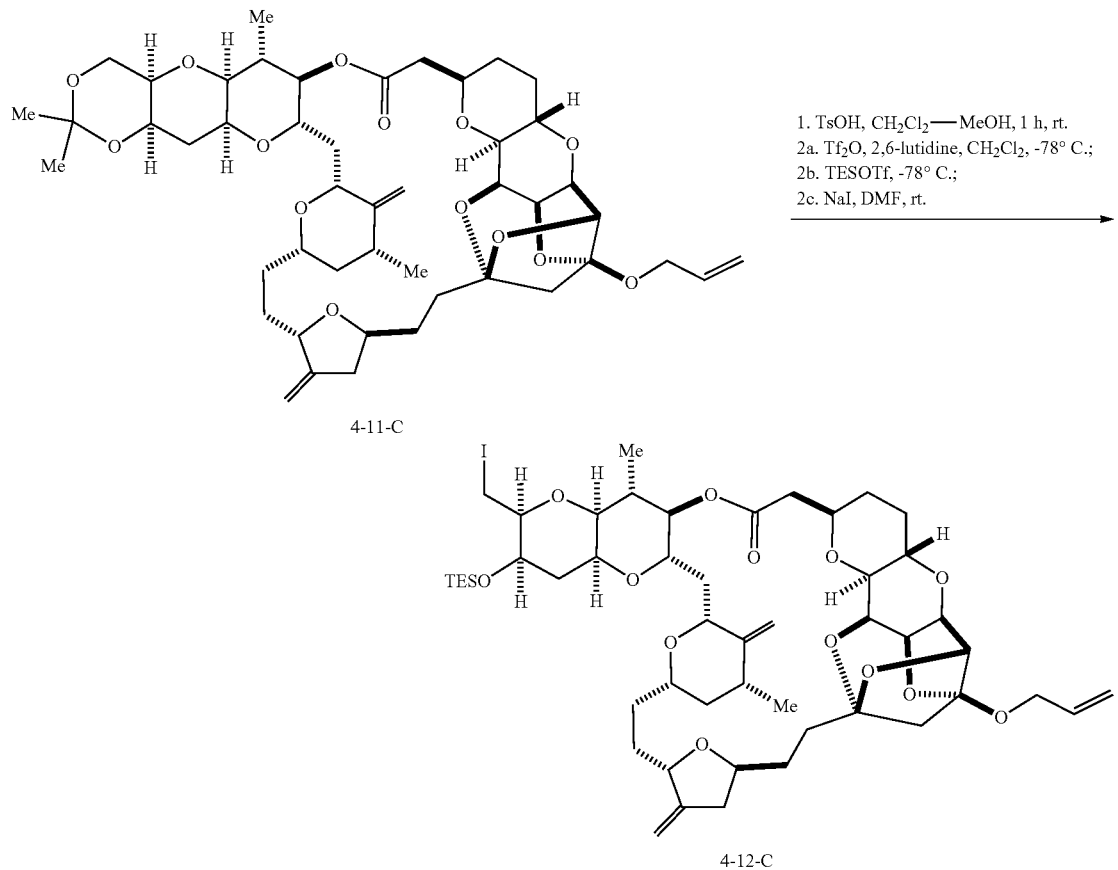

4-11-C

1. TsOH, CH$_2$Cl$_2$—MeOH, 1 h, rt.
2a. Tf$_2$O, 2,6-lutidine, CH$_2$Cl$_2$, -78° C.;
2b. TESOTf, -78° C.;
2c. NaI, DMF, rt.

4-12-C

To a stirred solution of 4-11-C(700 g, 0.819 mmol, 1 eq., dr=~20:1) in CH$_2$Cl$_2$ (8.2 mL) and MeOH (8.2 mL) was added p-TsOH.H$_2$O (3.1 mg, 0.016 mmol, 2 mol %) at room temperature. After being stirred for 1 h, the reaction was quenched with Et$_3$N (0.1 mL) and concentrated under reduced pressure. The residue was dissolved in EtOAc and sat. NaHCO$_3$ aq. The organic layer was separated and the aqueous layer was extracted with EtOAc. The combined organic layer was washed with brine, dried over Na$_2$SO$_4$, (dr=~20:1), as a colorless solid. The C20-epimer was separated by HPLC purification (Column: DuPont Instruments ZORBAL SIL 21.2 mm×25 cm (880952-101), Solvent: 2% iPrOH in Hexanes, Flow rate: 10.0 mL/min., Detection: UV at 254 nm and 220 nm, $t_{R(desired)}$=22.8 min. $t_{R(C20-epimer)}$=28.0 min.). 4-12-C: colorless solid, [α]$^{20}_D$ −46.8 (c 1.0, CHCl$_3$). MP: 84-86° C. (recrystallized from H$_2$O-iPrOH). $^1$H NMR (600 MHz, C$_6$D$_6$) δ: 5.75 (1H, dddd, J=17.3, 10.5, 5.1, 5.1 Hz), 5.15 (1H, ddd, J=17.4, 1.8, 1.8

Hz), 5.14 (1H, s), 5.11 (1H, s), 4.97 (1H, ddd, J=10.2, 1.8, 1.8 Hz), 4.90 (1H, s), 4.77-4.72 (3H, m), 4.62 (1H, d, J=11.2 Hz), 4.49 (1H, ddd, J=10.2, 10.2, 4.4 Hz), 4.35 (1H, ddd, J=1.8, 1.8, 1.8 Hz), 4.31 (1H, d, J=4.8 Hz), 4.11 (1H, dd, J=6.6, 4.8 Hz), 4.0-3.97 (1H, m), 3.83-3.80 (1H, m), 3.74 (1H, d, J=11.4 Hz), 3.72 (1H, ddd, J=5.4, 1.8, 1.8 Hz), 3.70-3.67 (2H, m), 3.32-3.27 (3H, m), 3.19 (1H, ddd, J=6.6, 6.6, 1.8 Hz), 3.03 (1H, dd, J=4.8, 3.6 Hz), 2.74 (1H, dd, J=17.4, 7.8 Hz), 2.71-2.67 (1H, m), 2.56 (1H, dd, J=9.6, 1.8 Hz), 2.33 (1H, dd, J=16.8, 4.2 Hz), 2.29-2.20 (5H, m), 2.23-1.97 (8H, m), 1.93-1.89 (1H, m), 1.72-1.66 (1H, m), 1.53-1.28 (8H, m), 1.14 (3H, d, J=7.2 Hz), 1.05 (1H, dd, J=12.6, 10.8 Hz), 1.00 (9H, t, J=8.4 Hz), 0.98 (3H, d, J=7.2 Hz), 0.66 (6H, q, J=7.8 Hz) ppm. $^{13}$C NMR (125 MHz, $C_6D_6$) δ: 171.4, 153.0, 152.6, 134.6, 128.3, 116.6, 116.2, 109.3, 105.0, 103.7, 83.3, 79.8, 78.6, 77.9, 77.7, 76.0, 75.6, 75.1, 75.0, 74.7, 74.1, 73.9, 70.0, 68.4, 65.9, 64.9, 63.9, 51.7, 43.9, 41.3, 39.4, 39.3, 38.9, 36.3, 36.2, 35.9, 32.5, 31.1, 30.7, 30.5, 28.5, 18.1, 16.6, 7.3 (×3), 5.7, 5.3 (×3) ppm. IR (film): 2952, 2948, 2875, 1733, 1457, 1338, 1218, 1138, 1073, 831 $cm^{-1}$. HRMS (ESI) m/z: [M+Na]$^+$ calcd for $C_{50}H_{75}IO_{13}SiNa$, 1061.3914; found, 1061.3919.

Synthesis of Left Halves

One of the central questions was how to construct the [6,6]-spiroketal in a stereoselective manner. Based on precedents, the oxy-Michael process of E→F under the basic conditions was used (FIG. 15). The first precedent was found in the synthetic work on polyether antibiotic (−)-A23187 (calcimycin) (see, e.g., Negri, D. P.; Kishi, Y. Tetrahedron Lett., 1987, 28, 1063); on treatment with a catalytic amount of NaOMe, G was transferred exclusively to H, the relative stereochemistry of which corresponded to that of F.

The second precedent was found in halichondrin syntheses. As the model study for the original enone route, the oxy-Michael reaction on I was studied; on treatment with DBU and LiCl in $CH_2Cl_2$, I gave selectively J, which isomerized to K on treatment with DBU and LiCl in MeCN or DBU and LiBr in $CH_2Cl_2$. Alternatively, K was obtained directly from I on treatment with Hunig base, LiBr in $CH_2Cl_2$ MeCN. These results indicated that J was as the kinetically controlled product, whereas K was as the thermodynamically controlled product. The stereochemistry of J and K was reduced from NOE experiments; in particular, a strong cross peak was observed between C39-H and C48-H of J-a, whereas a strong cross peak was detected between C40-H and C48-H of K-a, cf. red double-headed arrows.

A primitive estimation was made on the relative stability of J and K, on the basis of the literature-known data on A-values of cyclohexane and tetrahydropyran, destabilization energy due to 1,3-diaxial interaction, and destabilization-energy due to boat-conformation. The preferred conformation of K was assumed to be K-a, whereas that of J to be either J-a, J-b, or half-boat conformer (not shown). For the simplicity of analysis, conformers K-a, J-a, and J-b were used. Around the structure indicated by a dotted box, all of them had the same structural arrangement, including the double stereoelectronic stabilization. Therefore, this structural moiety was excluded from the analysis. A-value for Me-group at 2-position of tetrahydropyran was reported to be 2.86 kcal/mol, which was roughly 1.6 times of A-value for Me-group of cyclohexane (see, e.g., Eliel, E. L.; Hargrave, K. D.; Pietrusiewicz, K. M.; Manoharan, M. J. Am. Chem. Soc. 1982, 104, 3635). 1,3-Diaxial interaction of $CH_2R$/OMe on cyclohexane was known around 1.9 kcal/mol, which would correspond to −3 kcal/mol (1.6×1.9 kcal/mol) on tetrahydropyran (see, e.g., Corey, E. J.; Feiner, N. F. J. Org. Chem. 1980, 45, 765 and references cited therein). In addition, a boat conformer of cyclohexane and tetrahydropyran was estimated to be destabilized by 5.5 and 3.9 kcal/mol, respectively, relative to the corresponding chair conformer. Thus, we would assume the destabilization due to the boat conformation in J-b to be in the range of 3.9~5.5 kcal/mol (see, e.g., Eliel, E. L.; Allinger, N. L.; Angyal, S. J.; Morrison, G. A. Conformational Analysis; John Wiley: New York, 1965, p 244). Counting these factors, K was roughly estimated to be energetically favored over J by 3~4 kcal/mol.

To test the feasibility of the synthetic plan proposed above, studied first was the synthesis of 2-pyridyl thioester 8 for two reasons. First, γ-lactone 3 was readily available from 2, which was the starting material for the synthesis of C27-C37 building block and available from D-galactal (1) in a large quantity (see, e.g., Chen, C.-L.; Namba, K.; Kishi, Y. Org. Lett. 2009, 11, 409). Second, 2-pyridyl thioester 8 should be a good model substrate to study the following Zr/Ni-mediated one-pot ketone synthesis.

Figure 16:
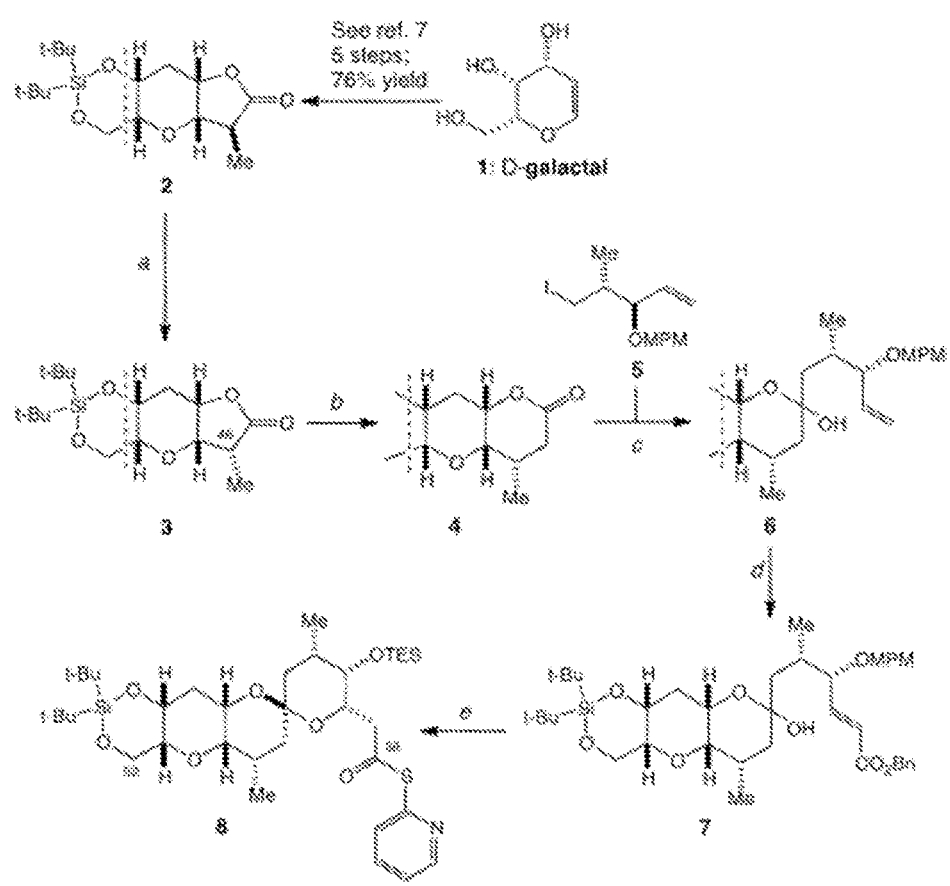
FIG. 16 shows exemplary synthesis of a left half of halichondrin analogs. Reagents and conditions: a. 1. TBSOTf (2.5 equiv.), Et$_3$N (5 equiv.), CH$_2$Cl$_2$, 0° C.~-rt, 3 hours. 2. NH$_4$Cl aq., EtOAc, THF, 50° C., 3 hours (100% for 2 steps). b. 1. DIBAL (1.3 equiv.), CH$_2$Cl$_2$, –78° C., 40 minutes. 2. MePPh$_3$Br (4 equiv.), t-BuOK (3 equiv.), THF, 0° C.~rt, 1.5 hours (96% for 2 steps). 3. 9-BBN (2.5 eq.), THF, rt, 1.5 hours then NaBO$_3$.H$_2$O aq. 4. TEMPO (10 mol %), PhI(OAc)$_2$ (3 equiv.), NaHCO$_3$ (10 equiv.), 4° C., 15 hours (97% for 2 steps). c. 5 (1.4 equiv.), t-BuLi (2.6 equiv.), THF, –78° C., 15 min (90%). d. 1. OsO$_4$ (10 mol %), NMMO (2 equiv.), H$_2$O, acetone, rt, 21 hours. 2. Pb(OAc)$_4$ (1.2 equiv.), K$_2$CO$_3$ (3 equiv.), CH$_2$Cl$_2$, rt, 1 hour (83% for 2 steps). 3. (MeO)$_2$P(=O)CH$_2$CO$_2$Bn (4 equiv.), K$_3$PO$_4$ (3 equiv.), rt, 23 hours. e. LiBr (10 equiv.), DBU (5 equiv.), BnOAc (10 equiv.), MeCN, rt, 12 hr, 2. DDQ (2 equiv.), CH$_2$Cl$_2$, pH 7 buffer, rt, 40 min (75% for 3 steps). 3. TESCl (2 equiv.), imidazole (4 equiv.), CH$_2$Cl$_2$, rt, 16 hours. 4. H$_2$ (1 atm), Pd/C, EtOAc, rt, 45 min, 5. (PyS)$_2$ (1.4 equiv.), PPh$_3$ (1.2 equiv.), CH$_2$Cl$_2$, rt, 17 hr (96% for 5 steps). Abbreviation: DIBAL=diisobutylaluminium hydride; 9-BBN=9-borabicyclononane; TEMPO=2,2,6,6-tetramethyl-1-piperidinyloxy; NMMO or NMO=4-methylmorpholine N-oxide.

FIG. 16 summarizes the synthesis of 8 from γ-lactone 3. Thus, γ-lactone 3 was straightforwardly transformed to δ-lactone 4 in an excellent overall yield. The coupling of 4 and 5-5 was achieved by slow addition of t-BuLi into a mixture of the two substrates in THF. The unsaturated benzyl ester group was incorporated on 6 in 3 steps, i.e., (1) dihydroxylation of the terminal olefin, (2) oxidative cleavage, and (3) Horner-Emmons reaction, to furnish 7 in an excellent overall yield. Alternatively, the transformation of 6 into 7 was realized in one step with metathesis (see, e.g., Trnka, T. M.; Grubbs, R. H. Acc. Chem. Res. 2001, 34, 18; Schrock, R. R. Adv. Syn. Catal. 2007, 349, 41; Hoveyda, A. H.; Zhugralin, A. R. Nature 2007, 450, 243; Araki, M.; Sakata, S.; Takei, H.; Mukaiyama, T. Bull. Chem. Soc. Jpn. 1974, 47, 1777). Because of the cost-effectiveness, the former three-step procedure was chosen for preparative purpose.

The behavior of 7 in oxy-Michael process was similar to the case of I into K. On treatment with DBU and LiBr in MeCN at room temperature, 7 initially gave a 2:1 mixture of kinetically- and thermodynamically-controlled products, which equilibrated almost exclusively to the thermodynamically controlled product at room temperature for 12 hours. In this transformation, the benzyl ester was partially hydrolyzed, but it was found that the hydrolysis of benzyl ester was completely suppressed by addition of BnOAc. Preparatively, on treatment with DBU (5 equiv)/LiBr (10 equiv)/BnOAc (10 equiv.), 7 gave the desired, thermodynamically controlled product with in an excellent overall yield. The stereochemistry of oxy-Michael product was confirmed by NOE experiments; a strong cross peak was observed between C40-H and C48-H. Finally, the necessary functional group adjustment was made in four steps, i.e., (1) deprotection of C41 MPM group, (2) protection of the resultant alcohol with TES, (3) debenzylation, and (4) thioester formation. 2-Pyridyl thioester 8 thus obtained was fully characterized and was found stable to store at −20° C. in dark. The overall yield of 8 from 3 was >50% in a 5-g scale preparation.

FIG. 17 summarizes the synthesis of left half in the halichondrin series. This synthesis was designed on the basis of the knowledge gained in the synthesis of C38-C52 building block discussed in the preceding section, coupled with the original synthesis of the left half of halichondrin B. Epoxy γ-lactone 9 was synthesized from L-gulono-γ-lactone by the method reported in 1992 (see, e.g., Buszek, K. R.; Fang, F. G.; Forsyth, C. J.; Jung, S. H.; Kishi, Y.; Scola, P. M.; Yoon, S. K. Tetrahedron Lett. 1992, 33, 1553), whereas cis-vinyl iodide 5-10 was prepared from commercially available (S)-glycidol in 4 steps. Then, 9 and 10 were coupled with use of a standard Cu-mediated chemistry. With use of 1.8 equivalent of 10, γ-lactone 11 was isolated in 81% yield. The homoallylic alcohol in 11 was epoxidized with Sharpless VO(TMHD)$_2$-mediated method, followed by TES-protection of the C48 alcohol, to give epoxy-γ-lactone 12 in 85% overall yield from 11, with >50:1 stereoselectivity (see, e.g., Sharpless, K. B.; Michaelson, R. C. J. Am. Chem. Soc. 1973, 95, 6136). The next coupling of 12 with 5 was best achieved by slow addition of t-BuLi into a mixture of the two substrates in THF, to give 13 in 85% yield, which existed as a mixture of ketol (major) and keto/alcohol (minor). Among acids tested, (PhO)$_2$P(=O)OH was found to be most effective in facilitating an intramolecular epoxide-ring opening by the masked alcohol at C47. With minor modifications on the transformation outlined in FIG. 16, 14 was transformed to the left half 17. Thus, the terminal olefin of 14 was converted to unsaturated benzyl ester 16. In this series, it was necessary to unmask the protecting group of the C48 alcohol; on treatment with (PhO)$_2$P(=O)OH, two TES-groups in 14 were selectively removed, to furnish 15.

Unsaturated benzyl ester 15 was subjected to oxy-Michael reaction under the condition optimized with 7 (FIG. 16), to furnish the desired product 16 in 86% yield. The stereochemical behavior of 16 in the oxy-Michael reaction was found to be very similar to that of 7, including the overall stereoselectivity and the equilibration of the kinetically-controlled product into the thermodynamically-controlled product. In this series, however, one-minor by-product was isolated in ~8% yield. The spectroscopic analysis (HRMS, $^1$H- and $^{13}$C-NMR, IR) suggested this minor product to be 18, which likely arose via the carbanion-attack to the unsaturated benzyl ester, cf., the red arrow in L. The structure information of 18 immediately suggested a possibility of eliminating or suppressing the by-product formation with use of organocatalysts recently reported by Asano, Matsubara and coworkers (see, e.g., Yoneda, N.; Fukata, Y.; Asano, K.; Matsubara, S. Angew. Chem. Int. Ed, 2015, 54, 15497). Indeed, an addition of non-chiral thiourea M had an expected effect, to give a 2:1 mixture of two diastereomers, free from 18. In principle, a chiral thioure should enforce preferentially to form one of the two diastereomers. In practice, however, the asymmetric induction was only modest with chiral organocatalysts. Thus, the 2:1 mixture was subjected to the equilibrating condition, to furnish almost exclusively 16 in 93% overall yield from 15. Obviously, the equilibration took place via the retro-oxy-Michael/oxy-Michael process. Curiously, however, there was no detectable amount of 18 formed in the equilibration step. Structurally, compared with 7, 15 had one additional free-hydroxyl group at C51. That additional free-hydroxyl group might affect the overall outcome in the oxy-Michael reaction, because it was carried out under basic conditions. However, it was demonstrated that the substrate with the C51-alcohol protected with TBS did exhibit virtually identical reactivity profiles as 15 did. Finally, the left-half 17 in the halichondrin series was obtained uneventfully from 16 in 82% overall yield.

FIG. 18 summarizes the synthesis of left half in the homohalichondrin series. Once again, this synthesis was based on the knowledge gained through the previous work (see, e.g., Fang, F. G.; Kishi, Y.; Matelich, M. C.; Scola, P. M. Tetrahedron Lett. 1992, 33, 1557). The synthesis began with γ-lactone 3, which was transformed to 21 via 20 by standard synthetic operations. Sharpless asymmetric epoxidation (see, e.g., Katsuki, T.; Sharpless, K. B. J. Am. Chem. Soc. 1980, 102, 5974) was used stereoselectively to install the C$_{53}$-C$_{55}$ moiety. Namely, asymmetric epoxidation of the allylic alcohol of 21, followed by acid treatment, gave triol 22 in an excellent overall yield. Based on the absolute stereochemistry of the epoxide introduced by Sharpless asymmetric epoxidation, the stereochemistry of 22 was assigned as indicated, which was confirmed by X-ray analysis of its C55 mono-3,5-dinitrobenzoate. This experiment proved the C53/C54-stereochemistry previously proposed for the homohalichondrins from NMR analysis. Triol 22 was transferred to 6-lactone 23 and then to unsaturated benzyl ester 24 in a good overall yield. The overall behavior of 24 in the intramolecular oxy-Michael to construct the [6,6]-spiroketal was similar to that observed on 15. Lastly, 2-pyridyl thioester 26 was secured from 25 as before.

FIG. 19 summarizes the synthesis of left half in the norhalichondrin series. With two modifications, this synthesis was carried out as the previous cases. First, the C53 terminal in the norhalichondrin series was a carboxylic acid, which was introduced via oxidation of the primary alcohol selectively prepared from 29. Second, TES-group was chosen to protect the alcohol at C50. Notably, the behavior of unsaturated benzyl ester 28 in the oxy-Michael transformation was found to be virtually identical with that of 7. 2-Thiopyridine ester 32 thus synthesized was isolated via neutral silica gel chromatography and fully characterized.

Experimental Procedures for Synthesis of Left Halves Halichondrin Analogs

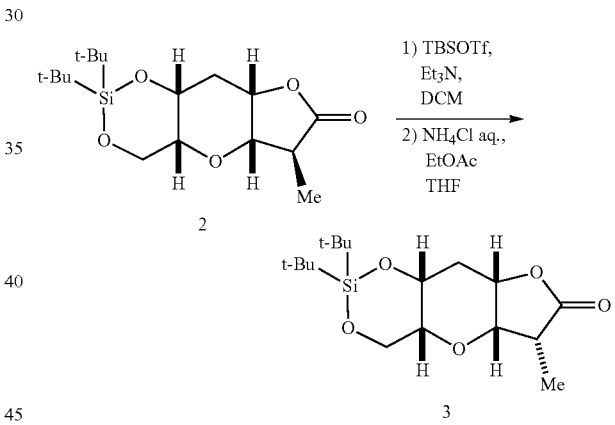

To a stirred solution of lactone 2 (10.0 g, 29.2 mmol, 1 eq.) and Et$_3$N (20.0 mL, 143 mmol, 5.0 eq.) in CH$_2$Cl$_2$ (100 mL) was added TBSOTf (17.0 mL, 74.0 mmol, 2.5 eq.) at 0° C. After being stirred for 3 h at room temperature, the reaction was quenched with sat. NaHCO$_3$ aq. The organic layer was separated and the aqueous layer was extracted with CH$_2$Cl$_2$. The combined organic layer was dried over Na$_2$SO$_4$, filtered, and concentrated under reduced pressure. The obtained crude material was used in the next reaction without further purification.

The crude silyl enol ether (calculated as 29.2 mmol, 1 eq.) was dissolved in a mixture of EtOAc (200 mL), THF (30 mL), and sat. NH$_4$Cl aq. (300 mL). After being stirred for 3 h at 50° C., the mixture was cooled to room temperature. The organic layer was separated and the aqueous layer was extracted with EtOAc. The combined organic layer was dried over Na$_2$SO$_4$, filtered, and concentrated under reduced pressure. The crude lactone was recrystallized from CH$_2$Cl$_2$/Hexanes to give lactone 3 (9.68 g from 1$^{st}$ recrystallization and 300 mg from 2$^{nd}$ recrystallization: total 9.98 g, 29.1 mmol, 100% for 2 steps) as a colorless crystal. The spectroscopic data obtained are consistent with those previously reported in the literature.

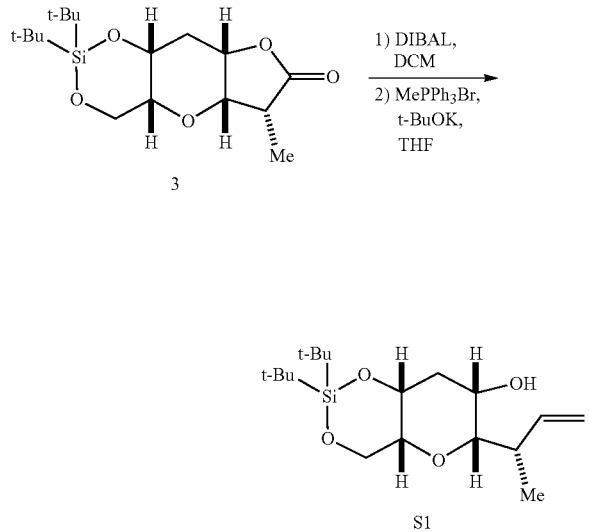

To a stirred solution of 3 (4.3 g, 12.6 mmol, 1 eq.) in CH$_2$Cl$_2$ (63 mL) at −78° C. was added DIBAL solution (16.4 mL of 1.0 M in hexanes, 16.4 mmol, 1.3 eq.). After being stirred for 40 min, the reaction was quenched with MeOH at the same temperature. Then 10% Rochelle's salt aq. was added. The mixture was stirred for 2 h at room temperature to give a clear biphasic mixture. The organic layer was separated and the aqueous layer was extracted with EtOAc. The combined organic layer was dried over Na$_2$SO$_4$, filtered, and concentrated under reduced pressure to give a crude lactol, which was used in the next reaction without further purification. To a suspension of Ph$_3$PCH$_3$Br (18.0 g, 50.4 mmol, 4 eq.) in THF (50 mL) was added t-BuOK (4.24 g, 37.8 mmol, 3 eq.) at 0° C. A solution of the crude lactol (calculated as 12.6 mmol) in THF (13 mL) was added into the reaction mixture, and then the ice bath was removed. After being stirred for 1.5 h at room temperature, the reaction was quenched with sat. NH$_4$Cl aq. The organic layer was separated and the aqueous layer was extracted with EtOAc. The combined organic layer was dried over Na$_2$SO$_4$, filtered, and concentrated under reduced pressure. The residue was dissolved in hexanes-EtOAc (10:1) and passed through a pad of silica gel (9% EtOAc in Hexanes) to give S-1 (4.15 g, 12.1 mmol, 96% for 2 steps) as a colorless solid. S-1: $[\alpha]^{20}_D$ −36.8 (c 1.14, CHCl$_3$). MP: 90-93° C. (recrystallized from Hexanes). $^1$H NMR (600 MHz, C$_6$D$_6$) δ: 6.19 (1H, ddd, J=17.3, 10.6, 6.7 Hz), 5.20-5.11 (2H, m), 4.13 (1H, d, J=12.3 Hz), 3.93 (1H, dd, J=2.9, 2.9 Hz), 3.84 (1H, dd, J=12.3, 2.9 Hz), 3.71 (1H, d, J=10.6 Hz), 3.58 (1H, m), 3.00 (1H, m), 2.74 (1H, d, J=9.4 Hz), 2.64 (1H, d, J=2.9 Hz), 2.18 (1H, ddd, J=14.7, 2.9, 2.9 Hz), 1.18 (9H, s), 1.15 (1H, ddd, J=14.7, 3.2, 3.2 Hz), 1.08 (3H, d, J=6.5 Hz), 1.05 (9H, s) ppm. $^{13}$C NMR (125 MHz, C$_6$D$_6$) δ: 142.6, 113.5, 85.5, 76.5, 69.7, 68.6, 64.2, 38.6, 36.9, 27.9, 27.5, 23.3, 20.6, 15.0 ppm. FTIR (film): 3503, 2960, 2933, 2858, 1474, 1132, 1091, 1022, 950, 908, 844, 825, 766, 651 cm$^{-1}$. HRMS (ESI) m/z: [M+Na]$^+$ calcd for C$_{18}$H$_{34}$O$_4$SiNa, 365.2119; found, 365.2116.

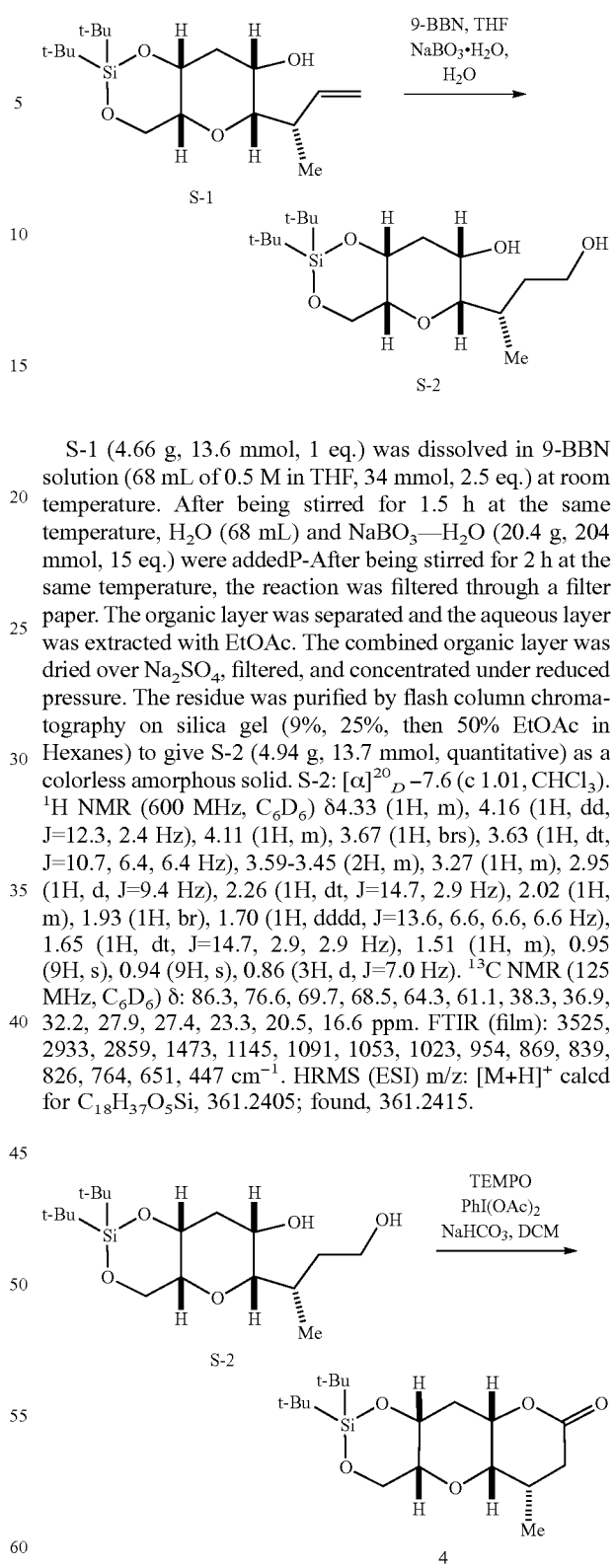

S-1 (4.66 g, 13.6 mmol, 1 eq.) was dissolved in 9-BBN solution (68 mL of 0.5 M in THF, 34 mmol, 2.5 eq.) at room temperature. After being stirred for 1.5 h at the same temperature, H$_2$O (68 mL) and NaBO$_3$—H$_2$O (20.4 g, 204 mmol, 15 eq.) were addedP-After being stirred for 2 h at the same temperature, the reaction was filtered through a filter paper. The organic layer was separated and the aqueous layer was extracted with EtOAc. The combined organic layer was dried over Na$_2$SO$_4$, filtered, and concentrated under reduced pressure. The residue was purified by flash column chromatography on silica gel (9%, 25%, then 50% EtOAc in Hexanes) to give S-2 (4.94 g, 13.7 mmol, quantitative) as a colorless amorphous solid. S-2: $[\alpha]^{20}_D$ −7.6 (c 1.01, CHCl$_3$). $^1$H NMR (600 MHz, C$_6$D$_6$) δ4.33 (1H, m), 4.16 (1H, dd, J=12.3, 2.4 Hz), 4.11 (1H, m), 3.67 (1H, brs), 3.63 (1H, dt, J=10.7, 6.4, 6.4 Hz), 3.59-3.45 (2H, m), 3.27 (1H, m), 2.95 (1H, d, J=9.4 Hz), 2.26 (1H, dt, J=14.7, 2.9 Hz), 2.02 (1H, m), 1.93 (1H, br), 1.70 (1H, dddd, J=13.6, 6.6, 6.6, 6.6 Hz), 1.65 (1H, dt, J=14.7, 2.9, 2.9 Hz), 1.51 (1H, m), 0.95 (9H, s), 0.94 (9H, s), 0.86 (3H, d, J=7.0 Hz). $^{13}$C NMR (125 MHz, C$_6$D$_6$) δ: 86.3, 76.6, 69.7, 68.5, 64.3, 61.1, 38.3, 36.9, 32.2, 27.9, 27.4, 23.3, 20.5, 16.6 ppm. FTIR (film): 3525, 2933, 2859, 1473, 1145, 1091, 1053, 1023, 954, 869, 839, 826, 764, 651, 447 cm$^{-1}$. HRMS (ESI) m/z: [M+H]$^+$ calcd for C$_{18}$H$_{37}$O$_5$Si, 361.2405; found, 361.2415.

To a stirred solution of S-2 (calculated as 13.6 mmol) in CH$_2$Cl$_2$ (136 mL) was added NaHCO$_3$ (11.4 g, 136 mmol, 10 eq.). The mixture was cooled to 4° C., then PhI(OAc)$_2$ (13.1 g, 40.8 mmol, 3 eq.) and TEMPO (213 mg, 1.36 mmol, 10 mol %) were added. After being stirred for 15 h at the same temperature, the reaction was quenched with 10% Na$_2$S$_2$O$_3$ aq. and sat. NaHCO$_3$ aq. The organic layer was separated and the aqueous layer was extracted with EtOAc. The combined organic layer was dried over Na$_2$SO$_4$, filtered, and concentrated under reduced pressure. The residue was purified by flash column chromatography on silica gel (0%, 9%, 17%, then 33% EtOAc in Hexanes) to give 4 (4.68 g, 13.1 mmol, 97% in 2 steps) as a colorless solid. 4: [α]$^{20}_D$ −12.7 (c 2.29, CHCl$_3$). MP: 147-150° C. (recrystallized from Hexanes-EtOAc). $^1$H NMR (600 MHz, C$_6$D$_6$) δ4.11 (1H, dd, J=12.9, 1.2 Hz), 3.96 (1H, dd, J=12.6, 3.2 Hz), 3.89 (1H, m), 3.43 (1H, m), 2.55 (1H, m), 2.53 (1H, m), 2.43 (1H, dd, J=17.0, 13.5 Hz), 2.28-2.20 (2H, m), 1.29 (1H, m), 1.21 (9H, s), 1.13-1.07 (10H, m), 0.76 (3H, d, J=6.5 Hz). 13C NMR (150 MHz, C$_6$D$_6$) δ: 169.0, 77.1, 75.0, 73.3, 68.0, 66.5, 35.9, 33.9, 31.3, 28.1, 27.2, 23.4, 20.4, 16.7 ppm. FTIR (film): 2933, 2857, 1727, 1474, 1364, 1180, 1136, 1109, 1045, 976, 829, 770, 645, 443 cm$^{-1}$. HRMS (ESI) m/z: [M+Na]$^+$ calcd for C$_{18}$H$_{32}$NaO$_5$Si, 379.1911; found, 379.1912.

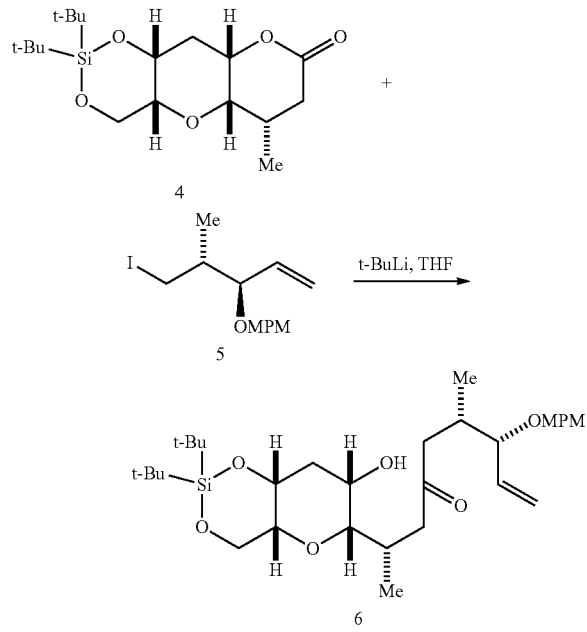

A solution of 4 (1.0 g, 2.80 mmol) and 5 (1.36 g, 3.93 mmol, 1.4 eq.) in THF was degassed by bubbling with Ar. To the solution was added t-BuLi solution (4.23 mL of 1.7 M in pentane, 7.29 mmol, 2.6 eq.) dropwise at −78° C. over 10 min. After being stirred for 15 min at the same temperature, the reaction was quenched with sat. NH$_4$Cl aq. The organic layer was separated and the aqueous layer was extracted with EtOAc. The combined organic layer was washed with brine, dried over Na$_2$SO$_4$, filtered, and concentrated under reduced pressure. The residue was purified by flash column chromatography on silica gel (10% then 30% EtOAc in Hexanes) to give 6 (1.46 g, 2.53 mmol, 90%) as colorless oil. 6 was obtained as an equilibrium mixture of ketone form and ketal form (ca. 4:1 ratio in C$_6$D$_6$). Spectral data only for major ketone form are shown here. 6: [α]$^{20}_D$ −17.4 (c 1.44, CHCl$_3$). $^1$H NMR (600 MHz, C$_6$D$_6$) δ: 7.26 (2H, d, J=8.7 Hz), 6.83 (2H, d, J=8.7 Hz), 5.63 (1H, ddd, J=17.1, 10.8, 7.8 Hz), 5.14-5.09 (2H, m), 4.53 (1H, d, J=11.4 Hz), 4.21 (1H, d, J=11.4 Hz), 4.10 (1H, d, J=12.6 Hz), 3.93 (1H, dd, J=2.7, 2.7 Hz), 3.85 (1H, dd, J=12.6, 3.0 Hz), 3.64 (1H, d, J=10.2 Hz), 3.57 (1H, d, J=10.8 Hz), 3.48 (1H, dd, J=7.2, 7.2 Hz), 3.34 (3H, s), 2.81-2.68 (4H, m), 2.64 (1H, s), 2.50-2.46 (1H, m), 2.28 (1H, dd, J=15.3, 7.5 Hz), 2.24 (1H, dd, J=16.5, 8.7 Hz), 2.15 (1H, ddd, J=14.4, 2.7, 2.7 Hz), 1.16 (9H, s), 1.16-1.13 (1H, m), 1.04 (9H, s), 1.02 (3H, d, J=6.6 Hz), 0.97 (3H, d, J=7.2 Hz) ppm. 13C NMR (125 MHz, C$_6$D$_6$) δ: 209.1, 159.6, 137.8, 131.3, 129.5, 118.1, 114.0, 84.9, 84.2, 76.5, 70.2, 69.7, 68.5, 64.1, 54.8, 47.3, 46.2, 37.0, 34.1, 31.4, 27.9, 27.5, 23.3, 20.5, 16.5, 16.1 ppm. FTIR (film): 3527, 2933, 2858, 1708, 1613, 1513, 1473, 1247, 1146, 1091, 1022, 956, 652, 447 cm$^{-1}$. HRMS (ESI) m/z: [M+Na]$^+$ calcd for C$_{32}$H$_{52}$NaO$_7$Si, 599.3375; found, 599.3376.

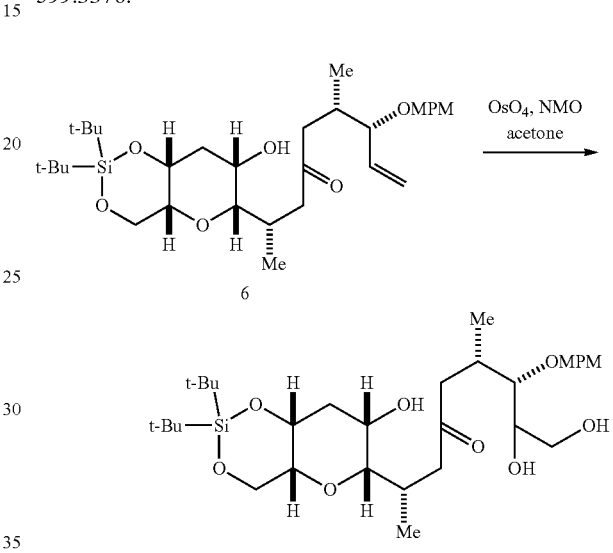

To a stirred solution of 6 (1.0 g, 1.73 mmol, 1 eq.) in acetone (17.4 mL) were added NMMO (405 mg, 3.46 mmol, 2 eq.) and OsO$_4$ solution (8.8 mL of 0.02 M in H$_2$O, 0.173 mmol, 10 mol %) at room temperature. After being stirred for 21 h at the same temperature, the mixture was diluted with water. The organic layer was separated and the aqueous layer was extracted with EtOAc. The combined organic layer was dried over Na$_2$SO$_4$, filtered, and concentrated under reduced pressure. The residue was passed through a pad of silica gel (EtOAc) and concentrated under reduced pressure. The obtained crude material was used in the next reaction without further purification. To a stirred solution of diol (calculated as 1.73 mmol) in CH$_2$Cl$_2$ (17.3 mL) was added K$_2$CO$_3$ (717 mg, 5.19 mmol, 3 eq.) and Pb(OAc)$_4$ (920 mg, 2.08 mmol, 1.2 eq.) at room temperature. After being stirred for 1 h at the same temperature, the reaction mixture was passed through a pad of silica gel (EtOAc). The filtrate was concentrated under reduced pressure. The residue was purified by flash column chromatography on silica gel (0%, 9%, 17%, then 25% EtOAc in Hexanes) to give S-3 (826 mg, 1.43 mmol, 83% for 2 steps) as colorless oil. S-3 was obtained as an equilibrium mixture of hemiacetal (ca. 4:1 ratio in C$_6$D$_6$). S-3: [α]$^{20}_D$ −39.3 (c 1.01, CHCl$_3$). $^1$H NMR (600 MHz, C$_6$D$_6$) δ: 7.19-7.16 (2H, m), 6.78-6.75 (2H, m), 5.41 (0.2H, dd, 11.1, 1.5 Hz), 4.93 (0.8H, dd, J=13.2, 1.8 Hz), 4.54 (0.8H, d, J=10.8 Hz), 4.44 (0.2H, d, J=11.4 Hz), 4.31 (0.8H, d, J=10.8 Hz), 4.26 (0.2H, d, J=11.4 Hz), 4.21-4.17 (1.2H, m), 3.99 (0.8H, dd, J=12.3, 2.7 Hz), 3.98 (0.2H, dd, J=12.6, 3.6 Hz), 3.90-3.89 (0.8H, m), 3.87-3.86 (0.2H, m), 3.69 (0.2H, d, J=10.8 Hz), 3.62 (0.8H, d, J=4.2 Hz), 3.36 (0.8H, d, J=12.6 Hz), 3.62 (0.8H, d, 4.2

Hz), 3.36 (0.8H, d, J=12.6 Hz), 3.29 (0.6H, s), 3.28 (2.4H, s), 3.19 (0.8H, s), 2.81 (0.2H, d, J=3.0 Hz), 2.77 (0.8H, d, J=2.4 Hz), 2.63 (0.8H, dd, J=1.5, 1.5 Hz), 2.61 (0.2H, dd, J=1.8, 1.8 Hz), 2.47-2.42 (0.2H, m), 2.34-2.25 (1.8H, m), 2.09 (0.8H, ddd, J=15.0, 1.8, 1.8 Hz), 2.00 (0.2H, ddd, J=15.0, 1.8, 1.8 Hz), 1.91-1.88 (0.4H, m), 1.74-1.61 (2.8H, m), 1.53-1.49 (1H, m), 1.42 (0.2H, ddd, J=15.6, 4.2, 4.2 Hz), 1.36 (0.8H, ddd, J=15.0, 4.5, 4.5 Hz), 1.29 (7.2H, s), 1.27 (1.8H, s), 1.14 (7.2H, s), 1.13 (1.8H, s), 1.07 (0.6H, d, J=6.6 Hz), 1.03 (2.4H, d, J=7.2 Hz), 1.01 (2.4H, d, J=7.2 Hz), 1.00 (0.6H, d, J=6.6 Hz) ppm. $^{13}$C NMR (125 MHz, C$_6$D$_6$) δ: 159.9, 159.7, 131.2, 129.6, 129.5, 128.5, 114.3, 114.0, 99.0, 98.4, 93.9, 91.2, 80.2, 78.6, 77.5, 77.4, 76.0, 72.2, 68.6, 68.5, 67.2, 67.0, 64.7, 64.0, 54.7, 38.5, 37.5, 37.4, 36.9, 36.4, 36.3, 29.5, 29.0, 27.8, 27.6, 23.41, 23.38, 23.1, 20.9, 17.9, 17.5, 17.2 ppm. FTIR (film): 3512, 2931, 2856, 1612, 1514, 1474, 1246, 1195, 1127, 1094, 1043, 1014, 966, 942, 828, 769, 735, 651, 441 cm$^{-1}$. HRMS (ESI) m/z: [M+Na]$^+$ calcd for C$_{31}$H$_{50}$NaO$_8$Si, 601.3167; found, 601.3168.

The residue was purified by flash column chromatography on silica gel (0%, 9%, 13%, the 17% EtOAc in Hexanes) to give alcohol S-4 (160 mg, 0.271 mmol, 75% for 3 steps) as colorless oil. S-4: [α]$^{20}_D$ −51.3 (c 1.0, CHCl$_3$). $^1$H NMR (600 MHz, C$_6$D$_6$) δ: 7.24-7.01 (5H, m), 5.07 (1H, d, J=12.3 Hz), 4.98 (1H, d, J=12.3 Hz), 4.30 (1H, m), 4.22 (1H, d, J=12.9 Hz), 4.16 (1H, dd, J=10.0, 2.9 Hz), 4.00 (1H, dd, J=12.6, 2.6 Hz), 3.93 (1H, m), 3.87 (1H, m), 2.99 (1H, d, J=8.2 Hz), 2.92-2.84 (2H, m), 2.71 (1H, brs), 2.32 (1H, dd, J=16.1, 3.2 Hz), 2.28 (1H, d, J=15.3 Hz), 2.18 (1H, m), 2.11 (1H, m), 1.74 (1H, dd, J=13.5, 4.1 Hz), 1.66 (1H, dd, J=12.9, 12.9 Hz), 1.55 (1H, ddd, J=15.4, 4.5, 4.5 Hz), 1.36-1.20 (11H, m), 1.13 (9H, s), 1.05 (3H, d, J=7.0 Hz), 0.92 (3H, d, J=6.5 Hz) ppm. $^{13}$C NMR (125 MHz, C$_6$D$_6$) δ: 171.6, 136.7, 128.7, 128.5, 126.9, 92.3, 77.52, 77.48, 70.5, 69.4, 68.6, 67.2, 66.1, 63.7, 37.42, 37.38, 36.5, 36.4, 29.8, 29.1, 27.8, 27.6, 23.4, 20.9, 17.6, 17.4 ppm. IR (film): 3473, 2957, 2931, 2857, 1736, 1131, 1017, 974 cm$^{-1}$. HRMS (ESI) m/z: [M+Na]$^+$ calcd for C$_{32}$H$_{50}$NaO$_8$Si, 613.3167; found, 613.3169.

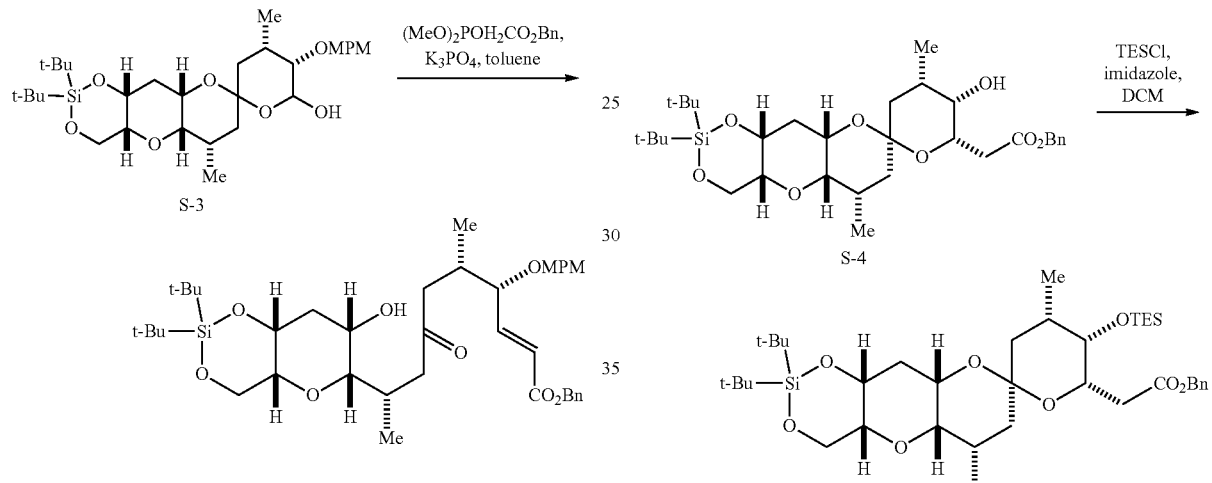

To a stirred solution of S-3 (208 mg, 0.359 mmol, 1 eq.) in toluene (3.6 mL) were added benzyl dimethylphosphonoacetate (0.30 mL, 1.44 mmol, 4 eq.) and K$_3$PO$_4$ (232 mg, 1.08 mmol, 3 eq.) at room temperature. After being stirred for 23 h at the same temperature, the reaction mixture was passed through a pad of silica gel (50% EtOAc in Hexanes) to give crude unsaturated ester (7) (as a ~3:1 mixture of E/Z isomers). The crude material was used in the next reaction without further purification.

To a stirred solution of the crude 7 (calculated as 0.359 mmol, 1 eq.), BnOAc (541 mg, 3.6 mmol, 10 eq.), and LiBr (313 mg, 3.6 mmol, 10 eq.) in MeCN (3.6 mL) was added DBU (0.269 μL, 1.80 mmol, 5 eq.) at room temperature. After being stirred for 12 h at the same temperature, the reaction was quenched with sat. NH$_4$Cl aq. The organic layer was separated and the aqueous layer was extracted with EtOAc. The combined organic layer was washed with brine, dried over Na$_2$SO$_4$, filtered, and concentrated under reduced pressure to give a crude spiro acetal, which was used in the next reaction without further purification. To a stirred solution of the crude spiro acetal (calculated as 0.359 mmol) in CH$_2$Cl$_2$ (3.6 mL) and phosphate buffer (pH=7, 0.7 mL) was added DDQ (163 mg, 0.72 mmol, 2 eq.). After being stirred for 40 min, the reaction was quenched with 10% Na$_2$S$_2$O$_3$ aq. and sat. NaHCO$_3$ aq. The organic layer was separated and the aqueous layer was extracted with CH$_2$Cl$_2$. The combined organic layer was dried over Na$_2$SO$_4$, filtered, and concentrated under reduced pressure.

To a stirred solution of S-4 (141 mg, 0.239 mmol, 1 eq.) in CH$_2$Cl$_2$ (2.4 mL, 0.1 M) were added imidazole (65 mg, 0.96 mmol, 4 eq.) and TESCl (80.2 μL, 0.48 mmol, 2 eq.) at room temperature. After being stirred for 16 h at the same temperature, the reaction was quenched with MeOH. The mixture was concentrated and passed through a pad of silica gel (25% EtOAc in Hexanes), and concentrated under reduced pressure to give to give a crude TES ether, which was used in the next reaction without further purification.

To a stirred solution of the crude TES ether (calculated as 0.239 mmol) in EtOAc (3.5 mL) was added wet 10% Pd/C (15 mg). The reaction was stirred under 1 atmosphere of hydrogen for 45 min at room temperature. The mixture was degassed and filled with N$_2$, passed through a pad of silica gel (EtOAc), and concentrated under reduced pressure to give a crude acid, which was used in the next reaction without further purification.

To a stirred solution of the crude acid (calculated as 0.239 mmol) in CH$_2$Cl$_2$ (2.4 mL, 0.1 M) were added PPh$_3$ (94 mg, 0.389 mmol, 1.2 eq.) and (PyS)$_2$ (73.7 mg, 0.335 mmol, 1.4 eq.) at room temperature. After being stirred for 17 h at the same temperature, the reaction mixture was concentrated under reduced pressure. The residue was purified by flash column chromatography on neutral silica gel (0%, 9%, then 17% EtOAc in Hexanes) to give thioester 8 (162 mg, 0.229 mmol, 96% for 3 steps), which contained 2% of (PyS)$_2$. The disulfide impurity can be removed by additional column chromatography (0%, 1%, 2%, 3%, then 9% EtOAc in CH$_2$Cl$_2$) or HPLC (Column: DuPont Instruments ZORBAL SIL 21.2 mm×25 cm (880952-101), Solvent: 3% iPrOH in Hexanes, Flow rate: 10.0 mL/min, Detection: UV at 254 nm and 220 nm, t$_R$=15 min. The product was obtained as pale yellow foam. 8: [α]$^{20}_D$ −74.3 (c 1.0, CHCl$_3$). $^1$H NMR (500 MHz, C$_6$D$_6$) δ: 8.33 (1H, m), 7.52 (1H, m), 6.94 (1H, m), 6.47 (1H, m), 4.25-4.16 (2H, m), 3.99 (1H, dd, J=12.4, 2.7 Hz), 3.97-3.91 (2H, m), 3.27 (1H, m), 3.19 (1H, brs), 2.91 (1H, m), 2.72 (1H, brs), 2.59 (1H, dd, J=14.9, 2.2 Hz), 2.34 (2H, d, J=14.6 Hz), 2.24 (1H, m), 1.77-1.60 (4H, m), 1.52 (1H, m), 1.31 (9H, s), 1.13 (9H, s), 1.04-0.96 (12H, m), 0.93 (3H, m), 0.59 (6H, q, J=7.8 Hz) ppm. $^{13}$C NMR (125 MHz, C$_6$D$_6$) δ: 194.7, 152.7, 150.6, 136.5, 128.5, 123.1, 97.4, 77.7, 77.5, 72.5, 70.0, 68.6, 67.3, 63.9, 47.8, 37.5, 36.7, 36.5, 30.5, 29.1, 27.8, 27.7, 23.4, 21.0, 18.5, 17.3, 7.4, 5.9 ppm. IR (film): 2955, 2931, 2874, 2857, 1708, 1132, 1035, 974 cm$^{-1}$. HRMS (ESI) m/z: [M+H]$^+$ calcd for C$_{36}$H$_{62}$O$_7$SSi$_2$, 708.3780; found, 708.3779.
Halichondrin Left Halves

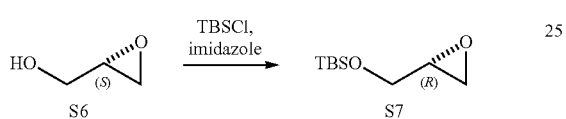

To a solution of (S)-glycidol S6 (6.70 g, 90.0 mmol; AK Scientific) in dichloromethane (250 mL) was added imidazole (7.40 g, 108 mmol) and TBSCl (14.9 g, 99.0 mmol) at 0° C. The reaction was stirred for 6 hr at room temperature before quenched with water (200 mL), and the resulting two layers were separated. The organic layer was dried over anhydrous Na$_2$SO$_4$, and filtered, concentrated under reduced pressure to give a crude oil. Purification over SiO$_2$ (hexanes/ethyl acetate=50/1) gave S7 as a clear oil (16.2 g, 95%). S7: [α]$_D$=−2.2 (c 1.0, CHCl$_3$); $^1$H NMR (500 MHz, CDCl$_3$) δ: 3.85 (1H, dd, J=9.6, 3.2 Hz), 3.66 (1H, dd, J=11.9, 5.0 Hz), 3.09 (1H, ddd, J=7.5, 4.4, 3.0 Hz), 2.77 (1H, dd, J=5.1, 4.5 Hz), 2.64 (1H, dd, J=5.2, 2.6 Hz), 0.9 (9H, s), 0.09 (3H, s), 0.08 (3H, s) ppm. $^{13}$C NMR (125 MHz, CDCl$_3$) δ: 63.7, 52.4, 44.4, 25.8, 18.3, −5.3, −5.4 ppm. HRMS (ESI) m/z: [M+H]$^+$ calcd for C$_9$H$_{21}$O$_2$Si, 189.1305; found 189.1299.

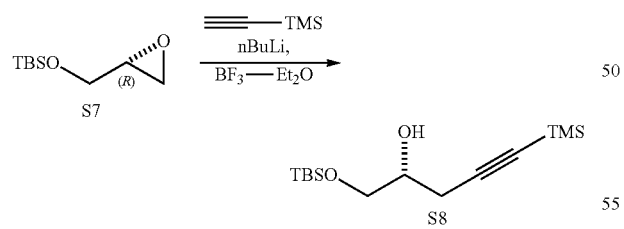

A solution of trimethylsilyl acetylene (23.8 mL, 167 mmol; Oakwood) in dry THF (76.0 mL) was cooled to −78° C. under Ar atmosphere and treated with n-BuLi (2.50 M in hexane, 61.3 mL, 159 mmol). After 30 min, BF$_3$.OEt$_2$ (18.9 mL, 159 mmol) was added dropwise followed by slow addition of a solution of epoxide S7 (15.0 g, 79.7 mmol) in THF (30.0 mL). The reaction mixture was stirred for 1 h at the same temperature before addition of sat'd-NaHCO$_3$ (100 mL) and diethyl ether (300 mL). The resulting biphasic solution was warmed up to rt, and the layers were separated. The organic layer was dried over anhydrous Na$_2$SO$_4$, filtered, and concentrated under reduced pressure to give crude oil. Purification over SiO$_2$ (hexanes/ethyl acetate=10/1) gave S8 as a clear oil (20.5 g, 90%). S8: [α]$^2$=−15.6 (c 1.0, CHCl$_3$); $^1$H NMR (500 MHz, CDCl$_3$): δ 3.82-3.78 (1H, m), 3.73 (1H, dd, J=10.0, 4.5 Hz), 3.67 (1H, dd, J=9.5, 5.5 Hz), 2.52-2.44 (2H, m), 0.92 (9H, s), 0.16 (9H, s), 0.10 (6H, s) ppm. $^{13}$C NMR (125 MHz, CDCl$_3$): δ 102.8, 87.0, 70.1, 65.4, 25.9, 24.5, 18.3, 0.02, −5.4, −5.4 ppm. HRMS (ESI) m/z: [M+Na]$^+$ calcd for C$_{14}$H$_{30}$NaO$_2$Si$_2$ 309.1677; found 309.1677.

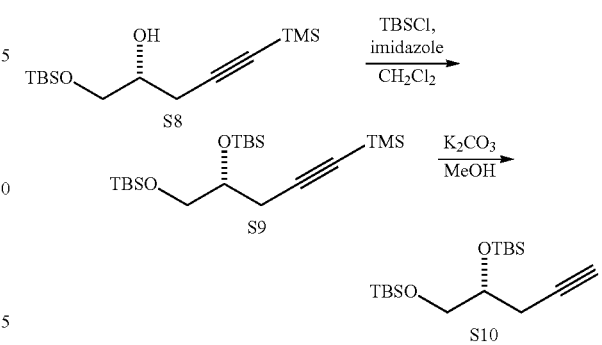

To a solution of alcohol S8 (20.5 g, 71.5 mmol) and imidazole (7.3 g, 107 mmol) in dichloromethane (300 mL) was added TBSCl (14.0 g, 92.9 mmol) at 0° C. The reaction was stirred for 6 hr at rt before addition of water (100 mL). The mixture was extracted with hexanes (200 mL), and the organic layer was dried over anhydrous Na$_2$SO$_4$, filtered, and concentrated under reduced pressure to give the crude product S9 which was used in next step without further purification.

To a solution of S9 in methanol (240 mL) was treated with potassium carbonate (11.9 g, 85.8 mmol) at rt. After 6 h, the reaction was diluted with hexanes (200 mL) and filtered through a pad of Celite®. Concentration under reduced pressure gave a crude oil, which was subject to purification over SiO$_2$ (hexanes/ethyl acetate=50/1) to give S10 as a clear oil (21.2 g, 90% for 2 steps). S10: [α]$^2$=+6.0 (c 1.0, CHCl$_3$). $^1$H NMR (500 MHz, CDCl$_3$) δ: 3.81 (1H, quint, J=5.5 Hz), 3.53-3.52 (2H, m), 2.46 (1H, ddd, J=14.0, 5.5, 2.5 Hz), 2.29 (1H, ddd, J=14.0, 6.0, 2.5 Hz), 1.94 (1H, t, J=2.5), 0.89 (18H, s), 0.12 (3H, s), 0.08 (3H, s), 0.06 (3H, s), 0.05 (3H, s). $^{13}$C NMR (125 MHz, CDCl$_3$) δ: 81.7, 71.8, 69.6, 66.4, 25.9, 25.8, 24.3, 18.3, 18.1, −4.5, −4.7, −5.4, −5.4 ppm. FTIR (film): 2955, 2929, 2886, 2857, 2124, 1472, 1361, 1253, 1116, 1078, 832, 773, 637 cm$^{-1}$. HRMS (ESI) m/z: [M+H]$^+$ calcd for C$_{17}$H$_{37}$O$_2$Si$_2$ 329.2327; found 329.2328.

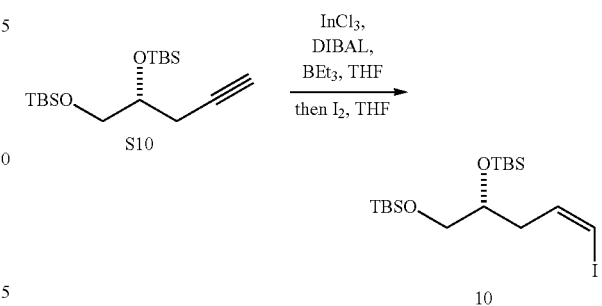

Anhydrous indium trichloride (16.4 g, 74.0 mmol; Alfa Aesar 99.99%) was placed in flask and heated with hot gun in vacuo for 3 min.[3] The indium salt was dissolved with THF (220 mL) at 0° C. under an argon atmosphere. The solution turned to a white suspension upon cooling to −78° C. DIBAL (1.0 M in hexane, 71.3 mL, 71.3 mmol) was then added dropwise to suspension at −78° C. The mixture was stirred for 2.5 hr to prepare dichloroindium hydride. S10 (18.1 g, 54.8 mmol) and triethyborane (1.0 M hexane solution, 11.0 mL, 11.0 mmol; Aldrich) were added to the reaction mixture and the resulting mixture was stirred for 4.5 hr at −78° C. Iodine (41.8 g, 164 mmol) in THF (80.0 mL) was added to the reaction mixture. After being stirred for 20 min at −78° C., the reaction was poured into saturated NaHCO$_3$ solution. Na$_2$S$_2$O$_3$ solution was added to consume excess iodine. Then saturated potassium sodium tartrate solution was added and stirring vigorously for 1 hr. The mixture was extracted with hexane and ethyl acetate (4:1, 1000 mL) twice. The organic layer was dried over anhydrous Na$_2$SO$_4$, filtered, and concentrated under reduced pressure to give crude oil. Purification over SiO$_2$ (hexanes/ethyl acetate=100/1) gave 10 as a clear oil (21.3 g, 85%, Z/E>99: 1)[2]. 10: colorless oil. $[\alpha]^2$=+3.0 (c 0.9, CHCl$_3$). $^1$H NMR (500 MHz, CDCl$_3$) δ: 6.29-6.24 (2H, m), 3.77 (1H, quint, J=5.4 Hz), 3.51 (1H, dd, J=10.2, 6.6 Hz), 3.40 (1H, dd, J=10.2, 6.6 Hz), 0.88 (9H, s), 0.86 (9H, s), 0.05 (3H, s), 0.04 (3H, s), 0.04 (3H, s), 0.03 (3H, s) ppm. $^{13}$C NMR (125 MHz, CDCl$_3$) δ: 138.0, 83.7, 71.9, 67.0, 39.8, 26.0, 25.9, 18.4, 18.1, −4.4, −4.7, −5.3, −5.3 ppm. FTIP (film): 2954, 2928, 2885, 2857, 1610, 1471, 1389, 1306, 1113, 1081, 831, 772 cm$^{-1}$. HRMS (ESI) m/z: [M+H]$^+$ calcd for C$_{17}$H$_{38}$IO$_2$Si$_2$ 457.1450; found 457.1455.

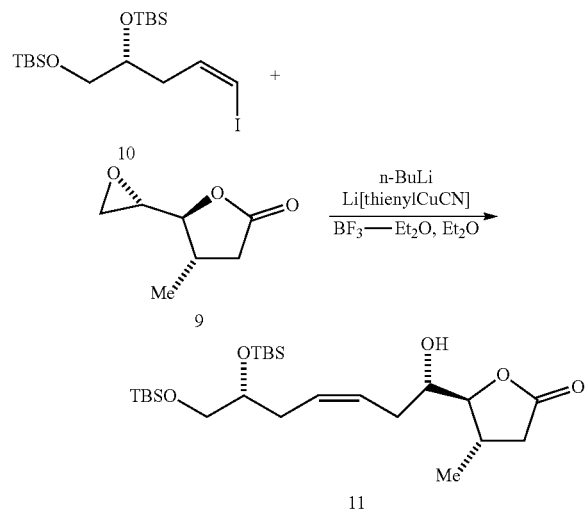

To a solution of vinyl iodide 10 (5.79 g, 12.7 mmol, 1.8 equiv.) in anhydrous Et$_2$O (64 mL) was added n-BuLi (2.52 M in hexane, 4.8 mL, 1.75 equiv.; Aldrich) dropwise at −78° C. under Ar atmosphere, and the clear mixture was stirred for 1 h at the same temperature. Li 2-thienylcyanocuprate (0.25 M in THF, 53.4 mL, 2.0 equiv.; Aldrich) was slowly added over 10 min at −78° C., which was stirred for 30 min before addition of BF$_3$.Et$_2$O (0.87 mL, 7.04 mmol, 1.6 equiv.). After 20 min, a solution of epoxide 9 (1000 mg, 7.04 mmol, 1.0 equiv.) in anhydrous Et$_2$O (5.0 mL) was added dropwise at −78° C., and the yellow reaction mixture was stirred for 1 hr at the same temperature. The reaction was quenched by slow addition of a mixture of sat. NH$_4$Cl aq. (90 mL) and 30% aq. NH$_4$OH (10 mL) at 0° C. and stirred 2 hr at rt. The biphasic mixture was diluted with Et$_2$O (200 mL), and layers were separated, and organic layer was dried over Na$_2$SO$_4$ and concentrated under reduced pressure. The residue was purified by flash column chromatography on silica gel (25% EtOAc in Hexanes) to afford 11 as a oil (2.69 g, 81%). 11: $[\alpha]^2$=+13.0 (c 1.0, CDCl$_3$). $^1$H NMR (600 MHz, C$_6$D$_6$) δ: 5.74 (1H, dd, J=10.8, 8.4 Hz), 5.47 (1H, dd, J=10.8, 7.8 Hz), 3.83-3.79 (m, 1H), 3.63 (1H, dd, J=9.9, 5.1 Hz), 3.56 (1H, dd, J=10.2, 6.6 Hz), 3.45 (1H, dd, J=6.0, 2.4 Hz), 3.25-3.24 (1H, m), 2.50-2.35 (3H, m), 2.37 (1H, dd, J=16.8, 9.0 Hz), 2.23-2.14 (2H, m), 1.95 (1H, d, J=6.0 Hz), 1.59 (1H, dd, J=17.1, 8.1 Hz), 1.00 (9H, s), 0.99 (9H, s), 0.53 (3H, d, J=7.2 Hz), 0.13 (3H, s), 0.12 (3H, s), 0.10 (3H, s), 0.09 (3H, s) ppm. $^{13}$C NMR (150 MHz, C$_6$D$_6$) δ: 175.5, 129.6, 127.1, 87.8, 73.3, 70.9, 67.3, 36.8, 32.8, 32.5, 31.3, 26.1 (×3), 26.2 (×3), 18.6, 18.4, 18.1, −4.2, −4.4, −5.1, −5.2 ppm. FTIP (film): 3450, 2958, 2930, 2858, 1778, 1472, 1428, 1389, 1361, 1252, 1113, 835, 776, 738, 703 cm$^{-1}$. HRMS (ESI) m/z: [M+Na]$^+$ calcd for C$_{24}$H$_{48}$O$_5$NaSi$_2$$^+$ 495.2932; found 495.2940.

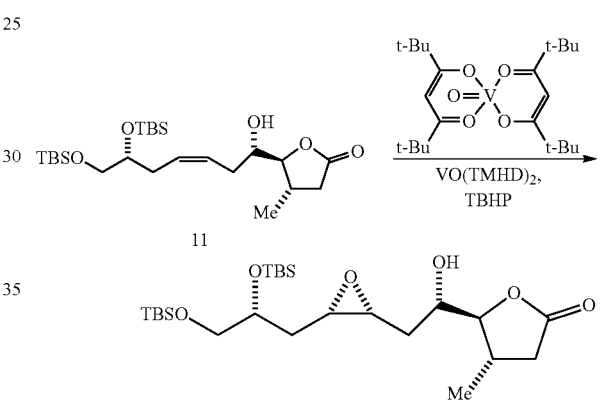

To a solution of alkene 11 (490 mg, 1.04 mmol, 1.0 equiv.) in toluene (10 mL) was added VO(TMHD)$_2$ (23 mg, 5 mol %) and tert-butylhydrogenperoxide (TBHP) (5.5 M in decane, 380 μL, 2.0 equiv.; Aldrich) to form a reddish solution. The reaction mixture was stirred for 5.5 hr at rt before quenched with sat. Na$_2$S$_2$O$_3$/NaHCO$_3$ solution (v:v=1:1). The resulting biphasic mixture was diluted with Et$_2$O (10 mL), and the layers were separated. The organic layer was dried over anhydrous Na$_2$SO$_4$, concentrated, and purified by flash column chromatography on silica gel (33% EtOAc in Hexanes) to afford S11 as a colorless oil (450 g, 89%, dr>50:1). S11: $[\alpha]^2$=+26.0 (c 1.0, CHCl$_3$). $^1$H NMR (600 MHz, C$_6$D$_6$) δ: 3.92 (1H, quint, J=5.4 Hz), 3.70 (1H, dd, J=10.2, 5.1 Hz), 3.66-3.62 (2H, m), 3.76 (1H, dd, J=9.9, 6.3 Hz), 3.14-3.11 (2H, m), 2.97 (1H, dt, J=14.4, 4.2 Hz), 2.47 (1H, dd, J=18.0, 9.6 Hz), 2.31-2.24 (1H, m), 1.84 (1H, dt, J=14.4, 4.8 Hz), 1.77-1.62 (4H, m), 0.97 (9H, s), 0.96 (9H, s), 0.67 (3H, d, J=6.6 Hz), 0.12 (3H, s), 0.11 (3H, s), 0.08 (3H, s), 0.07 (3H, s) ppm. $^{13}$C NMR (150 MHz, C$_6$D$_6$) δ: 176.1, 88.3, 72.2, 70.5, 67.5, 53.7, 53.4, 36.8, 33.2, 31.9, 31.2, 26.2 (×3), 26.1 (×3), 18.6, 18.5, 18.4, −4.2, −4.6, −5.2, −5.2 ppm. FTIP (film): 3450, 2955, 2929, 2857, 1779, 1472, 1463, 1388, 1361, 1253, 1115, 835, 776, 738 cm$^{-1}$. HRMS (ESI) m/z: [M+Na]$^+$ calcd for C$_{24}$H$_{48}$O$_6$NaSi$_2$$^+$ 511.2882; found 511.2877.

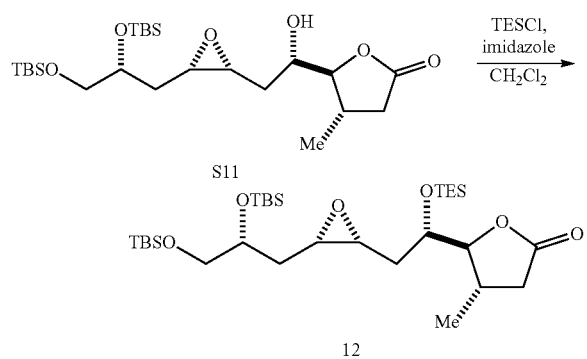

To a solution of S11 (450 mg, 0.92 mmol, 1.0 equiv.) and imidazole (251 mg) in dichloromethane (9.2 mL) was added TESCl (308 μL) at 0° C. The reaction was stirred for 1 hr at 0° C. before quenched with sat. NaHCO₃. The biphasic mixture was diluted with dichloromethane, and the layers were separated. The organic layer was dried over anhydrous Na₂SO₄, filtered, and concentrated under reduced pressure to give a crude oil. Purification over SiO₂ (9% EtOAc in Hexanes) afforded 12 as a clear oil (528 mg, 95%). 12: $[\alpha]^2=+26.9$ (c 1.0, CHCl₃). ¹H NMR (500 MHz, C₆D₆) δ: 3.97 (1H, quint, J=5.4 Hz), 3.94 (1H, dd, J=5.0, 3.5 Hz), 3.89-3.85 (1H, m), 3.76 (1H, dd, J=10.0, 5.5 Hz), 3.65 (1H, dd, J=10.5, 6.0 Hz), 3.15 (1H, dt, J=7.5, 4.0 Hz), 2.92 (1H, dt, J=9.0, 4.0 Hz), 2.40 (1H, dd, J=17.2, 9.2 Hz), 2.13-2.09 (1H, m), 2.04 (1H, ddd, J=14.0, 7.5, 3.5 Hz), 1.95 (1H, ddd, J=14.5, 5.5, 4.5 Hz), 1.71-1.64 (2H, m), 1.59 (1H, ddd, J=13.5, 8.0, 4.5 Hz), 1.00 (9H, s), 0.98 (9H, s), 0.97 (9H, t, J=8.5 Hz), 0.68 (3H, d, J=6.5 Hz), 0.58 (6H, q, J=8.0 Hz), 0.14 (3H, s), 0.13 (3H, s), 0.11 (3H, s), 0.09 (3H, s) ppm. ¹³C NMR (125 MHz, C₆D₆) δ: 175.3, 86.9, 72.2, 71.7, 67.7, 53.7, 52.4, 36.8, 33.5, 32.4, 31.2, 26.2 (×3), 26.1 (×3), 19.2, 18.6, 18.3, 7.1, 7.0, 6.3, 5.3, −4.2, −4.7, −5.2, −5.2 ppm. FTIP (film): 2955, 2929, 2878, 2857, 1781, 1472, 1463, 1388, 1361, 1250, 1097, 1005, 832, 774, 735 cm⁻¹. HRMS (ESI) m/z: [M+Na]⁺ calcd for C₃₀H₆₂O₆NaSi₃₊625.3746; found 625.3748.

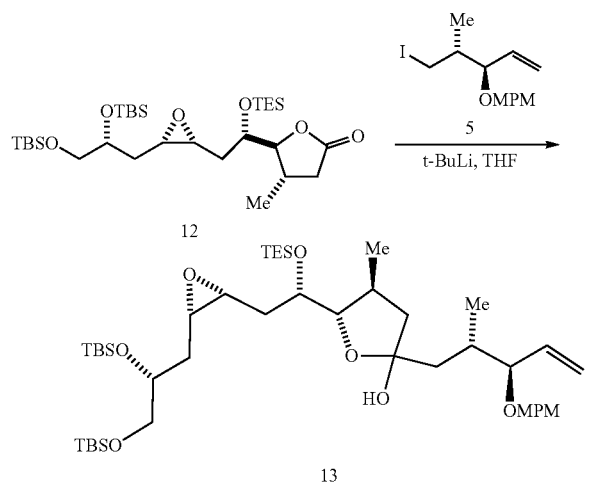

A solution of 12 (193 mg, 0.32 mmol) and 5 (155 mg, 0.45 mmol, 1.4 eq.) in THF was degassed by bubbling with Ar. To the solution was added t-BuLi solution (0.49 mL of 1.7 M in pentane, 14.6 mmol, 2.6 eq.) dropwise at −78° C. over 10 min. After being stirred for 15 min at the same temperature, the reaction was quenched with sat. NH₄Cl aq. The organic layer was separated and the aqueous layer was extracted with EtOAc. The combined organic layer was washed with brine, dried over Na₂SO₄, filtered, and concentrated under reduced pressure. The residue was purified by flash column chromatography on silica gel (10% then 30% EtOAc in Hexanes) to give 13 (225 mg, 0.27 mmol, 85%) as colorless oil. 13 was obtained as an equilibrium mixture of ketone form and ketal form (ca. 1:1 ratio).

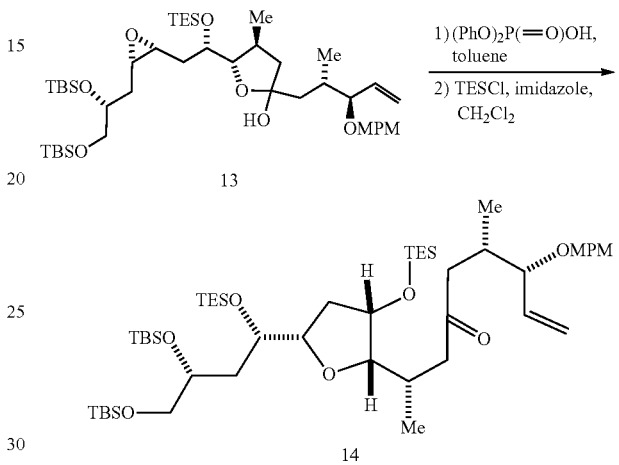

To a solution of 13 (500 mg, 0.607 mmol) in 10.1 mL of toluene, (PhO)₂P(═O)OH (15.2 mg in 2 mL toluene) was added at 0° C., The resulting mixture was stirred at room temperature for 12 hr before it was quenched by 5 mL of saturated aqueous NaHCO₃. The organic layer was removed, and the aqueous layer was extracted with ethyl acetate (30 mL) three times. The combined organic layers were dried over Na₂SO₄, filtered and concentrated. The resulting oil was then dissolved in 6 mL of dichloromethane before the addition of imidazole (413 mg, 6.07 mmol) and TESCl (509 μL, 3.04 mmol) at 0° C. The resulting mixture was stirred at room temperature for 2 hr before it was quenched by 5 mL of saturated aqueous NH₄Cl. The organic layer was removed, and the aqueous layer was extracted with ethyl acetate (30 mL) three times. The combined organic layers were dried over MgSO₄, filtered and concentrated. The residue was purified by flash column chromatography on silica gel (9% EtOAc in Hexanes) afforded 14 as a clear oil (484 mg, 85% for 2 steps). 14: $[\alpha]=-5.8$ (c 1.1, CHCl₃). ¹H NMR (600 MHz, C₆D₆) δ: 7.24 (1H, d, J=8.4 Hz), 6.82 (1H, d, J=9.0 Hz), 5.63 (1H, ddd, J=17.4, 10.8, 7.8 Hz), 5.13 (1H, dd, J=8.4, 3.0 Hz), 5.10 (1H, d, J=10.2 Hz), 4.54 (1H, d, J=10.8 Hz), 4.27-4.24 (1H, m), 4.21 (1H, d, J=7.6 Hz), 4.06-4.03 (1H, m), 4.00-3.98 (1H, m), 3.83 (1H, dd, J=10.5, 3.3 Hz), 3.76 (1H, q, J=4.8 Hz), 3.72 (1H, dd, J=10.2, 6.0 Hz), 3.49 (1H, t, J=6.9 Hz), 3.33 (3H, s), 3.12 (1H, dd, J=8.4, 4.2 Hz), 3.04 (1H, dd, J=16.8, 3.0 Hz), 2.77-2.71 (2H, m), 2.59-2.53 (1H, m), 2.36 (1H, dd, J=16.2, 10.2 Hz), 2.31 (1H, dd, J=16.8, 9.0 Hz), 2.00-1.91 (2H, m), 1.76 (1H, ddd, J=12.6, 7.8, 3.6 Hz), 1.59 (1H, ddd, J=12.6, 7.2, 2.4 Hz), 1.14 (9H, t, J=7.8 Hz), 1.08 (9H, s), 1.03 (9H, s), 1.01 (3H, d, J=5.4 Hz), 0.99 (1H, t, J=8.4 Hz), 0.82 (3H, s), 0.81 (3H, q, J=7.8 Hz), 0.57 (6H, q, J=7.8 Hz), 0.28 (3H, s), 0.28 (3H, s), 0.15 (6H, s) ppm. ¹³C NMR (150 MHz, C₆D₆) δ: 208.4, 159.7, 137.8, 131.4, 129.5, 118.1, 114.0, 87.4, 84.1, 81.3, 72.7, 72.2, 71.3, 70.3, 68.2, 54.8, 47.6, 46.4, 39.1, 39.0, 33.9, 28.9, 26.3 (×6), 18.7, 18.5, 17.4, 16.6, 7.9, 7.2, 5.8, 5.3, −3.9, −4.2, −5.0, −5.1 ppm. FTIP (film): 2956, 2932, 2880, 2855, 1713, 1615, 1514, 1463, 1381, 1361, 1249, 1079, 1039, 944, 833, 775, 736 cm$^{-1}$. HRMS (ESI) m/z: [M+Na]$^+$ calcd for $C_{50}H_{96}O_8NaSi_4^+$ 959.6074; found 959.6070.

through a pad of SiO$_2$ with EtOAc/hexanes (1/1), and concentrated to give S12 (1.65 g, 1.51 mmol, 82% for 3 steps, ~8:1 mixture of E/Z isomers). S12: $[\alpha]^{22}_D$ =−7.0 (c 0.9, CHCl$_3$). $^1$H NMR (600 MHz, C$_6$D$_6$) δ: 7.24 (2H, d, J=7.2 Hz), 7.15 (2H, d, J=8.4 Hz), 7.10 (2H, dd, J=7.2, 7.2 Hz), 7.05 (1H, t, J=7.2 Hz), 7.00 (1H, dd, J=15.5, 6.3 Hz), 6.59 (2H, d, J=8.4 Hz), 6.13 (1H, d, J=15.5 Hz), 5.10 (1H,

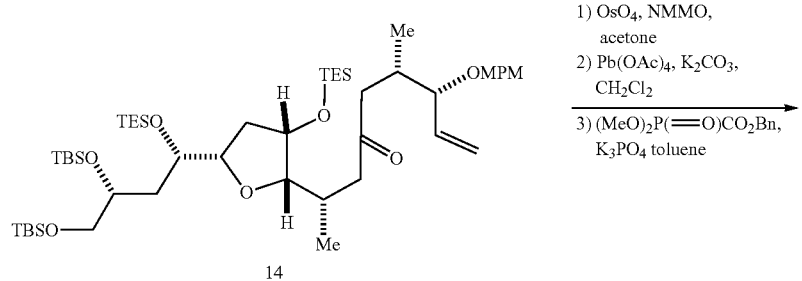

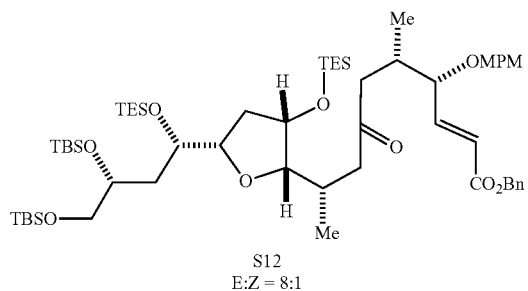

S12
E:Z = 8:1

To a solution of 14 (1.80 g, 1.92 mmol, 1.0 equiv.) in acetone (19.2 mL) was added NMMO (449 mg, 3.84 mmol, 2.0 equiv.) and aqueous solution of OsO$_4$ (4.88 mL, 0.096 mmol, 5 mg/mL H$_2$O, 5 mol %). The reaction mixture was stirred for 15 hr, and then quenched with Na$_2$SO$_3$ aq. The mixture was extracted twice with EtOAc, dried over Na$_2$SO$_4$, filtered, and concentrated. The residue was passed through a pad of SiO$_2$ with EtOAc and concentrated. Without further purification the crude material was used in the next reaction.

To a solution of diol (estimated as 1.92 mmol, 1.0 equiv.) in DCM (19.2 mL) was added K$_2$CO$_3$ (2.66 g, 19.2 mmol, 10 equiv.) and Pb(OAc)$_4$ (1.36 g, 3.07 mmol, 1.6 equiv.). After being stirred for 1 hr, the reaction mixture was passed through SiO$_2$ pad with EtOAc and concentrated. Without further purification the crude material was used in the next reaction.

To a solution of aldehyde (estimated as 1.92 mmol, 1.0 equiv.) in toluene (19.2 mL) at room temperature was added (MeO)$_2$P(=O)CH$_2$CO$_2$Bn (2.0 mL, 9.6 mmol, 5.0 equiv.) and K$_3$PO$_4$ (4.08 g, 19.2 mmol, 10 equiv.). After being stirred for additional 12 h, the reaction mixture was passed d, J=12.0 Hz), 5.06 (1H, d, J=12.0 Hz), 4.30 (1H, d, J=12.0 Hz), 4.27-4.24 (1H, m), 4.03 (1H, d, J=12.0 Hz), 4.00-3.97 (1H, m), 3.97-3.94 (1H, m), 3.78 (1H, dd, J=10.6, 3.8 Hz), 3.71 (1H, q, J=7.8 Hz), 3.65 (1H, dd, J=16.8, 6.6 Hz), 3.55 (1H, t, J=6.9 Hz), 3.27 (3H, s), 3.05 (1H, dd, J=12.6, 4.2 Hz), 2.93 (1H, dd, J=16.8, 3.0 Hz), 2.66-2.61 (1H, m), 2.50-2.44 (2H, m), 2.21 (1H, dd, J=8.4, 8.4 Hz), 2.19 (1H, dd, J=8.4, 8.4 Hz), 2.00-1.88 (2H, m), 1.70 (1H, ddd, J=12.6, 7.8, 3.6 Hz), 1.55 (1H, ddd, J=12.6, 7.2, 2.4 Hz), 1.08 (9H, t, J=7.8 Hz), 1.03 (9H, s), 0.98 (9H, s), 0.96 (3H, d, J=5.4 Hz), 0.93 (1H, t, J=8.4 Hz), 0.88 (3H, q, J=7.8 Hz), 0.76 (3H, q, J=7.8 Hz), 0.52 (6H, q, J=7.8 Hz), 0.23 (6H, s), 0.20 (6H, s) ppm. $^{13}$C NMR (150 MHz, C$_6$D$_6$) δ: 207.8, 165.5, 159.8, 147.7, 136.6, 130.6, 129.6, 128.69, 128.66, 128.3, 123.3, 114.0, 87.3, 81.6, 81.2, 72.6, 72.1, 71.2, 68.2, 66.4, 54.7, 47.6, 45.7, 39.0, 38.96, 33.5, 28.8, 26.2 (×6), 18.6, 18.4, 17.2, 16.5, 7.4, 7.2, 5.8, 5.2, −4.0, −4.3, −5.1, −5.2 ppm. FTIP (film): 2954, 2929, 2876, 2856, 1720, 1655, 1612, 1514, 1462, 1381, 1301, 1249, 1158, 1079, 1005, 835, 776, 740 cm$^{-1}$. HRMS (ESI) m/z: [M+Na]$^+$ calcd for $C_{50}H_{96}O_8NaSi_4^+$ 959.6074; found 959.6070.

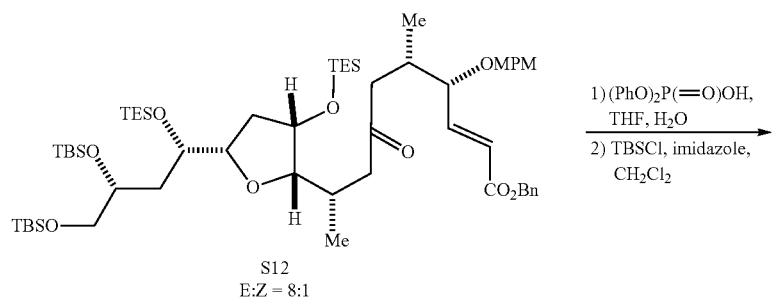

S12
E:Z = 8:1

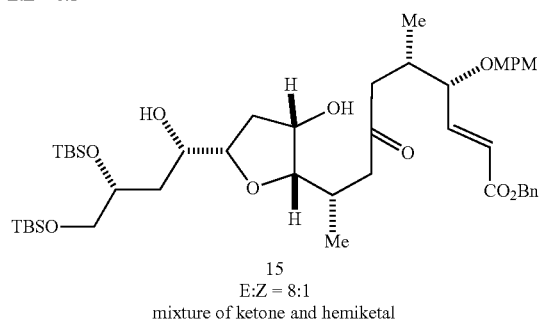

15
E:Z = 8:1
mixture of ketone and hemiketal

To a THF-H$_2$O (4:1, 0.05 M) solution of S12 (1.65 g, 1.51 mmol, 1 eq.), (PhO)$_2$P(=O)OH (113 mg, 0.45 mmol, 0.3 eq.) was added at 0° C. The resulting mixture was stirred at room temperature for 24 hr before it was quenched by 5 mL of saturated aqueous NaHCO$_3$. The organic layer was removed, and the aqueous layer was extracted with ethyl acetate (30 mL) three times. The combined organic layers were dried over Na$_2$SO$_4$, filtered and concentrated. The resulting oil was then dissolved in 6 mL of dichloromethane before the addition of imidazole (414 mg, 7.55 mol, 5 eq.) and TBSCl (274 mg, 1.81 mmol, 1.2 eq.) at 0° C. The resulting mixture was stirred at room temperature for 1 hour before it was quenched by 5 mL of saturated aqueous NH$_4$Cl. The organic layer was removed, and the aqueous layer was extracted with ethyl acetate (30 mL) three times. The combined organic layers were dried over MgSO$_4$, filtered and concentrated. Purification over SiO$_2$ (30% EtOAc in Hexanes) afforded 15 as a clear oil (1.02 g, 1.21 mmol, 80% for 2 steps). 15 was obtained as an equilibrium mixture of ketone form and ketal form (ca. 1:1 ratio in C$_6$D$_6$) alone with ~8:1 mixture of E/Z isomers,

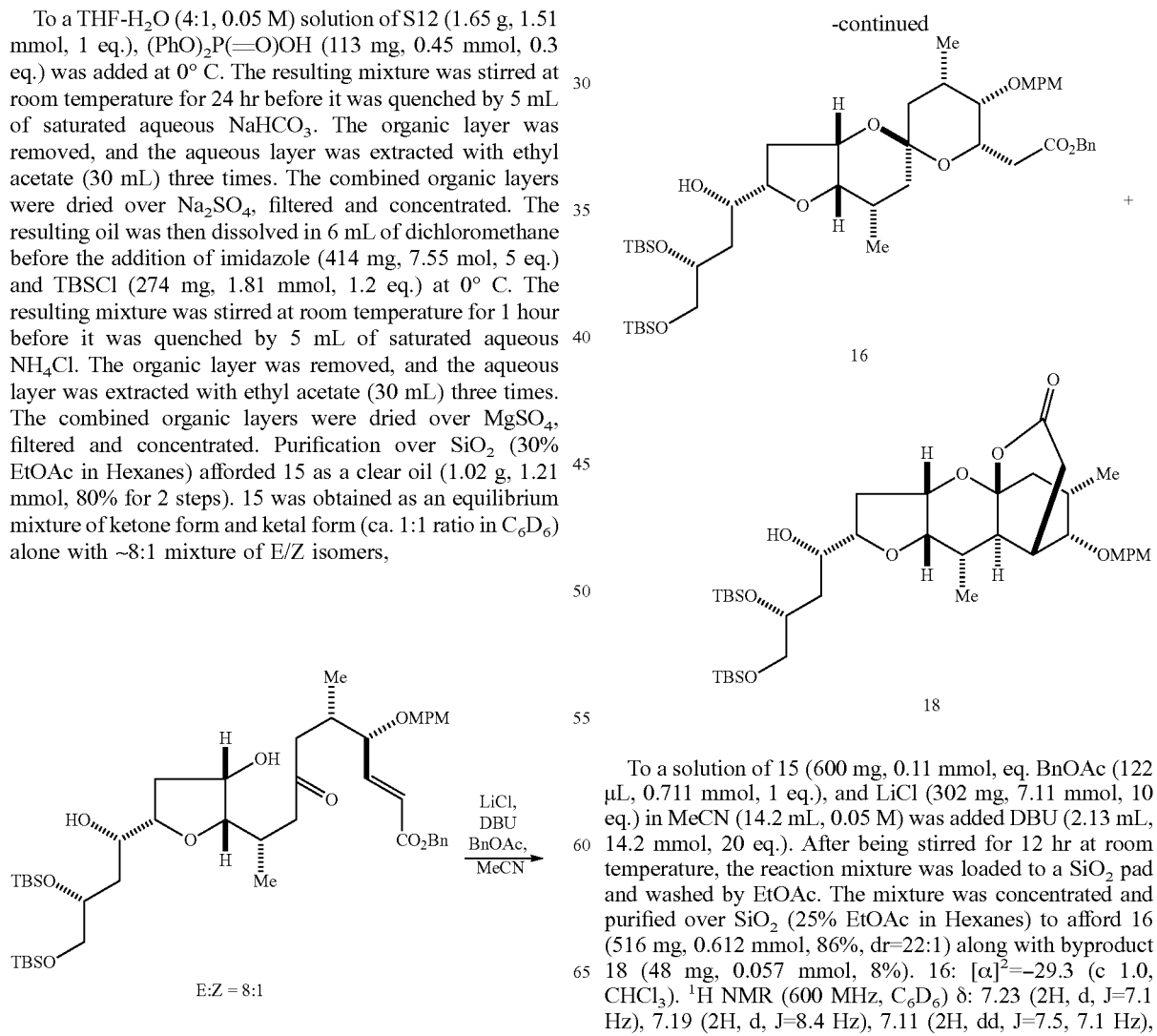

To a solution of 15 (600 mg, 0.11 mmol, eq. BnOAc (122 μL, 0.711 mmol, 1 eq.), and LiCl (302 mg, 7.11 mmol, 10 eq.) in MeCN (14.2 mL, 0.05 M) was added DBU (2.13 mL, 14.2 mmol, 20 eq.). After being stirred for 12 hr at room temperature, the reaction mixture was loaded to a SiO$_2$ pad and washed by EtOAc. The mixture was concentrated and purified over SiO$_2$ (25% EtOAc in Hexanes) to afford 16 (516 mg, 0.612 mmol, 86%, dr=22:1) along with byproduct 18 (48 mg, 0.057 mmol, 8%). 16: [α]$^2$=−29.3 (c 1.0, CHCl$_3$). $^1$H NMR (600 MHz, C$_6$D$_6$) δ: 7.23 (2H, d, J=7.1 Hz), 7.19 (2H, d, J=8.4 Hz), 7.11 (2H, dd, J=7.5, 7.1 Hz), 7.06 (1H, dd, J=7d, J 7.5, 7.5 Hz), 6.76 (2H, d, J=8.4 Hz), 5.09 (1H, d, J=12.0 Hz), 5.00 (1H, d, J=12.0 Hz), 4.27-4.21 (2H, m), 4.15 (2H, d, J=7.6 Hz), 3.95-3.77 (4H, m), 3.36 (1H, dd, J=6.3, 3.6 Hz), 3.26 (1H, dd, J=10.2, 2.4 Hz), 3.25 (3H, s), 2.89 (1H, dd, J=15.0, 10.2 Hz), 2.77 (1H, s), 2.19 (1H, dd, J=16.2, 3.0 Hz), 2.18-2.09 (1H, m), 2.08-2.02 (1H, m), 1.93-1.84 (2H, m), 1.57 (1H, t, J=12.9 Hz), 1.49 (1H, t, J=12.9 Hz), 1.38 (1H, dd, J=12.0, 3.0 Hz), 1.31 (1H, dd, J=12.8, 3.0 Hz), 1.14 (9H, t, J=7.8 Hz), 1.08 (9H, s), 1.03 (9H, s), 1.01 (3H, d, J=5.4 Hz), 0.88 (1H, t, J=8.4 Hz), 0.82 (3H, q, J=7.8 Hz), 0.81 (3H, q, J=7.8 Hz), 0.57 (6H, q, J=7.8 Hz), 0.28 (3H, s), 0.28 (3H, s), 0.15 (6H, s) ppm. $^{13}$C NMR (150 MHz, C$_6$D$_6$) δ: 171.5, 159.8, 136.6, 131.0, 129.7, 128.8, 128.7, 128.4, 114.0, 97.4, 80.5, 79.8, 78.1, 75.4, 72.2, 71.9, 70.7, 70.2, 67.9, 66.2, 54.7, 39.0, 37.9, 37.5, 37.0, 35.7, 30.5, 26.3 (×6), 18.7, 18.5, 18.2, 18.0, 7.2, 4.9, −4.0, −4.4, −5.1, −5.1 ppm. FTIP (film): 3545, 2956, 2927, 2856, 1736, 1613, 1514, 1462, 1381, 1303, 1249, 1096, 1038, 944, 835, 777 cm$^{-1}$. HRMS (ESI) m/z: [M+Na]$^+$ calcd for C$_{46}$H$_{74}$O$_{10}$NaSi$_2^+$ 865.4713; found 865.4723. 18 (C-Michael product): [α]$_D^{22}$=−10.0 (c 0.95, CHCl$_3$). $^1$H NMR (600 MHz, C$_6$D$_6$) δ: 7.14 (1H, d, J=8.4 Hz), 6.82 (1H, d, J=9.0 Hz), 4.18 (1H, d, J=12.0 Hz), 4.18-4.15 (1H, m), 4.12 (1H, d, J=12.0 Hz), 4.06 (1H, dd, J=4.8, 1.8 Hz), 3.95-3.92 (1H, m), 3.83-3.78 (1H, m), 3.77-3.71 (1H, m), 3.34 (3H, s), 3.06 (1H, dd, J=3.0, 2.4 Hz), 2.91 (1H, dd, J=4.8, 2.4 Hz), 2.82 (1H, dd, J=3.0, 3.0 Hz), 2.21 (1H, dd, J=12.6, 2.4 Hz), 2.17 (1H, dd, J=19.2, 8.4 Hz), 2.02 (1H, dd, J=8.1, 3.3 Hz), 1.90-1.83 (3H, m), 1.80-1.74 (2H, m), 1.70 (1H, ddd, J=14.4, 9.6, 4.8 Hz), 1.56-1.52 (1H, m), 1.35-1.30 (2H, m), 1.03 (9H, s), 0.99 (9H, s), 0.81 (3H, d, J=6.6 Hz), 0.78 (1H, d, J=6.0 Hz), 0.16 (6H, s), 0.11 (3H, s), 0.10 (3H, s) ppm. $^{13}$C NMR (125 MHz, C$_6$D$_6$): δ 169.1, 159.8, 131.0, 129.3, 129.3, 114.1, 114.1, 103.9, 81.1, 80.5, 79.7, 72.9, 71.8, 71.1, 70.8, 67.7, 54.8, 40.7, 38.2, 35.1, 33.0, 30.6, 29.5, 29.2, 27.4, 26.2 (×6), 16.8, 14.4, −4.2, −4.5, −5.1, −5.2 ppm. FTIP (film): 3507, 2954, 2929, 2879, 2856, 1732, 1612, 1513, 1462, 1382, 1363, 1210, 1158, 1068, 1004, 944, 834, 777 cm$^{-1}$. HRMS (ESI) m/z: [M+Na]$^+$ calcd for C$_{46}$H$_{74}$O$_{11}$NaSi$_2^+$ 865.4713; found 865.4721.

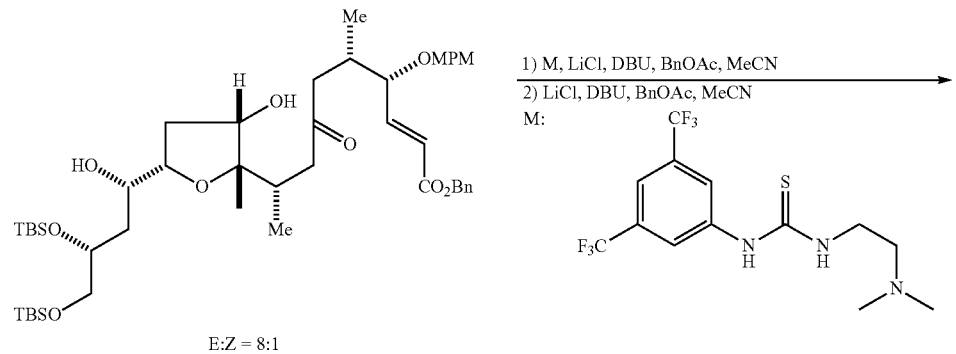

E:Z = 8:1

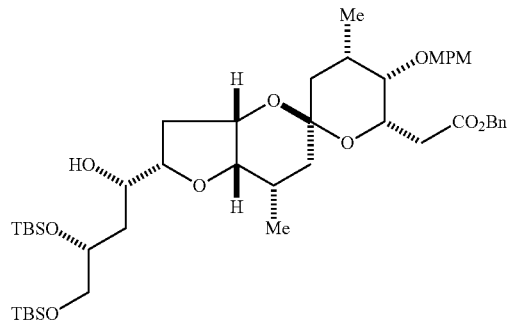

16

To a solution of 15 (60 mg, 0.071 mmol, 1 eq.), thiourea catalyst M (12.7 mg, 0.036 mmol, 0.5 eq.), BnOAc (12 μL, 0.0710 mmol, 1 eq.), and LiCl (30.2 mg, 0.711 mmol, 10 eq.) in MeCN (1.4 mL, 0.05 M) was added DBU (0.21 mL, 1.42 mmol, 20 eq.). After being stirred for 2 hr at room temperature, the reaction mixture was loaded to a SiO$_2$ pad and washed by 33% EtOAc in Hexanes. The mixture was concentrated and dissolved in 1.4 mL of dichloromethane before the addition of BnOAc (12 μL, 0.0710 mmol, 1 eq.), LiCl (30.2 mg, 0.711 mmol, 10 eq.) and DBU (0.21 mL, 1.42 mmol, 20 eq.). After being stirred for 24 hr at room temperature, the reaction mixture was loaded to a SiO$_2$ pad and washed by EtOAc. The mixture was concentrated and purified over SiO$_2$ (25% EtOAc in Hexanes) to afford 16 (55.8 mg, 0.066 mmol, 93%, dr>25:1).

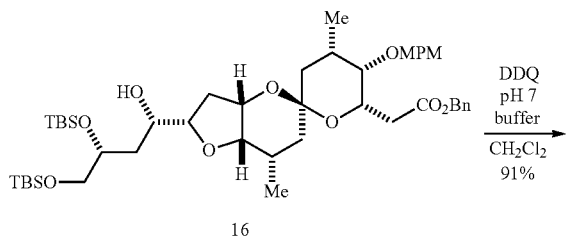

16

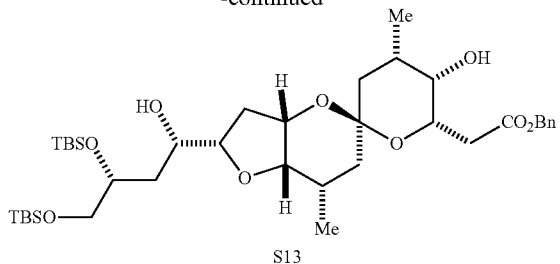

S13

To a solution of 16 (650 mg, 0.77 mmol) in dichloromethane (15 mL) and phosphate buffer (pH=7, 2.5 mL) was added DDQ (437 mg, 1.93 mmol). After being stirred for 40 min, the reaction was quenched with 10% aqueous $Na_2S_2O_3$ and saturated aqueous $NaHCO_3$. The mixture was extracted twice with DCM, dried over $Na_2SO_4$, filtered, and concentrated. The residue was purified by flash column chromatography on neutral silica gel (33% EtOAc in Hexanes) to afford S13 (518 mg, 0.72 mmol, 93%) as a colorless oil. S13: $[\alpha]D=-31.2$ (c 4.0, $CHCl_3$). $^1$H NMR (600 MHz, $C_6D_6$) δ: 7.23 (2H, d, J=7.1 Hz), 7.11 (2H, dd, J=7.5, 7.1 Hz), 7.06 (1H, dd, J=7.5, 7.5 Hz), 5.09 (1H, d, J=12.0 Hz), 5.00 (1H, d, J=12.0 Hz), 4.22-4.18 (2H, m), 4.02 (1H, ddd, J=6.6, 3.6, 1.2 Hz), 3.95-3.74 (4H, m), 3.26 (1H, d, J=2.4 Hz), 3.22 (1H, dd, J=2.4, 2.4 Hz), 2.87 (1H, d, J=8.4 Hz), 2.78 (1H, dd, J=15.9, 10.9 Hz), 2.21 (1H, dd, J=14.6, 3.0 Hz), 2.11-2.06 (1H, m), 2.00-1.92 (3H, m), 1.85-1.78 (1H, m), 1.49 (1H, t, J=12.9 Hz), 1.30 (1H, dd, J=14.4, 4.8 Hz), 1.17 (1H, dd, J=14.4, 4.8 Hz), 1.15 (1H, d, J=4.0 Hz), 1.11 (1H, d, J=12.6 Hz), 1.00 (3H, d, J=6.6 Hz), 0.99 (9H, s), 0.96 (9H, s), 0.75 (3H, d, J=6.6 Hz), 0.15 (3H, s), 0.12 (3H, s), 0.08 (3H, s), 0.07 (3H, s) ppm. $^{13}$C NMR (150 MHz, $C_6D_6$) δ: 171.4, 128.8, 128.7, 128.4, 97.2, 80.5, 79.6, 72.1, 71.9, 70.7, 70.1, 69.9, 67.8, 66.2, 38.9, 37.3, 37.0, 37.0, 35.6, 30.0, 26.3 (×6), 18.6, 18.4, 18.2, 17.5, −4.1, −4.5, −5.1, −5.1 ppm. FTIP (film): 3560, 2955, 2928, 2856, 1737, 1471, 1376, 1361, 1252, 1099, 1016, 835, 777 cm$^{-1}$. HRMS (ESI) m/z: $[M+Na]^+$ calcd for $C_{38}H_{66}O_9NaSi_{2+}$ 745.4138; found 745.4143.

hr at room temperature, the reaction was quenched with MeOH. The mixture was concentrated and purified by flash column chromatography on neutral silica gel (10% EtOAc in Hexanes) to give S14 (632 mg, 0.66 mmol, 96%) as a colorless oil. S14: $[\alpha]D=-44.3$ (c 1.0, $CHCl_3$). $^1$H NMR (600 MHz, $C_6D_6$) δ: 7.23 (2H, d, J=7.1 Hz), 7.11 (2H, dd, J=7.5, 7.1 Hz), 7.06 (1H, dd, J=7.5, 7.5 Hz), 5.09 (1H, d, J=12.0 Hz), 5.00 (1H, d, J=12.0 Hz), 4.23 (1H, dd, J=5.7, 2.1 Hz), 4.20-4.16 (1H, m), 4.11 (1H, dd, J=9.6, 2.4 Hz), 4.08 (1H, ddd, J=9.6, 7.2, 3.0 Hz), 3.83 (1H, ddd, J=8.4, 5.4, 5.4 Hz), 3.76 (1H, dd, J=10.2, 3.0 Hz), 3.70 (1H, dd, J=10.2, 5.4 Hz), 3.21 (1H, s), 3.19 (1H, d, J=3.0 Hz), 2.84 (1H, dd, J=15.6, 10.2 Hz), 2.25 (1H, dd, J=15.0, 3.6 Hz), 2.22-2.16 (1H, m), 2.15-2.11 (1H, m), 1.96 (1H, ddd, J=13.8, 8.4, 3.0 Hz), 1.88 (1H, ddd, J=13.6, 9.6, 6.0 Hz), 1.83 (1H, dd, J=13.8, 6.0 Hz), 1.73 (1H, ddd, J=13.8, 9.0, 4.2 Hz), 1.59 (1H, t, J=13.2 Hz), 1.52 (1H, t, J=13.2 Hz), 1.40 (1H, t, J=4.2 Hz), 1.37 (1H, t, J=4.2 Hz), 1.06 (9H, t, J=7.8 Hz), 1.04 (9H, s), 1.00 (3H, d, J=6.6 Hz), 0.98 (9H, s), 0.92 (1H, t, J=8.4 Hz), 0.87 (3H, d, J=7.2 Hz), 0.74 (6H, t, J=8.4 Hz), 0.53 (6H, t, J=8.8 Hz), 0.22 (3H, s), 0.22 (3H, s), 0.09 (6H, s) ppm. $^{13}$C NMR (150 MHz, $C_6D_6$) δ: 171.4, 136.7, 128.9, 128.7, 128.4, 97.0, 81.4, 80.3, 72.2, 72.1, 71.7, 71.5, 70.3, 68.3, 66.3, 38.3, 38.2, 37.6, 37.6, 35.4, 30.7, 26.3 (×6), 18.6, 18.4, 18.2, 18.2, 7.4, 7.3, 5.8, 5.7, −4.1, −4.2, −5.1, −5.2 ppm. FTIP (film): 2954, 2928, 2877, 2857, 1740, 1471, 1388, 1361, 1211, 1160, 1099, 1081, 1039, 944, 834 cm$^{-1}$. HRMS (ESI) m/z: $[M+Na]^+$ calcd for $C_{50}H_{96}O_8NaSi_4^+$ 959.6074; found 959.6070.

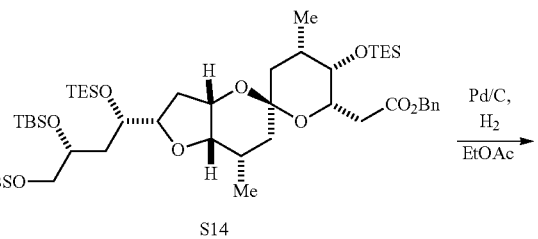

S14

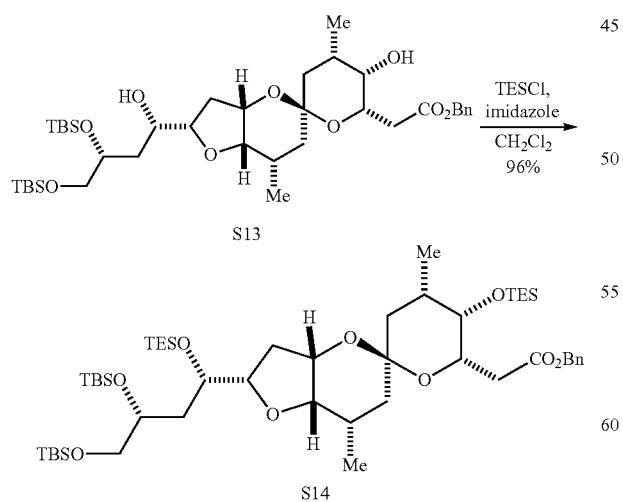

S13

S14

To a solution of S13 (495 mg, 0.685 mmol) in dichloromethane (7 mL) was added imidazole (233 mg, 3.43 mmol) and TESCl (0.35 mL, 2.06 mmol). After being for 2

S15

To a solution of S14 (330 mg, 0.347 mmol) in EtOAc (3.5 mL) was added Pd/C (33 mg, 10 wt %). The reaction flask was filled with $H_2$ with lab balloon and stirred for 45 min at room temperature. The mixture was passed through a pad of $SiO_2$ with EtOAc, and concentrated. Without further purification the crude acid S15 was used in the next reaction.

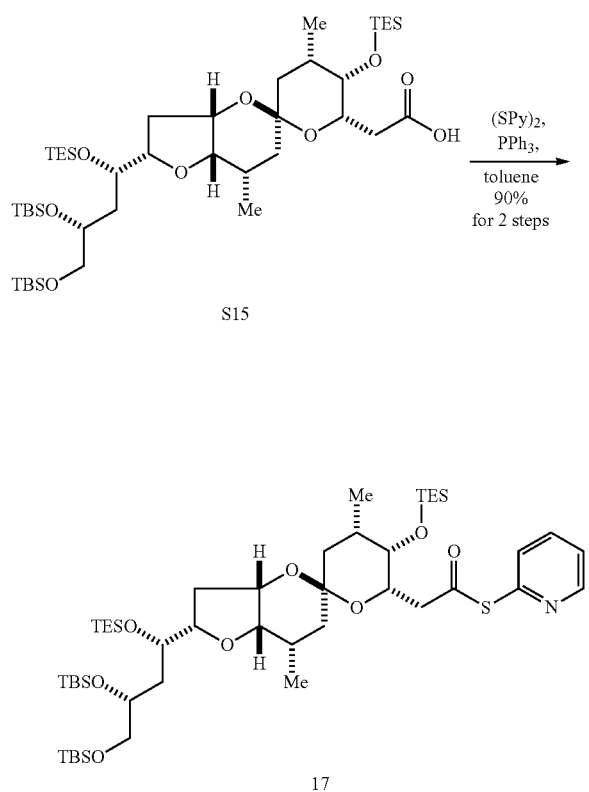

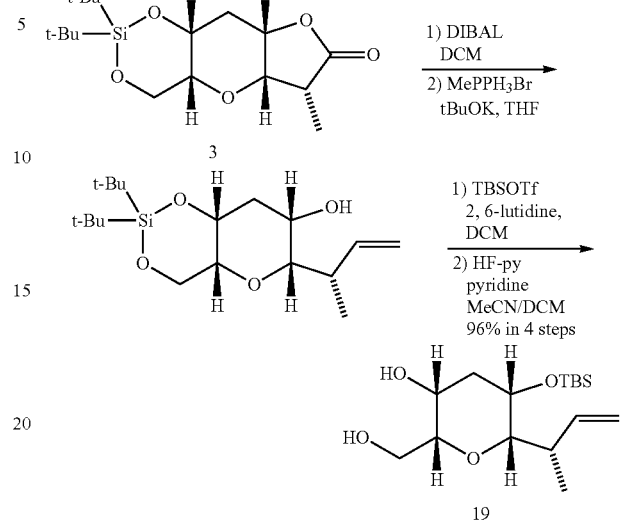

Homohalichondrin Left Halves

To a solution of crude acid S15 (estimated as 0.347 mmol) in toluene (3.5 mL) was added PPh$_3$ (118 mg, 0.45 mmol, 1.3 eq.) and (PyS)$_2$ (107 mg, 0.49 mmol, 1.4 eq.).[2] After being stirred for 3 hr at room temperature, the reaction mixture was concentrated. Flash column chromatography of the residue (neutral SiO$_2$, hexanes/EtOAc=I/O, 10/1, 5/1) to give 17 (297 mg, 0.312 mmol, 90% for 2 steps) as a colorless oil. 17: $[\alpha]^2$=−75.7 (c 0.4, CHCl$_3$). $^1$H NMR (600 MHz, C$_6$D$_6$) δ: 8.32 (1H, dd, J=4.2, 1.8 Hz), 7.54 (1H, d, J=7.8 Hz), 6.96 (1H, ddd, J=7.8, 7.8, 1.4 Hz), 6.47 (1H, dd, J=7.8, 4.2 Hz), 4.34 (1H, dd, J=6.0, 1.8 Hz), 4.24-4.21 (1H, m), 4.17 (1H, dd, J=10.2, 2.4 Hz), 4.12 (1H, dd, J=9.0, 6.6, 3.0 Hz), 3.85 (1H, dt, J=9.0, 6.0 Hz), 3.80 (1H, dd, J=10.8, 3.0 Hz), 3.74 (1H, dd, J=10.8, 4.0 Hz), 3.36 (1H, dd, J=2.4, 2.4 Hz), 3.23 (1H, dd, J=14.7, 9.6 Hz), 3.15 (1H, s), 2.59-2.55 (1H, m), 2.53 (1H, dd, J=14.4, 3.0 Hz), 2.16-2.11 (1H, m), 2.00 (1H, ddd, J=13.8, 9.0, 3.0 Hz), 1.94 (1H, ddd, J=13.8, 9.0, 5.4 Hz), 1.88 (1H, dd, J=13.8, 6.0 Hz), 1.77 (1H, ddd, J=13.2, 8.4, 4.2 Hz), 1.65 (1H, dd, J=13.2, 12.6 Hz), 1.60 (1H, dd, J=13.2, 12.6 Hz), 1.52 (1H, dd, J=13.2, 4.8 Hz), 1.44 (1H, dd, J=12.9, 3.4 Hz), 1.10 (9H, t, J=8.4 Hz), 1.09 (9H, s), 1.07 (3H, d, J=7.2 Hz), 1.03 (9H, s), 0.99 (9H, t, J=7.8 Hz), 0.91 (3H, d, J=6.6 Hz), 0.77 (6H, q, J=7.8 Hz), 0.57 (6H, q, J=7.8 Hz), 0.27 (6H, s), 0.137 (3H, s), 0.136 (3H, s) ppm. $^{13}$C NMR (125 MHz, C$_6$D$_6$) δ: 194.7, 152.6, 150.6, 136.5, 129.8, 123.2, 97.2, 81.4, 80.4, 72.3, 72.0, 71.9, 71.5, 70.5, 68.3, 47.6, 38.2, 37.7, 37.6, 35.3, 30.7, 26.3 (×3), 26.3 (×3), 18.6, 18.5, 18.5, 18.3, 7.4 (×6), 5.8 (×2), 5.7 (×6), −4.0, −4.2, −5.1, −5.2 ppm. FTIR (film): 2956, 2926, 2877, 1716, 1573, 1471, 1251, 837 775, 775, 728 cm$^{-1}$. HRMS (ESI) m/z: [M+H]$^+$ calcd for C$_{48}$H$_{92}$NO$_8$SSi$_4$, 954.5615; found, 954.5612.

To a stirred solution of lactone 3 (5.01 g, 14.6 mmol, 1 eq.) in CH$_2$Cl$_2$ (70 mL) was added DIBAL solution (19.0 mL of 1 M in Hexanes, 19.0 mmol, 1.3 eq.) at −78° C. over 15 min. After being stirred for 15 min at the same temperature, MeOH (2.0 mL), sat. Rochelle's salt aq. (70 mL), and EtOAc (70 mL) were added sequentially. The resulting solution was stirred for 2 h at room temperature to give a clear biphasic solution. The organic layer was separated and the aqueous layer was extracted with EtOAc. The combined organic layer was dried over Na$_2$SO$_4$, filtered, and concentrated under reduced pressure to give a crude lactol as a colorless solid, which was used in the next reaction without further purification.

To a stirred suspension of MePPh$_3$Br (21.0 g, 58.8 mmol, 4 eq.) in THF (50 mL) was added tBuOK (4.9 g, 43.7 mmol, 3 eq.) at 0° C. After being stirred for 1 h at room temperature, the yellow solution was re-cooled to 0° C. To this ylide solution was added a solution of the crude lactol (calculated as 14.6 mmol, 1 eq.) in THF (25 mL). After being stirred for 20 min at room temperature, the reaction was quenched with sat. NH$_4$Cl aq. (50 mL) and H$_2$O (20 mL). After adding Et$_2$O (100 mL), the organic layer was separated. The aqueous layer was extracted with Et$_2$O. The combined organic layer was dried over Na$_2$SO$_4$, filtered, and concentrated under reduced pressure. The obtained crude material was dissolved in minimum amount of CH$_2$Cl$_2$ (ca. 5 mL) and passed through a pad of silica gel (20% EtOAc in Hexanes). The filtrate was concentrated under reduced pressure to give a crude alcohol as a colorless solid, which was used in the next reaction without further purification.

To a stirred solution of the crude alcohol (calculated as 14.6 mmol, 1 eq.) and 2,6-lutidine (3.4 mL, 29.2 mmol, 2 eq.) in CH$_2$Cl$_2$ (70 mL) was added TBSOTf (4.4 mL, 19.2 mmol 1.3 eq.) at 0° C. After being stirred for 30 min at 0° C., the ice bath was removed and the reaction mixture was stirred for additional 30 min at room temperature. The reaction was quenched with brine and diluted with Et$_2$O (200 mL). The organic layer was separated and washed with 1N HCl, sat. NaHCO$_3$ aq., and brine, sequentially. The organic layer was dried over Na$_2$SO$_4$, filtered, and concentrated under reduced pressure to give a crude TBS ether as pale yellow oil, which was used in the next reaction without further purification.

A buffered HF.Py solution was prepared by adding HF.Py (3.0 mL of ~70% HF in pyridine, ca. 114 mmol, ca. 8 eq.) to a mixture of pyridine (15 mL) and MeCN (20 mL) at 0° C. To a stirred solution of the crude TBS ether (calculated as 14.6 mmol, 1 eq.) in MeCN (50 mL) and $CH_2Cl_2$ (30 mL) was added the buffered HF.Py solution at −10° C. over 15 min. After being stirred for 30 min at the same temperature, the reaction was warmed up to room temperature. After being stirred for 1 h at the same temperature, the mixture was cooled to 0° C. and quenched with sat. $NaHCO_3$ aq. carefully. The organic layer was separated and the aqueous layer was extracted with EtOAc. The combined organic layer was dried over $Na_2SO_4$, filtered, and concentrated under reduced pressure. The obtained crude material was purified by flash column chromatography on silica gel (25% then 50% EtOAc in Hexanes) to give diol 19 (4.43 g, 14.0 mmol, 96% for 4 steps) as a colorless amorphous solid. 19: $[\alpha]^{20}_D$ −36.7 (c 1.06, $CHCl_3$). $^1$H NMR (600 MHz, $C_6D_6$) δ: 6.01 (1H, ddd, J=16.9, 10.5, 6.2 Hz), 5.10 (1H, d, J=16.9 Hz), 5.05 (1H, d, J=10.5 Hz), 4.04 (1H, ddd, J=11.1, 7.8, 3.0 Hz), 3.77 (1H, ddd, J=11.1, 9.2, 4.4 Hz), 3.57 (1H, brs), 3.51-3.46 (2H, m), 3.18 (1H, dd, J=7.5, 4.5 Hz), 2.68-2.66 (2H, m), 2.01 (1H, dd, J=8.4, 3.0 Hz), 1.95 (1H, ddd, J=14.6, 2.7, 2.7 Hz), 1.12 (1H, ddd, J=14.6, 2.7, 2.7 Hz), 0.90 (9H, s), 0.82 (3H, d, J=5.4 Hz), 0.07 (3H, s), −0.06 (3H, s) ppm. $^{13}$C NMR (125 MHz, $C_6D_6$) δ: 141.9, 114.0, 84.2, 81.7, 66.9, 65.7, 63.4, 38.1, 37.1, 25.9, 18.2, 15.7, −3.8, −5.1 ppm. FTIR (film): 3527, 3259, 2960, 2929, 2858, 1256, 1090, 1056, 879, 776 cm$^{-1}$. HRMS (ESI) m/z: [M+H]$^+$ calcd for $C_{16}H_{33}O_4Si$, 317.2143; found, 317.2145.

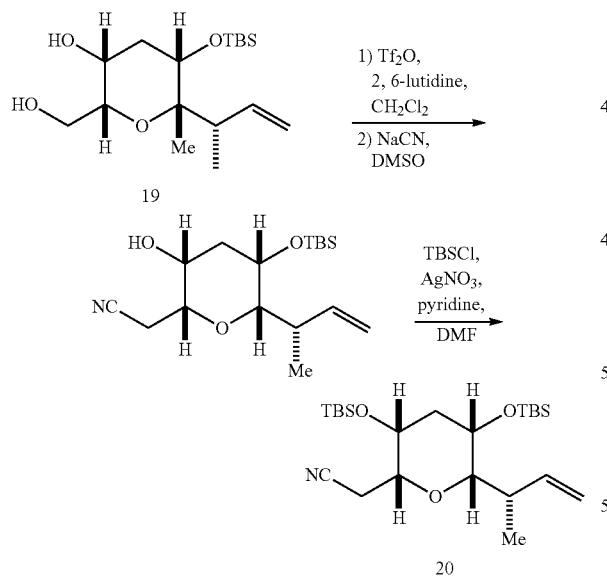

To a stirred solution of diol 19 (7.30 g, 23.1 mmol, 1 eq.) and 2,6-lutidine (10.8 mL, 92.7 mmol, 4 eq.) in $CH_2Cl_2$ (150 mL) was added $Tf_2O$ (4.7 mL, 27.9 mmol, 1.2 eq.) at −78° C. After being stirred for 10 min at the same temperature, the reaction was quenched with MeOH (1.0 mL) and brine (100 mL). After adding $Et_2O$ (500 mL), the organic layer was separated from the aqueous layer and washed with 1N HCl and brine sequentially. The organic layer was dried over $Na_2SO_4$, filtered, and concentrated under reduced pressure to give a crude triflate as wine red oil, which was dissolved in DMSO (150 mL) immediately without further purification.

To the DMSO solution of crude triflate (calculated as 23.1 mmol, 1 eq.) was added NaCN (11.3 g, 230 mmol, 10 eq.) at room temperature. After being stirred for 1 h at the same temperature, the reaction mixture was filtered through a paper and the filter cake was washed with EtOAc thoroughly. The filtrate was washed with $H_2O$ and brine. The organic layer was dried over $Na_2SO_4$, filtered, and concentrated under reduced pressure. The residue was passed through a pad of silica gel (20% EtOAc in Hexanes) to give a crude nitrile as a pink oil, which was used in the next step without further purification.

To a stirred solution of the crude nitrile (calculated as 23.1 mmol, 1 eq.) and pyridine (15.0 mL, 186 mmol, 8 eq.) in DMF (80 mL) were added TBSCl (10.4 g, 69.0 mmol, 3 eq.) and $AgNO_3$ (11.8 g, 69.5 mmol, 3 eq.) at 0° C. After being stirred for 30 min at 0° C., the cooling bath was removed and the reaction mixture was stirred for 18 h at room temperature. The reaction mixture was diluted with $Et_2O$ (100 mL) and filtered through a bed of Celite. The filter cake was washed thoroughly with $Et_2O$. The filtrate was washed with $H_2O$ and brine. The organic layer was dried over $Na_2SO_4$, filtered, and concentrated under reduced pressure. The obtained crude material was purified by flash column chromatography on silica gel (0% then 10% EtOAc in Hexanes) to give bis-TBS 20 (8.87 g, 20.2 mmol, 87% for 3 steps) as a colorless solid. 20: $[\alpha]^{20}_D$ −6.7 (c 1.07, $CHCl_3$). MP: 65-67° C. (recrystallized from $Et_2O$). $^1$H NMR (600 MHz, $C_6D_6$) δ: 6.31 (1H, ddd, J=17.4, 10.8, 6.6 Hz), 5.19 (1H, d, J=10.8 Hz), 5.15 (1H, d, J=17.4 Hz), 3.52 (1H, brs), 3.23-3.22 (1H, m), 3.11 (1H, ddd, J=8.0, 5.9, 2.0 Hz), 2.82-2.77 (1H, m), 2.66 (1H, d, J=9.6 Hz), 2.40 (1H, dd, J=16.8, 7.8 Hz), 2.07 (1H, dd, J=16.8, 5.4 Hz), 1.80 (1H, ddd, J=15.4, 2.7, 2.7 Hz), 1.32 (1H, ddd, J=15.4, 4.7, 4.7 Hz), 0.98 (9H, s), 0.93 (3H, d, J=6.6 Hz), 0.89 (9H, s), 0.10 (3H, s), 0.01 (3H, s), −0.01 (3H, s), −0.07 (3H, s) ppm. $^{13}$C NMR (125 MHz, $C_6D_6$) δ: 141.7, 117.9, 113.9, 85.2, 77.1, 65.0, 64.4, 38.3, 37.2, 26.4, 20.6, 18.4, 18.3, 15.9, −2.5, −3.5, −5.00, −5.03 ppm. FTIR (film): 2955, 2930, 2886, 2857, 1473, 1388, 1254, 1139, 1099, 1022, 835, cm$^{-1}$. HRMS (ESI) m/z: [M+Na]$^+$ calcd for $C_{23}H_{45}NO_3Si_2Na$, 462.2830; found, 462.2831.

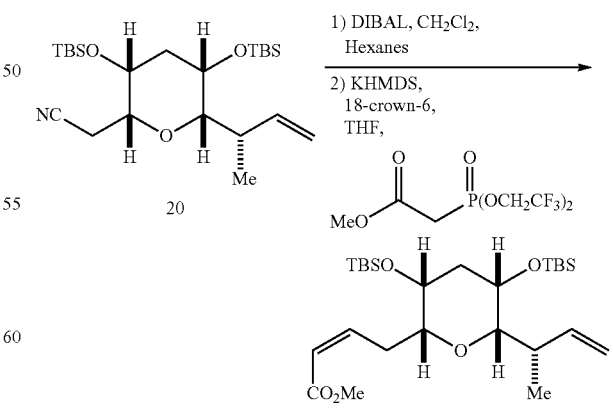

To a stirred solution of bis-TBS 20 (8.77 g, 19.9 mmol, 1 eq.) in Hexanes (150 mL) and $CH_2Cl_2$ (50 mL) was added DIBAL solution (22.0 mL of 1 M in Hexanes, 22.0 mmol, 1.1 eq.) at −78° C. After being stirred for 30 min at the same temperature, the reaction was quenched with MeOH (1.0 mL) and sat. Rochelle's salt aq. (200 mL). The mixture was stirred for 1.5 h at room temperature to give a clear biphasic mixture. The organic layer was separated and the aqueous layer was extracted with Et$_2$O. The combined organic layer was dried over Na$_2$SO$_4$, filtered, and concentrated under reduced pressure. The obtained crude material was passed through a pad of silica gel (20% EtOAc in Hexanes) to give a crude aldehyde as a colorless oil, which was used in the next reaction without further purification.

To a stirred solution of methyl bis(2,2,2-trifluoroethyl) phosphonoacetate (6.3 mL, 29.8 mmol, 1.5 eq.) and 18-crown-6 ether (42.0 g, 159 mmol, 8 eq.) in THF (400 mL) was added KHMDS solution (60 mL of 0.5 M in toluene, 30 mmol, 1.5 eq.) at −78° C. After being stirred for 30 min at −78° C., the resulting mixture was added to a solution of the crude aldehyde (calculated as 19.9 mmol, 1 eq.) in THF (100 mL) and stirred for 30 min at the same temperature. The reaction was quenched with sat. NH$_4$Cl aq. and diluted with Hexanes (400 mL). The organic layer was separated and the aqueous layer was extracted with Et$_2$O/Hexanes (1:1). The combined organic layer was dried over Na$_2$SO$_4$, filtered, and concentrated under reduced pressure. The obtained crude material was purified by flash column chromatography on silica gel (0% then 2% EtOAc in Hexanes) to give α,β-unsaturated ester S16 (8.37 g, 16.8 mmol, 84% for 2 steps) as a colorless oil. Only Z-isomer was obtained exclusively. S16: [α]$^{20}_D$ +42.0 (c 1.03, CHCl$_3$). $^1$H NMR (600 MHz, C$_6$D$_6$) δ: 6.67-6.63 (1H, m), 6.16 (1H, ddd, J=17.6, 10.2, 6.6 Hz), 5.91 (1H, dd, J=11.1, 1.5 Hz), 5.11 (1H, dd, J=17.6, 1.5 Hz), 5.09 (1H, dd, J=10.2, 1.5 Hz). 3.60 (1H, d, 1.8 Hz), 3.454-3.447 (1H, m), 3.34 (3H, s), 3.34-3.30 (1H, m), 3.13 (1H, d, 10.8 Hz), 3.03-2.97 (1H, m), 2.89-2.83 (1H, m), 2.68 (1H, d, 9.0 Hz), 1.92 (1H, d, 14.6 Hz), 1.45 (1H, ddd, 14.6, 4.5, 4.5 Hz), 1.03 (9H, s), 1.01 (9H, s), 0.93 (3H, d, J=7.2 Hz), 0.19 (3H, s), 0.16 (3H, s), 0.12 (3H, s), 0.04 (3H, s) ppm. $^{13}$C NMR (125 MHz, C$_6$D$_6$) δ: 166.6, 149.3, 142.6, 119.9, 113.4, 85.3, 81.0, 66.7, 64.7, 50.5, 39.0, 37.6, 32.5, 26.7, 26.4, 18.6, 18.5, 15.9, −2.3, −3.6, −4.6, −5.0 ppm. FTIR (film): 2951, 2929, 2857, 1723, 1644, 1253, 1091, 951, 836, 771 cm$^{-1}$. HRMS (ESI) m/z: [M+Na]$^+$ calcd for C$_{26}$H$_{50}$O$_5$Si$_2$Na, 521.3089; found, 521.3087.

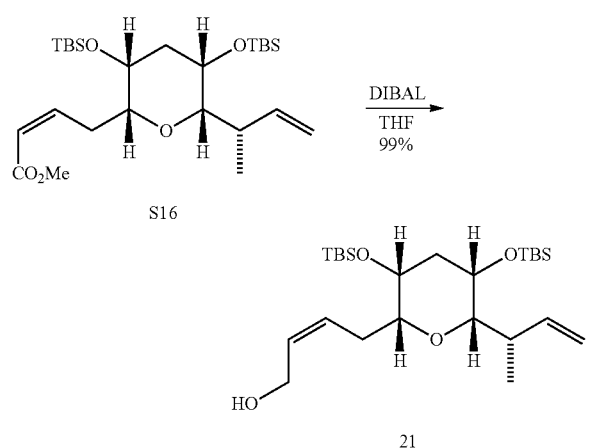

S16

To a stirred solution of ester S16 (8.30 g, 16.6 mmol, 1 eq.) in THF (200 mL) was added DIBAL solution (66 mL of 1 M in hexanes, 66.0 mmol, 4 eq.) at −78° C. After being stirred for 10 min at the same temperature, the reaction mixture was warmed to 0° C. and stirred for additional 30 min. The reaction was quenched with acetone (5.0 mL) and sat. Rochelle's salt aq. (200 mL). The resulting mixture was stirred for 2 h at room temperature to give a clear biphasic solution. The organic layer was separated and the aqueous layer was extracted with EtOAc. The combined organic layer was dried over Na$_2$SO$_4$, filtered, and concentrated under reduced pressure. The obtained crude material was purified by flash column chromatography on silica gel (11% EtOAc in Hexanes) to give allyl alcohol 21 (7.72 g, 16.4 mmol, 99%) as a colorless solid. 21: [ ]$^{20}_D$ −16.6 (c 1.00, CHCl$_3$). MP: 60-62° C. (recrystallized from Et$_2$O). $^1$H NMR (600 MHz, C$_6$D$_6$) δ: 6.24 (1H, ddd, J=17.4, 10.5, 6.9 Hz), 5.83-5.81 (1H, m), 5.77-5.74 (1H, m), 5.18-5.14 (2H, m), 4.23-4.20 (1H, m), 4.14-4.10 (1H, m), 3.62 (1H, d, J=1.2 Hz), 3.349-3.345 (1H, m), 3.05 (1H, d, J=9.6 Hz), 2.89-2.80 (2H, m), 2.72 (1H, d, J=9.0 Hz), 1.96 (1H, dd, J=14.4, 6.6 Hz), 1.91 (1H, ddd, J=14.6, 2.4, 2.4 Hz), 1.78-1.77 (1H, m), 1.49 (1H, ddd, J=14.6, 4.7, 4.7 Hz), 1.01 (18H, s), 0.95 (3H, d, J=7.2 Hz), 0.15 (3H, s), 0.08 (3H, s), 0.05 (3H, s), 0.004 (3H, s) ppm. $^{13}$C NMR (125 MHz, C$_6$D$_6$) δ: 142.4, 131.4, 129.2, 113.6, 85.1, 80.6, 66.7, 65.0, 58.8, 39.1, 37.5, 30.5, 26.5, 26.4, 18.53, 18.50, 16.0, −2.3, −3.5, −4.7, −5.0 ppm. FTIR (film): 2952, 2929, 2855, 1463, 1252, 1138, 1003, 833, 768 cm$^{-1}$. HRMS (ESI) m/z: [M+Na]$^+$ calcd for C$_{25}$H$_{50}$O$_4$Si$_2$Na, 493.3140; found, 493.3142.

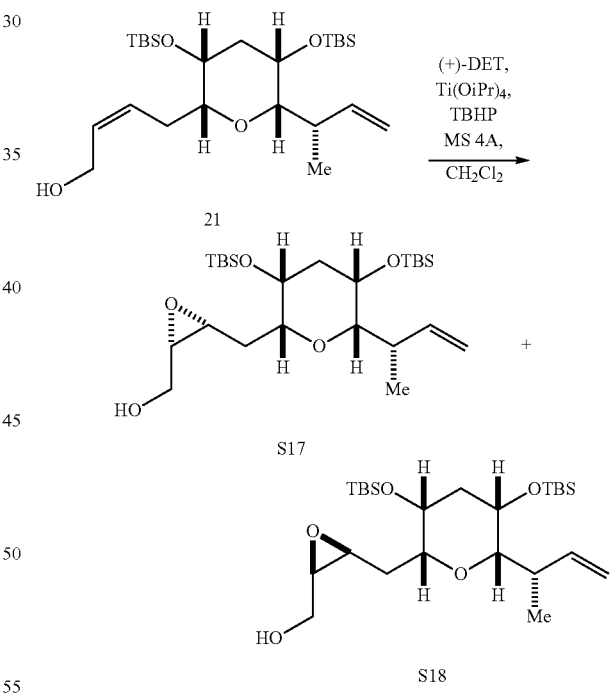

To a stirred suspension of molecular sieve 4A (1.5 g, activated powder) in CH$_2$Cl$_2$ (50 mL) were added Ti(OiPr)$_4$ (0.72 mL, 2.43 mmol, 15 mol %) and a solution of (+)-DET (0.55 mL, 3.21 mmol, 20 mol %) in CH$_2$Cl$_2$ (5.0 mL) at −20° C. After being stirred for 15 min at the same temperature, to the reaction mixture was added TBHP solution (4.5 mL of ~5.5 M in decane over molecular sieve 4A, ca. 24.8 mmol, ca. 1.5 eq.) and stirred for 30 min. In a separate flask, a solution of allyl alcohol 21 (7.65 g, 16.2 mmol, 1 eq.) in CH$_2$Cl$_2$ (80 mL) was cooled to −78° C. To this cooled allyl alcohol solution was added the above catalyst solution via cannula and rinsed with CH$_2$Cl$_2$ (30 mL). After being stirred for 10 min at −78° C., the reaction mixture was warmed to −10° C. and stirred for 15 h. The reaction flask was removed from cooling bath, and Et$_2$O (200 mL) was added to the cold reaction mixture with stirring, followed by addition of sat. Na$_2$SO$_4$ aq. (2.5 mL). After being stirred for 2 h at room temperature, the mixture was filtered through a pad of Celite, and the filter cake was washed with EtOAc thoroughly. After removal of solvent under reduced pressure, the obtained crude material was purified by flash column chromatography on silica gel (0%, 5%, 10%, 11%, then 20% EtOAc in Hexanes) to give epoxy alcohol S17 (6.81 g, 14.0 mmol, 86%) as a colorless solid and its undesired diastereomer S18 (862 mg, 1.77 mmol, 11%) as a colorless solid. S17: [α]$^{20}_D$ −26.0 (c 1.08, CHCl$_3$). MP: 78-79° C. (recrystallized from Hexanes/EtOAc). $^1$HNMR (600 MHz, C$_6$D$_6$) δ: 6.09-6.03 (1H, m), 5.21 (1H, d, J=18.0 Hz), 5.11 (1H, d, J=10.8 Hz), 3.92-3.88 (1H, m), 3.65 (1H, ddd, J=11.4, 7.8, 3.0 Hz), 3.58 (1H, s), 3.239-3.235 (1H, m), 3.17-3.12 (2H, m), 3.08 (1H, J=4.1, 4.1, 4.1 Hz), 2.78-2.71 (2H, m), 2.64 (1H, d, J=9.6 Hz), 2.13 (1H, ddd, J=14.1, 11.4, 8.4 Hz), 1.84 (1H, ddd, J=15.0, 2.4, 2.4 Hz), 1.57-1.53 (1H, m), 1.41 (1H, ddd, J=15.0, 4.2, 4.2 Hz), 1.01 (9H, s), 0.98 (9H, s), 0.90 (3H, d, J=6.6 Hz), 0.13 (3H, s), 0.03 (3H, s), 0.02 (3H, s), −0.06 (3H, s) ppm. $^{13}$C NMR (125 MHz, C$_6$D$_6$) δ: 142.1, 114.1, 85.35, 85.33, 78.8, 66.2, 64.5, 60.9, 56.1, 54.7, 38.8, 37.6, 30.3, 26.5, 26.3, 18.4, 16.0, −2.3, −3.7, −4.8, −5.1 ppm. FTIR (film): 2952, 2929, 2856, 1252, 1011, 833, 768 cm$^{-1}$. HRMS (ESI) m/z: [M+NH$_4$]$^+$ calcd for C$_{25}$H$_{54}$NO$_5$Si$_2$, 504.3535; found, 504.3527. Diastereomer S18: [α]$^{20}_D$ +11.9 (c 1.00, CHCl$_3$). MP: 89-91° C. (recrystallized from Et$_2$O). $^1$H NMR (600 MHz, C$_6$D$_6$) δ: 6.19 (1H, ddd, J=17.4, 10.7, 6.9 Hz), 5.17 (1H, ddd, J=17.4, 1.8, 1.8 Hz), 5.12 (1H, d, J=10.7 Hz), 3.70-3.68 (1H, m), 3.65 (1H, ddd, J=11.4, 6.0, 6.0 Hz), 3.59 (1H, ddd, J=11.4, 5.4, 5.4 Hz), 3.49 (1H, dd, J=8.4, 4.8 Hz), 3.44 (1H, ddd, J=7.8, 4.2, 4.2 Hz), 3.41 (1H, ddd, J=8.4, 3.6, 3.6 Hz), 3.02 (1H, dd, J=10.8, 5.4 Hz), 2.89-2.83 (1H, m), 2.76 (1H, dd, J=10.2, 2.4 Hz), 2.44 (1H, ddd, J=13.8, 8.4, 5.1 Hz), 1.95 (1H, ddd, J=14.4, 4.8, 3.6 Hz), 1.65 (1H, ddd, J=14.4, 4.8, 4.8 Hz), 1.57 (1H, ddd, J=14.4, 7.8, 3.6 Hz), 1.59-1.50 (1H, m), 1.04 (9H, s), 0.98-0.97 (12H, m), 0.16 (3H, s), 0.07 (3H, s), 0.06 (3H, s), 0.00 (3H, s) ppm. $^{13}$C NMR (125 MHz, C$_6$D$_6$) δ: 142.3, 113.7, 84.4, 79.2, 66.5, 65.3, 60.7, 56.0, 54.5, 39.1, 37.4, 30.9, 26.4, 26.3, 18.5, 18.4, 15.9, −2.5, −3.8, −4.8, −5.0 ppm. FTIR (film): 3448, 2953, 2929, 2857, 1463, 1253, 1128, 1088, 1005, 902, 833, 770, 735 cm$^{-1}$. HRMS (ESI) m/z: [M+Na]$^+$ calcd for C$_{25}$H$_{50}$O$_5$Si$_2$Na, 509.3089; found, 509.3088.

To a stirred solution of epoxy alcohol S17 (6.73 g, 13.8 mmol, 1 eq.) in THF (20.0 mL) were added molecular sieves 4A (4.0 g, activated pellet) and TBAF solution (80.0 mL of 1 M in THF, 80.0 mmol, 5.8 eq.) at room temperature. After being stirred for 12 h at the same temperature, CaCO$_3$ (20.0 g), DOWEX 50WX8-400 (60.0 g), MeOH (10 mL), and THF (100 mL) were added sequentially. After being stirred for 1.5 h at room temperature, the mixture was filtered through a pad of Celite, and the filtrand was washed with EtOAc thoroughly. After removal of solvent under reduced pressure, the obtained crude material was purified by flash column chromatography on silica gel (CH$_2$Cl$_2$ then EtOAc) to give triol 22 (3.73 g, 13.3 mmol, 96%) as a colorless amorphous solid. 22: [α]$^{20}_D$ −64.8 (c 1.00, CHCl$_3$). $^1$H NMR (600 MHz, CD$_3$OD) δ: 5.96 (1H, ddd, J=17.5, 10.5, 7.1 Hz), 5.03 (1H, ddd, 17.5, 1.6, 1.6 Hz), 4.97 (1H, ddd, J=10.5, 1.6, 1.5 Hz), 4.35 (1H, ddd, 9.5, 6.9, 4.1 Hz), 4.05 (1H, d, J=3.0 Hz), 3.93 (1H, s), 3.73 (1H, dd, J=3.0, 3.0 Hz), 3.61 (1H, dd, J=11.1, 5.7 Hz), 3.57 (1H, dd, 11.1, 5.7 Hz), 3.46 (1H, dd, J=6.0, 6.0, 4.2 Hz), 3.01 (1H, d, J=9.0 Hz), 2.50-2.44 (1H, m), 2.31 (1H, ddd, J=15.5, 2.4, 2.4 Hz), 2.09 (1H, ddd, 13.2, 9.2, 3.8 Hz), 2.04 (1H, dd, J=13.2, 6.6 Hz), 1.89 (1H, ddd, J=15.5, 3.8, 3.8 Hz), 0.99 (3H, d, J=7.2 Hz) ppm. $^{13}$C NMR (125 MHz, CD$_3$OD) δ: 143.5, 113.8, 82.8, 79.3, 79.0, 77.4, 74.9, 64.8, 64.6, 39.4, 36.6, 33.1, 15.6 ppm. FTIR (film): 3387, 2935, 2886, 1638, 1415, 1093, 1032, 838 cm$^{-1}$. HRMS (ESI) m/z: [M+Na]$^+$ calcd for C$_{13}$H$_{22}$O$_5$Na, 281.1359; found, 281.1359. The stereochemistry of triol 22 was confirmed by X-ray crystallographic analysis on its 3,5-dinitrobenzoate derivative S19.

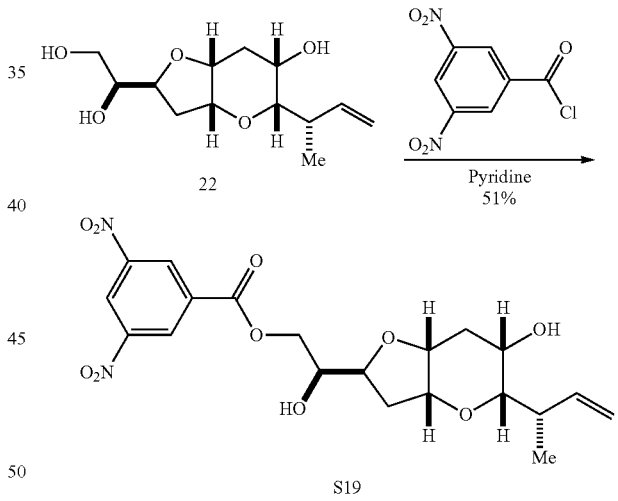

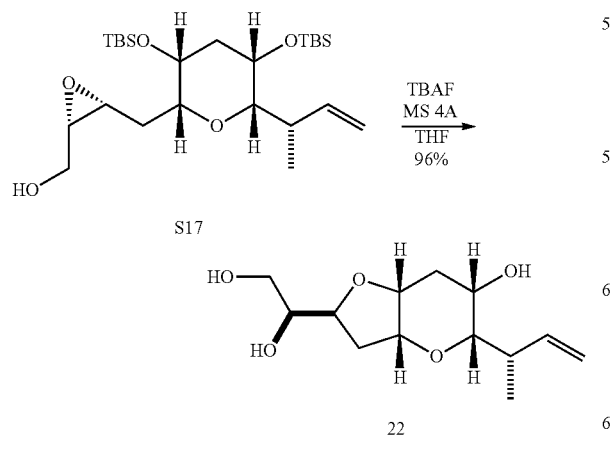

To a stirred solution of triol 22 (16.4 mg, 0.0635 mmol) in pyridine (0.50 mL) was added 3,5-dinitrobenzoyl chloride (20.0 mg, 0.0867 mmol, 1.4 eq.) at room temperature. After being stirred for 5 h at the same temperature, the resultant reaction mixture was diluted with EtOAc and was washed with 1N HCl, sat. NaHCO$_3$ aq., and brine sequentially. The organic layer was dried over Na$_2$SO$_4$, filtered, and concentrated under reduced pressure. The obtained crude material was purified by PTLC (EtOAc) to give dinitrobenzoate S19 (14.7 mg, 0.0325 mmol, 51%) as a colorless solid. Recrystallization from Hexanes/EtOAc gave a single crystal suitable for X-ray diffraction studies. S19: [α]$^{20}_D$ −51.3 (c 0.735, CHCl$_3$). MP: 127-129° C. (recrystallized from Hexanes/EtOAc). $^1$H NMR (600 MHz, C$_6$D$_6$) δ: 8.70 (2H, d, J=2.1 Hz), 8.48 (1H, t, J=2.1 Hz), 6.13 (1H, ddd, J=16.5, 10.3, 6.9 Hz), 5.18 (1H, d, J=16.5 Hz), 5.14 (1H, d, J=10.3 Hz), 4.28 (1H, dd, J=11.4, 7.2 Hz), 4.00-3.95 (2H, m), 3.55 (1H, ddd, J=10.2, 3.0, 3.0 Hz), 3.48 (1H, d, J=3.0 Hz), 3.38 (1H, s), 3.29-3.26 (1H, m), 2.97 (1H, d, J=10.8 Hz), 2.86-2.82 (1H, m), 2.61 (1H, d, J=9.0 Hz), 2.22 (1H, d, J=15.3 Hz), 2.01-1.96 (1H, m), 1.86 (1H, dd, J=12.8, 6.9 Hz), 1.68 (1H, ddd, J=12.8, 9.6, 3.6 Hz), 1.20 (1H, ddd, J=15.3, 3.3, 3.3 Hz), 1.03 (3H, d, J=7.2 Hz) ppm. $^{13}$C NMR (125 MHz, C$_6$D$_6$) δ: 162.7, 148.3, 142.5, 133.0, 128.8, 122.1, 113.8, 82.1, 78.0, 77.6, 77.2, 71.4, 68.4, 63.5, 38.7, 36.1, 32.3, 15.3 ppm. FTIR (film): 3489, 3423, 3100, 2919, 1733, 1545, 1345, 1282, 1170, 1095, 921, 721 cm$^{-1}$. HRMS (ESI) m/z: [M+NH$_4$]$^+$ calcd for C$_{20}$H$_{28}$N3O$_{10}$, 470.1769; found, 470.1779.

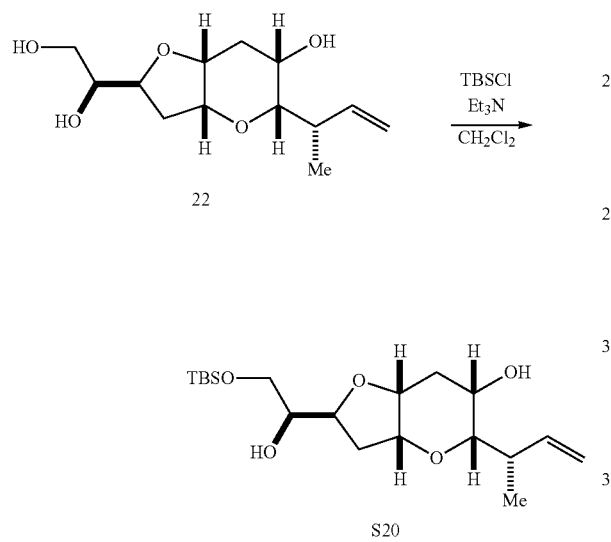

To a stirred solution of triol 22 (480 mg, 1.71 mmol, 1 eq.) in CH$_2$Cl$_2$ (9.0 mL) were added Et$_3$N (0.95 mL, 6.82 mml, 4 eq.) and TBSCl (385 mg, 2.55 mmol, 1.5 eq.) at room temperature. After being stirred for 5 h, to the reaction mixture was added TBSCl (200 mg, 1.33 mmol, 0.8 eq.) and stirred for an additional 15 h. The reaction was quenched with sat. NaHCO$_3$ aq. The organic layer was separated and the aqueous layer was extracted with EtOAc. The combined organic layer was dried over Na$_2$SO$_4$, filtered, and concentrated under reduced pressure. The obtained crude material was purified by flash column chromatography on silica gel (17% then 25% EtOAc in Hexanes) to give TBS ether S20 (633 mg, 1.70 mmol, 99%) as a colorless solid. S20: [α]$^{20}_D$ −41.6 (c 1.00, CHCl$_3$). MP: 55-58° C. (recrystallized from Et$_2$O). $^1$H NMR (600 MHz, CD$_3$OD) δ: 5.97 (1H, ddd, J=17.4, 10.5, 7.5 Hz), 5.04 (1H, d, J=17.4 Hz), 4.98 (1H, d, J=10.5 Hz), 4.41-4.38 (1H, m), 4.05 (1H, s), 3.93 (1H, s), 3.73 (1H, s), 3.72-3.66 (2H, m), 3.45 (1H, dd, J=9.3, 5.7 Hz), 3.02 (1H, d, J=9.0 Hz), 2.50-2.44 (1H, m), 2.32 (1H, d, J=15.2 Hz), 2.13 (1H, ddd, J=13.1, 9.6, 3.4 Hz), 2.04 (1H, dd, J=13.1, 7.2 Hz), 1.89 (1H, ddd, J=15.2, 3.3, 3.3 Hz), 0.99 (3H, d, J=7.2 Hz), 0.92 (9H, s), 0.09 (6H, s) ppm. $^{13}$C NMR (125 MHz, CD$_3$OD) δ: 143.4, 113.9, 82.8, 79.3, 78.6, 77.6, 74.8, 65.7, 65.0, 39.5, 36.5, 33.0, 26.4, 19.2, 15.6, −5.2, −5.3 ppm. FTIR (film): 3504, 2953, 2930, 2886, 2857, 1255, 1095, 837, 755 cm$^{-1}$. HRMS (ESI) m/z: [M+Na]$^+$ calcd for C$_{19}$H$_{36}$O$_5$SiNa, 395.2224; found, 395.2225.

To a stirred solution of TBS ether S20 (540 mg, 1.45 mmol, 1 eq.) in CH$_2$Cl$_2$ (20 mL) were added imidazole (300 mg, 4.41 mmol, 3 eq.) and TESCl (0.29 mL, 1.73 mmol, 1.2 eq.) at 0° C. After being stirred for 15 min at 0° C., the reaction was quenched with brine. After separation of the organic layer, the aqueous layer was extracted with Et$_2$O. The combined organic layer was dried over Na$_2$SO$_4$, filtered, and concentrated under reduced pressure. The residue was dissolved in hexanes and filtered through a plug of silica gel (20% EtOAc in Hexanes) to give a crude TES ether as pale yellow oil, which was used in the next step without further purification.

The crude TES ether (calculated as 1.45 mmol, 1 eq.) was cooled to 0° C. and dissolved in pre-cooled 9-BBN solution (9.0 mL of 0.5 M in THF, 4.50 mmol, 3 eq., ca. 5° C.). After being stirred for 5 min at 0° C., the ice bath was removed and the reaction mixture was stirred for 1 h at room temperature. The reaction mixture was cooled to 0° C. and quenched with H$_2$O (10 mL). After adding NaBO$_3$·H$_2$O (2.60 g, 26.0 mmol, 18 eq.) at the same temperature, the resulting mixture was stirred vigorously for 1 h at room temperature. The mixture was diluted with brine (10 mL) and EtOAc (20 mL). The organic layer was separated and the aqueous layer was extracted with EtOAc. The combined organic layer was dried over Na$_2$SO$_4$, filtered, and concentrated under reduced pressure. The obtained crude material was purified by flash column chromatography on neutral silica gel (CH$_2$Cl$_2$ then 0%, 9%, 17%, 20%, 25%, then 33% EtOAc in Hexanes) to give diol S21 (689 mg, 1.36 mmol, 94% for 2 steps) as a colorless oil. S21: [α]$^{20}_D$ +3.27 (c 1.04, CHCl$_3$). $^1$H NMR (600 MHz, CD$_3$OD) δ: 4.36 (1H, ddd, J=8.1, 8.1, 3.6 Hz), 4.07 (1H, d, J=3.0 Hz), 3.90 (1H, s), 3.73 (1H, s), 3.70 (1H, dd, J=9.9, 6.3 Hz), 3.68-3.59 (4H, m), 2.96 (1H, d, J=9.6 Hz), 2.29 (1H, d, J=15.0 Hz), 2.09 (1H, ddd, J=13.2, 9.0, 4.2 Hz), 2.04 (1H, dd, J=13.2, 6.6 Hz), 2.03-1.98 (1H, m), 1.91-1.87 (2H, m), 1.40-1.34 (1H, m), 0.98 (9H, t, J=7.8 Hz), 0.92-0.90 (12H, m), 0.65 (6H, q, J=7.8 Hz), 0.084 (3H, s), 0.079 (3H, s) ppm. $^{13}$C NMR (125 MHz, CD$_3$OD) δ: 83.3, 78.4, 79.2, 77.5, 76.8, 66.2, 65.1, 61.5, 37.4, 36.5, 33.0, 32.3, 26.44, 26.38, 19.2, 15.7, 7.3, 6.0, −5.2 ppm. FTIR (film): 3518, 2952, 2931, 2876, 1252, 1092, 835, 777, 741 cm$^{-1}$. HRMS (ESI) m/z: [M+Na]$^+$ calcd for C$_{25}$H$_{52}$O$_6$Si$_2$Na, 527.3195; found, 527.3194.

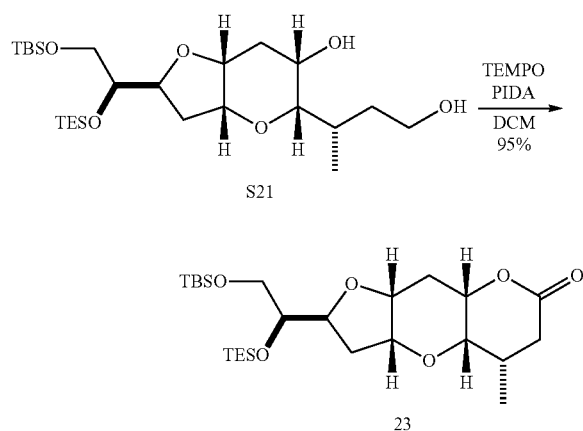

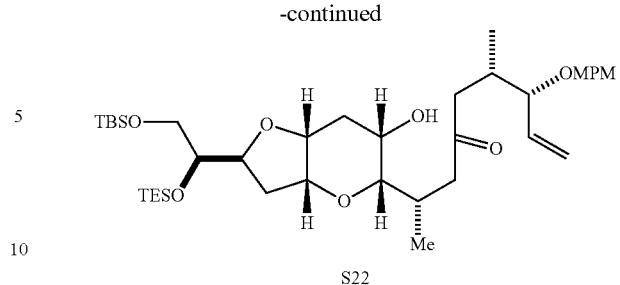

To a stirred solution of diol S21 (202 mg, 0.400 mmol) in CH$_2$Cl$_2$ (5.0 mL) were added TEMPO (12.5 mg, 20 mol %) and PIDA (390 mg, 3 eq.) at room temperature. After being stirred for 36 h, the reaction was quenched with sat. NaHCO$_3$ aq. and sat. Na$_2$S$_2$O$_3$ aq. The organic layer was separated and the aqueous layer was extracted with EtOAc. The combined organic layer was dried over Na$_2$SO$_4$, filtered, and concentrated under reduced pressure. The obtained crude material was purified by flash column chromatography on neutral silica gel (0%, 9%, 20%, 25%, then 33% EtOAc in Hexanes) to give lactone 23 (191 mg, 0.381 mmol, 95%) as a colorless oil. 23: [α]$^{20}_D$ −30.0 (c 1.02, CHCl$_3$). $^1$H NMR (600 MHz, C$_6$D$_6$) δ: 4.44-4.41 (1H, m), 3.95-3.92 (1H, m), 3.85-3.82 (1H, m), 3.70-3.66 (2H, m), 3.54 (1H, d, J=1.8 Hz), 3.46 (1H, brs), 2.52 (1H, s), 2.36-2.31 (2H, m), 2.16 (1H, dd, J=18.0, 6.0 Hz), 2.05-2.00 (1H, m), 1.90 (1H, dd, J=12.9, 6.6 Hz), 1.34-1.30 (1H, m), 1.17 (1H, ddd, J=15.8, 3.9, 3.9 Hz), 1.04 (9H, t, J=7.8 Hz), 1.00 (9H, s), 0.76 (3H, d, J=6.6 Hz), 0.68 (6H, q, J=7.8 Hz), 0.18 (3H, s), 0.15 (3H, s) ppm. $^{13}$C NMR (125 MHz, C$_6$D$_6$) δ: 168.4, 78.2, 77.9, 75.8, 73.8, 73.0, 71.4, 65.8, 35.6, 33.0, 31.3, 30.9, 26.2, 18.6, 16.7, 7.2, 5.6, −5.2-5.3 ppm. FTIR (film): 2953, 2929, 2877, 1730, 1461, 1246, 1117, 1085, 1002, 856, 776, 741, 668 cm$^{-1}$. HRMS (ESI) m/z: [M+H]$^+$ calcd for C$_{25}$H$_{49}$O$_6$Si$_2$, 501.3062; found, 501.3063.

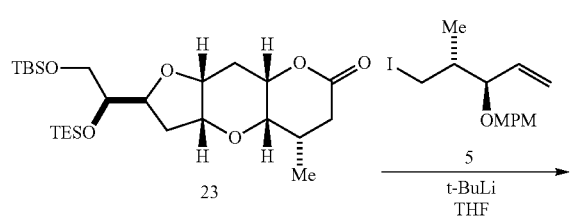

To a stirred solution of lactone 23 (467 mg, 0.932 mmol) and iodide (420 mg, 1.3 eq.) in THF (6.0 mL) was added tBuLi solution (1.3 mL of 1.7 M in pentane, 2.21 mmol, 2.5 eq.) over 20 min at −78° C. After being stirred for 30 min, the reaction was quenched with sat. NH$_4$Cl aq. and stirred for 10 min at room temperature. The organic layer was separated and the aqueous layer was extracted with EtOAc. The combined organic layer was dried over Na$_2$SO$_4$, filtered, and concentrated under reduced pressure. The obtained crude material was purified by flash column chromatography on neutral silica gel (0%, 5%, 7%, then 17% EtOAc in Hexanes) to give ketone, which contained a small amount of impurity. The pure compound, which exists as an equilibrium mixture of ketone and hemiacetal (ca. 10:1 ratio in C$_6$D$_6$) was obtained for analytical purpose by PTLC (Hexanes/EtOAc=2:1). Spectral data only for major ketone form of S22 are shown here. S22: [α]$^{20}_D$ −1.4 (c 1.13, CHCl$_3$). $^1$H NMR (600 MHz, C$_6$D$_6$) δ: 7.28 (2H, d, J=8.1 Hz), 6.85 (2H, d, J=8.1 Hz), 5.64 (1H, ddd, J=16.8, 9.0, 7.5 Hz), 5.13 (1H, d, J=9.0 Hz), 5.11 (1H, d, J=16.8 Hz), 4.57 (1H, d, J=11.4 Hz), 4.49 (1H, ddd, J=6.3, 6.3, 3.3 Hz), 4.23 (1H, d, J=10.8 Hz), 3.83 (1H, dd, J=9.9, 6.3 Hz), 3.75 (1H, dd, J=10.8, 6.0 Hz), 3.74 (1H, s), 3.63 (1H, d, J=3.0 Hz), 3.60-3.55 (2H, m), 3.47 (1H, dd, J=7.5, 7.5 Hz), 3.37 (1H, d, J=10.8 Hz), 3.33 (3H, s), 2.79 (1H, dd, J=16.8, 4.2 Hz), 2.77-2.69 (3H, m), 2.52-2.50 (1H, m), 2.30 (1H, d, J=15.6 Hz), 2.24 (1H, dd, J=16.8, 7.5 Hz), 2.20 (1H, dd, J=16.8, 8.7 Hz), 2.04 (1H, dd, J=12.9, 6.9 Hz), 1.96 (1H, ddd, J=12.6, 9.0, 4.2 Hz), 1.24 (1H, ddd, J=15.3, 3.0, 3.0 Hz), 1.12 (1H, dd, J=8.4, 8.4 Hz), 1.01 (9H, t, J=7.8 Hz), 10.1-0.95 (6H, m), 0.95 (9H, s), 0.63 (6H, q, J=7.8 Hz), 0.09 (3H, s), 0.08 (3H, s) ppm. $^{13}$C NMR (125 MHz, C$_6$D$_6$) δ: 208.7, 159.6, 137.9, 131.3, 129.5, 119.0, 114.0, 84.1, 82.0, 78.2, 78.1, 76.7, 75.8, 70.2, 65.5, 63.7, 54.8, 47.8, 46.0, 35.6, 34.0, 32.4, 31.4, 26.1, 18.5, 16.6, 16.3, 7.2, 5.5, −5.3 ppm. FTIR (film): 3518, 2953, 2932, 2876, 1709, 1613, 1514, 1463, 1413, 1248, 1092, 1037, 835, 778, 741 cm$^{-1}$. HRMS (ESI) m/z: [M+Na]$^+$ calcd for C$_{39}$H$_{68}$O$_8$Si$_2$Na, 743.4345; found, 743.4414.

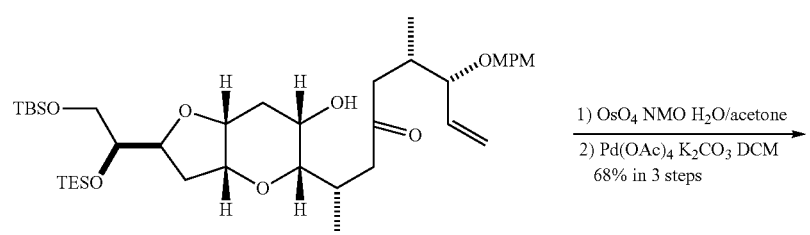

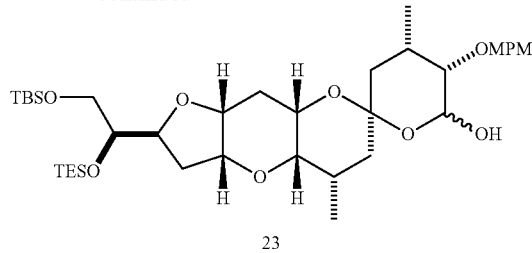

23

To a stirred solution of the crude ketone (calculated as 0.932 mmol, 1 eq.) in acetone (5.0 mL) were added OsO$_4$ solution (5.0 mL of 0.02 M in H$_2$O, 0.100 mmol, 10 mol %) and NMO (220 mg, 1.89 mmol, 2 eq.) at room temperature. After being stirred for 4 h at the same temperature, the reaction was quenched with Na$_2$SO$_3$ (1.5 g) and diluted with brine. After being stirred for 30 min at room temperature, the organic layer was separated and the aqueous layer was extracted with EtOAc. The combined organic layer was dried over Na$_2$SO$_4$, filtered, and concentrated under reduced pressure to give a crude diol as a brown oil, which was used in the next step without further purification.

To a solution of the crude diol (calculated as 0.932 mmol, 1 eq.) in CH$_2$Cl$_2$ (19 mL) were added K$_2$CO$_3$ (1.3 g, 9.41 mmol, 10 eq.) and Pb(OAc)$_4$ (620 mg, 1.40 mmol, 1.5 eq.) at room temperature. After being stirred for 15 min at the same temperature, the reaction was diluted with Hexanes/EtOAc (2:1) and filtered through a pad of SiO$_2$ (33% EtOAc in Hexanes). After evaporation of organic solvent, the obtained crude material was purified by flash column chromatography on neutral silica gel (0%, 5%, 9%, 13%, then 17% EtOAc in Hexanes) to give hemiacetal S23 (461 mg, 0.638 mmol, 68% for 3 steps) as pale brown oil. The product was obtained as an equilibrium mixture of hemiacetal (ca. 3:7 ratio in C$_6$D$_6$). S23: $[\alpha]^{20}_D$ −35.8 (c 1.04, CHCl$_3$). $^1$H NMR (600 MHz, C$_6$D$_6$) δ: 7.17-7.15 (2H, m), 6.80-6.74 (2H, m), 5.44 (0.3H, dd, J=11.7, 1.5 Hz), 4.92 (0.7H, dd, J=12.6, 1.5 Hz), 4.52 (0.7H, d, J=11.1 Hz), 4.45-4.39 (1.3H, m), 4.32 (0.7H, d, J=11.1 Hz), 4.23 (0.3H, d, J=11.4 Hz), 4.09 (0.3H, d, J=3.0 Hz), 3.95 (0.3H, d, J=10.8 Hz), 3.83-3.80 (1H, m), 3.77-3.74 (1H, m), 3.69-3.60 (3H, m), 3.56 (0.7H, d, J=4.2 Hz), 3.33 (0.3H, s), 3.29-3.27 (4H, m), 3.16 (0.7H, s), 2.74-2.72 (1H, m), 2.62-2.56 (0.3H. m), 2.35-2.25 (1.7H, m), 2.18 (0.7H, d, J=15.0 Hz), 2.10-2.00 (1.3H, m), 1.92-1.80 (1.3H, m), 1.72-1.59 (1.7H, m), 1.54 (0.7H, dd, J=12.6, 4.2 Hz), 1.51-1.48 (1H, m), 1.45-1.38 (1H, m), 1.11-1.07 (9.9H, m), 1.04-0.98 (14.1H, m), 0.77-0.72 (6H, m), 0.121-0.09 (6H, m) ppm. $^{13}$C NMR (125 MHz, C$_6$D$_6$) δ: 159.9, 159.7, 131.2, 129.7, 129.5, 114.2, 114.0, 98.9, 98.2, 93.8, 91.3, 80.1, 79.1, 79.0, 78.5, 77.8, 77.7, 76.8, 76.0, 74.1, 73.9, 73.4, 73.1, 72.2, 66.1, 64.8, 64.0, 54.7, 38.4, 38.2, 37.7, 37.3, 36.4, 31.5, 31.3, 29.7, 29.2, 26.2, 26.1, 23.2, 18.6, 17.8, 17.5, 17.44, 17.39, 7.3, 7.2, 5.7, 5.5, −5.1, −5.3 ppm. FTIR (film): 3507, 2953, 2928, 2874, 1514, 1462, 1248, 1090, 1035, 1013, 835, 776, 742 cm$^{−1}$. HRMS (ESI) m/z: [M+NH$_4$]$^+$ calcd for C$_{38}$H$_{70}$NO$_9$Si$_2$, 740.4584; found, 740.4608.

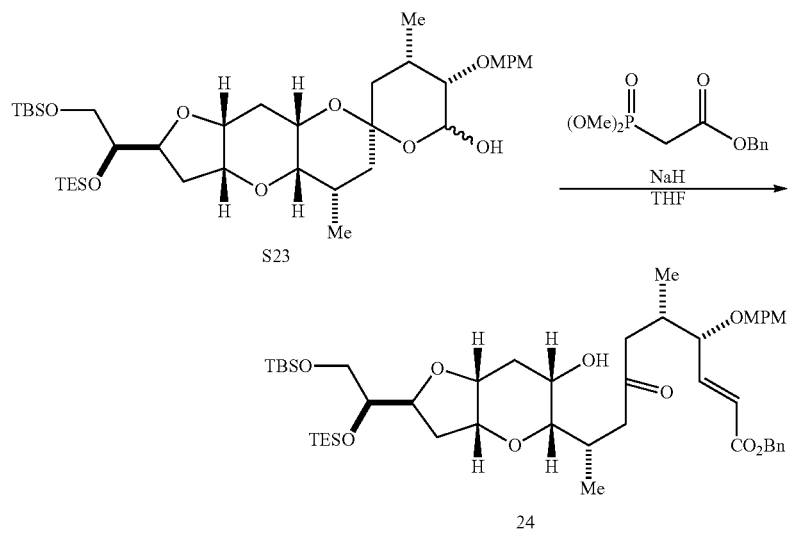

24

To a stirred solution of hemiacetal S23 (461 mg, 0.638 mmol, 1 eq.) and benzyl dimethylphosphonoacetate (0.67 mL, 3.19 mmol, 5 eq.) in THF (26.0 mL) was added NaH (100 mg of 60% in mineral oil, 2.50 mmol, 4 eq.) at 0° C. After being stirred for 3 h at the same temperature, the reaction was quenched with sat. NH$_4$Cl aq. The organic layer was separated and the aqueous layer was extracted with Hexanes/EtOAc (1:1). The combined organic layer was dried over Na$_2$SO$_4$, filtered, and concentrated under reduced pressure. The obtained crude material was purified by flash column chromatography on neutral silica gel (0%, 5%, 9%, 13%, then 17% EtOAc in Hexanes) to give unsaturated ester 24 (479 mg, 0.560 mmol, 88%) as colorless oil. 24: $[\alpha]^{20}_D$ −21.7 (c 1.00, CHCl$_3$). $^1$H NMR (600 MHz, C$_6$D$_6$) δ: 7.24

(2H, d, J=7.2 Hz), 7.15 (2H, d, J=8.4 Hz), 7.10 (2H, dd, J=7.2, 7.2 Hz), 7.05 (1H, t, J=7.2 Hz), 7.04 (1H, dd, J=15.5, 6.3 Hz), 6.79 (2H, d, J=8.4 Hz), 6.20 (1H, d, J=15.5 Hz), 5.14 (1H, d, J=12.0 Hz), 5.10 (1H, d, J=12.0 Hz), 4.48 (1H, ddd, J=8.1, 8.1, 3.4 Hz), 4.38 (1H, d, J=12.0 Hz), 4.10 (1H, d, J=12.0 Hz), 3.83 (1H, dd, J=9.9, 6.3 Hz), 3.77-3.74 (2H, m), 3.63-3.59 (3H, m), 3.55 (1H, ddd, J=10.8, 3.0, 3.0 Hz), 3.35-3.32 (4H, m), 2.70-2.64 (3H, m), 2.54 (1H, dd, J=16.8, 4.8 Hz), 2.47-2.43 (1H, m), 2.29 (1H, d, J=15.6 Hz), 2.15-2.08 (2H, m), 2.04-1.95 (2H, m), 1.25 (1H, ddd, J=15.0, 3.6, 3.6 Hz), 1.10 (1H, dd, J=7.8, 7.8 Hz), 1.01 (9H, t, J=8.1 Hz), 0.95 (9H, s), 0.92 (3H, d, J=6.6 Hz), 0.86 (3H, d, J=6.6 Hz), 0.64 (6H, q, J=8.1 Hz), 0.08 (3H, s), 0.07 (3H, s) ppm. $^{13}$C NMR (150 MHz, C$_6$D$_6$) δ: 208.2, 165.6, 159.8, 147.8, 136.6, 130.6, 129.7, 128.70, 128.66, 128.3, 123.3, 114.1, 81.9, 81.5, 78.2, 78.1, 76.7, 75.9, 71.1, 66.4, 65.5, 63.7, 54.7, 47.6, 45.5, 35.6, 33.6, 32.4, 31.4, 26.1, 18.5, 16.4, 16.3, 7.2, 5.5, −5.3 ppm. FTIR (film): 3526, 2953, 2933, 2876, 1719, 1612, 1513, 1462, 1249, 1160, 1093, 1036, 836, 778, 741, 697 cm$^{-1}$. HRMS (ESI) m/z: [M+Na]$^+$ calcd for C$_{47}$H$_{74}$O$_{10}$Si$_2$Na, 877.4713; found, 877.4713.

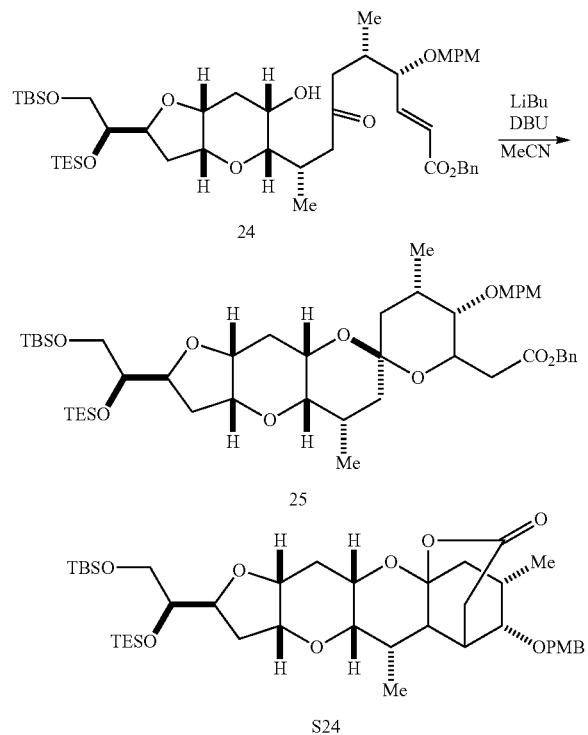

To a stirred solution of unsaturated ester 24 (132 mg, 0.154 mmol, 1 eq.) in MeCN (3.0 mL) were added LiBr (134 mg, 1.54 mmol, 10 eq.) and DBU (0.46 mL, 3.08 mmol, 20 eq.) at room temperature. After being stirred for 11 h at the same temperature, hexanes (3.0 mL) and H$_2$O (3.0 mL) were added to the reaction mixture. The organic layer was separated and the aqueous layer was extracted with hexanes. The combined organic layer was dried over Na$_2$SO$_4$, filtered, and concentrated under reduced pressure. The obtained crude material was purified by flash column chromatography on neutral silica gel (0%, 5%, 6%, then 9% EtOAc in Hexanes) to give spiro ketal 25 (92.1 mg, 0.108 mmol, 70%) as colorless oil and C-Michael addition product S24 (6.7 mg, 0.00897 mmol, 6%) as colorless oil. 25: [α]$^{20}_D$ −32.5 (c 1.00, CHCl$_3$). $^1$H NMR (600 MHz, C$_6$D$_6$) δ: 7.23 (2H, d, J=7.1 Hz), 7.19 (2H, d, J=8.4 Hz), 7.11 (2H, dd, J=7.5, 7.1 Hz), 7.06 (1H, dd, J=7.5, 7.5 Hz), 6.76 (2H, d, J=8.4 Hz), 5.09 (1H, d, J=12.0 Hz), 5.00 (1H, d, J=12.0 Hz), 4.44 (1H, ddd, J=10.2, 4.8, 4.8 Hz), 4.31 (1H, d, J=10.2 Hz), 4.23-4.21 (2H, m), 3.83-3.79 (2H, m), 3.75 (dd, J=10.2, 6.0 Hz), 3.72-3.68 (3H, m), 3.30 (3H, s), 2.96 (1H, dd, J=15.6, 9.6 Hz), 2.85 (1H, s), 2.80 (1H, d, J=2.4 Hz), 2.38-2.35 (2H, m), 2.28 (1H, dd, J=15.6, 3.6 Hz), 2.17-2.13 (1H, m), 2.05 (1H, dd, J=12.3, 6.3 Hz), 1.85 (1H, ddd, J=13.2, 9.6, 4.2 Hz), 1.70-1.62 (2H, m), 1.59-1.55 (2H, m), 1.43 (1H, dd, J=13.2, 4.2 Hz), 1.11 (9H, t, J=8.1 Hz), 1.01 (3H, d, J=4.2 Hz), 1.00-0.99 (12H, m), 0.76 (6H, q, J=8.1 Hz), 0.120 (3H, s), 0.116 (3H, s) ppm. $^{13}$C NMR (125 MHz, C$_6$D$_6$) δ: 171.6, 159.7, 136.8, 131.3, 129.7, 128.72, 128.66, 114.0, 97.0, 79.1, 78.5, 77.9, 76.8, 75.3, 74.2, 73.5, 69.6, 66.15, 66.06, 63.7, 54.7, 38.2, 37.7, 37.3, 36.5, 31.5, 30.6, 29.3, 26.2, 18.6, 18.2, 17.6, 7.4, 5.7, −5.1, −5.3 ppm. FTIR (film): 2954, 2928, 2874, 1737, 1514, 1462, 1249, 1088, 1018, 836, 742 cm$^{-1}$. HRMS (ESI) m/z: [M+Na]$^+$ calcd for C$_{47}$H$_{74}$O$_{10}$Si$_2$Na, 877.4713; found, 877.4712. C-Michael product S25: [α]$^{20}_D$ −79.5 (c 0.855, CHCl$_3$). $^1$H NMR (600 MHz, C$_6$D$_6$) δ: 7.10 (2H, d, J=8.7 Hz), 6.79 (2H, d, J=8.7 Hz), 4.42 (1H, ddd, J=9.6, 6.2, 3.5 Hz), 4.20 (1H, d, J=12.0 Hz), 4.11 (1H, d, J=12.0 Hz), 3.87 (1H, dd, J=10.2, 6.0 Hz), 3.78 (1H, dd, J=10.2, 5.4 Hz), 3.69-3.66 (3H, m), 3.61 (1H, dd, J=2.7, 2.7 Hz), 3.32 (3H, s), 2.86 (1H, dd, J=3.3, 3.3 Hz), 2.62 (1H, d, J=2.4 Hz), 2.38 (1H, dd, J=12.6, 3.0 Hz), 2.30 (1H, d, J=15.6 Hz), 2.23 (1H, dd, J=19.2, 7.8 Hz), 2.05 (1H, ddd, J=13.6, 3.6, 3.6 Hz), 1.99-1.89 (4H, m), 1.81 (1H, d, J=19.2 Hz), 1.63-1.58 (1H, m), 1.30-1.25 (2H, m), 1.06 (9H, t, J=7.8 Hz), 0.98 (9H, s), 0.84 (3H, d, J=6.6 Hz), 0.82 (3H, d, J=6.0 Hz), 0.70 (6H, q, J=7.8 Hz), 0.114 (3H, s), 0.112 (3H, s) ppm. $^{13}$C NMR (125 MHz, C$_6$D$_6$) δ: 169.7, 159.7, 131.1, 129.4, 114.0, 104.9, 80.6, 78.7, 78.2, 76.1, 74.0, 73.7, 71.1, 65.9, 65.2, 54.7, 40.8, 36.0, 33.1, 30.9, 30.7, 30.5, 29.5, 29.4, 26.2, 18.6, 16.9, 13.9, 7.3, 5.6, −5.1, −5.2 ppm. FTIR (film): 2954, 2931, 2876, 1729, 1612, 1514, 1462, 1302, 1247, 1205, 1157, 1133, 1090, 1038, 992, 937, 835, 777, 742 cm$^{-1}$. HRMS (ESI) m/z: [M+Na]$^+$ calcd for C$_{40}$H$_{66}$O$_9$Si$_2$Na, 769.4138; found, 769.4146.

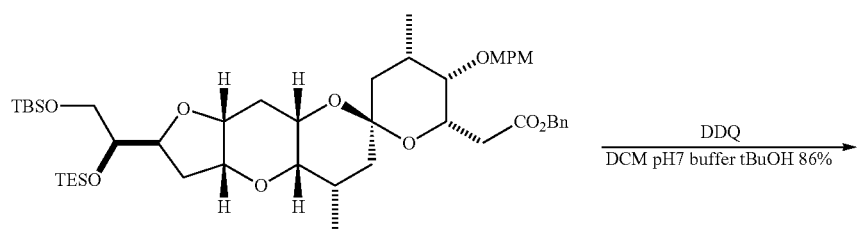

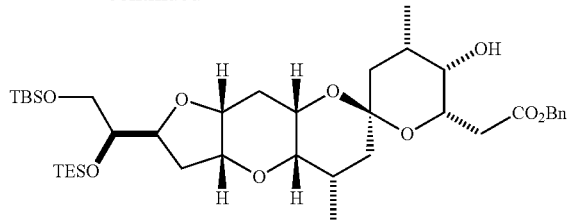

S25

To a stirred solution of MPM ether 25 (248 mg, 0.290 mmol, 1 eq.) in CH$_2$Cl$_2$ (6.0 mL), phosphate buffer (0.60 mL, pH7), and tBuOH (0.60 mL) was added DDQ (200 mg, 0.881 mmol, 3 eq.) at room temperature. After being stirred for 15 min at the same temperature, the reaction was quenched with sat. NaHCO$_3$ aq. The organic layer was separated and the aqueous layer was extracted with CH$_2$Cl$_2$. The combined organic layer was dried over Na$_2$SO$_4$, filtered, and concentrated under reduced pressure. The obtained crude material was purified by flash column chromatography on neutral silica gel (0%, 7%, then 9% EtOAc in Hexanes) to give alcohol S25 (183 mg, 0.249 mmol, 86%) as a colorless oil. S25: $[\alpha]^{20}_D$ −45.6 (c 1.01, CHCl$_3$). $^1$H NMR (600 MHz, C$_6$D$_6$) δ: 7.21 (2H, d, J=7.5 Hz), 7.11 (2H, dd, J=7.5, 7.5 Hz), 7.06 (1H, t, J=7.5 Hz), 5.07 (1H, d, J=12.6 Hz), 4.97 (1H, d, J=12.6 Hz), 4.43 (1H, ddd, J=10.2, 5.3, 5.3 Hz), 4.14 (1H, dd, J=9.6, 3.0 Hz), 3.82 (1H, dd, J=9.6, 5.4 Hz), 3.77-3.74 (2H, m), 3.70-3.67 (3H, m), 2.96 (1H, d, J=8.4 Hz), 2.86 (1H, dd, J=15.6, 10.2 Hz), 2.77 (1H, d, J=1.8 Hz), 2.33-2.28 (2H, m), 2.22-2.17 (1H, m), 2.12-2.04 (2H, m), 1.86 (1H, ddd, J=12.8, 10.2, 4.2 Hz), 1.61 (1H, dd, J=12.9, 12.9 Hz), 1.09 (9H, t, J=7.9 Hz), 1.05 (3H, d, J=6.6 Hz), 0.99 (9H, s), 0.93 (3H, d, J=7.2 Hz), 0.75 (6H, q, J=7.9 Hz), 0.12 (3H, s), 0.12 (3H, s) ppm. $^{13}$C NMR (125 MHz, C$_6$D$_6$) δ: 171.5, 136.7, 128.64, 128.57, 97.0, 79.0, 77.9, 76.8, 74.1, 73.3, 70.5, 69.3, 66.09, 66.06, 63.7, 37.4, 37.31, 37.27, 36.4, 30.2, 29.2, 26.2, 18.6, 17.65, 17.62, 7.3, 5.7, −5.1, −5.3 ppm. FTIR (film): 3469, 2953, 2928, 2874, 1736, 1498, 1251, 1128, 1017, 835, 776, 740 cm$^{-1}$. HRMS (ESI) m/z: [M+Na]$^+$ calcd for C$_{39}$H$_{66}$O$_9$Si$_2$Na, 757.4138; found, 757.4135.

To a stirred solution of alcohol S25 (183 mg, 0.249 mmol, 1 eq.) in CH$_2$Cl$_2$ (3.0 mL) were added imidazole (50.0 mg, 0734 mmol, 3 eq.) and TESCl (60 μL, 0.357 mmol, 1.5 eq.) at room temperature. After being stirred for 4 h at the same temperature, the reaction was quenched with sat. NaHCO$_3$ aq. The organic layer was separated and the aqueous layer was extracted with EtOAc. The combined organic layer was dried over Na$_2$SO$_4$, filtered, and concentrated under reduced pressure. The obtained crude material was purified by flash column chromatography on neutral silica gel (0%, 3%, then 5% EtOAc in Hexanes) to give TES ether S26 (205 mg, 0.241 mmol, 97%) as a colorless oil. S26: $[\alpha]^{20}_D$ −49.1 (c 1.00, CHCl$_3$). $^1$H NMR (600 MHz, C$_6$D$_6$) δ: 7.26 (2H, d, J=7.2 Hz), 7.10 (2H, dd, J=7.2, 7.2 Hz), 7.05 (1H, t, J=7.2 Hz), 5.14 (1H, d, J=12.3 Hz), 5.02 (1H, d, J=12.3 Hz), 4.46 (1H, ddd, J=9.8, 5.1, 5.1 Hz), 4.17 (1H, dd, J=10.2, 3.0 Hz), 3.84-3.80 (2H, m), 3.77 (1H, dd, J=10.2, 5.4 Hz), 3.73 (1H, d, J=1.8 Hz), 3.71-3.69 (2H, m), 3.22 (1H, s), 2.92 (1H, dd, J=15.3, 9.1 Hz), 2.80 (1H, s), 2.38 (1H, d, J=15.6 Hz), 2.30-2.27 (2H, m), 2.16-2.11 (1H, m), 2.06 (1H, dd, J=12.9, 6.3 Hz), 1.87 (1H, ddd, J=13.2, 9.6, 4.2 Hz), 1.69-1.61 (2H, m), 1.59 (1H, ddd, J=15.2, 4.7, 4.7 Hz), 1.53 (1H, dd, J=12.6, 3.6 Hz), 1.46 (1H, dd, J=12.3, 3.9 Hz), 1.11 (9H, t, J=7.9 Hz), 1.00 (9H, s), 1.00-0.95 (12H, m), 0.93 (3H, d, J=7.2 Hz), 0.76 (6H, q, J=7.9 Hz), 0.56 (6H, q, J=7.9 Hz), 0.131 (3H, s), 0.127 (3H, s) ppm. 13C NMR (125 MHz, C$_6$D$_6$) δ: 171.6, 136.8, 128.75, 128.67, 128.3, 96.9, 79.0, 77.9, 76.8, 74.2, 73.6, 72.4, 69.9, 66.2, 66.1, 63.6, 38.3, 37.5, 37.4, 36.4, 31.5, 30.7, 29.3, 26.2, 18.6, 17.5, 7.4, 5.8, 5.7, −5.1, −5.3 ppm. FTIR (film): 2953, 2928, 2875, 1738, 1498, 1240, 1033, 1001, 974, 834, 737, 677 cm$^{-1}$. HRMS (ESI) m/z: [M+H]$^+$ calcd for C$_{45}$H$_{81}$O$_9$Si$_3$, 849.5183; found, 849.5184.

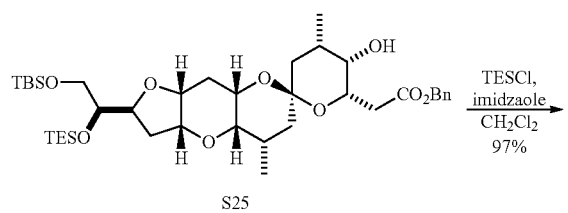

S25

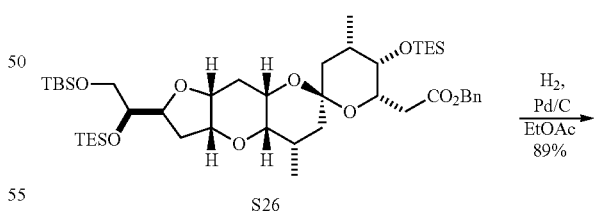

S26

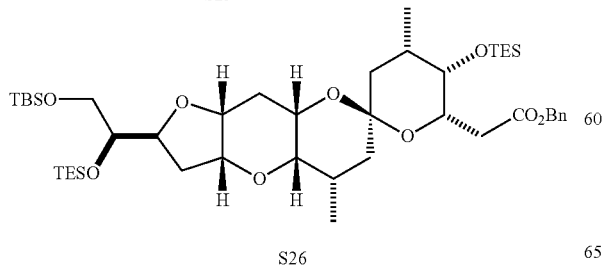

S26

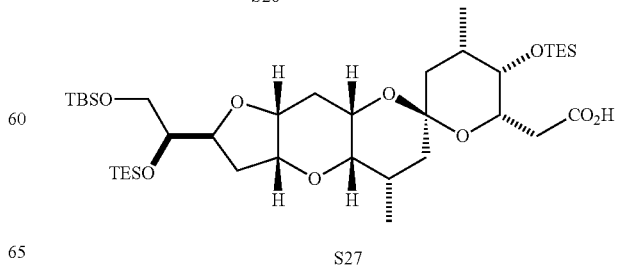

S27

To a stirred solution of Benzyl ester S26 (230 mg, 0.271 mmol, 1 eq.) in EtOAc (10.0 mL) was added wet 10% Pd/C (23 mg, 10% w/w) at room temperature. The reaction was stirred under 1 atmosphere of hydrogen for 2 h. The resulting mixture was filtered through a pad of Celite (EtOAc). The organic solvent was removed under reduced pressure to give a crude mixture, which was purified by flash column chromatography on neutral silica gel (0%, 5%, then 33% EtOAc in Hexanes) to give carboxylic acid S27 (183 mg, 0.241 mmol, 89%) as a colorless oil. S27: $[\alpha]^{20}_D$ −54.8 (c 1.06, CHCl$_3$). $^1$H NMR (500 MHz, C$_6$D$_6$) δ: 4.45 (1H, ddd, J=10.0, 5.0, 5.0 Hz), 4.12 (1H, dd, J=9.8, 2.8 Hz), 3.89 (1H, d, J=3.5 Hz), 3.81 (1H, dd, J=11.0, 5.0 Hz), 3.76-3.73 (2H, m), 3.70-3.67 (2H, m), 3.24 (1H, s), 2.89 (1H, d, J=1.5 Hz), 2.87 (1H, dd, J=16.0, 3.0 Hz), 2.40 (1H, d, J=15.5 Hz), 2.34 (1H, dd, J=16.0, 3.0 Hz), 2.32-2.21 (2H, m), 2.04 (1H, dd, J=12.8, 5.8 Hz), 1.87 (1H, ddd, J=13.5, 9.5, 4.0 Hz), 1.70-1.62 (3H, m), 1.53 (1H, dd, J=12.5, 4.0 Hz), 1.47 (1H, dd, J=13.0, 4.0 Hz), 1.09 (9H, t, J=8.0 Hz), 1.00 (3H, d, J=7.0 Hz), 0.99 (9H, s), 0.97 (9H, t, J=8.0 Hz), 0.92 (3H, d, J=7.0 Hz), 0.75 (6H, q, J=8.0 Hz), 0.57 (6H, q, J=8.0 Hz), 0.120 (3H, s), 0.115 (3H, s) ppm. $^{13}$C NMR (125 MHz, C$_6$D$_6$) δ: 178.1, 97.1, 79.0, 77.9, 76.7, 74.3, 73.6, 72.3, 69.6, 66.1, 63.8, 38.0, 37.5, 37.4, 36.4, 31.5, 30.7, 29.4, 26.2, 18.6, 17.5, 7.3, 5.8, 5.7, −5.1, −5.3 ppm. FTIR (film): 3120, 2953, 2928, 2875, 1731, 1713, 1461, 1415, 1309, 1078, 1033, 1004, 833, 776, 724 cm$^{-1}$. HRMS (ESI) m/z: [M+H]$^+$ calcd for C$_3$gH$_{75}$O9Si$_3$, 759.4713; found, 759.4724.

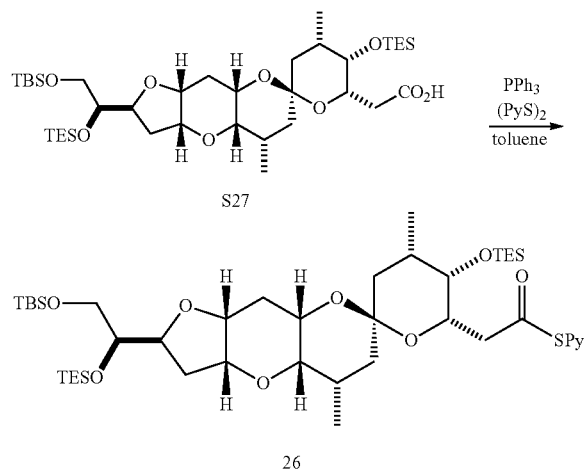

To a stirred solution of carboxylic acid S27 (183 mg, 0.241 mmol, 1 eq.) in toluene (1.2 mL) were added PPh$_3$ (190 mg, 0.724 mmol, 3 eq.) and (PyS)$_2$ (64.0 mg, 0.290 mmol, 1.2 eq.) at room temperature. After being stirred for 12 h at the same temperature, the resulting reaction mixture was directly subjected to column chromatography on neutral silica gel (0%, 3%, 5%, then 6% EtOAc in Hexanes) to give pyridinethiol ester 26 (199 mg, 0.233 mmol, 97%) as pale yellow oil. 26: $[\alpha]^{20}_D$ −65.7 (c 1.00, CHCl$_3$). $^1$H NMR (600 MHz, C$_6$D$_6$) δ: 8.33 (1H, dd, J=5.0, 1.4 Hz), 7.54 (1H, d, J=8.1 Hz), 6.96 (1H, ddd, J=8.1, 7.6, 1.4 Hz), 6.47 (1H, dd, J=7.6, 5.0 Hz), 4.45 (1H, ddd, J=9.8, 5.1, 5.1 Hz), 4.17 (1H, dd, J=10.2, 2.4 Hz), 3.88 (1H, d, J=3.6 Hz), 3.81 (1H, dd, J=10.5, 5.1 Hz), 3.75 (1H, dd, J=10.5, 5.7 Hz), 3.71-3.65 (3H, m), 3.25 (1H, dd, J=15.0, 10.2 Hz), 3.10 (1H, s), 2.82 (1H, d, J=1.8 Hz), 2.53 (1H, dd, J=15.0, 2.4 Hz), 2.39-2.34 (2H, m), 2.27-2.23 (1H, m), 2.04 (1H, dd, J=12.9, 5.7 Hz), 1.85 (1H, ddd, J=13.4, 9.8, 3.8 Hz), 1.70-1.60 (3H, m), 1.54-1.50 (2H, m), 1.10 (9H, t, J=7.8 Hz), 0.99-0.97 (21H, m), 0.91 (3H, d, J=6.0 Hz), 0.75 (6H, q, J=8.0 Hz), 0.56 (6H, q, J=7.8 Hz), 0.121 (3H, s), 0.119 (3H, s) ppm. $^{13}$C NMR (125 MHz, C$_6$D$_6$) δ: 194.6, 152.8, 150.6, 136.5, 129.8, 123.1, 97.1, 79.0, 77.9, 76.8, 74.2, 73.6, 72.5, 69.9, 66.1, 63.8, 47.8, 37.5, 37.4, 36.4, 31.4, 30.7, 29.3, 26.2, 18.6, 18.5, 17.5, 7.4, 7.3, 5.9, 5.7, −5.1, −5.3 ppm. FTIR (film): 2953, 2928, 2875, 1708, 1572, 1420, 1250, 1033, 1001, 834, 775, 736, 723 cm$^{-1}$. HRMS (ESI) m/z: [M+Na]$^+$ calcd for C$_{43}$H$_{77}$NO$_8$SSi$_3$Na, 874.4570; found, 874.4573.

Norhalichondrin Left Halves

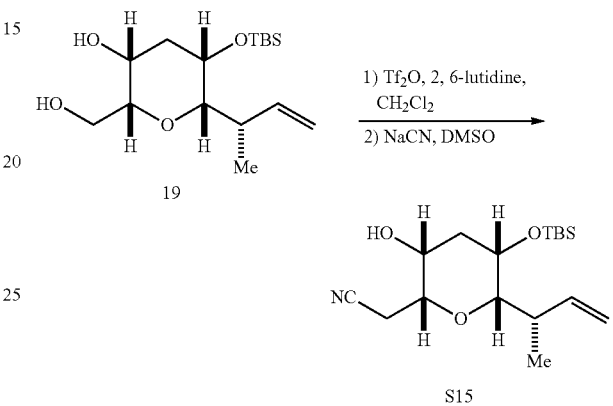

To a stirred solution of diol 19 (3.65 g, 11.6 mmol, 1 eq.) and 2,6-lutidine (5.4 mL, 46.4 mmol, 4 eq.) in CH$_2$Cl$_2$ (75 mL) was added Tf$_2$O (2.4 mL, 27.9 mmol, 1.2 eq.) at −78° C. After being stirred for 10 min at the same temperature, the reaction was quenched with MeOH (0.5 mL) and brine (50 mL). After being added Et$_2$O (250 mL), the organic layer was separated from aqueous layer and washed with 1N HCl and brine sequentially. The organic layer was dried over Na$_2$SO$_4$, filtered, and concentrated under reduced pressure to give a crude triflate as wine red oil, which was dissolved in DMSO (75 mL) immediately without further purification.

To the DMSO solution of crude triflate (estimated as 11.6 mmol, 1 eq.) was added NaCN (5.7 g, 115 mmol, 10 eq.) at room temperature. After being stirred for 1 hr at the same temperature, the reaction mixture was filtered through a paper and the filter cake was washed with EtOAc thoroughly. The filtrate was washed with H$_2$O and brine. The organic layer was dried over Na$_2$SO$_4$, filtered, and concentrated under reduced pressure. The residue was purified by flash column chromatography on silica gel (0%, 5%, 10%, then 25% EtOAc in Hexanes) to give S15 (3.26 g, 10.1 mmol, 87% for 2 steps) as a colorless oil. S15: $[\alpha]^{20}_D$ −24.0 (c 1.00, CHCl$_3$). $^1$H NMR (600 MHz, C$_6$D$_6$) δ: 6.18 (1H, m), 5.15 (1H, d, J=9.6 Hz), 5.11 (1H, d, J=15.4 Hz), 3.48 (1H, s), 3.39 (1H, d, J=11.4 Hz), 3.21 (1H, d, J=11.4 Hz), 2.97 (1H, dd, J=6.6, 6.4 Hz), 2.61-2.55 (2H, m), 2.33 (1H, dd, J=16.2, 8.4 Hz), 2.09 (1H, dd, J=15.0, 7.8 Hz), 1.88 (1H, d, J=15.2 Hz), 0.99 (1H, d, J=12.6 Hz), 0.88 (9H, s), 0.80 (3H, d, J=5.8 Hz), 0.03 (3H, s), −0.09 (3H, s) ppm. $^{13}$C NMR (150 MHz, C$_6$D$_6$) δ: 141.2, 117.6, 114.1, 84.7, 76.9, 66.4, 65.8, 37.5, 36.3, 25.8, 20.4, 18.1, 15.3, −4.0, −5.1 ppm. FTIR (film): 3515, 2956, 2930, 2897, 2858, 1473, 1433, 1365, 1255, 1168, 1122, 1082, 1046, 995, 978, 940, 834, 775, 736, 688, 474 cm$^{-1}$. HRMS (ESI) m/z: [M+Na]$^+$ calcd for C$_{17}$H$_{31}$NO$_3$SiNa, 348.1965; found, 348.1969.

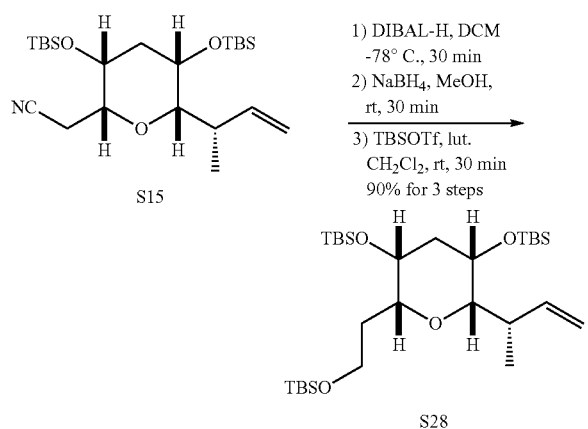

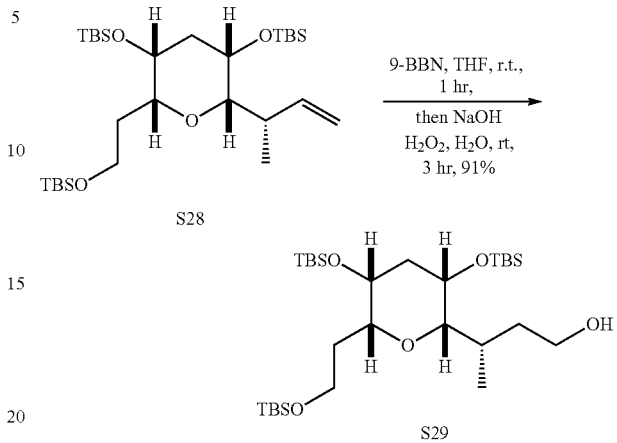

To a stirred solution of S15 (3.25 g, 10.0 mmol, 1 eq.) in CH$_2$Cl$_2$ (150 mL) were added DIBAL solution (45 ml of 1 M in hexanes, 45.0 mmol, 4.5 eq.) at −78° C. under Ar atmosphere. After being stirred for 30 min at the same temperature, 150 mL of sat. Rochelle's salt aq. was added and the temperature was allowed to increase to room temperature. After being stirred for 1 h at the same temperature, the mixture was diluted with EtOAc. The organic layer was separated and the aqueous layer was extracted with EtOAc. The combined organic layer was dried over Na$_2$SO$_4$, filtered, and concentrated under reduced pressure to give a crude aldehyde, which was used in the next reaction without further purification.

To a stirred solution of the crude aldehyde (calculated as 10.0 mmol, 1 eq.) in CH$_2$Cl$_2$ (150 mL) were added NaBH$_4$ (1.89 g, 50.0 mmol, 5 eq.) at 0° C. After being stirred for 30 min at room temperature, the reaction was quenched with AcOH (2.8 mL) and the resultant mixture was concentrated under reduced pressure. The residue was passed through a pad of silica gel (5% MeOH in CH$_2$Cl$_2$) to give a crude alcohol, which was used in the next reaction after concentration without further purification.

To a stirred solution of the crude alcohol (calculated as 10.0 mmol, 1 eq.) in CH$_2$Cl$_2$ (100 mL) were added 2,6-lutidne (3.75 g, 35.0 mmol, 3.5 eq.) and TESOTf (7.93 g, 30.0 mmol, 3 eq.) at 0° C. After being stirred for 30 min at room temperature, MeOH (1 mL) was added and the resultant mixture was diluted with 200 mL of CH$_2$Cl$_2$. The resultant mixture was washed with 1N HCl and sat. NaHCO$_3$ aq. The organic layer was dried over MgSO$_4$, filtered, and concentrated under reduced pressure. The residue was purified by flash column chromatography on silica gel (0%, 5%, 10%, then 15% EtOAc in Hexanes) to give S28 (5.03 g, 9.00 mmol, 90% for 3 steps) as a colorless oil. S28: [α]$^{20}_D$ +3.4 (c 1.00, CHCl$_3$). $^1$H NMR (600 MHz, C$_6$D$_6$) δ: 6.27 (1H, m), 5.17 (1H, ddd, J=17.4, 1.8, 1.6 Hz), 5.16 (1H, dd, J=10.8, 1.8 Hz), 4.00 (1H, m), 3.82 (1H, m), 3.67 (1H, quin, J=2.0 Hz), 3.49 (1H, ddd, J=10.8, 1.8, 1.6 Hz), 2.89 (1H, m), 2.84 (1H, dd, J=9.0, 1.8 Hz), 2.18 (1H, m), 1.94 (1H, ddd, J=15.8, 2.3, 2.0 Hz), 1.65 (1H, m), 1.54 (1H, dt, J=15.6, 4.4 Hz), 1.03 (9H, s), 1.022 (9H, s), 1.020 (9H, s), 0.98 (3H, d, J=6.6 Hz), 0.17 (3H, s), 0.15 (3H, s), 0.12 (3H, s), 0.08 (3H, s), 0.06 (3H, s), 0.02 (3H, s) ppm. $^{13}$C NMR (150 MHz, C$_6$D$_6$) δ: 143.0, 113.4, 85.1, 77.4, 66.3, 65.0, 60.3, 39.3, 37.8, 36.1, 18.6, 18.5, 16.1, −2.2, −3.4, −4.7, −5.00, −5.02, −5.10 ppm. FTIR (film): 2953, 2928, 2844, 2856, 1472, 1462, 1387, 1251, 1020, 958, 938, 886, 808, 768, 705, 674, 662 cm$^{-1}$. HRMS (ESI) m/z: [M+H]$^+$ calcd for C$_{29}$H$_{63}$O$_4$Si$_3$, 559.4034; found, 559.4063.

To a stirred solution of the S28 (4.9 g, 8.78 mmol, 1 eq.) in THF (16 mL) was added 9-BBN solution (17.6 mL of 0.5 M in THF, 8.8 mmol, 2 eq.) at 0° C. After being stirred for 1 h at room temperature, 2 N NaOH aq. (21 mL) was added, followed by 9 M H$_2$O$_2$ aq. very slowly at 0° C. After being stirred for 30 min at room temperature, the resultant mixture was quenched with sat. Na$_2$S$_2$O$_3$ aq. The organic layer was separated and the aqueous layer was extracted with Et$_2$O. The combined organic layer was dried over MgSO$_4$, filtered, and concentrated under reduced pressure. The crude product was purified by flash column chromatography on silica gel (0%, 5%, 10%, then 20% EtOAc in Hexanes) to give S29 (4.61 g, 7.99 mmol, 91%) as a white solid.

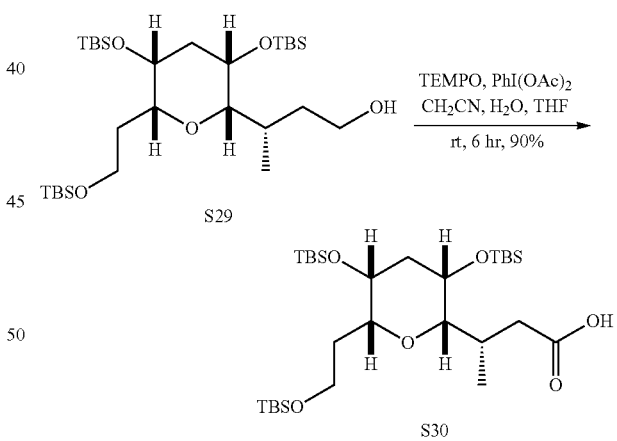

To a stirred solution of alcohol S29 (1.6 g, 2.81 mmol, 1 eq.) in THF/CH$_3$CN/H$_2$O (3.5 mL/13 mL/13 mL) were added TEMPO (220 mg, 1.41 mmol, 0.5 eq.) and PhI(OAc)$_2$ (4.53 g, 14.1 mmol, 5 eq.) at room temperature. After being stirred for 5 h at the same temperature, the resultant mixture was quenched with sat. Na$_2$S$_2$O$_3$ aq. The organic layer was separated and the aqueous layer was extracted with Et$_2$O. The combined organic layer was dried over MgSO$_4$, filtered, and concentrated under reduced pressure. The crude product was purified by flash column chromatography on silica gel (0%, 5%, 10%, then 25% EtOAc in Hexanes) to give acid S30 (1.49 g, 2.53 mmol, 90%) as an amorphous solid. S30:

[α]$^{20D}$+34.0 (c 1.00, CHCl$_3$). $^1$H NMR (600 MHz, C$_6$D$_6$) δ: 3.90 (1H, td, J=9.6, 4.2 Hz), 3.79 (1H, m), 3.61 (1H, s), 3.46 (1H, d, J=10.8 Hz), 3.40 (1H, s), 3.01 (1H, dd, J=16.2, 4.2 Hz), 2.82 (1H, d, J=4.2 Hz), 2.66 (1H, m), 2.35 (1H, dd, J=16.2, 7.2 Hz), 2.15 (1H, m), 1.89 (1H, d, J=14.4 Hz), 1.65 (1H, m), 1.49 (1H, dt, J=14.4, 4.9 Hz), 1.04 (9H, s), 1.03 (9H, s), 1.02 (9H, s), 0.96 (3H, d, J=7.2 Hz), 0.15 (3H, s), 0.14 (3H, s), 0.13 (3H, s), 0.08 (3H, s), 0.06 (3H, s), 0.01 (3H, s) ppm. $^{13}$C NMR (150 MHz, C$_6$D$_6$) δ: 180.2, 84.1, 77.6, 67.3, 64.9, 60.6, 39.4, 37.8, 36.0, 30.8, 26.7, 26.5, 26.3, 18.6, 18.5, 18.4, 16.8, −2.6, −3.4, −4.8, −5.0, −5.1, −5.2 ppm. FTIR (film): 2953, 2929, 2885, 2857, 1708, 1472, 1463, 1386, 1253, 1098, 1020, 938, 886, 772 cm$^{-1}$. HRMS (ESI) m/z: [M+H]$^+$ calcd for C$_{29}$H$_{63}$O$_6$Si$_3$, 591.3927; found, 591.3921.

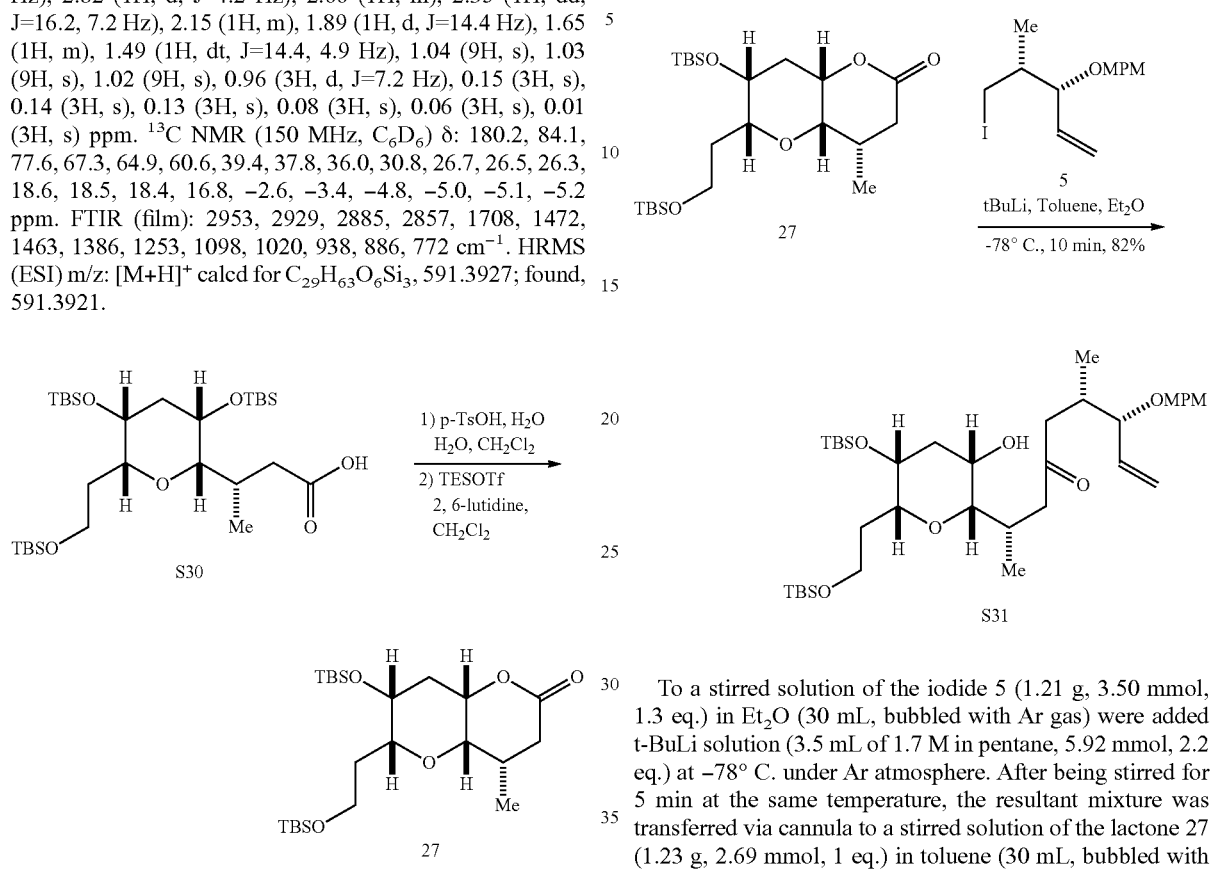

To a stirred solution of acid S30 (2.50 g, 4.23 mmol, 1 eq.) in CH$_2$Cl$_2$ (40 mL) were added p-TsOH.H$_2$O (805 mg, 4.23 mmol, 1 eq.) and H$_2$O (0.76 mL, 42.3 mmol, 10 eq.) at room temperature. After being stirred for 24 h at the same temperature, the resultant mixture was directly concentrated under reduced pressure to give a crude lactone. The crude product was used in the next step without any purification.

To a stirred solution of the crude lactone (calculated as 4.23 mmol, 1 eq.) in CH$_2$Cl$_2$ (100 mL) were added 2,6-lutidne (5.43 g, 50.8 mmol, 12 eq.) and TESOTf (11.2 g, 42.3 mmol, 10 eq.) at 0° C. After being stirred for 1 h at room temperature, MeOH (3 mL) was added and the resultant mixture was diluted with 200 mL of CH$_2$Cl$_2$. The resultant mixture was washed with sat. NH$_4$Cl aq. and sat. NaHCO$_3$ aq. The organic layer was dried over Na$_2$SO$_4$, filtered, and concentrated under reduced pressure. The residue was purified by flash column chromatography on silica gel (0%, 5%, 10%, then 15% EtOAc in Hexanes) to give bis-TES 27 (1.46 g, 3.20 mmol, 76% for 2 steps) as a colorless oil. 27: [α]$^{20}_D$ +25.5 (c 1.00, CHCl$_3$). $^1$H NMR (600 MHz, C$_6$D$_6$) δ: 3.80 (1H, td, J=9.6, 4.4 Hz), 3.70 (1H, m), 3.61 (1H, s), 3.37 (1H, dd, J=10.2, 3.0 Hz), 3.33 (1H, s), 2.82 (1H, s), 2.46 (1H, dd, J=17.2, 12.0 Hz), 2.13 (1H, dd, J=17.2, 4.6 Hz), 2.09-2.02 (2H, m), 1.67 (1H, m), 1.32 (1H, m), 1.20 (1H, dt, J=14.4, 4.5 Hz), 1.09-1.01 (18H, m), 0.79 (3H, d, J=6.6 Hz), 0.75-0.61 (12H, m) ppm. $^{13}$C NMR (150 MHz, C$_6$D$_6$) δ: 168.5, 75.6, 74.3, 73.4, 66.2, 59.2, 36.3, 36.0, 33.0, 31.4, 26.2, 16.6, 7.2, 5.3, 4.8 ppm. FTIR (film): 2954, 2934, 2911, 2876, 1734, 1459, 1414, 1376, 1239, 1197, 1097, 1032, 938, 780, 726 cm$^{-1}$. HRMS (ESI) m/z: [M+H]$^+$ calcd for C$_{23}$H$_{47}$O$_5$Si$_2$, 459.2957; found, 459.2946.

To a stirred solution of the iodide 5 (1.21 g, 3.50 mmol, 1.3 eq.) in Et$_2$O (30 mL, bubbled with Ar gas) were added t-BuLi solution (3.5 mL of 1.7 M in pentane, 5.92 mmol, 2.2 eq.) at −78° C. under Ar atmosphere. After being stirred for 5 min at the same temperature, the resultant mixture was transferred via cannula to a stirred solution of the lactone 27 (1.23 g, 2.69 mmol, 1 eq.) in toluene (30 mL, bubbled with Ar gas) at −78° C. under Ar atmosphere. After being stirred for 10 min at the same temperature, the resultant mixture was quenched with sat. NaHCO$_3$ aq. The organic layer was separated and the aqueous layer was extracted with EtOAc. The combined organic layer was dried over Na$_2$SO$_4$, filtered, and concentrated under reduced pressure. The crude product was purified by flash column chromatography on neutral silica gel (0%, 5%, 10%, then 15% EtOAc in Hexanes) to give ketone/hemiketal mixture S31 (1.48 g, 2.19 mmol, 82%) as a colorless oil. S31: [α]$^{20}_D$ +2.8 (c 1.00, CHCl$_3$). $^1$H NMR (500 MHz, C$_6$D$_6$) δ: 7.27 (2H, d, J=9.6 Hz), 6.85 (2H, d, J=9.6 Hz), 5.64 (1H, m), 5.16-5.05 (2H, m), 4.55 (1H, d, J=13.8 Hz), 4.23 (1H, d, J=13.8 Hz), 3.94-3.87 (1H, m), 3.84-3.78 (1H, m), 3.70-3.61 (2H, m), 3.49 (1H, t, J=7.8 Hz), 3.44 (1H, d, J=11.4 Hz), 3.40 (1H, s), 3.34 (3H, s), 2.98 (1H, dd, J=18.0, 3.6 Hz), 2.91-2.85 (1H, m), 2.81 (1H, d, J=10.8 Hz), 2.74 (1H, dd, J=18.0, 3.6 Hz), 2.55-2.48 (1H, m), 2.30-2.18 (2H, m), 2.13-2.05 (1H, m), 2.02 (1H, dt, J=17.4, 2.0 Hz), 1.68-1.60 (1H, m), 1.28 (1H, dt, J=17.4, 2.0 Hz), 1.08 (9H, t, J=8.4 Hz), 0.99 (3H, d, J=7.8 Hz), 0.97 (3H, d, J=7.8 Hz), 0.93 (9H, t, J=8.4 Hz), 0.70 (6H, q, J=8.4 Hz), 0.51 (6H, q, J=8.4 Hz) ppm. $^{13}$C NMR (125 MHz, C$_6$D$_6$) δ: 208.9, 159.7, 137.9, 131.4, 129.5, 117.9, 114.0, 84.6, 84.0, 77.0, 70.2, 69.7, 65.0, 59.7, 54.8, 47.9, 46.0, 37.7, 36.5, 34.0, 31.3, 16.5, 16.2, 7.2, 7.0, 5.0, 4.9 ppm. FTIR (film): 3523, 2955, 2935, 2912, 2876, 1711, 1613, 1514, 1459, 1413, 1376, 1301, 1247, 1085, 1003, 819, 743 cm$^{-1}$. HRMS (ESI) m/z: [M+Na]$^+$ calcd for C$_{37}$H$_{66}$O$_7$Si$_2$Na, 701.4245; found, 701.4268.

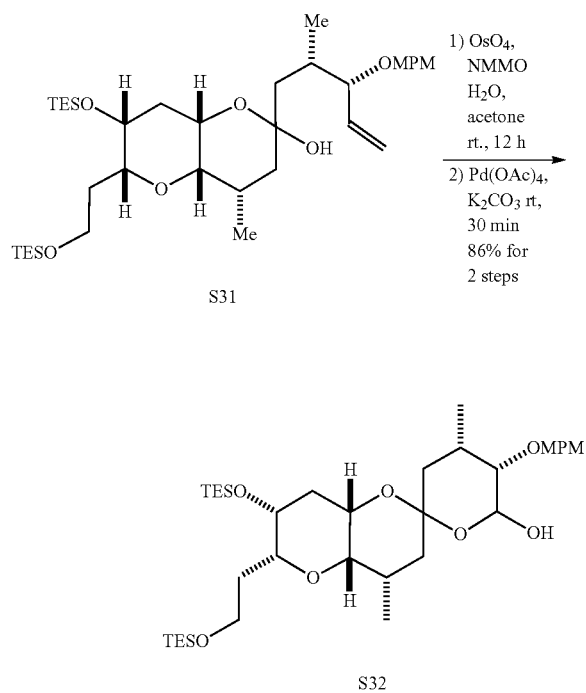

S31

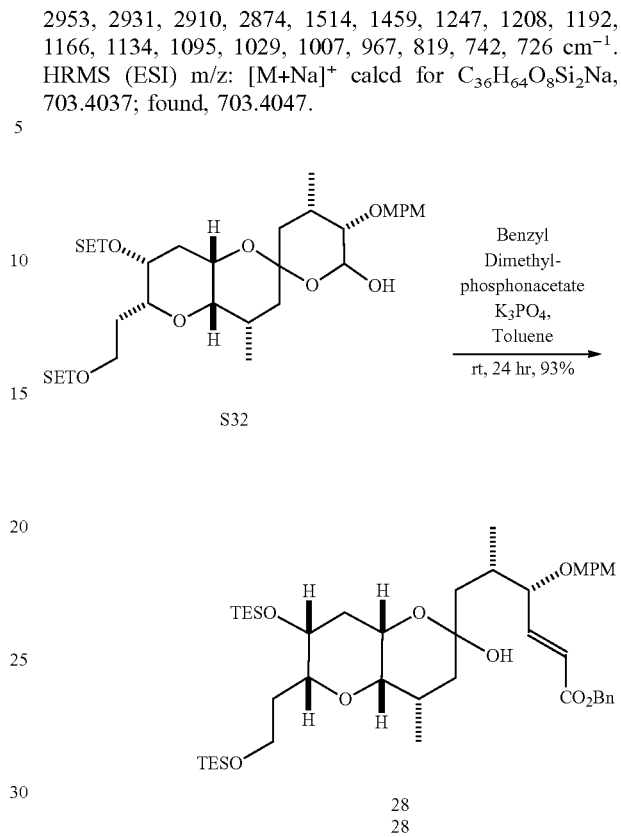

S32

2953, 2931, 2910, 2874, 1514, 1459, 1247, 1208, 1192, 1166, 1134, 1095, 1029, 1007, 967, 819, 742, 726 cm$^{-1}$. HRMS (ESI) m/z: [M+Na]$^+$ calcd for $C_{36}H_{64}O_8Si_2Na$, 703.4037; found, 703.4047.

To a stirred solution of S31 (1.17 g, 1.73 mmol, 1 eq.) in acetone (17.3 mL) were added NMMO (405 mg, 3.46 mmol, 2 eq.) and OsO$_4$ solution (4.4 mL of 0.02 M in H$_2$O, 0.088 mmol, 5 mol %) at room temperature. After being stirred for 12 h at the same temperature, the mixture was diluted with water. The organic layer was separated and the aqueous layer was extracted with EtOAc. The combined organic layer was dried over Na$_2$SO$_4$, filtered, and concentrated under reduced pressure. The residue was passed through a pad of silica gel (EtOAc) and concentrated under reduced pressure to give a crude diol, which was used in the next reaction without further purification.

To a stirred solution of diol (calculated as 1.73 mmol, 1 eq.) in CH$_2$Cl$_2$ (17.3 mL) was added K$_2$CO$_3$ (2.39 g, 17.3 mmol, 10 eq.) and Pb(OAc)$_4$ (1.53 g, 3.46 mmol, 2 eq.) at room temperature. After being stirred for 1 h at the same temperature, the reaction mixture was passed through a pad of silica gel (EtOAc). The filtrate was concentrated under reduced pressure. The residue was purified by flash column chromatography on silica gel (0%, 9%, 17%, then 25% EtOAc in Hexanes) to give S32 (1.0 g, 1.48 mmol, 86% for 2 steps) as colorless oil. S32 was obtained as an equilibrium mixture of hemiacetal. S32: [α]$^{20}_D$ −20.0 (c 1.00, CHCl$_3$). $^1$H NMR (600 MHz, C$_6$D$_6$) δ: 7.16 (2H, d, J=8.4 Hz), 6.76 (2H, d, J=8.4 Hz), 5.44 (0.28H, d, J=9.6 Hz), 4.91 (0.72H, d, J=9.6 Hz), 4.54 (0.72H, d, J=9.6 Hz), 4.46 (0.28H, d, J=9.6 Hz), 4.36 (0.72H, d, J=9.6 Hz), 4.26 (0.28H, d, J=9.6 Hz), 4.11 (0.28H, s), 3.98-3.86 (1.28H, m), 3.85-3.76 (1H, m), 3.60 (0.78H, s), 3.46-3.36 (2H, m), 3.30 (0.84H, s), 3.29 (2.16H, s), 3.22 (0.28H, s), 3.20 (0.72H, s), 2.99 (0.28H, s), 2.96 (0.72H, s), 2.64 (0.28H, m), 2.34 (1.72H, m), 2.23-2.11 (1H, m), 1.92-1.76 (1.28H, m), 1.76-1.60 (3.27H, m), 1.54 (1H, m), 1.50-1.40 (2H, m), 1.15-0.98 (24H, m), 0.74-0.54 (12H, m) ppm. $^{13}$C NMR (125 MHz, C$_6$D$_6$) δ: 159.9, 131.2, 129.7, 129.6, 114.3, 114.0, 99.0, 98.2, 93.9, 91.3, 80.1, 78.5, 76.4, 76.3, 76.0, 75.9, 75.8, 72.1, 67.0, 66.9, 66.0, 65.2, 59.6, 59.5, 54.7, 38.5, 38.4, 37.8, 37.7, 36.6, 36.4, 30.1, 29.0, 23.5, 17.8, 17.5, 17.3, 7.3, 7.2, 5.5, 5.4, 4.8 ppm. FTIR (film):

To a stirred solution of S32 (700 mg, 1.029 mmol, 1 eq.) in toluene (10 mL) were added benzyl dimethylphosphonoacetate (0.86 mL, 4.116 mmol, 4 eq.) and K$_3$PO$_4$ (660 mg, 3.087 mmol, 3 eq.) at room temperature. After being stirred for 36 h at the same temperature, the reaction mixture was passed through a pad of silica gel (50% EtOAc in Hexanes) to give crude 28, which was further purified by flash column chromatography on neutral silica gel (0%, 5%, 6%, then 9% EtOAc in Hexanes) to give a ~8:1 mixture of E/Z isomers 28 (776 mg, 0.956 mmol, 93%) as a colorless oil. Some of the pure E isomer was isolated for characterization purpose by further chromatography. The Mixture of E/Z isomer was directly used in the next step. 28: [α]$^{20}_D$ −2.2 (c 1.00, CHCl$_3$). $^1$H NMR (600 MHz, C$_6$D$_6$) δ: 7.24 (2H, d, J=7.8 Hz), 7.15 (2H, d, J=7.8 Hz), 7.11 (2H, t, J=7.8 Hz), 7.05 (1H, m), 6.79 (2H, d, J=7.8 Hz), 6.19 (1H, d, J=15.6 Hz), 5.12 (2H, q, J=12.0 Hz), 4.37 (1H, d, J=12.0 Hz), 4.11 (1H, d, J=12.0 Hz), 3.92-3.87 (1H, m), 3.83-3.78 (1H, m), 3.68-3.57 (3H, m), 3.46-3.41 (2H, m), 3.33 (3H, s), 2.91 (1H, dd, J=15.0, 2.0 Hz), 2.85-2.78 (2H, m), 2.52 (1H, dd, J=17.4, 4.5 Hz), 2.49-2.44 (1H, m), 2.21-2.10 (2H, m), 2.08 (1H, td, J=10.2, 6.0 Hz), 2.03 (1H, d, J=14.4 Hz), 1.68-1.61 (1H, m), 1.29 (1H, d, J=14.4 Hz), 1.07 (9H, t, J=8.4 Hz), 0.97 (3H, d, J=7.8 Hz), 0.93 (9H, t, J=8.4 Hz), 0.86 (3H, d, J=7.8 Hz), 0.69 (6H, q, J=8.4 Hz), 0.52 (6H, q, J=8.4 Hz) ppm. $^{13}$C NMR (150 MHz, C$_6$D$_6$) δ: 208.3, 165.6, 159.8, 147.8, 136.7, 130.7, 129.7, 128.7, 128.6, 128.3, 123.3, 114.0, 84.5, 81.6, 76.9, 71.2, 69.6, 66.4, 65.0, 59.6, 54.8, 47.8, 45.6, 37.8, 36.5, 33.7, 31.2, 16.3, 16.2 7.2, 7.0, 5.1, 4.9 ppm. FTIR (film): 3511, 2954, 2912, 2876, 1720, 1514, 1458, 1413, 1376, 1248, 1165, 1085, 1004, 820, 743, 729, 698 cm$^{-1}$. HRMS (ESI) m/z: [M+Na]$^+$ calcd for $C_{45}H_{72}O_9Si_2Na$, 835.4613; found, 835.4622.

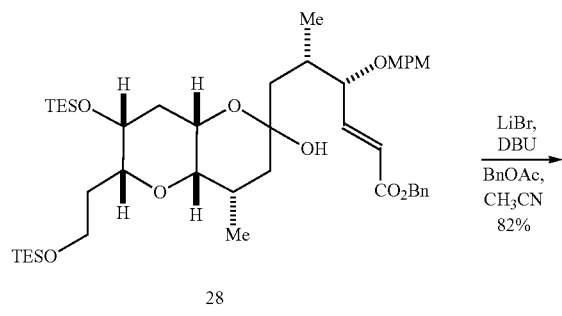

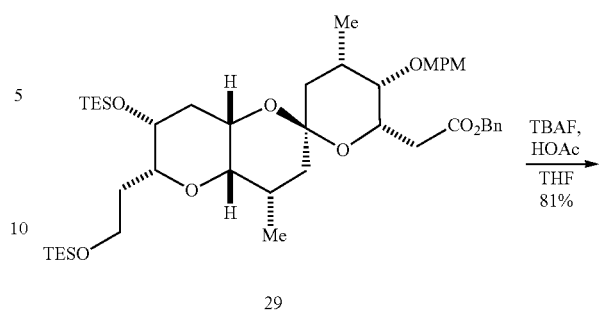

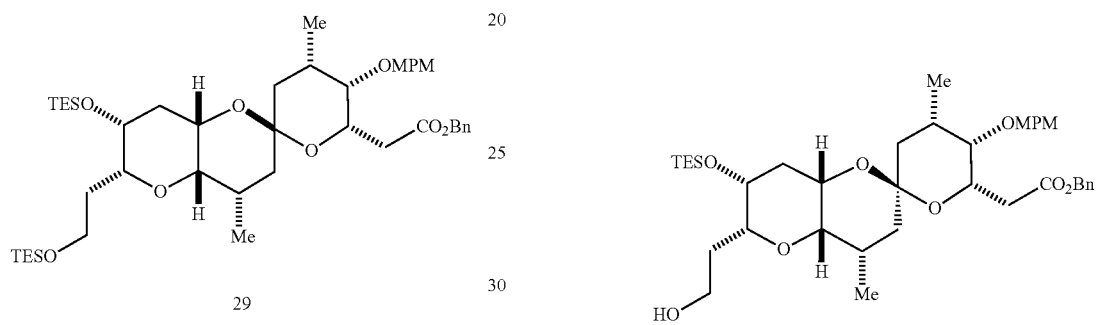

To a stirred solution of unsaturated ester 28 (800 mg, 0.985 mmol, 1 eq.) in MeCN (3.0 mL) were added BnOAc (296 mg, 1.97 mmol, 2 eq.), LiBr (857 mg, 9.85 mmol, 10 eq.), and DBU (0.74 mL, 4.93 mmol, 5 eq.) at room temperature. After being stirred for 12 h at the same temperature, hexanes (3.0 mL) and H$_2$O (3.0 mL) were added to the reaction mixture. The organic layer was separated and the aqueous layer was extracted with hexanes. The combined organic layer was dried over Na$_2$SO$_4$, filtered, and concentrated under reduced pressure. The obtained crude material was purified by flash column chromatography on neutral silica gel (0%, 5%, 6%, then 9% EtOAc in Hexanes) to give spiro ketal 29 (658 mg, 0.810 mmol, 82%) as colorless oil. 29: $[\alpha]^{20}_D$ −28.1 (c 1.00, CHCl$_3$). $^1$H NMR (600 MHz, C$_6$D$_6$) δ: 7.24 (2H, d, J=7.8 Hz), 7.20 (2H, d, J=7.8 Hz), 7.13 (2H, t, J=7.8 Hz), 7.09 (1H, q, J=7.8 Hz), 6.77 (2H, d, J=7.8 Hz), 5.09 (1H, d, J=14.4 Hz), 5.00 (1H, d, J=14.4 Hz), 4.33 (1H, d, J=11.0 Hz), 4.28-4.21 (2H, m), 3.94 (1H, m), 3.88-3.78 (2H, m), 3.48 (1H, d, J=10.8 Hz), 3.42 (1H, m), 3.30 (3H, s), 3.04 (1H, s), 2.97 (1H, dd, J=14.4, 10.8 Hz), 2.90 (1H, s), 2.38 (1H, m), 2.31 (1H, dd, J=17.0, 2.5 Hz), 2.26-2.16 (2H, m), 2.04 (1H, d, J=15.0 Hz), 1.77-1.64 (3H, m), 1.61-1.55 (2H, m), 1.42 (1H, dd, J=12.6, 3.1 Hz), 1.12-1.04 (21H, m), 1.02 (3H, d, J=6.6 Hz), 0.67 (12H, q, J=8.4 Hz) ppm. $^{13}$C NMR (150 MHz, C$_6$D$_6$) δ: 171.7, 159.7, 136.8, 131.3, 129.7, 128.8, 128.6, 128.3, 114.0, 97.0, 78.6, 76.4, 76.2, 75.3, 69.8, 67.2, 66.1, 64.9, 59.6, 54.7, 38.2, 37.7, 37.4, 36.7, 36.4, 30.9, 29.2, 18.2, 17.4, 7.3, 7.2, 5.5, 4.9 ppm. FTIR (film): 2953, 2978, 2911, 2874, 1736, 1613, 1514, 1458, 1414, 1396, 1371, 1303, 1246, 11246, 1207, 1190, 1165, 1128, 1095, 1032, 1010, 974, 822, 741, 727, 698, 671 cm$^{-1}$. HRMS (ESI) m/z: [M+Na]$^+$ calcd for C$_{45}$H$_{72}$O$_9$Si$_2$Na, 835.4613; found, 835.4598.

To a stirred solution of TES ether 29 (600 mg 0.738 mmol, 1 eq.) in CH$_2$Cl$_2$ (5 mL) was added TBAF (1.107 mL, 1 M solution in THF, 1.107 mmol, 1.5 eq.) at 0° C. After being stirred for 5 hr at the same temperature, without concentration, the reaction mixture was directly subjected to the flash column chromatography on neutral silica gel (0%, 5%, then 10% EtOAc in Hexanes) to give ester S33 (418 mg, 0.598 mmol, 81%) as a colorless oil. S33: $[\alpha]^{20}_D$ −46.0 (c 1.00, CHCl$_3$). $^1$H NMR (600 MHz, C$_6$D$_6$) δ: 7.24 (2H, d, J=7.8 Hz), 7.20 (2H, d, J=7.8 Hz), 7.13 (2H, t, J=7.8 Hz), 7.09 (1H, q, J=7.8 Hz), 6.77 (2H, d, J=7.8 Hz), 5.09 (1H, d, J=14.4 Hz), 5.00 (1H, d, J=14.4 Hz), 4.33 (1H, d, J=11.0 Hz), 4.28-4.21 (2H, m), 3.85-3.79 (2H, m), 3.77-3.72 (1H, m), 3.29 (3H, s), 3.21 (1H, d, J=8.4 Hz), 2.99-2.93 (2H, m), 2.88 (1H, s), 2.36 (1H, s), 2.28 (1H, dd, J=16.2, 3.0 Hz), 2.24 (1H, m), 2.16-2.08 (2H, m), 2.01 (1H, d, J=13.8 Hz), 1.69-1.54 (3H, m), 1.50 (1H, dt, J=13.8, 2.1 Hz), 1.36 (2H, dd, J=12.6, 3.0 Hz), 1.08 (9H, t, J=8.4 Hz), 1.03 (3H, d, J=7.2 Hz), 0.97 (3H, d, J=7.2 Hz), 0.65 (6H, q, J=8.4 Hz) ppm. $^{13}$C NMR (150 MHz, C$_6$D$_6$) δ: 171.7, 159.8, 136.8, 131.2, 129.7, 128.7, 128.6, 128.3, 114.0, 97.0, 80.1, 78.5, 76.6, 75.3, 69.8, 66.9, 66.1, 64.6, 61.3, 54.8, 38.1, 37.7, 37.3, 36.4, 35.1, 30.9, 28.9, 18.2, 17.6, 7.3, 5.5 ppm. FTIR (film): 2954, 2928, 2911, 2874, 1736, 1612, 1514, 1457, 1420, 1304, 1247, 1208, 1163, 1086, 1064, 1038, 1010, 821, 740, 699 cm$^{-1}$. HRMS (ESI) m/z: [M+H]$^+$ calcd for C$_{39}$H$_{59}$O9Si, 699.3923; found, 699.3937.

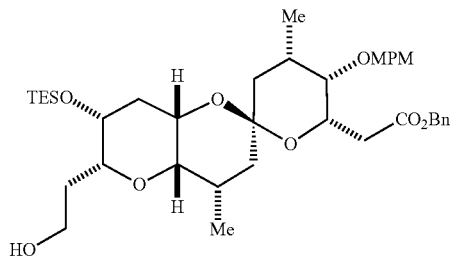

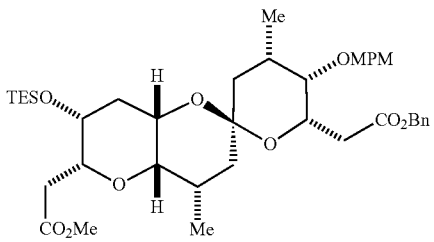

S33

To a stirred solution of alcohol S33 (400 mg, 0.573 mmol, 1 eq.) in CH$_2$Cl$_2$ (10 mL) were added NaHCO$_3$ (480 mg, 5.73 mmol, 10 eq.) and Dess-Martin periodinane (486 mg, 1.146 mmol, 2 eq.) subsequently at room temperature. After being stirred for 30 min at the same temperature, the reaction was quenched with sat. NaHCO$_3$ aq. The organic layer was separated and the aqueous layer was extracted with CH$_2$Cl$_2$. The combined organic layer was dried over Na$_2$SO$_4$, filtered, and concentrated under reduced pressure. The obtained crude material was passed through a SiO$_2$ to give the crude aldehyde which was used in the next step without further purification. To a stirred solution of the crude aldehyde (estimated as 0.573 mmol, 1 eq.) in a mixed solvent (9 mL of t-BuOH, 2 mL of water and 2 mL of 2-methyl-2-butene) were added NaH$_2$PO$_3$·H$_2$O (316 mg, 2.292 mmol, 4 eq.) and NaClO$_2$ (156 mg, 1.719 mmol, 3 eq.) subsequently at room temperature. After being stirred for 30 min at the same temperature, the reaction was quenched with sat. NaHCO$_3$ aq. The organic layer was separated and the aqueous layer was extracted with EtOAc. The combined organic layer was dried over Na$_2$SO$_4$, filtered, and concentrated under reduced pressure. The obtained crude acid was used in the next step without further purification. To a stirred solution of the crude acid (estimated as 0.573 mmol, 1 eq.) in a mixed solvent (15 mL of benzene and 3 mL of MeOH) was added TMSCH$_2$N$_2$ solution (0.81 mL of 2 M in Et$_2$O, 1.72 mmol, 3 eq.) at room temperature. After being stirred for 5 min at the same temperature, the reaction was quenched with HOAc (0.1 mL) at 0° C. After concentration, the obtained crude material was purified by flash column chromatography on neutral silica gel (0%, 3%, then 5% EtOAc in Hexanes) to give ester 30 (362 mg, 0.499 mmol, 87% for 3 steps) as a colorless oil. 30: [α]$^{20}_D$ −35.6 (c 1.00, CHCl$_3$). $^1$H NMR (600 MHz, C$_6$D$_6$) δ: 7.24 (2H, d, J=7.8 Hz), 7.20 (2H, d, J=7.8 Hz), 7.13 (2H, t, J=7.8 Hz), 7.09 (1H, q, J=7.8 Hz), 6.77 (2H, d, J=7.8 Hz), 5.09 (1H, d, J=14.4 Hz), 5.00 (1H, d, J=14.4 Hz), 4.33 (1H, d, J=11.0 Hz), 4.28-4.21 (2H, m), 3.78 (1H, s), 3.74 (1H, d, J=8.4 Hz), 3.59 (1H, s), 3.38 (3H, s), 3.30 (3H, s), 2.99 (1H, s), 2.95 (1H, dd, J=12.2, 10.8 Hz), 2.91 (1H, s), 2.83 (1H, dd, J=16.2, 7.2 Hz), 2.58 (1H, dd, J=16.2, 6.0 Hz), 2.36 (1H, s), 2.31 (1H, dd, J=16.2, 3.2 Hz), 2.13 (1H, s), 2.01 (1H, d, J=15.0 Hz), 1.66 (2H, td, J=12.6, 2.0 Hz), 1.58-1.51 (2H, m), 1.38 (1H, dd, J=12.6, 3.2 Hz), 1.06 (9H, t, J=8.4 Hz), 1.05 (3H, d, J=6.0 Hz), 1.00 (3H, d, J=6.0 Hz), 0.64 (6H, q, J=8.4 Hz) ppm. $^{13}$C NMR (150 MHz, C$_6$D$_6$) δ: 171.8, 171.7, 159.7, 136.7, 131.3, 129.7, 128.8, 128.7, 128.3, 114.0, 97.0, 78.5, 77.1, 76.4, 75.3, 69.8, 66.1, 65.7, 64.4, 54.8, 50.9, 38.0, 37.7, 37.3, 37.2, 36.2, 30.9, 28.9, 18.2, 17.6, 7.3, 5.4 ppm. FTIR (film): 2952, 2924, 2874, 2854, 1737, 1613, 1514, 1457, 1436, 1397, 1371, 1302, 1246, 1207, 1163, 1085, 1038, 944, 738, 698 cm$^{-1}$. HRMS (ESI) m/z: [M+Na]$^+$ calcd for C$_{40}$H$_{58}$O$_{10}$SiNa, 749.3697; found, 749.3720.

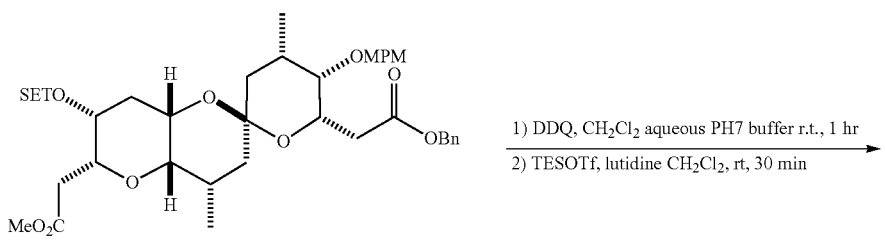

30

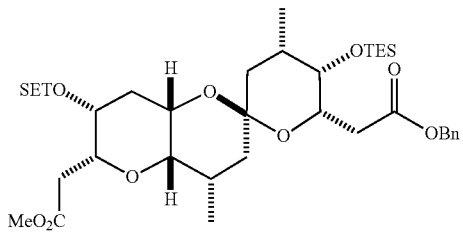

31

To a stirred solution of MPM ether 30 (350 mg, 0.482 mmol, 1 eq.) in CH$_2$Cl$_2$ (10 mL), phosphate buffer (3 mL, pH7) was added DDQ (219 mg, 0.964 mmol, 2 eq.) at room temperature. After being stirred for 1 h at the same temperature, the reaction was quenched with sat. NaHCO$_3$ aq. The organic layer was separated and the aqueous layer was extracted with CH$_2$Cl$_2$. The combined organic layer was dried over Na$_2$SO$_4$, filtered, and concentrated under reduced pressure. The obtained crude material was passed through a SiO$_2$ to give the crude alcohol, which was used in the next step without further purification.

To a stirred solution of the crude alcohol (calculated as 0.482 mmol, 1 eq.) in CH$_2$Cl$_2$ (5.0 mL) were added 2,6-lutidine (129 mg, 1.205 mmol, 2.5 eq.) and TESOTf (255 mg, 0.964 mmol, 2 eq.) at room temperature maintained with a water bath. After being stirred for 30 min at the same temperature, the reaction was quenched with sat. NaHCO$_3$ aq. The organic layer was separated and the aqueous layer was extracted with EtOAc. The combined organic layer was dried over Na$_2$SO$_4$, filtered, and concentrated under reduced pressure. The obtained crude material was purified by flash column chromatography on neutral silica gel (0%, 3%, then 5% EtOAc in Hexanes) to give TES ether 31 (288 mg, 0.400 mmol, 97%) as a colorless oil. 31: [α]$^{20}_D$ −52.1 (c 1.00, CHCl$_3$). $^1$H NMR (600 MHz, C$_6$D$_6$) δ: 7.26 (2H, d, J=7.8 Hz), 7.11 (2H, t, J=7.8 Hz), 7.05 (1H, q, J=7.8 Hz), 5.09 (1H, d, J=14.4 Hz), 5.00 (1H, d, J=14.4 Hz), 4.18 (1H, dd, J=10.2, 4.0 Hz), 3.80 (1H, s), 3.74 (1H, td, J=6.6, 1.5 Hz), 3.61 (1H, s), 3.38 (3H, s), 3.29 (1H, s), 2.98 (1H, s), 2.91 (1H, dd, J=13.8, 12.0 Hz), 2.84 (1H, dd, J=15.0, 8.4 Hz), 2.60 (1H, dd, J=15.0, 5.5 Hz), 2.35-2.29 (2H, m), 2.15-2.07 (1H, m), 2.03 (1H, dd, J=15.0, 3.0 Hz), 1.68 (1H, t, J=13.8 Hz), 1.64 (1H, t, J=13.8 Hz), 1.58-1.51 (2H, m), 1.40 (1H, dd, J=13.2, 4.3 Hz), 1.07 (9H, t, J=8.4 Hz), 0.99 (3H, d, J=7.2 Hz), 0.96 (3H, d, J=7.2 Hz), 0.95 (9H, t, J=8.4 Hz), 0.65 (6H, q, J=8.4 Hz), 0.56 (6H, q, J=8.4 Hz) ppm. $^{13}$C NMR (150 MHz, C$_6$D$_6$) δ: 171.8, 171.6, 136.7, 128.8, 128.7, 128.3, 96.9, 77.2, 76.4, 72.5, 70.1, 66.2, 65.6, 64.4, 38.3, 37.5, 37.4, 37.2, 36.3, 31.0, 28.9, 18.5, 17.1, 7.3, 7.2, 5.8, 5.4 ppm. FTIR (film): 2955, 2925, 2876, 1739, 1457, 1372, 1304, 1266, 1240, 1208, 1160, 1130, 1086, 1063, 1036, 947, 856, 740, 697 cm$^{-1}$. HRMS (ESI) m/z: [M+Na]$^+$ calcd for C$_{38}$H$_{64}$O$_9$Si$_2$Na, 743.3987; found, 743.4003.

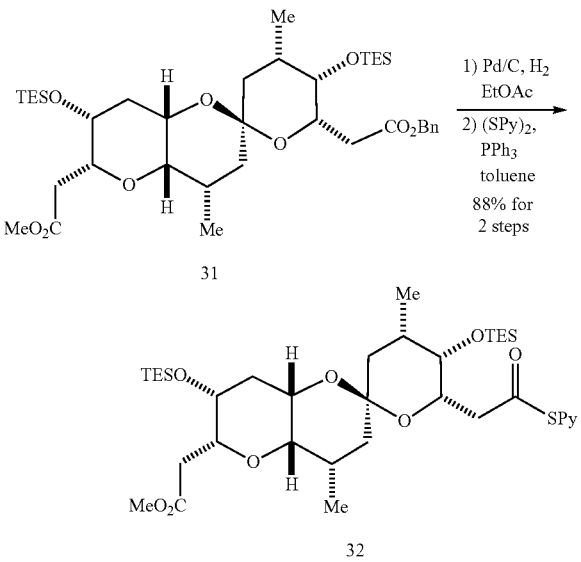

To a stirred solution of Benzyl ester 31 (250 mg, 0.347 mmol, 1 eq.) in EtOAc (10.0 mL) was added wet 10% Pd/C (25 mg, 10% w/w) at room temperature. The reaction was stirred under 1 atmosphere of hydrogen for 2 h at the same temperature. The resulting mixture was filtered through a pad of Celite (EtOAc). The organic solvent was removed under reduced pressure to give a crude acid, which was used in the next step without further purification.

To a stirred solution of the crude carboxylic acid (calculated as 0.347 mmol, 1 eq.) in toluene (1.2 mL) were added PPh$_3$ (110 mg, 0.416 mmol, 1.2 eq.) and (PyS)$_2$ (107 mg, 0.486 mmol, 1.4 eq.) at room temperature. After being stirred for 12 h at the same temperature, the resulting reaction mixture was directly subjected to column chromatography on neutral silica gel (0%, 3%, 5%, then 6% EtOAc in Hexanes) to give pyridinethiol ester 5-32 (221 mg, 0.306 mmol, 88% for 2 steps) as colorless oil. 5-32: [α]$^{20}_D$ −62.1 (c 1.0, CHCl$_3$). $^1$H NMR (600 MHz, C$_6$D$_6$) δ: 8.32 (1H, dd, J=4.5, 1.3 Hz), 7.52 (1H, d, J=7.8 Hz), 6.97 (1H, td, J=7.8, 1.5 Hz), 6.48 (1H, m), 4.19 (1H, dd, J=9.6, 2.8 Hz), 3.88 (1H, t, J=1.6 Hz), 3.72 (1H, m), 3.58 (1H, t, J=1.6 Hz), 3.37 (3H, s), 3.23 (1H, dd, J=13.8, 10.2 Hz), 3.17 (1H, brs), 3.04

(1H, J=2.4 Hz, 1H), 2.82 (1H, dd, J=13.8, 7.2 Hz), 2.59-2.53 (2H, m), 2.41-2.34 (1H, m), 2.27 (1H, m), 2.03 (1H, dt, J=14.4, 2.4 Hz), 1.70 (1H, t, J=13.2 Hz), 1.63 (1H, t, J=13.2 Hz), 1.59 (1H, dt, J=15.0, 3.5 Hz), 1.53 (1H, dd, J=13.2, 5.2 Hz), 1.45 (1H, dd, J=13.2, 5.2 Hz), 1.06 (9H, t, J=8.4 Hz), 1.00 (3H, d, J=6.0 Hz), 0.98 (9H, t, J=8.4 Hz), 0.93 (3H, d, J=6.6 Hz), 0.64 (6H, q, J=8.4, 1.1 Hz), 0.56 (6H, q, J=8.4 Hz) ppm. $^{13}$C NMR (150 MHz, C$_6$D$_6$) δ: 194.7, 152.7, 150.6, 136.5, 128.5, 123.1, 97.4, 77.7, 77.5, 72.5, 70.0, 68.6, 67.3, 63.9, 47.8, 37.5, 36.7, 36.5, 30.5, 29.1, 27.8, 27.7, 23.4, 21.0, 18.5, 17.3, 7.4, 5.9 ppm. IR (film): 2955, 2931, 2874, 2857, 1708, 1132, 1035, 974 cm$^{-1}$. HRMS (ESI) m/z: [M+Na]$^+$ calcd for C$_{36}$H$_{61}$NO$_8$SSi$_2$Na, 746.3554; found, 746.3578.

Additional Experimental Procedures for Preparing Compound (1) and Other Compounds

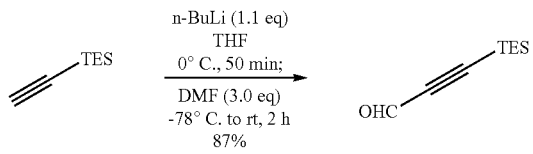

To a stirred solution of (triethylsilyl)acetylene (25.7 g, 183 mmol) in THF (250 mL) was added n-BuLi (2.5 M in hexane, 80.0 mL, 201 mmol) dropwise over 20 min at 0° C. After stirring for 50 min, DMF (42.0 mL, 549 mmol) was added to a mixture at −78° C. The reaction mixture was allowed to warm up to room temperature and stirred for 2 h. The reaction was quenched with 3M HCl (185 mL) at 0° C. The mixture was diluted with EtOAc (260 mL), washed with H$_2$O (190 mL) four times and brine one time. The organic layer was dried over anhydrous sodium sulfate, filtered, and concentrated under reduced pressure. Finally, crude oil was purified by distillation (−63° C.) to afford desired aldehyde (26.9 g, 160 mmol, 87%) as a colorless oil; $^1$H NMR (400 MHz, CDCl$_3$) δ 9.18 (s, 1H), 1.02 (t, J=7.6 Hz, 9H), 0.69 (q, J=7.6 Hz, 6H); $^{13}$C NMR (100 MHz, CDCl$_3$) δ 176.8, 103.5, 101.6, 7.2, 3.7; IR (neat) 2958, 2877, 2151, 1667, 995, 723, 677.

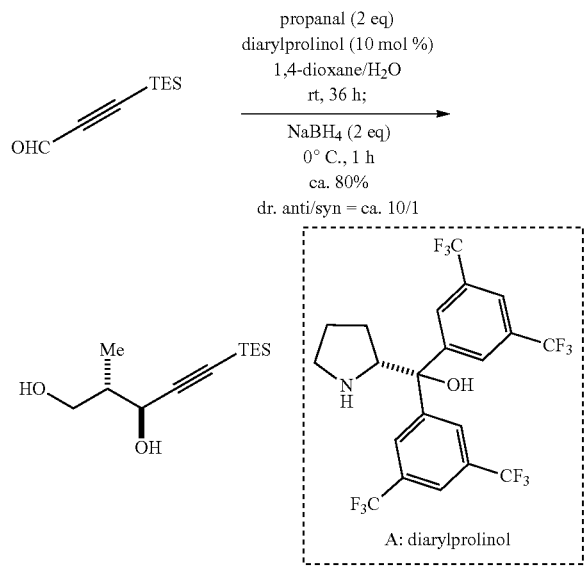

To a stirred mixture of alkynyl aldehyde (25.4 g, 151 mmol), propanal (21.7 mL, 302 mmol), and water (8.20 mL, 453 mmol) in 1,4-dioxane (150 mL) was added diarylprolinol A (7.90 g, 15.1 mmol; Hayashim Y; Itoh, T.; Aratake, S.; Ishikawa, H. Angew, Chem. Int. Ed. 2008, 47, 2082). After stirring for 36 h at room temperature, NaBH$_4$ (11.4 g, 302 mmol) was added to a mixture at 0° C. After stirring for 1 h at 0° C., the reaction was quenched with H$_2$O (54 mL), brine (320 mL) and the reaction mixture was extracted with EtOAc five times. The combined organic extracts were dried over anhydrous sodium sulfate, filtered, and concentrated under reduced pressure. The resulting oil was filtered through a pad of silica gel (450 g) and washed with a mixture of hexanes/EtOAc=10/1, then 1/1. The filtrate was concentrated again under reduced pressure. The residue (27.7 g, ca. 121 mmol, ca. 80%) was subject to the next reaction without further purification.

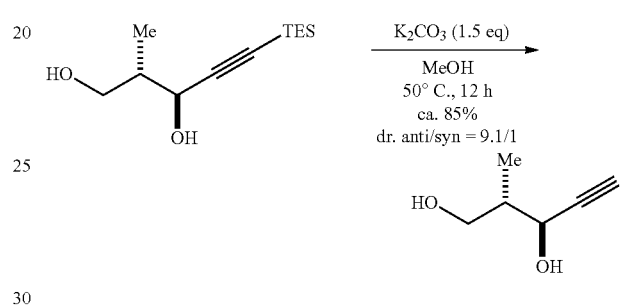

To a stirred solution of the crude diol (27.7 g, ca. 121 mmol) in MeOH (400 mL) was added K$_2$CO$_3$ (25.2 g, 182 mmol) at room temperature. The resulting mixture was heated at 50° C. and stirred for 12 h. After cooling to room temperature, the solvent was removed under reduced pressure. The resulting oil was diluted with CH$_2$Cl$_2$ and filtered through a pad of silica gel (130 g) to remove K$_2$CO$_3$. The precipitate was washed with CH$_2$Cl$_2$/MeOH=10/1 and the filtrate was concentrated under reduced pressure. The resulting oil was filtered through a pad of silica gel (160 g) again and washed with a mixture of hexanes/EtOAc=5/1, then 1/2. The filtrate was concentrated again under reduced pressure. The residue (11.7 g, ca. 103 mmol, ca. 85%) was subject to the next reaction without further purification.

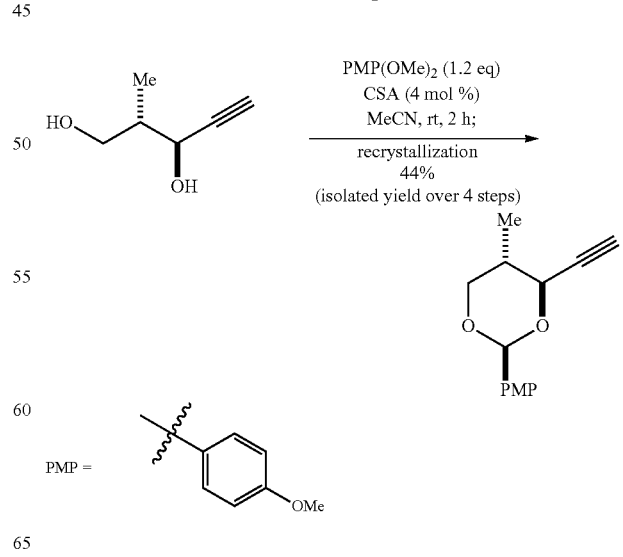

To a stirred mixture of the crude diol (11.7 g, ca. 103 mmol) and p-methoxybenzylidenedimethylacetal (22.0 mL, 124 mmol) in MeCN (180 mL) was added a catalytic amount of CSA (0.96 g, 4.12 mmol) at room temperature. After stirring for 2 h, the reaction mixture was quenched with Et$_3$N (2.9 mL, 20.6 mmol), filtered through a pad of silica gel (70 g), washed with CH$_2$Cl$_2$ and concentrated under reduced pressure. The residue was purified by crystallization from hexanes/CH$_2$Cl$_2$ to afford desired anti compound (15.5 g, 66.8 mmol, 44% over 4 steps from alkynyl aldehyde) as a white pure crystal; [α]$_D^{20}$+3.00 (c 1.0, MeOH); $^1$H NMR (400 MHz, CDCl$_3$) δ 7.42 (d, J=8.4 Hz, 2H), 6.88 (d, J=8.4 Hz, 2H), 5.43 (s, 1H), 4.21-4.15 (m, 2H), 3.80 (s, 3H), 3.51 (dd, J=11.2, 11.2 Hz, 1H), 2.53 (d, J=2.4 Hz, 1H), 2.19-2.17 (m, 1H), 0.95 (d, J=7.2 Hz, 3H); $^{13}$C NMR (100 MHz, CDCl$_3$) δ 160.1, 130.2, 127.6, 113.6, 101.5, 80.7, 74.3, 73.7, 72.7, 55.3, 35.1, 12.5; IR (neat) 3263, 2963, 2838, 1614, 1519, 1247, 1024, 997, 834.

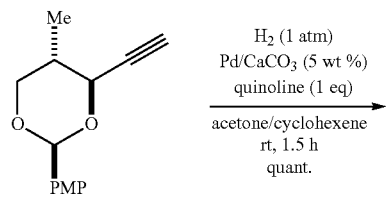

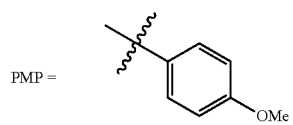

To a stirred solution of alkyne (15.5 g, 66.8 mmol) in a mixture of acetone (480 mL) and cyclohexene (160 mL) was added quinoline (7.90 mL, 66.8 mmol) and 5 wt % Pd/CaCO$_3$ poisoned with Pb (0.775 g, 5 wt %) at room temperature. The flask containing a mixture was charged with hydrogen gas (1 atm) at room temperature, vigorously stirred for 1.5 h and filtered through a pad of Celite. The filter cake was washed with EtOAc and the filtrate was concentrated under reduced pressure. The residue was filtered through a pad of silica gel (230 g) and washed with a mixture of hexanes/EtOAc=20/1. The filtrate was concentrated again under reduced pressure to afford pure alkene (15.6 g, 66.7 mmol, quant.); a white solid; [α]$_D^{20}$+65.4 (c 1.0, CHCl$_3$); $^1$H NMR (400 MHz, CDCl$_3$) δ 7.44 (d, J=8.8 Hz, 2H), 6.89 (d, J=8.8 Hz, 2H), 5.94-5.85 (m, 1H), 5.51 (s, 1H), 5.36 (d, J=17.2 Hz, 1H), 5.26 (d, J=10.4 Hz, 1H), 4.16 (dd, J=11.6, 4.8 Hz, 1H), 3.89 (dd, J=11.4, 4.8 Hz, 1H), 3.80 (s, 3H), 3.54 (dd, J=11.6, 11.4 Hz, 1H), 1.93-1.87 (m, 1H), 0.79 (d, J=6.8 Hz, 3H); $^{13}$C NMR (100 MHz, CDCl$_3$) δ 159.9, 136.0, 131.0, 127.5, 118.0, 113.6, 101.0, 84.7, 73.0, 55.3, 33.9, 12.3; IR (neat) 2965, 1612, 1516, 1248, 1140, 1034, 815.

To a stirred solution of the starting material (445 g, 1.885 mol) in dichloromethane (750 mL) under N$_2$ atmosphere was added Et$_3$N (790 mL, 5.656 mol) at room temperature. To this mixture, a solution of p-bromobenzenesulfonyl chloride (730 g, 2.828 mol) in dichloromethane (600 mL) was added dropwise below 41° C. After being stirred for 2 hrs at 35-40° C., the mixture was poured into a mixture of n-heptane (2 L) and water (1.5 L) and stirred for 5 min to give a biphasic mixture. The separated aqueous layer was extracted with a mixture of n-heptane/EtOAc=2/1 (v/v) twice. The combined organic layer was washed with 1M HCl aq. and saturated NaHCO$_3$ aq. The organic layer was concentrated under reduced pressure to give a crude material as a solid. To this solid was added MTBE (870 mL) and n-heptane (2.6 L) and heated to 49° C. to dissolve the solid. The mixture was slowly cooled to room temperature and stirred for 16 hrs. After further stirred below 3° C. for 1 hr, the resulting suspension was filtrated and rinsed with cold n-heptane/MTBE=9/1 (v/v). The crystals were dried under reduced pressure at 30° C. to give the desired compound (740.6 g, 1.626 mol, 86%). $^1$H-NMR (500 MHz, CDCl$_3$) δ ppm 7.75 (2H, d, J=8.5 Hz), 7.67 (2H, d, J=8.5 Hz), 7.14 (2H, d, J=8.5 Hz), 6.86 (2H, d, J=8.5 Hz), 5.60-5.67 (1H, m), 5.33 (1H, dd, J=10.5, 2.0 Hz), 5.23 (1H, d, J=17.5 Hz), 4.46 (1H, d, J=11.0 Hz), 4.14 (1H, d, J=11.0 Hz), 4.14 (1H, dd, J=9.0, 4.0 Hz), 4.10 (1H, dd, J=9.0, 4.0 Hz), 3.82 (3H, s), 3.57 (1H, dd, J=8.0, 8.0 Hz), 1.92-2.00 (1H, m), 0.90 (3H, d, J=7.0 Hz).

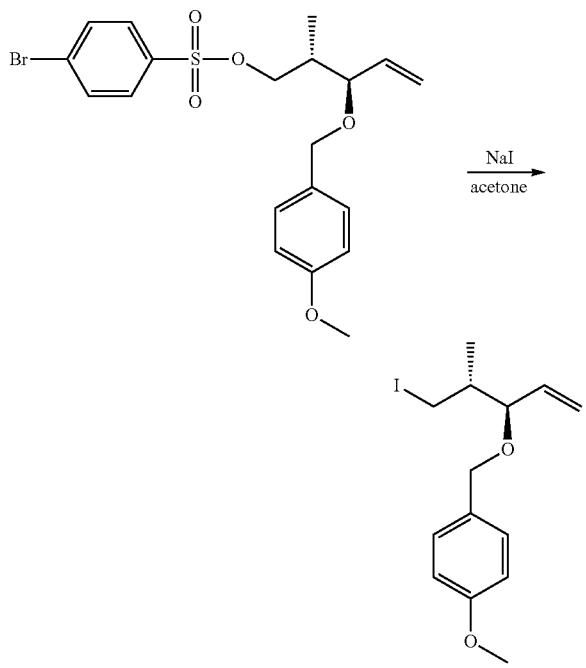

To a stirred solution of the starting material (730.6 g, 1.604 mol) in acetone (2.2) was added NaI (721 g, 4.813 mol) at room temperature under $N_2$ atmosphere and heated to 45° C. After being stirred for 2.5 hrs, the mixture was cooled below 30° C. followed by addition of n-heptane (2.2 L) and water (2.2 L) to give a biphasic mixture. The organic layer was separated and the aqueous layer was extracted with a mixture of n-heptane/EtOAc=4/1 (v/v) twice. The combined organic layer was washed with a mixture of aqueous solution containing 6% $NaHCO_3$ and 3% $Na_2S_2O_3$ aq. The organic layer was concentrated under reduced pressure and azeotroped with n-heptane. The residue was purified by column chromatography on neutral silica gel (10 kg, eluent: 0%, 2% then 5% EtOAc in n-heptane). The collected fractions were concentrated to give the desired product (551 g, 1.591 mol, 99%). $^1$H-NMR (500 MHz, $CDCl_3$) δ ppm 7.28 (2H, d, J=9.0 Hz), 6.88 (2H, d, J=9.0 Hz), 5.69-5.76 (1H, m), 5.35 (1H, dd, J=10.0, 1.5 Hz), 5.29 (1H, d, J=17.5 Hz), 4.51 (1H, d, J=11.0Hz), 4.28 (1H, d, 11.0 Hz), 3.82 (3H, s), 3.53 (1H, dd, J=8.0, 8.0 Hz), 3.46 (1H, dd, J=9.0, 6.0 Hz), 3.34 (1H, dd, J=9.0, 3.5 Hz), 1.51-1.59 (1H, m), 0.94 (3H, d, J=7.0 Hz).

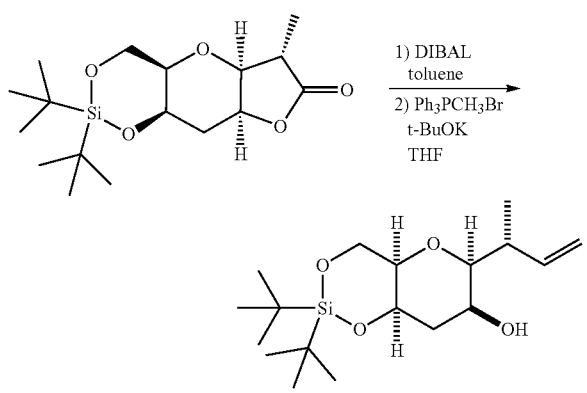

To a stirred solution of lactone (500 g, 1.46 mol) in toluene (5 L) was added DIBAL solution (1.83 L of 1M in toluene, 1.83 mol) at −71~−62° C. under $N_2$ atmosphere. After being stirred for 15 min, the reaction was quenched with EtOAc (500 mL) at −69~−65° C. Then the mixture was warmed up to −23° C. and 30% Rochelle's salt aq. (5 L) was added at −23~8° C. The mixture was stirred for 30 min at room temperature to give a biphasic mixture. The organic layer was separated and washed sequentially with water and 5% NaCl aq. The combined aqueous layers were extracted with EtOAc. The combined organic layers were concentrated and azeotroped with toluene twice under reduced pressure to give a crude lactol, which was used in the next reaction without further purification.

To a suspension of $Ph_3PCH_3Br$ (2086 g, 5.84 mol) in THF (4 L) was added t-BuOK (491.5 g, 4.38 mol) at 3° C. under $N_2$ atmosphere. A solution of the crude lactol (calculated as 1.46 mol) in THF (1 L) was added into the reaction mixture at 1~9° C. After being stirred for 20 min at 3~7° C., the reaction was quenched with water (125 mL) below 14° C. Then iPrOAc (5 L) and water (2.4 L) were added to give a biphasic mixture. The organic layer was separated and washed with 5% NaCl aq. The organic layer was concentrated under reduced pressure. The residue was added toluene (1 L) and n-heptane (1 L) and stirred for 16 hrs at 0° C. The precipitated solid was removed by filtration and filtrated solution was concentrated under reduced pressure. The residue was purified by column chromatography on neutral silica gel (3.0 kg, eluent: 0%, 5%, 7%, 9% then 12% EtOAc in n-heptane) to give the desired compound (440 g, 1.28 mol, 88% in 2 steps). $^1$H-NMR (500 MHz, $CDCl_3$) δ: 5.70-5.77 (1H, ddd, J=17, 10.5, 8.0 Hz), 5.18 (1H, ddd, J=17, 1.5, 1.5 Hz), 5.05 (1H, dd, J=10.5, 1.5 Hz), 4.42 (1H, dd, J=3.0, 3.0 Hz), 4.27 (1H, dd, J=15, 2.5 Hz), 4.23 (1H, dd, J=15, 1.5 Hz), 3.70-3.74 (1H, m), 3.62 (1H, d, J=10.5 Hz), 3.32 (1H, m), 2.97 (1H, dd, J=9.5, 1.3 Hz), 2.72-2.80 (1H, m), 2.33 (1H, ddd, J=15.0, 3.0, 3.0 Hz), 1.67 (1H, ddd, 15.0, 3.0, 3.0 Hz), 1.12 (3H, d, J=6.5 Hz), 1.07 (9H, s), 1.06 (9H, s)

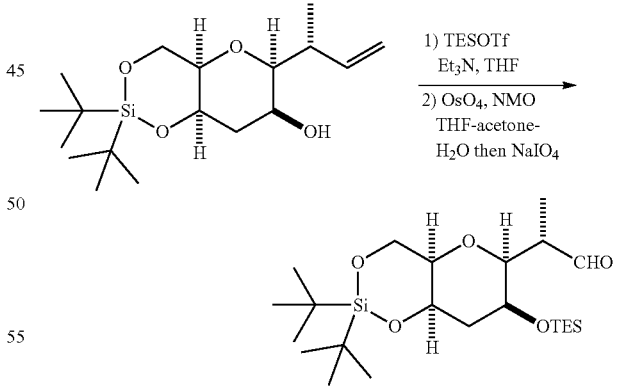

To a stirred solution of the starting material (440 g, 1.28 mol) in THF (3.7 L) was added triethylamine (367 mL, 2.63 mol) at 20° C. under $N_2$ atmosphere and cooled to 3° C. To this mixture, TESOTf (354 mL, 1.54 mol) was added dropwise below 7° C. and stirred for 8 min at the same temperature. The reaction was quenched with 3.5% $NaHCO_3$ (4.4 L) aq. below 18° C. followed by addition of EtOAc (2.2 L) and n-heptane (2.2 L) to give a biphasic mixture. The organic layer was separated and washed with 5% NaCl aq. The organic layer was dried over Na₂SO₄, filtered and concentrated under reduced pressure to give a crude material, which was used in the next reaction without further purification.

A solution of the crude (calculated as 1.28 mol) in THF (2.1 L) and acetone (2.1 L) was added NMO (464 g, 3.96 mol) followed by addition of water (0.5 L) at room temperature. To this mixture, 4% OsO₄ aq. (194 mL, 32 mmol) was added and stirred for 19 hrs at room temperature. Then water (2.1 L) and NaIO₄ (847 g, 3.96 mol) were added to this mixture and further stirred for 70 min at room temperature. To this mixture, n-heptane (2.9 L) and water (1.2 L) were added and stirred for 5 min at room temperature to a give biphasic mixture. The organic layer was separated and aqueous layer was extracted with n-heptane. The combined organic layers were added to 20% Na₂SO₃ aq. and the resulting biphasic mixture was stirred for 30 min at room temperature. The organic layer was separated and washed sequentially with 10% Na₂SO₃ aq., water, 5% NaCl aq. The organic layer was dried over Na₂SO₄, filtered, concentrated under reduced pressure. The residue was purified by column chromatography on neutral silica gel (5.9 kg, eluent: 0%, 5%, then 10% EtOAc in n-heptane). The collected fractions were concentrated and the resulting aldehyde was solidified by cooling with ice-water bath to give the aldehyde (502.8 g, 1.10 mol, 86% in 2 steps). ¹H-NMR (500 MHz, CDCl₃) δ: 9.84 (1H, s), 4.29-4.31 (1H, m), 4.28 (1H, dd, J=12.5, 3.0 Hz), 4.21 (1H, dd, J=12.5, 1.5 Hz), 3.86-3.88 (1H, m), 3.57 (1H, dd, J=7.5, 2.5 Hz), 3.29-3.32 (1H, m), 2.80-2.86 (1H, dq, J=7.5 Hz, 7.5 Hz), 2.21-2.25 (1H, ddd, J=15.0, 2.5, 2.5 Hz), 1.77-1.81 (1H, ddd, J=15.0, 4.0, 4.0 Hz), 1.16 (3H, d, J=7.5 Hz), 1.07 (9H, s), 1.04 (9H, s), 0.96-1.00 (9H, m), 0.58-0.67 (6H, m).

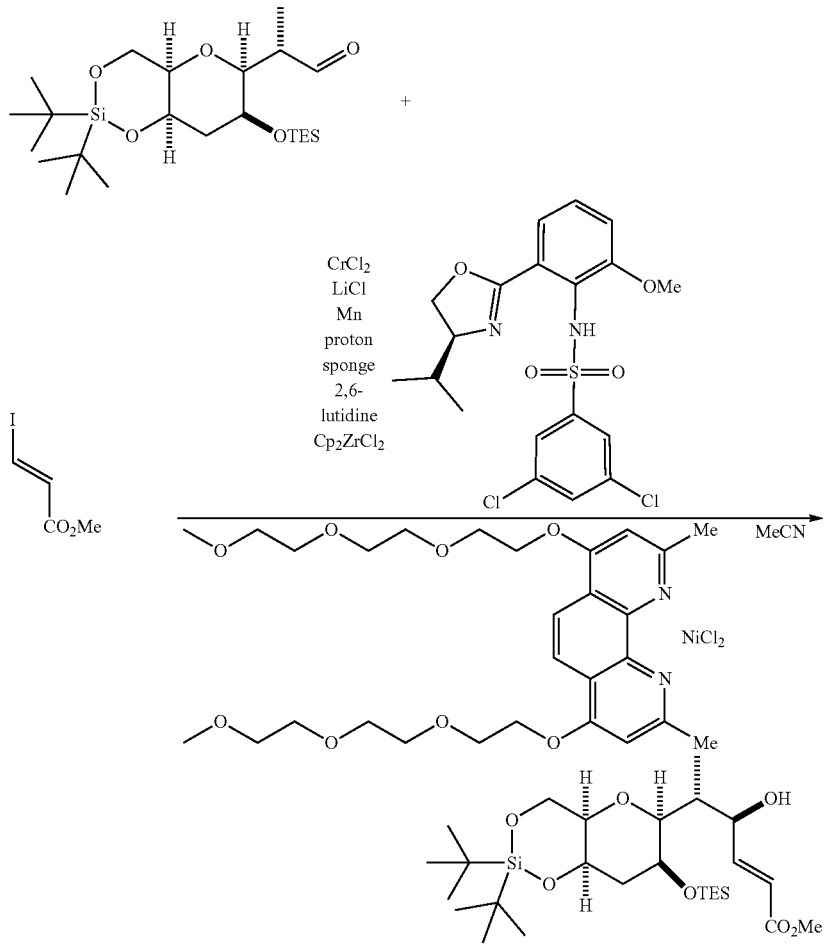

In a glove box, CrCl₂ (22 mg, 0.18 mmol), proton sponge (42 mg, 0.20 mmol), sulfonamide ligand (88 mg, 0.20 mmol) were added in a well-dried round bottomed flask and added anhydrous MeCN (3.0 mL). The mixture was stirred in the glove box at room temperature.

In another flask, the aldehyde (500 mg, 0.90 mmol) was added toluene. After azeotropic removal of toluene, the flask was brought in the glove box followed by addition of vinyl iodide (477 mg, 2.25 mmol), Mn (198 mg, 3.60 mmol), LiCl (76 mg, 1.80 mmol), Cp₂ZrCl₂ (289 mg, 0.99 mmol) and 2,6-lutidine (0.21 mL, 1.80 mmol). To this flask, the Cr solution prepared above was added followed by addition of Ni catalyst (3.0 mg, 4.5 μmol). The mixture was stirred vigorously for 145 min at 30° C. The flask was taken out of the glove box and Florisil® (1 g) was added to this mixture at room temperature. After dilution with n-heptane/EtOAc=1/1 (v/v) (5 mL), the suspension was stirred vigorously for 35 min at room temperature and passed through a neutral silica gel (5 g) pad. The desired product was eluted with EtOAc and collected solution was concentrated under reduced pressure. The residue was purified by column chromatography on neutral silica gel (10 g, eluent; 0%, 10%, 20%, 33% then 50% EtOAc in n-heptane). The collected fractions were concentrated to give the desired product (462 mg, 0.85 mmol, 94%).

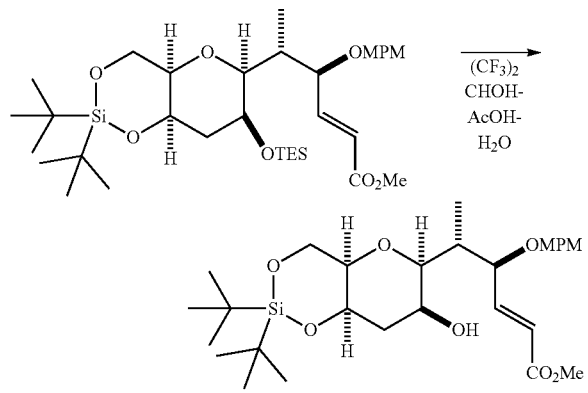

To a stirred solution of the starting material (636.6 g, 0.957 mol) in hexafluoroisopropanol (HFIP) (1.6 L) and water (160 mL) were added AcOH (55 mL, 0.957 mol) at 5° C. under $N_2$ atmosphere. The mixture was stirred for 30 min below 5° C. and 3 hrs at room temperature. The reaction was quenched with 5% $NaHCO_3$ aq. (5 L) followed by addition of n-heptane (5 L). After separation of the organic layer, the aqueous and HFIP layer were combined and extracted with n-heptane twice. Three organic layers were combined and washed with 5% NaCl aq. The organic layer was dried over $Na_2SO_4$, filtered and concentrated. The residue was purified by column chromatography on neutral silica gel (8.5 kg, eluent: 0%, 9.1%, 11% then 17% EtOAc in n-heptane). The collected fractions were concentrated to give the desired alcohol (480 g, 0.871 mol, 91%).

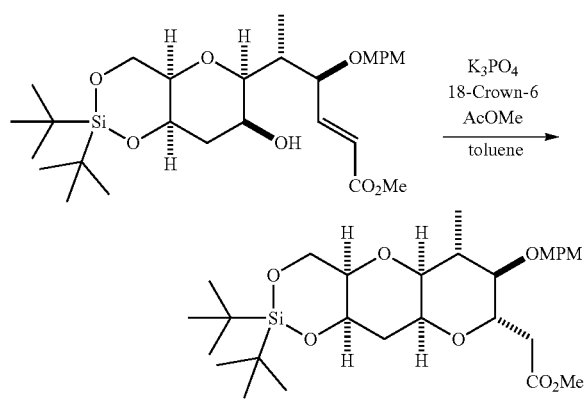

The starting material (480.0 g, 0.872 mol) was azeotroped with toluene (1.4 L) twice and added toluene (4.8 L). After addition of MeOAc (480 mL), the mixture was cooled to 1° C. and kept under $N_2$ atmosphere until used. In another flask was added $K_3PO_4$ (92.5 g, 0.436 mol), 18-crown-6 (345.5 g, 1.307 mol) and MeOH (480 mL). This mixture was sonicated for 20 min and concentrated under reduced pressure. The resulting mixture was azeotroped with toluene (480 mL) three times and toluene (2.4 L) was added to the mixture and filtrated. The filtrated solution was added dropwise to the solution of the starting material prepared above below 4° C. After being stirred for 16 min below 5° C., the mixture was poured into chilled water (2.4 L) followed by addition of iPrOAc (2.4 L), water (2.4 L) and NaCl (100 g) to give a biphasic mixture. The separated organic layer was washed with 5% NaCl aq. The organic layer was dried over $Na_2SO_4$, filtered and concentrated. The residue was purified by column chromatography on neutral silica gel (8.6 kg, eluent: 0%, 9.1%, 17%, 25% then 33% EtOAc in n-heptane). The pure fractions were concentrated to give the oxy-Michael product (293 g, 0.531 mol, 61% in 2 steps).

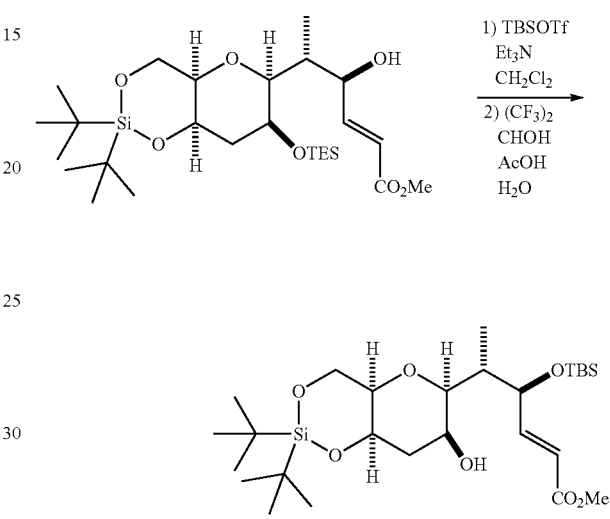

To a stirred solution of the starting material (41.3 g, 75.8 mmol) in dichloromethane (206 mL) was added $Et_3N$ (25.4 mL, 181.9 mmol) at 1° C. under $N_2$ atmosphere. To this mixture, TBSOTf (20.9 mL, 91.0 mmol) was added dropwise below 10° C. After being stirred for 30 min at 0° C., the reaction was quenched with 10% $NaHCO_3$ aq. (206 mL) below 17° C. The mixture was extracted with n-heptane and the resulting organic phase was washed with water and 5% NaCl aq. The organic layer was dried over $Na_2SO_4$, filtered and concentrated to give a crude oil, which was used in the next step without further purification. To this crude material (calculated as 75.8 mmol) were added HFIP (124 mL) and water (12.5 mL). After cooling to 4° C., AcOH (4.4 mL) was added and the resulting mixture was stirred for 30 min at 0° C. and another 1.5 hrs at room temperature under $N_2$ atmosphere. The mixture was quenched with 5% $NaHCO_3$ aq. (400 mL) followed by addition of n-heptane (400 mL) to give a biphasic mixture. The organic phase was separated and washed with 5% NaCl aq. The organic layer was dried over $Na_2SO_4$, filtered and concentrated. The residue was purified by column chromatography on neutral silica gel (750 g, eluent: 0%, 4.8%, 9.1% then 11% EtOAc in n-heptane). The collected fractions were concentrated to give the desired product (40.5 g, 74.2 mmol, 98%). $^1$H-NMR (500 MHz, $CDCl_3$) δ: 7.01 (1H, dd, J=16.0, 5.0 Hz), 5.98 (1H, dd, J=16.0, 2.5 Hz), 4.43-4.45 (1H, m), 4.40 (1H, dd, J=2.5, 2.5 Hz), 4.23 (1H, dd, J=13.0, 3.0 Hz), 4.16 (1H, dd, J=13.0, 1.0 Hz), 3.75 (3H, s), 3.73-3.76 (1H, m), 3.59 (1H, d, J=11.0 Hz), 3.28-3.29 (2H, m), 2.33 (1H, ddd, J=14.5, 2.5, 2.5 Hz), 2.10-2.18 (1H, m), 1.73 (1H, ddd, J=15.0, 3.5, 3.5 Hz), 1.04-1.06 (21H, m), 0.90 (9H, s), 0.03 (3H, s), 0.02 (3H, s).

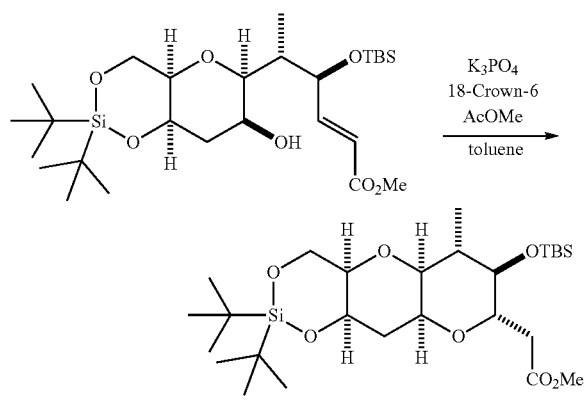

In N$_2$ atmosphere, K$_3$PO$_4$ (0.624 g, 2.94 mmol), 18-crown-6 (2.33 g, 8.82 mmol) and MeOH (15 mL) were added in a flask and sonicated for 6 min. After the mixture was concentrated under reduced pressure, the mixture was azeotroped with toluene (20 mL) three times. The residue was added toluene (15 mL) and kept under N$_2$ atmosphere at room temperature.

In another flask, the starting material (5.34 g, 9.80 mmol) was azeotroped with toluene (53 mL) twice and the residue was added toluene (53 mL) followed by MeOAc (5.3 mL). After the mixture was cooled below 3° C., the solution containing K$_3$PO$_4$ prepared above was added dropwise to the solution of the starting material below 3° C. over 40 min. The mixture was poured into a mixture of cold EtOAc/water=1/1 (v/v) (106 mL) to give a biphasic mixture. The organic layer was separated and the aqueous layer was extracted with EtOAc. The combined organic layer was washed with water and 5% NaCl aq. The separated organic layer was dried over Na$_2$SO$_4$, filtrated and concentrated under reduced pressure. The residue was purified by column chromatography on neutral silica gel (80 g, eluent: 0%, 5%, 7%, 10% then 15% EtOAc in n-heptane). The collected fractions were concentrated to give the desired product (4.35 g, 7.98 mmol, 81%). $^1$H-NMR (500 MHz, CDCl$_3$) δ: 4.30 (1H, ddd, J=8.0, 3.5, 3.5 Hz), 4.13 (1H, dd, J=12.5, 5.5 Hz), 4.09 (1H, dd, J=12.5, 3.0 Hz) 3.87 (1H, ddd, J=9.0. 9.0, 3.0 Hz), 3.79 (1H, ddd, J=7.5, 4.5, 4.5 Hz), 3.70 (3H, s), 3.60 (1H, ddd, J=5.5, 3.5, 3.5 Hz), 3.34 (1H, dd, J=8.0, 5.0 Hz), 3.30 (1H, dd, J=10.0, 8.5 Hz), 2.71 (1H, dd, J=14.5, 3.0 Hz), 2.41 (1H, dd, J=14.5, 10.0 Hz), 2.11 (1H, ddd, J=13.5, 8.0, 8.0 Hz), 1.98 (1H, ddd, J=13.5, 4.5, 4.5 Hz), 1.77-1.85 (1H, m), 1.10 (3H, d, J=6.5 Hz), 1.06 (9H, s), 1.02 (9H, s), 0.90 (9H, s), 0.09 (3H, s), 0.06 (3H, s).

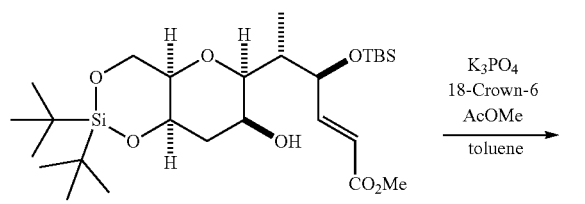

In N$_2$ atmosphere, K$_3$PO$_4$ (4.73 g, 22.27 mmol), 18-crown-6 (17.66 g, 66.81 mmol) and MeOH (120 mL) were added in a flask and sonicated for 8 min. After the mixture was concentrated under reduced pressure, the mixture was azeotroped with toluene (120 mL) three times. The residue was added toluene (150 mL) and kept under N$_2$ atmosphere at room temperature until used.

In another flask, the starting material (40.45 g, 74.24 mmol) was azeotroped with toluene (120 mL) twice and the residue was added toluene (400 mL) followed by MeOAc (40 mL). After the mixture was cooled below 3° C., the solution containing K$_3$PO$_4$ prepared above was added dropwise to the solution of the starting material below 3° C. over 90 min. The mixture was poured into a mixture of cold EtOAc/water=1/1 (v/v) (800 mL) to give biphasic mixture. The organic layer was separated and the aqueous layer was extracted with EtOAc (200 mL). The combined organic layer was washed with 5 wt % NaCl aq. The separated organic layer was dried over Na$_2$SO$_4$, filtrated and concentrated under reduced pressure. The residue was purified by column chromatography on neutral silica gel (600 g, eluent: 0%, 9%, 11%, then 14% EtOAc in n-heptane). The collected fractions were concentrated to give the desired product (23.36 g, 42.9 mmol) as a colorless oil. Then, the inseparable fractions were combined and the solvent was removed under reduced pressure. The residue was re-purified by column chromatography on neutral silica gel (300 g, eluent: 0%, 9%, 11%, then 14% EtOAc in n-heptane). The collected fractions were concentrated to give the desired product (9.90 g, 18.17 mmol) as a colorless oil. Both desired compound were combined to give the desired product (33.26 g, 61.04 mmol, 82%).

The desired product (6.13 g, 11.25 mmol) was added MeOH (50 mL) and the mixture was azeotroped under reduced pressure at 40° C. The residual solid was added MeOH (36.8 mL) and the slurry was warmed up to 50° C. After the slurry became a clear solution, the solution was cooled to 35° C. and seed was added. After a solution became cloudy, the mixture was stirred at room temperature for 30 min and then water (7.4 mL) was added to the mixture. After being stirred at room temperature for 3 hrs, the generated crystal was collected by suction and washed with cold MeOH/water=5/1 (v/v) (40 mL). The crystal was dried at 40° C. under reduced pressure for 2 hrs to give the desired product (5.48 g, 10.06 mmol, 89%). $^1$H-NMR (500 MHz, CDCl$_3$) δ: 4.30 (1H, ddd, J=8.0, 3.5, 3.5 Hz), 4.13 (1H, dd, J=12.5, 5.5 Hz), 4.09 (1H, dd, J=12.5, 3.0 Hz) 3.87 (1H, ddd, J=9.0, 9.0, 3.0 Hz), 3.79 (1H, ddd, J=7.5, 4.5, 4.5 Hz), 3.70 (3H, s), 3.60 (1H, ddd, J=5.5, 3.5, 3.5 Hz), 3.34 (1H, dd, J=8.0, 5.0 Hz), 3.30 (1H, dd, J=10.0, 8.5 Hz), 2.71 (1H, dd, J=14.5, 3.0 Hz), 2.41 (1H, dd, J=14.5, 10.0 Hz), 2.11 (1H, ddd, J=13.5, 8.0, 8.0 Hz), 1.98 (1H, ddd, J=13.5, 4.5, 4.5 Hz), 1.77-1.85 (1H, m), 1.10 (3H, d, J=6.5 Hz), 1.06 (9H, s), 1.02 (9H, s), 0.90 (9H, s), 0.09 (3H, s), 0.06 (3H, s).

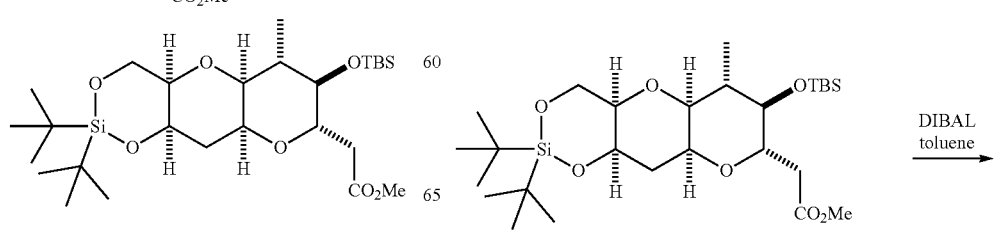

-continued

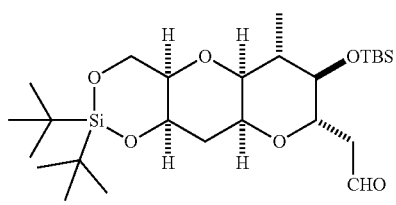

The starting material (12 g, 22.02 mmol) was azeotroped with toluene (36 mL) twice and the residue was added toluene (240 mL). After the mixture was cooled below −70° C., DIBAL solution (26.4 mL of 1M in toluene, 26.43 mmol) was added to the mixture at −73~−71° C. under $N_2$ atmosphere. After being stirred for 32 min, the reaction was quenched with acetone (12 mL) at −75~−74° C. Then the mixture was warmed up to −30° C. and 30 wt % Rochelle's salt aq. (180 mL) was added at −29~4° C. The mixture was stirred for 3 hrs at room temperature to give a biphasic mixture. The organic layer was separated and washed with 5 wt % NaCl aq. The separated organic layer was dried over $Na_2SO_4$, filtrated and concentrated under reduced pressure to give a crude aldehyde (14.18 g), which was used as 100% yield in the next reaction without further purification.

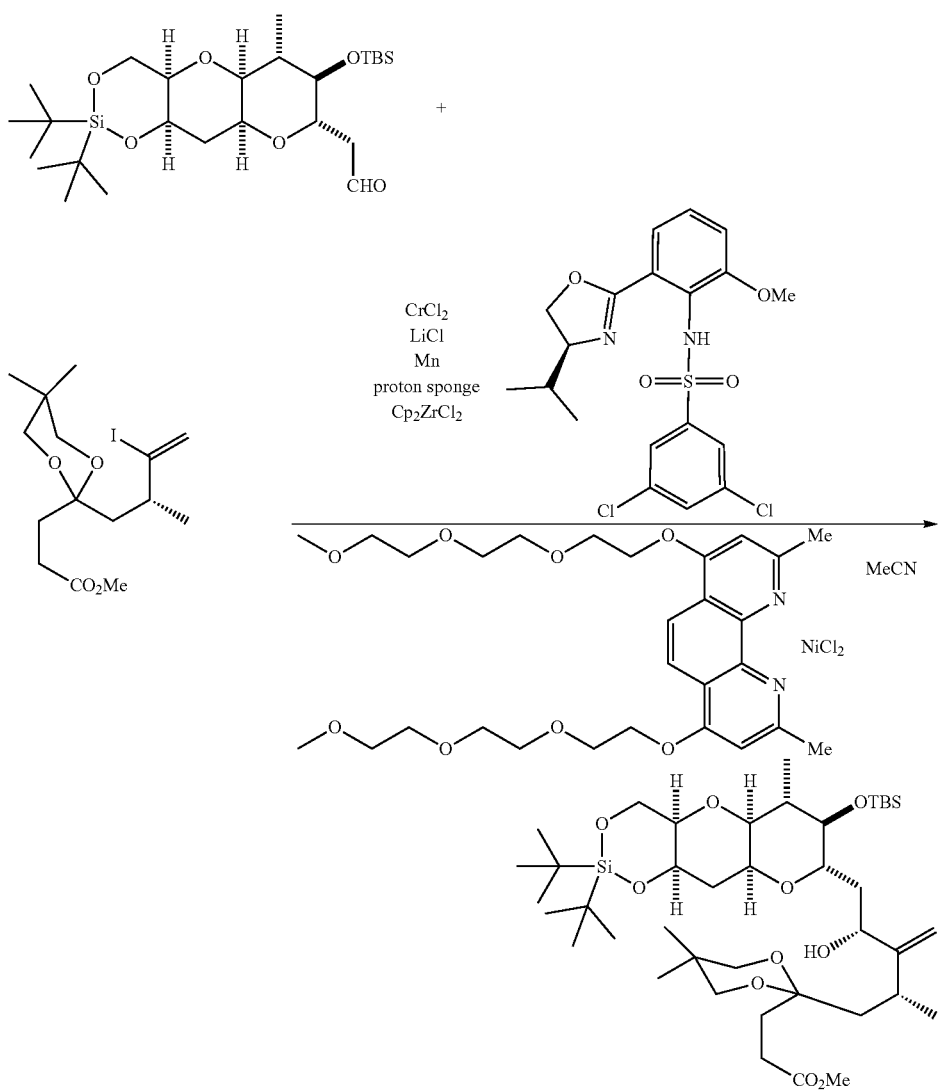

In a glove bag, $CrCl_2$ (541 mg, 4.41 mmol), proton sponge (1.04 g, 4.85 mmol), sulfonamide ligand (2.15 g, 4.85 mmol) were added in a well-dried round bottomed flask. After taking flask out from glove bag, anhydrous MeCN (90.7 mL) was added under $N_2$ atmosphere. The mixture was stirred at room temperature until used.

In another flask, the aldehyde (11.34 g, 22.03 mmol) and vinyl iodide (10.47 g, 26.43 mmol) were added toluene. After azeotropic removal of toluene (twice), the residual mixtures were added Mn (4.84 g, 88.10 mmol), LiCl (1.87 g, 44.05 mmol) and $Cp_2ZrCl_2$ (7.08 g, 24.23 mmol) and then the flask was purged by $N_2$ gas. To this flask, the Cr solution prepared above was added. After the mixture was warmed up to 40° C., solution of Ni catalyst (730 uL (prepared as 100 mg/mL MeCN in advance), 0.11 mmol) was added. During stirring vigorously for 19 hrs at 40° C., additional Ni catalyst (Y. Kishi et. al, Journal of the American Chemical Society (2015), 137(19), 6219-6225) (365 uL, 0.06 mmol) was added 6 times to complete the reaction. The mixture was added iPrOAc (120 mL) followed by a mixture of 5 wt %

NaHCO₃ and 5 wt % D,L-serine aqueous solution (120 mL) at 40° C. After stirring for 4 hrs at 40° C., the mixture was cooled to room temperature and passed through Celite (25 g) with iPrOAc (600 mL) washing to give biphasic mixture. The organic layer was separated and the organic layer was washed with 5 wt % NaHCO₃ aq., water and 5% NaCl aq. The separated organic layer was dried over Na₂SO₄, filtrated and concentrated under reduced pressure to give a crude desired product (25.26 g), which was used as 100% yield in the next reaction without further purification.

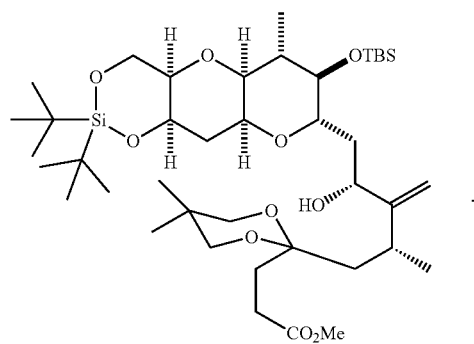

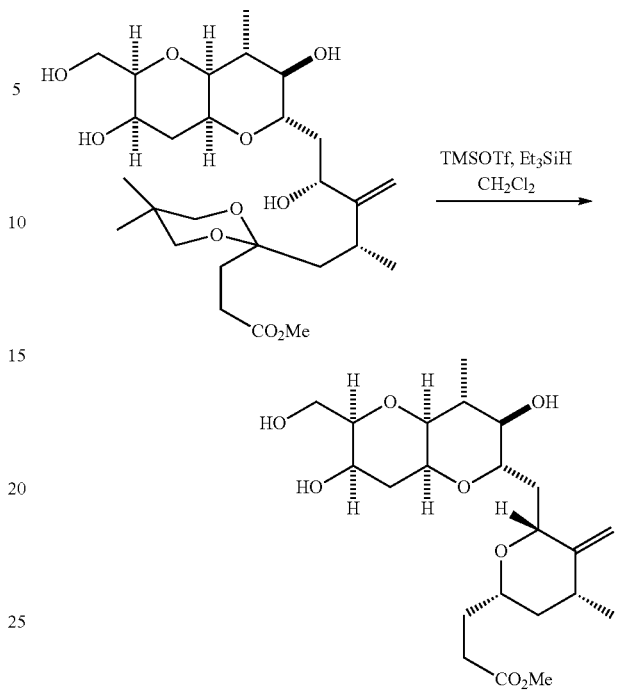

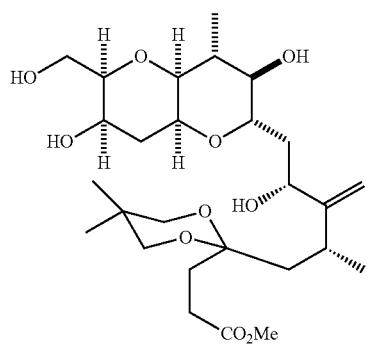

To a stirred solution of the starting material (17.3 g, 22.03 mmol) in THF (52 ml) was added TBAF (88 mL of 1M in THF, 88.13 mmol) at 0° C. After stirring for 15 hrs at room temperature, the mixture was added EtOAc (180 mL) followed by 10 wt % NH₄Cl aq. (180 mL) to give biphasic mixture. The organic layer was separated and the aqueous layer was extracted with EtOAc (180 mL) twice. The combined organic layer was washed with saturated NaCl aq. The separated organic layer was dried over Na₂SO₄, filtrated and concentrated under reduced pressure. The residue was purified by column chromatography on NH-silica gel (120 g, eluent: 0%, 20%, 50%, 100% EtOAc in n-heptane and then 5% MeOH in EtOAc). The collected fractions were concentrated to give the desired product (17.46 g, including impurities), which was used as 100% yield in the next reaction without further purification.

The starting material (11.69 g, 22.03 mmol) was azeotroped with toluene (35 mL) twice and the residue was added CH₂Cl₂ (117 mL) followed by Et₃SiH (17.6 mL, 110.14 mmol) at rt. After the mixture was cooled below −70° C., TMSOTf (16.0 mL, 88.11 mmol) was added to the mixture at −72~−70° C. under N₂ atmosphere. After being stirred for 30 min, the reaction mixture was warmed up to 0° C. After being stirred for 27 min at 0° C., the reaction mixture was quenched with water (117 mL) below 14° C. and then the mixture was stirred at room temperature. After being stirred for 25 min, saturated NaHCO₃ aq. (58 mL) was added and the mixture was stirred for 25 min at room temperature to give a biphasic mixture. The organic layer was separated and the aqueous layer was extracted with CH₂Cl₂ (117 mL). The combined organic layer was dried over Na₂SO₄, filtrated and concentrated under reduced pressure to give a crude desired product (18.95 g), which was used as 100% yield in the next reaction without further purification.

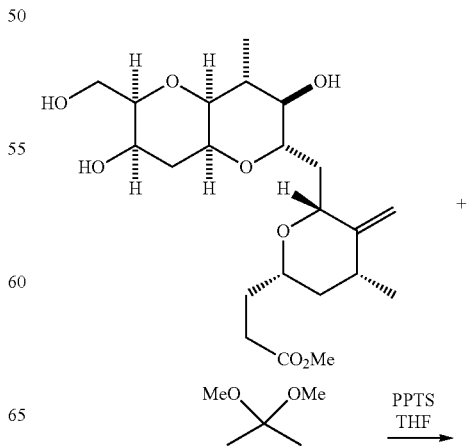

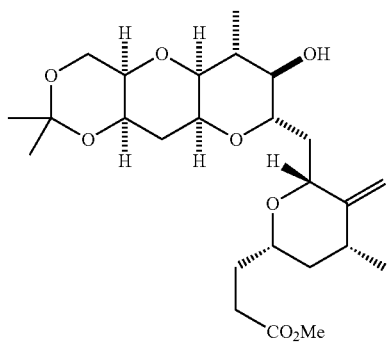

The starting material (9.44 g, 22.03 mmol) was azeotroped with toluene (30 mL) twice and the residue was added THF (94 mL), 2,2-dimethoxypropane (10.84 mL, 88.13 mmol) and PPTS (277 mg, 1.10 mmol) at room temperature. After being stirred at 40° C. under N₂ atmosphere for 4.5 hrs, the reaction mixture was cooled to room temperature and then the reaction mixture was diluted with EtOAc (100 mL) followed by saturated NaHCO₃ aq. (100 mL). After being stirred for 15 min, a biphasic mixture was obtained. The organic layer was separated and the aqueous layer was extracted with EtOAc (100 mL). The combined organic layer was washed with saturated NaCl aq. The separated organic layer was dried over Na₂SO₄, filtrated and concentrated under reduced pressure to give a crude desired product (18.95 g)

A crude desired product (18.95 g) was purified by ODS-column chromatography on YMC-GEL (100 g, eluent: 3%, 40% MeCN in water). The collected fractions were extracted by CH₂Cl₂ (500 mL+250 mL) and the combined organic layer was dried over Na₂SO₄, filtrated and concentrated under reduced pressure to give the desired product (12.00 g, including impurities).

A crude desired product (12.00 g) was purified by column chromatography on neutral silica gel (150 g, eluent: 0%, 20%, 33%, 50%, and 66% EtOAc in n-heptane). The collected fractions were concentrated to give a crude desired product (4.56 g, including impurities).

A crude desired product (4.56 g) was added a mixture of n-hexane/EtOAc=9/1 (v/v) (45 mL) and the slurry was warmed up to 60° C. After the slurry became a clear solution, the solution was cooled to 45° C. and seed was added. After a solution became cloudy, the mixture was stirred at room temperature for 50 min and then the mixture was stirred at 0° C. for 65 min and then stirred at −10° C. for 17.5 hrs. The generated crystal was collected by suction and washed with cold n-hexane (13.5 mL). The crystal was dried at 40° C. under reduced pressure to give the desired product (3.57 g, 7.62 mmol, 35% in 5 steps). ¹H-NMR (500 MHz, CDCl₃) δ: 4.88 (1H, s), 4.82 (1H, d, J=2.0 Hz), 4.18 (1H, q, J=5.5 Hz), 4.03 (1H, dd, J=12.5, 3.0 Hz), 4.00-3.95 (2H, m), 3.88 (1H, dd, J=6.0, 4.0 Hz), 3.86 (1H, dd, J=12.0, 2.5 Hz), 3.67 (3H, s), 3.64-3.57 (1H, m), 3.55 (1H, d, J=8.5 Hz), 3.42 (1H, t, J=3.0 Hz), 3.36 (1H, dt, J=8.0, 5.5 Hz), 3.26 (1H, q, J=2.5 Hz), 2.54-2.40 (2H, m), 2.33-2.23 (1H, m), 2.19-2.11 (2H, m), 2.10-2.00 (2H, m), 1.86-1.68 (4H, m), 1.44 (3H, s), 1.43 (3H, s), 1.16 (3H, d, J=8.0 Hz), 1.15-1.09 (1H, m), 1.08 (3H, d, J=6.0 Hz).

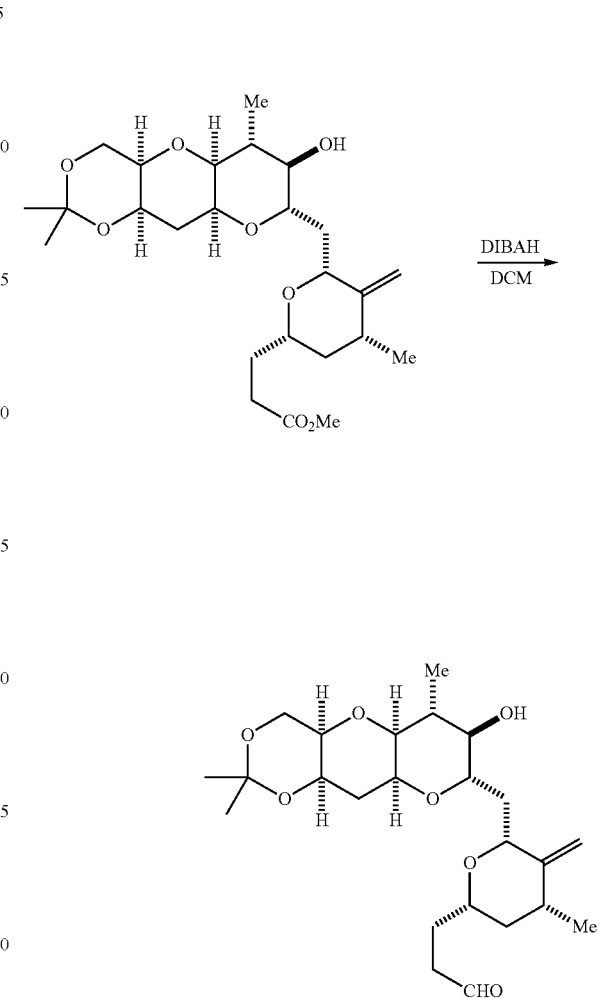

To a stirred solution of starting material (52.0 g, 0.11 mol) in dichloromethane (1.04 L) was added DIBAL solution (253 mL of 1M in toluene, 0.255 mol) at −74.3~−71.5° C. under N₂ atmosphere. After being stirred for 76 min, the reaction was quenched with acetone (24.5 mL) at −75.2~−73.8° C. After being stirred for additional 9 min, MeOH (27.0 mL) was added to the reaction at −74.2~−73.5° C., followed by addition of BHT (52.0 mg). Then the mixture was warmed up to −20° C. and added to 40 wt % Rochelle's salt aq. (1.04 kg), then EtOAc (936 mL) was added to the mixture. The mixture was stirred for 85 min at room temperature to give a biphasic mixture. The organic layer was separated and re-extracted with EtOAc (520 mL). Combined organic layer was washed with 20 wt % NaCl aq. (520 g). After addition of BHT (52.0 mg), the organic layer was concentrated and azeotroped with toluene (208 mL) and MeCN (156 mL) under reduced pressure to give a crude aldehyde, which was used in the next reaction without further purification (assumed as 90% yield, 0.1 mol).

491    492
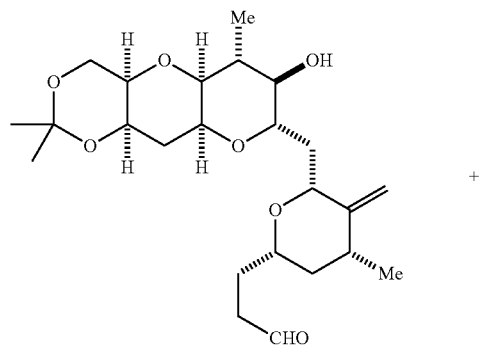
+
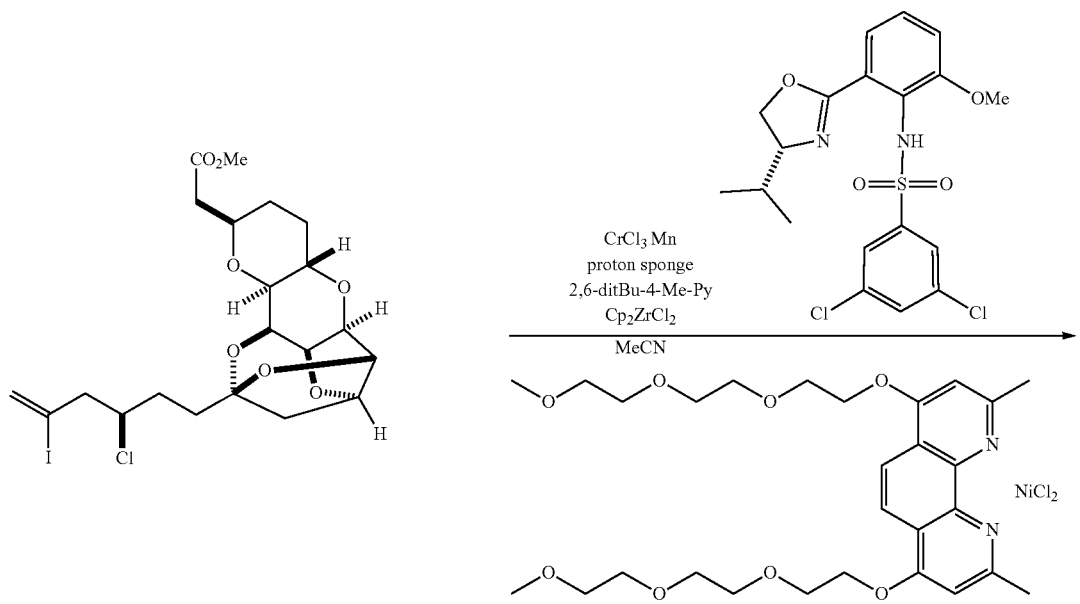
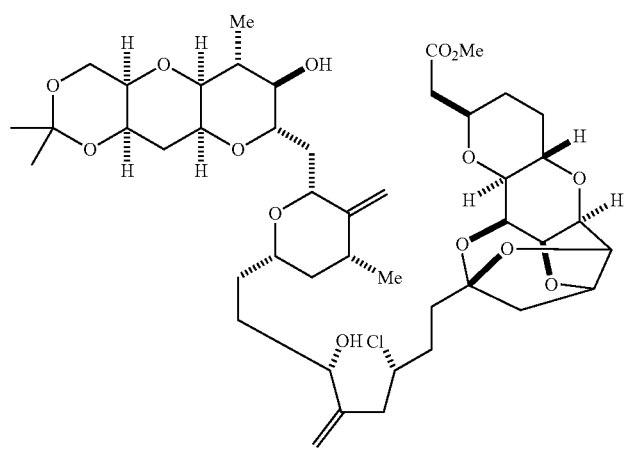

To a reactor, CrCl$_3$ (3.16 g, 20 mmol), proton sponge (4.71 g, 22 mmol), sulfonamide ligand (9.74 g, 22 mmol), Mn (11.0 g, 200 mmol) and Cp$_2$ZrCl$_2$ (75.9 g, 260 mmol) were charged, then reactor was purged with Argon. To the reactor, anhydrous MeCN (263 mL) was added and stirred for 70 min at 30° C. To a reaction, Ni-complex (662 mg, 1.0 mmol) in anhydrous MeCN (6.6 mL) was added. Then, a mixture of the aldehyde (43.8 g, 100 mmol), vinyl iodide (63.2 g, 114 mmol) and 2,6-di-tert-butyl-2-methyl pyridine (41.0 g, 200 mmol) in anhydrous MeCN (131 mL), which were azeotroped with MeCN (219 mL) in advance, was added. After substrates addition, Ni-complex (661 mg, 1.0 mmol) in anhydrous MeCN (6.57 mL) was added twice to complete the reaction. To the reaction, toluene (876 mL) was added, then cooled to 0° C. To the mixture, water (788 mL) and 20 wt % citric acid aq. (87.5 g) was added at around 14° C. for 20 min. After removal of the aqueous layer, the organic layer was passed through hyflo super-cell (35.0 g) then washed with toluene (876 mL). Combined organic layer was washed with 33% MeCN aq. (876 mL) followed by a mixture of 5 wt % NaHCO$_3$–10 wt % Na$_2$SO$_4$ aqueous solution (438 g). Organic layer was concentrated under reduced pressure. The residue was purified by column chromatography on silica gel (1900 g, eluent; 10%, 25%, 50%, 67% then 100% EtOAc in n-heptane). The collected fractions were concentrated to give the desired product (79.4 g, 92 mmol, 82% in two steps).$^1$H-NMR (500 MHz, CDCl$_3$) δ: 5.16 (1H, s), 4.97 (1H, s), 4.87 (1H, s), 4.82 (1H, s), 4.70 (1H, t, J=4.7 Hz), 4.63 (1H, t, J=4.5 Hz), 4.43 (1H, d, J=1.8 Hz), 4.18-4.33 (4H, m), 3.93-4.10 (5H, m), 3.78-3.92 (3H, m), 3.68 (3H, s), 3.59 (1H, d, J=3.0 Hz), 3.19-3.48 (3H, m), 2.85-2.98 (2H, m), 2.56-2.71 (2H, m), 2.48 (1H, dd, 15.1, 6.0 Hz), 2.41 (1H, dd, J=15.6, 5.8 Hz), 1.93-2.33 (11H, m), 1.51-1.92 (10H, m), 1.36-1.50 (8H, m), 1.14 (3H, d, J=7.5 Hz), 1.08 (3H, d, J=6.3 Hz).

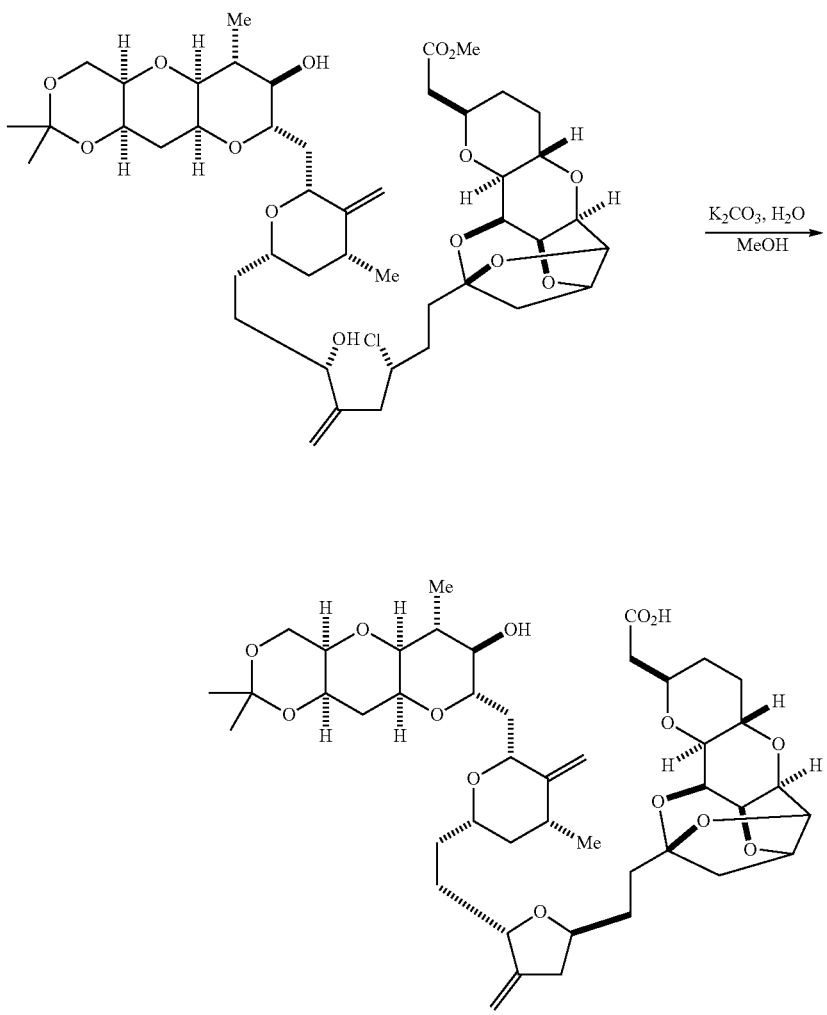

To a stirred solution of the starting material (79.3 g, 91.4 mmol) in MeOH (793 mL) was added K$_2$CO$_3$ (63.2 g, 0.457 mol) at room temperature under N$_2$ atmosphere. After heated to 55° C., the mixture was stirred for 3 hr, then water (24.7 mL, 1.37 mol) was added at same temperature. After being stirred for 20 hr, the reaction was cooled to room temperature, then toluene (1.59 L) and water (1.59 L) was added. Aqueous layer was washed with toluene (1.59 L) twice. To the resulted aqueous layer, dichloromethane (1.59 L) and 25 wt % NH$_4$Cl aq. (2.38 kg) were added. After separation of two layers, the aqueous layer was re-extracted with dichloromethane (2.38 L). Combined organic layer was concentrated and azeotroped with toluene (397 mL) to give a crude seco acid, which was used in the next reaction without further purification.

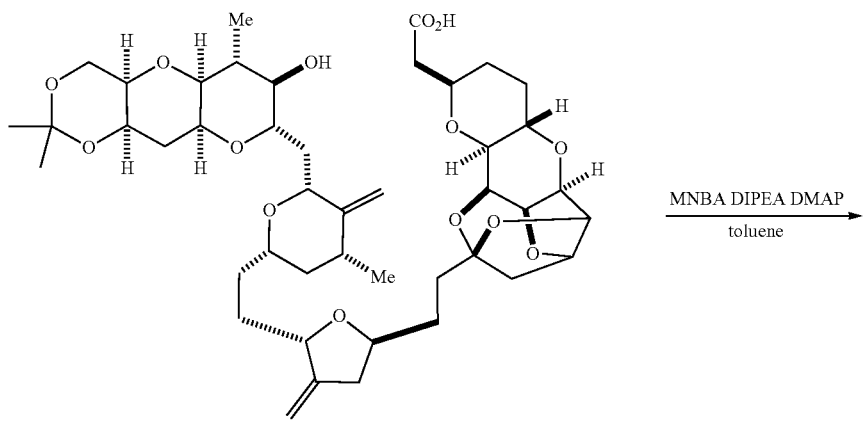

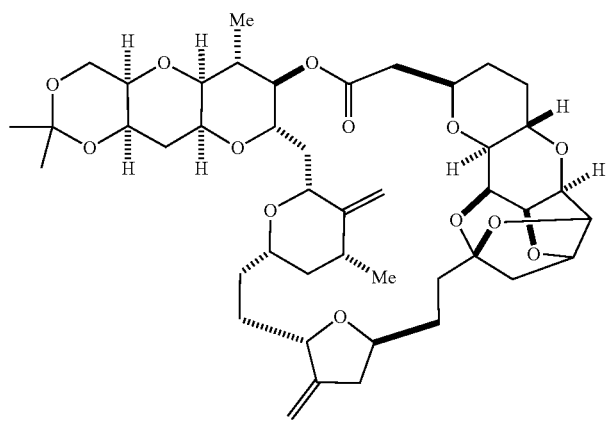

To a stirred solution of N,N-dimethylaminopyridine (DMAP, 67.0 g, 549 mmol) in toluene (5.60 L) was added N,N-diisopropylethylamine (DIPEA, 95.6 mL, 549 mmol) and 2-methyl-6-nitrobenzoic anhydride (MNBA, 94.4 g, 274 mmol) at 25° C. under $N_2$ atmosphere, then heated to 80° C. To the mixture, starting material (74.7 g, 91.4 mmol) in toluene (1.49 L) was added dropwise for 6 hr. After cooled to 25° C., the mixture was washed with 50 vol % DMF aq. (1.49 L) twice. The second 50% DMF aqueous layer was re-extracted with toluene (500 mL). Combined organic layer was washed with 20 wt % $NH_4Cl$ aq. (1.49 kg) twice, each aqueous layer was re-extracted with EtOAc (750 mL). Combined organic layer was washed with 20 wt % NaCl aq. (374 g) and re-extracted with EtOAc (750 mL). Combined organic layer was concentrated and azeotroped with MeCN (200 mL). The residue was dissolved in dichloromethane (448 mL) and concentrated. The resulted high concentrated dichloromethane solution was added to MeCN (1.05 L) at 0° C. under $N_2$ atmosphere. Resulted precipitation was filtered and washed with MeCN (224 mL) followed by drying at 40° C. gave a desired macrolactone (41.5 g, 51.9 mmol, 56.8% in two steps).

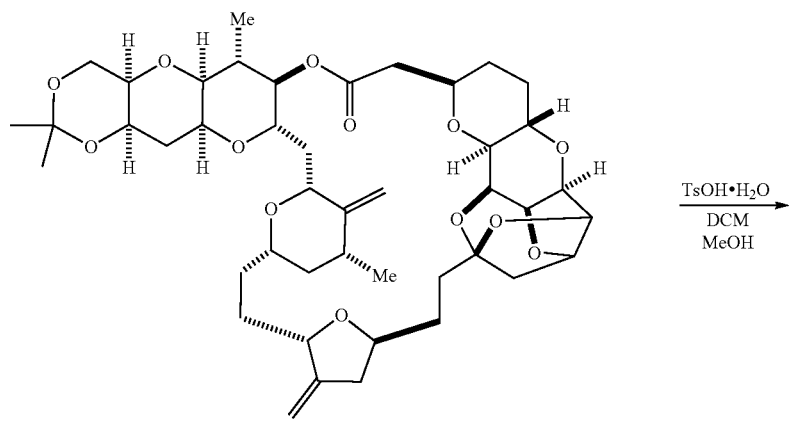

-continued

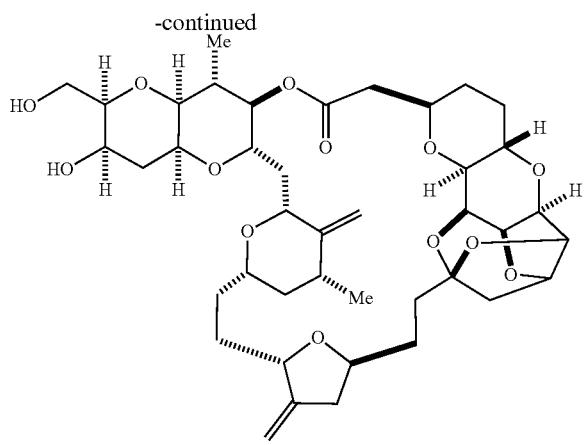

To a stirred solution of starting material (40.5 g, 50.7 mmol) in dichloromethane (312 mL) and MeOH (579 mL) was added p-toluenesulfonic acid monohydrate (194 mg, 1.0 mmol) at 25° C. under $N_2$ atmosphere for 4 hr. The reaction was passed through NH-silica gel (40.5 g), then rinsed with a mixture of dichloromethane (1.01 L) and MeOH (1.01 L). Combined filtrate was concentrated and azeotroped with toluene (81 mL) twice to give a desired diol, which was used in the next reaction without further purification.

under $N_2$ atmosphere. After stirred for 10 min, triethylsilyl trifluoromethanesulfonate (TESOTf, 99 μL, 0.438 mmol) was added to the reaction, then warmed to −40° C. After stirred for 70 min, NaI (235 mg, 1.57 mmol) and 1,3-dimethyl-2-imidazolidinone (DMI, 4.75 mL) was added, then warmed to room temperature. After stirred for 4 hr, toluene (7.13 mL) and cold water (4.75 mL) was added to the reaction. After separated aqueous layer, organic layer was washed with water (4.75 mL), 5 wt % citric acid aq.

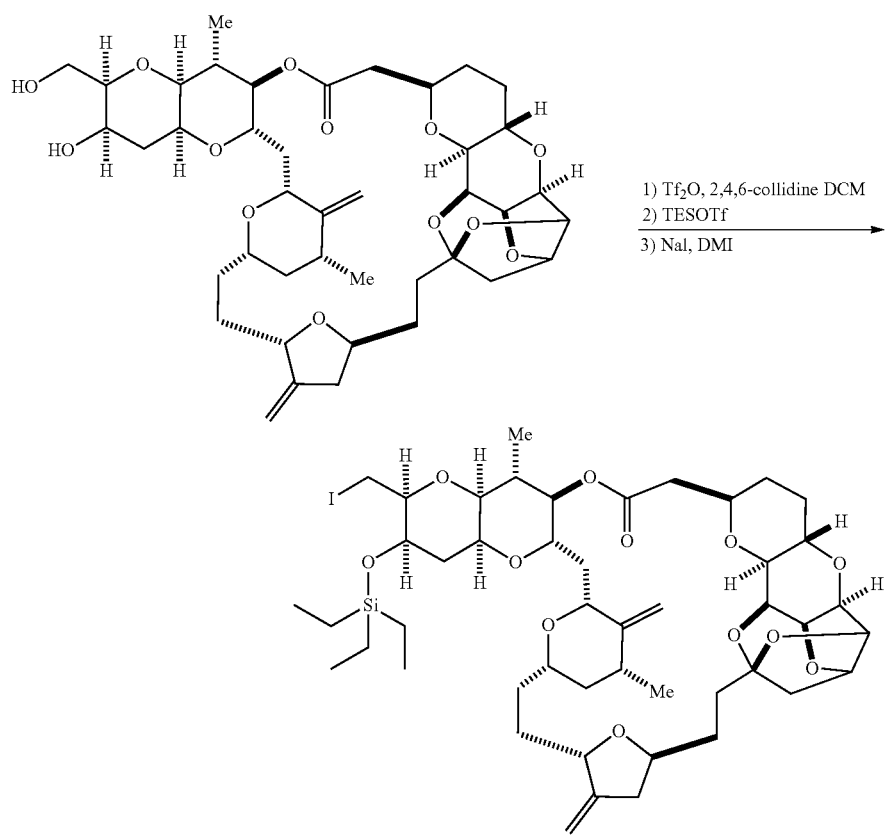

To a solution of starting material (238 mg, 0.313 mmol) and 2,4,6-collidine (2070 L, 1.57 mmol) in anhydrous dichloromethane (2.38 mL) was added trifluoromethanesulfonic anhydride (Tf$_2$O, 73.7 μL, 0.438 mmol) at −78° C.

(2.38 mL) followed by a mixture of 5 wt % NaHCO$_3$–10 wt % Na$_2$SO$_4$ aqueous solution (1.19 mL). The organic layer was concentrated under reduced pressure. The residue was purified by column chromatography on silica gel (6 g, eluent; 10%, 20%, then 30% EtOAc in n-heptane). The collected fractions were concentrated. The residue was crystallized from dichloromethane (0.24 mL) and 1-propanol (4.75 mL) at 0° C. Resulted precipitation was filtered and washed with 1-propanol to give desired iodide (250 mg, 0.254 mmol).

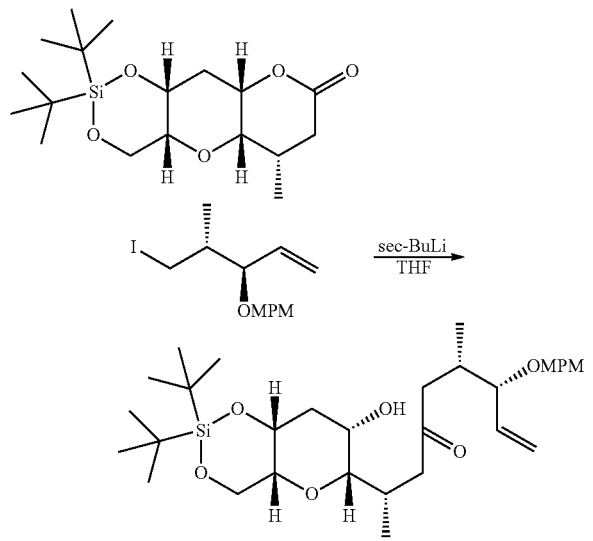

To a mixture of lactone (55 g, 154 mmol) and iodide (58.75 g, 170 mmol) was added THF (550 ml) and the reaction mixture was cooled in dry ice-EtOH bath. Sec-BuLi (1.03M solution in cyclohexane, 315 mL, 324 mmol) was gradually added at −73.2~−58.5° C. during 33 min and stirred for 30 min. After addition of sat.NH₄Cl (550 mL) at −74.2~−11.2° C. during 3 min, dry ice bath was removed. The reaction mixture was diluted with AcOEt (550 mL) and water (220 mL) and stirred in water bath for 40 min. The resulting layers were separated and the organic layer was washed with sat.NaCl (165 mL) and separated organic layer was concentrated in vacuum. The residue was azeotroped with n-heptane (110 mL×3). The residue was purified by column chromatography on neutral silica gel (1.1 kg, eluent: 0%, 5%, 10%, 15% then 25% EtOAc in n-heptane) to give desired compound (71.82 g, 125 mmol, 81%).

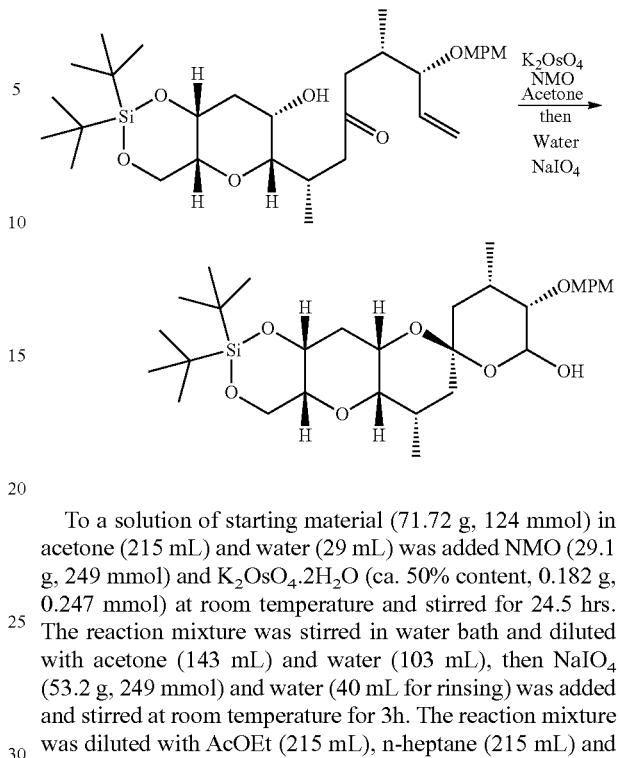

To a solution of starting material (71.72 g, 124 mmol) in acetone (215 mL) and water (29 mL) was added NMO (29.1 g, 249 mmol) and K₂OsO₄.2H₂O (ca. 50% content, 0.182 g, 0.247 mmol) at room temperature and stirred for 24.5 hrs. The reaction mixture was stirred in water bath and diluted with acetone (143 mL) and water (103 mL), then NaIO₄ (53.2 g, 249 mmol) and water (40 mL for rinsing) was added and stirred at room temperature for 3h. The reaction mixture was diluted with AcOEt (215 mL), n-heptane (215 mL) and water (430 mL). The resulting insoluble material was removed by decantation followed by filtration through cotton plug. The filtrate was separated and the aqueous layer was extracted with n-heptane/AcOEt=1/1 (v/v) (286 mL). The combined organic layer was washed twice with sat.Na₂S₂O₃ (215 mL) and washed with sat.NaCl (143 mL) and concentrated in vacuum. The residue was passed through a pad of neutral silica gel (143 g, eluent: 66% EtOAc in n-heptane) to give desired compound (71.3 g, 123 mmol, 99%).

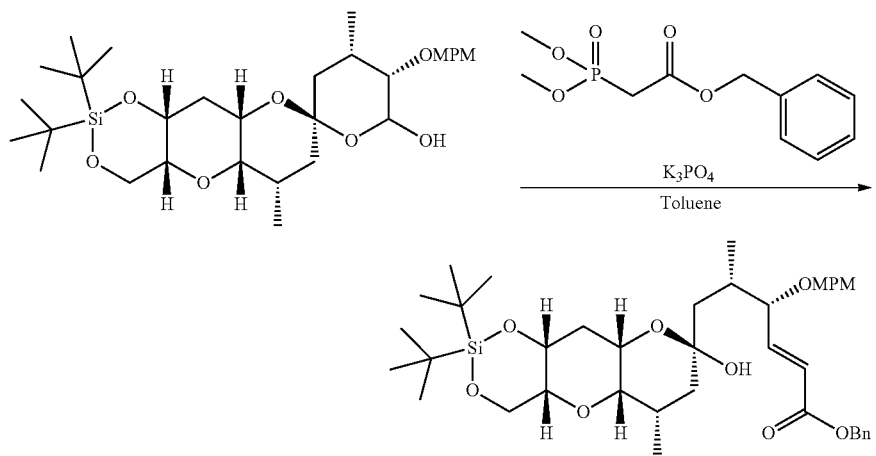

To a mixture of starting material (71.23 g, 123 mmol) and K₃PO₄ (78.4 g, 369 mmol) and toluene (214 mL) was added dimethyl(benzyloxycarbonyl)methyl phosphonate (127.1 g, 492 mmol). The reaction mixture was purged by N₂ (balloon) and stirred at 30° C. for 48 hrs. Additional K₃PO₄ (26.13 g, 123 mmol) and dimethyl(benzyloxycarbonyl)m- ethyl phosphonate (26.1 mL, 123 mmol) were added and stirred at 30° C. for 26 hrs. The reaction mixture was cooled in water bath and diluted with MTBE (712 mL) and quenched with sat.NH$_4$Cl (50 mL) at 21-36° C. The reaction mixture was cooled in ice-water bath and sat.NH$_4$Cl (662 mL) and water (214 mL) were successively added. The resulting layers were separated and the aqueous layer was extracted with MTBE (712 mL). The combined organic layer was washed with sat.NaCl (356 mL) and concentrated in vacuum. The residue was azeotroped with toluene (178 mL). The residue was purified by column chromatography on neutral silica gel (1.1 kg, eluent: 0%, 8%, 15% then 25% EtOAc in n-heptane) to give desired compound (72.63 g, 102 mmol, 83%, a mixture of E/Z isomers).$^1$H-NMR (500 MHz, CDCl$_3$) δ: 7.30-7.44 (5H, m), 7.23 (2H, d, J=8.6 Hz), 6.84-6.92 (3H, m), 6.06 (1H, dd, J=15.9, 1.2 Hz), 5.18-5.24 (2H, m), 4.50 (1H, d, J=11.6 Hz), 4.39 (1H, t, J=2.8 Hz), 4.27 (1H, d, J=11 Hz), 4.18-4.24 (1H, m), 4.10-4.16 (1H, m), 3.81 (3H, s), 3.72-3.79 (2H, m), 3.60 (1H, d, J=10.4 Hz), 3.26 (1H, m), 3.01-3.06 (1H, m), 2.73 (1H, dd, J=15.0, 4.6 Hz), 2.44-2.59 (2H, m), 2.21-2.39 (4H, m), 1.72 (1H, dt, J=14.7, 3.1 Hz), 1.05 (18H, s), 0.91 (6H, dd, J=14.7, 6.7 Hz).

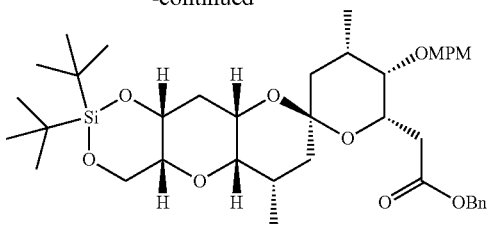

A solution of the starting material (72.5 g, 102 mmol) and AcOBn (72.9 mL, 510 mmol) in MeCN (1087 mL) was cooled in ice-water bath. LiBr (88.5 g, 1019 mmol) was added at 10.1-16.5° C. during 3 min and DBU (76.1 mL, 510 mmol) was added at 11.8-15.4° C. The reaction mixture was stirred at room temperature for 2 hrs. Then, the reaction mixture was stirred at 30° C. for 23 hrs. The reaction mixture was cooled in ice-water bath and diluted with MTBE (362 mL) and quenched with sat.NH$_4$Cl (362 mL) at 7.4-13.7° C. and water (145 mL). The resulting layers were separated and the organic layer was washed with sat.NaCl (254 mL) and dried over anhydrous Na$_2$SO$_4$. After filtration, the filtrate was concentrated in vacuum. The residue was purified by column chromatography on neutral silica gel (1.1 kg, eluent: 0%, 3%, 10%, 20% then 35% MTBE in n-heptane) to give a desired compound (64.07 g, 90 mmol, 88%). $^1$H-NMR (500 MHz, CDCl$_3$) δ: 7.31-7.40 (5H, m), 7.23-7.27 (2H, m), 6.86 (2H, d, J=8.6 Hz), 5.01-5.18 (2H, m), 4.41-4.57 (2H, m), 4.24-4.33 (1H, m), 4.16-4.22 (2H, m), 4.08 (1H, ddd, J=9.3, 4.7, 1.2 Hz), 3.80 (3H, s), 3.51-3.54 (1H, m), 3.25 (1H, brs), 3.15-3.20 (1H, m), 2.97 (1H, d, J=2.5 Hz), 2.72 (1H, dd, J=15.6, 9.5 Hz), 2.28-2.42 (2H, m), 2.07 (1H, dt, J=15.3, 1.8 Hz), 1.87-2.00 (1H, m), 1.69 (1H, dt, J=15.3, 4.6 Hz), 1.45-1.58 (3H, m), 1.36-1.42 (1H, m), 1.05 (9H, s), 1.03 (9H, s), 0.95 (3H, d, J=6.7 Hz), 0.89 (3H, d, J=6.7 Hz).

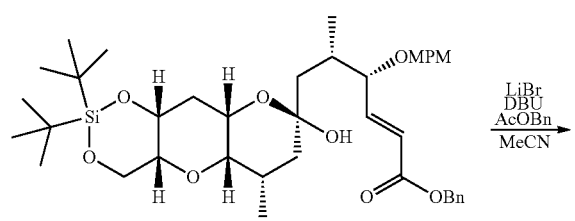

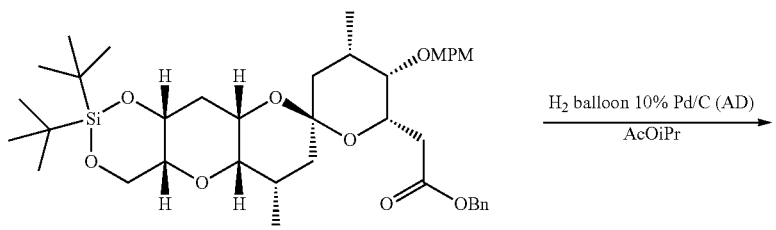

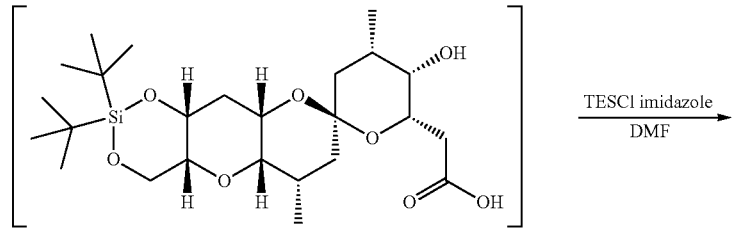

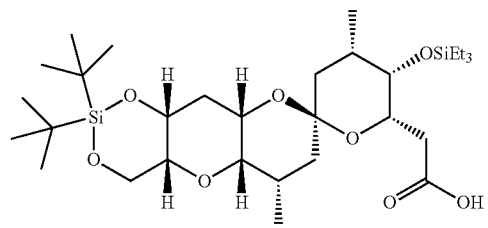

The starting material (64 g, 90 mmol) was dissolved in ⁱPrOAc (1280 mL) and purged by N₂ (balloon). 10% Pd/C (AD, Kawaken Fine Chemicals, 6.4 g) was added and purged by H₂ (balloon) and stirred at room temperature for 24 hrs. The catalyst was filtered through Hyflo Supercel (64 g) and washed with ⁱPrOAc (1280 mL). The filtrate was concentrated to ca. half volume. ⁱPrOAc (1280 mL) was added and concentrated to ca. half volume. ⁱPrOAc (1280 mL) was added again and concentrated to ca. half volume. DMF (500 mL) was added to the residual solution and concentrated in vacuum for 1 hr until removal of ⁱPrOAc to give desired seco acid as DMF solution (ca. 500 mL). This solution of the seco acid (calculated as 90 mmol) was diluted with DMF (140 mL) and imidazole (36.77 g, 540 mmol) was added. The reaction mixture was cooled in ice-water bath and TESCl (45.3 mL, 270 mmol) was slowly added at 2.1-4.2° C. during 13 min, then stirred in water bath for 80 min. The reaction mixture was cooled in ice-water bath and quenched with sat.NaHCO₃ (384 mL) at 4.8~13.8° C. during 24 min and stirred in water bath for 1 hr. The reaction mixture was diluted with n-heptane (640 mL) and water (768 mL) and the resulting layers were separated. The organic layer was successively washed with sat.NH₄Cl (384 mL), water (640 mL), 10% NaCl (384 mL) and concentrated in vacuum. The residue was purified by column chromatography on neutral silica gel (640 g, eluent: 0%, then 67% MTBE in n-heptane) to give the desired compound (61.55 g). To this compound was added cyclopentyl methyl ether (32 mL) and MeCN (94 mL) and heated at 50° C. to dissolve the solid. To this solution was slowly added MeCN (514 mL) during 1 hr. The mixture was slowly cooled to room temperature and stirred for 2 hrs. After further stirred at 0° C. for 1 hr followed by −20° C. for 14 hrs. The resulting suspension was filtrated and rinsed with cold (ca. −20° C.) MeCN (92 mL). The crystals were dried under reduced pressure at 40° C. to give the desired compound (47.68 g, 78 mmol, 86%) as a white solid. ¹H-NMR (500 MHz, CDCl₃) δ: 4.13-4.31 (3H, m), 3.96-4.06 (1H, m), 3.49-3.65 (2H, m), 3.12-3.24 (2H, m), 2.69 (1H, dd, J=15.8, 10.0 Hz), 2.39 (1H, dd, J=15.8, 3.7 Hz), 2.20-2.31 (1H, m), 2.08-2.15 (1H, m), 1.98-2.07 (1H, m), 1.81 (1H, dt, J=15.2, 4.4 Hz), 1.47-1.57 (3H, m), 1.39-1.45 (1H, m), 1.03 (9H, s), 1.02 (9H, s), 0.94-0.99 (12H, m), 0.86 (3H, d, J=6.9 Hz), 0.59-0.66 (6H, m).

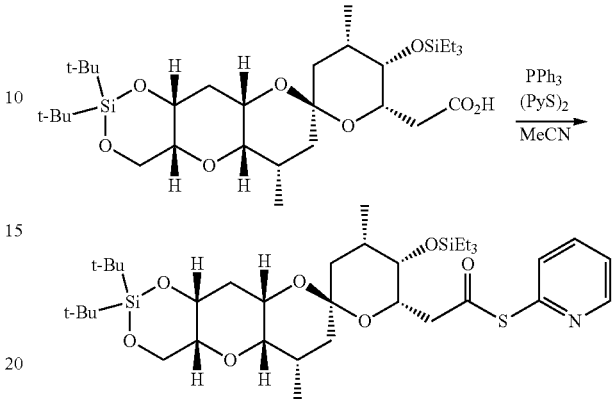

To a solution of starting material (35.1 g, 57.1 mmol) and triphenylphosphine (35.8 g, 136 mmol) in dehydrated acetonitrile (350 mL) was added 2,2'-dipyridyldisulfide (15.1 g, 68.5 mmol) at 0° C. (bath) under nitrogen atmosphere. After warmed up to 25° C., the mixture was stirred for 17.5h and the reaction was quenched with n-heptane (1050 mL) and water (350 mL) to give a biphasic mixture. The organic layer was separated and washed with 5 times 75 vol % acetonitrile aqueous solution (351 mL) and once with saturated sodium chloride aqueous solution (175 mL). Then, the organic layer was concentrated to dryness. The residue was purified by column chromatography on silica-gel (1900 g, eluent: 0%, 10% ethyl acetate in n-heptane) to give desired compound (38.6 g, 54.5 mmol, 96%).

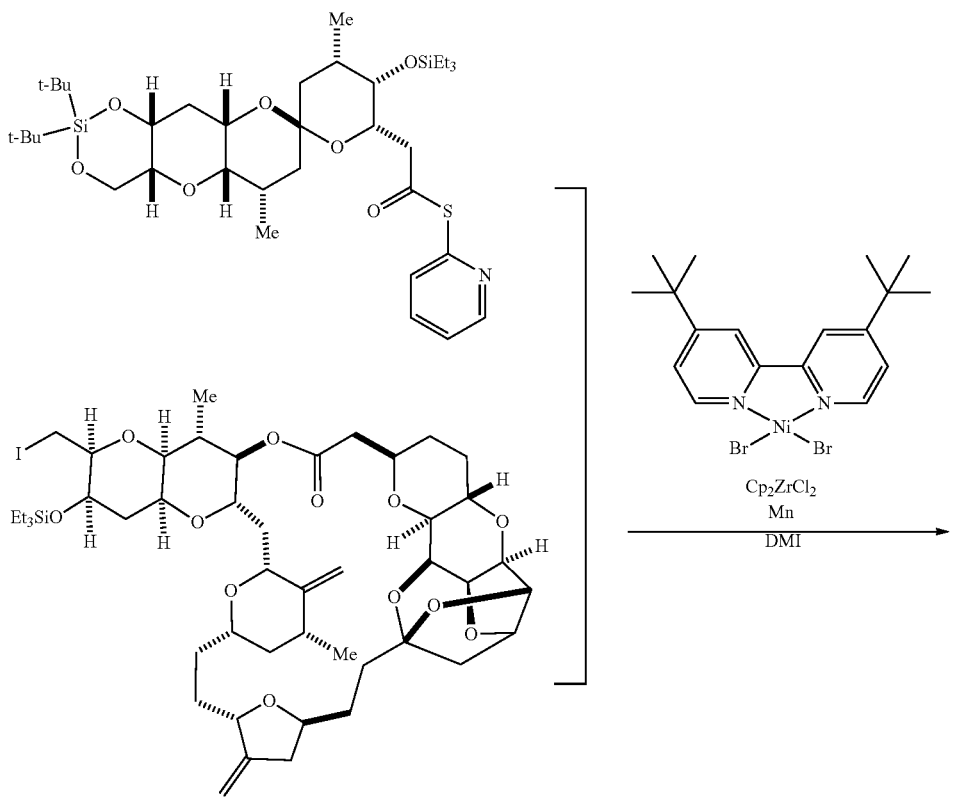

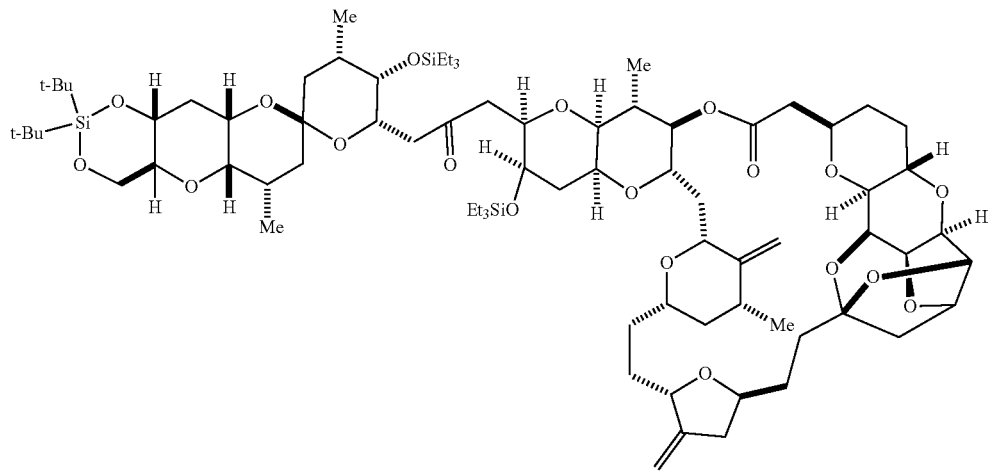

Preparation of Nickel Catalyst Solution.

A solution of nickel(II) bromide (5.00 g, 22.9 mmol) and 4,4'-di-tert-butyl-2,2'-dipyridyl (6.15 g, 22.9 mmol) in dehydrated ethanol (100 mL) was stirred at 80° C. for 18h under argon atmosphere. After the reaction mixture was cooled to room temperature, the reaction mixture was concentrated to dryness. The residue was dried in vacuum at 150° C. (bath) for 70h. Then, dehydrated DMI (62 mL) was added to give nickel catalyst solution (used as 0.37 mol/L). See, e.g., Dr. Daniel J. Weix et. al., Chem. Eur. J. 2016, 22, 11564-11567)

Coupling Reaction.

To a solution of iodide (30.1 g, 30.6 mmol), thioester (30.4 g, 42.9 mmol), bis(cyclopentadienyl)zirconium(IV) dichloride (31.3 g, 107 mmol) and manganese (11.7 g, 214 mmol) in dehydrated DMI (270 mL) was added nickel catalyst solution (30 mL, 0.37 mol/L in DMI, 11.1 mmol) prepared above under argon atmosphere. After being stirred at 30° C. (bath) for 4h under argon atmosphere, the reaction was quenched with heptane (600 mL), 10 wt % citric acid aqueous solution (600 mL) below 22° C. (0° C. bath). Then Celite®545 (15.0 g) was added and the mixture was stirred at 0° C. for 1h. Then the mixture was passed through short pad of Celite®545 (60.0 g) and the Celite®545 pad was washed with heptane (1500 mL) to give biphasic mixture. The aqueous layer was separated and extracted with heptane (90 mL). The combined organic layer was washed with a mixture of 5 wt % sodium bicarbonate and 10 wt % sodium sulfate aqueous solution (150 mL) and then concentrated to dryness. The residue was purified by column chromatography on silica-gel (1500 g, eluent: 10%, then 30% ethyl acetate in heptane) to give desired compound (36.6 g, 25.2 mmol, 82%).

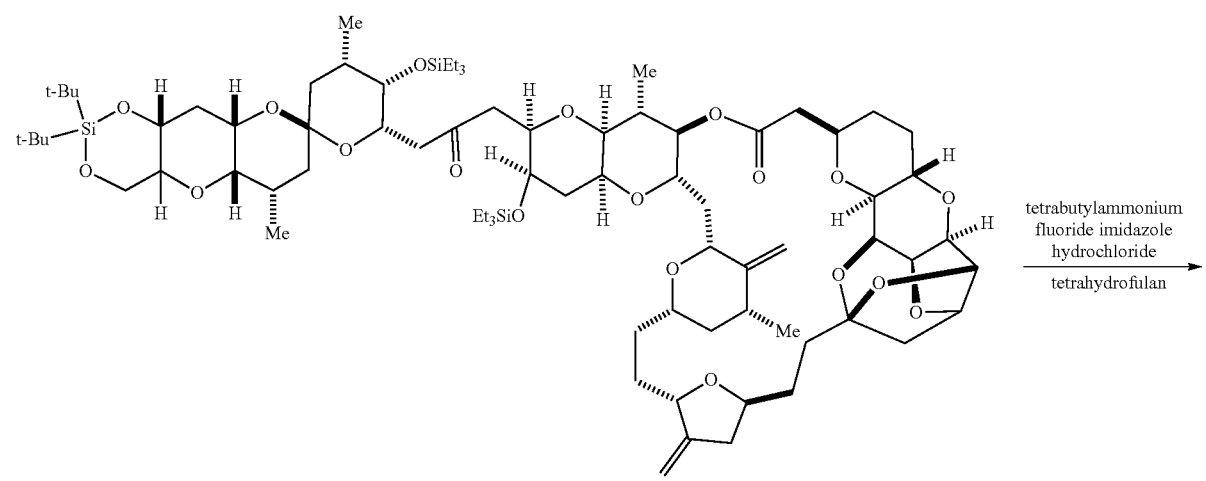

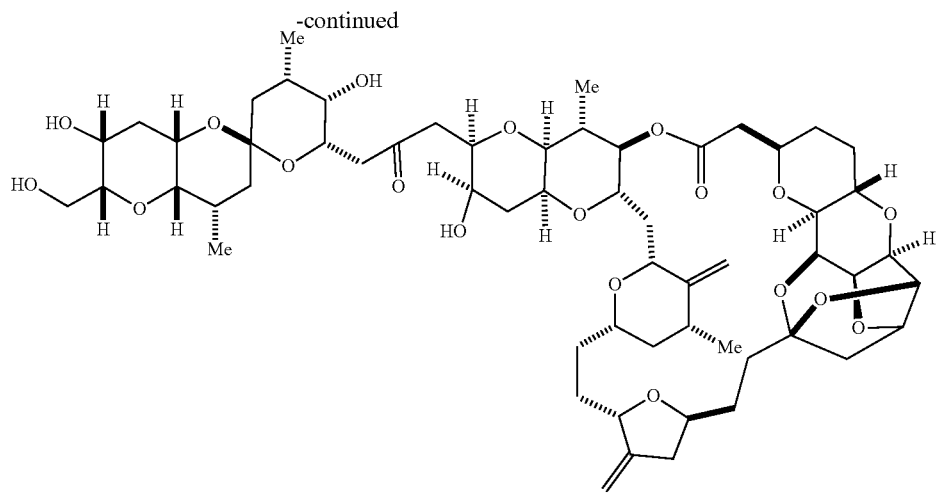

To a solution of starting material (35.5 g, 24.4 mmol) in THF (365 mL) was added a mixture of imidazole hydrochloride (12.9 g, 123 mmol) and tetrabutylammonium fluoride (244 mL, 1.0 mol/L in THF, 244 mmol) at 25° C. (bath) under nitrogen atmosphere. After being stirred at 25° C. for 19h, the reaction was quenched with toluene (710 mL) and 10 wt % sodium chloride aqueous solution (710 mL) to give a biphasic mixture. The aqueous layer was separated and extracted with toluene (178 mL). The combined organic layer was washed with water (71 mL) and then concentrated to dryness. The residue was purified by column chromatography on silica gel (1500 g, eluent: 10% to 100% ethyl acetate in heptane, then, 10% methanol in ethyl acetate) to give desired compound (25.5 g, 23.5 mmol, 96%).

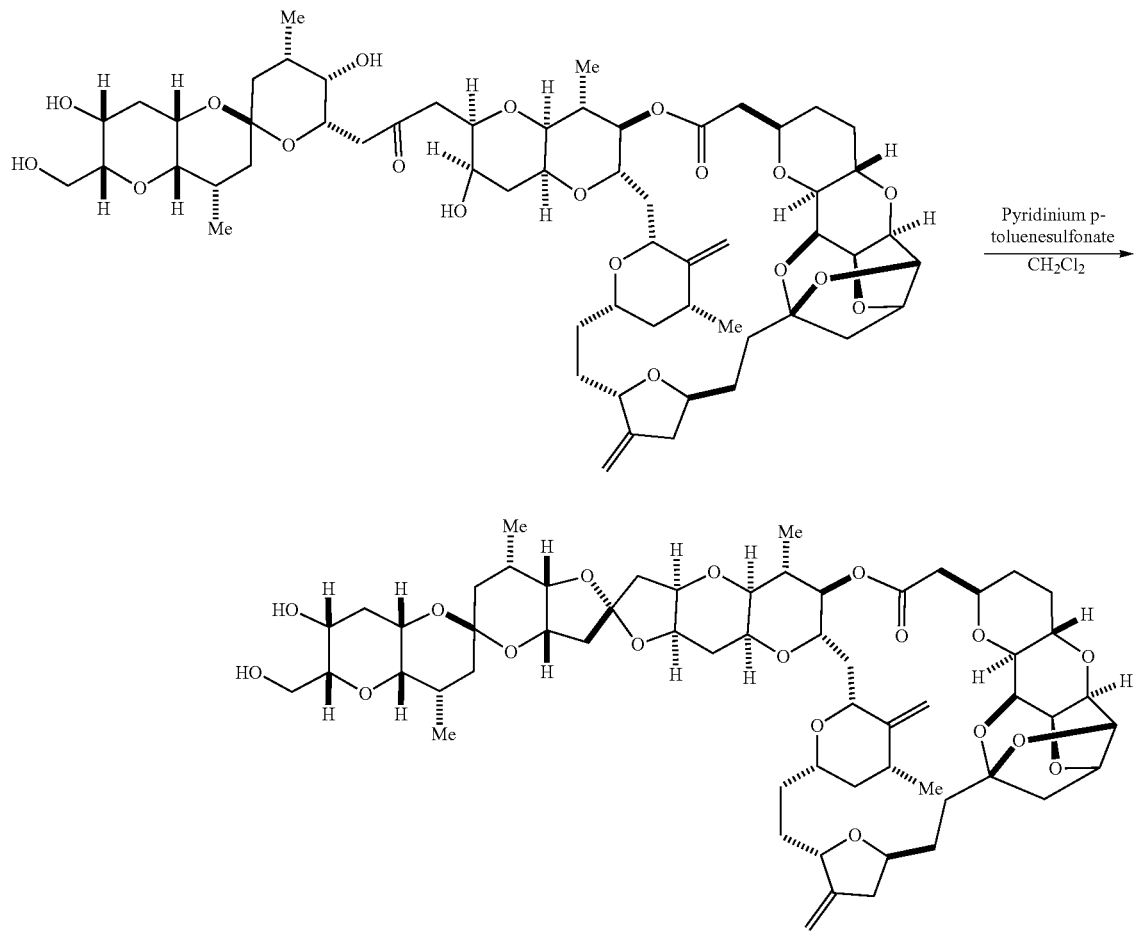

To a solution of desired compound (25.4 g, 23.4 mmol) in dichloromethane (765 mL) was added pyridinium p-toluenesulfonate (29.5 g, 117 mmol) at 10° C. under nitrogen atmosphere. After being stirred at 9-11° C. for 3h, the reaction was quenched with water (508 mL) to give a biphasic mixture. The aqueous layer was re-extracted with dichloromethane (25 mL). The combined organic layer was washed with water (508 mL) followed by a mixture of 5 wt % sodium bicarbonate and 10 wt % sodium sulfate aqueous solution (127 mL). Then, the organic layer was concentrated to dryness. The residue was purified by column chromatography on silica gel (1500 g, eluent: 10%, 95%, 100% ethyl acetate in heptane) to give the desired compound (23.8 g). This compound was purified again by column chromatography on ODS (950 g, eluent: 30%, 65%, 100% acetonitrile in water). The fractions containing desired compound were combined and acetonitrile was removed to some extent under reduced pressure. The resulting aqueous solution was extracted with ethyl acetate (1524 mL+762 mL) and the combined organic layer was concentrated to dryness to give desired compound (18.1 g, 17.0 mmol, 73%).

To a solution of starting material (15.2 g, 14.2 mmol) in dichloromethane (30 mL) was added triethylamine (12.3 mL, 88.5 mmol), dibutyltin oxide (2.13 g, 8.56 mmol) and p-toluenesulfonyl chloride (8.16 g, 42.8 mmol) successively at 25° C. After being stirred at 25° C. for 3h, the reaction mixture was passed through glass-filter. The filtrate was directly purified by column chromatography on silica gel (750 g, eluent: 10%, 30%, 50%, 70%, 85% ethyl acetate in heptane) to give desired compound (17.4 g, 14.2 mmol, quant.). $^1$H NMR (600 MHz, BENZENE-$d_6$) δ ppm 0.86 (d, J=6.8 Hz, 3H) 0.95 (d, J=6.8 Hz, 3H) 1.00-1.05 (m, 4H) 1.07-1.17 (m, 4H) 1.19 (br td, J=14.7, 3.0 Hz, 1H) 1.26-1.49 (m, 8H) 1.54 (t, J=13.0 Hz, 1H) 1.61-1.67 (m, 2H) 1.75-2.39 (m, 25H) 2.62-2.75 (m, 5H) 3.25 (br s, 1H) 3.27 (br s, 1H) 3.35 (t, J=6.0 Hz, 1H) 3.39 (dt, J=10.8, 5.6 Hz, 1H) 3.44 (br d, J=11.0 Hz, 1H) 3.50 (d, J=11.3 Hz, 1H) 3.55 (br s, 1H) 3.62 (dd, J=6.2, 4.3 Hz, 1H) 3.78 (br t, J=9.6 Hz, 1H) 3.83 (br t, J=6.0 Hz, 1H) 3.86-3.96 (m, 3H) 3.99-4.11 (m, 3H) 4.14 (m, 1H) 4.27 (br s, 1H) 4.36-4.44 (m, 2H) 4.49 (m, 1H) 4.55-4.61 (m, 2H) 4.80 (s, 1H) 4.86-4.91 (m, 2H) 4.95 (br s, 1H) 5.02 (br s, 1H) 6.65 (d, J=7.9 Hz, 2H) 7.80 (d, J=7.9 Hz, 2H).

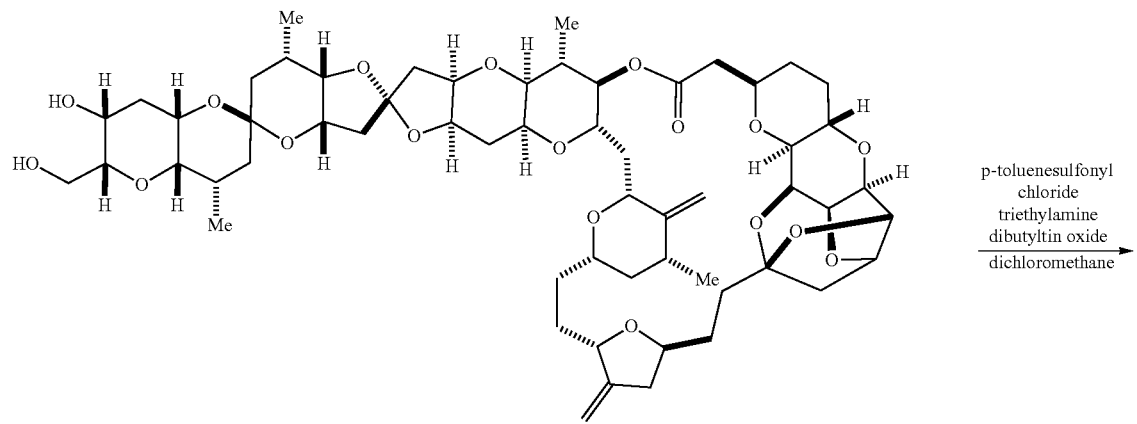

p-toluenesulfonyl chloride
triethylamine
dibutyltin oxide
dichloromethane

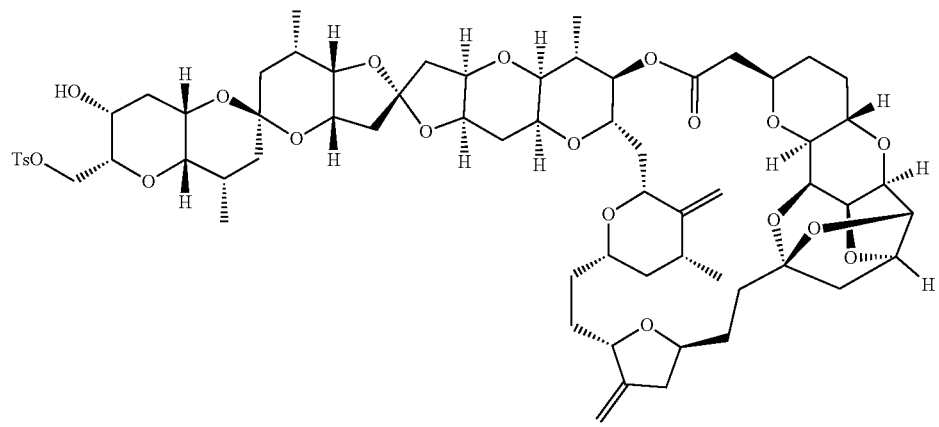

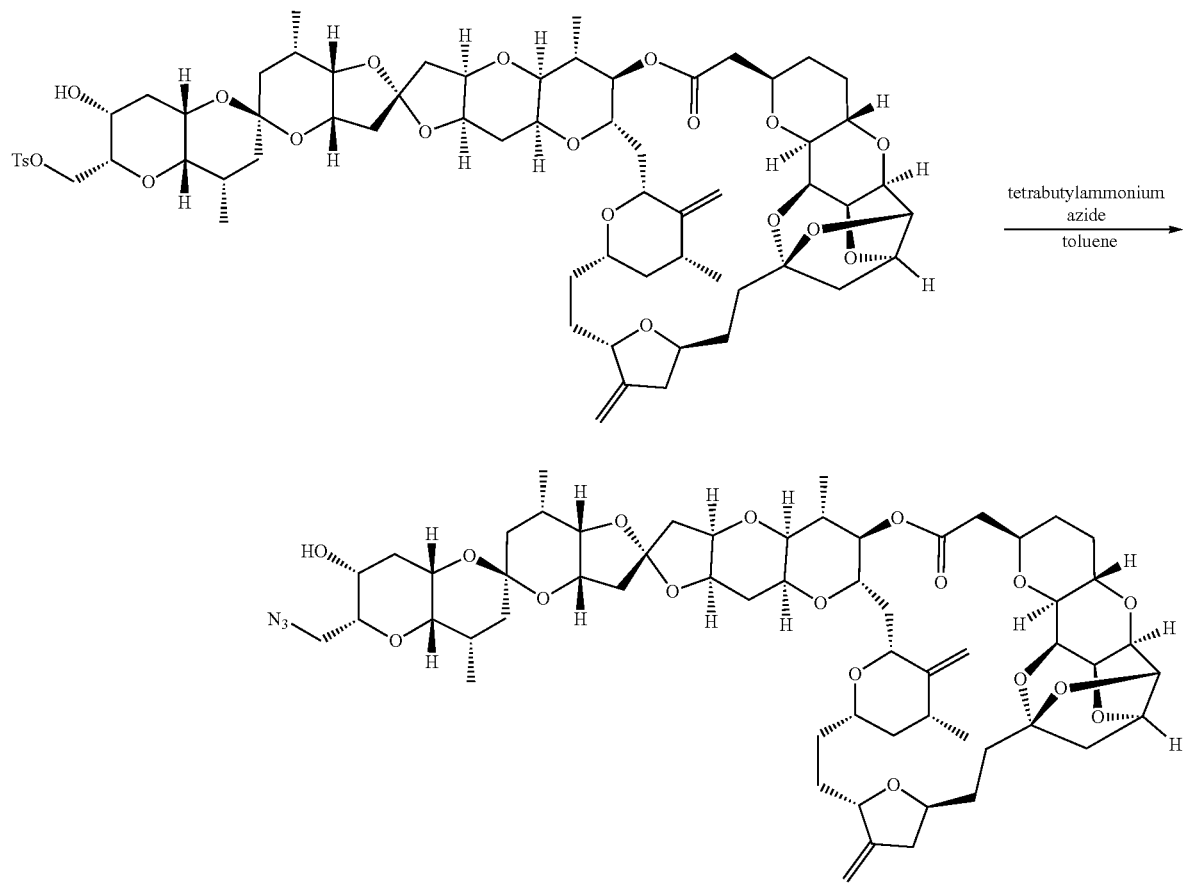

To a solution of starting material (17.3 g, 14.2 mmol) in toluene (121 mL) was added tetrabutylammonium azide (32.2 g, 113 mmol) at room temperature under nitrogen atmosphere. After being stirred at 100° C. (bath) for 5h, the reaction mixture was cooled to room temperature and tetrahydrofuran (52 mL) was added to give a homogenous solution. The solution was directly purified by column chromatography on silica gel (750 g, eluent: 10%, 50%, 70%, 80% ethyl acetate in heptane) to give desired compound (15.5 g, 14.2 mmol, quant.). $^1$H NMR (600 MHz, BENZENE-d6) δ ppm 0.97-1.05 (m, 9H) 1.08-1.37 (m, 8H) 1.39-1.55 (m, 5H) 1.58-1.71 (m, 3H) 1.78-1.88 (m, 2H) 1.91-2.08 (m, 8H) 2.09-2.40 (m, 13H) 2.62-2.75 (m, 4H) 2.78 (d, J=2.3 Hz, 1H) 2.97 (dd, J=13.0, 4.0 Hz, 1H) 3.09 (dd, J=8.3, 3.8 Hz, 1H) 3.26 (br d, J=11.3 Hz, 1H) 3.30 (t, J=2.6 Hz, 1H) 3.32 (br s, 1H) 3.40 (dt, J=10.8, 5.6 Hz, 1H) 3.56 (d, J=11.0 Hz, 1H) 3.58-3.65 (m, 3H) 3.78 (br dd, J=10.8, 8.9 Hz, 1H) 3.83 (br dd, J=7.2, 5.7 Hz, 1H) 3.86-3.99 (m, 3H) 4.01-4.11 (m, 3H) 4.14 (t, J=4.5 Hz, 1H) 4.28 (dd, J=3.8, 1.5 Hz, 1H) 4.50 (m, 1H) 4.56-4.62 (m, 2H) 4.80 (br s, 1H) 4.86-4.92 (m, 2H) 4.96 (br d, J=1.9 Hz, 1H) 5.02 (br d, J=1.5 Hz, 1H).

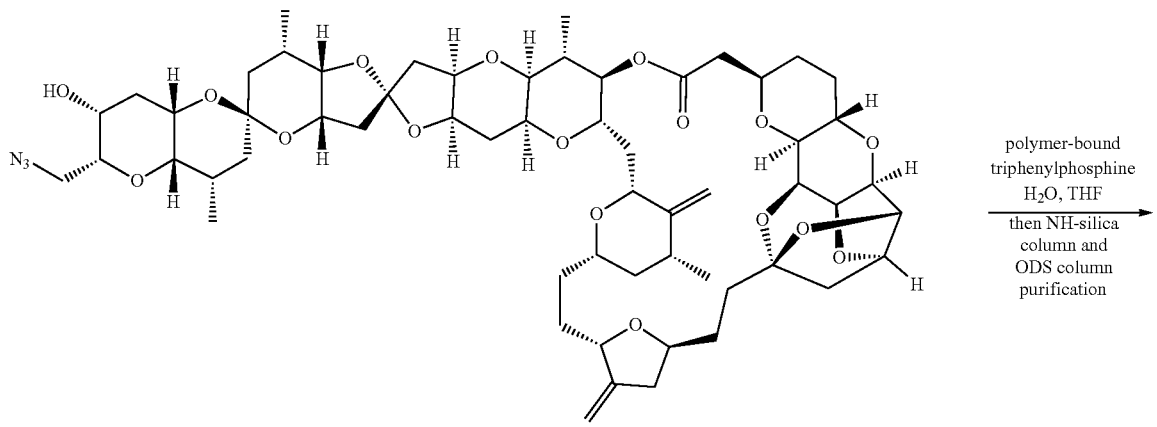

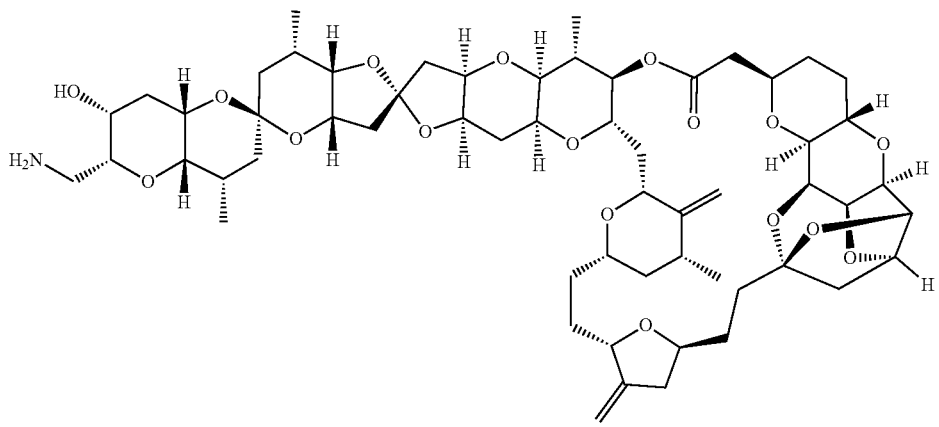

To a solution of starting material (15.4 g, 14.1 mmol) in a mixture of THF (92 mL) and water (10 mL) was added polymer-bound triphenylphosphine (20.4 g, 2.07 mmol/g, 42.2 mmol) at 25° C. After being stirred at 25° C. for 70h, the reaction mixture was passed through glass-filter. The filtrate was concentrated to dryness. The residue was purified by column chromatography on NH-silica-gel (900 g, eluent: 50%, 100% MTBE in heptane, then 3%, 10% methanol MTBE) to give desired compound (14.1 g, 13.2 mmol, 94%) as a white solid. The desired compound was further purified by column chromatography on ODS (400 g, eluent: 1%, 70%, 100% 0.05 vol % acetic acid/acetonitrile in 0.05 vol % acetic acid/water). The fractions containing desired compound were combined and dichloromethane (3304 mL), 20 wt % sodium chloride aqueous solution (661 mL) and saturated sodium bicarbonate aqueous solution (1322 mL) were added to give biphasic mixture. Then, the aqueous layer was extracted with dichloromethane (830 mL). The combined organic layer was washed with water (165 mL) and concentrated to dryness to give desired compound (12.4 g, 11.6 mmol, 88%). After the compound was dissolved in dichloromethane (25 mL) and pentane (25 mL), half of the solution was added to pentane (984 mL) at 0° C. with stirring to precipitate desired compound. After removal of approximately 271 mL of solvent under slightly reduced pressure, pentane (246 mL) was added. After removal of approximately 246 mL of solvent under slightly reduced pressure, pentane (246 mL) was added. To this mixture was added remaining half of the desired compound solution at 0° C. with stirring to further precipitate the desired compound. After removal of approximately 271 mL of solvent under slightly reduced pressure, pentane (246 mL) was added. After removal of approximately 246 mL of solvent under slightly reduced pressure, pentane (246 mL) was added. The resulting slurry was filtrated, dried at 40° C. gave the desired compound (11.5 g, 93%).

$^1$H NMR (600 MHz, METHANOL-$d_4$) δ ppm 0.98 (d, J=7.2 Hz, 3H) 1.00 (d, J=6.8 Hz, 3H) 1.02 (m, 1H) 1.05 (d, J=6.8 Hz, 3H) 1.09 (d, J=6.4 Hz, 3H) 1.28-1.45 (m, 5H) 1.46-1.59 (m, 4H) 1.57-1.63 (m, 1H) 1.65-1.71 (m, 1H) 1.70-1.75 (m, 2H) 1.79-1.86 (m, 2H) 1.91 (dt, J=14.9, 3.1 Hz, 1H) 1.94-2.11 (m, 8H) 2.14-2.34 (m, 9H) 2.39 (dd, J=13.2, 6.0 Hz, 1H) 2.44 (dd, J=17.4, 1.9 Hz, 1H) 2.56 (dd, J=17.6, 9.6 Hz, 1H) 2.69 (dd, J=13.2, 4.2 Hz, 1H) 2.79 (ddq, J=15.9, 7.6, 2.0 Hz, 1H) 2.92 (dd, J=13.2, 8.3 Hz, 1H) 2.97 (dd, J=9.6, 1.7 Hz, 1H) 3.21 (dd, J=6.4, 4.9 Hz, 1H) 3.29 (m, 1H) 3.34 (dd, J=8.3, 4.15 Hz, 1H) 3.58 (br. s., 1H) 3.60 (br. d, J=11.3 Hz, 1H) 3.68-3.73 (m, 2H) 3.80 (br. s., 1H) 3.84-3.90 (m, 2H) 3.98 (d, J=2.3 Hz, 1H) 4.03-4.13 (m, 4H) 4.17 (dd, J=6.4, 4.9 Hz, 1H) 4.24 (ddd, J=11.3, 4.5, 1.5 Hz, 1H) 4.29 (dd, J=4.0, 1.9 Hz, 1H) 4.32 (td, J=10.2, 4.2 Hz, 1H) 4.44 (br. d, J=11.0 Hz, 1H) 4.59 (t, J=4.5 Hz, 1H) 4.62 (dd, J=7.4, 4.7 Hz, 1H) 4.69 (t, J=4.7 Hz, 1H) 4.80 (br. s., 1H) 4.87 (s, 1H) 5.00 (br. s., 1H) 5.05 (br. d, J=1.1 Hz, 1H).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of preparing a compound of Formula (H3-A):

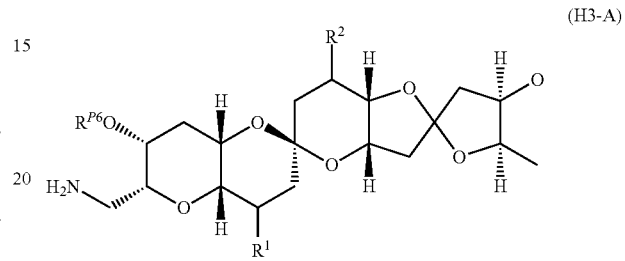

(H3-A)

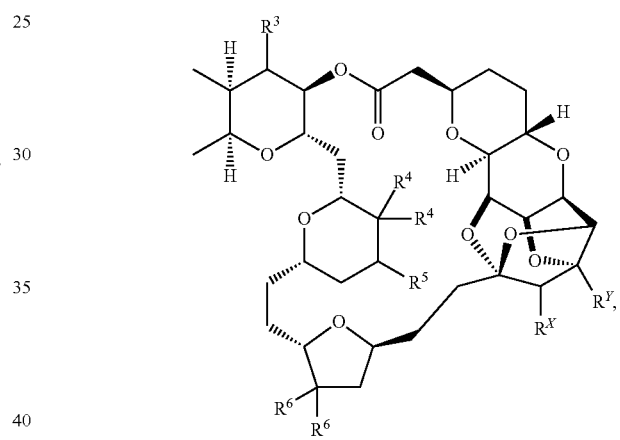

or a salt thereof, the method comprising reducing a compound of Formula (H3-N3):

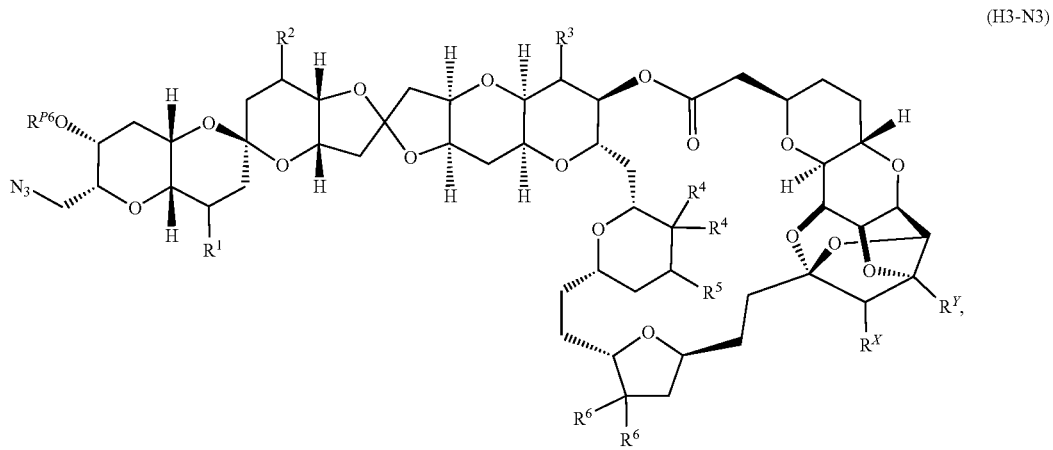

(H3-N3)

or a salt thereof, wherein:

R$^1$, R$^2$, R$^3$, and R$^5$ are each independently hydrogen, halogen, or optionally substituted alkyl;

each instance of R$^4$ is independently hydrogen, halogen, or optionally substituted alkyl, or two R$^4$ groups are taken together to form:

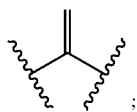 [SMILES: *C(*)=C]

each instance of R$^6$ is independently hydrogen, halogen, or optionally substituted alkyl, or two R$^6$ groups are taken together to form:

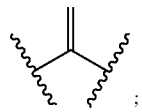 [SMILES: *C(*)=C]

R$^{P6}$ is hydrogen, optionally substituted alkyl, optionally substituted acyl, or an oxygen protecting group;

R$^X$ is hydrogen or —OR$^{Xa}$, wherein R$^{Xa}$ is hydrogen, optionally substituted alkyl, optionally substituted acyl, or an oxygen protecting group; and R$^Y$ is hydrogen or —OR$^{Ya}$, wherein R$^{Ya}$ is hydrogen, optionally substituted alkyl, optionally substituted acyl, or an oxygen protecting group;

optionally wherein R$^{Xa}$ and R$^{Ya}$ are joined together with their intervening atoms to form optionally substituted heterocyclyl.

2. The method of claim 1 further comprising a step of reacting a compound of Formula (H3-L):

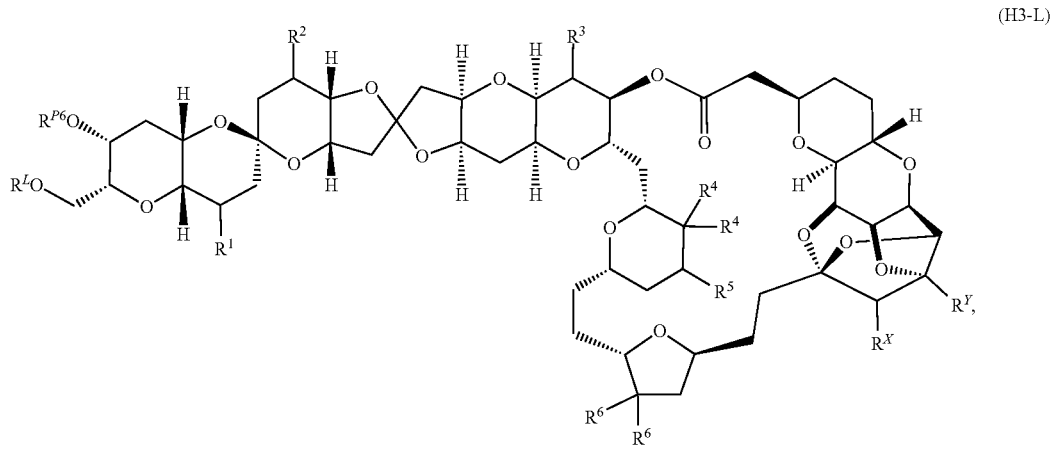

or a salt thereof, in the presence of an azide, to yield a compound of Formula (H3-N3):

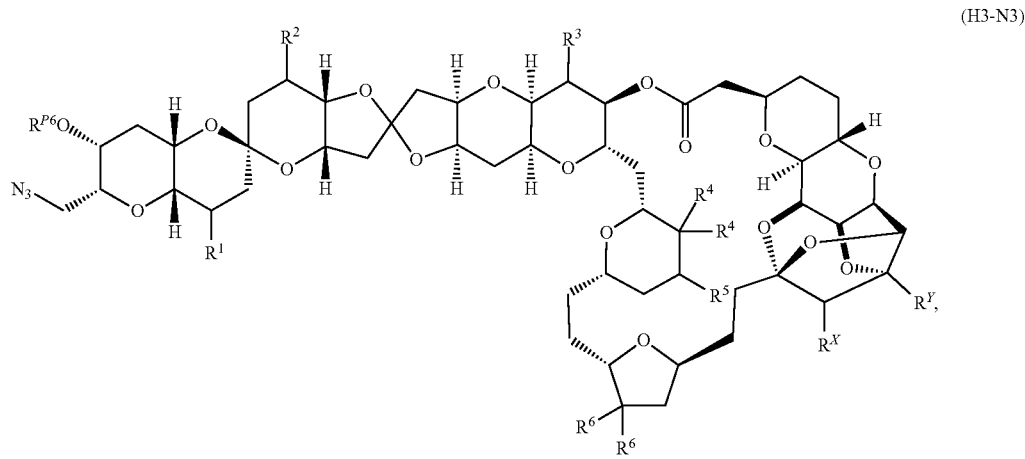

or a salt thereof, wherein:
R$^L$ is optionally substituted sulfonyl, optionally substituted sulfinyl, optionally substituted phosphoryl, or optionally substituted acyl;
R$^1$, R$^2$, R$^3$, and R$^5$ are each independently hydrogen, halogen, or optionally substituted alkyl;
each instance of R$^4$ is independently hydrogen, halogen, or optionally substituted alkyl, or two R$^4$ groups are taken together to form:

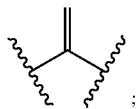 [SMILES: *C(*)=C]

each instance of R$^6$ is independently hydrogen, halogen, or optionally substituted alkyl, or two R$^6$ groups are taken together to form:

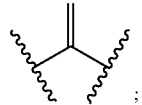 [SMILES: *C(*)=C]

R$^{P6}$ is hydrogen, optionally substituted alkyl, optionally substituted acyl, or an oxygen protecting group;
R$^X$ is hydrogen or —OR$^{Xa}$, wherein R$^{Xa}$ is hydrogen, optionally substituted alkyl, optionally substituted acyl, or an oxygen protecting group; and
R$^Y$ is hydrogen or —OR$^{Ya}$, wherein R$^{Ya}$ is hydrogen, optionally substituted alkyl, optionally substituted acyl, or an oxygen protecting group;
optionally wherein R$^{Xa}$ and R$^{Ya}$ are joined together with their intervening atoms to form optionally substituted heterocyclyl.

3. The method of claim 2 further comprising a step of reacting a compound of Formula (H3-OH):

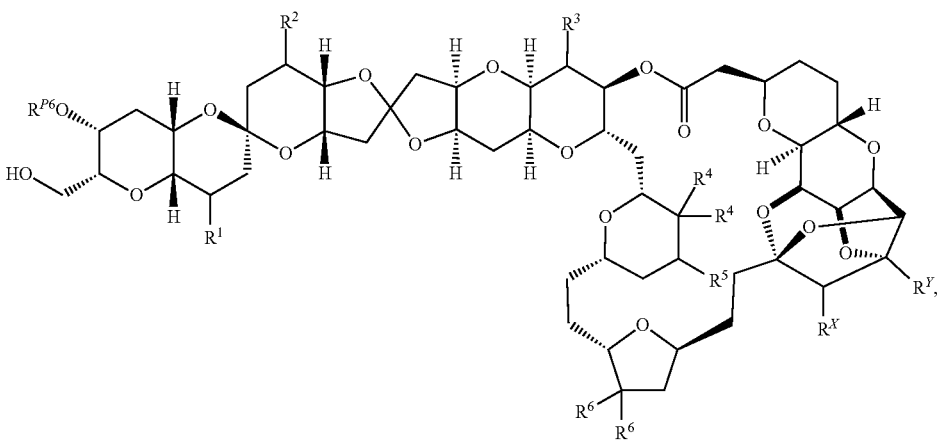

(H3-OH)

or a salt thereof, in the presence of a reagent of the formula X$^L$-R$^L$, to yield a compound of Formula (H3-L):

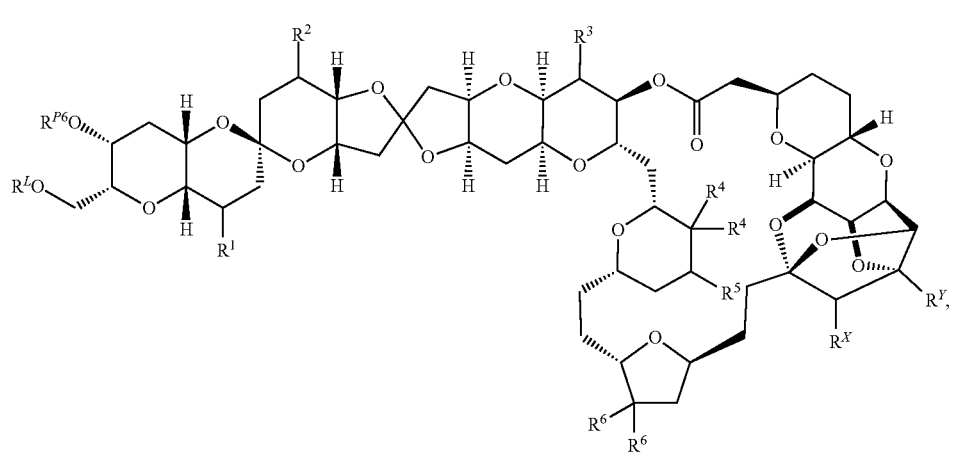

(H3-L)

521 or a salt thereof, wherein:
R$^L$ is optionally substituted sulfonyl, optionally substituted sulfinyl, optionally substituted phosphoryl, or optionally substituted acyl;
X$^L$ is halogen or a leaving group;
R$^1$, R$^2$, R$^3$, and R$^5$ are each independently hydrogen, halogen, or optionally substituted alkyl;
each instance of R$^4$ is independently hydrogen, halogen, or optionally substituted alkyl, or two R$^4$ groups are taken together to form:

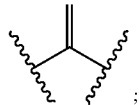 [SMILES: *C(*)=C]

each instance of R$^6$ is independently hydrogen, halogen, or optionally substituted alkyl, or two R$^6$ groups are taken together to form:

522

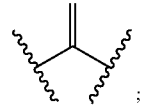 [SMILES: *C(*)=C]

R$^{P6}$ is hydrogen, optionally substituted alkyl, optionally substituted acyl, or an oxygen protecting group;
R$^X$ is hydrogen or —OR$^{Xa}$, wherein R$^{Xa}$ is hydrogen, optionally substituted alkyl, optionally substituted acyl, or an oxygen protecting group; and
R$^Y$ is hydrogen or —OR$^{Ya}$, wherein R$^{Ya}$ is hydrogen, optionally substituted alkyl, optionally substituted acyl, or an oxygen protecting group;
optionally wherein R$^{Xa}$ and R$^{Ya}$ are joined together with their intervening atoms to form optionally substituted heterocyclyl.

4. A method of preparing Compound (1):

Compound (1)

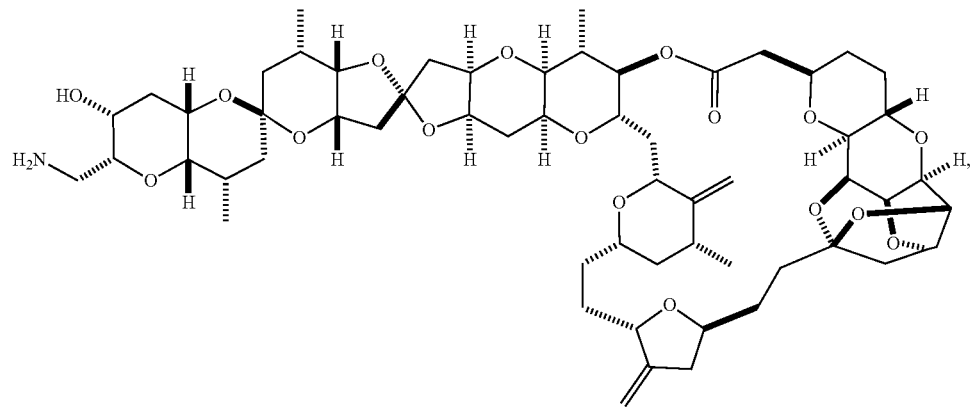

or a salt thereof, the method comprising reducing Compound (B):

(B)

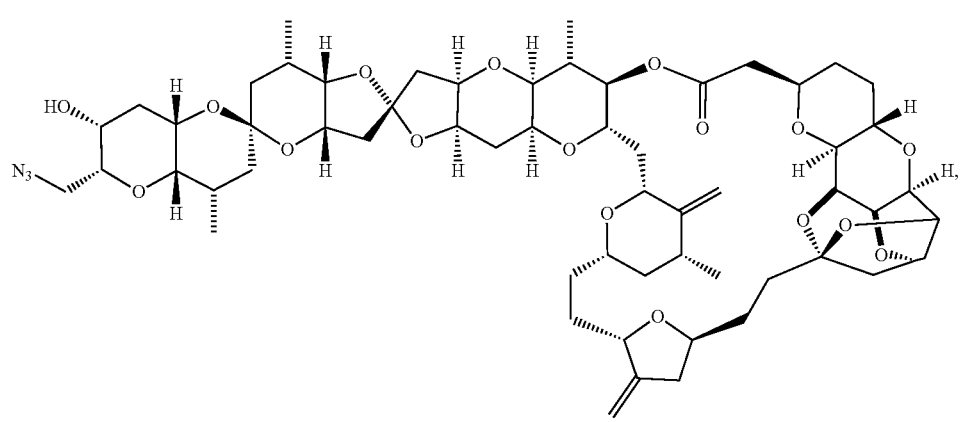

or a salt thereof.

5. The method of claim 4 further comprising a step of reacting a compound of Formula (A):
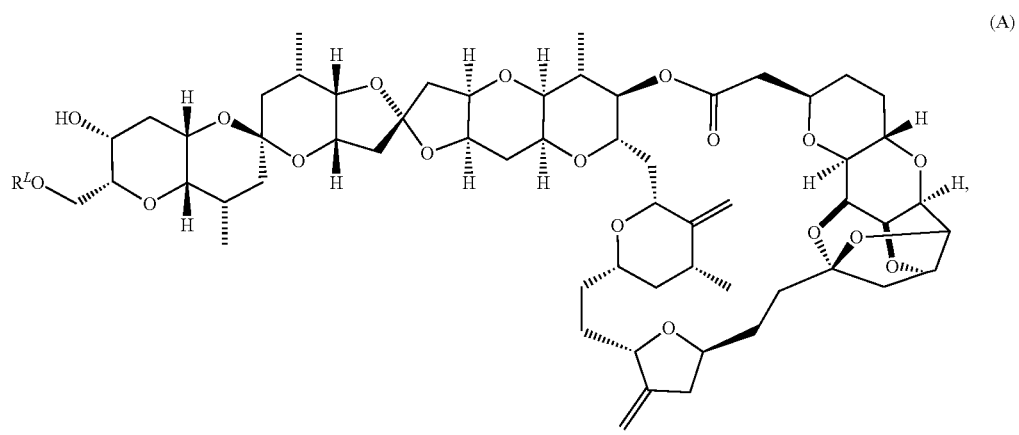
(A)
or a salt thereof, in the presence of an azide, to yield Compound (B):
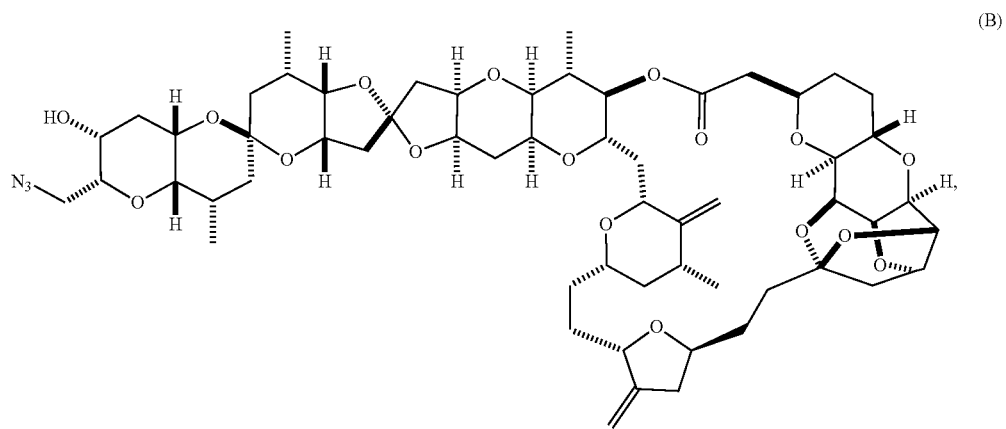
(B)

or a salt thereof, wherein:
R$^L$ is optionally substituted sulfonyl, optionally substituted sulfinyl, optionally substituted phosphoryl, or optionally substituted acyl.

6. The method of claim 5 further comprising a step of reacting Compound (2):

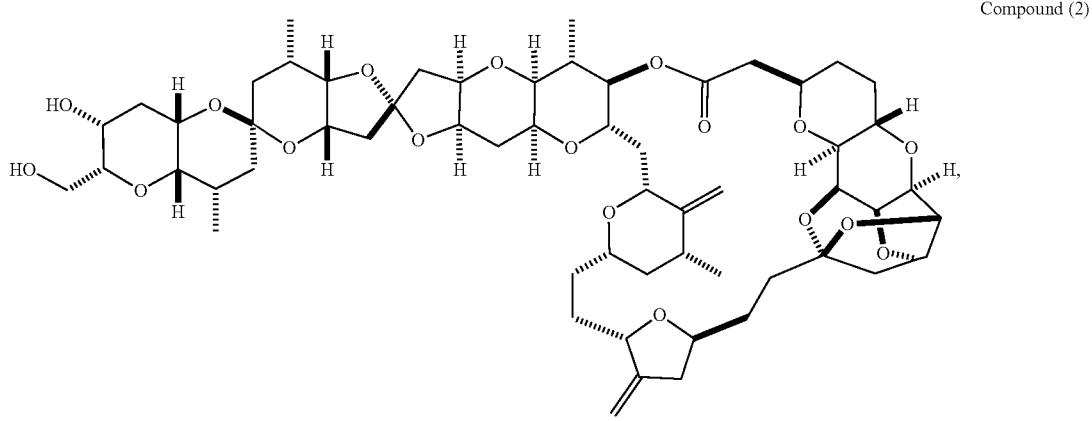

Compound (2)

or a salt thereof, in the presence of a reagent of the formula X$^L$-R$^L$, to yield a compound of Formula (A):

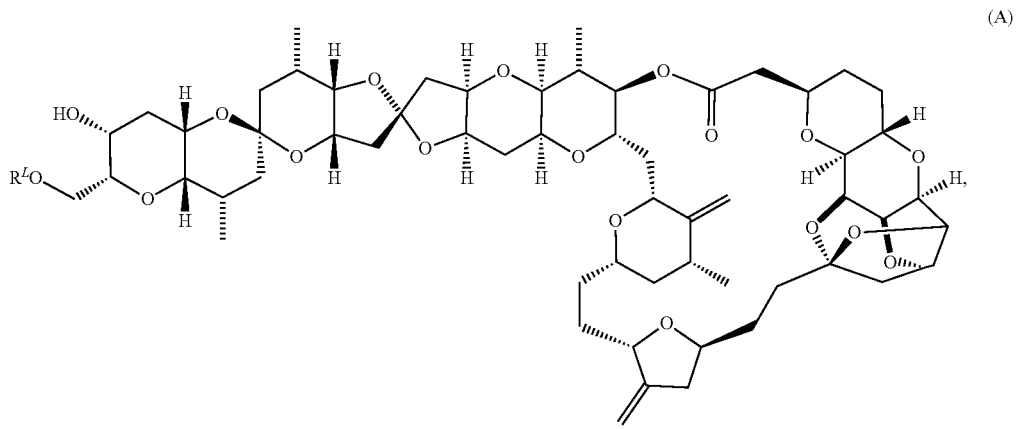

(A)

or a salt thereof, wherein:
X$^L$ is halogen or a leaving group; and
R$^L$ is optionally substituted sulfonyl, optionally substituted sulfinyl, optionally substituted phosphoryl, or optionally substituted acyl.

7. The method of claim 1, wherein the step of reducing is carried out in the presence of:
(i) palladium and H2;
(ii) a hydride source; or
(iii) a phosphine reagent.

8. The method of claim 1, wherein the step of reducing is carried out in the presence of a phosphine reagent.

9. The method of claim 8, wherein the phosphine reagent is a trialkylphosphine or triarylphosphine.

10. The method of claim 8, wherein the phosphine reagent is triphenylphosphine (Ph$_3$P).

11. The method of claim 8, wherein the phosphine reagent is polymer-bound triphenylphosphine (Ph$_3$P).

12. The method of claim 8, wherein at least one equivalent of the phosphine reagent is present with respect to the compound of Formula (H3-N3) or salt thereof.

13. The method of claim 8, wherein the step of reducing is carried out in the presence of water.

14. The method of claim 1, wherein the step of reducing is carried out in tetrahydrofuran (THF).

15. The method of claim 1, wherein the compound of Formula (H3-A), or salt thereof, is purified and isolated by precipitation.

16. The method of claim 1, wherein R$^{P6}$ is hydrogen.

17. The method of claim 1, wherein:
$R^1$, $R^2$, $R^3$, and $R^5$ are each independently $C_{1-6}$ alkyl;
two $R^4$ groups are taken together to form:

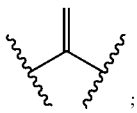 [SMILES: *C(*)=C]
;

and
two $R^6$ groups are taken together to form:

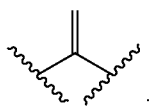
.

18. The method of claim 1, wherein:
$R^1$, $R^2$, $R^3$, and $R^5$ are methyl;
two $R^4$ groups are taken together to form:

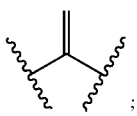 [SMILES: *C(*)=C]
;

and two $R^6$ groups are taken together to form:

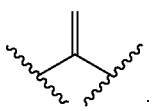 [SMILES: *C(*)=C]
.

19. The method of claim 1, wherein $R^X$ and $R^Y$ are both hydrogen.

20. The method of claim 4, wherein the step of reducing is carried out in the presence of:
(i) palladium and H2;
(ii) a hydride source; or
(iii) a phosphine reagent.

21. The method of claim 4, wherein the step of reducing is carried out in the presence of a phosphine reagent.

22. The method of claim 21, wherein the phosphine reagent is a trialkylphosphine or triarylphosphine.

23. The method of claim 21, wherein the phosphine reagent is triphenylphosphine ($Ph_3P$).

24. The method of claim 21, wherein the phosphine reagent is polymer-bound triphenylphosphine ($Ph_3P$).

25. The method of claim 21, wherein at least one equivalent of the phosphine reagent is present with respect to Compound (B) or salt thereof.

26. The method of claim 21, wherein the step of reducing is carried out in the presence of water.

27. The method of claim 4, wherein the step of reducing is carried out in tetrahydrofuran (THF).

28. The method of claim 4, wherein the step of reducing is carried out in the presence of triphenylphosphine ($Ph_3P$) and water, in tetrahydrofuran (THF), at a temperature ranging from 0° C. to 50° C.

29. The method of claim 4, wherein the step of reducing is carried out in the presence of triphenylphosphine ($Ph_3P$) and water, in tetrahydrofuran (THF), at a temperature of approximately 25° C.

30. The method of claim 4, wherein Compound (1), or salt thereof, is purified and isolated by precipitation.

31. The method of claim 2, wherein the azide is sodium azide, potassium azide, or a tetraalkylammonium azide.

32. The method of claim 2, wherein the azide is a tetraalkylammonium azide.

33. The method of claim 2, wherein the azide is tetrabutylammonium azide ([n-$Bu_4N]N_3$).

34. The method of claim 2, wherein the step of reacting is carried out in toluene.

35. The method of claim 5, wherein the compound of Formula (A) is the following:

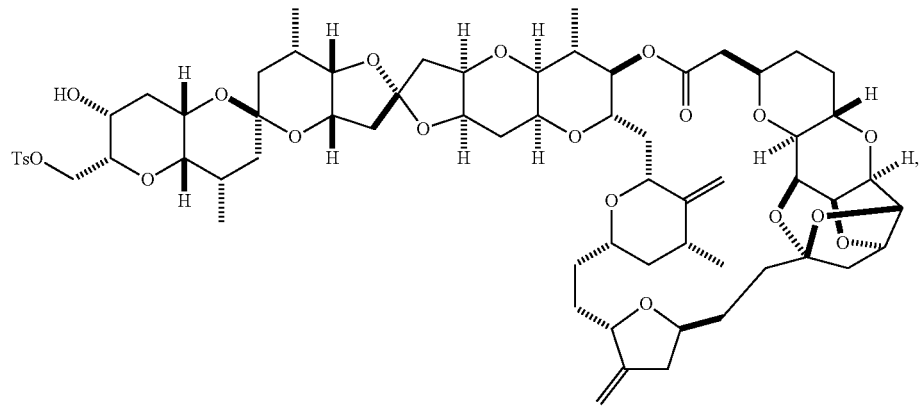

or a salt thereof.

36. The method of claim 5, wherein the azide is sodium azide, potassium azide, or a tetraalkylammonium azide.

37. The method of claim 5, wherein the azide is a tetraalkylammonium azide.

38. The method of claim 5, wherein the azide is tetrabutylammonium azide ([n-$Bu_4N]N_3$).

39. The method of claim 5, wherein the step of reacting is carried out in toluene.

40. The method of claim 35, wherein the step of reacting is carried out in the presence of tetrabutylammonium azide.

41. The method of claim 35, wherein the step of reacting is carried out in the presence of tetrabutylammonium azide, in toluene, at a temperature ranging from room temperature to 150° C.

42. The method of claim 3, wherein reagent of the formula $X^L$-$R^L$ is a sulfonyl halide; $R^L$ is optionally substituted sulfonyl; and $X^L$ is halogen.

43. The method of claim 3, wherein reagent of the formula $X^L$-$R^L$ is tosyl chloride (TsCl).

44. The method of claim 3, wherein the step of reacting is carried out in the presence of a base.

45. The method of claim 44, wherein the base is a trialkylamine base, a pyridine base, or an imidazole base.

46. The method of claim 44, wherein the base is triethylamine (TEA).

47. The method of claim 3, wherein the step of reacting is carried out in the presence of a Lewis acid.

48. The method of claim 47, wherein the Lewis acid is dibutyltin oxide.

49. The method of claim 3, wherein the step of reacting is carried out in dichloromethane (DCM).

50. The method of claim 6, wherein the compound of Formula (A) is the following:

55. The method of claim 53, wherein the base is triethylamine (TEA).

56. The method of claim 6, wherein the step of reacting is carried out in the presence of a Lewis acid.

57. The method of claim 56, wherein the Lewis acid is dibutyltin oxide.

58. The method of claim 6, wherein the step of reacting is carried out in dichloromethane (DCM).

59. The method of claim 50, wherein the step of reacting is carried out in the presence of p-toluenesulfonyl chloride (TsCl), triethylamine (TEA), and dibutyltin oxide.

60. The method of claim 50, wherein the step of reacting is carried out in the presence of p-toluenesulfonyl chloride (TsCl), triethylamine (TEA), and dibutyltin oxide, in dichloromethane (DCM), at a temperature ranging from 0° C. to 50° C.

61. The method of claim 1, wherein the step of reducing is carried out in the presence of triphenylphosphine ($Ph_3P$) and water, in tetrahydrofuran (THF), at a temperature ranging from 0° C. to 50° C.

62. The method of claim 1, wherein the step of reducing is carried out in the presence of triphenylphosphine ($Ph_3P$) and water, in tetrahydrofuran (THF), at a temperature of approximately 25° C.

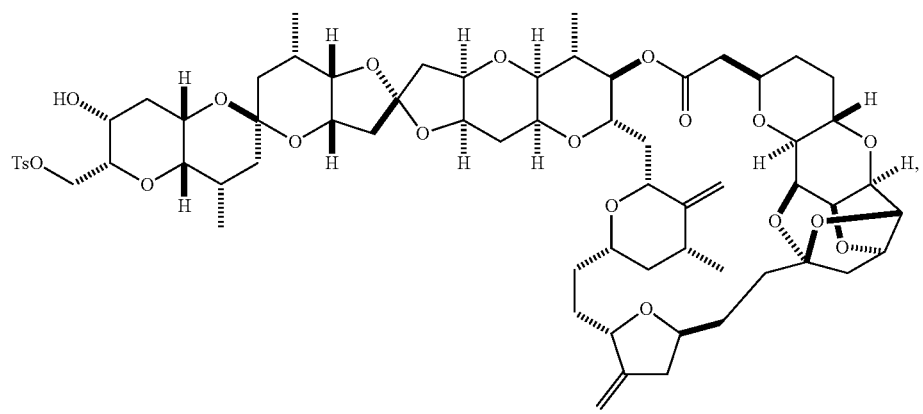

or a salt thereof.

51. The method of claim 6, wherein reagent of the formula $X^L$-$R^L$ is a sulfonyl halide; $R^L$ is optionally substituted sulfonyl; and $X^L$ is halogen.

52. The method of claim 6, wherein reagent of the formula $X^L$-$R^L$ is tosyl chloride (TsCl).

53. The method of claim 6, wherein the step of reacting is carried out in the presence of a base.

54. The method of claim 53, wherein the base is a trialkylamine base, a pyridine base, or an imidazole base.

63. The method of claim 5, wherein the step of reacting is carried out in the presence of tetrabutylammonium azide, in toluene, at a temperature ranging from room temperature to 150° C.

64. The method of claim 35, wherein the azide is sodium azide, potassium azide, or a tetraalkylammonium azide.

65. The method of claim 35, wherein the azide is a tetraalkylammonium azide.

66. The method of claim 35, wherein the step of reacting is carried out in toluene.

* * * * *

UNITED STATES PATENT AND TRADEMARK OFFICE
CERTIFICATE OF CORRECTION

PATENT NO. : 11,548,898 B2  
APPLICATION NO. : 16/628504  
DATED : January 10, 2023  
INVENTOR(S) : Yoshito Kishi et al.

Page 1 of 8

It is certified that error appears in the above-identified patent and that said Letters Patent is hereby corrected as shown below:

In the Specification

At Column 19, Lines 5-8, the text: "("heteroC$_{23}$ alkenyl")" should be replaced with --("heteroC$_{2-3}$ alkenyl")--.

At Column 20, Lines 4-6, the text: "("heteroC$_{24}$ alkynyl")" should be replaced with --("heteroC$_{2-4}$ alkynyl")--.

At Column 22, Lines 52-56, the text: "having 6, 10, or 14 t electrons" should be replaced with --having 6, 10, or 14 π electrons--.

At Column 23, Lines 7-14, the text: "having 6, 10, or 14 nt electrons" should be replaced with --having 6, 10, or 14 π electrons--.

At Column 25, Line 24, the text: "–C(=O)NR$^{bb}$ SO$_2$R$^{aa}$" should be replaced with -- –C(=O)NR$^{bb}$SO$_2$R$^{aa}$--.

At Column 26, Line 61, the text: "–NH(C$_{1-6}$ alkyl)$_2^+$X, –NH$_2$(C$_{1-6}$ alkyl)$^+$X" should be replaced with -- –NH(C$_{1-6}$ alkyl)$_2^+$X$^-$, –NH$_2$(C$_{1-6}$ alkyl)$^+$X$^-$--.

At Column 27, Line 24, the text: "–NH(C$_{1-6}$ alkyl)$_2^+$X" should be replaced with -- –NH(C$_{1-6}$ alkyl)$_2^+$X$^-$--.

At Column 27, Line 28, the text: "–CO$_2$(C$_{1-6}$ alkyl)" should be replaced with -- –OCO$_2$(C$_{1-6}$ alkyl)--.

At Column 27, Line 64, the text: –OP(=O)(ORc)$_2$" should be replaced with -- –OP(=O)(OR$^{cc}$)$_2$--.

At Column 28, Lines 10-11, the text: "wherein R$^{aa}$, R$^{bb}$ and RC are as defined herein" should be replaced with --wherein R$^{aa}$, R$^{bb}$ and R$^{cc}$ are as defined herein--.

Signed and Sealed this  
Twenty-fourth Day of December, 2024

Derrick Brent  
*Acting Director of the United States Patent and Trademark Office*

CERTIFICATE OF CORRECTION (continued)
U.S. Pat. No. 11,548,898 B2

At Column 28, Line 18, the text: "–NR$^{bb}$(=NR$^{bb}$)N(R$^{bb}$)$_2$" should be replaced with -- –NR$^{bb}$C(=NR$^{bb}$)N(R$^{bb}$)$_2$--.

At Column 28, Lines 26-27, the text: "wherein R$^{bb}$ and X are as defined herein." should be replaced with --wherein Rbb and X⁻ are as defined herein.--.

At Column 31, Lines 7-8, the text: "3-trimethyl silylethanesulfonamide (SES)" should be replaced with --β-trimethylsilylethanesulfonamide (SES)--.

At Column 31, Lines 32-33, the text: "N-p-methoxyb enzylideneamine" should be replaced with --N-p-methoxybenzylideneamine--.

At Column 33, Line 30, the text: "–CO$_2$R" should be replaced with -- –CO$_2$R$^{aa}$--.

At Column 34, Line 26, the text: "–OC(=NR$^{bb}$)Ra, –OC(=NR$^{bb}$)OR" should be replaced with -- –OC(=NR$^{bb}$)R$^{aa}$, –OC(=NR$^{bb}$)OR$^{aa}$--.

At Column 36, Line 65, the text: "bearing a ca-OR" should be replaced with --bearing a α-OR--.

At Column 38, Line 26, the text: "CHzCl$_2$-MeOH" should be replaced with --CH$_2$Cl$_2$-MeOH--.

At Column 40, Line 5, the text: "C$_{38}$-C$_{53}$ building block" should be replaced with --C38-C53 building block--.

At Column 45, Line 22, the text: "NiX$_2$e(ligand);" should be replaced with --NiX$_2$•(ligand);--.

At Column 92, Line 47, the text: "(HI3-2-I)" should be replaced with --(H3-2-I)--.

At Column 119, Line 3, the text: "OR$^7$ with the group" should be replaced with --OR$^{P7}$ with the group--.

At Column 119, Lines 24-31, the sentences: "In certain embodiments, the group –OR$^7$ is a leaving group. In certain embodiments, the group –OR$^7$ is –O-sulfonyl. In certain embodiments, the group –OR$^7$ is –OMs. In certain embodiments, the group –OR$^7$ is –OTs. In certain embodiments, the group –OR$^{P7}$ is –OTf. In certain embodiments, the group –OR$^7$ is –O-acyl. In certain embodiments, the group –OR$^7$ is –O-phosphoryl." should be replaced with: --In certain embodiments, the group –OR$^{P7}$ is a leaving group. In certain embodiments, the group –OR$^{P7}$ is –O-sulfonyl. In certain embodiments, the group –OR$^{P7}$ is –OMs. In certain embodiments, the group –OR$^{P7}$ is –OTs. In certain embodiments, the group –OR$^{P7}$ is –OTf. In certain embodiments, the group –OR$^{P7}$ is –O-acyl. In certain embodiments, the group –OR$^{P7}$ is –O-phosphoryl.--.

At Column 121, Line 67, the text: "the acid isp-toluenesulfonic acid" should be replaced with --the acid is *p*-toluenesulfonic acid--.

At Column 128, Line 27, the text: "two R$^6$ groups" should be replaced with --two R$^4$ groups--.

CERTIFICATE OF CORRECTION (continued)
U.S. Pat. No. 11,548,898 B2

At Column 133, Line 25, the text: "Lewis acid is AgOTfIn certain" should be replaced with --Lewis acid is AgOTf. In certain--.

At Column 161, Line 14, the text: "and $R^{Pl0}$ is TES." should be replaced with --and $R^{P10}$ is TES.--.

At Column 171, Line 31, the text: "group R from," should be replaced with --group $R^{P4}$ from,--.

At Column 175, Line 26, the text: "Homer-Wadsworth" should be replaced with --Horner-Wadsworth--.

At Column 184, Line 25, the text: "In certain embodiments, $R^1$, $R^{P3}$, and $R^{P4}$" should be replaced with --In certain embodiments, $R^{P1}$, $R^{P3}$, and $R^{P4}$--.

At Column 188, Line 26, the text: "Homer-Wadsworth" should be replaced with --Horner-Wadsworth--.

At Column 189, Lines 40-53, the text and formula: "In certain embodiments, the organometallic reagent is a lithium reagent (*e.g.*, to convert the compound 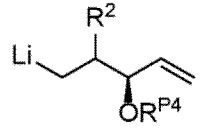 of the Formula (L-5-5) to a compound of the formula: $OR^{P4}$ for addition to the compound of Formula (L-5-4))." should be replaced with: --In certain embodiments, the organometallic reagent is a lithium reagent (*e.g.*, to convert the compound of the Formula (L-5-5) to a compound of the formula: 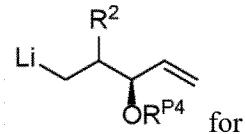 for addition to the compound of Formula (L-5-4)).--.

At Column 190, Line 3, the text: "$R^1$ is TBS" should be replaced with --$R^{P1}$ is TBS--.

At Column 193, Line 8, the text: "4A molecular sieves" should be replaced with --4Å molecular sieves--.

At Column 195, Line 21, the text: "(*i.e.*, H)" should be replaced with --(*i.e.*, H⁻)--.

At Column 195, Line 45, the text: "Homer-Wadsworth" should be replaced with --Horner-Wadsworth--.

At Column 206, Line 8, the text: "Homer-Wadsworth" should be replaced with --Horner-Wadsworth--.

At Column 219, Line 43, the text: "Homer-Wadsworth" should be replaced with --Horner-Wadsworth--.

At Column 223, Line 67, the text: "Formula L-5-4):" should be replaced with --Formula (L-5-4):--.

CERTIFICATE OF CORRECTION (continued)
U.S. Pat. No. 11,548,898 B2

At Column 226, Line 3, the text: "N,N-dii sopropylethylamine" should be replaced with --N,N-diisopropylethylamine--.

At Column 231, Line 27, the text: "$R^{P1}$, $R^{P2}$, $R^{P3}$, $R^4$, and $R^{P5}$" should be replaced with --$R^{P1}$, $R^{P2}$, $R^{P3}$, $R^{P4}$, and $R^{P5}$--.

At Column 234, Line 18, the text: "–$OR^X$" should be replaced with -- –$OR^{Xa}$--.

At Column 235, Line 10, the text: "–$OR^X$" should be replaced with -- –$OR^{Xa}$--.

At Column 271, Lines 50-51, the text: "substituted alkyl. In certain embodiments, In certain embodiments, $R^7$ is optionally substituted $C_{1-6}$ alkyl." should be replaced with --substituted alkyl. In certain embodiments, $R^7$ is optionally substituted $C_{1-6}$ alkyl.--.

At Column 272, Lines 7-8, the text: "substituted alkyl. In certain embodiments, In certain embodiments, $R^8$ is optionally substituted $C_{1-6}$ alkyl." should be replaced with --substituted alkyl. In certain embodiments, $R^8$ is optionally substituted $C_{1-6}$ alkyl.--.

At Column 273, Lines 36-38, the text: "substituted alkyl. In certain embodiments, In certain embodiments, $R^{P1}$ is optionally substituted $C_{1-6}$ alkyl" should be replaced with --substituted alkyl. In certain embodiments, $R^{P1}$ is optionally substituted $C_{1-6}$ alkyl.--.

At Column 280, Line 35, the text: "$R^{P\circ\ 0}$" should be replaced with --$R^{P10}$--.

At Column 282, Line 19, the text: "$CpzZrCl_2$" should be replaced with --$Cp_2ZrCl_2$--.

At Column 282, Line 31, the text: "$CpzZrCl_2$" should be replaced with --$Cp_2ZrCl_2$--.

At Column 283, Lines 10-11, the text: "relevant group at the a-position" should be replaced with --relevant group at the α-position--.

At Column 283, Line 65, the text: "permanganate, orp-anisaldehyde." should be replaced with --permanganate, or *p*-anisaldehyde.--.

At Column 288, Line 30, the text: "H NMR" should be replaced with --$^1$H NMR--.

At Column 291, Line 43, the text: "R)-(5-(4-methoxyphenyl)-3-oxo-1-phenylpentyl)carbamate (8k)" should be replaced with --(R)-(5-(4-methoxyphenyl)-3-oxo-1-phenylpentyl)carbamate (8k)--.

At Column 292, Line 2, the text: "methyl (R)-2-((tert-butoxycarbonyl)amino)-6-(4-methoxyphenyl)-4-oxohexanoate (8l)" should be replaced with --methyl (R)-2-((tert-butoxycarbonyl)amino)-6-(4-methoxyphenyl)-4-oxohexanoate (8l)--.

At Column 296, Line 28, the text: "6-chloro-1-(4-methoxyphenyl)hexan-3-one (10l)" should be replaced with --6-chloro-1-(4-methoxyphenyl)hexan-3-one (10l)--.

CERTIFICATE OF CORRECTION (continued)
U.S. Pat. No. 11,548,898 B2

At Column 298, Line 45, the text: "6=7.09" should be replaced with --$\delta = 7.09$--.

At Column 298, Line 49, the text: "6=210.9" should be replaced with --$\delta = 210.9$--.

At Column 302, Lines 1-2, the text: "((S)-2-C+(S)-2-D→(2,4)-2-E)-coupling" should be replaced with --(($S$)-2-C + ($S$)-2-D → ($\Sigma,\Sigma$)-2-E)-coupling--.

At Column 310, Line 42, the text: "C38-Epi-2-11:" should be replaced with --C38-*epi*-2-11:--.

At Column 319, Line 1, the text: "C38-Epi-Halichondrin B:" should be replaced with --C38-*epi*-Halichondrin B:--.

At Column 322, Line 12, the text: "[ ]$^{20}$$_D$ -68.4" should be replaced with --$[\alpha]^{20}_D$ -68.4--.

At Column 325, Line 5, the text: "at room temperature.$^3$" should be replaced with --at room temperature.--.

At Column 333, Line 34, the text: "38-Epi-Homohalichondrin B (C38-Epi-19):" should be replaced with --38-*epi*-Homohalichondrin B (C38-*epi*-19):--.

At Column 334, Line 42, the text: "15.2 μm. FTIR (film):" should be replaced with --15.2 pm. FTIR (film):--.

At Column 339, Line 26, the text: "were added.$^1$" should be replaced with --were added.--.

At Column 341, Line 1, the text: "38-Epi-Halichondrin A (C38-Epi-20):" should be replaced with --38-*epi*-Halichondrin A (C38-*epi*-20):--.

At Column 346, Line 66, the text: "at room temperature.$^3$" should be replaced with --at room temperature.--.

At Column 347, Line 14, the text: "(c 0.37, MeOH)$^1$H" should be replaced with --(*c* 0.37, MeOH) $^1$H--.

At Column 348, Line 1, the text: "38-Epi-Norhalichondrin A (C38-Epi-21):" should be replaced with --38-*epi*-Norhalichondrin A (C38-*epi*-21):--.

At Column 351, Line 66, the text: "[i]$^{20}$$_D$ -73.0" should be replaced with --$[\alpha]^{20}_D$ -73.0--.

At Column 355, Line 33, the text: "38-Epi-Homohalichondrin A (C38-Epi-22):" should be replaced with --38-*epi*-Homohalichondrin A (C38-*epi*-22):--.

At Column 361, Line 41, the text: "were added.$^1$" should be replaced with --were added.--.

At Column 363, Line 24, the text: "38-Epi-Halichondrin C (C38-Epi-23):" should be replaced with --38-*epi*-Halichondrin C (C38-*epi*-23):--.

At Column 365, Line 43, the text: "[i]$^{20}$$_D$ -64.8" should be replaced with --[α]$^{20}$$_D$ -64.8--.

At Column 374, Line 35, the text: "the $C_{19}$-$C_{20}$ bond" should be replaced with --the C19-C20 bond--.

At Column 374, Lines 65-66, the text: "as the maj or product" should be replaced with --as the major product--.

At Column 375, Line 49, the text: "The $C_{19}$-$C_{20}$ bond" should be replaced with --The C19-C20 bond--.

At Column 375, Line 64, the text: "CpzZrCl$_2$" should be replaced with --Cp$_2$ZrCl$_2$--.

At Column 376, Line 5, the text: "Cl" should be replaced with --C1--.

At Column 376, Line 35, the text: "Cl" should be replaced with --C1--.

At Column 376, Line 67, the text: "300-500 mg" should be replaced with --300~500 mg--.

At Column 377, Line 38-43, the text: "The chiral centers at C17 and C25 originated from the chiral centers present in $C_1$-$C_{19}$ and $C_{20}$-$C_{26}$ building blocks. Thus, use of C17-epi-$C_1$-$C_{19}$ building block gave the stereoisomer at C17, whereas use of the antipode of $C_{20}$-$C_{26}$ building block gave the minor stereoisomers at C25." should be replaced with: --The chiral centers at C17 and C25 originated from the chiral centers present in C1-C19 and C20-C26 building blocks. Thus, use of C17-*epi*-C1-C19 building block gave the stereoisomer at C17, whereas use of the antipode of C20-C26 building block gave the minor stereoisomers at C25.--.

At Column 377, Line 48, the text: "$C_1$-$C_{19}$" should be replaced with --C1-C19--.

At Column 382, Line 50, the text: "[α]20D+18.8" should be replaced with --[α]$^{20}$$_D$ +18.8--.

At Column 388, Line 60, the text: "(1H, d, J 7.2 Hz)" should be replaced with --(1H, d, *J* = 7.2 Hz)--.

At Column 417, Line 31, the text: "ofNaOMe" should be replaced with --of NaOMe--.

At Column 417, Lines 65-66, the text: "-3 kcal/mol (1.6×1.9 kcal/mol)" should be replaced with --~3 kcal/mol (1.6 × 1.9 kcal/mol)--.

At Column 418, Line 22, the text: "6-lactone" should be replaced with --δ-lactone--.

At Column 420, Line 1, the text: "$C_{53}$-$C_{55}$" should be replaced with --C53-C55--.

At Column 420, Line 10, the text: "6-lactone" should be replaced with --δ-lactone--.

At Column 422, Line 22, the text: "were addedP-After" should be replaced with --were added. After--.

At Column 426, Line 49, the text: "pressure to give to give a crude TES ether" should be replaced

CERTIFICATE OF CORRECTION (continued)
U.S. Pat. No. 11,548,898 B2 with --pressure to give a crude TES ether--.

At Column 427, Line 6, the text: "$t_R{=}^{15}$ min." should be replaced with --$t_R$ = 15 min.--.

At Column 427, Line 39, the text: "[α]$_D$=–2.2" should be replaced with --$[\alpha]_D^{22} = -2.2$--.

At Column 428, Line 5, the text: "[α]$^2$=–15.6" should be replaced with --$[\alpha]_D^{22} = -15.6$--.

At Column 428, Line 43, the text: "[α]$^2$=+6.0" should be replaced with --$[\alpha]_D^{22} = +6.0$--.

At Column 429, Line 3, the text: "3 min.$^3$" should be replaced with --3 min.--.

At Column 429, Line 23, the text: "[α]$^2$=+3.0" should be replaced with --$[\alpha]_D^{22} = +3.0$--.

At Column 430, Line 8, the text: "[α]$^2$=+13.0" should be replaced with --$[\alpha]_D^{22} = +13.0$--.

At Column 430, Line 54, the text: "[α]$^2$=+26.0" should be replaced with --$[\alpha]_D^{22} = +26.0$--.

At Column 431, Line 26, the text: "[α]$^2$=+26.9" should be replaced with --$[\alpha]_D^{22} = +26.9$--.

At Column 431, Line 41, the text: "$C_{30}H_{62}O_6NaSi_3$+625.3746" should be replaced with --$C_{30}H_{62}O_6NaSi_3^+$ 625.3746--.

At Column 432, Line 51, the text: "[α]=–5.8" should be replaced with --$[\alpha]_D^{22} = -5.8$--.

At Column 436, Line 57, the text: "(600 mg, 0.11 mmol, eq. BnOAc" should be replaced with --(600 mg, 0.711 mmol, 1 eq.), BnOAc--.

At Column 436, Line 65, the text: "[α]$^2$=–29.3" should be replaced with --$[\alpha]_D^{22} = -29.3$--.

At Column 438, Line 6, the text: "$C_{46}H_{74}O_{11}NaSi_2^+$" should be replaced with --$C_{46}H_{74}O_{10}NaSi_2^+$--.

At Column 439, Line 22, the text: "[α]D=–3.12" should be replaced with --$[\alpha]_D^{22} = -31.2$--.

At Column 440, Line 5, the text: "[α]D=–44.3" should be replaced with --$[\alpha]_D^{22} = -44.3$--.

At Column 441, Line 36, the text: "(107 mg, 0.49 mmol, 1.4 eq.).$^2$" should be replaced with --(107 mg, 0.49 mmol, 1.4 eq.).--.

At Column 441, Lines 40, the text: "(neutral SiO$_2$, hexanes/EtOAc=I/O, 10/1, 5/1)" should be replaced with --(neutral SiO$_2$, hexanes/EtOAc = 1/0, 10/1, 5/1)--.

CERTIFICATE OF CORRECTION (continued)
U.S. Pat. No. 11,548,898 B2

At Column 441, Line 42, the text: "$[\alpha]^2$=−75.7" should be replaced with --$[\alpha]_D^{22} = -75.7$--.

At Column 446, Line 12, the text: "$[\ ]^{20}{}_D$ -16.6" should be replaced with --$[\alpha]^{20}{}_D$ -16.6--.

At Column 449, Line 13, the text: "$C_{20}H_{28}N3O_{10}$" should be replaced with --$C_{20}H_{28}N_3O_{10}$--.

At Column 456, Line 33, the text: "$C_{47}H_{74 10}Si_2Na$" should be replaced with --$C_{47}H_{74}O_{10}Si_2Na$--.

At Column 463, Line 1, the text: "$[\alpha]^{20D}$ +34.0" should be replaced with --$[\alpha]^{20}{}_D$ +34.0--.

At Column 475, Line 9, the text: "$[\alpha]D^{20}$+3.00" should be replaced with --$[\alpha]_D{}^{20}$ +3.00--.

At Column 477, Line 29, the text: "in acetone (2.2)" should be replaced with --in acetone (2.2L)--.

At Column 483, Line 31, the text: "EtOAc/water=l/1 (v/v) (106mL)" should be replaced with --EtOAc/water=1/1 (v/v) (106mL)--.

In the Claims

In Claim 2, Column 520, Line 15, the text: "$R^{Ya}$are" should be replaced with --$R^{Ya}$ are--.

In Claim 3, Column 522, Line 16, the text: "$R^{Ya}$are" should be replaced with --$R^{Ya}$ are--.